United States Patent
Chabriere et al.

(10) Patent No.: US 10,072,252 B2
(45) Date of Patent: Sep. 11, 2018

(54) SULFOLOBAL PHOSPHOTRIESTERASE-LIKE (PLL) LACTONASES ACTIVITY HAVING ENHANCED PROPERTIES AND THE USES THEREOF

(71) Applicants: CENTRE NATIONAL DE LA RECHERCHE SCIENTIFIQUE, Paris (FR); UNIVERSITE D'AIX-MARSEILLE, Marseilles (FR)

(72) Inventors: Eric Chabriere, Marseilles (FR); Mikael Elias, Florange (FR); Julien Hiblot, Marseilles (FR); Didier Raoult, Marseilles (FR)

(73) Assignees: CENTRE NATIONAL DE LA RECHERCHE SCIENTIFIQUE, Paris (FR); UNIVERSITE D'AIX-MARSEILLE, Marseilles (FR)

( * ) Notice: Subject to any disclaimer, the term of this patent is extended or adjusted under 35 U.S.C. 154(b) by 141 days.

(21) Appl. No.: 14/782,703

(22) PCT Filed: Apr. 14, 2014

(86) PCT No.: PCT/EP2014/057554
§ 371 (c)(1),
(2) Date: Oct. 6, 2015

(87) PCT Pub. No.: WO2014/167140
PCT Pub. Date: Oct. 16, 2014

(65) Prior Publication Data
US 2016/0115462 A1    Apr. 28, 2016

(30) Foreign Application Priority Data
Apr. 12, 2013   (EP) ................................ 13305483

(51) Int. Cl.
C12N 9/16       (2006.01)
A01N 63/00      (2006.01)
A61K 38/00      (2006.01)

(52) U.S. Cl.
CPC .............. *C12N 9/16* (2013.01); *A01N 63/00* (2013.01); *C12Y 301/08001* (2013.01); *A61K 38/00* (2013.01); *C12Y 301/08* (2013.01)

(58) Field of Classification Search
None
See application file for complete search history.

(56) References Cited

U.S. PATENT DOCUMENTS

2010/0333221 A1    12/2010  Chabriere et al.
2013/0071394 A1 *   3/2013  Troyer et al. .......... A61K 38/47
                                                       424/134.1

FOREIGN PATENT DOCUMENTS

WO    2008/145865 A2    12/2008

OTHER PUBLICATIONS

Hiblot et al.,"Structural and Enzymatic characterization of the lactonase SisLac from Sulfolobus islandicus", PLoS ONE 7(10): e47028.*
Luigia Merone et al.: "A thermostable phosphotriesterase from the archaeon Sulfolobus solfataricus: cloning, overexpression and properties", Extremophiles, Life Under Extreme Conditions, Springer-Verlag, TO,vol. 9, No. 4, Aug. 1, 2005 (Aug. 1, 2005), pp. 297-305, XP019374100, ISSN: 1433-4909, DOI: 10.1007/500792-005-0445-4 the whole document.
Database UniProt [Online] Apr. 29, 2008 (Apr. 29, 2008), "Sub Name: Full=QsdA;" XP002716054, retrieved from EBI accession No. UNIPROT:B1N7B2 Database accession No. B1N7B2 sequence.
Janek Bzdrenga et al.: "SacPox from the thermoacidophilic crenarchaeon Sulfolobus acidocaldarius is a proficientlactonase", BMC Research Notes, vol. 7, No. I, Jan. 1, 2014 (Jan. 1, 2014) , p. 333, XP055126943, ISSN: 1756-0500, DOI: 10.1186/1756-0500-7-333.
Julien Hiblot et al.: "Differential Active Site Loop Conformations Mediate Promiscuous Activities in the Lactonase SsOPox" PLOS ONE, vol. 8, No. 9, Sep. 23, 2013 (Sep. 23, 2013), p. e75272, XP055126945, ISSN: 1932-6203, DOI: 10.1371/journal.pone.0075272.
Database UniProt [Online], Mar. 6, 2013 (Mar. 6, 2013), "SubName: Full=N-acylhomoserine I actonase;" XP002702545, retrieved from EBI accession No. UNI PROT: L7KJL9 Database accession No. L7KJL9, the whole document.
International Search Report, dated Jul. 15, 2014, from corresponding PCT application.
EP Search Report, dated Nov. 8, 2013, from corresponding EP application.

* cited by examiner

*Primary Examiner* — Anand U Desai
(74) *Attorney, Agent, or Firm* — Young & Thompson

(57) ABSTRACT

Mutated hyperthermophilic PTE having a lactonase activity derived from a hyperthermophilic phosphotriesterase corresponding to the consensus sequence of SEQ ID NO: 1, the mutated PTE including the at least one mutation chosen amongst 53 putative positions and the mutated PTE having enhanced properties. Also provided are compositions including the mutated hyperthermophilic PTE and the uses thereof, notably as bioscavenger of organophosphate compounds or as quorum quencher of the bacteria using lactones to communicate.

Figure 4:
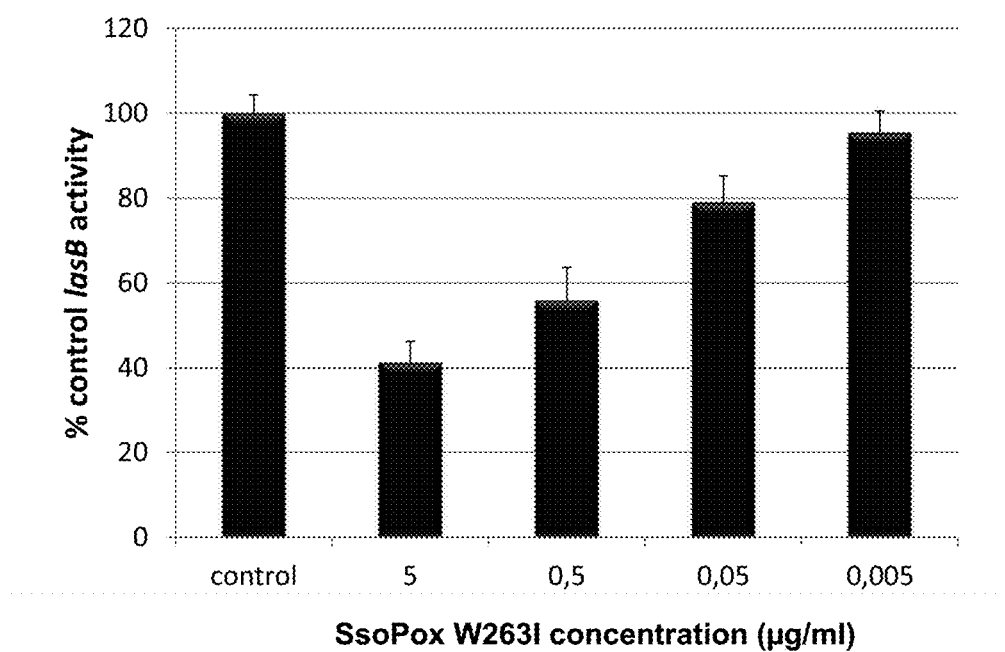

22 Claims, 9 Drawing Sheets
Specification includes a Sequence Listing.

FIGURE 1
A.
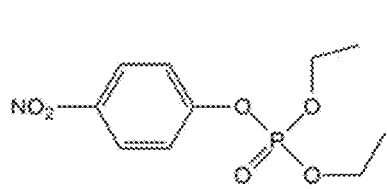
B.
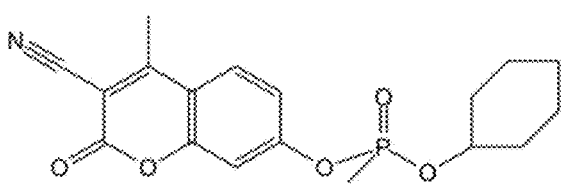
C.
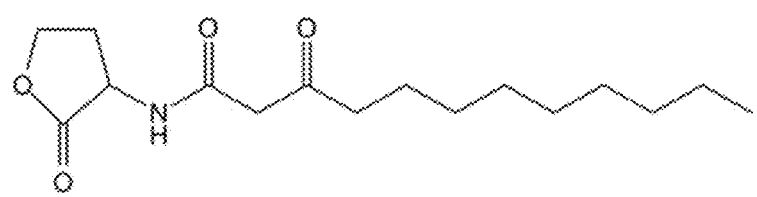
D.
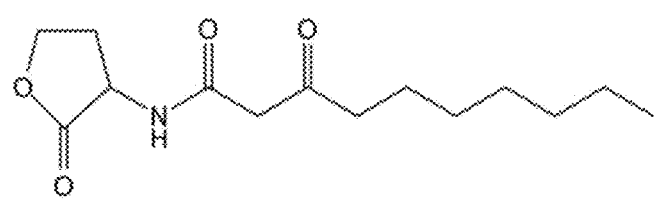
F.
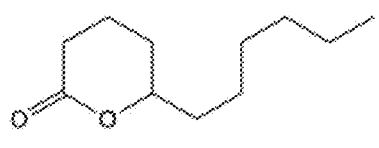
E.
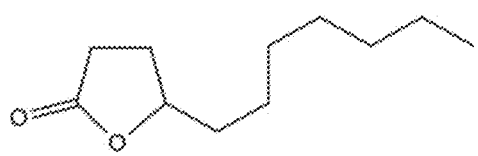

FIGURE 2-A
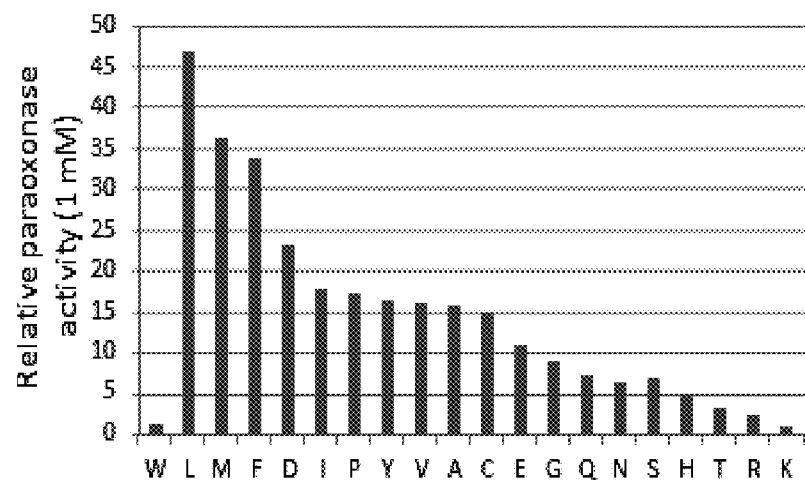
FIGURE 2-B
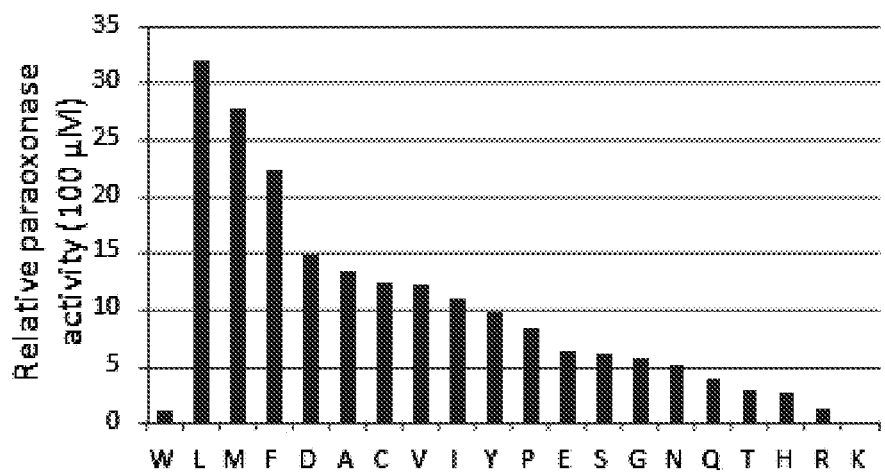

FIGURE 2-C
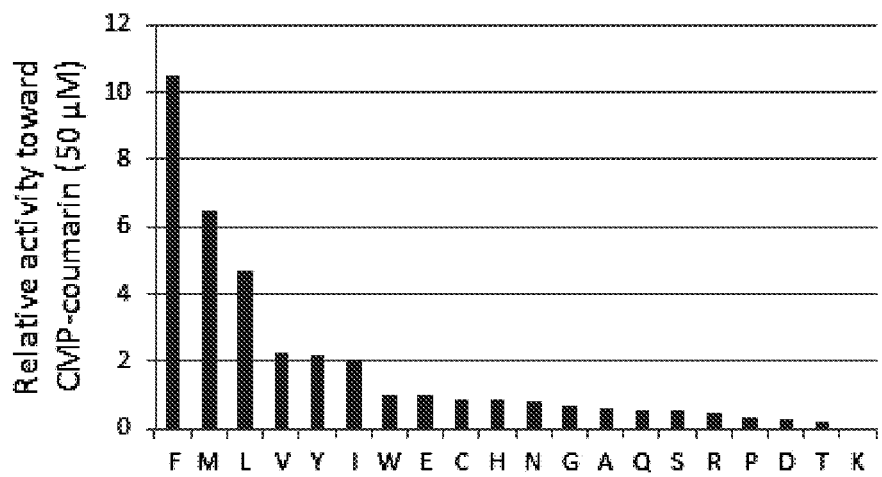
FIGURE 2-D
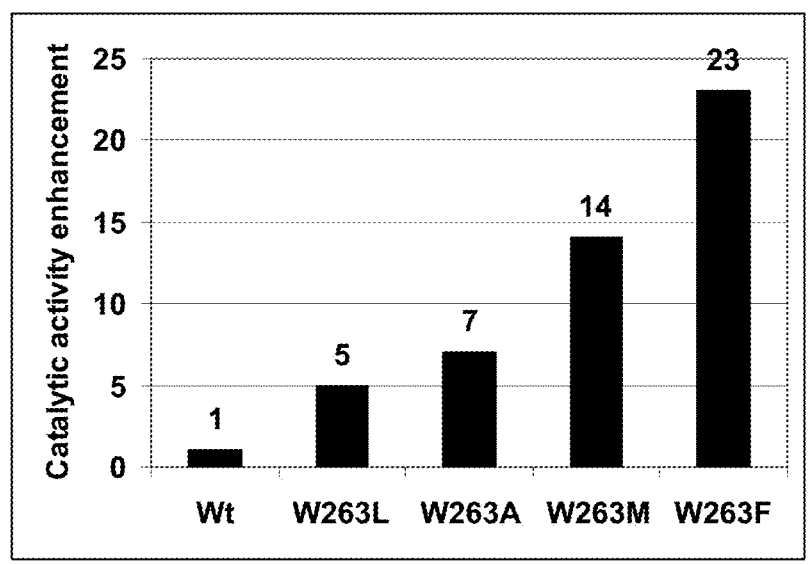

FIGURE 3-A
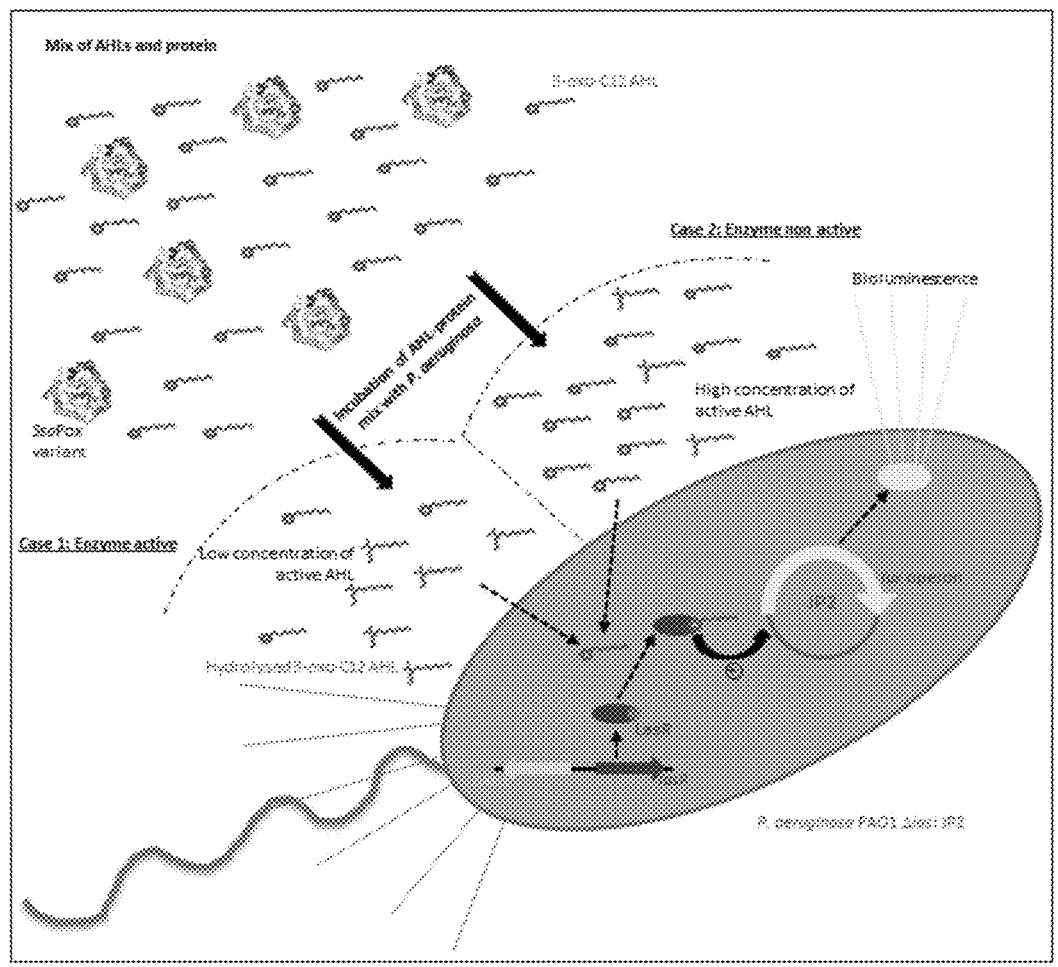

FIGURE 3-B
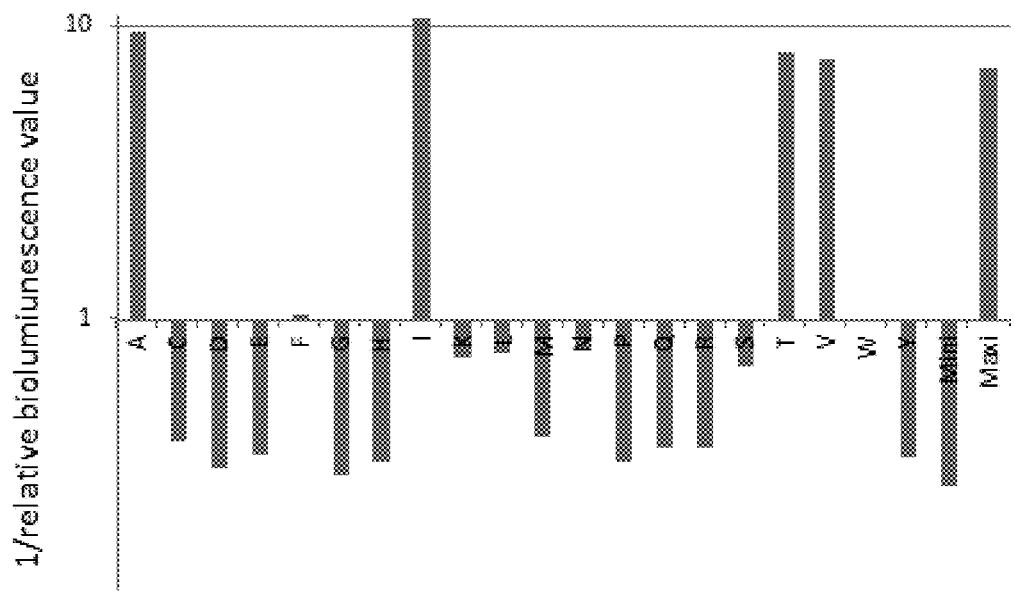
FIGURE 3-C
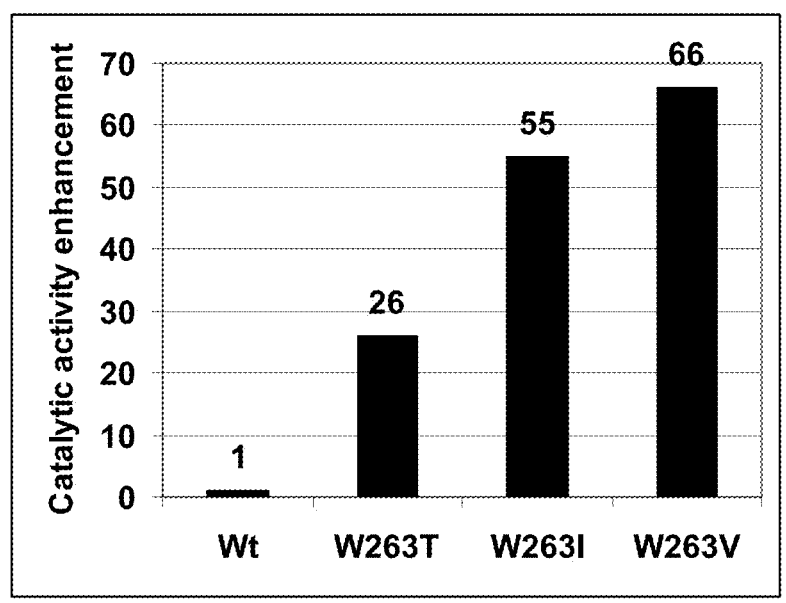

FIGURE 7
A
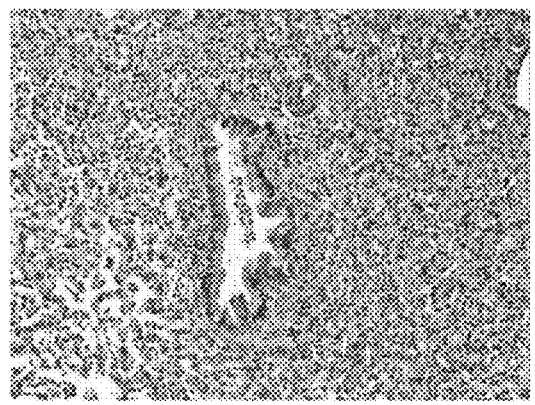
B
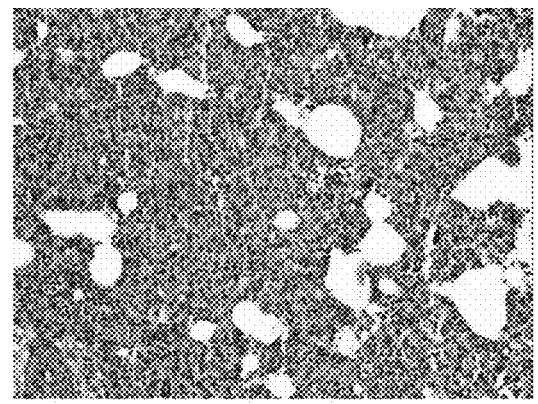
C
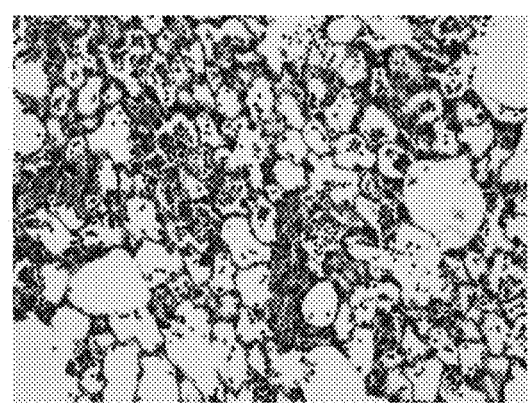

SEQUENCE LISTING

```
<160> NUMBER OF SEQ ID NOS: 313

<210> SEQ ID NO 1
<211> LENGTH: 316
<212> TYPE: PRT
<213> ORGANISM: Unknown
<220> FEATURE:
<223> OTHER INFORMATION: Sulfolobus
<220> FEATURE:
<221> NAME/KEY: misc_feature
<222> LOCATION: (2)..(2)
<223> OTHER INFORMATION: A or blank
<220> FEATURE:
<221> NAME/KEY: misc_feature
<222> LOCATION: (3)..(3)
<223> OTHER INFORMATION: T or blank
<220> FEATURE:
<221> NAME/KEY: misc_feature
<222> LOCATION: (4)..(4)
<223> OTHER INFORMATION: R or K
<220> FEATURE:
```

```
<221> NAME/KEY: misc_feature
<222> LOCATION: (11)..(11)
<223> OTHER INFORMATION: D or G or E
<220> FEATURE:
<221> NAME/KEY: misc_feature
<222> LOCATION: (12)..(12)
<223> OTHER INFORMATION: S or E or P
<220> FEATURE:
<221> NAME/KEY: misc_feature
<222> LOCATION: (14)..(14)
<223> OTHER INFORMATION: E or S
<220> FEATURE:
<221> NAME/KEY: misc_feature
<222> LOCATION: (15)..(15)
<223> OTHER INFORMATION: S or P or A
<220> FEATURE:
<221> NAME/KEY: misc_feature
<222> LOCATION: (16)..(16)
<223> OTHER INFORMATION: K or G or E
<220> FEATURE:
<221> NAME/KEY: misc_feature
<222> LOCATION: (17)..(17)
<223> OTHER INFORMATION: D or E
<220> FEATURE:
<221> NAME/KEY: misc_feature
<222> LOCATION: (18)..(18)
<223> OTHER INFORMATION: I or M
<220> FEATURE:
<221> NAME/KEY: misc_feature
<222> LOCATION: (33)..(33)
<223> OTHER INFORMATION: A or P
<220> FEATURE:
<221> NAME/KEY: misc_feature
<222> LOCATION: (36)..(36)
<223> OTHER INFORMATION: Q or Y
<220> FEATURE:
<221> NAME/KEY: misc_feature
<222> LOCATION: (48)..(48)
<223> OTHER INFORMATION: F or L
<220> FEATURE:
<221> NAME/KEY: misc_feature
<222> LOCATION: (49)..(49)
<223> OTHER INFORMATION: R or K
<220> FEATURE:
<221> NAME/KEY: misc_feature
<222> LOCATION: (57)..(57)
<223> OTHER INFORMATION: R or T
<220> FEATURE:
<221> NAME/KEY: misc_feature
<222> LOCATION: (58)..(58)
<223> OTHER INFORMATION: A or I
<220> FEATURE:
<221> NAME/KEY: misc_feature
<222> LOCATION: (60)..(60)
<223> OTHER INFORMATION: Q or S
<220> FEATURE:
<221> NAME/KEY: misc_feature
<222> LOCATION: (61)..(61)
<223> OTHER INFORMATION: F or Y
<220> FEATURE:
<221> NAME/KEY: misc_feature
<222> LOCATION: (81)..(81)
<223> OTHER INFORMATION: M or S
<220> FEATURE:
<221> NAME/KEY: misc_feature
<222> LOCATION: (87)..(87)
<223> OTHER INFORMATION: A or E or T
<220> FEATURE:
<221> NAME/KEY: misc_feature
<222> LOCATION: (92)..(92)
<223> OTHER INFORMATION: L or V
<220> FEATURE:
<221> NAME/KEY: misc_feature
<222> LOCATION: (93)..(93)
<223> OTHER INFORMATION: V or I
<220> FEATURE:
<221> NAME/KEY: misc_feature
<222> LOCATION: (95)..(95)
<223> OTHER INFORMATION: G or A
```

```
<220> FEATURE:
<221> NAME/KEY: misc_feature
<222> LOCATION: (98)..(98)
<223> OTHER INFORMATION: I or L
<220> FEATURE:
<221> NAME/KEY: misc_feature
<222> LOCATION: (100)..(100)
<223> OTHER INFORMATION: I or T
<220> FEATURE:
<221> NAME/KEY: misc_feature
<222> LOCATION: (102)..(102)
<223> OTHER INFORMATION: I or T or V
<220> FEATURE:
<221> NAME/KEY: misc_feature
<222> LOCATION: (107)..(107)
<223> OTHER INFORMATION: Y or F
<220> FEATURE:
<221> NAME/KEY: misc_feature
<222> LOCATION: (109)..(109)
<223> OTHER INFORMATION: L or N
<220> FEATURE:
<221> NAME/KEY: misc_feature
<222> LOCATION: (110)..(110)
<223> OTHER INFORMATION: N or G
<220> FEATURE:
<221> NAME/KEY: misc_feature
<222> LOCATION: (113)..(113)
<223> OTHER INFORMATION: I or L
<220> FEATURE:
<221> NAME/KEY: misc_feature
<222> LOCATION: (114)..(114)
<223> OTHER INFORMATION: D or E
<220> FEATURE:
<221> NAME/KEY: misc_feature
<222> LOCATION: (118)..(118)
<223> OTHER INFORMATION: D or E
<220> FEATURE:
<221> NAME/KEY: misc_feature
<222> LOCATION: (120)..(120)
<223> OTHER INFORMATION: F or L
<220> FEATURE:
<221> NAME/KEY: misc_feature
<222> LOCATION: (126)..(126)
<223> OTHER INFORMATION: E or K
<220> FEATURE:
<221> NAME/KEY: misc_feature
<222> LOCATION: (130)..(130)
<223> OTHER INFORMATION: G or A
<220> FEATURE:
<221> NAME/KEY: misc_feature
<222> LOCATION: (132)..(132)
<223> OTHER INFORMATION: L or N or S
<220> FEATURE:
<221> NAME/KEY: misc_feature
<222> LOCATION: (134)..(134)
<223> OTHER INFORMATION: K or R
<220> FEATURE:
<221> NAME/KEY: misc_feature
<222> LOCATION: (138)..(138)
<223> OTHER INFORMATION: V or I
<220> FEATURE:
<221> NAME/KEY: misc_feature
<222> LOCATION: (140)..(140)
<223> OTHER INFORMATION: I or V
<220> FEATURE:
<221> NAME/KEY: misc_feature
<222> LOCATION: (149)..(149)
<223> OTHER INFORMATION: K or R
<220> FEATURE:
<221> NAME/KEY: misc_feature
<222> LOCATION: (153)..(153)
<223> OTHER INFORMATION: K or R
<220> FEATURE:
<221> NAME/KEY: misc_feature
<222> LOCATION: (154)..(154)
<223> OTHER INFORMATION: V or A
<220> FEATURE:
<221> NAME/KEY: misc_feature
<222> LOCATION: (161)..(161)
```

```
<223> OTHER INFORMATION: A or T
<220> FEATURE:
<221> NAME/KEY: misc_feature
<222> LOCATION: (162)..(162)
<223> OTHER INFORMATION: N or Q or H
<220> FEATURE:
<221> NAME/KEY: misc_feature
<222> LOCATION: (165)..(165)
<223> OTHER INFORMATION: T or A
<220> FEATURE:
<221> NAME/KEY: misc_feature
<222> LOCATION: (166)..(166)
<223> OTHER INFORMATION: K or N
<220> FEATURE:
<221> NAME/KEY: misc_feature
<222> LOCATION: (178)..(178)
<223> OTHER INFORMATION: N or G
<220> FEATURE:
<221> NAME/KEY: misc_feature
<222> LOCATION: (183)..(183)
<223> OTHER INFORMATION: Q or E
<220> FEATURE:
<221> NAME/KEY: misc_feature
<222> LOCATION: (188)..(188)
<223> OTHER INFORMATION: T or M
<220> FEATURE:
<221> NAME/KEY: misc_feature
<222> LOCATION: (196)..(196)
<223> OTHER INFORMATION: K or R
<220> FEATURE:
<221> NAME/KEY: misc_feature
<222> LOCATION: (197)..(197)
<223> OTHER INFORMATION: I or V
<220> FEATURE:
<221> NAME/KEY: misc_feature
<222> LOCATION: (208)..(208)
<223> OTHER INFORMATION: I or V or T
<220> FEATURE:
<221> NAME/KEY: misc_feature
<222> LOCATION: (221)..(221)
<223> OTHER INFORMATION: I or V
<220> FEATURE:
<221> NAME/KEY: misc_feature
<222> LOCATION: (234)..(234)
<223> OTHER INFORMATION: V or I
<220> FEATURE:
<221> NAME/KEY: misc_feature
<222> LOCATION: (240)..(240)
<223> OTHER INFORMATION: T or V
<220> FEATURE:
<221> NAME/KEY: misc_feature
<222> LOCATION: (241)..(241)
<223> OTHER INFORMATION: T or L
<220> FEATURE:
<221> NAME/KEY: misc_feature
<222> LOCATION: (243)..(243)
<223> OTHER INFORMATION: R or K
<220> FEATURE:
<221> NAME/KEY: misc_feature
<222> LOCATION: (250)..(250)
<223> OTHER INFORMATION: S or L
<220> FEATURE:
<221> NAME/KEY: misc_feature
<222> LOCATION: (252)..(252)
<223> OTHER INFORMATION: K or R
<220> FEATURE:
<221> NAME/KEY: misc_feature
<222> LOCATION: (255)..(255)
<223> OTHER INFORMATION: I or V
<220> FEATURE:
<221> NAME/KEY: misc_feature
<222> LOCATION: (257)..(257)
<223> OTHER INFORMATION: H or Q
<220> FEATURE:
<221> NAME/KEY: misc_feature
<222> LOCATION: (267)..(267)
<223> OTHER INFORMATION: T or I
<220> FEATURE:
<221> NAME/KEY: misc_feature
```

```
<222> LOCATION: (269)..(269)
<223> OTHER INFORMATION: K or R
<220> FEATURE:
<221> NAME/KEY: misc_feature
<222> LOCATION: (272)..(272)
<223> OTHER INFORMATION: Y or L
<220> FEATURE:
<221> NAME/KEY: misc_feature
<222> LOCATION: (279)..(279)
<223> OTHER INFORMATION: R or K
<220> FEATURE:
<221> NAME/KEY: misc_feature
<222> LOCATION: (282)..(282)
<223> OTHER INFORMATION: I or M
<220> FEATURE:
<221> NAME/KEY: misc_feature
<222> LOCATION: (283)..(283)
<223> OTHER INFORMATION: T or S or A
<220> FEATURE:
<221> NAME/KEY: misc_feature
<222> LOCATION: (287)..(287)
<223> OTHER INFORMATION: E or T
<220> FEATURE:
<221> NAME/KEY: misc_feature
<222> LOCATION: (289)..(289)
<223> OTHER INFORMATION: T or V
<220> FEATURE:
<221> NAME/KEY: misc_feature
<222> LOCATION: (292)..(292)
<223> OTHER INFORMATION: F or S
<220> FEATURE:
<221> NAME/KEY: misc_feature
<222> LOCATION: (293)..(293)
<223> OTHER INFORMATION: L or I
<220> FEATURE:
<221> NAME/KEY: misc_feature
<222> LOCATION: (295)..(295)
<223> OTHER INFORMATION: R or K
<220> FEATURE:
<221> NAME/KEY: misc_feature
<222> LOCATION: (296)..(296)
<223> OTHER INFORMATION: N or A
<220> FEATURE:
<221> NAME/KEY: misc_feature
<222> LOCATION: (299)..(299)
<223> OTHER INFORMATION: N or T or S
<220> FEATURE:
<221> NAME/KEY: misc_feature
<222> LOCATION: (300)..(300)
<223> OTHER INFORMATION: E or D
<220> FEATURE:
<221> NAME/KEY: misc_feature
<222> LOCATION: (302)..(302)
<223> OTHER INFORMATION: V or Q
<220> FEATURE:
<221> NAME/KEY: misc_feature
<222> LOCATION: (303)..(303)
<223> OTHER INFORMATION: I or L
<220> FEATURE:
<221> NAME/KEY: misc_feature
<222> LOCATION: (304)..(304)
<223> OTHER INFORMATION: A or H or D
<220> FEATURE:
<221> NAME/KEY: misc_feature
<222> LOCATION: (305)..(305)
<223> OTHER INFORMATION: T or V or I
<220> FEATURE:
<221> NAME/KEY: misc_feature
<222> LOCATION: (308)..(308)
<223> OTHER INFORMATION: K or V
<220> FEATURE:
<221> NAME/KEY: misc_feature
<222> LOCATION: (309)..(309)
<223> OTHER INFORMATION: E or K
<220> FEATURE:
<221> NAME/KEY: misc_feature
<222> LOCATION: (312)..(312)
<223> OTHER INFORMATION: K or A
<220> FEATURE:
```

```
<221> NAME/KEY: misc_feature
<222> LOCATION: (313)..(313)
<223> OTHER INFORMATION: K or R
<220> FEATURE:
<221> NAME/KEY: misc_feature
<222> LOCATION: (314)..(314)
<223> OTHER INFORMATION: F or L

<400> SEQUENCE: 1

Met Xaa Xaa Xaa Ile Pro Leu Val Gly Lys Xaa Xaa Ile Xaa Xaa Xaa
1               5                   10                  15

Xaa Xaa Gly Phe Thr Leu Ile His Glu His Leu Arg Val Phe Ser Glu
            20                  25                  30

Xaa Val Arg Xaa Gln Trp Pro His Leu Tyr Asn Glu Asp Glu Glu Xaa
        35                  40                  45

Xaa Asn Ala Val Asn Glu Val Lys Xaa Xaa Met Xaa Xaa Gly Val Lys
    50                  55                  60

Thr Ile Val Asp Pro Thr Val Met Gly Leu Gly Arg Asp Ile Arg Phe
65                  70                  75                  80

Xaa Glu Lys Val Val Lys Xaa Thr Gly Ile Asn Xaa Xaa Ala Xaa Thr
                85                  90                  95

Gly Xaa Tyr Xaa Tyr Xaa Asp Leu Pro Phe Xaa Phe Xaa Xaa Arg Ser
            100                 105                 110

Xaa Xaa Glu Ile Ala Xaa Leu Xaa Ile His Asp Ile Lys Xaa Gly Ile
        115                 120                 125

Gln Xaa Thr Xaa Asn Xaa Ala Gly Phe Xaa Lys Xaa Ala Ala Asp Glu
    130                 135                 140

Pro Gly Ile Thr Xaa Asp Val Glu Xaa Xaa Ile Arg Ala Ala Ala Ile
145                 150                 155                 160

Xaa Xaa Lys Glu Xaa Xaa Val Pro Ile Ile Thr His Ser Asn Ala His
                165                 170                 175

Asn Xaa Thr Gly Leu Glu Xaa Gln Arg Ile Leu Xaa Glu Glu Gly Val
            180                 185                 190

Asp Pro Gly Xaa Xaa Leu Ile Gly His Leu Gly Asp Thr Asp Asn Xaa
            195                 200                 205

Asp Tyr Ile Lys Lys Ile Ala Asp Lys Gly Ser Phe Xaa Gly Leu Asp
        210                 215                 220

Arg Tyr Gly Leu Asp Leu Phe Leu Pro Xaa Asp Lys Arg Asn Glu Xaa
225                 230                 235                 240

Xaa Leu Xaa Leu Ile Lys Asp Gly Tyr Xaa Asp Xaa Ile Met Xaa Ser
        245                 250                 255

Xaa Asp Tyr Cys Cys Thr Ile Asp Trp Gly Xaa Ala Xaa Pro Glu Xaa
            260                 265                 270

Lys Pro Lys Leu Ala Pro Xaa Trp Ser Xaa Xaa Leu Ile Phe Xaa Asp
            275                 280                 285

Xaa Ile Pro Xaa Xaa Lys Xaa Xaa Gly Val Xaa Xaa Glu Xaa Xaa Xaa
    290                 295                 300

Xaa Ile Phe Xaa Xaa Asn Pro Xaa Xaa Xaa Phe Ser
305                 310                 315

<210> SEQ ID NO 2
<211> LENGTH: 945
<212> TYPE: DNA
<213> ORGANISM: Sulfolobus solfataricus

<400> SEQUENCE: 2
atgcgcattc cgctggttgg taaagatagc attgaaagca agatattgg ctttaccctg      60
```

```
attcatgaac atctgcgtgt ttttagcgaa gcagttcgtc agcagtggcc tcatctgtat    120
aatgaagatg aagaatttcg caatgccgtg aatgaagtta acgtgcaat gcagtttggc    180
gttaaaacca ttgttgatcc gaccgttatg ggtctgggtc gtgatattcg ttttatggaa    240
aaagttgtga agccaccgg cattaatctg gttgcaggca ccggtattta tatttatatc    300
gatctgccgt tttatttct gaatcgcagc attgatgaaa ttgccgacct gtttattcat    360
gatattaaag aaggcattca gggcaccctg aataaagcag gttttgttaa aattgcagcc    420
gatgaaccgg gtattaccaa agatgttgaa aaagttattc gtgcagcagc cattgccaat    480
aaagaaacca aagttccgat tattacccat agcaatgccc ataataatac cggtctggaa    540
cagcagcgta ttctgaccga agaaggtgtg gatccgggta aaattctgat tggtcatctg    600
ggtgataccg ataatatcga ttatatcaaa aaaattgccg ataaaggcag ctttattggt    660
ctggatcgtt atggtctgga cctgtttctg ccggttgata aacgtaatga accaccctg    720
cgcctgatta agatggtta tagcgataaa attatgatta gccatgatta ttgctgcacc    780
attgattggg gcaccgcaaa accggaatat aaaccgaaac tggcaccgcg ttggagcatt    840
accctgattt ttgaagatac aattccgttt ctgaaacgca atggtgttaa tgaagaagtg    900
attgccacca ttttaaaga aaatccgaaa aaattcttta gctaa                    945
```

<210> SEQ ID NO 3
<211> LENGTH: 314
<212> TYPE: PRT
<213> ORGANISM: Sulfolobus solfataricus

<400> SEQUENCE: 3

```
Met Arg Ile Pro Leu Val Gly Lys Asp Ser Ile Glu Ser Lys Asp Ile
1               5                   10                  15

Gly Phe Thr Leu Ile His Glu His Leu Arg Val Phe Ser Glu Ala Val
            20                  25                  30

Arg Gln Gln Trp Pro His Leu Tyr Asn Glu Asp Glu Glu Phe Arg Asn
        35                  40                  45

Ala Val Asn Glu Val Lys Arg Ala Met Gln Phe Gly Val Lys Thr Ile
    50                  55                  60

Val Asp Pro Thr Val Met Gly Leu Gly Arg Asp Ile Arg Phe Met Glu
65                  70                  75                  80

Lys Val Val Lys Ala Thr Gly Ile Asn Leu Val Ala Gly Thr Gly Ile
                85                  90                  95

Tyr Ile Tyr Ile Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Gly
        115                 120                 125

Thr Leu Asn Lys Ala Gly Phe Val Lys Ile Ala Ala Asp Glu Pro Gly
    130                 135                 140

Ile Thr Lys Asp Val Glu Lys Val Ile Arg Ala Ala Ile Ala Asn
145                 150                 155                 160

Lys Glu Thr Lys Val Pro Ile Ile Thr His Ser Asn Ala His Asn Asn
                165                 170                 175

Thr Gly Leu Glu Gln Gln Arg Ile Leu Thr Glu Glu Gly Val Asp Pro
            180                 185                 190

Gly Lys Ile Leu Ile Gly His Leu Gly Asp Thr Asp Asn Ile Asp Tyr
        195                 200                 205

Ile Lys Lys Ile Ala Asp Lys Gly Ser Phe Ile Gly Leu Asp Arg Tyr
```

```
                    210                 215                 220
Gly Leu Asp Leu Phe Leu Pro Val Asp Lys Arg Asn Glu Thr Thr Leu
225                 230                 235                 240

Arg Leu Ile Lys Asp Gly Tyr Ser Asp Lys Ile Met Ile Ser His Asp
                245                 250                 255

Tyr Cys Cys Thr Ile Asp Trp Gly Thr Ala Lys Pro Glu Tyr Lys Pro
                260                 265                 270

Lys Leu Ala Pro Arg Trp Ser Ile Thr Leu Ile Phe Glu Asp Thr Ile
            275                 280                 285

Pro Phe Leu Lys Arg Asn Gly Val Asn Glu Glu Val Ile Ala Thr Ile
            290                 295                 300

Phe Lys Glu Asn Pro Lys Lys Phe Phe Ser
305                 310
```

<210> SEQ ID NO 4
<211> LENGTH: 948
<212> TYPE: DNA
<213> ORGANISM: Sulfolobus acidocaldarius

<400> SEQUENCE: 4

```
atgaccaaaa ttccgctggt tggtaaaggt gaaattagtc cgggtgaaat gggttttacc      60
ctgattcatg aacatctgcg tgtttttagc gaaccggtgc gttatcagtg gcctcatctg     120
tataatgaag atgaagaact gaaaaacgcc gtgaacgaag tgaaaaccat tatgagctat     180
ggcgttaaaa ccattgttga tccgaccgtt atgggtctgg tcgtgatat cgttttagt      240
gaaaaagtgg tgaaagaaac cggcattaat gttattgcag caaccggtct gtatacctat     300
accgatctgc cgttttttttt caatggtcgt agcctggaag aaattgcaga actgctgatc     360
cacgatatca aaaaaggtat tcagggcacc aataatcgtg cgggtttat caaagttgca     420
gcagatgaac cgggtattac ccgtgatgtt gaacgtgcaa ttcgtgcagc agcaattgca     480
cagaaagaaa caaatgttcc gattatcacc catagcaatg cacataatgg caccggtctg     540
gaacagcagc gtattctgat ggaagaaggt gtggatccgg tcgtgttct gattggtcat     600
ctgggtgata ccgataacgt ggactacatc aaaaaaatcg cagataaagg tagctttgtt     660
ggcctggatc gctatggtct ggacctgttt ctgccgattg ataaacgtaa tgaagttctg     720
ctgaaactga tcaaagatgg ttatctggat cgtattatgg tgagccagga ttattgttgt     780
accattgatt ggggtattgc caaaccggaa tataaaccga actggcaccg gaaatggtca     840
atgagcctga tttttaccga tgtgattccg agcattaaac gtgccggtgt taccgatgaa     900
cagctgcatg tgattttttgt taaaaatccg gcacgcctgt ttagctga                 948
```

<210> SEQ ID NO 5
<211> LENGTH: 315
<212> TYPE: PRT
<213> ORGANISM: Sulfolobus acidocaldarius

<400> SEQUENCE: 5

```
Met Thr Lys Ile Pro Leu Val Gly Lys Gly Glu Ile Ser Pro Gly Glu
1               5                   10                  15

Met Gly Phe Thr Leu Ile His Glu His Leu Arg Val Phe Ser Glu Pro
                20                  25                  30

Val Arg Tyr Gln Trp Pro His Leu Tyr Asn Glu Asp Glu Glu Leu Lys
            35                  40                  45

Asn Ala Val Asn Glu Val Lys Thr Ile Met Ser Tyr Gly Val Lys Thr
        50                  55                  60
```

Ile Val Asp Pro Thr Val Met Gly Leu Gly Arg Asp Ile Arg Phe Ser
65                  70                  75                  80

Glu Lys Val Val Lys Glu Thr Gly Ile Asn Val Ile Ala Ala Thr Gly
            85                  90                  95

Leu Tyr Thr Tyr Thr Asp Leu Pro Phe Phe Phe Asn Gly Arg Ser Leu
            100                 105                 110

Glu Glu Ile Ala Glu Leu Leu Ile His Asp Ile Lys Lys Gly Ile Gln
            115                 120                 125

Gly Thr Asn Asn Arg Ala Gly Phe Ile Lys Val Ala Ala Asp Glu Pro
130                 135                 140

Gly Ile Thr Arg Asp Val Glu Arg Ala Ile Arg Ala Ala Ala Ile Ala
145                 150                 155                 160

Gln Lys Glu Thr Asn Val Pro Ile Ile Thr His Ser Asn Ala His Asn
            165                 170                 175

Gly Thr Gly Leu Glu Gln Gln Arg Ile Leu Met Glu Glu Gly Val Asp
            180                 185                 190

Pro Gly Arg Val Leu Ile Gly His Leu Gly Asp Thr Asp Asn Val Asp
            195                 200                 205

Tyr Ile Lys Lys Ile Ala Asp Lys Gly Ser Phe Val Gly Leu Asp Arg
210                 215                 220

Tyr Gly Leu Asp Leu Phe Leu Pro Ile Asp Lys Arg Asn Glu Val Leu
225                 230                 235                 240

Leu Lys Leu Ile Lys Asp Gly Tyr Leu Asp Arg Ile Met Val Ser Gln
            245                 250                 255

Asp Tyr Cys Cys Thr Ile Asp Trp Gly Ile Ala Lys Pro Glu Tyr Lys
            260                 265                 270

Pro Lys Leu Ala Pro Lys Trp Ser Met Ser Leu Ile Phe Thr Asp Val
            275                 280                 285

Ile Pro Ser Ile Lys Arg Ala Gly Val Thr Asp Glu Gln Leu His Val
            290                 295                 300

Ile Phe Val Lys Asn Pro Ala Arg Leu Phe Ser
305                 310                 315

<210> SEQ ID NO 6
<211> LENGTH: 945
<212> TYPE: DNA
<213> ORGANISM: Sulfolobus islandicus

<400> SEQUENCE: 6
atgcgtattc cgctggttgg taaagaaccg attgaagccg aagatatggg ttttaccctg     60
attcatgaac atctgcgtgt ttttagcgaa gcagttcgtt atcagtggcc tcatctgtat    120
aatgaagatg aagaactgcg taatgccgtt aatgaagtta acgtgccat gcagtttggt    180 gttaaaacca ttgttgatcc gaccgttatg ggtctgggtc gtgatattcg ctttatggaa    240
aaagttgtga aaccaccggg tattaatctg gttgcaggca ccggtattta tttatgtg    300 gatctgccgt tttattttct gaaccgcagc attgatgaaa ttgccgacct gtttattcat    360
gatattaaag aaggtattca ggcaaccagc aataaagccg gttttgtgaa aattgcagcc    420
gatgaaccgg gtattaccaa agatgtggaa aaagttattc gtgcagcagc cattacccat    480
aaagaagcca agttccgat tattacccat agcaatgccc ataataatac cggtctggaa    540
gaacagcgta ttctgatgga agaaggtgtt gatccgggta aaattctgat tggtcatctg    600
ggtgataccg ataataccga ttatattaaa aaaattgccg ataaaggcag ctttattggt    660

```
ctggatcgtt atggtctgga cctgtttctg ccggttgata acgtaatga aaccaccctg      720 aaactgatta agatggcta tagcgatcgc attatgatca gccatgatta ttgttgtacc      780
attgattggg gcaccgcacg tccggaactg aaaccgaaac tggcaccgcg ttggagcatg      840
gcactgattt ttgaagatac cattccgttt ctgaaaaaaa atggcgtgag cgaagaagtg      900
atcgatatta ttttcaaaga aaacccgaaa aaattcttta gctaa                     945
```

<210> SEQ ID NO 7
<211> LENGTH: 314
<212> TYPE: PRT
<213> ORGANISM: Sulfolobus islandicus

<400> SEQUENCE: 7

```
Met Arg Ile Pro Leu Val Gly Lys Glu Pro Ile Glu Ala Glu Asp Met
1               5                   10                  15

Gly Phe Thr Leu Ile His Glu His Leu Arg Val Phe Ser Glu Ala Val
            20                  25                  30

Arg Tyr Gln Trp Pro His Leu Tyr Asn Glu Asp Glu Glu Leu Arg Asn
        35                  40                  45

Ala Val Asn Glu Val Lys Arg Ala Met Gln Phe Gly Val Lys Thr Ile
    50                  55                  60

Val Asp Pro Thr Val Met Gly Leu Gly Arg Asp Ile Arg Phe Met Glu
65                  70                  75                  80

Lys Val Val Lys Thr Thr Gly Ile Asn Leu Val Ala Gly Thr Gly Ile
                85                  90                  95

Tyr Ile Tyr Val Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Ala
        115                 120                 125

Thr Ser Asn Lys Ala Gly Phe Val Lys Ile Ala Ala Asp Glu Pro Gly
    130                 135                 140

Ile Thr Lys Asp Val Glu Lys Val Ile Arg Ala Ala Ile Thr His
145                 150                 155                 160

Lys Glu Ala Lys Val Pro Ile Ile Thr His Ser Asn Ala His Asn Asn
                165                 170                 175

Thr Gly Leu Glu Glu Gln Arg Ile Leu Met Glu Glu Gly Val Asp Pro
            180                 185                 190

Gly Lys Ile Leu Ile Gly His Leu Gly Asp Thr Asp Asn Thr Asp Tyr
        195                 200                 205

Ile Lys Lys Ile Ala Asp Lys Gly Ser Phe Ile Gly Leu Asp Arg Tyr
    210                 215                 220

Gly Leu Asp Leu Phe Leu Pro Val Asp Lys Arg Asn Glu Thr Thr Leu
225                 230                 235                 240

Lys Leu Ile Lys Asp Gly Tyr Ser Asp Arg Ile Met Ile Ser His Asp
                245                 250                 255

Tyr Cys Cys Thr Ile Asp Trp Gly Thr Ala Arg Pro Glu Leu Lys Pro
            260                 265                 270

Lys Leu Ala Pro Arg Trp Ser Met Ala Leu Ile Phe Glu Asp Thr Ile
        275                 280                 285

Pro Phe Leu Lys Lys Asn Gly Val Ser Glu Glu Val Ile Asp Ile Ile
    290                 295                 300

Phe Lys Glu Asn Pro Lys Lys Phe Phe Ser
305                 310
```

<210> SEQ ID NO 8
<211> LENGTH: 945
<212> TYPE: DNA
<213> ORGANISM: Sulfolobus solfataricus

<400> SEQUENCE: 8

| | | | | | |
|---|---|---|---|---|---|
| atgcgcattc | cgctggttgg | taaagatagc | attgaaagca | agatattgg | ctttaccctg | 60 |
| attcatgaac | atctgcgtgt | ttttagcgaa | gcagttcgtc | agcagtggcc | tcatctgtat | 120 |
| aatgaagatg | aagaatttcg | caatgccgtg | aatgaagtta | acgtgcaat | gcagtttggc | 180 |
| gttaaaacca | ttgttgatcc | gaccgttatg | ggtctgggtc | gtgatattcg | ttttatggaa | 240 |
| aaagttgtga | agccaccgg | cattaatctg | gttgcaggca | ccggtattta | tatttatatc | 300 |
| gatctgccgt | tttattttct | gaatcgcagc | attgatgaaa | ttgccgacct | gtttattcat | 360 |
| gatattaaag | aaggcattca | gggcaccctg | aataaagcag | gttttgttaa | aattgcagcc | 420 |
| gatgaaccgg | gtattaccaa | agatgttgaa | aaagttattc | gtgcagcagc | cattgccaat | 480 |
| aaagaaacca | agttccgat | tattacccat | agcaatgccc | ataataatac | cggtctggaa | 540 |
| cagcagcgta | ttctgaccga | agaaggtgtg | gatccgggta | aaattctgat | ggtcatctg | 600 |
| ggtgataccg | ataatatcga | ttatatcaaa | aaaattgccg | ataaaggcag | ctttattggt | 660 |
| ctggatcgtt | atggtctgga | cctgtttctg | ccggttgata | acgtaatga | aaccaccctg | 720 |
| cgcctgatta | aagatggtta | tagcgataaa | attatgatta | gccatgatta | ttgctgcacc | 780 |
| attgatatgg | gcaccgcaaa | accggaatat | aaaccgaaac | tggcaccgcg | cttggagcatt | 840 |
| accctgattt | ttgaagatac | aattccgttt | ctgaaacgca | atggtgttaa | tgaagaagtg | 900 |
| attgccacca | tttttaaaga | aaatccgaaa | aaattcttta | gctaa | | 945 |

<210> SEQ ID NO 9
<211> LENGTH: 314
<212> TYPE: PRT
<213> ORGANISM: Sulfolobus solfataricus

<400> SEQUENCE: 9

Met Arg Ile Pro Leu Val Gly Lys Asp Ser Ile Glu Ser Lys Asp Ile
1               5                   10                  15

Gly Phe Thr Leu Ile His Glu His Leu Arg Val Phe Ser Glu Ala Val
                20                  25                  30

Arg Gln Gln Trp Pro His Leu Tyr Asn Glu Asp Glu Glu Phe Arg Asn
            35                  40                  45

Ala Val Asn Glu Val Lys Arg Ala Met Gln Phe Gly Val Lys Thr Ile
        50                  55                  60

Val Asp Pro Thr Val Met Gly Leu Gly Arg Asp Ile Arg Phe Met Glu
65                  70                  75                  80

Lys Val Val Lys Ala Thr Gly Ile Asn Leu Val Ala Gly Thr Gly Ile
                85                  90                  95

Tyr Ile Tyr Ile Asp Leu Pro Phe Tyr Phe Leu Asn Arg Ser Ile Asp
                100                 105                 110

Glu Ile Ala Asp Leu Phe Ile His Asp Ile Lys Glu Gly Ile Gln Gly
            115                 120                 125

Thr Leu Asn Lys Ala Gly Phe Val Lys Ile Ala Ala Asp Glu Pro Gly
        130                 135                 140

Ile Thr Lys Asp Val Glu Lys Val Ile Arg Ala Ala Ile Ala Asn
145                 150                 155                 160

Lys Glu Thr Lys Val Pro Ile Ile Thr His Ser Asn Ala His Asn Asn
                165                 170                 175

Thr Gly Leu Glu Gln Gln Arg Ile Leu Thr Glu Gly Val Asp Pro
                180                 185                 190

Gly Lys Ile Leu Ile Gly His Leu Gly Asp Thr Asp Asn Ile Asp Tyr
            195                 200                 205

Ile Lys Lys Ile Ala Asp Lys Gly Ser Phe Ile Gly Leu Asp Arg Tyr
210                 215                 220

Gly Leu Asp Leu Phe Leu Pro Val Lys Arg Asn Glu Thr Thr Leu
225                 230                 235                 240

Arg Leu Ile Lys Asp Gly Tyr Ser Asp Lys Ile Met Ile Ser His Asp
                245                 250                 255

Tyr Cys Cys Thr Ile Asp Met Gly Thr Ala Lys Pro Glu Tyr Lys Pro
            260                 265                 270

Lys Leu Ala Pro Arg Trp Ser Ile Thr Leu Ile Phe Glu Asp Thr Ile
        275                 280                 285

Pro Phe Leu Lys Arg Asn Gly Val Asn Glu Glu Val Ile Ala Thr Ile
    290                 295                 300

Phe Lys Glu Asn Pro Lys Lys Phe Phe Ser
305                 310

<210> SEQ ID NO 10
<211> LENGTH: 945
<212> TYPE: DNA
<213> ORGANISM: Sulfolobus solfataricus

<400> SEQUENCE: 10
atgcgcattc cgctggttgg taaagatagc attgaaagca agatattgg ctttaccctg        60 attcatgaac atctgcgtgt ttttagcgaa gcagttcgtc agcagtggcc tcatctgtat       120
aatgaagatg aagaatttcg caatgccgtg aatgaagtta acgtgcaat gcagtttggc        180 gttaaaacca ttgttgatcc gaccgttatg ggtctgggtc gtgatattcg ttttatggaa       240
aaagttgtga agccaccggg cattaatctg gttgcaggca ccggtattta tatttatatc      300
gatctgccgt tttatttttct gaatcgcagc attgatgaaa ttgccgacct gttttattcat    360 gatattaaag aaggcattca gggcaccctg aataaagcag gttttgttaa aattgcagcc      420
gatgaaccgg gtattaccaa agatgttgaa aaagttattc gtgcagcagc cattgccaat      480
aaagaaacca agttccgat tattacccat agcaatgccc ataataatac cggtctggaa       540
cagcagcgta ttctgaccga agaaggtgtg gatccgggta aaattctgat tggtcatctg      600
ggtgataccg ataatatcga ttatatcaaa aaaattgccg ataaaggcag ctttattggt       660
ctggatcgtt atggtctgga cctgtttctg ccggttgata acgtaatga aaccaccctg        720 cgcctgatta agatggtta tagcgataaa attatgatta gccatgatta ttgctgcacc       780
attgatctgg gcaccgcaaa accggaatat aaaccgaaac tggcaccgcg ttggagcatt       840
accctgattt ttgaagatac aattccgttt ctgaaacgca atggtgttaa tgaagaagtg       900
attgccacca tttttaaaga aaatccgaaa aaattcttta gctaa                      945

<210> SEQ ID NO 11
<211> LENGTH: 314
<212> TYPE: PRT
<213> ORGANISM: Sulfolobus solfataricus

<400> SEQUENCE: 11

Met Arg Ile Pro Leu Val Gly Lys Asp Ser Ile Glu Ser Lys Asp Ile
1               5                   10                  15

```
Gly Phe Thr Leu Ile His Glu His Leu Arg Val Phe Ser Glu Ala Val
                20                  25                  30

Arg Gln Gln Trp Pro His Leu Tyr Asn Glu Asp Glu Glu Phe Arg Asn
            35                  40                  45

Ala Val Asn Glu Val Lys Arg Ala Met Gln Phe Gly Val Lys Thr Ile
        50                  55                  60

Val Asp Pro Thr Val Met Gly Leu Gly Arg Asp Ile Arg Phe Met Glu
65                  70                  75                  80

Lys Val Val Lys Ala Thr Gly Ile Asn Leu Val Ala Gly Thr Gly Ile
                85                  90                  95

Tyr Ile Tyr Ile Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Gly
        115                 120                 125

Thr Leu Asn Lys Ala Gly Phe Val Lys Ile Ala Ala Asp Glu Pro Gly
    130                 135                 140

Ile Thr Lys Asp Val Glu Lys Val Ile Arg Ala Ala Ile Ala Asn
145                 150                 155                 160

Lys Glu Thr Lys Val Pro Ile Ile Thr His Ser Asn Ala His Asn Asn
                165                 170                 175

Thr Gly Leu Glu Gln Gln Arg Ile Leu Thr Glu Glu Gly Val Asp Pro
            180                 185                 190

Gly Lys Ile Leu Ile Gly His Leu Gly Asp Thr Asp Asn Ile Asp Tyr
        195                 200                 205

Ile Lys Lys Ile Ala Asp Lys Gly Ser Phe Ile Gly Leu Asp Arg Tyr
    210                 215                 220

Gly Leu Asp Leu Phe Leu Pro Val Asp Lys Arg Asn Glu Thr Thr Leu
225                 230                 235                 240

Arg Leu Ile Lys Asp Gly Tyr Ser Asp Lys Ile Met Ile Ser His Asp
                245                 250                 255

Tyr Cys Cys Thr Ile Asp Leu Gly Thr Ala Lys Pro Glu Tyr Lys Pro
            260                 265                 270

Lys Leu Ala Pro Arg Trp Ser Ile Thr Leu Ile Phe Glu Asp Thr Ile
        275                 280                 285

Pro Phe Leu Lys Arg Asn Gly Val Asn Glu Glu Val Ile Ala Thr Ile
    290                 295                 300

Phe Lys Glu Asn Pro Lys Lys Phe Phe Ser
305                 310

<210> SEQ ID NO 12
<211> LENGTH: 945
<212> TYPE: DNA
<213> ORGANISM: Sulfolobus solfataricus

<400> SEQUENCE: 12
atgcgcattc cgctggttgg taaagatagc attgaaagca agatattgg ctttaccctg     60 attcatgaac atctgcgtgt ttttagcgaa gcagttcgtc agcagtggcc tcatctgtat   120
aatgaagatg aagaatttcg caatgccgtg aatgaagtta acgtgcaat gcagtttggc    180 gttaaaacca ttgttgatcc gaccgttatg ggtctgggtc gtgatattcg ttttatggaa   240
aaagttgtga agccaccgg cattaatctg gttgcaggca ccggtattta tatttatatc   300
gatctgccgt tttatttct gaatcgcagc attgatgaaa ttgccgacct gtttattcat   360
gatattaaag aaggcattca gggcaccctg aataaagcag gttttgttaa aattgcagcc   420
```

```
gatgaaccgg gtattaccaa agatgttgaa aaagttattc gtgcagcagc cattgccaat    480
aaagaaacca agttccgat tattacccat agcaatgccc ataataatac cggtctggaa     540
cagcagcgta ttctgaccga agaaggtgtg gatccgggta aaattctgat tggtcatctg    600
ggtgataccg ataatatcga ttatatcaaa aaaattgccg ataaaggcag ctttattggt    660
ctggatcgtt atggtctgga cctgtttctg ccggttgata acgtaatga aaccaccctg     720 cgcctgatta agatggtta tagcgataaa attatgatta gccatgatta ttgctgcacc    780
attgatgcag gcaccgcaaa accggaatat aaaccgaaac tggcaccgcg ttggagcatt    840
accctgattt ttgaagatac aattccgttt ctgaaacgca atggtgttaa tgaagaagtg    900
attgccacca tttttaaaga aaatccgaaa aaattcttta gctaa                    945
```

<210> SEQ ID NO 13
<211> LENGTH: 314
<212> TYPE: PRT
<213> ORGANISM: Sulfolobus solfataricus

<400> SEQUENCE: 13

```
Met Arg Ile Pro Leu Val Gly Lys Asp Ser Ile Glu Ser Lys Asp Ile
1               5                   10                  15

Gly Phe Thr Leu Ile His Glu His Leu Arg Val Phe Ser Glu Ala Val
            20                  25                  30

Arg Gln Gln Trp Pro His Leu Tyr Asn Glu Asp Glu Glu Phe Arg Asn
        35                  40                  45

Ala Val Asn Glu Val Lys Arg Ala Met Gln Phe Gly Val Lys Thr Ile
    50                  55                  60

Val Asp Pro Thr Val Met Gly Leu Gly Arg Asp Ile Arg Phe Met Glu
65                  70                  75                  80

Lys Val Val Lys Ala Thr Gly Ile Asn Leu Val Ala Gly Thr Gly Ile
                85                  90                  95

Tyr Ile Tyr Ile Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Gly
        115                 120                 125

Thr Leu Asn Lys Ala Gly Phe Val Lys Ile Ala Ala Asp Glu Pro Gly
    130                 135                 140

Ile Thr Lys Asp Val Glu Lys Val Ile Arg Ala Ala Ile Ala Asn
145                 150                 155                 160

Lys Glu Thr Lys Val Pro Ile Ile Thr His Ser Asn Ala His Asn Asn
                165                 170                 175

Thr Gly Leu Glu Gln Gln Arg Ile Leu Thr Glu Glu Gly Val Asp Pro
            180                 185                 190

Gly Lys Ile Leu Ile Gly His Leu Gly Asp Thr Asp Asn Ile Asp Tyr
        195                 200                 205

Ile Lys Lys Ile Ala Asp Lys Gly Ser Phe Ile Gly Leu Asp Arg Tyr
    210                 215                 220

Gly Leu Asp Leu Phe Leu Pro Val Asp Lys Arg Asn Glu Thr Thr Leu
225                 230                 235                 240

Arg Leu Ile Lys Asp Gly Tyr Ser Asp Lys Ile Met Ile Ser His Asp
                245                 250                 255

Tyr Cys Cys Thr Ile Asp Ala Gly Thr Ala Lys Pro Glu Tyr Lys Pro
            260                 265                 270

Lys Leu Ala Pro Arg Trp Ser Ile Thr Leu Ile Phe Glu Asp Thr Ile
        275                 280                 285
```

Pro Phe Leu Lys Arg Asn Gly Val Asn Glu Glu Val Ile Ala Thr Ile
    290                 295                 300

Phe Lys Glu Asn Pro Lys Lys Phe Phe Ser
305                 310

<210> SEQ ID NO 14
<211> LENGTH: 945
<212> TYPE: DNA
<213> ORGANISM: Sulfolobus solfataricus

<400> SEQUENCE: 14

```
atgcgcattc cgctggttgg taaagatagc attgaaagca agatattgg  ctttaccctg      60
attcatgaac atctgcgtgt ttttagcgaa gcagttcgtc agcagtggcc tcatctgtat     120
aatgaagatg aagaatttcg caatgccgtg aatgaagtta acgtgcaat gcagtttggc     180
gttaaaacca ttgttgatcc gaccgttatg ggtctgggtc gtgatattcg ttttatggaa     240
aaagttgtga agccaccgg cattaatctg gttgcaggca ccggtattta tatttatatc     300
gatctgccgt tttattttct gaatcgcagc attgatgaaa ttgccgacct gtttattcat     360
gatattaaag aaggcattca gggcaccctg aataaagcag ttttgttaa aattgcagcc     420
gatgaaccgg gtattaccaa agatgttgaa aaagttattc gtgcagcagc cattgccaat     480
aaagaaacca aagttccgat tattacccat agcaatgccc ataataatac cggtctggaa     540
cagcagcgta ttctgaccga agaaggtgtg gatccgggta aaattctgat tggtcatctg     600
ggtgataccg ataatatcga ttatatcaaa aaaattgccg ataaaggcag ctttattggt     660
ctggatcgtt atggtctgga cctgtttctg ccggttgata acgtaatga aaccacccctg     720
cgcctgatta aagatggtta tagcgataaa attatgatta gccatgatta ttgctgcacc     780
attgatattg gcaccgcaaa accggaatat aaaccgaaac tggcaccgcg ttggagcatt     840
accctgattt ttgaagatac aattccgttt ctgaaacgca atggtgttaa tgaagaagtg     900
attgccacca ttttttaaaga aaatccgaaa aaattcttta gctaa                    945
```

<210> SEQ ID NO 15
<211> LENGTH: 314
<212> TYPE: PRT
<213> ORGANISM: Sulfolobus solfataricus

<400> SEQUENCE: 15

Met Arg Ile Pro Leu Val Gly Lys Asp Ser Ile Glu Ser Lys Asp Ile
1               5                  10                  15

Gly Phe Thr Leu Ile His Glu His Leu Arg Val Phe Ser Glu Ala Val
            20                  25                  30

Arg Gln Gln Trp Pro His Leu Tyr Asn Glu Asp Glu Glu Phe Arg Asn
        35                  40                  45

Ala Val Asn Glu Val Lys Arg Ala Met Gln Phe Gly Val Lys Thr Ile
    50                  55                  60

Val Asp Pro Thr Val Met Gly Leu Gly Arg Asp Ile Arg Phe Met Glu
65                  70                  75                  80

Lys Val Val Lys Ala Thr Gly Ile Asn Leu Val Ala Gly Thr Gly Ile
                85                  90                  95

Tyr Ile Tyr Ile Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Gly
        115                 120                 125

```
Thr Leu Asn Lys Ala Gly Phe Val Lys Ile Ala Ala Asp Glu Pro Gly
    130                 135                 140

Ile Thr Lys Asp Val Glu Lys Val Ile Arg Ala Ala Ile Ala Asn
145                 150                 155                 160

Lys Glu Thr Lys Val Pro Ile Ile Thr His Ser Asn Ala His Asn Asn
                165                 170                 175

Thr Gly Leu Glu Gln Gln Arg Ile Leu Thr Glu Gly Val Asp Pro
            180                 185                 190

Gly Lys Ile Leu Ile Gly His Leu Gly Asp Thr Asp Asn Ile Asp Tyr
                195                 200                 205

Ile Lys Lys Ile Ala Asp Lys Gly Ser Phe Ile Gly Leu Asp Arg Tyr
210                 215                 220

Gly Leu Asp Leu Phe Leu Pro Val Asp Lys Arg Asn Glu Thr Thr Leu
225                 230                 235                 240

Arg Leu Ile Lys Asp Gly Tyr Ser Asp Lys Ile Met Ile Ser His Asp
                245                 250                 255

Tyr Cys Cys Thr Ile Asp Ile Gly Thr Ala Lys Pro Glu Tyr Lys Pro
                260                 265                 270

Lys Leu Ala Pro Arg Trp Ser Ile Thr Leu Ile Phe Glu Asp Thr Ile
            275                 280                 285

Pro Phe Leu Lys Arg Asn Gly Val Asn Glu Glu Val Ile Ala Thr Ile
            290                 295                 300

Phe Lys Glu Asn Pro Lys Lys Phe Phe Ser
305                 310

<210> SEQ ID NO 16
<211> LENGTH: 945
<212> TYPE: DNA
<213> ORGANISM: Sulfolobus solfataricus

<400> SEQUENCE: 16
atgcgcattc cgctggttgg taaagatagc attgaaagca agatattgg ctttaccctg      60
attcatgaac atctgcgtgt ttttagcgaa gcagttcgtc agcagtggcc tcatctgtat    120
aatgaagatg aagaatttcg caatgccgtg aatgaagtta acgtgcaat gcagtttggc     180
gttaaaacca ttgttgatcc gaccgttatg ggtctgggtc gtgatattcg ttttatggaa    240
aaagttgtga agccaccgg cattaatctg gttgcaggca ccggtattta tatttatatc    300
gatctgccgt tttatttct gaatcgcagc attgatgaaa ttgccgacct gtttattcat    360
gatattaaag aaggcattca gggcacccct aataaagcag ttttgttaa aattgcagcc    420
gatgaaccgg gtattaccaa agatgttgaa aaagttattc gtgcagcagc cattgccaat    480
aaagaaacca agttccgat tattacccat agcaatgccc ataataatac cggtctggaa    540
cagcagcgta ttctgaccga agaaggtgtg gatccgggta aaattctgat tggtcatctg    600
ggtgataccg ataatatcga ttatatcaaa aaaattgccg ataaaggcag ctttattggt    660
ctggatcgtt atggtctgga cctgtttctg ccggttgata acgtaatga accaccctg     720
cgcctgatta agatggttta tagcgataaa attatgatta ccatgatta ttgctgcacc    780
attgatgttg gcaccgcaaa accggaatat aaaccgaaac tggcaccgcg ttggagcatt    840
accctgattt ttgaagatac aattccgttt ctgaaacgca atggtgttaa tgaagaagtg    900
attgccacca ttttttaaaga aaatccgaaa aaattctta gctaa                    945

<210> SEQ ID NO 17
<211> LENGTH: 314
```

<212> TYPE: PRT
<213> ORGANISM: Sulfolobus solfataricus

<400> SEQUENCE: 17

Met Arg Ile Pro Leu Val Gly Lys Asp Ser Ile Glu Ser Lys Asp Ile
1               5                   10                  15

Gly Phe Thr Leu Ile His Glu His Leu Arg Val Phe Ser Glu Ala Val
            20                  25                  30

Arg Gln Gln Trp Pro His Leu Tyr Asn Glu Asp Glu Glu Phe Arg Asn
        35                  40                  45

Ala Val Asn Glu Val Lys Arg Ala Met Gln Phe Gly Val Lys Thr Ile
    50                  55                  60

Val Asp Pro Thr Val Met Gly Leu Gly Arg Asp Ile Arg Phe Met Glu
65                  70                  75                  80

Lys Val Val Lys Ala Thr Gly Ile Asn Leu Val Ala Gly Thr Gly Ile
                85                  90                  95

Tyr Ile Tyr Ile Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Gly
        115                 120                 125

Thr Leu Asn Lys Ala Gly Phe Val Lys Ile Ala Ala Asp Glu Pro Gly
    130                 135                 140

Ile Thr Lys Asp Val Glu Lys Val Ile Arg Ala Ala Ile Ala Asn
145                 150                 155                 160

Lys Glu Thr Lys Val Pro Ile Ile Thr His Ser Asn Ala His Asn Asn
                165                 170                 175

Thr Gly Leu Glu Gln Gln Arg Ile Leu Thr Glu Glu Gly Val Asp Pro
            180                 185                 190

Gly Lys Ile Leu Ile Gly His Leu Gly Asp Thr Asp Asn Ile Asp Tyr
        195                 200                 205

Ile Lys Lys Ile Ala Asp Lys Gly Ser Phe Ile Gly Leu Asp Arg Tyr
    210                 215                 220

Gly Leu Asp Leu Phe Leu Pro Val Asp Lys Arg Asn Glu Thr Thr Leu
225                 230                 235                 240

Arg Leu Ile Lys Asp Gly Tyr Ser Asp Lys Ile Met Ile Ser His Asp
                245                 250                 255

Tyr Cys Cys Thr Ile Asp Val Gly Thr Ala Lys Pro Gly Tyr Lys Pro
            260                 265                 270

Lys Leu Ala Pro Arg Trp Ser Ile Thr Leu Ile Phe Glu Asp Thr Ile
        275                 280                 285

Pro Phe Leu Lys Arg Asn Gly Val Asn Glu Glu Val Ile Ala Thr Ile
    290                 295                 300

Phe Lys Glu Asn Pro Lys Lys Phe Phe Ser
305                 310

<210> SEQ ID NO 18
<211> LENGTH: 945
<212> TYPE: DNA
<213> ORGANISM: Sulfolobus solfataricus

<400> SEQUENCE: 18
atgcgcattc cgctggttgg taaagatagc attgaaagca agatattgg ctttaccctg     60 attcatgaac atctgcgtgt ttttagcgaa gcagttcgtc agcagtggcc tcatctgtat    120
aatgaagatg aagaatttcg caatgccgtg aatgaagtta acgtgcaat gcagtttggc    180

-continued

```
gttaaaacca ttgttgatcc gaccgttatg ggtctgggtc gtgatattcg ttttatggaa    240
aaagttgtga aagccaccgg cattaatctg gttgcaggca ccggtattta tatttatatc    300
gatctgccgt tttatttct gaatcgcagc attgatgaaa ttgccgacct gtttattcat    360
gatattaaag aaggcattca gggcaccctg aataaagcag gttttgttaa aattgcagcc    420
gatgaaccgg gtattaccaa agatgttgaa aaagttattc gtgcagcagc cattgccaat    480
aaagaaacca agttccgat tattacccat agcaatgccc ataataatac cggtctggaa    540
cagcagcgta ttctgaccga agaaggtgtg gatccgggta aaattctgat tggtcatctg    600
ggtgataccg ataatatcga ttatatcaaa aaaattgccg ataaaggcag ctttattggt    660
ctggatcgtt atggtctgga cctgtttctg ccggttgata acgtaatga accacccctg    720 cgcctgatta agatggtta tagcgataaa attatgatta gccatgatta ttgctgcacc    780
attgataccg gcaccgcaaa accggaatat aaaccgaaac tggcaccgcg ttggagcatt    840
accctgattt ttgaagatac aattccgttt ctgaaacgca atggtgttaa tgaagaagtg    900
attgccacca tttttaaaga aaatccgaaa aaattcttta gctaa                    945
```

<210> SEQ ID NO 19
<211> LENGTH: 314
<212> TYPE: PRT
<213> ORGANISM: Sulfolobus solfataricus

<400> SEQUENCE: 19

```
Met Arg Ile Pro Leu Val Gly Lys Asp Ser Ile Glu Ser Lys Asp Ile
1               5                   10                  15

Gly Phe Thr Leu Ile His Glu His Leu Arg Val Phe Ser Glu Ala Val
            20                  25                  30

Arg Gln Gln Trp Pro His Leu Tyr Asn Glu Asp Glu Glu Phe Arg Asn
        35                  40                  45

Ala Val Asn Glu Val Lys Arg Ala Met Gln Phe Gly Val Lys Thr Ile
    50                  55                  60

Val Asp Pro Thr Val Met Gly Leu Gly Arg Asp Ile Arg Phe Met Glu
65                  70                  75                  80

Lys Val Val Lys Ala Thr Gly Ile Asn Leu Val Ala Gly Thr Gly Ile
                85                  90                  95

Tyr Ile Tyr Ile Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Gly
        115                 120                 125

Thr Leu Asn Lys Ala Gly Phe Val Lys Ile Ala Ala Asp Glu Pro Gly
    130                 135                 140

Ile Thr Lys Asp Val Glu Lys Val Ile Arg Ala Ala Ile Ala Asn
145                 150                 155                 160

Lys Glu Thr Lys Val Pro Ile Ile Thr His Ser Asn Ala His Asn Asn
                165                 170                 175

Thr Gly Leu Glu Gln Gln Arg Ile Leu Thr Glu Glu Gly Val Asp Pro
            180                 185                 190

Gly Lys Ile Leu Ile Gly His Leu Gly Asp Thr Asp Asn Ile Asp Tyr
        195                 200                 205

Ile Lys Lys Ile Ala Asp Lys Gly Ser Phe Ile Gly Leu Asp Arg Tyr
    210                 215                 220

Gly Leu Asp Leu Phe Leu Pro Val Asp Lys Arg Asn Glu Thr Thr Leu
225                 230                 235                 240
```

```
Arg Leu Ile Lys Asp Gly Tyr Ser Asp Lys Ile Met Ile Ser His Asp
                245                 250                 255
Tyr Cys Cys Thr Ile Asp Thr Gly Thr Ala Lys Pro Glu Tyr Lys Pro
            260                 265                 270
Lys Leu Ala Pro Arg Trp Ser Ile Thr Leu Ile Phe Glu Asp Thr Ile
        275                 280                 285
Pro Phe Leu Lys Arg Asn Gly Val Asn Glu Glu Val Ile Ala Thr Ile
    290                 295                 300
Phe Lys Glu Asn Pro Lys Lys Phe Phe Ser
305                 310
```

<210> SEQ ID NO 20
<211> LENGTH: 945
<212> TYPE: DNA
<213> ORGANISM: Sulfolobus solfataricus

<400> SEQUENCE: 20

```
atgcgcattc cgctggttgg taaagatagc attgaaagca agatattgg ctttacctg      60
attcatgaac atctgcgtgt ttttagcgaa gcagttcgtc agcagtggcc tcatctgtat    120
aatgaagatg aagaatttcg caatgccgtg aatgaagtta acgtgcaat gcagtttggc    180
gttaaaacca ttgttgatcc gaccgttatg ggtctgggtc gtgatattcg ttttatggaa    240
aaagttgtga agccaccggg cattaatctg gttgcaggca ccggtattta tatttatatc    300
gatctgccgt tttatttct gaatcgcagc attgatgaaa ttgccgacct gtttattcat    360
gatattaaag aaggcattca gggcacccctg aataaagcag gttttgttaa aattgcagcc    420
gatgaaccgg gtattaccaa agatgttgaa aaagttattc gtgcagcagc cattgccaat    480
aaagaaacca agttccgat tattacccat agcaatgccc ataataatac cggtctggaa    540
cagcagcgta ttctgaccga gaaggtgtg gatccgggta aaattctgat tggtcatctg    600
ggtgataccg ataatatcga ttatatcaaa aaaattgccg ataaaggcag ctttattggt    660
ctggatcgtt atggtctgga cctgttctg ccggttgata acgtaatga aaccaccctg    720
cgcctgatta agatggtta tagcgataaa attatgatta gccatgatta tctgtgcacc    780
tttgatgcag gcaccgcaaa accggaatat aaaccgaaac tggcaccgcg ttggagcatt    840
accctgattt tgaagatac aattccgttt ctgaaacgca atggtgttaa tgaagaagtg    900
attgccacca ttttaaga aaatccgaaa aaattcttta gctaa                     945
```

<210> SEQ ID NO 21
<211> LENGTH: 314
<212> TYPE: PRT
<213> ORGANISM: Sulfolobus solfataricus

<400> SEQUENCE: 21

```
Met Arg Ile Pro Leu Val Gly Lys Asp Ser Ile Glu Ser Lys Asp Ile
1               5                   10                  15
Gly Phe Thr Leu Ile His Glu His Leu Arg Val Phe Ser Glu Ala Val
                20                  25                  30
Arg Gln Gln Trp Pro His Leu Tyr Asn Glu Asp Glu Glu Phe Arg Asn
            35                  40                  45
Ala Val Asn Glu Val Lys Arg Ala Met Gln Phe Gly Val Lys Thr Ile
        50                  55                  60
Val Asp Pro Thr Val Met Gly Leu Gly Arg Asp Ile Arg Phe Met Glu
65                  70                  75                  80
Lys Val Val Lys Ala Thr Gly Ile Asn Leu Val Ala Gly Thr Gly Ile
```

```
                85                  90                  95
Tyr Ile Tyr Ile Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Gly
            115                 120                 125

Thr Leu Asn Lys Ala Gly Phe Val Lys Ile Ala Ala Asp Glu Pro Gly
            130                 135                 140

Ile Thr Lys Asp Val Glu Lys Val Ile Arg Ala Ala Ile Ala Asn
145                 150                 155                 160

Lys Glu Thr Lys Val Pro Ile Ile Thr His Ser Asn Ala His Asn Asn
                165                 170                 175

Thr Gly Leu Glu Gln Gln Arg Ile Leu Thr Glu Gly Val Asp Pro
            180                 185                 190

Gly Lys Ile Leu Ile Gly His Leu Gly Asp Thr Asp Asn Ile Asp Tyr
            195                 200                 205

Ile Lys Lys Ile Ala Asp Lys Gly Ser Phe Ile Gly Leu Asp Arg Tyr
            210                 215                 220

Gly Leu Asp Leu Phe Leu Pro Val Asp Lys Arg Asn Glu Thr Thr Leu
225                 230                 235                 240

Arg Leu Ile Lys Asp Gly Tyr Ser Asp Lys Ile Met Ile Ser His Asp
                245                 250                 255

Tyr Leu Cys Thr Phe Asp Ala Gly Thr Ala Lys Pro Gly Tyr Lys Pro
            260                 265                 270

Lys Leu Ala Pro Arg Trp Ser Ile Thr Leu Ile Phe Glu Asp Thr Ile
            275                 280                 285

Pro Phe Leu Lys Arg Asn Gly Val Asn Glu Glu Val Ile Ala Thr Ile
            290                 295                 300

Phe Lys Glu Asn Pro Lys Lys Phe Phe Ser
305                 310

<210> SEQ ID NO 22
<211> LENGTH: 948
<212> TYPE: DNA
<213> ORGANISM: Sulfolobus solfataricus

<400> SEQUENCE: 22
atgcgcattc cgctggttgg taaagatagc attgaaagca agatattgg ctttaccctg      60
attcatgaac atctgcgtgc atttagcgaa gcagttcgtc agcagtggcc tcatctgtat    120
aatgaagatg aagaatttcg caatgccgtg aatgaagtta acgtgcaat gcagtttggc     180
gttaaaacca ttgttgatcc gaccgttatg ggtctgggtc gtgatattcg ttttatggaa    240
aaagttgtga agccaccgg cattaatctg gttgcaggca ccggtatttg gatttatatc     300
gatctgccgt tttattttct gaatcgcagc attgatgaaa ttgccgacct gtttattcat    360
gatattaaag aaggcattca gggcacccctg aataaagcag gttttgttaa aattgcagcc   420
gatgaaccgg gtattaccaa agatgttgaa aaagttattc gtgcagcagc cattgccaat    480
aaagaaacca agttccgat tattacccat agcaatgccc ataataatac cggtctggaa     540
cagcagcgta ttctgaccga agaaggtgtg gatccgggta aaattctgat tggtcatctg    600
ggtgataccg ataatatcga ttatatcaaa aaaattgccg ataaaggcag ctttattggt    660
ctggatcgtt atggtctgga catgtttctg ccggttgata acgtaatga accaccctg      720
cgcctgatta agatggtta tagcgataaa attatgatta gccatgatta ttgctgcacc    780
attgatatgg gcaccgcaaa accggaatat aaaccgaaac tggcaccgcg ttggagcatt   840
```

```
accctgattt ttgaagatac aattccgttt ctgaaacgca atggtgttaa tgaagaagtg    900
attgccacca tttttaaaga aaatccgaaa aaattcttta gctaataa                 948
```

<210> SEQ ID NO 23
<211> LENGTH: 314
<212> TYPE: PRT
<213> ORGANISM: Sulfolobus solfataricus

<400> SEQUENCE: 23

```
Met Arg Ile Pro Leu Val Gly Lys Asp Ser Ile Glu Ser Lys Asp Ile
1               5                   10                  15

Gly Phe Thr Leu Ile His Glu His Leu Arg Ala Phe Ser Glu Ala Val
                20                  25                  30

Arg Gln Gln Trp Pro His Leu Tyr Asn Glu Asp Glu Glu Phe Arg Asn
        35                  40                  45

Ala Val Asn Glu Val Lys Arg Ala Met Gln Phe Gly Val Lys Thr Ile
    50                  55                  60

Val Asp Pro Thr Val Met Gly Leu Gly Arg Asp Ile Arg Phe Met Glu
65                  70                  75                  80

Lys Val Val Lys Ala Thr Gly Ile Asn Leu Val Ala Gly Thr Gly Ile
                85                  90                  95

Trp Ile Tyr Ile Asp Leu Pro Phe Tyr Phe Leu Asn Arg Ser Ile Asp
                100                 105                 110

Glu Ile Ala Asp Leu Phe Ile His Asp Ile Lys Glu Gly Ile Gln Gly
        115                 120                 125

Thr Leu Asn Lys Ala Gly Phe Val Lys Ile Ala Ala Asp Glu Pro Gly
    130                 135                 140

Ile Thr Lys Asp Val Glu Lys Val Ile Arg Ala Ala Ile Ala Asn
145                 150                 155                 160

Lys Glu Thr Lys Val Pro Ile Ile Thr His Ser Asn Ala His Asn Asn
                165                 170                 175

Thr Gly Leu Glu Gln Gln Arg Ile Leu Thr Glu Glu Gly Val Asp Pro
            180                 185                 190

Gly Lys Ile Leu Ile Gly His Leu Gly Asp Thr Asp Asn Ile Asp Tyr
        195                 200                 205

Ile Lys Lys Ile Ala Asp Lys Gly Ser Phe Ile Gly Leu Asp Arg Tyr
    210                 215                 220

Gly Leu Asp Met Phe Leu Pro Val Asp Lys Arg Asn Glu Thr Thr Leu
225                 230                 235                 240

Arg Leu Ile Lys Asp Gly Tyr Ser Asp Lys Ile Met Ile Ser His Asp
                245                 250                 255

Tyr Cys Cys Thr Ile Asp Met Gly Thr Ala Lys Pro Gly Tyr Lys Pro
            260                 265                 270

Lys Leu Ala Pro Arg Trp Ser Ile Thr Leu Ile Phe Glu Asp Thr Ile
        275                 280                 285

Pro Phe Leu Lys Arg Asn Gly Val Asn Glu Val Ile Ala Thr Ile
    290                 295                 300

Phe Lys Glu Asn Pro Lys Lys Phe Phe Ser
305                 310
```

<210> SEQ ID NO 24
<211> LENGTH: 945
<212> TYPE: DNA
<213> ORGANISM: Sulfolobus solfataricus

<400> SEQUENCE: 24

```
atgcgcattc cgctggttgg taaagatagc attgaaagca agatattgg ctttaccctg      60
attcatgaac atctgcgtgc atttagcgaa gcagttcgtc agcagtggcc tcatctgtat     120
aatgaagatg aagaatttcg caatgccgtg aatgaagtta acgtgcaat gcagtttggc      180
gttaaaacca ttgttgatcc gaccgttatg ggtctgggtc gtgatattcg ttttatggaa     240
aaagttgtga agccaccgg cattaatctg gttgcaggca ccggtatttg gatttatatc      300
gatctgccgt tttatttct gaatcgcagc attgatgaaa ttgccgacct gtttattcat      360
gatattaaag aaggcattca gggcaccctg aataaagcag gttttgttaa aattgcagcc     420
gatgaaccgg gtattaccaa agatgttgaa aaagttattc gtgcagcagc cattgccaat     480
aaagaaacca agttccgat tattacccat agcaatgccc ataataatac cggtctggaa      540
cagcagcgta ttctgaccga agaaggtgtg gatccgggta aaattctgat tggtcatctg     600
ggtgataccg ataatatcga ttatatcaaa aaaattgccg ataaaggcag ctttattggt     660
ctggatcgtt atggtctgga cctgtttctg ccggttgata acgtaatga aaccaccctg      720
cgcctgatta agatggtta tagcgataaa attatgatta gccatgatta ttgctgcacc     780
attgatctgg gcaccgcaaa accggaatat aaaccgaaac tggcaccgcg ttggagcact     840
accctgattt ttgaagatac aattccgttt ctgaaacgca atggtgttaa tgaagaagtg     900
attgccacca tttttaaaga aaatccgaaa aaattcttta gctaa                     945
```

<210> SEQ ID NO 25
<211> LENGTH: 314
<212> TYPE: PRT
<213> ORGANISM: Sulfolobus solfataricus

<400> SEQUENCE: 25

```
Met Arg Ile Pro Leu Val Gly Lys Asp Ser Ile Glu Ser Lys Asp Ile
 1               5                  10                  15

Gly Phe Thr Leu Ile His Glu His Leu Arg Ala Phe Ser Glu Ala Val
                20                  25                  30

Arg Gln Gln Trp Pro His Leu Tyr Asn Glu Asp Glu Glu Phe Arg Asn
            35                  40                  45

Ala Val Asn Glu Val Lys Arg Ala Met Gln Phe Gly Val Lys Thr Ile
        50                  55                  60

Val Asp Pro Thr Val Met Gly Leu Gly Arg Asp Ile Arg Phe Met Glu
 65                  70                  75                  80

Lys Val Val Lys Ala Thr Gly Ile Asn Leu Val Ala Gly Thr Gly Ile
                85                  90                  95

Trp Ile Tyr Ile Asp Leu Pro Phe Tyr Phe Leu Asn Arg Ser Ile Asp
                100                 105                 110

Glu Ile Ala Asp Leu Phe Ile His Asp Ile Lys Glu Gly Ile Gln Gly
            115                 120                 125

Thr Leu Asn Lys Ala Gly Phe Val Lys Ile Ala Ala Asp Glu Pro Gly
        130                 135                 140

Ile Thr Lys Asp Val Glu Lys Val Ile Arg Ala Ala Ile Ala Asn
145                 150                 155                 160

Lys Glu Thr Lys Val Pro Ile Ile Thr His Ser Asn Ala His Asn Asn
                165                 170                 175

Thr Gly Leu Glu Gln Gln Arg Ile Leu Thr Glu Glu Gly Val Asp Pro
            180                 185                 190

Gly Lys Ile Leu Ile Gly His Leu Gly Asp Thr Asp Asn Ile Asp Tyr
```

```
                195                 200                 205
Ile Lys Lys Ile Ala Asp Lys Gly Ser Phe Ile Gly Leu Asp Arg Tyr
        210                 215                 220

Gly Leu Asp Leu Phe Leu Pro Val Asp Lys Arg Asn Glu Thr Thr Leu
225                 230                 235                 240

Arg Leu Ile Lys Asp Gly Tyr Ser Asp Lys Ile Met Ile Ser His Asp
                245                 250                 255

Tyr Cys Cys Thr Ile Asp Leu Gly Thr Ala Lys Pro Glu Tyr Lys Pro
        260                 265                 270

Lys Leu Ala Pro Arg Trp Ser Thr Thr Leu Ile Phe Glu Asp Thr Ile
            275                 280                 285

Pro Phe Leu Lys Arg Asn Gly Val Asn Glu Glu Val Ile Ala Thr Ile
        290                 295                 300

Phe Lys Glu Asn Pro Lys Lys Phe Phe Ser
305                 310

<210> SEQ ID NO 26
<211> LENGTH: 948
<212> TYPE: DNA
<213> ORGANISM: Sulfolobus solfataricus

<400> SEQUENCE: 26
atgcgcattc cgctggttgg taaagatagc attgaaagca agatattgg ctttaccctg      60
attcatgaac atctgcgtgt ttttagcgaa gcagttcgtc agcagtggcc tcatctgtat     120
aatgaagatg aagaacttcg caatgccgtg aatgaagtta acgtgcaat gcagtttggc     180
gttaaaacca ttgttgatcc gaccgttatg ggtctgggtc gtgatattcg ttttatggaa     240
aaagttgtga agccaccgg cattaatctg gttgcaggca ccggtatta tatttatatc     300
gatctgccgt tttatttct gaatcgcagc attgatgaaa ttgccgacct gtttattcat     360
gatattaaag aaggcattca gggcacccct aataaagcag ttttgttaa aattgcagcc     420
gatgaaccgg gtattaccaa agatgttgaa aaagttattc gtgcagcagc cattgccaat     480
aaagaaacca agttccgat tattacccat agcaatgccc ataataatac cggtctggaa     540
cagcagcgta ttctgaccga agaaggtgtg gatccgggta aaattctgat ggtcatctg     600
ggtgataccg ataatatcga ttatatcaaa aaaattgccg ataaaggcag ctttattggt     660
ctggatcgtt atggtctgga cctgtttctg ccggttgata acgtaatga accaccctg     720
cgcctgatta agatggtta tagcgataaa attatgatta gccatgatta tgcctgcacc     780
attgatatgg gcaccgcaaa accggaatat aaaccgaaac tggcaccgcg ttggagcact     840
accctgattt ttgaagatac aattccgttt ctgaaacgca atggtgttaa tgaagaagtg     900
attgccacca ttttaaaga aaatccgaaa aaattcttta gctaataa                948

<210> SEQ ID NO 27
<211> LENGTH: 314
<212> TYPE: PRT
<213> ORGANISM: Sulfolobus solfataricus

<400> SEQUENCE: 27

Met Arg Ile Pro Leu Val Gly Lys Asp Ser Ile Glu Ser Lys Asp Ile
1               5                   10                  15

Gly Phe Thr Leu Ile His Glu His Leu Arg Val Phe Ser Glu Ala Val
            20                  25                  30

Arg Gln Gln Trp Pro His Leu Tyr Asn Glu Asp Glu Glu Leu Arg Asn
        35                  40                  45
```

```
Ala Val Asn Glu Val Lys Arg Ala Met Gln Phe Gly Val Lys Thr Ile
 50                  55                  60
Val Asp Pro Thr Val Met Gly Leu Gly Arg Asp Ile Arg Phe Met Glu
 65                  70                  75                  80
Lys Val Val Lys Ala Thr Gly Ile Asn Leu Val Ala Gly Thr Gly Ile
                 85                  90                  95
Tyr Ile Tyr Ile Asp Leu Pro Phe Tyr Phe Leu Asn Arg Ser Ile Asp
            100                 105                 110
Glu Ile Ala Asp Leu Phe Ile His Asp Ile Lys Glu Gly Ile Gln Gly
            115                 120                 125
Thr Leu Asn Lys Ala Gly Phe Val Lys Ile Ala Ala Asp Glu Pro Gly
130                 135                 140
Ile Thr Lys Asp Val Glu Lys Val Ile Arg Ala Ala Ile Ala Asn
145                 150                 155                 160
Lys Glu Thr Lys Val Pro Ile Ile Thr His Ser Asn Ala His Asn Asn
                165                 170                 175
Thr Gly Leu Glu Gln Gln Arg Ile Leu Thr Glu Gly Val Asp Pro
            180                 185                 190
Gly Lys Ile Leu Ile Gly His Leu Gly Asp Thr Asp Asn Ile Asp Tyr
            195                 200                 205
Ile Lys Lys Ile Ala Asp Lys Gly Ser Phe Ile Gly Leu Asp Arg Tyr
210                 215                 220
Gly Leu Asp Leu Phe Leu Pro Val Asp Lys Arg Asn Glu Thr Thr Leu
225                 230                 235                 240
Arg Leu Ile Lys Asp Gly Tyr Ser Asp Lys Ile Met Ile Ser His Asp
                245                 250                 255
Tyr Ala Cys Thr Ile Asp Met Gly Thr Ala Lys Pro Glu Tyr Lys Pro
            260                 265                 270
Lys Leu Ala Pro Arg Trp Ser Thr Thr Leu Ile Phe Glu Asp Thr Ile
            275                 280                 285
Pro Phe Leu Lys Arg Asn Gly Val Asn Glu Glu Val Ile Ala Thr Ile
290                 295                 300
Phe Lys Glu Asn Pro Lys Lys Phe Phe Ser
305                 310

<210> SEQ ID NO 28
<211> LENGTH: 948
<212> TYPE: DNA
<213> ORGANISM: Sulfolobus solfataricus

<400> SEQUENCE: 28
atgcgcattc cgctggttgg taaagatagc attgaaagca agatattgg ctttaccctg      60
attcatgaac atctgcgtgc atttagcgaa gcagttcgtc agcagtggcc tcatctgtat    120
aatgaagatg aagaatttcg caatgccgtg aatgaagtta acgtgcaat gcagtttggc    180
gttaaaacca ttgttgatcc gaccgttatg ggtctgggtc gtgatactcg ttttatggaa    240
aaagttgtga agccaccgg cattaatctg gttgcaggca ccggtatttg gatttttatc    300
gatctgccgt ttatttttct gaatcgcagc attgatgaaa ttgccgacct gtttattcat    360
gatattaaag aaggcattca gggcaccccg aataaagcag ttttgttaa aattgcagcc    420
gatgaaccgg gtattaccaa agatgttgaa aaagttattc gtgcagcagc cattgccaat    480
aaagaaacca agttccgat tattacccat agcaatgccc ataataatac cggtctggaa    540
cagcagcgta ttctgaccga agaaggtgtg gatccgggta aaattctgat tggtcatctg    600
```

```
ggtgataccg ataatatcga ttatatcaaa aaaattgccg ataaaggcag ctttattggt    660
ctggatcgtt atggtgtgga cctgtttctg ccggttgata acgtaatga aaccaccctg    720 cgcctgatta agatggtta tagcgataaa attatgatta gccatgatta ttgctgcacc    780
attgattggg gcaccgcaaa accggaatat aaaccgaaac tggcaccgcg ttggagcatt    840
accctgattt ttgaagatac aattccgttt ctgaaacgca atggtgttaa tgaagaagtg    900
attgccacca ttttaaaga aatccgaaa aaattcttta gctaataa                948
```

<210> SEQ ID NO 29
<211> LENGTH: 314
<212> TYPE: PRT
<213> ORGANISM: Sulfolobus solfataricus

<400> SEQUENCE: 29

```
Met Arg Ile Pro Leu Val Gly Lys Asp Ser Ile Glu Ser Lys Asp Ile
1               5                   10                  15

Gly Phe Thr Leu Ile His Glu His Leu Arg Ala Phe Ser Glu Ala Val
            20                  25                  30

Arg Gln Gln Trp Pro His Leu Tyr Asn Glu Asp Glu Glu Phe Arg Asn
        35                  40                  45

Ala Val Asn Glu Val Lys Arg Ala Met Gln Phe Gly Val Lys Thr Ile
    50                  55                  60

Val Asp Pro Thr Val Met Gly Leu Gly Arg Asp Thr Arg Phe Met Glu
65                  70                  75                  80

Lys Val Val Lys Ala Thr Gly Ile Asn Leu Val Ala Gly Thr Gly Ile
                85                  90                  95

Trp Ile Phe Ile Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Gly
        115                 120                 125

Thr Pro Asn Lys Ala Gly Phe Val Lys Ile Ala Ala Asp Glu Pro Gly
    130                 135                 140

Ile Thr Lys Asp Val Glu Lys Val Ile Arg Ala Ala Ile Ala Asn
145                 150                 155                 160

Lys Glu Thr Lys Val Pro Ile Ile Thr His Ser Asn Ala His Asn Asn
                165                 170                 175

Thr Gly Leu Glu Gln Gln Arg Ile Leu Thr Glu Glu Gly Val Asp Pro
            180                 185                 190

Gly Lys Ile Leu Ile Gly His Leu Gly Asp Thr Asp Asn Ile Asp Tyr
        195                 200                 205

Ile Lys Lys Ile Ala Asp Lys Gly Ser Phe Ile Gly Leu Asp Arg Tyr
    210                 215                 220

Gly Val Asp Leu Phe Leu Pro Val Asp Lys Arg Asn Glu Thr Thr Leu
225                 230                 235                 240

Arg Leu Ile Lys Asp Gly Tyr Ser Asp Lys Ile Met Ile Ser His Asp
                245                 250                 255

Tyr Cys Cys Thr Ile Asp Trp Gly Thr Ala Lys Pro Glu Tyr Lys Pro
            260                 265                 270

Lys Leu Ala Pro Arg Trp Ser Ile Thr Leu Ile Phe Glu Asp Thr Ile
        275                 280                 285

Pro Phe Leu Lys Arg Asn Gly Val Asn Glu Glu Val Ile Ala Thr Ile
    290                 295                 300

Phe Lys Glu Asn Pro Lys Lys Phe Phe Ser
```

<210> SEQ ID NO 30
<211> LENGTH: 948
<212> TYPE: DNA
<213> ORGANISM: Sulfolobus solfataricus

<400> SEQUENCE: 30

```
atgcgcattc cgctggttgg taaagatagc attgaaagca agatattgg ctttaccctg      60
attcatgaac atctgcgtgt ttttagcgaa gcagttcgtc agcagtggcc ccatctgtat     120
aatgaagatg aagaatttcg caatgccgtg aatgaagtta acgtgcaat gcagtttggc     180
gttaaaacca ttgttgatcc gaccgttatg ggtattggtc gtgatattcg ttttatggaa     240
aaagttgtga agccaccgg cattaatctg gttgcaggca ccggtattta tatttttatc     300
gatctgccgt tttatttcct gaatcgcagc attgatgaaa ttgccgacct gtttattcat     360
gatttaaaag aaggcattca gggcaccctg aataaagcag gttttgttaa aattgcagcc     420
gatgaaccgg gtattaccaa agatgttgaa aaagtcattc gtgcagcagc cattgccaat     480
aaagaaacca aagttccgat tattacccat agcaatgccc ataataatac cggtctggaa     540
cagcagcgta ttctgaccga agaaggtgtg gatccgggta aaattctgat tggtcatctg     600
ggtgataccg ataatatcga ttatatcaaa aaaattgccg ataaaggcag ctttattggt     660
ctggatcgtt atggtctgga catgtctctg ccggttgata acgtaatga accaccctg      720
cgcctgatta agatggttta tagcgataaa attatgatta ccatgatta ttgctgcacc     780
attgatctgg gcaccgcaaa accggaatat aaaccgaaac tggcaccgcg ttggagcatt     840
accctgattt ttgaagatac aattccgttt ctgaaacgca atggtgttaa tgaagaagtg     900
attgccacca ttttttaaaga aaatccgaaa aaattcttta gctaataa                948
```

<210> SEQ ID NO 31
<211> LENGTH: 314
<212> TYPE: PRT
<213> ORGANISM: Sulfolobus solfataricus

<400> SEQUENCE: 31

```
Met Arg Ile Pro Leu Val Gly Lys Asp Ser Ile Glu Ser Lys Asp Ile
1               5                   10                  15
Gly Phe Thr Leu Ile His Glu His Leu Arg Val Phe Ser Glu Ala Val
                20                  25                  30
Arg Gln Gln Trp Pro His Leu Tyr Asn Glu Asp Glu Glu Phe Arg Asn
            35                  40                  45
Ala Val Asn Glu Val Lys Arg Ala Met Gln Phe Gly Val Lys Thr Ile
        50                  55                  60
Val Asp Pro Thr Val Met Gly Ile Gly Arg Asp Ile Arg Phe Met Glu
65                  70                  75                  80
Lys Val Val Lys Ala Thr Gly Ile Asn Leu Val Ala Gly Thr Gly Ile
                85                  90                  95
Tyr Ile Phe Ile Asp Leu Pro Phe Tyr Phe Leu Asn Arg Ser Ile Asp
                100                 105                 110
Glu Ile Ala Asp Leu Phe Ile His Asp Leu Lys Glu Gly Ile Gln Gly
            115                 120                 125
Thr Leu Asn Lys Ala Gly Phe Val Lys Ile Ala Ala Asp Glu Pro Gly
        130                 135                 140
Ile Thr Lys Asp Val Glu Lys Val Ile Arg Ala Ala Ala Ile Ala Asn
145                 150                 155                 160
```

```
Lys Glu Thr Lys Val Pro Ile Ile Thr His Ser Asn Ala His Asn Asn
                165                 170                 175
Thr Gly Leu Glu Gln Gln Arg Ile Leu Thr Glu Gly Val Asp Pro
            180                 185                 190
Gly Lys Ile Leu Ile Gly His Leu Gly Asp Thr Asp Asn Ile Asp Tyr
            195                 200                 205
Ile Lys Lys Ile Ala Asp Lys Gly Ser Phe Ile Gly Leu Asp Arg Tyr
    210                 215                 220
Gly Leu Asp Met Ser Leu Pro Val Asp Lys Arg Asn Glu Thr Thr Leu
225                 230                 235                 240
Arg Leu Ile Lys Asp Gly Tyr Ser Asp Lys Ile Met Ile Ser His Asp
                245                 250                 255
Tyr Cys Cys Thr Ile Asp Leu Gly Thr Ala Lys Pro Glu Tyr Lys Pro
                260                 265                 270
Lys Leu Ala Pro Arg Trp Ser Ile Thr Leu Ile Phe Glu Asp Thr Ile
            275                 280                 285
Pro Phe Leu Lys Arg Asn Gly Val Asn Glu Glu Val Ile Ala Thr Ile
        290                 295                 300
Phe Lys Glu Asn Pro Lys Lys Phe Phe Ser
305                 310

<210> SEQ ID NO 32
<211> LENGTH: 945
<212> TYPE: DNA
<213> ORGANISM: Sulfolobus solfataricus

<400> SEQUENCE: 32
atgcgcattc cgctggttgg taaagatagc attgaaagca aagatattgg ctttaccctg      60
attcatgaac atctgcgtgt ttttagcgaa gcagttcgtc agcagtggcc ccatctgtat     120
aatgaagatg aagaatttcg caatgccgtg aatgaagtta acgtgcaat gcagtttggc     180
gttaaaacca ttgttgatcc gagtgttatg ggtattggtc gtgatattcg ttttatggaa     240
aaagttgtga agccaccggc attaatctg gttgcaggca ccggtattta tatttatatc     300
gatctgccgt tttattttct gaatcgcagc attgatgaaa ttgccgacct gtttattcat     360
gatattaaag aaggcattca gggcaccccg aataaagcag gttttgttaa aattgcagcc     420
gatgaaccgg gtattaccaa agatgttgaa aaagttattc gtgcagcagc cattgccaat     480
aaagaaacca agttccgat tattacccat agcaatgccc ataataatac cggtctggaa     540
cagcagcgta ttctgaccga agaaggtgtg gatccgggta aaattctgat tggtcatctg     600
ggtgataccg ataatatcga ttatatcaaa aaaattgccg ataaaggcag ctttattggt     660
ctggatcgtt atggtctgga catgtctctg ccggttgata acgtaatga accaccctg      720
cgcctgatta agatggttta tagcgataaa attatgatta gccatgatta ttgctgcacc     780
attgatatgg gcaccgcaaa accggaatat aaaccgaaac cggcaccgcg ttggagcatt     840
accctgattt ttgaagatac aattccgttt ctgaaacgca atggtgttaa tgaagaagtg     900
attgccacca ttttaaaga aaatccgaaa aaattcttta gctaa                     945

<210> SEQ ID NO 33
<211> LENGTH: 314
<212> TYPE: PRT
<213> ORGANISM: Sulfolobus solfataricus

<400> SEQUENCE: 33
```

```
Met Arg Ile Pro Leu Val Gly Lys Asp Ser Ile Glu Ser Lys Asp Ile
1               5                   10                  15

Gly Phe Thr Leu Ile His Glu His Leu Arg Val Phe Ser Glu Ala Val
            20                  25                  30

Arg Gln Gln Trp Pro His Leu Tyr Asn Glu Asp Glu Phe Arg Asn
                35                  40                  45

Ala Val Asn Glu Val Lys Arg Ala Met Gln Phe Gly Val Lys Thr Ile
    50                  55                  60

Val Asp Pro Ser Val Met Gly Ile Gly Arg Asp Ile Arg Phe Met Glu
65                  70                  75                  80

Lys Val Val Lys Ala Thr Gly Ile Asn Leu Val Ala Gly Thr Gly Ile
                85                  90                  95

Tyr Ile Tyr Ile Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Gly
            115                 120                 125

Thr Pro Asn Lys Ala Gly Phe Val Lys Ile Ala Ala Asp Glu Pro Gly
    130                 135                 140

Ile Thr Lys Asp Val Glu Lys Val Ile Arg Ala Ala Ile Ala Asn
145                 150                 155                 160

Lys Glu Thr Lys Val Pro Ile Ile Thr His Ser Asn Ala His Asn Asn
                165                 170                 175

Thr Gly Leu Glu Gln Gln Arg Ile Leu Thr Glu Gly Val Asp Pro
            180                 185                 190

Gly Lys Ile Leu Ile Gly His Leu Gly Asp Thr Asp Asn Ile Asp Tyr
            195                 200                 205

Ile Lys Lys Ile Ala Asp Lys Gly Ser Phe Ile Gly Leu Asp Arg Tyr
210                 215                 220

Gly Leu Asp Met Ser Leu Pro Val Asp Lys Arg Asn Glu Thr Thr Leu
225                 230                 235                 240

Arg Leu Ile Lys Asp Gly Tyr Ser Asp Lys Ile Met Ile Ser His Asp
                245                 250                 255

Tyr Cys Cys Thr Ile Asp Met Gly Thr Ala Lys Pro Glu Tyr Lys Pro
                260                 265                 270

Lys Pro Ala Pro Arg Trp Ser Ile Thr Leu Ile Phe Glu Asp Thr Ile
            275                 280                 285

Pro Phe Leu Lys Arg Asn Gly Val Asn Glu Glu Val Ile Ala Thr Ile
        290                 295                 300

Phe Lys Glu Asn Pro Lys Lys Phe Phe Ser
305                 310
```

<210> SEQ ID NO 34
<211> LENGTH: 945
<212> TYPE: DNA
<213> ORGANISM: Sulfolobus solfataricus

<400> SEQUENCE: 34

```
atgcgcattc cgctggttgg taaagatagc attgaaagca agatatttgg ctttacccctg    60 attcatgaac atctgcgtgt ttttagcgaa gcagttcgtc agcagtggcc tcatctgtat   120
aatgaagatg aagaatttcg caatgccgtg aatgaagtta acgtgcaat gcagtttggc   180 gttaaaacca ttgttgatcc gagtgttatg ggtctgggtc gtgatactcg ttttatggaa   240
aaagttgtga agccaccggg cattaatctg gttgcaggcc ccgtatttg gattttttatc   300 gatctgccgt tttatttttct gaatcgcagc attgatgaaa ttgccgacct gtttattcat   360
```

```
gatattaaag aaggcattca gggcaccctg aataaagcag gttttgttaa aattgcagcc    420
gatgaaccgg gtattaccaa agatgttgaa aaagttattc gtgcagcagc cattgccaat    480
aaagaaacca agttccgat tattacccat agcaatgccc ataataatac cggtctggaa     540
cagcagcgta ttctgaccga agaaggtgtg atcccgggta aaattctgat tggtcatctg    600
ggtgataccg ataatatcga ttatatcaaa aaaattgccg ataaaggcag ctttattggt    660
ctggatcgtt atggtctgga catgtttctg ccggttgata acgtaatga accaccctg     720 cgcctgatta agatggtta tagcgataaa attatgatta gccatgatta ttgctgcacc    780
attgatctgg gcaccgcaaa accggaatat aaaccgaaac tggcaccgcg ttggagcatt    840
accctgattt ttgaagatac aattccgttt ctgaaacgca atggtgttaa tgaagaagtg    900
attgccacca ttttttaaaga aaatccgaaa aaattcttta gctaa                  945
```

<210> SEQ ID NO 35
<211> LENGTH: 314
<212> TYPE: PRT
<213> ORGANISM: Sulfolobus solfataricus

<400> SEQUENCE: 35

```
Met Arg Ile Pro Leu Val Gly Lys Asp Ser Ile Glu Ser Lys Asp Ile
1               5                   10                  15

Gly Phe Thr Leu Ile His Glu His Leu Arg Val Phe Ser Glu Ala Val
            20                  25                  30

Arg Gln Gln Trp Pro His Leu Tyr Asn Glu Asp Glu Glu Phe Arg Asn
        35                  40                  45

Ala Val Asn Glu Val Lys Arg Ala Met Gln Phe Gly Val Lys Thr Ile
    50                  55                  60

Val Asp Pro Ser Val Met Gly Leu Gly Arg Asp Thr Arg Phe Met Glu
65                  70                  75                  80

Lys Val Val Lys Ala Thr Gly Ile Asn Leu Val Ala Gly Thr Gly Ile
                85                  90                  95

Trp Ile Phe Ile Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Gly
        115                 120                 125

Thr Leu Asn Lys Ala Gly Phe Val Lys Ile Ala Ala Asp Glu Pro Gly
    130                 135                 140

Ile Thr Lys Asp Val Glu Lys Val Ile Arg Ala Ala Ile Ala Asn
145                 150                 155                 160

Lys Glu Thr Lys Val Pro Ile Ile Thr His Ser Asn Ala His Asn Asn
                165                 170                 175

Thr Gly Leu Glu Gln Gln Arg Ile Leu Thr Glu Glu Gly Val Asp Pro
            180                 185                 190

Gly Lys Ile Leu Ile Gly His Leu Gly Asp Thr Asp Asn Ile Asp Tyr
        195                 200                 205

Ile Lys Lys Ile Ala Asp Lys Gly Ser Phe Ile Gly Leu Asp Arg Tyr
    210                 215                 220

Gly Leu Asp Met Phe Leu Pro Val Asp Lys Arg Asn Glu Thr Thr Leu
225                 230                 235                 240

Arg Leu Ile Lys Asp Gly Tyr Ser Asp Lys Ile Met Ile Ser His Asp
                245                 250                 255

Tyr Cys Cys Thr Ile Asp Leu Gly Thr Ala Lys Pro Glu Tyr Lys Pro
            260                 265                 270
```

Lys Leu Ala Pro Arg Trp Ser Ile Thr Leu Ile Phe Glu Asp Thr Ile
        275                 280                 285

Pro Phe Leu Lys Arg Asn Gly Val Asn Glu Glu Val Ile Ala Thr Ile
        290                 295                 300

Phe Lys Glu Asn Pro Lys Lys Phe Phe Ser
305                 310

<210> SEQ ID NO 36
<211> LENGTH: 945
<212> TYPE: DNA
<213> ORGANISM: Sulfolobus solfataricus

<400> SEQUENCE: 36

```
atgcgcattc cgctggttgg tgaagatagc attgaaagca agatattgg ctttaccctg      60
attcatgaac atctgcgtgt ttttagcgaa gcagttcgtc agcagtggcc tcatctgtat    120
aatgaagatg aagaacttcg caatgccgtg aatgaagtta acgtgcaat gcagtttggc    180
gttaaaacca ttgttgatcc gaccgttatg ggtctgggtc gtgatattcg ttttatggaa    240
aaagttgtga agccaccgg cattaatctg gttgcaggca ccggtatttg attttatc      300
gatctgccgt tttattttct gaatcgcagc attgatgaaa ttgccgacct gtttattcat    360
gatattaaag aaggcattca gggcacccctg aataaagcag gttttgttaa aattgcagcc    420
gatgaaccgg gtattaccaa agatgttgaa aaagttattc gtgcagcagc cattgccaat    480
aaagaaacca agttccgat tattacccat agcaatgccc ataataatac cggtctggaa    540
cagcagcgta ttctgaccga agaaggtgtg atcccgggta aaattctgat tggtcatctg    600
ggtgataccg ataatatcga ttatatcaaa aaaattgccg ataaaggcag ctttattggt    660
ctggatcgtt atggtctgga catgtttctg ccggttgata acgtaatga accacccctg    720
cgcctgatta agatggttta tagcgataaa attatgatta gccatgatta ttgctgcacc    780
attgattggg gcaccgcaaa accggaatat aaaccgaaac tggcaccgcg ttggagcatt    840
accctgattt ttgaagatac aattccgttt ctgaaacgca atggtgttaa tgaagaagtg    900
attgccacca tttttaaaga aaatccgaaa aaattcttta gctaa                   945
```

<210> SEQ ID NO 37
<211> LENGTH: 314
<212> TYPE: PRT
<213> ORGANISM: Sulfolobus solfataricus

<400> SEQUENCE: 37

Met Arg Ile Pro Leu Val Gly Glu Asp Ser Ile Glu Ser Lys Asp Ile
1               5                   10                  15

Gly Phe Thr Leu Ile His Glu His Leu Arg Val Phe Ser Glu Ala Val
            20                  25                  30

Arg Gln Gln Trp Pro His Leu Tyr Asn Glu Asp Glu Glu Leu Arg Asn
        35                  40                  45

Ala Val Asn Glu Val Lys Arg Ala Met Gln Phe Gly Val Lys Thr Ile
    50                  55                  60

Val Asp Pro Thr Val Met Gly Leu Gly Arg Asp Ile Arg Phe Met Glu
65                  70                  75                  80

Lys Val Val Lys Ala Thr Gly Ile Asn Leu Val Ala Gly Thr Gly Ile
                85                  90                  95

Trp Ile Phe Ile Asp Leu Pro Tyr Phe Leu Asn Arg Ser Ile Asp
                100                 105                 110

```
Glu Ile Ala Asp Leu Phe Ile His Asp Ile Lys Glu Gly Ile Gln Gly
            115                 120                 125
Thr Leu Asn Lys Ala Gly Phe Val Lys Ile Ala Ala Asp Glu Pro Gly
        130                 135                 140
Ile Thr Lys Asp Val Glu Lys Val Ile Arg Ala Ala Ile Ala Asn
145                 150                 155                 160
Lys Glu Thr Lys Val Pro Ile Ile Thr His Ser Asn Ala His Asn Asn
                165                 170                 175
Thr Gly Leu Glu Gln Gln Arg Ile Leu Thr Glu Glu Val Asp Pro
            180                 185                 190
Gly Lys Ile Leu Ile Gly His Leu Gly Asp Thr Asp Asn Ile Asp Tyr
        195                 200                 205
Ile Lys Lys Ile Ala Asp Lys Gly Ser Phe Ile Gly Leu Asp Arg Tyr
    210                 215                 220
Gly Leu Asp Met Phe Leu Pro Val Asp Lys Arg Asn Glu Thr Thr Leu
225                 230                 235                 240
Arg Leu Ile Lys Asp Gly Tyr Ser Asp Lys Ile Met Ile Ser His Asp
                245                 250                 255
Tyr Cys Cys Thr Ile Asp Trp Gly Thr Ala Lys Pro Glu Tyr Lys Pro
            260                 265                 270
Lys Leu Ala Pro Arg Trp Ser Ile Thr Leu Ile Phe Glu Asp Thr Ile
        275                 280                 285
Pro Phe Leu Lys Arg Asn Gly Val Asn Glu Val Ile Ala Thr Ile
    290                 295                 300
Phe Lys Glu Asn Pro Lys Lys Phe Phe Ser
305                 310

<210> SEQ ID NO 38
<211> LENGTH: 945
<212> TYPE: DNA
<213> ORGANISM: Sulfolobus solfataricus

<400> SEQUENCE: 38
atgcgcattc cgctggttgg taaagatagc attgaaagca aagatattgg ctttaccctg      60
attcatgaac atctgcgtgt ttttagcgaa gcagttcgtc agcagtggcc tcatctgtat     120
aatgaagatg aagaatttcg caatgccgtg aatgaagtta acgtgcaat gcagtttggc      180
gttaaaacca ttgttgatcc gaccgttatg ggtattggtc gtgatattcg ttttatggaa     240
aaagttgtga agccaccgg cattaatctg gttgcaggca ccggtattta tatttatatc      300
gatctgccgt ttattttct gaatcgcagc attgatgaaa ttgccgacct gtttattcat      360
gatattaaag aaggcattca gggcacccctg aataaagcag ttttgttaa aattgcagcc     420
gatgaaccgg gtattaccaa agatgttgaa aaagttattc gtgcagcagc cattgccaat     480
aaagaaacca agttccgat tattacccat agcaatgccc ataataatac cggtctggaa      540
cagcagcgta ttctgaccga agaaggtgtg gatccgggta aaattctgat tggtcatctg     600
ggtgataccg ataatatcga ttatatcaaa aaaattgccg ataaaggcag ctttattggt     660
ctggatcgtt atggtctgga cctgtttctg ccggttgata acgtaatga accaccctg       720
cgcctgatta aagatggtta tagcgataaa attatgatta gccatgatta ttgctgcacc     780
attgattttg gcaccgcaaa accggaatat aaaccgaaac tggcaccgcg ttggagcatt     840
accctgattt ttgaagatac aattccgttt ctgaaacgca atggtgttaa tgaagaagtg     900
attgccacca ttttttaaaga aaatccgaaa aaattcttta gctaa                    945
```

<210> SEQ ID NO 39
<211> LENGTH: 314
<212> TYPE: PRT
<213> ORGANISM: Sulfolobus solfataricus

<400> SEQUENCE: 39

```
Met Arg Ile Pro Leu Val Gly Lys Asp Ser Ile Glu Ser Lys Asp Ile
1               5                   10                  15

Gly Phe Thr Leu Ile His Glu His Leu Arg Val Phe Ser Glu Ala Val
            20                  25                  30

Arg Gln Gln Trp Pro His Leu Tyr Asn Glu Asp Glu Phe Arg Asn
        35                  40                  45

Ala Val Asn Glu Val Lys Arg Ala Met Gln Phe Gly Val Lys Thr Ile
    50                  55                  60

Val Asp Pro Thr Val Met Gly Ile Gly Arg Asp Ile Arg Phe Met Glu
65                  70                  75                  80

Lys Val Val Lys Ala Thr Gly Ile Asn Leu Val Ala Gly Thr Gly Ile
                85                  90                  95

Tyr Ile Tyr Ile Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Gly
        115                 120                 125

Thr Leu Asn Lys Ala Gly Phe Val Lys Ile Ala Ala Asp Glu Pro Gly
130                 135                 140

Ile Thr Lys Asp Val Glu Lys Val Ile Arg Ala Ala Ile Ala Asn
145                 150                 155                 160

Lys Glu Thr Lys Val Pro Ile Ile Thr His Ser Asn Ala His Asn Asn
                165                 170                 175

Thr Gly Leu Glu Gln Gln Arg Ile Leu Thr Glu Glu Gly Val Asp Pro
            180                 185                 190

Gly Lys Ile Leu Ile Gly His Leu Gly Asp Thr Asp Asn Ile Asp Tyr
        195                 200                 205

Ile Lys Lys Ile Ala Asp Lys Gly Ser Phe Ile Gly Leu Asp Arg Tyr
    210                 215                 220

Gly Leu Asp Leu Phe Leu Pro Val Asp Lys Arg Asn Glu Thr Thr Leu
225                 230                 235                 240

Arg Leu Ile Lys Asp Gly Tyr Ser Asp Lys Ile Met Ile Ser His Asp
                245                 250                 255

Tyr Cys Cys Thr Ile Asp Phe Gly Thr Ala Lys Pro Glu Tyr Lys Pro
            260                 265                 270

Lys Leu Ala Pro Arg Trp Ser Ile Thr Leu Ile Phe Glu Asp Thr Ile
        275                 280                 285

Pro Phe Leu Lys Arg Asn Gly Val Asn Glu Val Ile Ala Thr Ile
    290                 295                 300

Phe Lys Glu Asn Pro Lys Lys Phe Phe Ser
305                 310
```

<210> SEQ ID NO 40
<211> LENGTH: 945
<212> TYPE: DNA
<213> ORGANISM: Sulfolobus solfataricus

<400> SEQUENCE: 40

```
atgcgcattc cgctggttgg taaagatagc attgaaagca agatattgg ctttacccctg      60 attcatgaac atctgcgtgt tttttagcgaa gcagttcgtc agcagtggcc tcatctgtat    120
```

```
aatgaagatg aagaatttcg caatgccgtg aatgaagtta aacgtgcaat gcagtttggc    180
gttaaaacca ttgttgatcc gagtgttatg ggtctgggtc gtgatattcg ttttatggaa    240
aaagttgtga agccaccgg cattaatctg gttgcaggca ccggtatttg attttttatc     300
gatctgccgt tttattttct gaatcgcagc attgatgaaa ttgccgacct gtttattcat    360
gatattaaag aaggcattca gggcaccccg aataaagcag gttttgttaa aattgcagcc    420
gatgaaccgg gtattaccaa agatgttgaa aaagttattc gtgcagcagc cattgccaat    480
aaagaaacca agttccgat tattacccat agcaatgccc ataataatac cggtctggaa     540
cagcagcgta ttctgaccga agaaggtgtg gatccgggta aaattctgat tggtcatctg    600
ggtgataccg ataatatcga ttatatcaaa aaaattgccg ataaaggcag ctttattggt    660
ctggatcgtt atggtctgga catgtttctg ccggttgata acgtaatga accacctg       720
cgcctgatta agatggtta tagcgataaa attatgatta gccatgatta ttgctgcacc    780
attgattggg gcaccgcaaa accggaatat aaaccgaaac tggcaccgcg ttggagcatt    840
accctgattt ttgaagatac aattccgttt ctgaaacgca atggtgttaa tgaagaagtg    900
attgccacca ttttaaaga aatccgaaa aaattcttta gctaa                      945
```

<210> SEQ ID NO 41
<211> LENGTH: 314
<212> TYPE: PRT
<213> ORGANISM: Sulfolobus solfataricus

<400> SEQUENCE: 41

```
Met Arg Ile Pro Leu Val Gly Lys Asp Ser Ile Glu Ser Lys Asp Ile
1               5                   10                  15

Gly Phe Thr Leu Ile His Glu His Leu Arg Val Phe Ser Glu Ala Val
            20                  25                  30

Arg Gln Gln Trp Pro His Leu Tyr Asn Glu Asp Glu Glu Phe Arg Asn
        35                  40                  45

Ala Val Asn Glu Val Lys Arg Ala Met Gln Phe Gly Val Lys Thr Ile
    50                  55                  60

Val Asp Pro Ser Val Met Gly Leu Gly Arg Asp Ile Arg Phe Met Glu
65                  70                  75                  80

Lys Val Val Lys Ala Thr Gly Ile Asn Leu Val Ala Gly Thr Gly Ile
                85                  90                  95

Trp Ile Phe Ile Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Gly
        115                 120                 125

Thr Pro Asn Lys Ala Gly Phe Val Lys Ile Ala Ala Asp Glu Pro Gly
    130                 135                 140

Ile Thr Lys Asp Val Glu Lys Val Ile Arg Ala Ala Ile Ala Asn
145                 150                 155                 160

Lys Glu Thr Lys Val Pro Ile Ile Thr His Ser Asn Ala His Asn Asn
                165                 170                 175

Thr Gly Leu Glu Gln Gln Arg Ile Leu Thr Glu Glu Gly Val Asp Pro
            180                 185                 190

Gly Lys Ile Leu Ile Gly His Leu Gly Asp Thr Asp Asn Ile Asp Tyr
        195                 200                 205

Ile Lys Lys Ile Ala Asp Lys Gly Ser Phe Ile Gly Leu Asp Arg Tyr
    210                 215                 220
```

```
Gly Leu Asp Met Phe Leu Pro Val Asp Lys Arg Asn Glu Thr Thr Leu
225                 230                 235                 240

Arg Leu Ile Lys Asp Gly Tyr Ser Asp Lys Ile Met Ile Ser His Asp
            245                 250                 255

Tyr Cys Cys Thr Ile Asp Trp Gly Thr Ala Lys Pro Glu Tyr Lys Pro
        260                 265                 270

Lys Leu Ala Pro Arg Trp Ser Ile Thr Leu Ile Phe Glu Asp Thr Ile
    275                 280                 285

Pro Phe Leu Lys Arg Asn Gly Val Asn Glu Val Ile Ala Thr Ile
290                 295                 300

Phe Lys Glu Asn Pro Lys Lys Phe Phe Ser
305                 310
```

<210> SEQ ID NO 42
<211> LENGTH: 945
<212> TYPE: DNA
<213> ORGANISM: Sulfolobus solfataricus

<400> SEQUENCE: 42

```
atgcgcattc cgctggttgg taaagatagc attgaaagca agatattgg ctttaccctg    60
attcatgaac atctgcgtgc atttagcgaa gcagttcgtc agcagtggcc tcatctgtat   120
aatgaagatg aagaacttcg caatgccgtg aatgaagtta acgtgcaat gcagtttggc   180
gttaaaacca ttgttgatcc gaccgttatg ggtctgggtc gtgatattcg ttttatggaa   240
aaagttgtga agccaccgg cattaatctg gttgcaggca ccggtatttta tatttatatc   300
gatctgccgt tttattttct gaatcgcagc attgatgaaa ttgccgacct gtttattcat   360
gatattaaag aaggcattca gggcaccctg aataaagcag gttttgttaa aattgcagcc   420
gatgaaccgg gtattaccaa agatgttgaa aaagttattc gtgcagcagc cattgccaat   480
aaagaaaacca agttccgat tattacccat agcaatgccc ataataatac cggtctggaa   540
cagcagcgta ttctgaccga agaaggtgtg atcccgggta aaattctgat ggtcatctg   600
ggtgataccg ataatatcga ttatatcaaa aaaattgccg ataaaggcag ctttattggt   660
ctggatcgtt atggtgtgga cctgtttctg ccggttgata acgtaatga accaccctg   720
cgcctgatta agatggtta tagcgataaa attatgatta gccatgatta tgctgcacc   780
attgatctgg gcaccgcaaa accggaatat aaaccgaaac tggcaccgcg ttggagcatt   840
accctaattt tgaagatac aattccgttt ctgaaacgca atggtgttaa tgaagaagtg   900
attgccacca ttttaaaga aaatccgaaa aaattctta gctaa                    945
```

<210> SEQ ID NO 43
<211> LENGTH: 314
<212> TYPE: PRT
<213> ORGANISM: Sulfolobus solfataricus

<400> SEQUENCE: 43

```
Met Arg Ile Pro Leu Val Gly Lys Asp Ser Ile Glu Ser Lys Asp Ile
1               5                   10                  15

Gly Phe Thr Leu Ile His Glu His Leu Arg Ala Phe Ser Glu Ala Val
            20                  25                  30

Arg Gln Gln Trp Pro His Leu Tyr Asn Glu Asp Glu Glu Leu Arg Asn
        35                  40                  45

Ala Val Asn Glu Val Lys Arg Ala Met Gln Phe Gly Val Lys Thr Ile
    50                  55                  60

Val Asp Pro Thr Val Met Gly Leu Gly Arg Asp Ile Arg Phe Met Glu
```

```
                65                  70                  75                  80
Lys Val Val Lys Ala Thr Gly Ile Asn Leu Val Ala Gly Thr Gly Ile
                    85                  90                  95

Tyr Ile Tyr Ile Asp Leu Pro Phe Tyr Phe Leu Asn Arg Ser Ile Asp
                    100                 105                 110

Glu Ile Ala Asp Leu Phe Ile His Asp Ile Lys Glu Gly Ile Gln Gly
                    115                 120                 125

Thr Leu Asn Lys Ala Gly Phe Val Lys Ile Ala Ala Asp Glu Pro Gly
            130                 135                 140

Ile Thr Lys Asp Val Glu Lys Val Ile Arg Ala Ala Ile Ala Asn
145                 150                 155                 160

Lys Glu Thr Lys Val Pro Ile Ile Thr His Ser Asn Ala His Asn Asn
                165                 170                 175

Thr Gly Leu Glu Gln Gln Arg Ile Leu Thr Glu Glu Gly Val Asp Pro
                    180                 185                 190

Gly Lys Ile Leu Ile Gly His Leu Gly Asp Thr Asp Asn Ile Asp Tyr
                    195                 200                 205

Ile Lys Lys Ile Ala Asp Lys Gly Ser Phe Ile Gly Leu Asp Arg Tyr
            210                 215                 220

Gly Val Asp Leu Phe Leu Pro Val Asp Lys Arg Asn Glu Thr Thr Leu
225                 230                 235                 240

Arg Leu Ile Lys Asp Gly Tyr Ser Asp Lys Ile Met Ile Ser His Asp
                245                 250                 255

Tyr Cys Cys Thr Ile Asp Leu Gly Thr Ala Lys Pro Glu Tyr Lys Pro
                    260                 265                 270

Lys Leu Ala Pro Arg Trp Ser Ile Thr Leu Ile Phe Glu Asp Thr Ile
                    275                 280                 285

Pro Phe Leu Lys Arg Asn Gly Val Asn Glu Glu Val Ile Ala Thr Ile
            290                 295                 300

Phe Lys Glu Asn Pro Lys Lys Phe Phe Ser
305                 310
```

<210> SEQ ID NO 44
<211> LENGTH: 945
<212> TYPE: DNA
<213> ORGANISM: Sulfolobus solfataricus

<400> SEQUENCE: 44

```
atgcgcattc cgctggttgg taaagatagc attgaaagca agatattgg ctttaccctg      60
attcatgaac atctgcgtgt ttttagcgaa gcagttcgtc agcagtggcc tcatctgtat     120
aatgaagatg aagaatttcg caatgccgtg aatgaagtta acgtgcaat gcagtttggc     180
gttaaaacca ttgttgatgt gagtgttatg ggtctgggtc gtgatattcg ttttatggaa     240
aaagttgtga agccaccgg cattaatctg gttgcaggca ccggtatttg attttttatc     300
gatctgccgt tttatttct gaatcgcagc attgatgaaa ttgccgacct gtttattcat     360
gatattaaag aaggcattca gggcaccctg aataaagcag gttttgttaa aattgcagcc     420
gatgaaccgg gtattaccaa agatgttgag aaagttattc gtgcagcagc cattgccaat     480
aaagaaacca agttccgat tattacccat agcaatgccc ataataatac cggtctggaa     540
cagcagcgta ttctgaccga gaaggtgtg gatccgggta aaattctgat tggtcatctg     600
ggtgataccg ataatatcga ttatatcaaa aaaattgccg ataaaggcag ctttattggt     660
ctggatcgtt atggtctgga catgtttctg ccggttgata acgtaatga accacccctg     720
```

```
cgcctgatta aagatggtta tagcgataaa attatgatta gccatgatta tgcctgcacc      780
attgatctgg gcaccgcaaa accggaatat aaaccgaaac tggcaccgcg ttggagcact      840
accctgattt ttgaagatac aattccgttt ctgaaacgca atggtgttaa tgaagaagtg      900
attgccacca ttttaaaga aaatccgaaa aaattcttta gctaa                      945
```

```
<210> SEQ ID NO 45
<211> LENGTH: 314
<212> TYPE: PRT
<213> ORGANISM: Sulfolobus solfataricus

<400> SEQUENCE: 45

Met Arg Ile Pro Leu Val Gly Lys Asp Ser Ile Glu Ser Lys Asp Ile
1               5                   10                  15

Gly Phe Thr Leu Ile His Glu His Leu Arg Val Phe Ser Glu Ala Val
                20                  25                  30

Arg Gln Gln Trp Pro His Leu Tyr Asn Glu Asp Glu Glu Phe Arg Asn
            35                  40                  45

Ala Val Asn Glu Val Lys Arg Ala Met Gln Phe Gly Val Lys Thr Ile
        50                  55                  60

Val Asp Val Ser Val Met Gly Leu Gly Arg Asp Ile Arg Phe Met Glu
65                  70                  75                  80

Lys Val Val Lys Ala Thr Gly Ile Asn Leu Val Ala Gly Thr Gly Ile
                85                  90                  95

Trp Ile Phe Ile Asp Leu Pro Phe Tyr Phe Leu Asn Arg Ser Ile Asp
                100                 105                 110

Glu Ile Ala Asp Leu Phe Ile His Asp Ile Lys Glu Gly Ile Gln Gly
            115                 120                 125

Thr Leu Asn Lys Ala Gly Phe Val Lys Ile Ala Ala Asp Glu Pro Gly
        130                 135                 140

Ile Thr Lys Asp Val Glu Lys Val Ile Arg Ala Ala Ile Ala Asn
145                 150                 155                 160

Lys Glu Thr Lys Val Pro Ile Ile Thr His Ser Asn Ala His Asn Asn
                165                 170                 175

Thr Gly Leu Glu Gln Gln Arg Ile Leu Thr Glu Glu Gly Val Asp Pro
            180                 185                 190

Gly Lys Ile Leu Ile Gly His Leu Gly Asp Thr Asp Asn Ile Asp Tyr
        195                 200                 205

Ile Lys Lys Ile Ala Asp Lys Gly Ser Phe Ile Gly Leu Asp Arg Tyr
    210                 215                 220

Gly Leu Asp Met Phe Leu Pro Val Asp Lys Arg Asn Glu Thr Thr Leu
225                 230                 235                 240

Arg Leu Ile Lys Asp Gly Tyr Ser Asp Lys Ile Met Ile Ser His Asp
                245                 250                 255

Tyr Ala Cys Thr Ile Asp Leu Gly Thr Ala Lys Pro Glu Tyr Lys Pro
            260                 265                 270

Lys Leu Ala Pro Arg Trp Ser Thr Thr Leu Ile Phe Glu Asp Thr Ile
        275                 280                 285

Pro Phe Leu Lys Arg Asn Gly Val Asn Glu Glu Val Ile Ala Thr Ile
    290                 295                 300

Phe Lys Glu Asn Pro Lys Lys Phe Phe Ser
305                 310

<210> SEQ ID NO 46
<211> LENGTH: 945
```

-continued

<210> SEQ ID NO 46
<211> LENGTH: 945
<212> TYPE: DNA
<213> ORGANISM: Sulfolobus solfataricus

<400> SEQUENCE: 46

```
atgcgcattc cgctggttgg taaagatagc attgaaagca agatattgg ctttaccctg       60
attcatgaac atctgcgtgt ttttagcgaa gcagttcgtc agcagtggcc tcatctgtat      120
aatgaagatg aagaacttcg caatgccgtg aatgaagtta acgtgcaat gcagtttggc      180
gttaaaacca ttgttgatcc gagtgttatg ggtctgggtc gtgatattcg ttttatggaa      240
aaagttgtga agccaccgg cattaatctg gttgcaggca ccggtatttg gattttatc      300
gatctgccgt tttattttct gaatcgcagc attgatgaaa ttgccgacct gtttattcat      360
gatattaaag aaggcattca gggcaccccg aataaagcag gttttgttaa aattgcagct      420
gatgaaccgg gtattaccaa agatgttgaa aaagttattc gtgcagcagc cattgccaat      480
aaagaaacca atgttccgat tattacccat agcaatgccc ataataatac cggtctggaa      540
cagcagcgta ttctgaccga agaaggtgtg gatccgggta aaattctgat tggtcatctg      600
ggtgataccg ataatatcga ttatatcaaa aaaattgccg ataaaggcag ctttattggt      660
ctggatcgtt atggtgtgga cctgtttctg ccggttgata acgtaatga accaccctg      720
cgcctgatta agatggtta tagcgataaa attatgatta gccatgatta ttgctgcacc      780
attgatatgg gcaccgcaaa accggaatat aaaccgaaac tggcaccgcg ttggagcatt      840
accctgattt ttgaagatac aattccgttt ctgaaacgca tggtgttaa tgaagaagtg      900
attgccacca ttttaaaga aaatccgaaa aaattcttta gctaa                     945
```

<210> SEQ ID NO 47
<211> LENGTH: 314
<212> TYPE: PRT
<213> ORGANISM: Sulfolobus solfataricus

<400> SEQUENCE: 47

Met Arg Ile Pro Leu Val Gly Lys Asp Ser Ile Glu Ser Lys Asp Ile
1               5                   10                  15

Gly Phe Thr Leu Ile His Glu His Leu Arg Val Phe Ser Glu Ala Val
            20                  25                  30

Arg Gln Gln Trp Pro His Leu Tyr Asn Glu Asp Glu Glu Leu Arg Asn
        35                  40                  45

Ala Val Asn Glu Val Lys Arg Ala Met Gln Phe Gly Val Lys Thr Ile
    50                  55                  60

Val Asp Pro Ser Val Met Gly Leu Gly Arg Asp Ile Arg Phe Met Glu
65                  70                  75                  80

Lys Val Val Lys Ala Thr Gly Ile Asn Leu Val Ala Gly Thr Gly Ile
                85                  90                  95

Trp Ile Phe Ile Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Gly
        115                 120                 125

Thr Pro Asn Lys Ala Gly Phe Val Lys Ile Ala Ala Asp Glu Pro Gly
    130                 135                 140

Ile Thr Lys Asp Val Glu Lys Val Ile Arg Ala Ala Ile Ala Asn
145                 150                 155                 160

Lys Glu Thr Asn Val Pro Ile Ile Thr His Ser Asn Ala His Asn Asn
                165                 170                 175

Thr Gly Leu Glu Gln Gln Arg Ile Leu Thr Glu Glu Gly Val Asp Pro

```
                180             185                 190
Gly Lys Ile Leu Ile Gly His Leu Gly Asp Thr Asp Asn Ile Asp Tyr
            195                 200                 205

Ile Lys Lys Ile Ala Asp Lys Gly Ser Phe Ile Gly Leu Asp Arg Tyr
            210                 215                 220

Gly Val Asp Leu Phe Leu Pro Val Asp Lys Arg Asn Glu Thr Thr Leu
225                 230                 235                 240

Arg Leu Ile Lys Asp Gly Tyr Ser Asp Lys Ile Met Ile Ser His Asp
                245                 250                 255

Tyr Cys Cys Thr Ile Asp Met Gly Thr Ala Lys Pro Glu Tyr Lys Pro
                260                 265                 270

Lys Leu Ala Pro Arg Trp Ser Ile Thr Leu Ile Phe Glu Asp Thr Ile
            275                 280                 285

Pro Phe Leu Lys Arg Asn Gly Val Asn Glu Glu Val Ile Ala Thr Ile
            290                 295                 300

Phe Lys Glu Asn Pro Lys Lys Phe Phe Ser
305                 310
```

<210> SEQ ID NO 48
<211> LENGTH: 945
<212> TYPE: DNA
<213> ORGANISM: Sulfolobus solfataricus

<400> SEQUENCE: 48

```
atgcgcattc cgctggttgg taaagatagc attgaaagca agatattgg ctttaccctg    60
attcatgaac atctgcgtgt ttttagcgaa gcagttcgtc agcagtggcc ccatctgtat   120
aatgaagatg aagaatttcg caatgccgtg aatgaagtta acgtgcaat gcagtttggc   180
gttaaaacca ttgttgatcc gagtgttatg ggtattggtc gtgatattcg ttttatggaa   240
aaagttgtga agccaccgg cattaatctg gttgcaggca ccggtatttg gatttttatc   300
gatctgccgt tttattttct gaatcgcagc attgatgaaa ttgccgacct gtttattcat   360
gatattaaag aaggcattca gggcaccccg aataaagcag ttttgttaa aattgcagcc   420
gatgaaccgg gtattaccaa agatgttgaa aaagttattc gtgcagcagc cattgccaat   480
aaagaaacca agttccgat tattacccat agcaatgccc ataataatac cggtctggaa   540
cagcagcgta ttctgaccga agaaggtgtg atcccgggta aaattctgat tggtcatctg   600
ggtgataccg ataatatcga ttatatcaaa aaaattgccg ataaaggcag ctttattggt   660
ctggatcgtt atggtctgga cctgtttctg ccggttgata acgtaatga accaccctg    720
cgcctgatta agatggttta tagcgataaa attatgatta gccatgatta ttgctgcacc   780
attgattggg gcaccgcaaa accggaatat aaaccgaaac tggcaccgcg ttggagcatt   840
acccctgattt ttgaagatac aattccgttt ctgaaacgca atggtgttaa tgaagaagtg   900
attgccacca tttttaaaga aaatccgaaa aaattcttta gctaa                  945
```

<210> SEQ ID NO 49
<211> LENGTH: 314
<212> TYPE: PRT
<213> ORGANISM: Sulfolobus solfataricus

<400> SEQUENCE: 49

```
Met Arg Ile Pro Leu Val Gly Lys Asp Ser Ile Glu Ser Lys Asp Ile
1               5                   10                  15

Gly Phe Thr Leu Ile His Glu His Leu Arg Val Phe Ser Glu Ala Val
            20                  25                  30
```

Arg Gln Gln Trp Pro His Leu Tyr Asn Glu Asp Glu Phe Arg Asn
        35                  40                  45

Ala Val Asn Glu Val Lys Arg Ala Met Gln Phe Gly Val Lys Thr Ile
 50                  55                  60

Val Asp Pro Ser Val Met Gly Ile Gly Arg Asp Ile Arg Phe Met Glu
 65                  70                  75                  80

Lys Val Val Lys Ala Thr Gly Ile Asn Leu Val Ala Gly Thr Gly Ile
                 85                  90                  95

Trp Ile Phe Ile Asp Leu Pro Phe Tyr Phe Leu Asn Arg Ser Ile Asp
                100                 105                 110

Glu Ile Ala Asp Leu Phe Ile His Asp Ile Lys Glu Gly Ile Gln Gly
                115                 120                 125

Thr Pro Asn Lys Ala Gly Phe Val Lys Ile Ala Ala Asp Glu Pro Gly
        130                 135                 140

Ile Thr Lys Asp Val Glu Lys Val Ile Arg Ala Ala Ile Ala Asn
145                 150                 155                 160

Lys Glu Thr Lys Val Pro Ile Ile Thr His Ser Asn Ala His Asn Asn
                165                 170                 175

Thr Gly Leu Glu Gln Gln Arg Ile Leu Thr Glu Glu Gly Val Asp Pro
        180                 185                 190

Gly Lys Ile Leu Ile Gly His Leu Gly Asp Thr Asp Asn Ile Asp Tyr
            195                 200                 205

Ile Lys Lys Ile Ala Asp Lys Gly Ser Phe Ile Gly Leu Asp Arg Tyr
        210                 215                 220

Gly Leu Asp Leu Phe Leu Pro Val Asp Lys Arg Asn Glu Thr Thr Leu
225                 230                 235                 240

Arg Leu Ile Lys Asp Gly Tyr Ser Asp Lys Ile Met Ile Ser His Asp
                245                 250                 255

Tyr Cys Cys Thr Ile Asp Trp Gly Thr Ala Lys Pro Glu Tyr Lys Pro
                260                 265                 270

Lys Leu Ala Pro Arg Trp Ser Ile Thr Leu Ile Phe Glu Asp Thr Ile
        275                 280                 285

Pro Phe Leu Lys Arg Asn Gly Val Asn Glu Val Ile Ala Thr Ile
        290                 295                 300

Phe Lys Glu Asn Pro Lys Lys Phe Phe Ser
305                 310

<210> SEQ ID NO 50
<211> LENGTH: 948
<212> TYPE: DNA
<213> ORGANISM: Sulfolobus acidocaldarius

<400> SEQUENCE: 50
atgaccaaaa ttccgctggt tggtaaaggt gaaattagtc cgggtgaaat gggttttacc      60
ctgattcatg aacatctgcg tgtttttagc gaaccggtgc gttatcagtg gcctcatctg     120
tataatgaag atgaagaact gaaaaacgcc gtgaacgaag tgaaaaccat tatgagctat     180
ggcgttaaaa ccattgttga tccgaccgtt atgggtctgg tcgtgatat cgtttttagt      240
gaaaaagtgg tgaaagaaac cggcattaat gttattgcag caaccggtct gtatacctat     300
accgatctgc gtttttttt caatggtcgt agcctggaag aaattgcaga actgctgatc     360
cacgatatca aaaaggtat tcagggcacc aataatcgtg cgggttttat caaagttgca     420
gcagatgaac cgggtattac ccgtgatgtt gaacgtgcaa ttcgtgcagc agcaattgca     480

```
cagaaagaaa caaatgttcc gattatcacc catagcaatg cacataatgg caccggtctg      540
gaacagcagc gtattctgat ggaagaaggt gtggatccgg tcgtgttct gattggtcat       600 ctgggtgata ccgataacgt ggactacatc aaaaaaatcg cagataaagg tagctttgtt     660
ggcctggatc gctatggtct ggacctgttt ctgccgattg ataaacgtaa tgaagttctg     720
ctgaaactga tcaaagatgg ttatctggat cgtattatgg tgagccagga ttattgttgt    780
accattgatt ttggtattgc caaaccggaa tataaaccga aactggcacc gaaatggtca    840
atgagcctga ttttaccga tgtgattccg agcattaaac gtgccggtgt taccgatgaa     900
cagctgcatg tgattttgt taaaaatccg gcacgcctgt ttagctga                 948
```

<210> SEQ ID NO 51
<211> LENGTH: 315
<212> TYPE: PRT
<213> ORGANISM: Sulfolobus acidocaldarius

<400> SEQUENCE: 51

Met Thr Lys Ile Pro Leu Val Gly Lys Gly Glu Ile Ser Pro Gly Glu
1               5                   10                  15

Met Gly Phe Thr Leu Ile His Glu His Leu Arg Val Phe Ser Glu Pro
            20                  25                  30

Val Arg Tyr Gln Trp Pro His Leu Tyr Asn Glu Asp Glu Glu Leu Lys
        35                  40                  45

Asn Ala Val Asn Glu Val Lys Thr Ile Met Ser Tyr Gly Val Lys Thr
    50                  55                  60

Ile Val Asp Pro Thr Val Met Gly Leu Gly Arg Asp Ile Arg Phe Ser
65                  70                  75                  80

Glu Lys Val Val Lys Glu Thr Gly Ile Asn Val Ile Ala Ala Thr Gly
                85                  90                  95

Leu Tyr Thr Tyr Thr Asp Leu Pro Phe Phe Phe Asn Gly Arg Ser Leu
            100                 105                 110

Glu Glu Ile Ala Glu Leu Leu Ile His Asp Ile Lys Lys Gly Ile Gln
        115                 120                 125

Gly Thr Asn Asn Arg Ala Gly Phe Ile Lys Val Ala Ala Asp Glu Pro
    130                 135                 140

Gly Ile Thr Arg Asp Val Glu Arg Ala Ile Arg Ala Ala Ile Ala
145                 150                 155                 160

Gln Lys Glu Thr Asn Val Pro Ile Ile Thr His Ser Asn Ala His Asn
                165                 170                 175

Gly Thr Gly Leu Glu Gln Gln Arg Ile Leu Met Glu Glu Gly Val Asp
            180                 185                 190

Pro Gly Arg Val Leu Ile Gly His Leu Gly Asp Thr Asp Asn Val Asp
        195                 200                 205

Tyr Ile Lys Lys Ile Ala Asp Lys Gly Ser Phe Val Gly Leu Asp Arg
    210                 215                 220

Tyr Gly Leu Asp Leu Phe Leu Pro Ile Asp Lys Arg Asn Glu Val Leu
225                 230                 235                 240

Leu Lys Leu Ile Lys Asp Gly Tyr Leu Asp Arg Ile Met Val Ser Gln
                245                 250                 255

Asp Tyr Cys Cys Thr Ile Asp Phe Gly Ile Ala Lys Pro Glu Tyr Lys
            260                 265                 270

Pro Lys Leu Ala Pro Lys Trp Ser Met Ser Leu Ile Phe Thr Asp Val
        275                 280                 285

Ile Pro Ser Ile Lys Arg Ala Gly Val Thr Asp Glu Gln Leu His Val

```
                290              295              300
Ile Phe Val Lys Asn Pro Ala Arg Leu Phe Ser
305                 310              315
```

<210> SEQ ID NO 52
<211> LENGTH: 948
<212> TYPE: DNA
<213> ORGANISM: Sulfolobus acidocaldarius

<400> SEQUENCE: 52

```
atgaccaaaa ttccgctggt tggtaaaggt gaaattagtc cgggtgaaat gggttttacc    60
ctgattcatg aacatctgcg tgtttttagc gaaccggtgc gttatcagtg gcctcatctg   120
tataatgaag atgaagaact gaaaaacgcc gtgaacgaag tgaaaaccat tatgagctat   180
ggcgttaaaa ccattgttga tccgaccgtt atgggtctgg gtcgtgatat tcgttttagt   240
gaaaaagtgg tgaaagaaac cggcattaat gttattgcag caaccggtct gtataccTat   300
accgatctgc cgttttttt caatggtcgt agcctggaag aaattgcaga actgctgatc   360
cacgatatca aaaaaggtat tcagggcacc aataatcgtg cgggttttat caaagttgca   420
gcagatgaac cgggtattac ccgtgatgtt gaacgtgcaa ttcgtgcagc agcaattgca   480
cagaaagaaa caaatgttcc gattatcacc catagcaatg cacataatgg caccggtctg   540
gaacagcagc gtattctgat ggaagaaggt gtggatccgg tcgtgttct gattggtcat   600
ctgggtgata ccgataacgt ggactacatc aaaaaaatcg cagataaagg tagctttgtt   660
ggcctggatc gctatggtct ggacctgtttt ctgccgattg ataaacgtaa tgaagttctg   720
ctgaaactga tcaaagatgg ttatctggat cgtattatgt gagccagga ttattgttgt   780
accattgata tgggtattgc caaaccggaa tataaaccga aactggcacc gaaatggtca   840
atgagcctga ttttaccga tgtgattccg agcattaaac gtgccggtgt taccgatgaa   900
cagctgcatg tgattttgt taaaaatccg gcacgcctgt ttagctga               948
```

<210> SEQ ID NO 53
<211> LENGTH: 315
<212> TYPE: PRT
<213> ORGANISM: Sulfolobus acidocaldarius

<400> SEQUENCE: 53

```
Met Thr Lys Ile Pro Leu Val Gly Lys Gly Glu Ile Ser Pro Gly Glu
1               5                   10                  15

Met Gly Phe Thr Leu Ile His Glu His Leu Arg Val Phe Ser Glu Pro
            20                  25                  30

Val Arg Tyr Gln Trp Pro His Leu Tyr Asn Glu Asp Glu Glu Leu Lys
        35                  40                  45

Asn Ala Val Asn Glu Val Lys Thr Ile Met Ser Tyr Gly Val Lys Thr
    50                  55                  60

Ile Val Asp Pro Thr Val Met Gly Leu Gly Arg Asp Ile Arg Phe Ser
65                  70                  75                  80

Glu Lys Val Val Lys Glu Thr Gly Ile Asn Val Ile Ala Ala Thr Gly
                85                  90                  95

Leu Tyr Thr Tyr Thr Asp Leu Pro Phe Phe Asn Gly Arg Ser Leu
            100                 105                 110

Glu Glu Ile Ala Glu Leu Leu Ile His Asp Ile Lys Lys Gly Ile Gln
        115                 120                 125

Gly Thr Asn Asn Arg Ala Gly Phe Ile Lys Val Ala Ala Asp Glu Pro
    130                 135                 140
```

```
Gly Ile Thr Arg Asp Val Glu Arg Ala Ile Arg Ala Ala Ala Ile Ala
145                 150                 155                 160

Gln Lys Glu Thr Asn Val Pro Ile Ile Thr His Ser Asn Ala His Asn
            165                 170                 175

Gly Thr Gly Leu Glu Gln Gln Arg Ile Leu Met Glu Glu Gly Val Asp
        180                 185                 190

Pro Gly Arg Val Leu Ile Gly His Leu Gly Asp Thr Asp Asn Val Asp
            195                 200                 205

Tyr Ile Lys Lys Ile Ala Asp Lys Gly Ser Phe Val Gly Leu Asp Arg
210                 215                 220

Tyr Gly Leu Asp Leu Phe Leu Pro Ile Asp Lys Arg Asn Glu Val Leu
225                 230                 235                 240

Leu Lys Leu Ile Lys Asp Gly Tyr Leu Asp Arg Ile Met Val Ser Gln
                245                 250                 255

Asp Tyr Cys Cys Thr Ile Asp Met Gly Ile Ala Lys Pro Glu Tyr Lys
            260                 265                 270

Pro Lys Leu Ala Pro Lys Trp Ser Met Ser Leu Ile Phe Thr Asp Val
            275                 280                 285

Ile Pro Ser Ile Lys Arg Ala Gly Val Thr Asp Glu Gln Leu His Val
    290                 295                 300

Ile Phe Val Lys Asn Pro Ala Arg Leu Phe Ser
305                 310                 315

<210> SEQ ID NO 54
<211> LENGTH: 948
<212> TYPE: DNA
<213> ORGANISM: Sulfolobus acidocaldarius

<400> SEQUENCE: 54
atgaccaaaa ttccgctggt tggtaaaggt gaaattagtc cgggtgaaat gggttttacc      60
ctgattcatg aacatctgcg tgttttagc gaaccggtgc gttatcagtg gcctcatctg     120
tataatgaag atgaagaact gaaaaacgcc gtgaacgaag tgaaaaccat tatgagctat     180
ggcgttaaaa ccattgttga tccgaccgtt atgggtctgg tcgtgatat cgttttagt      240
gaaaaagtgg tgaaagaaac cggcattaat gttattgcag caaccggtct gtataccat     300
accgatctgc cgtttttttt caatggtcgt agcctggaag aaattgcaga actgctgatc     360
cacgatatca aaaaaggtat tcagggcacc aataatcgtg cgggttttat caaagttgca     420
gcagatgaac cgggtattac ccgtgatgtt gaacgtgcaa ttcgtgcagc agcaattgca     480
cagaaagaaa caaatgttcc gattatcacc catagcaatg cacataatgg caccggtctg     540
gaacagcagc gtattctgat ggaagaaggt gtggatccgg tcgtgttct gattggtcat     600
ctgggtgata ccgataacgt ggactacatc aaaaaaatcg cagataaagg tagctttgtt     660
ggcctggatc gctatggtct ggacctgttt ctgccgattg ataaacgtaa tgaagttctg     720
ctgaaactga tcaaagatgg ttatctggat cgtattatgg tgagccagga ttattgttgt     780
accattgatc tgggtattgc caaaccggaa tataaaccga aactggcacc gaaatggtca     840
atgagcctga ttttaccga tgtgattccg agcattaaac gtgccggtgt taccgatgaa     900
cagctgcatg tgattttgt taaaaatccg gcacgcctgt ttagctga                  948

<210> SEQ ID NO 55
<211> LENGTH: 315
<212> TYPE: PRT
<213> ORGANISM: Sulfolobus acidocaldarius
```

<400> SEQUENCE: 55

```
Met Thr Lys Ile Pro Leu Val Gly Lys Gly Glu Ile Ser Pro Gly Glu
1               5                   10                  15

Met Gly Phe Thr Leu Ile His Glu His Leu Arg Val Phe Ser Glu Pro
            20                  25                  30

Val Arg Tyr Gln Trp Pro His Leu Tyr Asn Glu Asp Glu Leu Lys
        35                  40                  45

Asn Ala Val Asn Glu Val Lys Thr Ile Met Ser Tyr Gly Val Lys Thr
    50                  55                  60

Ile Val Asp Pro Thr Val Met Gly Leu Gly Arg Asp Ile Arg Phe Ser
65                  70                  75                  80

Glu Lys Val Val Lys Glu Thr Gly Ile Asn Val Ile Ala Ala Thr Gly
                85                  90                  95

Leu Tyr Thr Tyr Thr Asp Leu Pro Phe Phe Asn Gly Arg Ser Leu
            100                 105                 110

Glu Glu Ile Ala Glu Leu Leu Ile His Asp Ile Lys Lys Gly Ile Gln
            115                 120                 125

Gly Thr Asn Asn Arg Ala Gly Phe Ile Lys Val Ala Ala Asp Glu Pro
    130                 135                 140

Gly Ile Thr Arg Asp Val Glu Arg Ala Ile Arg Ala Ala Ile Ala
145                 150                 155                 160

Gln Lys Glu Thr Asn Val Pro Ile Ile Thr His Ser Asn Ala His Asn
                165                 170                 175

Gly Thr Gly Leu Glu Gln Gln Arg Ile Leu Met Glu Glu Gly Val Asp
            180                 185                 190

Pro Gly Arg Val Leu Ile Gly His Leu Gly Asp Thr Asp Asn Val Asp
        195                 200                 205

Tyr Ile Lys Lys Ile Ala Asp Lys Gly Ser Phe Val Gly Leu Asp Arg
210                 215                 220

Tyr Gly Leu Asp Leu Phe Leu Pro Ile Asp Lys Arg Asn Glu Val Leu
225                 230                 235                 240

Leu Lys Leu Ile Lys Asp Gly Tyr Leu Asp Arg Ile Met Val Ser Gln
                245                 250                 255

Asp Tyr Cys Cys Thr Ile Asp Leu Gly Ile Ala Lys Pro Glu Tyr Lys
            260                 265                 270

Pro Lys Leu Ala Pro Lys Trp Ser Met Ser Leu Ile Phe Thr Asp Val
        275                 280                 285

Ile Pro Ser Ile Lys Arg Ala Gly Val Thr Asp Glu Gln Leu His Val
    290                 295                 300

Ile Phe Val Lys Asn Pro Ala Arg Leu Phe Ser
305                 310                 315
```

<210> SEQ ID NO 56
<211> LENGTH: 948
<212> TYPE: DNA
<213> ORGANISM: Sulfolobus acidocaldarius

<400> SEQUENCE: 56

```
atgaccaaaa ttccgctggt tggtaaaggt gaaattagtc cgggtgaaat gggttttacc    60
ctgattcatg aacatctgcg tgttttagc gaaccggtgc gttatcagtg gcctcatctg   120
tataatgaag atgaagaact gaaaaacgcc gtgaacgaag tgaaaaccat tatgagctat   180
ggcgttaaaa ccattgttga tccgaccgtt atgggtctgg gtcgtgatat tcgttttagt   240
```

```
gaaaaagtgg tgaaagaaac cggcattaat gttattgcag caaccggtct gtataccttat   300 accgatctgc cgttttttt caatggtcgt agcctggaag aaattgcaga actgctgatc   360
cacgatatca aaaaaggtat tcagggcacc aataatcgtg cgggttttat caaagttgca   420
gcagatgaac cgggtattac ccgtgatgtt aacgtgcaa ttcgtgcagc agcaattgca   480
cagaaagaaa caaatgttcc gattatcacc catagcaatg cacataatgg caccggtctg   540
gaacagcagc gtattctgat ggaagaaggt gtggatccgg tcgtgttct gattggtcat   600 ctgggtgata ccgataacgt ggactacatc aaaaaaatcg cagataaagg tagctttgtt   660
ggcctggatc gctatggtct ggacctgttt ctgccgattg ataaacgtaa tgaagttctg   720
ctgaaactga tcaaagatgg ttatctggat cgtattatgg tgagccagga ttattgttgt   780
accattgatg caggtattgc caaaccggaa tataaaccga actggcaccc gaaatggtca   840
atgagcctga ttttttaccga tgtgattccg agcattaaac gtgccggtgt taccgatgaa   900
cagctgcatg tgattttttgt taaaaatccg gcacgcctgt ttagctga           948
```

<210> SEQ ID NO 57
<211> LENGTH: 315
<212> TYPE: PRT
<213> ORGANISM: Sulfolobus acidocaldarius

<400> SEQUENCE: 57

```
Met Thr Lys Ile Pro Leu Val Gly Lys Gly Glu Ile Ser Pro Gly Glu
1               5                   10                  15

Met Gly Phe Thr Leu Ile His Glu His Leu Arg Val Phe Ser Glu Pro
                20                  25                  30

Val Arg Tyr Gln Trp Pro His Leu Tyr Asn Glu Asp Glu Glu Leu Lys
            35                  40                  45

Asn Ala Val Asn Glu Val Lys Thr Ile Met Ser Tyr Gly Val Lys Thr
        50                  55                  60

Ile Val Asp Pro Thr Val Met Gly Leu Gly Arg Asp Ile Arg Phe Ser
65                  70                  75                  80

Glu Lys Val Val Lys Glu Thr Gly Ile Asn Val Ile Ala Ala Thr Gly
                85                  90                  95

Leu Tyr Thr Tyr Thr Asp Leu Pro Phe Phe Asn Gly Arg Ser Leu
                100                 105                 110

Glu Glu Ile Ala Glu Leu Leu Ile His Asp Ile Lys Lys Gly Ile Gln
            115                 120                 125

Gly Thr Asn Asn Arg Ala Gly Phe Ile Lys Val Ala Ala Asp Glu Pro
        130                 135                 140

Gly Ile Thr Arg Asp Val Glu Arg Ala Ile Arg Ala Ala Ile Ala
145                 150                 155                 160

Gln Lys Glu Thr Asn Val Pro Ile Ile Thr His Ser Asn Ala His Asn
                165                 170                 175

Gly Thr Gly Leu Glu Gln Gln Arg Ile Leu Met Glu Glu Gly Val Asp
            180                 185                 190

Pro Gly Arg Val Leu Ile Gly His Leu Gly Asp Thr Asp Asn Val Asp
        195                 200                 205

Tyr Ile Lys Lys Ile Ala Asp Lys Gly Ser Phe Val Gly Leu Asp Arg
        210                 215                 220

Tyr Gly Leu Asp Leu Phe Leu Pro Ile Asp Lys Arg Asn Glu Val Leu
225                 230                 235                 240

Leu Lys Leu Ile Lys Asp Gly Tyr Leu Asp Arg Ile Met Val Ser Gln
                245                 250                 255
```

```
Asp Tyr Cys Cys Thr Ile Asp Ala Gly Ile Ala Lys Pro Glu Tyr Lys
            260                 265                 270

Pro Lys Leu Ala Pro Lys Trp Ser Met Ser Leu Ile Phe Thr Asp Val
            275                 280                 285

Ile Pro Ser Ile Lys Arg Ala Gly Val Thr Asp Glu Gln Leu His Val
            290                 295                 300

Ile Phe Val Lys Asn Pro Ala Arg Leu Phe Ser
305                 310                 315

<210> SEQ ID NO 58
<211> LENGTH: 948
<212> TYPE: DNA
<213> ORGANISM: Sulfolobus acidocaldarius

<400> SEQUENCE: 58
atgaccaaaa ttccgctggt tggtaaaggt gaaattagtc cgggtgaaat gggttttacc      60
ctgattcatg aacatctgcg tgtttttagc gaaccggtgc gttatcagtg gcctcatctg     120
tataatgaag atgaagaact gaaaaacgcc gtgaacgaag tgaaaaccat tatgagctat     180
ggcgttaaaa ccattgttga tccgaccgtt atgggtctgg tcgtgatat cgtttttagt      240 gaaaaagtgg tgaaagaaac cggcattaat gttattgcag caaccggtct gtataccta     300 accgatctgc cgtttttttt caatggtcgt agcctggaag aaattgcaga actgctgatc     360
cacgatatca aaaaaggtat tcagggcacc aataatcgtg cgggttttat caaagttgca     420
gcagatgaac cgggtattac ccgtgatgtt aacgtgcaa ttcgtgcagc agcaattgca      480
cagaaagaaa caaatgttcc gattatcacc atagcaatg cacataatgg caccggtctg      540
gaacagcagc gtattctgat ggaagaaggt gtggatccgg tcgtgttct gattggtcat      600 ctgggtgata ccgataacgt ggactacatc aaaaaaatcg cagataaagg tagctttgtt     660
ggcctggatc gctatggtct ggacctgttt ctgccgattg ataaacgtaa tgaagttctg     720
ctgaaactga tcaaagatgg ttatctggat cgtattatgt gagccagga ttattgttgt      780 accattgata ttggtattgc caaaccggaa tataaaccga aactggcacc gaaatggtca     840
atgagcctga tttttaccga tgtgattccg agcattaaac gtgccggtgt taccgatgaa     900
cagctgcatg tgatttttgt taaaaatccg gcacgcctgt ttagctga                  948

<210> SEQ ID NO 59
<211> LENGTH: 315
<212> TYPE: PRT
<213> ORGANISM: Sulfolobus acidocaldarius

<400> SEQUENCE: 59

Met Thr Lys Ile Pro Leu Val Gly Lys Gly Glu Ile Ser Pro Gly Glu
1               5                   10                  15

Met Gly Phe Thr Leu Ile His Glu His Leu Arg Val Phe Ser Glu Pro
            20                  25                  30

Val Arg Tyr Gln Trp Pro His Leu Tyr Asn Glu Asp Glu Glu Leu Lys
        35                  40                  45

Asn Ala Val Asn Glu Val Lys Thr Ile Met Ser Tyr Gly Val Lys Thr
    50                  55                  60

Ile Val Asp Pro Thr Val Met Gly Leu Gly Arg Asp Ile Arg Phe Ser
65                  70                  75                  80

Glu Lys Val Val Lys Glu Thr Gly Ile Asn Val Ile Ala Ala Thr Gly
                85                  90                  95
```

Leu Tyr Thr Tyr Thr Asp Leu Pro Phe Phe Asn Gly Arg Ser Leu
            100                 105                 110

Glu Glu Ile Ala Glu Leu Leu Ile His Asp Ile Lys Lys Gly Ile Gln
        115                 120                 125

Gly Thr Asn Asn Arg Ala Gly Phe Ile Lys Val Ala Ala Asp Glu Pro
    130                 135                 140

Gly Ile Thr Arg Asp Val Glu Arg Ala Ile Arg Ala Ala Ile Ala
145                 150                 155                 160

Gln Lys Glu Thr Asn Val Pro Ile Ile Thr His Ser Asn Ala His Asn
                165                 170                 175

Gly Thr Gly Leu Glu Gln Gln Arg Ile Leu Met Glu Glu Gly Val Asp
            180                 185                 190

Pro Gly Arg Val Leu Ile Gly His Leu Gly Asp Thr Asp Asn Val Asp
        195                 200                 205

Tyr Ile Lys Lys Ile Ala Asp Lys Gly Ser Phe Val Gly Leu Asp Arg
    210                 215                 220

Tyr Gly Leu Asp Leu Phe Leu Pro Ile Asp Lys Arg Asn Glu Val Leu
225                 230                 235                 240

Leu Lys Leu Ile Lys Asp Gly Tyr Leu Asp Arg Ile Met Val Ser Gln
                245                 250                 255

Asp Tyr Cys Cys Thr Ile Asp Ile Gly Ile Ala Lys Pro Glu Tyr Lys
            260                 265                 270

Pro Lys Leu Ala Pro Lys Trp Ser Met Ser Leu Ile Phe Thr Asp Val
        275                 280                 285

Ile Pro Ser Ile Lys Arg Ala Gly Val Thr Asp Glu Gln Leu His Val
    290                 295                 300

Ile Phe Val Lys Asn Pro Ala Arg Leu Phe Ser
305                 310                 315

<210> SEQ ID NO 60
<211> LENGTH: 948
<212> TYPE: DNA
<213> ORGANISM: Sulfolobus acidocaldarius

<400> SEQUENCE: 60
atgaccaaaa ttccgctggt tggtaaaggt gaaattagtc cgggtgaaat gggttttacc     60
ctgattcatg aacatctgcg tgttttagc gaaccggtgc gttatcagtg gcctcatctg    120
tataatgaag atgaagaact gaaaaacgcc gtgaacgaag tgaaaaccat tatgagctat    180
ggcgttaaaa ccattgttga tccgaccgtt atgggtctgg tcgtgatat cgttttagt     240 gaaaaagtgg tgaaagaaac cggcattaat gttattgcag caaccggtct gtatacctat    300
accgatctgc cgttttttt caatggtcgt agcctggaag aaattgcaga actgctgatc    360
cacgatatca aaaaaggtat tcagggcacc aataatcgtg cgggttttat caaagttgca    420
gcagatgaac cgggtattac cgtgatgtt aacgtgcaa ttcgtgcagc agcaattgca    480
cagaaagaaa caaatgttcc gattatcacc catagcaatg cacataatgg caccggtctg    540
gaacagcagc gtattctgat ggaagaaggt gtggatccgg tcgtgttct gattggtcat    600 ctgggtgata ccgataacgt ggactacatc aaaaaaatcg cagataaagg tagctttgtt    660
ggcctggatc gctatggtct ggacctgttt ctgccgattg ataaacgtaa tgaagttctg    720
ctgaaactga tcaaagatgg ttatctggat cgtattatgg tgagccagga ttattgttgt    780
accattgatt tggtattgc caaaccggaa tataaaccga actggcacc gaaatggtca    840 atgagcctga ttttaccga tgtgattccg agcattaaac gtgccggtgt taccgatgaa    900
cagctgcatg tgatttttgt taaaaatccg gcacgcctgt ttagctga                948

<210> SEQ ID NO 61
<211> LENGTH: 315
<212> TYPE: PRT
<213> ORGANISM: Sulfolobus acidocaldarius

<400> SEQUENCE: 61

Met Thr Lys Ile Pro Leu Val Gly Lys Gly Glu Ile Ser Pro Gly Glu
1               5                   10                  15

Met Gly Phe Thr Leu Ile His Glu His Leu Arg Val Phe Ser Glu Pro
            20                  25                  30

Val Arg Tyr Gln Trp Pro His Leu Tyr Asn Glu Asp Glu Glu Leu Lys
        35                  40                  45

Asn Ala Val Asn Glu Val Lys Thr Ile Met Ser Tyr Gly Val Lys Thr
    50                  55                  60

Ile Val Asp Pro Thr Val Met Gly Leu Gly Arg Asp Ile Arg Phe Ser
65                  70                  75                  80

Glu Lys Val Val Lys Glu Thr Gly Ile Asn Val Ile Ala Ala Thr Gly
                85                  90                  95

Leu Tyr Thr Tyr Thr Asp Leu Pro Phe Phe Asn Gly Arg Ser Leu
            100                 105                 110

Glu Glu Ile Ala Glu Leu Leu Ile His Asp Ile Lys Lys Gly Ile Gln
        115                 120                 125

Gly Thr Asn Asn Arg Ala Gly Phe Ile Lys Val Ala Ala Asp Glu Pro
    130                 135                 140

Gly Ile Thr Arg Asp Val Glu Arg Ala Ile Arg Ala Ala Ile Ala
145                 150                 155                 160

Gln Lys Glu Thr Asn Val Pro Ile Ile Thr His Ser Asn Ala His Asn
                165                 170                 175

Gly Thr Gly Leu Glu Gln Gln Arg Ile Leu Met Glu Glu Gly Val Asp
            180                 185                 190

Pro Gly Arg Val Leu Ile Gly His Leu Gly Asp Thr Asp Asn Val Asp
        195                 200                 205

Tyr Ile Lys Lys Ile Ala Asp Lys Gly Ser Phe Val Gly Leu Asp Arg
    210                 215                 220

Tyr Gly Leu Asp Leu Phe Leu Pro Ile Asp Lys Arg Asn Glu Val Leu
225                 230                 235                 240

Leu Lys Leu Ile Lys Asp Gly Tyr Leu Asp Arg Ile Met Val Ser Gln
                245                 250                 255

Asp Tyr Cys Cys Thr Ile Asp Val Gly Ile Ala Lys Pro Glu Tyr Lys
            260                 265                 270

Pro Lys Leu Ala Pro Lys Trp Ser Met Ser Leu Ile Phe Thr Asp Val
        275                 280                 285

Ile Pro Ser Ile Lys Arg Ala Gly Val Thr Asp Glu Gln Leu His Val
    290                 295                 300

Ile Phe Val Lys Asn Pro Ala Arg Leu Phe Ser
305                 310                 315

<210> SEQ ID NO 62
<211> LENGTH: 948
<212> TYPE: DNA
<213> ORGANISM: Sulfolobus acidocaldarius

<400> SEQUENCE: 62

```
atgaccaaaa ttccgctggt tggtaaaggt gaaattagtc cgggtgaaat gggttttacc       60
ctgattcatg aacatctgcg tgtttttagc gaaccggtgc gttatcagtg gcctcatctg      120
tataatgaag atgaagaact gaaaaacgcc gtgaacgaag tgaaaaccat tatgagctat      180
ggcgttaaaa ccattgttga tccgaccgtt atgggtctgg gtcgtgatat tcgttttagt      240
gaaaaagtgg tgaaagaaac cggcattaat gttattgcag caaccggtct gtataccttat     300
accgatctgc cgtttttttt caatggtcgt agcctggaag aaattgcaga actgctgatc      360
cacgatatca aaaaaggtat tcagggcacc aataatcgtg cgggttttat caaagttgca      420
gcagatgaac cgggtattac ccgtgatgtt gaacgtgcaa ttcgtgcagc agcaattgca      480
cagaaagaaa caaatgttcc gattatcacc catagcaatg cacataatgg caccggtctg      540
gaacagcagc gtattctgat ggaagaaggt gtggatccgg tcgtgttct gattggtcat       600
ctgggtgata ccgataacgt ggactacatc aaaaaaatcg cagataaagg tagctttgtt      660
ggcctggatc gctatggtct ggacctgttt ctgccgattg ataaacgtaa tgaagttctg      720
ctgaaactga tcaaagatgg ttatctggat cgtattatgt gagccagga ttattgttgt       780
accattgata ccggtattgc caaaccggaa tataaaccga actggcacc gaaatggtca       840
atgagcctga tttttaccga tgtgattccg agcattaaac gtgccggtgt taccgatgaa      900
cagctgcatg tgattttgt taaaaatccg gcacgcctgt ttagctga                    948
```

<210> SEQ ID NO 63
<211> LENGTH: 315
<212> TYPE: PRT
<213> ORGANISM: Sulfolobus acidocaldarius

<400> SEQUENCE: 63

Met Thr Lys Ile Pro Leu Val Gly Lys Gly Glu Ile Ser Pro Gly Glu
1               5                   10                  15

Met Gly Phe Thr Leu Ile His Glu His Leu Arg Val Phe Ser Glu Pro
                20                  25                  30

Val Arg Tyr Gln Trp Pro His Leu Tyr Asn Glu Asp Glu Glu Leu Lys
            35                  40                  45

Asn Ala Val Asn Glu Val Lys Thr Ile Met Ser Tyr Gly Val Lys Thr
        50                  55                  60

Ile Val Asp Pro Thr Val Met Gly Leu Gly Arg Asp Ile Arg Phe Ser
65                  70                  75                  80

Glu Lys Val Val Lys Glu Thr Gly Ile Asn Val Ile Ala Ala Thr Gly
                85                  90                  95

Leu Tyr Thr Tyr Thr Asp Leu Pro Phe Phe Asn Gly Arg Ser Leu
            100                 105                 110

Glu Glu Ile Ala Glu Leu Leu Ile His Asp Ile Lys Lys Gly Ile Gln
        115                 120                 125

Gly Thr Asn Asn Arg Ala Gly Phe Ile Lys Val Ala Ala Asp Glu Pro
    130                 135                 140

Gly Ile Thr Arg Asp Val Glu Arg Ala Ile Arg Ala Ala Ala Ile Ala
145                 150                 155                 160

Gln Lys Glu Thr Asn Val Pro Ile Ile Thr His Ser Asn Ala His Asn
                165                 170                 175

Gly Thr Gly Leu Glu Gln Gln Arg Ile Leu Met Glu Glu Gly Val Asp
            180                 185                 190

Pro Gly Arg Val Leu Ile Gly His Leu Gly Asp Thr Asp Asn Val Asp
        195                 200                 205

```
Tyr Ile Lys Lys Ile Ala Asp Lys Gly Ser Phe Val Gly Leu Asp Arg
210                 215                 220

Tyr Gly Leu Asp Leu Phe Leu Pro Ile Asp Lys Arg Asn Glu Val Leu
225                 230                 235                 240

Leu Lys Leu Ile Lys Asp Gly Tyr Leu Asp Arg Ile Met Val Ser Gln
                245                 250                 255

Asp Tyr Cys Cys Thr Ile Asp Thr Gly Ile Ala Lys Pro Glu Tyr Lys
                260                 265                 270

Pro Lys Leu Ala Pro Lys Trp Ser Met Ser Leu Ile Phe Thr Asp Val
                275                 280                 285

Ile Pro Ser Ile Lys Arg Ala Gly Val Thr Asp Glu Gln Leu His Val
290                 295                 300

Ile Phe Val Lys Asn Pro Ala Arg Leu Phe Ser
305                 310                 315

<210> SEQ ID NO 64
<211> LENGTH: 951
<212> TYPE: DNA
<213> ORGANISM: Sulfolobus acidocaldarius

<400> SEQUENCE: 64
atgaccaaaa ttccgctggt tggtaaaggt gaaattagtc cgggtgaaat gggttttacc      60
ctgattcatg aacatctgcg tgttttagc gaaccggtgc gttatcagtg gcctcatctg      120
tataatgaag atgaagaact gaaaaacgcc gtgaacgaag tgaaaaccat tatgagctat     180
ggcgttaaaa ccattgttga tccgaccgtt atgggtctgg tcgtgatat cgttttagt       240 gaaaaagtgg tgaaagaaac cggcattaat gttattgcag caaccggtct gtataccat      300 accgatctgc cgtttttttt caatggtcgt agcctggaag aaattgcaga actgctgatc     360
cacgatatca aaaaaggtat tcagggcacc aataatcgtg cgggttttat caaagttgca    420
gcagatgaac cgggtattac ccgtgatgtt aacgtgcaa ttcgtgcagc agcaattgca     480
cagaaagaaa caaatgttcc gattatcacc catagcaatg cacataatgg caccggtctg    540
gaacagcagc gtattctgat ggaagaaggt gtggatccgg tcgtgttct gattggtcat     600 ctgggtgata ccgataacgt ggactacatc aaaaaaatcg cagataaagg tagctttgtt    660
ggcctggatc gctatggtct ggaccctgttt ctgccgattg ataaacgtaa tgaagttctg   720
ctgaaactga tcaaagatgg ttatctggat cgtattatgg tgagccagga ttatctgtgt   780
acctttgatg caggtattgc caaaccggaa tataaaccga actggcacc gaaatggtca    840 atgagcctga ttttaccga tgtgattccg agcattaaac gtgccggtgt taccgatgaa    900
cagctgcatg tgattttttgt taaaaatccg gcacgcctgt ttagctgata a            951

<210> SEQ ID NO 65
<211> LENGTH: 315
<212> TYPE: PRT
<213> ORGANISM: Sulfolobus acidocaldarius

<400> SEQUENCE: 65

Met Thr Lys Ile Pro Leu Val Gly Lys Gly Glu Ile Ser Pro Gly Glu
1               5                   10                  15

Met Gly Phe Thr Leu Ile His Glu His Leu Arg Val Phe Ser Glu Pro
                20                  25                  30

Val Arg Tyr Gln Trp Pro His Leu Tyr Asn Glu Asp Glu Glu Leu Lys
            35                  40                  45

Asn Ala Val Asn Glu Val Lys Thr Ile Met Ser Tyr Gly Val Lys Thr
```

```
            50                  55                  60
Ile Val Asp Pro Thr Val Met Gly Leu Gly Arg Asp Ile Arg Phe Ser
65                  70                  75                  80

Glu Lys Val Val Lys Glu Thr Gly Ile Asn Val Ile Ala Ala Thr Gly
                85                  90                  95

Leu Tyr Thr Tyr Thr Asp Leu Pro Phe Phe Asn Gly Arg Ser Leu
            100                 105                 110

Glu Glu Ile Ala Glu Leu Leu Ile His Asp Ile Lys Lys Gly Ile Gln
            115                 120                 125

Gly Thr Asn Asn Arg Ala Gly Phe Ile Lys Val Ala Ala Asp Glu Pro
        130                 135                 140

Gly Ile Thr Arg Asp Val Glu Arg Ala Ile Arg Ala Ala Ile Ala
145                 150                 155                 160

Gln Lys Glu Thr Asn Val Pro Ile Ile Thr His Ser Asn Ala His Asn
                165                 170                 175

Gly Thr Gly Leu Glu Gln Gln Arg Ile Leu Met Glu Glu Gly Val Asp
            180                 185                 190

Pro Gly Arg Val Leu Ile Gly His Leu Gly Asp Thr Asp Asn Val Asp
        195                 200                 205

Tyr Ile Lys Lys Ile Ala Asp Lys Gly Ser Phe Val Gly Leu Asp Arg
    210                 215                 220

Tyr Gly Leu Asp Leu Phe Leu Pro Ile Asp Lys Arg Asn Glu Val Leu
225                 230                 235                 240

Leu Lys Leu Ile Lys Asp Gly Tyr Leu Asp Arg Ile Met Val Ser Gln
                245                 250                 255

Asp Tyr Leu Cys Thr Phe Asp Ala Gly Ile Ala Lys Pro Glu Tyr Lys
            260                 265                 270

Pro Lys Leu Ala Pro Lys Trp Ser Met Ser Leu Ile Phe Thr Asp Val
        275                 280                 285

Ile Pro Ser Ile Lys Arg Ala Gly Val Thr Asp Glu Gln Leu His Val
    290                 295                 300

Ile Phe Val Lys Asn Pro Ala Arg Leu Phe Ser
305                 310                 315

<210> SEQ ID NO 66
<211> LENGTH: 951
<212> TYPE: DNA
<213> ORGANISM: Sulfolobus acidocaldarius

<400> SEQUENCE: 66
atgaccaaaa ttccgctggt tgtaaaggt gaaattagtc cgggtgaaat gggttttacc       60
ctgattcatg aacatctgcg tgcatttagc gaaccggtgc gttatcagtg gcctcatctg      120
tataatgaag atgaagaact gaaaaacgcc gtgaacgaag tgaaaaccat tatgagctat      180
ggcgttaaaa ccattgttga tccgaccgtt atgggtctgg tcgtgatat cgttttagt       240 gaaaaagtgg tgaaagaaac cggcattaat gttattgcag caaccggtct gtggacctat      300
accgatctgc cgtttttttt caatggtcgt agcctggaag aaattgcaga actgctgatc      360
cacgatatca aaaaggtat tcagggcacc aataatcgtg cggttttat caaagttgca      420 gcagatgaac cgggtattac ccgtgatgtt gaacgtgcaa ttcgtgcagc agcaattgca      480
cagaaagaaa caaatgttcc gattataacc catagcaatg cacataatgg caccggtctg      540
gaacagcagc gtattctgat ggaagaaggt gtggatccgg tcgtgttct gattggtcat      600 ctgggtgata ccgataacgt ggactacatc aaaaaaaatcg cagataaagg tagctttgtt      660
```

```
ggcctggatc gctatggtct ggacatgttt ctgccgattg ataaacgtaa tgaagttctg    720
ctgaaactga tcaaagatgg ttatctggat cgtattatgg tgagccagga ttattgttgt    780
accattgata tgggtattgc caaaccggaa tataaaccga aactggcacc gaaatggtca    840
atgagcctga tttttaccga tgtgattccg agcattaaac gtgccggtgt taccgatgaa    900
cagctgcatg tgattttttgt taaaaatccg gcacgcctgt ttagctgata a            951
```

<210> SEQ ID NO 67
<211> LENGTH: 315
<212> TYPE: PRT
<213> ORGANISM: Sulfolobus acidocaldarius

<400> SEQUENCE: 67

Met Thr Lys Ile Pro Leu Val Gly Lys Gly Glu Ile Ser Pro Gly Glu
1               5                   10                  15

Met Gly Phe Thr Leu Ile His Glu His Leu Arg Ala Phe Ser Glu Pro
            20                  25                  30

Val Arg Tyr Gln Trp Pro His Leu Tyr Asn Glu Asp Glu Glu Leu Lys
        35                  40                  45

Asn Ala Val Asn Glu Val Lys Thr Ile Met Ser Tyr Gly Val Lys Thr
    50                  55                  60

Ile Val Asp Pro Thr Val Met Gly Leu Gly Arg Asp Ile Arg Phe Ser
65                  70                  75                  80

Glu Lys Val Val Lys Glu Thr Gly Ile Asn Val Ile Ala Ala Thr Gly
                85                  90                  95

Leu Trp Thr Tyr Thr Asp Leu Pro Phe Phe Asn Gly Arg Ser Leu
            100                 105                 110

Glu Glu Ile Ala Glu Leu Leu Ile His Asp Ile Lys Lys Gly Ile Gln
        115                 120                 125

Gly Thr Asn Asn Arg Ala Gly Phe Ile Lys Val Ala Ala Asp Glu Pro
    130                 135                 140

Gly Ile Thr Arg Asp Val Glu Arg Ala Ile Arg Ala Ala Ile Ala
145                 150                 155                 160

Gln Lys Glu Thr Asn Val Pro Ile Ile Thr His Ser Asn Ala His Asn
                165                 170                 175

Gly Thr Gly Leu Glu Gln Gln Arg Ile Leu Met Glu Glu Gly Val Asp
            180                 185                 190

Pro Gly Arg Val Leu Ile Gly His Leu Gly Asp Thr Asp Asn Val Asp
        195                 200                 205

Tyr Ile Lys Lys Ile Ala Asp Lys Gly Ser Phe Val Gly Leu Asp Arg
    210                 215                 220

Tyr Gly Leu Asp Met Phe Leu Pro Ile Asp Lys Arg Asn Glu Val Leu
225                 230                 235                 240

Leu Lys Leu Ile Lys Asp Gly Tyr Leu Asp Arg Ile Met Val Ser Gln
                245                 250                 255

Asp Tyr Cys Cys Thr Ile Asp Met Gly Ile Ala Lys Pro Glu Tyr Lys
            260                 265                 270

Pro Lys Leu Ala Pro Lys Trp Ser Met Ser Leu Ile Phe Thr Asp Val
        275                 280                 285

Ile Pro Ser Ile Lys Arg Ala Gly Val Thr Asp Glu Gln Leu His Val
    290                 295                 300

Ile Phe Val Lys Asn Pro Ala Arg Leu Phe Ser
305                 310                 315

<210> SEQ ID NO 68
<211> LENGTH: 951
<212> TYPE: DNA
<213> ORGANISM: Sulfolobus acidocaldarius

<400> SEQUENCE: 68

```
atgaccaaaa ttccgctggt tggtaaaggt gaaattagtc cgggtgaaat gggttttacc      60
ctgattcatg aacatctgcg tgcatttagc gaaccggtgc gttatcagtg gcctcatctg     120
tataatgaag atgaagaact gaaaaacgcc gtgaacgaag tgaaaaccat tatgagctat     180
ggcgttaaaa ccattgttga tccgaccgtt atgggtctgg gtcgtgatat tcgttttagt     240
gaaaaagtgg tgaaagaaac cggcattaat gttattgcag caaccggtct gtggacctat     300
accgatctgc cgtttttttt caatggtcgt agcctggaag aaattgcaga actgctgatc     360
cacgatatca aaaaaggtat tcagggcacc aataatcgtg cgggttttat caaagttgca     420
gcagatgaac cgggtattac ccgtgatgtt aacgtgcaa ttcgtgcagc agcaattgca     480
cagaaagaaa caaatgttcc gattatcacc catagcaatg cacataatgg caccggtctg     540
gaacagcagc gtattctgat ggaagaaggt gtggatccgg tcgtgttct gattggtcat     600
ctgggtgata ccgataacgt ggactacatc aaaaaaatcg cagataaagg tagctttgtt     660
ggcctggatc gctatggtct ggacctgttt ctgccgattg ataaacgtaa tgaagttctg     720
ctgaaactga tcaagatgg ttatctggat cgtattatgg tgagccagga ttattgttgt     780
accattgatc tgggtattgc caaaccggaa tataaaccga actggcacc gaaatggtca     840
acgagcctga tttttaccga tgtgattccg agcattaaac gtgccggtgt taccgatgaa     900
cagctgcatg tgattttgt taaaaatccg gcacgcctgt ttagctgata a              951
```

<210> SEQ ID NO 69
<211> LENGTH: 315
<212> TYPE: PRT
<213> ORGANISM: Sulfolobus acidocaldarius

<400> SEQUENCE: 69

```
Met Thr Lys Ile Pro Leu Val Gly Lys Gly Glu Ile Ser Pro Gly Glu
1               5                   10                  15

Met Gly Phe Thr Leu Ile His Glu His Leu Arg Ala Phe Ser Glu Pro
            20                  25                  30

Val Arg Tyr Gln Trp Pro His Leu Tyr Asn Glu Asp Glu Glu Leu Lys
        35                  40                  45

Asn Ala Val Asn Glu Val Lys Thr Ile Met Ser Tyr Gly Val Lys Thr
    50                  55                  60

Ile Val Asp Pro Thr Val Met Gly Leu Gly Arg Asp Ile Arg Phe Ser
65                  70                  75                  80

Glu Lys Val Val Lys Glu Thr Gly Ile Asn Val Ile Ala Ala Thr Gly
                85                  90                  95

Leu Trp Thr Tyr Thr Asp Leu Pro Phe Phe Phe Asn Gly Arg Ser Leu
            100                 105                 110

Glu Glu Ile Ala Glu Leu Leu Ile His Asp Ile Lys Lys Gly Ile Gln
        115                 120                 125

Gly Thr Asn Asn Arg Ala Gly Phe Ile Lys Val Ala Ala Asp Glu Pro
    130                 135                 140

Gly Ile Thr Arg Asp Val Glu Arg Ala Ile Arg Ala Ala Ala Ile Ala
145                 150                 155                 160

Gln Lys Glu Thr Asn Val Pro Ile Ile Thr His Ser Asn Ala His Asn
```

```
              165                 170                 175
Gly Thr Gly Leu Glu Gln Gln Arg Ile Leu Met Glu Glu Gly Val Asp
            180                 185                 190

Pro Gly Arg Val Leu Ile Gly His Leu Gly Asp Thr Asp Asn Val Asp
            195                 200                 205

Tyr Ile Lys Lys Ile Ala Asp Lys Gly Ser Phe Val Gly Leu Asp Arg
        210                 215                 220

Tyr Gly Leu Asp Leu Phe Leu Pro Ile Asp Lys Arg Asn Glu Val Leu
225                 230                 235                 240

Leu Lys Leu Ile Lys Asp Gly Tyr Leu Asp Arg Ile Met Val Ser Gln
                245                 250                 255

Asp Tyr Cys Cys Thr Ile Asp Leu Gly Ile Ala Lys Pro Glu Tyr Lys
            260                 265                 270

Pro Lys Leu Ala Pro Lys Trp Ser Thr Ser Leu Ile Phe Thr Asp Val
            275                 280                 285

Ile Pro Ser Ile Lys Arg Ala Gly Val Thr Asp Glu Gln Leu His Val
        290                 295                 300

Ile Phe Val Lys Asn Pro Ala Arg Leu Phe Ser
305                 310                 315

<210> SEQ ID NO 70
<211> LENGTH: 951
<212> TYPE: DNA
<213> ORGANISM: Sulfolobus acidocaldarius

<400> SEQUENCE: 70
atgaccaaaa ttccgctggt tggtaaaggt gaaattagtc cgggtgaaat gggttttacc      60
ctgattcatg aacatctgcg tgtttttagc gaaccggtgc gttatcagtg gcctcatctg     120
tataatgaag atgaagaact gaaaaacgcc gtgaacgaag tgaaaaccat tatgagctat     180
ggcgttaaaa ccattgttga tccgaccgtt atgggtctgg tcgtgatat tcgttttagt     240 gaaaaagtgg tgaaagaaac cggcattaat gttattgcag caaccggtct gtataccatat    300 accgatctgc gtttttttt caatggtcgt agcctggaag aaattgcaga actgctgatc     360
cacgatatca aaaaaggtat tcagggcacc aataatcgtg cggtttttat caaagttgca     420
gcagatgaac cggtattac cgtgatgtt aacgtgcaa ttcgtgcagc agcaattgca       480
cagaaagaaa caaatgttcc gattatcacc atagcaatg cacataatgg caccggtctg     540
gaacagcagc gtattctgat ggaagaaggt gtggatccgg tcgtgttct gattggtcat     600 ctgggtgata ccgataacgt ggactacatc aaaaaaatcg cagataaagg tagctttgtt     660
ggcctggatc gctatggtct ggacctgttt ctgccgattg ataaacgtaa tgaagttctg     720
ctgaaactga tcaaagatgg ttatctggat cgtattatgg tgagccagga ttatgcttgt     780
accattgata tgggtattgc caaaccggaa tataaaccga actggcacc gaaatggtca     840 acgagcctga tttttaccga tgtgattccg agcattaaac gtgccggtgt taccgatgaa     900
cagctgcatg tgatttttgt taaaaatccg gcacgcctgt ttagctgata a              951

<210> SEQ ID NO 71
<211> LENGTH: 315
<212> TYPE: PRT
<213> ORGANISM: Sulfolobus acidocaldarius

<400> SEQUENCE: 71

Met Thr Lys Ile Pro Leu Val Gly Lys Gly Glu Ile Ser Pro Gly Glu
1               5                  10                  15
```

Met Gly Phe Thr Leu Ile His Glu His Leu Arg Val Phe Ser Glu Pro
            20                  25                  30

Val Arg Tyr Gln Trp Pro His Leu Tyr Asn Glu Asp Glu Leu Lys
35                  40                  45

Asn Ala Val Asn Glu Val Lys Thr Ile Met Ser Tyr Gly Val Lys Thr
50                  55                  60

Ile Val Asp Pro Thr Val Met Gly Leu Gly Arg Asp Ile Arg Phe Ser
65                  70                  75                  80

Glu Lys Val Val Lys Glu Thr Gly Ile Asn Val Ile Ala Ala Thr Gly
                85                  90                  95

Leu Tyr Thr Tyr Thr Asp Leu Pro Phe Phe Asn Gly Arg Ser Leu
            100                 105                 110

Glu Glu Ile Ala Glu Leu Leu Ile His Asp Ile Lys Lys Gly Ile Gln
            115                 120                 125

Gly Thr Asn Asn Arg Ala Gly Phe Ile Lys Val Ala Ala Asp Glu Pro
130                 135                 140

Gly Ile Thr Arg Asp Val Glu Arg Ala Ile Arg Ala Ala Ile Ala
145                 150                 155                 160

Gln Lys Glu Thr Asn Val Pro Ile Ile Thr His Ser Asn Ala His Asn
            165                 170                 175

Gly Thr Gly Leu Glu Gln Gln Arg Ile Leu Met Glu Glu Gly Val Asp
            180                 185                 190

Pro Gly Arg Val Leu Ile Gly His Leu Gly Asp Thr Asp Asn Val Asp
            195                 200                 205

Tyr Ile Lys Lys Ile Ala Asp Lys Gly Ser Phe Val Gly Leu Asp Arg
            210                 215                 220

Tyr Gly Leu Asp Leu Phe Leu Pro Ile Asp Lys Arg Asn Glu Val Leu
225                 230                 235                 240

Leu Lys Leu Ile Lys Asp Gly Tyr Leu Asp Arg Ile Met Val Ser Gln
            245                 250                 255

Asp Tyr Ala Cys Thr Ile Asp Met Gly Ile Ala Lys Pro Glu Tyr Lys
            260                 265                 270

Pro Lys Leu Ala Pro Lys Trp Ser Thr Ser Leu Ile Phe Thr Asp Val
            275                 280                 285

Ile Pro Ser Ile Lys Arg Ala Gly Val Thr Asp Glu Gln Leu His Val
290                 295                 300

Ile Phe Val Lys Asn Pro Ala Arg Leu Phe Ser
305                 310                 315

<210> SEQ ID NO 72
<211> LENGTH: 951
<212> TYPE: DNA
<213> ORGANISM: Sulfolobus acidocaldarius

<400> SEQUENCE: 72
atgaccaaaa ttccgctggt tggtaaaggt gaaattagtc cgggtgaaat gggttttacc     60
ctgattcatg aacatctgcg tgcatttagc gaaccggtgc gttatcagtg gcctcatctg    120
tataatgaag atgaagaact gaaaaacgcc gtgaacgaag tgaaaaccat tatgagctat    180
ggcgttaaaa ccattgttga tccgaccgtt atgggtctgg gtcgtgatac tcgttttagt    240
gaaaaagtgg tgaaagaaac cggcattaat gttattgcag caaccggtct gtggaccttt    300
accgatctgc cgttttttt caatggtcgt agcctggaag aaattgcaga actgctgatc    360
cacgatatca aaaaaggtat tcagggcacc ccgaatcgtg cgggttttat caaagttgca    420

```
gcagatgaac cgggtattac ccgtgatgtt gaacgtgcaa ttcgtgcagc agcaattgca      480
cagaaagaaa caaatgttcc gattatcacc catagcaatg cacataatgg caccggtctg      540
gaacagcagc gtattctgat ggaagaaggt gtggatccgg tcgtgttct gattggtcat       600 ctgggtgata ccgataacgt ggactacatc aaaaaaatcg cagataaagg tagctttgtt      660
ggcctggatc gctatggtgt ggacctgttt ctgccgattg ataaacgtaa tgaagttctg      720
ctgaaactga tcaaagatgg ttatctggat cgtattatgg tgagccagga ttattgttgt      780
accattgatt ggggtattgc caaaccggaa tataaaccga aactggcacc gaaatggtca      840
atgagcctga tttttaccga tgtgattccg agcattaaac gtgccggtgt taccgatgaa      900
cagctgcatg tgattttgt taaaaatccg gcacgcctgt ttagctgata a                951
```

<210> SEQ ID NO 73
<211> LENGTH: 315
<212> TYPE: PRT
<213> ORGANISM: Sulfolobus acidocaldarius

<400> SEQUENCE: 73

```
Met Thr Lys Ile Pro Leu Val Gly Lys Gly Glu Ile Ser Pro Gly Glu
1               5                   10                  15

Met Gly Phe Thr Leu Ile His Glu His Leu Arg Ala Phe Ser Glu Pro
            20                  25                  30

Val Arg Tyr Gln Trp Pro His Leu Tyr Asn Glu Asp Glu Glu Leu Lys
        35                  40                  45

Asn Ala Val Asn Glu Val Lys Thr Ile Met Ser Tyr Gly Val Lys Thr
    50                  55                  60

Ile Val Asp Pro Thr Val Met Gly Leu Gly Arg Asp Thr Arg Phe Ser
65                  70                  75                  80

Glu Lys Val Val Lys Glu Thr Gly Ile Asn Val Ile Ala Ala Thr Gly
                85                  90                  95

Leu Trp Thr Phe Thr Asp Leu Pro Phe Phe Asn Gly Arg Ser Leu
            100                 105                 110

Glu Glu Ile Ala Glu Leu Leu Ile His Asp Ile Lys Lys Gly Ile Gln
        115                 120                 125

Gly Thr Pro Asn Arg Ala Gly Phe Ile Lys Val Ala Ala Asp Glu Pro
    130                 135                 140

Gly Ile Thr Arg Asp Val Glu Arg Ala Ile Arg Ala Ala Ile Ala
145                 150                 155                 160

Gln Lys Glu Thr Asn Val Pro Ile Ile Thr His Ser Asn Ala His Asn
                165                 170                 175

Gly Thr Gly Leu Glu Gln Gln Arg Ile Leu Met Glu Glu Gly Val Asp
            180                 185                 190

Pro Gly Arg Val Leu Ile Gly His Leu Gly Asp Thr Asp Asn Val Asp
        195                 200                 205

Tyr Ile Lys Lys Ile Ala Asp Lys Gly Ser Phe Val Gly Leu Asp Arg
    210                 215                 220

Tyr Gly Val Asp Leu Phe Leu Pro Ile Asp Lys Arg Asn Glu Val Leu
225                 230                 235                 240

Leu Lys Leu Ile Lys Asp Gly Tyr Leu Asp Arg Ile Met Val Ser Gln
                245                 250                 255

Asp Tyr Cys Cys Thr Ile Asp Trp Gly Ile Ala Lys Pro Glu Tyr Lys
            260                 265                 270

Pro Lys Leu Ala Pro Lys Trp Ser Met Ser Leu Ile Phe Thr Asp Val
```

Ile Pro Ser Ile Lys Arg Ala Gly Val Thr Asp Glu Gln Leu His Val
            275                 280                 285
Ile Phe Val Lys Asn Pro Ala Arg Leu Phe Ser
    290                 295                 300
305             310             315

<210> SEQ ID NO 74
<211> LENGTH: 951
<212> TYPE: DNA
<213> ORGANISM: Sulfolobus acidocaldarius

<400> SEQUENCE: 74

```
atgaccaaaa ttccgctggt tggtaaaggt gaaattagtc cgggtgaaat gggttttacc      60
ctgattcatg aacatctgcg tgtttttagc gaaccggtgc gttatcagtg gccccatctg     120
tataatgaag atgaagaact gaaaaacgcc gtgaacgaag tgaaaaccat tatgagctat     180
ggcgttaaaa ccattgttga tccgaccgtt atgggtattg gtcgtgatat tcgttttagt     240
gaaaaagtgg tgaaagaaac cggcattaat gttattgcag caaccggtct gtatacctta     300
accgatctgc cgttttttttt caatggtcgt agcctggaag aaattgcaga actgctgatc     360
cacgatttaa aaaaaggtat tcagggcacc aataatcgtg cgggttttat caaagttgca     420
gcagatgaac cgggtattac ccgtgatgtt gaacgtgcca ttcgtgcagc agcaattgca     480
cagaaagaaa caaatgttcc gattatcacc catagcaatg cacataatgg caccggtctg     540
gaacagcagc gtattctgat ggaagaaggt gtggatccgg tcgtgttct gattggtcat     600
ctgggtgata ccgataacgt ggactacatc aaaaaaatcg cagataaagg tagctttgtt     660
ggcctggatc gctatggtct ggacatgtct ctgccgattg ataaacgtaa tgaagttctg     720
ctgaaactga tcaaagatgg ttatctggat cgtattatgg tgagccagga ttattgttgt     780
accattgatc tgggtattgc caaaccggaa tataaaccga actggcaccc gaaatggtca     840
atgagcctga ttttttaccga tgtgattccg agcattaaac gtgccggtgt taccgatgaa     900
cagctgcatg tgattttgt taaaaatccg gcacgcctgt ttagctgata a              951
```

<210> SEQ ID NO 75
<211> LENGTH: 315
<212> TYPE: PRT
<213> ORGANISM: Sulfolobus acidocaldarius

<400> SEQUENCE: 75

Met Thr Lys Ile Pro Leu Val Gly Lys Gly Glu Ile Ser Pro Gly Glu
1               5                   10                  15
Met Gly Phe Thr Leu Ile His Glu His Leu Arg Val Phe Ser Glu Pro
            20                  25                  30
Val Arg Tyr Gln Trp Pro His Leu Tyr Asn Glu Asp Glu Glu Leu Lys
        35                  40                  45
Asn Ala Val Asn Glu Val Lys Thr Ile Met Ser Tyr Gly Val Lys Thr
    50                  55                  60
Ile Val Asp Pro Thr Val Met Gly Ile Gly Arg Asp Ile Arg Phe Ser
65                  70                  75                  80
Glu Lys Val Val Lys Glu Thr Gly Ile Asn Val Ile Ala Ala Thr Gly
                85                  90                  95
Leu Tyr Thr Phe Thr Asp Leu Pro Phe Phe Phe Asn Gly Arg Ser Leu
            100                 105                 110
Glu Glu Ile Ala Glu Leu Leu Ile His Asp Leu Lys Lys Gly Ile Gln
        115                 120                 125

Gly Thr Asn Asn Arg Ala Gly Phe Ile Lys Val Ala Ala Asp Glu Pro
      130                 135                 140

Gly Ile Thr Arg Asp Val Glu Arg Ala Ile Arg Ala Ala Ile Ala
145                 150                 155                 160

Gln Lys Glu Thr Asn Val Pro Ile Ile Thr His Ser Asn Ala His Asn
                165                 170                 175

Gly Thr Gly Leu Glu Gln Gln Arg Ile Leu Met Glu Glu Gly Val Asp
            180                 185                 190

Pro Gly Arg Val Leu Ile Gly His Leu Gly Asp Thr Asp Asn Val Asp
        195                 200                 205

Tyr Ile Lys Lys Ile Ala Asp Lys Gly Ser Phe Val Gly Leu Asp Arg
    210                 215                 220

Tyr Gly Leu Asp Met Ser Leu Pro Ile Asp Lys Arg Asn Glu Val Leu
225                 230                 235                 240

Leu Lys Leu Ile Lys Asp Gly Tyr Leu Asp Arg Ile Met Val Ser Gln
                245                 250                 255

Asp Tyr Cys Cys Thr Ile Asp Leu Gly Ile Ala Lys Pro Glu Tyr Lys
            260                 265                 270

Pro Lys Leu Ala Pro Lys Trp Ser Met Ser Leu Ile Phe Thr Asp Val
        275                 280                 285

Ile Pro Ser Ile Lys Arg Ala Gly Val Thr Asp Glu Gln Leu His Val
    290                 295                 300

Ile Phe Val Lys Asn Pro Ala Arg Leu Phe Ser
305                 310                 315

<210> SEQ ID NO 76
<211> LENGTH: 951
<212> TYPE: DNA
<213> ORGANISM: Sulfolobus acidocaldarius

<400> SEQUENCE: 76
atgaccaaaa ttccgctggt tggtaaaggt gaaattagtc cgggtgaaat gggttttacc      60
ctgattcatg aacatctgcg tgtttttagc gaaccggtgc gttatcagtg gccccatctg     120
tataatgaag atgaagaact gaaaaacgcc gtgaacgaag tgaaaaccat tatgagctat     180
ggcgttaaaa ccattgttga tccgagtgtt atgggtattg tcgtgatat cgtttttagt      240
gaaaaagtgg tgaaagaaac cggcattaat gttattgcag caaccggtct gtatacctat     300
accgatctgc gtttttttt caatggtcgt agcctggaag aaattgcaga actgctgatc     360
cacgatatca aaaaaggtat tcagggcacc ccgaatcgtg cgggttttat caaagttgca     420
gcagatgaac cgggtattac ccgtgatgtt gaacgtgcaa ttcgtgcagc agcaattgca     480
cagaaagaaa caaatgttcc gattatcacc catagcaatg cacataatgg caccggtctg     540
gaacagcagc gtattctgat ggaagaaggt gtggatccgg tcgtgttct gattggtcat      600
ctgggtgata ccgataacgt ggactacatc aaaaaaatcg cagataaagg tagctttgtt     660
ggcctggatc gctatggtct ggacatgtct ctgccgattg ataaacgtaa tgaagttctg     720
ctgaaactga tcaaagatgg ttatctggat cgtattatgg tgagccagga ttattgttgt     780
accattgata tgggtattgc caaaccggaa tataaaccga accggcacc gaaatggtca      840
atgagcctga ttttaccga tgtgattccg agcattaaac gtgccggtgt taccgatgaa     900
cagctgcatg tgattttgt taaaaatccg gcacgcctgt ttagctgata a                951

<210> SEQ ID NO 77

<211> LENGTH: 315
<212> TYPE: PRT
<213> ORGANISM: Sulfolobus acidocaldarius

<400> SEQUENCE: 77

```
Met Thr Lys Ile Pro Leu Val Gly Lys Gly Glu Ile Ser Pro Gly Glu
1               5                   10                  15
Met Gly Phe Thr Leu Ile His Glu His Leu Arg Val Phe Ser Glu Pro
            20                  25                  30
Val Arg Tyr Gln Trp Pro His Leu Tyr Asn Glu Asp Glu Glu Leu Lys
        35                  40                  45
Asn Ala Val Asn Glu Val Lys Thr Ile Met Ser Tyr Gly Val Lys Thr
    50                  55                  60
Ile Val Asp Pro Ser Val Met Gly Ile Gly Arg Asp Ile Arg Phe Ser
65                  70                  75                  80
Glu Lys Val Val Lys Glu Thr Gly Ile Asn Val Ile Ala Ala Thr Gly
                85                  90                  95
Leu Tyr Thr Tyr Thr Asp Leu Pro Phe Phe Phe Asn Gly Arg Ser Leu
            100                 105                 110
Glu Glu Ile Ala Glu Leu Leu Ile His Asp Ile Lys Lys Gly Ile Gln
        115                 120                 125
Gly Thr Pro Asn Arg Ala Gly Phe Ile Lys Val Ala Ala Asp Glu Pro
    130                 135                 140
Gly Ile Thr Arg Asp Val Glu Arg Ala Ile Arg Ala Ala Ile Ala
145                 150                 155                 160
Gln Lys Glu Thr Asn Val Pro Ile Ile Thr His Ser Asn Ala His Asn
                165                 170                 175
Gly Thr Gly Leu Glu Gln Gln Arg Ile Leu Met Glu Glu Gly Val Asp
            180                 185                 190
Pro Gly Arg Val Leu Ile Gly His Leu Gly Asp Thr Asp Asn Val Asp
        195                 200                 205
Tyr Ile Lys Lys Ile Ala Asp Lys Gly Ser Phe Val Gly Leu Asp Arg
    210                 215                 220
Tyr Gly Leu Asp Met Ser Leu Pro Ile Asp Lys Arg Asn Glu Val Leu
225                 230                 235                 240
Leu Lys Leu Ile Lys Asp Gly Tyr Leu Asp Arg Ile Met Val Ser Gln
                245                 250                 255
Asp Tyr Cys Cys Thr Ile Asp Met Gly Ile Ala Lys Pro Glu Tyr Lys
            260                 265                 270
Pro Lys Pro Ala Pro Lys Trp Ser Met Ser Leu Ile Phe Thr Asp Val
        275                 280                 285
Ile Pro Ser Ile Lys Arg Ala Gly Val Thr Asp Glu Gln Leu His Val
    290                 295                 300
Ile Phe Val Lys Asn Pro Ala Arg Leu Phe Ser
305                 310                 315
```

<210> SEQ ID NO 78
<211> LENGTH: 951
<212> TYPE: DNA
<213> ORGANISM: Sulfolobus acidocaldarius

<400> SEQUENCE: 78

```
atgaccaaaa ttccgctggt tggtaaaggt gaaattagtc cgggtgaaat gggttttacc      60
ctgattcatg aacatctgcg tgttttagc gaaccggtgc gttatcagtg gcctcatctg     120
tataatgaag atgaagaact gaaaaacgcc gtgaacgaag tgaaaaccat tatgagctat     180
```

```
ggcgttaaaa ccattgttga tccgagtgtt atgggtctgg gtcgtgatac tcgttttagt        240
gaaaaagtgg tgaaagaaac cggcattaat gttattgcag caaccggtct gtggaccttt        300
accgatctgc cgttttttt caatggtcgt agcctggaag aaattgcaga actgctgatc         360
cacgatatca aaaaaggtat tcagggcacc aataatcgtg cgggttttat caaagttgca        420
gcagatgaac cgggtattac ccgtgatgtt gaacgtgcaa ttcgtgcagc agcaattgca        480
cagaaagaaa caaatgttcc gattatcacc catagcaatg cacataatgg caccggtctg        540
gaacagcagc gtattctgat ggaagaaggt gtggatccgg gtcgtgttct gattggtcat        600
ctgggtgata ccgataacgt ggactacatc aaaaaaatcg cagataaagg tagctttgtt        660
ggcctggatc gctatggtct ggacatgttt ctgccgattg ataaacgtaa tgaagttctg        720
ctgaaactga tcaaagatgg ttatctggat cgtattatgg tgagccagga ttattgttgt        780
accattgatc tgggtattgc caaaccggaa tataaaccga actggcacc gaaatggtca        840 atgagcctga ttttaccga tgtgattccg agcattaaac gtgccggtgt taccgatgaa        900
cagctgcatg tgattttgt taaaaatccg gcacgcctgt ttagctgata a                  951
```

<210> SEQ ID NO 79  
<211> LENGTH: 315  
<212> TYPE: PRT  
<213> ORGANISM: Sulfolobus acidocaldarius

<400> SEQUENCE: 79

```
Met Thr Lys Ile Pro Leu Val Gly Lys Gly Glu Ile Ser Pro Gly Glu
1               5                   10                  15

Met Gly Phe Thr Leu Ile His Glu His Leu Arg Val Phe Ser Glu Pro
                20                  25                  30

Val Arg Tyr Gln Trp Pro His Leu Tyr Asn Glu Asp Glu Glu Leu Lys
            35                  40                  45

Asn Ala Val Asn Glu Val Lys Thr Ile Met Ser Tyr Gly Val Lys Thr
        50                  55                  60

Ile Val Asp Pro Ser Val Met Gly Leu Gly Arg Asp Thr Arg Phe Ser
65                  70                  75                  80

Glu Lys Val Val Lys Glu Thr Gly Ile Asn Val Ile Ala Ala Thr Gly
                85                  90                  95

Leu Trp Thr Phe Thr Asp Leu Pro Phe Phe Asn Gly Arg Ser Leu
                100                 105                 110

Glu Glu Ile Ala Glu Leu Leu Ile His Asp Ile Lys Lys Gly Ile Gln
            115                 120                 125

Gly Thr Asn Asn Arg Ala Gly Phe Ile Lys Val Ala Ala Asp Glu Pro
        130                 135                 140

Gly Ile Thr Arg Asp Val Glu Arg Ala Ile Arg Ala Ala Ala Ile Ala
145                 150                 155                 160

Gln Lys Glu Thr Asn Val Pro Ile Ile Thr His Ser Asn Ala His Asn
                165                 170                 175

Gly Thr Gly Leu Glu Gln Gln Arg Ile Leu Met Glu Glu Gly Val Asp
            180                 185                 190

Pro Gly Arg Val Leu Ile Gly His Leu Gly Asp Thr Asp Asn Val Asp
        195                 200                 205

Tyr Ile Lys Lys Ile Ala Asp Lys Gly Ser Phe Val Gly Leu Asp Arg
    210                 215                 220

Tyr Gly Leu Asp Met Phe Leu Pro Ile Asp Lys Arg Asn Glu Val Leu
225                 230                 235                 240
```

```
Leu Lys Leu Ile Lys Asp Gly Tyr Leu Asp Arg Ile Met Val Ser Gln
            245                 250                 255

Asp Tyr Cys Cys Thr Ile Asp Leu Gly Ile Ala Lys Pro Glu Tyr Lys
            260                 265                 270

Pro Lys Leu Ala Pro Lys Trp Ser Met Ser Leu Ile Phe Thr Asp Val
            275                 280                 285

Ile Pro Ser Ile Lys Arg Ala Gly Val Thr Asp Glu Gln Leu His Val
            290                 295                 300

Ile Phe Val Lys Asn Pro Ala Arg Leu Phe Ser
305                 310                 315

<210> SEQ ID NO 80
<211> LENGTH: 951
<212> TYPE: DNA
<213> ORGANISM: Sulfolobus acidocaldarius

<400> SEQUENCE: 80
atgaccaaaa ttccgctggt tggtgaaggt gaaattagtc cgggtgaaat gggttttacc      60
ctgattcatg aacatctgcg tgttttagc gaaccggtgc gttatcagtg gcctcatctg     120
tataatgaag atgaagaact gaaaaacgcc gtgaacgaag tgaaaaccat tatgagctat     180
ggcgttaaaa ccattgttga tccgaccgtt atgggtctgg tcgtgatat tcgttttagt     240 gaaaaagtgg tgaaagaaac cggcattaat gttattgcag caaccggtct gtggaccttt     300
accgatctgc gtttttttt caatggtcgt agcctggaag aaattgcaga actgctgatc     360
cacgatatca aaaaaggtat tcagggcacc aataatcgtg cgggttttat caaagttgca     420
gcagatgaac cgggtattac ccgtgatgtt gaacgtgcaa ttcgtgcagc agcaattgca     480
cagaaagaaa caaatgttcc gattatcacc catagcaatg cacataatgg caccggtctg     540
gaacagcagc gtattctgat ggaagaaggt gtggatccgg tcgtgttct gattggtcat     600 ctgggtgata ccgataacgt ggactacatc aaaaaaatcg cagataaagg tagctttgtt     660
ggcctggatc gctatggtct ggacatgttt ctgccgattg ataaacgtaa tgaagttctg     720
ctgaaactga tcaaagatgg ttatctggat cgtattatgg tgagccagga ttattgttgt     780
accattgatt ggggtattgc caaaccggaa tataaaccga actggcacc gaaatggtca     840 atgagcctga ttttaccga tgtgattccg agcattaaac gtgccggtgt taccgatgaa     900
cagctgcatg tgatttttgt taaaaatccg gcacgcctgt ttagctgata a              951

<210> SEQ ID NO 81
<211> LENGTH: 315
<212> TYPE: PRT
<213> ORGANISM: Sulfolobus acidocaldarius

<400> SEQUENCE: 81

Met Thr Lys Ile Pro Leu Val Gly Glu Gly Glu Ile Ser Pro Gly Glu
1               5                   10                  15

Met Gly Phe Thr Leu Ile His Glu His Leu Arg Val Phe Ser Glu Pro
            20                  25                  30

Val Arg Tyr Gln Trp Pro His Leu Tyr Asn Glu Asp Glu Glu Leu Lys
        35                  40                  45

Asn Ala Val Asn Glu Val Lys Thr Ile Met Ser Tyr Gly Val Lys Thr
    50                  55                  60

Ile Val Asp Pro Thr Val Met Gly Leu Gly Arg Asp Ile Arg Phe Ser
65                  70                  75                  80
```

```
Glu Lys Val Val Lys Glu Thr Gly Ile Asn Val Ile Ala Ala Thr Gly
                 85                  90                  95

Leu Trp Thr Phe Thr Asp Leu Pro Phe Phe Asn Gly Arg Ser Leu
            100                 105                 110

Glu Glu Ile Ala Glu Leu Leu Ile His Asp Ile Lys Lys Gly Ile Gln
            115                 120                 125

Gly Thr Asn Asn Arg Ala Gly Phe Ile Lys Val Ala Ala Asp Glu Pro
        130                 135                 140

Gly Ile Thr Arg Asp Val Glu Arg Ala Ile Arg Ala Ala Ile Ala
145                 150                 155                 160

Gln Lys Glu Thr Asn Val Pro Ile Ile Thr His Ser Asn Ala His Asn
                165                 170                 175

Gly Thr Gly Leu Glu Gln Gln Arg Ile Leu Met Glu Glu Gly Val Asp
            180                 185                 190

Pro Gly Arg Val Leu Ile Gly His Leu Gly Asp Thr Asp Asn Val Asp
            195                 200                 205

Tyr Ile Lys Lys Ile Ala Asp Lys Gly Ser Phe Val Gly Leu Asp Arg
        210                 215                 220

Tyr Gly Leu Asp Met Phe Leu Pro Ile Asp Lys Arg Asn Glu Val Leu
225                 230                 235                 240

Leu Lys Leu Ile Lys Asp Gly Tyr Leu Asp Arg Ile Met Val Ser Gln
                245                 250                 255

Asp Tyr Cys Cys Thr Ile Asp Trp Gly Ile Ala Lys Pro Glu Tyr Lys
            260                 265                 270

Pro Lys Leu Ala Pro Lys Trp Ser Met Ser Leu Ile Phe Thr Asp Val
        275                 280                 285

Ile Pro Ser Ile Lys Arg Ala Gly Val Thr Asp Glu Gln Leu His Val
        290                 295                 300

Ile Phe Val Lys Asn Pro Ala Arg Leu Phe Ser
305                 310                 315

<210> SEQ ID NO 82
<211> LENGTH: 950
<212> TYPE: DNA
<213> ORGANISM: Sulfolobus acidocaldarius

<400> SEQUENCE: 82
atgaccaaaa ttccgctggt tggtaaaggt gaaattagtc cgggtgaaat gggttttacc      60
ctgattcatg aacatctgcg tgtttttagc gaaccggtgc gttatcagtg gcctcatctg     120
tataatgaag atgaagaact gaaaaacgcc gtgaacgaag tgaaaaccat tatgagctat     180
ggcgttaaaa ccattgttga tccgaccgtt atgggtattg tcgtgatat tcgttttagt     240 gaaaaagtgg tgaaagaaac cggcattaat gttattgcag caaccggtct gtatacctat     300
accgatctgc cgttttttttt caatggtcgt agcctggaag aaattgcaga actgctgatc     360
cacgatatca aaaaaggtat tcagggcacc aataatcgtg cgggttttat caaagttgca     420
gcagatgaac cgggtattac ccgtgatgtt gaacgtgcaa ttcgtgcagc agcaattgca     480
cagaaagaaa caaatgttcc gattatcacc catagcaatg cacataatgg caccggtctg     540 aacagcagc gtattctgat ggaagaaggt gtggatccgg tcgtgttct gattggtcat     600 ctgggtgata ccgataacgt ggactacatc aaaaaaatcg cagataaagg tagctttgtt     660
ggcctggatc gctatggtct ggacctgttt ctgccgattg ataaacgtaa tgaagttctg     720
ctgaaactga tcaaagatgg ttatctggat cgtattatgt gagccagga ttattgttgt     780
```

-continued

```
accattgatt ttggtattgc caaaccggaa tataaaccga aactggcacc gaaatggtca         840
atgagcctga ttttaccga tgtgattccg agcattaaac gtgccggtgt taccgatgaa          900
cagctgcatg tgattttgt taaaaatccg gcacgcctgt ttagctgaaa                     950
```

<210> SEQ ID NO 83
<211> LENGTH: 315
<212> TYPE: PRT
<213> ORGANISM: Sulfolobus acidocaldarius

<400> SEQUENCE: 83

```
Met Thr Lys Ile Pro Leu Val Gly Lys Gly Glu Ile Ser Pro Gly Glu
1               5                   10                  15

Met Gly Phe Thr Leu Ile His Glu His Leu Arg Val Phe Ser Glu Pro
            20                  25                  30

Val Arg Tyr Gln Trp Pro His Leu Tyr Asn Glu Asp Glu Glu Leu Lys
        35                  40                  45

Asn Ala Val Asn Glu Val Lys Thr Ile Met Ser Tyr Gly Val Lys Thr
    50                  55                  60

Ile Val Asp Pro Thr Val Met Gly Ile Gly Arg Asp Ile Arg Phe Ser
65                  70                  75                  80

Glu Lys Val Val Lys Glu Thr Gly Ile Asn Val Ile Ala Ala Thr Gly
                85                  90                  95

Leu Tyr Thr Tyr Thr Asp Leu Pro Phe Phe Phe Asn Gly Arg Ser Leu
            100                 105                 110

Glu Glu Ile Ala Glu Leu Leu Ile His Asp Ile Lys Lys Gly Ile Gln
        115                 120                 125

Gly Thr Asn Asn Arg Ala Gly Phe Ile Lys Val Ala Ala Asp Glu Pro
    130                 135                 140

Gly Ile Thr Arg Asp Val Glu Arg Ala Ile Arg Ala Ala Ile Ala
145                 150                 155                 160

Gln Lys Glu Thr Asn Val Pro Ile Ile Thr His Ser Asn Ala His Asn
                165                 170                 175

Gly Thr Gly Leu Glu Gln Gln Arg Ile Leu Met Glu Glu Gly Val Asp
            180                 185                 190

Pro Gly Arg Val Leu Ile Gly His Leu Gly Asp Thr Asp Asn Val Asp
        195                 200                 205

Tyr Ile Lys Lys Ile Ala Asp Lys Gly Ser Phe Val Gly Leu Asp Arg
    210                 215                 220

Tyr Gly Leu Asp Leu Phe Leu Pro Ile Asp Lys Arg Asn Glu Val Leu
225                 230                 235                 240

Leu Lys Leu Ile Lys Asp Gly Tyr Leu Asp Arg Ile Met Val Ser Gln
                245                 250                 255

Asp Tyr Cys Cys Thr Ile Asp Phe Gly Ile Ala Lys Pro Glu Tyr Lys
            260                 265                 270

Pro Lys Leu Ala Pro Lys Trp Ser Met Ser Leu Ile Phe Thr Asp Val
        275                 280                 285

Ile Pro Ser Ile Lys Arg Ala Gly Val Thr Asp Glu Gln Leu His Val
    290                 295                 300

Ile Phe Val Lys Asn Pro Ala Arg Leu Phe Ser
305                 310                 315
```

<210> SEQ ID NO 84
<211> LENGTH: 951
<212> TYPE: DNA
<213> ORGANISM: Sulfolobus acidocaldarius

<400> SEQUENCE: 84

```
atgaccaaaa ttccgctggt tggtaaaggt gaaattagtc cgggtgaaat gggttttacc     60
ctgattcatg aacatctgcg tgtttttagc gaaccggtgc gttatcagtg cctcatctg    120
tataatgaag atgaagaact gaaaaacgcc gtgaacgaag tgaaaaccat tatgagctat    180
ggcgttaaaa ccattgttga tccgagtgtt atgggtctgg tcgtgatat tcgttttagt    240
gaaaaagtgg tgaaagaaac cggcattaat gttattgcag caaccggtct gtggaccttt    300
accgatctgc cgtttttttt caatggtcgt agcctggaag aaattgcaga actgctgatc    360
cacgatatca aaaaaggtat tcagggcacc ccgaatcgtg cgggttttat caaagttgca    420
gcagatgaac cgggtattac ccgtgatgtt gaacgtgcaa ttcgtgcagc agcaattgca    480
cagaaagaaa caaatgttcc gattatcacc catagcaatg cacataatgg caccggtctg    540
gaacagcagc gtattctgat ggaagaaggt gtggatccgg tcgtgttct gattggtcat    600
ctgggtgata ccgataacgt ggactacatc aaaaaaatcg cagataaagg tagctttgtt    660
ggcctggatc gctatggtct ggacatgttt ctgccgattg ataaacgtaa tgaagttctg    720
ctgaaactga tcaaagatgg ttatctggat cgtattatgg tgagccagga ttattgttgt    780
accattgatt ggggtattgc caaaccggaa tataaaccga actggcacc gaaatggtca    840
atgagcctga ttttaccga tgtgattccg agcattaaac gtgccggtgt taccgatgaa    900
cagctgcatg tgattttgt taaaaatccg gcacgcctgt tagctgata a              951
```

<210> SEQ ID NO 85
<211> LENGTH: 315
<212> TYPE: PRT
<213> ORGANISM: Sulfolobus acidocaldarius

<400> SEQUENCE: 85

```
Met Thr Lys Ile Pro Leu Val Gly Lys Gly Glu Ile Ser Pro Gly Glu
1               5                   10                  15

Met Gly Phe Thr Leu Ile His Glu His Leu Arg Val Phe Ser Glu Pro
            20                  25                  30

Val Arg Tyr Gln Trp Pro His Leu Tyr Asn Glu Asp Glu Glu Leu Lys
        35                  40                  45

Asn Ala Val Asn Glu Val Lys Thr Ile Met Ser Tyr Gly Val Lys Thr
    50                  55                  60

Ile Val Asp Pro Ser Val Met Gly Leu Gly Arg Asp Ile Arg Phe Ser
65                  70                  75                  80

Glu Lys Val Val Lys Glu Thr Gly Ile Asn Val Ile Ala Ala Thr Gly
                85                  90                  95

Leu Trp Thr Phe Thr Asp Leu Pro Phe Phe Phe Asn Gly Arg Ser Leu
            100                 105                 110

Glu Glu Ile Ala Glu Leu Leu Ile His Asp Ile Lys Lys Gly Ile Gln
        115                 120                 125

Gly Thr Pro Asn Arg Ala Gly Phe Ile Lys Val Ala Ala Asp Glu Pro
    130                 135                 140

Gly Ile Thr Arg Asp Val Glu Arg Ala Ile Arg Ala Ala Ala Ile Ala
145                 150                 155                 160

Gln Lys Glu Thr Asn Val Pro Ile Ile Thr His Ser Asn Ala His Asn
                165                 170                 175

Gly Thr Gly Leu Glu Gln Gln Arg Ile Leu Met Glu Glu Gly Val Asp
            180                 185                 190
```

Pro Gly Arg Val Leu Ile Gly His Leu Gly Asp Thr Asp Asn Val Asp
        195                 200                 205

Tyr Ile Lys Lys Ile Ala Asp Lys Gly Ser Phe Val Gly Leu Asp Arg
        210                 215                 220

Tyr Gly Leu Asp Met Phe Leu Pro Ile Asp Lys Arg Asn Glu Val Leu
225                 230                 235                 240

Leu Lys Leu Ile Lys Asp Gly Tyr Leu Asp Arg Ile Met Val Ser Gln
                245                 250                 255

Asp Tyr Cys Cys Thr Ile Asp Trp Gly Ile Ala Lys Pro Glu Tyr Lys
                260                 265                 270

Pro Lys Leu Ala Pro Lys Trp Ser Met Ser Leu Ile Phe Thr Asp Val
        275                 280                 285

Ile Pro Ser Ile Lys Arg Ala Gly Val Thr Asp Glu Gln Leu His Val
        290                 295                 300

Ile Phe Val Lys Asn Pro Ala Arg Leu Phe Ser
305                 310                 315

<210> SEQ ID NO 86
<211> LENGTH: 951
<212> TYPE: DNA
<213> ORGANISM: Sulfolobus acidocaldarius

<400> SEQUENCE: 86

| | | | | | |
|---|---|---|---|---|---|
| atgaccaaaa | ttccgctggt | tggtaaaggt | gaaattagtc | cgggtgaaat | gggttttacc | 60 |
| ctgattcatg | aacatctgcg | tgcatttagc | gaaccggtgc | gttatcagtg | gcctcatctg | 120 |
| tataatgaag | atgaagaact | gaaaaacgcc | gtgaacgaag | tgaaaaccat | tatgagctat | 180 |
| ggcgttaaaa | ccattgttga | tccgaccgtt | atgggtctgg | tcgtgatat | cgttttagt | 240 |
| gaaaaagtgg | tgaaagaaac | cggcattaat | gttattgcag | caaccggtct | gtataccat | 300 |
| accgatctgc | gttttttttt | caatggtcgt | agcctggaag | aaattgcaga | actgctgatc | 360 |
| cacgatatca | aaaaaggtat | tcagggcacc | aataatcgtg | cgggttttat | caaagttgca | 420 |
| gcagatgaac | cgggtattac | ccgtgatgtt | gaacgtgcaa | ttcgtgcagc | agcaattgca | 480 |
| cagaaagaaa | caaatgttcc | gattatcacc | catagcaatg | cacataatgg | caccggtctg | 540 |
| gaacagcagc | gtattctgat | ggaagaaggt | gtggatccgg | tcgtgttct | gattggtcat | 600 |
| ctgggtgata | ccgataacgt | ggactacatc | aaaaaaatcg | cagataaagg | tagctttgtt | 660 |
| ggcctggatc | gctatggtgt | ggacctgttt | ctgccgattg | ataaacgtaa | tgaagttctg | 720 |
| ctgaaactga | tcaaagatgg | ttatctggat | cgtattatgg | tgagccagga | ttattgttgt | 780 |
| accattgatc | tgggtattgc | caaaccggaa | tataaaccga | actggcaccc | gaaatggtca | 840 |
| atgagcctaa | ttttaccga | tgtgattccg | agcattaaac | gtgccggtgt | accgatgaa | 900 |
| cagctgcatg | tgattttgt | taaaaatccg | gcacgcctgt | tagctgata | a | 951 |

<210> SEQ ID NO 87
<211> LENGTH: 315
<212> TYPE: PRT
<213> ORGANISM: Sulfolobus acidocaldarius

<400> SEQUENCE: 87

Met Thr Lys Ile Pro Leu Val Gly Lys Gly Glu Ile Ser Pro Gly Glu
1               5                   10                  15

Met Gly Phe Thr Leu Ile His Glu His Leu Arg Ala Phe Ser Glu Pro
            20                  25                  30

Val Arg Tyr Gln Trp Pro His Leu Tyr Asn Glu Asp Glu Glu Leu Lys

```
                     35                  40                  45
Asn Ala Val Asn Glu Val Lys Thr Ile Met Ser Tyr Gly Val Lys Thr
 50                  55                  60

Ile Val Asp Pro Thr Val Met Gly Leu Gly Arg Asp Ile Arg Phe Ser
 65                  70                  75                  80

Glu Lys Val Val Lys Glu Thr Gly Ile Asn Val Ile Ala Ala Thr Gly
                 85                  90                  95

Leu Tyr Thr Tyr Thr Asp Leu Pro Phe Phe Phe Asn Gly Arg Ser Leu
                100                 105                 110

Glu Glu Ile Ala Glu Leu Leu Ile His Asp Ile Lys Lys Gly Ile Gln
            115                 120                 125

Gly Thr Asn Asn Arg Ala Gly Phe Ile Lys Val Ala Ala Asp Glu Pro
        130                 135                 140

Gly Ile Thr Arg Asp Val Glu Arg Ala Ile Arg Ala Ala Ala Ile Ala
145                 150                 155                 160

Gln Lys Glu Thr Asn Val Pro Ile Ile Thr His Ser Asn Ala His Asn
                165                 170                 175

Gly Thr Gly Leu Glu Gln Gln Arg Ile Leu Met Glu Glu Gly Val Asp
            180                 185                 190

Pro Gly Arg Val Leu Ile Gly His Leu Gly Asp Thr Asp Asn Val Asp
        195                 200                 205

Tyr Ile Lys Lys Ile Ala Asp Lys Gly Ser Phe Val Gly Leu Asp Arg
    210                 215                 220

Tyr Gly Val Asp Leu Phe Leu Pro Ile Asp Lys Arg Asn Glu Val Leu
225                 230                 235                 240

Leu Lys Leu Ile Lys Asp Gly Tyr Leu Asp Arg Ile Met Val Ser Gln
                245                 250                 255

Asp Tyr Cys Cys Thr Ile Asp Leu Gly Ile Ala Lys Pro Glu Tyr Lys
            260                 265                 270

Pro Lys Leu Ala Pro Lys Trp Ser Met Ser Leu Ile Phe Thr Asp Val
        275                 280                 285

Ile Pro Ser Ile Lys Arg Ala Gly Val Thr Asp Glu Gln Leu His Val
    290                 295                 300

Ile Phe Val Lys Asn Pro Ala Arg Leu Phe Ser
305                 310                 315

<210> SEQ ID NO 88
<211> LENGTH: 951
<212> TYPE: DNA
<213> ORGANISM: Sulfolobus acidocaldarius

<400> SEQUENCE: 88
atgaccaaaa ttccgctggt tggtaaaggt gaaattagtc cgggtgaaat gggttttacc      60
ctgattcatg aacatctgcg tgttttagc gaaccggtgc gttatcagtg gcctcatctg     120
tataatgaag atgaagaact gaaaaacgcc gtgaacgaag tgaaaaccat tatgagctat     180
ggcgttaaaa ccattgttga tgtgagtgtt atgggtctgg gtcgtgatat cgttttagt     240 gaaaaagtgg tgaaagaaac cggcattaat gttattgcag caaccggtct gtggaccttt     300
accgatctgc cgttttttt caatggtcgt agcctggaag aaattgcaga actgctgatc     360
cacgatatca aaaaaggtat tcagggcacc aataatcgtg cgggttttat caaagttgca     420
gcagatgaac cgggtattac ccgtgatgtt gagcgtgcaa ttcgtgcagc agcaattgca     480
cagaaagaaa caaatgttcc gattatcacc catagcaatg cacataatgg caccggtctg     540
```

```
gaacagcagc gtattctgat ggaagaaggt gtggatccgg gtcgtgttct gattggtcat    600
ctgggtgata ccgataacgt ggactacatc aaaaaaatcg cagataaagg tagctttgtt    660
ggcctggatc gctatggtct ggacatgttt ctgccgattg ataaacgtaa tgaagttctg    720
ctgaaactga tcaaagatgg ttatctggat cgtattatgg tgagccagga ttatgcttgt    780
accattgatc tgggtattgc caaaccggaa tataaaccga aactggcacc gaaatggtca    840
acgagcctga ttttaccga tgtgattccg agcattaaac gtgccggtgt taccgatgaa    900
cagctgcatg tgattttgt taaaaatccg gcacgcctgt ttagctgata a               951
```

<210> SEQ ID NO 89
<211> LENGTH: 315
<212> TYPE: PRT
<213> ORGANISM: Sulfolobus acidocaldarius
<400> SEQUENCE: 89

```
Met Thr Lys Ile Pro Leu Val Gly Lys Gly Glu Ile Ser Pro Gly Glu
1               5                   10                  15

Met Gly Phe Thr Leu Ile His Glu His Leu Arg Val Phe Ser Glu Pro
            20                  25                  30

Val Arg Tyr Gln Trp Pro His Leu Tyr Asn Glu Asp Glu Glu Leu Lys
        35                  40                  45

Asn Ala Val Asn Glu Val Lys Thr Ile Met Ser Tyr Gly Val Lys Thr
    50                  55                  60

Ile Val Asp Val Ser Val Met Gly Leu Gly Arg Asp Ile Arg Phe Ser
65                  70                  75                  80

Glu Lys Val Val Lys Glu Thr Gly Ile Asn Val Ile Ala Ala Thr Gly
                85                  90                  95

Leu Trp Thr Phe Thr Asp Leu Pro Phe Phe Phe Asn Gly Arg Ser Leu
            100                 105                 110

Glu Glu Ile Ala Glu Leu Leu Ile His Asp Ile Lys Lys Gly Ile Gln
        115                 120                 125

Gly Thr Asn Asn Arg Ala Gly Phe Ile Lys Val Ala Ala Asp Glu Pro
    130                 135                 140

Gly Ile Thr Arg Asp Val Glu Arg Ala Ile Arg Ala Ala Ala Ile Ala
145                 150                 155                 160

Gln Lys Glu Thr Asn Val Pro Ile Ile Thr His Ser Asn Ala His Asn
                165                 170                 175

Gly Thr Gly Leu Glu Gln Gln Arg Ile Leu Met Glu Glu Gly Val Asp
            180                 185                 190

Pro Gly Arg Val Leu Ile Gly His Leu Gly Asp Thr Asp Asn Val Asp
        195                 200                 205

Tyr Ile Lys Lys Ile Ala Asp Lys Gly Ser Phe Val Gly Leu Asp Arg
    210                 215                 220

Tyr Gly Leu Asp Met Phe Leu Pro Ile Asp Lys Arg Asn Glu Val Leu
225                 230                 235                 240

Leu Lys Leu Ile Lys Asp Gly Tyr Leu Asp Arg Ile Met Val Ser Gln
                245                 250                 255

Asp Tyr Ala Cys Thr Ile Asp Leu Gly Ile Ala Lys Pro Glu Tyr Lys
            260                 265                 270

Pro Lys Leu Ala Pro Lys Trp Ser Thr Ser Leu Ile Phe Thr Asp Val
        275                 280                 285

Ile Pro Ser Ile Lys Arg Ala Gly Val Thr Asp Glu Gln Leu His Val
    290                 295                 300
```

Ile Phe Val Lys Asn Pro Ala Arg Leu Phe Ser
305                 310                 315

<210> SEQ ID NO 90
<211> LENGTH: 951
<212> TYPE: DNA
<213> ORGANISM: Sulfolobus acidocaldarius

<400> SEQUENCE: 90

```
atgaccaaaa ttccgctggt tggtaaaggt gaaattagtc cgggtgaaat gggttttacc      60
ctgattcatg aacatctgcg tgtttttagc gaaccggtgc gttatcagtg gcctcatctg     120
tataatgaag atgaagaact gaaaaacgcc gtgaacgaag tgaaaaccat tatgagctat     180
ggcgttaaaa ccattgttga tccgagtgtt atgggtctgg gtcgtgatat tcgttttagt     240
gaaaaagtgg tgaaagaaac cggcattaat gttattgcag caaccggtct gtggaccttt     300
accgatctgc cgttttttt caatggtcgt agcctggaag aaattgcaga actgctgatc     360
cacgatatca aaaaaggtat tcagggcacc ccgaatcgtg cgggttttat caaagttgca     420
gctgatgaac cgggtattac ccgtgatgtt gaacgtgcaa ttcgtgcagc agcaattgca     480
cagaaagaaa caaatgttcc gattatcacc catagcaatg cacataatgg caccggtctg     540
gaacagcagc gtattctgat ggaagaaggt gtggatccgg tcgtgttct gattggtcat     600
ctgggtgata ccgataacgt ggactacatc aaaaaaatcg cagataaagg tagctttgtt     660
ggcctggatc gctatggtgt ggacctgttt ctgccgattg ataaacgtaa tgaagttctg     720
ctgaaactga tcaaagatgg ttatctggat cgtattatgg tgagccagga ttattgttgt     780
accattgata tgggtattgc caaaccggaa tataaaccga actggcaccc gaaatggtca     840
atgagcctga ttttaccga tgtgattccg agcattaaac gtgccggtgt taccgatgaa     900
cagctgcatg tgattttgt taaaaatccg gcacgcctgt ttagctgata a               951
```

<210> SEQ ID NO 91
<211> LENGTH: 315
<212> TYPE: PRT
<213> ORGANISM: Sulfolobus acidocaldarius

<400> SEQUENCE: 91

Met Thr Lys Ile Pro Leu Val Gly Lys Gly Glu Ile Ser Pro Gly Glu
1               5                   10                  15

Met Gly Phe Thr Leu Ile His Glu His Leu Arg Val Phe Ser Glu Pro
            20                  25                  30

Val Arg Tyr Gln Trp Pro His Leu Tyr Asn Glu Asp Glu Glu Leu Lys
        35                  40                  45

Asn Ala Val Asn Glu Val Lys Thr Ile Met Ser Tyr Gly Val Lys Thr
    50                  55                  60

Ile Val Asp Pro Ser Val Met Gly Leu Gly Arg Asp Ile Arg Phe Ser
65                  70                  75                  80

Glu Lys Val Val Lys Glu Thr Gly Ile Asn Val Ile Ala Ala Thr Gly
                85                  90                  95

Leu Trp Thr Phe Thr Asp Leu Pro Phe Phe Phe Asn Gly Arg Ser Leu
            100                 105                 110

Glu Glu Ile Ala Glu Leu Leu Ile His Asp Ile Lys Lys Gly Ile Gln
        115                 120                 125

Gly Thr Pro Asn Arg Ala Gly Phe Ile Lys Val Ala Ala Asp Glu Pro
    130                 135                 140

Gly Ile Thr Arg Asp Val Glu Arg Ala Ile Arg Ala Ala Ala Ile Ala

```
                        145                 150                 155                 160
        Gln Lys Glu Thr Asn Val Pro Ile Ile Thr His Ser Asn Ala His Asn
                        165                 170                 175

Gly Thr Gly Leu Glu Gln Gln Arg Ile Leu Met Glu Glu Gly Val Asp
                        180                 185                 190

Pro Gly Arg Val Leu Ile Gly His Leu Gly Asp Thr Asp Asn Val Asp
                        195                 200                 205

Tyr Ile Lys Lys Ile Ala Asp Lys Gly Ser Phe Val Gly Leu Asp Arg
                        210                 215                 220

Tyr Gly Val Asp Leu Phe Leu Pro Ile Asp Lys Arg Asn Glu Val Leu
        225                 230                 235                 240

Leu Lys Leu Ile Lys Asp Gly Tyr Leu Asp Arg Ile Met Val Ser Gln
                        245                 250                 255

Asp Tyr Cys Cys Thr Ile Asp Met Gly Ile Ala Lys Pro Glu Tyr Lys
                        260                 265                 270

Pro Lys Leu Ala Pro Lys Trp Ser Met Ser Leu Ile Phe Thr Asp Val
                        275                 280                 285

Ile Pro Ser Ile Lys Arg Ala Gly Val Thr Asp Glu Gln Leu His Val
                        290                 295                 300

Ile Phe Val Lys Asn Pro Ala Arg Leu Phe Ser
        305                 310                 315
```

<210> SEQ ID NO 92
<211> LENGTH: 951
<212> TYPE: DNA
<213> ORGANISM: Sulfolobus acidocaldarius

<400> SEQUENCE: 92

```
atgaccaaaa ttccgctggt tggtaaaggt gaaattagtc cgggtgaaat gggttttacc      60
ctgattcatg aacatctgcg tgttttagc gaaccggtgc gttatcagtg gccccatctg     120
tataatgaag atgaagaact gaaaaacgcc gtgaacgaag tgaaaaccat tatgagctat     180
ggcgttaaaa ccattgttga tccgagtgtt atgggtattg gtcgtgatat cgttttagt     240
gaaaaagtgg tgaaagaaac cggcattaat gttattgcag caaccggtct gtggacctt     300
accgatctgc gttttttttt caatggtcgt agcctggaag aaattgcaga actgctgatc     360
cacgatatca aaaaaggtat tcagggcacc ccgaatcgtg cgggttttat caaagttgca     420
gcagatgaac cgggtattac ccgtgatgtt gaacgtgcaa ttcgtgcagc agcaattgca     480
cagaaagaaa caaatgttcc gattatcacc catagcaatg cacataatgg caccggtctg     540
gaacagcagc gtattctgat ggaagaaggt gtggatccgg tcgtgttct gattggtcat     600
ctgggtgata ccgataacgt ggactacatc aaaaaaatcg cagataaagg tagctttgtt     660
ggcctggatc gctatggtct ggacctgttt ctgccgattg ataaacgtaa tgaagttctg     720
ctgaaactga tcaaagatgg ttatctggat cgtattatgg tgagccagga ttattgttgt     780
accattgatt ggggtattgc caaaccggaa tataaaccga actggcacc gaaatggtca     840
atgagcctga ttttaccga tgtgattccg agcattaaac gtgccggtgt taccgatgaa     900
cagctgcatg tgatttttgt taaaaatccg gcacgcctgt ttagctgata a              951
```

<210> SEQ ID NO 93
<211> LENGTH: 315
<212> TYPE: PRT
<213> ORGANISM: Sulfolobus acidocaldarius

<400> SEQUENCE: 93

```
Met Thr Lys Ile Pro Leu Val Gly Lys Gly Glu Ile Ser Pro Gly Glu
1               5                   10                  15

Met Gly Phe Thr Leu Ile His Glu His Leu Arg Val Phe Ser Glu Pro
            20                  25                  30

Val Arg Tyr Gln Trp Pro His Leu Tyr Asn Glu Asp Glu Glu Leu Lys
        35                  40                  45

Asn Ala Val Asn Glu Val Lys Thr Ile Met Ser Tyr Gly Val Lys Thr
50                  55                  60

Ile Val Asp Pro Ser Val Met Gly Ile Gly Arg Asp Ile Arg Phe Ser
65                  70                  75                  80

Glu Lys Val Val Lys Glu Thr Gly Ile Asn Val Ile Ala Ala Thr Gly
                85                  90                  95

Leu Trp Thr Phe Thr Asp Leu Pro Phe Phe Phe Asn Gly Arg Ser Leu
            100                 105                 110

Glu Glu Ile Ala Glu Leu Leu Ile His Asp Ile Lys Lys Gly Ile Gln
        115                 120                 125

Gly Thr Pro Asn Arg Ala Gly Phe Ile Lys Val Ala Ala Asp Glu Pro
130                 135                 140

Gly Ile Thr Arg Asp Val Glu Arg Ala Ile Arg Ala Ala Ala Ile Ala
145                 150                 155                 160

Gln Lys Glu Thr Asn Val Pro Ile Ile Thr His Ser Asn Ala His Asn
                165                 170                 175

Gly Thr Gly Leu Glu Gln Gln Arg Ile Leu Met Glu Glu Gly Val Asp
            180                 185                 190

Pro Gly Arg Val Leu Ile Gly His Leu Gly Asp Thr Asp Asn Val Asp
        195                 200                 205

Tyr Ile Lys Lys Ile Ala Asp Lys Gly Ser Phe Val Gly Leu Asp Arg
210                 215                 220

Tyr Gly Leu Asp Leu Phe Leu Pro Ile Asp Lys Arg Asn Glu Val Leu
225                 230                 235                 240

Leu Lys Leu Ile Lys Asp Gly Tyr Leu Asp Arg Ile Met Val Ser Gln
                245                 250                 255

Asp Tyr Cys Cys Thr Ile Asp Trp Gly Ile Ala Lys Pro Glu Tyr Lys
            260                 265                 270

Pro Lys Leu Ala Pro Lys Trp Ser Met Ser Leu Ile Phe Thr Asp Val
        275                 280                 285

Ile Pro Ser Ile Lys Arg Ala Gly Val Thr Asp Glu Gln Leu His Val
290                 295                 300

Ile Phe Val Lys Asn Pro Ala Arg Leu Phe Ser
305                 310                 315

<210> SEQ ID NO 94
<211> LENGTH: 945
<212> TYPE: DNA
<213> ORGANISM: Sulfolobus islandicus

<400> SEQUENCE: 94
atgcgtattc cgctggttgg taaagaaccg attgaagccg aagatatggg ttttaccctg      60
attcatgaac atctgcgtgt ttttagcgaa gcagttcgtt atcagtggcc tcatctgtat     120
aatgaagatg aagaactgcg taatgccgtt aatgaagtta acgtgccat gcagtttggt      180 gttaaaacca ttgttgatcc gaccgttatg ggtctgggtc gtgatattcg ctttatggaa     240
aaagttgtga aaccaccgg tattaatctg gttgcaggca ccggtattta tttatgtg      300
```

```
gatctgccgt tttattttct gaaccgcagc attgatgaaa ttgccgacct gtttattcat      360
gatattaaag aaggtattca ggcaaccagc aataaagccg ttttgtgaa aattgcagcc       420 gatgaaccgg gtattaccaa agatgtggaa aaagttattc gtgcagcagc cattacccat     480
aaagaagcca agttccgat tattacccat agcaatgccc ataataatac cggtctggaa      540
gaacagcgta ttctgatgga agaaggtgtt gatccgggta aaattctgat tggtcatctg    600
ggtgataccg ataataccga ttatattaaa aaaattgccg ataaaggcag ctttattggt    660
ctggatcgtt atggtctgga cctgtttctg ccggttgata aacgtaatga aaccaccctg     720
aaactgatta agatggcta tagcgatcgc attatgatca gccatgatta ttgttgtacc     780
attgattttg gcaccgcacg tccggaactg aaaccgaaac tggcaccgcg ttggagcatg    840
gcactgattt ttgaagatac cattccgttt ctgaaaaaaa atggcgtgag cgaagaagtg   900
atcgatatta ttttcaaaga aaacccgaaa aaattcttta gctaa                     945
```

<210> SEQ ID NO 95
<211> LENGTH: 314
<212> TYPE: PRT
<213> ORGANISM: Sulfolobus islandicus

<400> SEQUENCE: 95

```
Met Arg Ile Pro Leu Val Gly Lys Glu Pro Ile Glu Ala Glu Asp Met
1               5                   10                  15

Gly Phe Thr Leu Ile His Glu His Leu Arg Val Phe Ser Glu Ala Val
            20                  25                  30

Arg Tyr Gln Trp Pro His Leu Tyr Asn Glu Asp Glu Glu Leu Arg Asn
        35                  40                  45

Ala Val Asn Glu Val Lys Arg Ala Met Gln Phe Gly Val Lys Thr Ile
    50                  55                  60

Val Asp Pro Thr Val Met Gly Leu Gly Arg Asp Ile Arg Phe Met Glu
65                  70                  75                  80

Lys Val Val Lys Thr Thr Gly Ile Asn Leu Val Ala Gly Thr Gly Ile
                85                  90                  95

Tyr Ile Tyr Val Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Ala
        115                 120                 125

Thr Ser Asn Lys Ala Gly Phe Val Lys Ile Ala Ala Asp Glu Pro Gly
    130                 135                 140

Ile Thr Lys Asp Val Glu Lys Val Ile Arg Ala Ala Ile Thr His
145                 150                 155                 160

Lys Glu Ala Lys Val Pro Ile Ile Thr His Ser Asn Ala His Asn Asn
                165                 170                 175

Thr Gly Leu Glu Glu Gln Arg Ile Leu Met Glu Glu Gly Val Asp Pro
            180                 185                 190

Gly Lys Ile Leu Ile Gly His Leu Gly Asp Thr Asp Asn Thr Asp Tyr
        195                 200                 205

Ile Lys Lys Ile Ala Asp Lys Gly Ser Phe Ile Gly Leu Asp Arg Tyr
    210                 215                 220

Gly Leu Asp Leu Phe Leu Pro Val Asp Lys Arg Asn Glu Thr Thr Leu
225                 230                 235                 240

Lys Leu Ile Lys Asp Gly Tyr Ser Asp Arg Ile Met Ile Ser His Asp
                245                 250                 255

Tyr Cys Cys Thr Ile Asp Phe Gly Thr Ala Arg Pro Glu Leu Lys Pro
```

```
            260                 265                 270
Lys Leu Ala Pro Arg Trp Ser Met Ala Leu Ile Phe Glu Asp Thr Ile
            275                 280                 285

Pro Phe Leu Lys Lys Asn Gly Val Ser Glu Val Ile Asp Ile Ile
        290                 295                 300

Phe Lys Glu Asn Pro Lys Lys Phe Phe Ser
305                 310
```

<210> SEQ ID NO 96
<211> LENGTH: 945
<212> TYPE: DNA
<213> ORGANISM: Sulfolobus islandicus

<400> SEQUENCE: 96

```
atgcgtattc cgctggttgg taaagaaccg attgaagccg aagatatggg ttttacccctg    60
attcatgaac atctgcgtgt ttttagcgaa gcagttcgtt atcagtggcc tcatctgtat   120
aatgaagatg aagaactgcg taatgccgtt aatgaagtta acgtgccat gcagtttggt    180
gttaaaacca ttgttgatcc gaccgttatg ggtctgggtc gtgatattcg ctttatggaa   240
aaagttgtga aaaccaccgg tattaatctg gttgcaggca ccggtattta tatttatgtg   300
gatctgccgt tttatttct gaaccgcagc attgatgaaa ttgccgacct gtttattcat   360
gatattaaag aaggtattca ggcaaccagc aataaagccg ttttgtgaa aattgcagcc    420
gatgaaccgg gtattaccaa agatgtggaa aaagttattc gtgcagcagc cattacccat   480
aaagaagcca agttccgat tattacccat agcaatgccc ataataatac cggtctggaa    540
gaacagcgta ttctgatgga agaaggtgtt gatccgggta aaattctgat tggtcatctg   600
ggtgataccg ataataccga ttatattaaa aaaattgccg ataaaggcag ctttattggt   660
ctggatcgtt atggtctgga cctgtttctg ccggttgata acgtaatga accaccctg     720
aaactgatta agatggcta tagcgatcgc attatgatca gccatgatta tgttgtacc    780
attgatatgg gcaccgcacg tccggaactg aaaccgaaac tggcaccgcg ttggagcatg   840
gcactgattt tgaagatac cattccgttt ctgaaaaaaa atggcgtgag cgaagaagtg   900
atcgatatta ttttcaaaga aaacccgaaa aaattccttta gctaa                945
```

<210> SEQ ID NO 97
<211> LENGTH: 314
<212> TYPE: PRT
<213> ORGANISM: Sulfolobus islandicus

<400> SEQUENCE: 97

```
Met Arg Ile Pro Leu Val Gly Lys Glu Pro Ile Glu Ala Glu Asp Met
1               5                   10                  15

Gly Phe Thr Leu Ile His Glu His Leu Arg Val Phe Ser Glu Ala Val
            20                  25                  30

Arg Tyr Gln Trp Pro His Leu Tyr Asn Glu Asp Glu Glu Leu Arg Asn
        35                  40                  45

Ala Val Asn Glu Val Lys Arg Ala Met Gln Phe Gly Val Lys Thr Ile
    50                  55                  60

Val Asp Pro Thr Val Met Gly Leu Gly Arg Asp Ile Arg Phe Met Glu
65                  70                  75                  80

Lys Val Val Lys Thr Thr Gly Ile Asn Leu Val Ala Gly Thr Gly Ile
                85                  90                  95

Tyr Ile Tyr Val Asp Leu Pro Phe Tyr Phe Leu Asn Arg Ser Ile Asp
            100                 105                 110
```

```
Glu Ile Ala Asp Leu Phe Ile His Asp Ile Lys Glu Gly Ile Gln Ala
            115                 120                 125

Thr Ser Asn Lys Ala Gly Phe Val Lys Ile Ala Ala Asp Glu Pro Gly
        130                 135                 140

Ile Thr Lys Asp Val Glu Lys Val Ile Arg Ala Ala Ile Thr His
145                 150                 155                 160

Lys Glu Ala Lys Val Pro Ile Ile Thr His Ser Asn Ala His Asn Asn
                165                 170                 175

Thr Gly Leu Glu Glu Gln Arg Ile Leu Met Glu Gly Val Asp Pro
        180                 185                 190

Gly Lys Ile Leu Ile Gly His Leu Gly Asp Thr Asp Asn Thr Asp Tyr
                195                 200                 205

Ile Lys Lys Ile Ala Asp Lys Gly Ser Phe Ile Gly Leu Asp Arg Tyr
        210                 215                 220

Gly Leu Asp Leu Phe Leu Pro Val Asp Lys Arg Asn Glu Thr Thr Leu
225                 230                 235                 240

Lys Leu Ile Lys Asp Gly Tyr Ser Asp Arg Ile Met Ile Ser His Asp
                245                 250                 255

Tyr Cys Cys Thr Ile Asp Met Gly Thr Ala Arg Pro Glu Leu Lys Pro
                260                 265                 270

Lys Leu Ala Pro Arg Trp Ser Met Ala Leu Ile Phe Glu Asp Thr Ile
                275                 280                 285

Pro Phe Leu Lys Lys Asn Gly Val Ser Glu Glu Val Ile Asp Ile Ile
        290                 295                 300

Phe Lys Glu Asn Pro Lys Lys Phe Phe Ser
305                 310

<210> SEQ ID NO 98
<211> LENGTH: 945
<212> TYPE: DNA
<213> ORGANISM: Sulfolobus islandicus

<400> SEQUENCE: 98
atgcgtattc cgctggttgg taaagaaccg attgaagccg aagatatggg ttttaccctg      60
attcatgaac atctgcgtgt ttttagcgaa gcagttcgtt atcagtggcc tcatctgtat     120
aatgaagatg aagaactgcg taatgccgtt aatgaagtta acgtgccat gcagtttggt     180
gttaaaacca ttgttgatcc gaccgttatg ggtctgggtc gtgatattcg ctttatggaa     240
aaagttgtga aaccaccggg tattaatctg gttgcaggca ccggtattta tatttatgtg     300
gatctgccgt tttattttct gaaccgcagc attgatgaaa ttgccgacct gtttattcat     360
gatattaaag aaggtattca ggcaaccagc aataaagccg gttttgtgaa aattgcagcc     420
gatgaaccgg gtattaccaa agatgtggaa aaagttattc gtgcagcagc cattacccat     480
aaagaagcca agttccgat tattacccat agcaatgccc ataataatac cggtctggaa     540
gaacagcgta ttctgatgga agaaggtgtt gatccgggta aaattctgat tggtcatctg     600
ggtgataccg ataataccga ttatattaaa aaaattgccg ataaaggcag ctttattggt     660
ctggatcgtt atggtctgga cctgtttctg ccggttgata acgtaatga accaccctg      720
aaactgatta agatggcta tagcgatcgc attatgatca gccatgatta ttgttgtacc     780
attgatctgg gcaccgcacg tccggaactg aaaccgaaac tggcaccgcg ttggagcatg     840
gcactgattt ttgaagatac cattccgttt ctgaaaaaaa atggcgtgag cgaagaagtg     900
atcgatatta ttttcaaaga aaacccgaaa aaattcttta gctaa                    945
```

<210> SEQ ID NO 99
<211> LENGTH: 314
<212> TYPE: PRT
<213> ORGANISM: Sulfolobus islandicus

<400> SEQUENCE: 99

| Met | Arg | Ile | Pro | Leu | Val | Gly | Lys | Glu | Pro | Ile | Glu | Ala | Glu | Asp | Met |
|---|---|---|---|---|---|---|---|---|---|---|---|---|---|---|---|
| 1 | | | | 5 | | | | | 10 | | | | | 15 | |

| Gly | Phe | Thr | Leu | Ile | His | Glu | His | Leu | Arg | Val | Phe | Ser | Glu | Ala | Val |
|---|---|---|---|---|---|---|---|---|---|---|---|---|---|---|---|
| | | | 20 | | | | | 25 | | | | | 30 | | |

| Arg | Tyr | Gln | Trp | Pro | His | Leu | Tyr | Asn | Glu | Asp | Glu | Glu | Leu | Arg | Asn |
|---|---|---|---|---|---|---|---|---|---|---|---|---|---|---|---|
| | | 35 | | | | | 40 | | | | | 45 | | | |

| Ala | Val | Asn | Glu | Val | Lys | Arg | Ala | Met | Gln | Phe | Gly | Val | Lys | Thr | Ile |
|---|---|---|---|---|---|---|---|---|---|---|---|---|---|---|---|
| | 50 | | | | | 55 | | | | | 60 | | | | |

| Val | Asp | Pro | Thr | Val | Met | Gly | Leu | Gly | Arg | Asp | Ile | Arg | Phe | Met | Glu |
|---|---|---|---|---|---|---|---|---|---|---|---|---|---|---|---|
| 65 | | | | | 70 | | | | | 75 | | | | | 80 |

| Lys | Val | Val | Lys | Thr | Thr | Gly | Ile | Asn | Leu | Val | Ala | Gly | Thr | Gly | Ile |
|---|---|---|---|---|---|---|---|---|---|---|---|---|---|---|---|
| | | | | 85 | | | | | 90 | | | | | 95 | |

| Tyr | Ile | Tyr | Val | Asp | Leu | Pro | Phe | Tyr | Phe | Leu | Asn | Arg | Ser | Ile | Asp |
|---|---|---|---|---|---|---|---|---|---|---|---|---|---|---|---|
| | | | 100 | | | | | 105 | | | | | 110 | | |

| Glu | Ile | Ala | Asp | Leu | Phe | Ile | His | Asp | Ile | Lys | Glu | Gly | Ile | Gln | Ala |
|---|---|---|---|---|---|---|---|---|---|---|---|---|---|---|---|
| | | 115 | | | | | 120 | | | | | 125 | | | |

| Thr | Ser | Asn | Lys | Ala | Gly | Phe | Val | Lys | Ile | Ala | Ala | Asp | Glu | Pro | Gly |
|---|---|---|---|---|---|---|---|---|---|---|---|---|---|---|---|
| | 130 | | | | | 135 | | | | | 140 | | | | |

| Ile | Thr | Lys | Asp | Val | Glu | Lys | Val | Ile | Arg | Ala | Ala | Ile | Thr | His |
|---|---|---|---|---|---|---|---|---|---|---|---|---|---|---|
| 145 | | | | | 150 | | | | | 155 | | | | | 160 |

| Lys | Glu | Ala | Lys | Val | Pro | Ile | Ile | Thr | His | Ser | Asn | Ala | His | Asn | Asn |
|---|---|---|---|---|---|---|---|---|---|---|---|---|---|---|---|
| | | | | 165 | | | | | 170 | | | | | 175 | |

| Thr | Gly | Leu | Glu | Glu | Gln | Arg | Ile | Leu | Met | Glu | Gly | Val | Asp | Pro |
|---|---|---|---|---|---|---|---|---|---|---|---|---|---|---|
| | | | 180 | | | | | 185 | | | | | 190 | |

| Gly | Lys | Ile | Leu | Ile | Gly | His | Leu | Gly | Asp | Thr | Asp | Asn | Thr | Asp | Tyr |
|---|---|---|---|---|---|---|---|---|---|---|---|---|---|---|---|
| | | 195 | | | | | 200 | | | | | 205 | | | |

| Ile | Lys | Lys | Ile | Ala | Asp | Lys | Gly | Ser | Phe | Ile | Gly | Leu | Asp | Arg | Tyr |
|---|---|---|---|---|---|---|---|---|---|---|---|---|---|---|---|
| | 210 | | | | | 215 | | | | | 220 | | | | |

| Gly | Leu | Asp | Leu | Phe | Leu | Pro | Val | Asp | Lys | Arg | Asn | Glu | Thr | Thr | Leu |
|---|---|---|---|---|---|---|---|---|---|---|---|---|---|---|---|
| 225 | | | | | 230 | | | | | 235 | | | | | 240 |

| Lys | Leu | Ile | Lys | Asp | Gly | Tyr | Ser | Asp | Arg | Ile | Met | Ile | Ser | His | Asp |
|---|---|---|---|---|---|---|---|---|---|---|---|---|---|---|---|
| | | | | 245 | | | | | 250 | | | | | 255 | |

| Tyr | Cys | Cys | Thr | Ile | Asp | Leu | Gly | Thr | Ala | Arg | Pro | Glu | Leu | Lys | Pro |
|---|---|---|---|---|---|---|---|---|---|---|---|---|---|---|---|
| | | | 260 | | | | | 265 | | | | | 270 | | |

| Lys | Leu | Ala | Pro | Arg | Trp | Ser | Met | Ala | Leu | Ile | Phe | Glu | Asp | Thr | Ile |
|---|---|---|---|---|---|---|---|---|---|---|---|---|---|---|---|
| | | 275 | | | | | 280 | | | | | 285 | | | |

| Pro | Phe | Leu | Lys | Lys | Asn | Gly | Val | Ser | Glu | Glu | Val | Ile | Asp | Ile | Ile |
|---|---|---|---|---|---|---|---|---|---|---|---|---|---|---|---|
| | 290 | | | | | 295 | | | | | 300 | | | | |

| Phe | Lys | Glu | Asn | Pro | Lys | Lys | Phe | Phe | Ser |
|---|---|---|---|---|---|---|---|---|---|
| 305 | | | | | 310 | | | | |

<210> SEQ ID NO 100
<211> LENGTH: 945
<212> TYPE: DNA
<213> ORGANISM: Sulfolobus islandicus

<400> SEQUENCE: 100
atgcgtattc cgctggttgg taaagaaccg attgaagccg aagatatggg ttttaccctg      60

```
attcatgaac atctgcgtgt ttttagcgaa gcagttcgtt atcagtggcc tcatctgtat    120
aatgaagatg aagaactgcg taatgccgtt aatgaagtta acgtgccat gcagtttggt    180
gttaaaacca ttgttgatcc gaccgttatg ggtctgggtc gtgatattcg ctttatggaa    240
aaagttgtga aaccaccgg tattaatctg gttgcaggca ccggtatttta tatttatgtg    300
gatctgccgt tttatttcct gaaccgcagc attgatgaaa ttgccgacct gtttattcat    360
gatattaaag aaggtattca ggcaaccagc aataaagccg ttttgtgaa aattgcagcc    420
gatgaaccgg gtattaccaa agatgtggaa aaagttattc gtgcagcagc cattacccat    480
aaagaagcca agttccgat tattacccat agcaatgccc ataataatac cggtctggaa    540
gaacagcgta ttctgatgga agaaggtgtt gatccgggta aaattctgat tggtcatctg    600
ggtgataccg ataataccga ttatattaaa aaaattgccg ataaaggcag ctttattggt    660
ctggatcgtt atggtctgga cctgtttctg ccggttgata acgtaatga accacctg    720
aaactgatta agatggcta tagcgatcgc attatgatca gccatgatta ttgttgtacc    780
attgatgcag gcaccgcacg tccggaactg aaaccgaaac tggcaccgcg ttggagcatg    840
gcactgattt ttgaagatac cattccgttt ctgaaaaaaa atggcgtgag cgaagaagtg    900
atcgatatta ttttcaaaga aaacccgaaa aaattcttta gctaa    945
```

<210> SEQ ID NO 101
<211> LENGTH: 314
<212> TYPE: PRT
<213> ORGANISM: Sulfolobus islandicus

<400> SEQUENCE: 101

```
Met Arg Ile Pro Leu Val Gly Lys Glu Pro Ile Glu Ala Glu Asp Met
1               5                   10                  15

Gly Phe Thr Leu Ile His Glu His Leu Arg Val Phe Ser Glu Ala Val
            20                  25                  30

Arg Tyr Gln Trp Pro His Leu Tyr Asn Glu Asp Glu Glu Leu Arg Asn
        35                  40                  45

Ala Val Asn Glu Val Lys Arg Ala Met Gln Phe Gly Val Lys Thr Ile
    50                  55                  60

Val Asp Pro Thr Val Met Gly Leu Gly Arg Asp Ile Arg Phe Met Glu
65                  70                  75                  80

Lys Val Val Lys Thr Thr Gly Ile Asn Leu Val Ala Gly Thr Gly Ile
                85                  90                  95

Tyr Ile Tyr Val Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Ala
        115                 120                 125

Thr Ser Asn Lys Ala Gly Phe Val Lys Ile Ala Ala Asp Glu Pro Gly
    130                 135                 140

Ile Thr Lys Asp Val Glu Lys Val Ile Arg Ala Ala Ile Thr His
145                 150                 155                 160

Lys Glu Ala Lys Val Pro Ile Ile Thr His Ser Asn Ala His Asn Asn
                165                 170                 175

Thr Gly Leu Glu Glu Gln Arg Ile Leu Met Glu Glu Gly Val Asp Pro
            180                 185                 190

Gly Lys Ile Leu Ile Gly His Leu Gly Asp Thr Asp Asn Thr Asp Tyr
        195                 200                 205

Ile Lys Lys Ile Ala Asp Lys Gly Ser Phe Ile Gly Leu Asp Arg Tyr
    210                 215                 220
```

Gly Leu Asp Leu Phe Leu Pro Val Asp Lys Arg Asn Glu Thr Thr Leu
225                 230                 235                 240

Lys Leu Ile Lys Asp Gly Tyr Ser Asp Arg Ile Met Ile Ser His Asp
            245                 250                 255

Tyr Cys Cys Thr Ile Asp Ala Gly Thr Ala Arg Pro Glu Leu Lys Pro
        260                 265                 270

Lys Leu Ala Pro Arg Trp Ser Met Ala Leu Ile Phe Glu Asp Thr Ile
    275                 280                 285

Pro Phe Leu Lys Lys Asn Gly Val Ser Glu Glu Val Ile Asp Ile Ile
290                 295                 300

Phe Lys Glu Asn Pro Lys Lys Phe Phe Ser
305                 310

<210> SEQ ID NO 102
<211> LENGTH: 945
<212> TYPE: DNA
<213> ORGANISM: Sulfolobus islandicus

<400> SEQUENCE: 102
atgcgtattc cgctggttgg taaagaaccg attgaagccg aagatatggg ttttacccctg    60
attcatgaac atctgcgtgt ttttagcgaa gcagttcgtt atcagtggcc tcatctgtat   120
aatgaagatg aagaactgcg taatgccgtt aatgaagtta acgtgccat gcagtttggt   180
gttaaaacca ttgttgatcc gaccgttatg ggtctgggtc gtgatattcg ctttatggaa   240
aaagttgtga aaccaccggg tattaatctg gttgcaggca ccggtatttta tatttatgtg   300
gatctgccgt tttatttct gaaccgcagc attgatgaaa ttgccgacct gtttattcat   360
gatattaaag aaggtattca ggcaaccagc aataaagccg gttttgtgaa aattgcagcc   420
gatgaaccgg gtattaccaa agatgtggaa aaagttattc gtgcagcagc cattacccat   480
aaagaagcca aagttccgat tattacccat agcaatgccc ataataatac cggtctggaa   540
gaacagcgta ttctgatgga agaaggtgtt gatccgggta aaattctgat ggtgcatctg   600
ggtgataccg ataataccga ttatattaaa aaaattgccg ataaaggcag ctttattggt   660
ctggatcgtt atggtctgga cctgtttctg ccggttgata acgtaatga accaccctg    720
aaactgatta agatggcta tagcgatcgc attatgatca gccatgatta ttgttgtacc   780
attgatattg caccgcacg tccggaactg aaaccgaaac tggcaccgcg tttggagcatg   840
gcactgattt ttgaagatac cattccgttt ctgaaaaaaa atggcgtgag cgaagaagtg   900
atcgatatta ttttcaaaga aaacccgaaa aaattcttta gctaa              945

<210> SEQ ID NO 103
<211> LENGTH: 314
<212> TYPE: PRT
<213> ORGANISM: Sulfolobus islandicus

<400> SEQUENCE: 103

Met Arg Ile Pro Leu Val Gly Lys Glu Pro Ile Glu Ala Glu Asp Met
1               5                   10                  15

Gly Phe Thr Leu Ile His Glu His Leu Arg Val Phe Ser Glu Ala Val
            20                  25                  30

Arg Tyr Gln Trp Pro His Leu Tyr Asn Glu Asp Glu Glu Leu Arg Asn
        35                  40                  45

Ala Val Asn Glu Val Lys Arg Ala Met Gln Phe Gly Val Lys Thr Ile
    50                  55                  60

```
Val Asp Pro Thr Val Met Gly Leu Gly Arg Asp Ile Arg Phe Met Glu
 65                  70                  75                  80

Lys Val Val Lys Thr Thr Gly Ile Asn Leu Val Ala Gly Thr Gly Ile
                 85                  90                  95

Tyr Ile Tyr Val Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Ala
        115                 120                 125

Thr Ser Asn Lys Ala Gly Phe Val Lys Ile Ala Ala Asp Glu Pro Gly
    130                 135                 140

Ile Thr Lys Asp Val Glu Lys Val Ile Arg Ala Ala Ile Thr His
145                 150                 155                 160

Lys Glu Ala Lys Val Pro Ile Ile Thr His Ser Asn Ala His Asn Asn
                165                 170                 175

Thr Gly Leu Glu Glu Gln Arg Ile Leu Met Glu Glu Gly Val Asp Pro
            180                 185                 190

Gly Lys Ile Leu Ile Gly His Leu Gly Asp Thr Asp Asn Thr Asp Tyr
        195                 200                 205

Ile Lys Lys Ile Ala Asp Lys Gly Ser Phe Ile Gly Leu Asp Arg Tyr
    210                 215                 220

Gly Leu Asp Leu Phe Leu Pro Val Asp Lys Arg Asn Glu Thr Thr Leu
225                 230                 235                 240

Lys Leu Ile Lys Asp Gly Tyr Ser Asp Arg Ile Met Ile Ser His Asp
                245                 250                 255

Tyr Cys Cys Thr Ile Asp Ile Gly Thr Ala Arg Pro Glu Leu Lys Pro
            260                 265                 270

Lys Leu Ala Pro Arg Trp Ser Met Ala Leu Ile Phe Glu Asp Thr Ile
        275                 280                 285

Pro Phe Leu Lys Lys Asn Gly Val Ser Glu Glu Val Ile Asp Ile Ile
    290                 295                 300

Phe Lys Glu Asn Pro Lys Lys Phe Phe Ser
305                 310

<210> SEQ ID NO 104
<211> LENGTH: 945
<212> TYPE: DNA
<213> ORGANISM: Sulfolobus islandicus

<400> SEQUENCE: 104
atgcgtattc cgctggttgg taaagaaccg attgaagccg aagatatggg ttttacccctg    60 attcatgaac atctgcgtgt ttttagcgaa gcagttcgtt atcagtggcc tcatctgtat    120
aatgaagatg aagaactgcg taatgccgtt aatgaagtta acgtgccat gcagtttggt    180 gttaaaacca ttgttgatcc gaccgttatg ggtctgggtc gtgatattcg ctttatggaa    240
aaagttgtga aaaccaccgg tattaatctg gttgcaggca ccggtattta tatttatgtg    300
gatctgccgt tttattttct gaaccgcagc attgatgaaa ttgccgacct gtttattcat    360
gatattaaag aaggtattca ggcaaccagc aataaagccg gttttgtgaa aattgcagcc    420
gatgaaccgg gtattaccaa agatgtggaa aaagttattc gtgcagcagc cattacccat    480
aaagaagcca agttccgat tattacccat agcaatgccc ataataatac cggtctggaa    540
gaacagcgta ttctgatgga agaaggtgtt gatccgggta aaattctgat tggtcatctg    600
ggtgataccg ataataccga ttatattaaa aaaattgccg ataaaggcag ctttattggt    660
ctggatcgtt atggtctgga cctgtttctg ccggttgata acgtaatga aaccacctg    720
```

```
aaactgatta aagatggcta tagcgatcgc attatgatca gccatgatta ttgttgtacc      780
attgatgttg gcaccgcacg tccggaactg aaaccgaaac tggcaccgcg ttggagcatg      840
gcactgattt ttgaagatac cattccgttt ctgaaaaaaa atggcgtgag cgaagaagtg      900
atcgatatta ttttcaaaga aaacccgaaa aaattcttta gctaa                     945
```

<210> SEQ ID NO 105
<211> LENGTH: 314
<212> TYPE: PRT
<213> ORGANISM: Sulfolobus islandicus

<400> SEQUENCE: 105

```
Met Arg Ile Pro Leu Val Gly Lys Glu Pro Ile Glu Ala Glu Asp Met
1               5                   10                  15

Gly Phe Thr Leu Ile His Glu His Leu Arg Val Phe Ser Glu Ala Val
                20                  25                  30

Arg Tyr Gln Trp Pro His Leu Tyr Asn Glu Asp Glu Glu Leu Arg Asn
            35                  40                  45

Ala Val Asn Glu Val Lys Arg Ala Met Gln Phe Gly Val Lys Thr Ile
        50                  55                  60

Val Asp Pro Thr Val Met Gly Leu Gly Arg Asp Ile Arg Phe Met Glu
65                  70                  75                  80

Lys Val Val Lys Thr Thr Gly Ile Asn Leu Val Ala Gly Thr Gly Ile
                85                  90                  95

Tyr Ile Tyr Val Asp Leu Pro Phe Tyr Phe Leu Asn Arg Ser Ile Asp
                100                 105                 110

Glu Ile Ala Asp Leu Phe Ile His Asp Ile Lys Glu Gly Ile Gln Ala
            115                 120                 125

Thr Ser Asn Lys Ala Gly Phe Val Lys Ile Ala Ala Asp Glu Pro Gly
        130                 135                 140

Ile Thr Lys Asp Val Glu Lys Val Ile Arg Ala Ala Ile Thr His
145                 150                 155                 160

Lys Glu Ala Lys Val Pro Ile Ile Thr His Ser Asn Ala His Asn Asn
                165                 170                 175

Thr Gly Leu Glu Glu Gln Arg Ile Leu Met Glu Glu Gly Val Asp Pro
            180                 185                 190

Gly Lys Ile Leu Ile Gly His Leu Gly Asp Thr Asp Asn Thr Asp Tyr
        195                 200                 205

Ile Lys Lys Ile Ala Asp Lys Gly Ser Phe Ile Gly Leu Asp Arg Tyr
    210                 215                 220

Gly Leu Asp Leu Phe Leu Pro Val Asp Lys Arg Asn Glu Thr Thr Leu
225                 230                 235                 240

Lys Leu Ile Lys Asp Gly Tyr Ser Asp Arg Ile Met Ile Ser His Asp
                245                 250                 255

Tyr Cys Cys Thr Ile Asp Val Gly Thr Ala Arg Pro Glu Leu Lys Pro
            260                 265                 270

Lys Leu Ala Pro Arg Trp Ser Met Ala Leu Ile Phe Glu Asp Thr Ile
        275                 280                 285

Pro Phe Leu Lys Lys Asn Gly Val Ser Glu Glu Val Ile Asp Ile Ile
    290                 295                 300

Phe Lys Glu Asn Pro Lys Lys Phe Phe Ser
305                 310
```

<210> SEQ ID NO 106

<211> LENGTH: 945
<212> TYPE: DNA
<213> ORGANISM: Sulfolobus islandicus

<400> SEQUENCE: 106

```
atgcgtattc cgctggttgg taaagaaccg attgaagccg aagatatggg ttttaccctg      60
attcatgaac atctgcgtgt ttttagcgaa gcagttcgtt atcagtggcc tcatctgtat     120
aatgaagatg aagaactgcg taatgccgtt aatgaagtta acgtgccat gcagtttggt      180
gttaaaacca ttgttgatcc gaccgttatg ggtctgggtc gtgatattcg ctttatggaa     240
aaagttgtga aaaccaccgg tattaatctg gttgcaggca ccggtattta tatttatgtg     300
gatctgccgt tttatttcct gaaccgcagc attgatgaaa ttgccgacct gtttattcat     360
gatattaaag aaggtattca ggcaaccagc aataaagccg ttttgtgaa aattgcagcc      420
gatgaaccgg gtattaccaa agatgtggaa aaagttattc gtgcagcagc cattacccat     480
aaagaagcca agttccgat tattacccat agcaatgccc ataataatac cggtctggaa      540
gaacagcgta ttctgatgga agaaggtgtt gatccgggta aaattctgat ggtcatctg      600
ggtgataccg ataataccga ttatattaaa aaaattgccg ataaaggcag ctttattggt     660
ctggatcgtt atggtctgga cctgtttctg ccggttgata acgtaatga accaccctg      720
aaactgatta agatggcta tagcgatcgc attatgatca gccatgatta ttgttgtacc     780
attgataccg gcaccgcacg tccggaactg aaaccgaaac tggcaccgcg ttggagcatg     840
gcactgattt ttgaagatac cattccgttt ctgaaaaaaa atggcgtgag cgaagaagtg     900
atcgatatta ttttcaaaga aaacccgaaa aaattcttta gctaa                    945
```

<210> SEQ ID NO 107
<211> LENGTH: 314
<212> TYPE: PRT
<213> ORGANISM: Sulfolobus islandicus

<400> SEQUENCE: 107

```
Met Arg Ile Pro Leu Val Gly Lys Glu Pro Ile Glu Ala Glu Asp Met
1               5                   10                  15

Gly Phe Thr Leu Ile His Glu His Leu Arg Val Phe Ser Glu Ala Val
            20                  25                  30

Arg Tyr Gln Trp Pro His Leu Tyr Asn Glu Asp Glu Glu Leu Arg Asn
        35                  40                  45

Ala Val Asn Glu Val Lys Arg Ala Met Gln Phe Gly Val Lys Thr Ile
    50                  55                  60

Val Asp Pro Thr Val Met Gly Leu Gly Arg Asp Ile Arg Phe Met Glu
65                  70                  75                  80

Lys Val Val Lys Thr Thr Gly Ile Asn Leu Val Ala Gly Thr Gly Ile
                85                  90                  95

Tyr Ile Tyr Val Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Ala
        115                 120                 125

Thr Ser Asn Lys Ala Gly Phe Val Lys Ile Ala Ala Asp Glu Pro Gly
    130                 135                 140

Ile Thr Lys Asp Val Glu Lys Val Ile Arg Ala Ala Ile Thr His
145                 150                 155                 160

Lys Glu Ala Lys Val Pro Ile Ile Thr His Ser Asn Ala His Asn Asn
                165                 170                 175
```

```
Thr Gly Leu Glu Glu Gln Arg Ile Leu Met Glu Gly Val Asp Pro
            180                 185                 190

Gly Lys Ile Leu Ile Gly His Leu Gly Asp Thr Asp Asn Thr Asp Tyr
            195                 200                 205

Ile Lys Lys Ile Ala Asp Lys Gly Ser Phe Ile Gly Leu Asp Arg Tyr
    210                 215                 220

Gly Leu Asp Leu Phe Leu Pro Val Asp Lys Arg Asn Glu Thr Thr Leu
225                 230                 235                 240

Lys Leu Ile Lys Asp Gly Tyr Ser Asp Arg Ile Met Ile Ser His Asp
                245                 250                 255

Tyr Cys Cys Thr Ile Asp Thr Gly Thr Ala Arg Pro Glu Leu Lys Pro
            260                 265                 270

Lys Leu Ala Pro Arg Trp Ser Met Ala Leu Ile Phe Glu Asp Thr Ile
            275                 280                 285

Pro Phe Leu Lys Lys Asn Gly Val Ser Glu Glu Val Ile Asp Ile Ile
            290                 295                 300

Phe Lys Glu Asn Pro Lys Lys Phe Phe Ser
305                 310

<210> SEQ ID NO 108
<211> LENGTH: 945
<212> TYPE: DNA
<213> ORGANISM: Sulfolobus islandicus

<400> SEQUENCE: 108
atgcgtattc cgctggttgg taaagaaccg attgaagccg aagatatggg ttttacccctg    60 attcatgaac atctgcgtgt ttttagcgaa gcagttcgtt atcagtggcc tcatctgtat   120
aatgaagatg aagaactgcg taatgccgtt aatgaagtta acgtgccat gcagtttggt    180 gttaaaacca ttgttgatcc gaccgttatg ggtctgggtc gtgatattcg ctttatggaa   240
aaagttgtga aaaccaccgg tattaatctg gttgcaggca ccggtattta tatttatgtg   300
gatctgccgt tttatttctc tgaaccgcag cattgatgaaa ttgccgacct gtttattcat   360
gatattaaag aaggtattca ggcaaccagc aataaagccg ttttgtgaa aattgcagcc    420 gatgaaccgg gtattaccaa agatgtggaa aaagttattc gtgcagcagc cattaccccat   480 aaagaagcca agttccgat tattacccat agcaatgccc ataataatac cggtctggaa   540
gaacagcgta ttctgatgga agaaggtgtt gatccgggta aaattctgat tggtcatctg   600
ggtgataccg ataataccga ttatattaaa aaaattgccg ataaaggcag ctttattggt   660
ctggatcgtt atggtctgga cctgtttctg ccggttgata acgtaatga accaccctg    720 aaactgatta agatggcta gcgatcgc attatgatca gccatgatta tctgtgtacc    780
tttgatgcag gcaccgcacg tccggaactg aaaccgaaac tggcaccgcg ttggagcatg   840
gcactgattt ttgaagatac cattccgttt ctgaaaaaaa atggcgtgag cgaagaagtg   900
atcgatatta ttttcaaaga aaacccgaaa aaattcttta gctaa                  945

<210> SEQ ID NO 109
<211> LENGTH: 314
<212> TYPE: PRT
<213> ORGANISM: Sulfolobus islandicus

<400> SEQUENCE: 109

Met Arg Ile Pro Leu Val Gly Lys Glu Pro Ile Glu Ala Glu Asp Met
1               5                   10                  15

Gly Phe Thr Leu Ile His Glu His Leu Arg Val Phe Ser Glu Ala Val
```

```
                      20                  25                  30
Arg Tyr Gln Trp Pro His Leu Tyr Asn Glu Asp Glu Leu Arg Asn
             35                  40                  45
Ala Val Asn Glu Val Lys Arg Ala Met Gln Phe Gly Val Lys Thr Ile
         50                  55                  60
Val Asp Pro Thr Val Met Gly Leu Gly Arg Asp Ile Arg Phe Met Glu
 65                  70                  75                  80
Lys Val Val Lys Thr Thr Gly Ile Asn Leu Val Ala Gly Thr Gly Ile
                 85                  90                  95
Tyr Ile Tyr Val Asp Leu Pro Phe Tyr Phe Leu Asn Arg Ser Ile Asp
            100                 105                 110
Glu Ile Ala Asp Leu Phe Ile His Asp Ile Lys Glu Gly Ile Gln Ala
        115                 120                 125
Thr Ser Asn Lys Ala Gly Phe Val Lys Ile Ala Ala Asp Glu Pro Gly
    130                 135                 140
Ile Thr Lys Asp Val Glu Lys Val Ile Arg Ala Ala Ile Thr His
145                 150                 155                 160
Lys Glu Ala Lys Val Pro Ile Ile Thr His Ser Asn Ala His Asn Asn
                165                 170                 175
Thr Gly Leu Glu Glu Gln Arg Ile Leu Met Glu Gly Val Asp Pro
            180                 185                 190
Gly Lys Ile Leu Ile Gly His Leu Gly Asp Thr Asp Asn Thr Asp Tyr
        195                 200                 205
Ile Lys Lys Ile Ala Asp Lys Gly Ser Phe Ile Gly Leu Asp Arg Tyr
    210                 215                 220
Gly Leu Asp Leu Phe Leu Pro Val Asp Lys Arg Asn Glu Thr Thr Leu
225                 230                 235                 240
Lys Leu Ile Lys Asp Gly Tyr Ser Asp Arg Ile Met Ile Ser His Asp
                245                 250                 255
Tyr Leu Cys Thr Phe Asp Ala Gly Thr Ala Arg Pro Glu Leu Lys Pro
            260                 265                 270
Lys Leu Ala Pro Arg Trp Ser Met Ala Leu Ile Phe Glu Asp Thr Ile
        275                 280                 285
Pro Phe Leu Lys Lys Asn Gly Val Ser Glu Glu Val Ile Asp Ile Ile
    290                 295                 300
Phe Lys Glu Asn Pro Lys Lys Phe Phe Ser
305                 310

<210> SEQ ID NO 110
<211> LENGTH: 945
<212> TYPE: DNA
<213> ORGANISM: Sulfolobus islandicus

<400> SEQUENCE: 110
atgcgtattc cgctggttgg taaagaaccg attgaagccg aagatatggg ttttaccctg      60
attcatgaac atctgcgtgc atttagcgaa gcagttcgtt atcagtggcc tcatctgtat     120
aatgaagatg aagaactgcg taatgccgtt aatgaagtta acgtgccat gcagtttggt     180
gttaaaacca ttgttgatcc gaccgttatg ggtctgggtc gtgatattcg ctttatggaa     240
aaagttgtga aaaccaccgg tattaatctg gttgcaggca ccggtatttg gatttatgtg     300
gatctgccgt tttatttct gaaccgcagc attgatgaaa ttgccgacct gtttattcat     360
gatattaaag aaggtattca ggcaaccagc aataaagccg gttttgtgaa aattgcagcc     420
gatgaaccgg gtattaccaa agatgtggaa aaagttattc gtgcagcagc cattacccat     480
```

```
aaagaagcca aagttccgat tattacccat agcaatgccc ataataatac cggtctggaa      540
gaacagcgta ttctgatgga agaaggtgtt gatccgggta aaattctgat tggtcatctg      600
ggtgataccg ataataccga ttatattaaa aaaattgccg ataaaggcag ctttattggt      660
ctggatcgtt atggtctgga catgtttctg ccggttgata acgtaatgaa accaccctg       720 aaactgatta agatggcta tagcgatcgc attatgatca gccatgatta ttgttgtacc       780
attgatatgg gcaccgcacg tccggaactg aaaccgaaac tggcaccgcg ttggagcatg      840
gcactgattt ttgaagatac cattccgttt ctgaaaaaaa atggcgtgag cgaagaagtg      900
atcgatatta ttttcaaaga aaacccgaaa aaattcttta gctaa                     945
```

<210> SEQ ID NO 111
<211> LENGTH: 314
<212> TYPE: PRT
<213> ORGANISM: Sulfolobus islandicus

<400> SEQUENCE: 111

```
Met Arg Ile Pro Leu Val Gly Lys Glu Pro Ile Glu Ala Glu Asp Met
1               5                   10                  15

Gly Phe Thr Leu Ile His Glu His Leu Arg Ala Phe Ser Glu Ala Val
            20                  25                  30

Arg Tyr Gln Trp Pro His Leu Tyr Asn Glu Asp Glu Leu Arg Asn
        35                  40                  45

Ala Val Asn Glu Val Lys Arg Ala Met Gln Phe Gly Val Lys Thr Ile
    50                  55                  60

Val Asp Pro Thr Val Met Gly Leu Gly Arg Asp Ile Arg Phe Met Glu
65                  70                  75                  80

Lys Val Val Lys Thr Thr Gly Ile Asn Leu Val Ala Gly Thr Gly Ile
                85                  90                  95

Trp Ile Tyr Val Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Ala
        115                 120                 125

Thr Ser Asn Lys Ala Gly Phe Val Lys Ile Ala Ala Asp Glu Pro Gly
    130                 135                 140

Ile Thr Lys Asp Val Glu Lys Val Ile Arg Ala Ala Ile Thr His
145                 150                 155                 160

Lys Glu Ala Lys Val Pro Ile Ile Thr His Ser Asn Ala His Asn Asn
                165                 170                 175

Thr Gly Leu Glu Glu Gln Arg Ile Leu Met Glu Gly Val Asp Pro
            180                 185                 190

Gly Lys Ile Leu Ile Gly His Leu Gly Asp Thr Asp Asn Thr Asp Tyr
        195                 200                 205

Ile Lys Lys Ile Ala Asp Lys Gly Ser Phe Ile Gly Leu Asp Arg Tyr
    210                 215                 220

Gly Leu Asp Met Phe Leu Pro Val Asp Lys Arg Asn Glu Thr Thr Leu
225                 230                 235                 240

Lys Leu Ile Lys Asp Gly Tyr Ser Asp Arg Ile Met Ile Ser His Asp
                245                 250                 255

Tyr Cys Cys Thr Ile Asp Met Gly Thr Ala Arg Pro Glu Leu Lys Pro
            260                 265                 270

Lys Leu Ala Pro Arg Trp Ser Met Ala Leu Ile Phe Glu Asp Thr Ile
        275                 280                 285
```

```
Pro Phe Leu Lys Lys Asn Gly Val Ser Glu Glu Val Ile Asp Ile Ile
        290                 295                 300

Phe Lys Glu Asn Pro Lys Lys Phe Phe Ser
305                 310
```

<210> SEQ ID NO 112
<211> LENGTH: 945
<212> TYPE: DNA
<213> ORGANISM: Sulfolobus islandicus

<400> SEQUENCE: 112

```
atgcgtattc cgctggttgg taaagaaccg attgaagccg aagatatggg ttttaccctg    60
attcatgaac atctgcgtgc atttagcgaa gcagttcgtt atcagtggcc tcatctgtat   120
aatgaagatg aagaactgcg taatgccgtt aatgaagtta acgtgccat gcagtttggt   180
gttaaaacca ttgttgatcc gaccgttatg ggtctgggtc gtgatattcg ctttatggaa   240
aaagttgtga aaccaccggg tattaatctg gttgcaggca ccggtatttg gatttatgtg   300
gatctgccgt tttatttct gaaccgcagc attgatgaaa ttgccgacct gtttattcat   360
gatattaaag aaggtattca ggcaaccagc aataaagccg gttttgtgaa aattgcagcc   420
gatgaaccgg gtattaccaa agatgtggaa aaagttattc gtgcagcagc cattacccat   480
aaagaagcca agttccgat tattacccat agcaatgccc ataataatac cggtctggaa   540
gaacagcgta ttctgatgga agaaggtgtt gatccgggta aaattctgat ggtcatctg   600
ggtgataccg ataataccga ttatattaaa aaaattgccg ataaaggcag ctttattggt   660
ctggatcgtt atggtctgga cctgtttctg ccggttgata acgtaatga accaccctg    720
aaactgatta agatggcta tagcgatcgc attatgatca gccatgatta ttgttgtacc   780
attgatctgg gcaccgcacg tccggaactg aaaccgaaac tggcaccgcg ttggagcacg   840
gcactgattt ttgaagatac cattccgttt ctgaaaaaaa atggcgtgag cgaagaagtg   900
atcgatatta ttttcaaaga aaacccgaaa aaattcttta gctaa                   945
```

<210> SEQ ID NO 113
<211> LENGTH: 314
<212> TYPE: PRT
<213> ORGANISM: Sulfolobus islandicus

<400> SEQUENCE: 113

```
Met Arg Ile Pro Leu Val Gly Lys Glu Pro Ile Glu Ala Glu Asp Met
1               5                  10                  15

Gly Phe Thr Leu Ile His Glu His Leu Arg Ala Phe Ser Glu Ala Val
            20                  25                  30

Arg Tyr Gln Trp Pro His Leu Tyr Asn Glu Asp Glu Glu Leu Arg Asn
        35                  40                  45

Ala Val Asn Glu Val Lys Arg Ala Met Gln Phe Gly Val Lys Thr Ile
    50                  55                  60

Val Asp Pro Thr Val Met Gly Leu Gly Arg Asp Ile Arg Phe Met Glu
65                  70                  75                  80

Lys Val Val Lys Thr Thr Gly Ile Asn Leu Val Ala Gly Thr Gly Ile
                85                  90                  95

Trp Ile Tyr Val Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Ala
        115                 120                 125

Thr Ser Asn Lys Ala Gly Phe Val Lys Ile Ala Ala Asp Glu Pro Gly
```

```
                  130                 135                 140
Ile Thr Lys Asp Val Glu Lys Val Ile Arg Ala Ala Ile Thr His
145                 150                 155                 160

Lys Glu Ala Lys Val Pro Ile Ile Thr His Ser Asn Ala His Asn Asn
                165                 170                 175

Thr Gly Leu Glu Glu Gln Arg Ile Leu Met Glu Glu Gly Val Asp Pro
                180                 185                 190

Gly Lys Ile Leu Ile Gly His Leu Gly Asp Thr Asp Asn Thr Asp Tyr
                195                 200                 205

Ile Lys Lys Ile Ala Asp Lys Gly Ser Phe Ile Gly Leu Asp Arg Tyr
                210                 215                 220

Gly Leu Asp Leu Phe Leu Pro Val Asp Lys Arg Asn Glu Thr Thr Leu
225                 230                 235                 240

Lys Leu Ile Lys Asp Gly Tyr Ser Asp Arg Ile Met Ile Ser His Asp
                245                 250                 255

Tyr Cys Cys Thr Ile Asp Leu Gly Thr Ala Arg Pro Glu Leu Lys Pro
                260                 265                 270

Lys Leu Ala Pro Arg Trp Ser Thr Ala Leu Ile Phe Glu Asp Thr Ile
                275                 280                 285

Pro Phe Leu Lys Lys Asn Gly Val Ser Glu Glu Val Ile Asp Ile Ile
                290                 295                 300

Phe Lys Glu Asn Pro Lys Lys Phe Phe Ser
305                 310
```

<210> SEQ ID NO 114
<211> LENGTH: 945
<212> TYPE: DNA
<213> ORGANISM: Sulfolobus islandicus

<400> SEQUENCE: 114

```
atgcgtattc cgctggttgg taaagaaccg attgaagccg aagatatggg ttttaccctg      60
attcatgaac atctgcgtgt ttttagcgaa gcagttcgtt atcagtggcc tcatctgtat     120
aatgaagatg aagaactgcg taatgccgtt aatgaagtta acgtgccat gcagtttggt      180
gttaaaacca ttgttgatcc gaccgttatg ggtctgggtc gtgatattcg ctttatggaa     240
aaagttgtga aaccaccggg tattaatctg gttgcaggca ccggtattta tatttatgtg     300
gatctgccgt ttattttcct gaaccgcagc attgatgaaa ttgccgacct gtttattcat     360
gatattaaag aaggtattca ggcaaccagc aataaagccg ttttgtgaa aattgcagcc      420
gatgaaccgg gtattaccaa agatgtggaa aagttattc gtgcagcagc cattacccat     480
aaagaagcca agttccgat tattacccat agcaatgccc ataataatac cggtctggaa      540
gaacagcgta ttctgatgga agaaggtgtt gatccgggta aaattctgat tggtcatctg     600
ggtgataccg ataataccga ttatattaaa aaaattgccg ataaaggcag ctttattggt     660
ctggatcgtt atggtctgga cctgtttctg ccggttgata acgtaatga accaccctg       720
aaactgatta agatggcta tagcgatcgc attatgatca gccatgatta tgcttgtacc     780
attgatatgg gcaccgcacg tccggaactg aaaccgaaac tggcaccgcg ttggagcacg    840
gcactgattt tgaagatac cattccgttt ctgaaaaaaa atggcgtgag cgaagaagtg     900
atcgatatta ttttcaaaga aaacccgaaa aaattcttta gctaa                   945
```

<210> SEQ ID NO 115
<211> LENGTH: 314
<212> TYPE: PRT

<213> ORGANISM: Sulfolobus islandicus

<400> SEQUENCE: 115

Met Arg Ile Pro Leu Val Gly Lys Glu Pro Ile Glu Ala Glu Asp Met
1               5                   10                  15
Gly Phe Thr Leu Ile His Glu His Leu Arg Val Phe Ser Glu Ala Val
            20                  25                  30
Arg Tyr Gln Trp Pro His Leu Tyr Asn Glu Asp Glu Leu Arg Asn
        35                  40                  45
Ala Val Asn Glu Val Lys Arg Ala Met Gln Phe Gly Val Lys Thr Ile
    50                  55                  60
Val Asp Pro Thr Val Met Gly Leu Gly Arg Asp Ile Arg Phe Met Glu
65                  70                  75                  80
Lys Val Val Lys Thr Thr Gly Ile Asn Leu Val Ala Gly Thr Gly Ile
                85                  90                  95
Tyr Ile Tyr Val Asp Leu Pro Phe Tyr Phe Leu Asn Arg Ser Ile Asp
            100                 105                 110
Glu Ile Ala Asp Leu Phe Ile His Asp Ile Lys Glu Gly Ile Gln Ala
        115                 120                 125
Thr Ser Asn Lys Ala Gly Phe Val Lys Ile Ala Ala Asp Glu Pro Gly
    130                 135                 140
Ile Thr Lys Asp Val Glu Lys Val Ile Arg Ala Ala Ile Thr His
145                 150                 155                 160
Lys Glu Ala Lys Val Pro Ile Ile Thr His Ser Asn Ala His Asn Asn
                165                 170                 175
Thr Gly Leu Glu Glu Gln Arg Ile Leu Met Glu Gly Val Asp Pro
            180                 185                 190
Gly Lys Ile Leu Ile Gly His Leu Gly Asp Thr Asp Asn Thr Asp Tyr
        195                 200                 205
Ile Lys Lys Ile Ala Asp Lys Gly Ser Phe Ile Gly Leu Asp Arg Tyr
    210                 215                 220
Gly Leu Asp Leu Phe Leu Pro Val Asp Lys Arg Asn Glu Thr Thr Leu
225                 230                 235                 240
Lys Leu Ile Lys Asp Gly Tyr Ser Asp Arg Ile Met Ile Ser His Asp
                245                 250                 255
Tyr Ala Cys Thr Ile Asp Met Gly Thr Ala Arg Pro Glu Leu Lys Pro
            260                 265                 270
Lys Leu Ala Pro Arg Trp Ser Thr Ala Leu Ile Phe Glu Asp Thr Ile
        275                 280                 285
Pro Phe Leu Lys Lys Asn Gly Val Ser Glu Glu Val Ile Asp Ile Ile
    290                 295                 300
Phe Lys Glu Asn Pro Lys Lys Phe Phe Ser
305                 310

<210> SEQ ID NO 116
<211> LENGTH: 945
<212> TYPE: DNA
<213> ORGANISM: Sulfolobus islandicus

<400> SEQUENCE: 116
atgcgtattc cgctggttgg taaagaaccg attgaagccg aagatatggg ttttaccctg    60
attcatgaac atctgcgtgc atttagcgaa gcagttcgtt atcagtggcc tcatctgtat   120
aatgaagatg aagaactgcg taatgccgtt aatgaagtta acgtgccat gcagtttggt   180 gttaaaacca ttgttgatcc gaccgttatg ggtctgggtc gtgatactcg ctttatggaa   240

-continued

```
aaagttgtga aaaccaccgg tattaatctg gttgcaggca ccggtatttg gattttgtgt    300
gatctgccgt tttattttct gaaccgcagc attgatgaaa ttgccgacct gtttattcat    360
gatattaaag aaggtattca ggcaacccccg aataaagccg ttttgtgaa aattgcagcc    420 gatgaaccgg gtattaccaa agatgtggaa aagttattc gtgcagcagc cattacccat    480
aaagaagcca agttccgat tattacccat agcaatgccc ataataatac cggtctggaa    540
gaacagcgta ttctgatgga agaaggtgtt gatccgggta aaattctgat tggtcatctg    600
ggtgataccg ataataccga ttatattaaa aaaattgccg ataaaggcag ctttattggt    660
ctggatcgtt atggtgtgga cctgttctg ccggttgata acgtaatga accaccctg      720 aaactgatta agatggcta tagcgatcgc attatgatca gccatgatta ttgttgtacc    780
attgattggg gcaccgcacg tccggaactg aaaccgaaac tggcaccgcg ttggagcatg    840
gcactgattt ttgaagatac cattccgttt ctgaaaaaaa atggcgtgag cgaagaagtg    900
atcgatatta ttttcaaaga aaacccgaaa aaattcttta gctaa                    945
```

<210> SEQ ID NO 117
<211> LENGTH: 314
<212> TYPE: PRT
<213> ORGANISM: Sulfolobus islandicus

<400> SEQUENCE: 117

```
Met Arg Ile Pro Leu Val Gly Lys Glu Pro Ile Glu Ala Glu Asp Met
1               5                   10                  15

Gly Phe Thr Leu Ile His Glu His Leu Arg Ala Phe Ser Glu Ala Val
            20                  25                  30

Arg Tyr Gln Trp Pro His Leu Tyr Asn Glu Asp Glu Glu Leu Arg Asn
        35                  40                  45

Ala Val Asn Glu Val Lys Arg Ala Met Gln Phe Gly Val Lys Thr Ile
    50                  55                  60

Val Asp Pro Thr Val Met Gly Leu Gly Arg Asp Thr Arg Phe Met Glu
65                  70                  75                  80

Lys Val Val Lys Thr Thr Gly Ile Asn Leu Val Ala Gly Thr Gly Ile
                85                  90                  95

Trp Ile Phe Val Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Ala
        115                 120                 125

Thr Pro Asn Lys Ala Gly Phe Val Lys Ile Ala Ala Asp Glu Pro Gly
    130                 135                 140

Ile Thr Lys Asp Val Glu Lys Val Ile Arg Ala Ala Ile Thr His
145                 150                 155                 160

Lys Glu Ala Lys Val Pro Ile Ile Thr His Ser Asn Ala His Asn Asn
                165                 170                 175

Thr Gly Leu Glu Glu Gln Arg Ile Leu Met Glu Glu Gly Val Asp Pro
            180                 185                 190

Gly Lys Ile Leu Ile Gly His Leu Gly Asp Thr Asp Asn Thr Asp Tyr
        195                 200                 205

Ile Lys Lys Ile Ala Asp Lys Gly Ser Phe Ile Gly Leu Asp Arg Tyr
    210                 215                 220

Gly Val Asp Leu Phe Leu Pro Val Asp Lys Arg Asn Glu Thr Thr Leu
225                 230                 235                 240

Lys Leu Ile Lys Asp Gly Tyr Ser Asp Arg Ile Met Ile Ser His Asp
```

```
            245                 250                 255
Tyr Cys Cys Thr Ile Asp Trp Gly Thr Ala Arg Pro Glu Leu Lys Pro
            260                 265                 270

Lys Leu Ala Pro Arg Trp Ser Met Ala Leu Ile Phe Glu Asp Thr Ile
            275                 280                 285

Pro Phe Leu Lys Lys Asn Gly Val Ser Glu Val Ile Asp Ile Ile
            290                 295                 300

Phe Lys Glu Asn Pro Lys Lys Phe Phe Ser
305                 310

<210> SEQ ID NO 118
<211> LENGTH: 945
<212> TYPE: DNA
<213> ORGANISM: Sulfolobus islandicus

<400> SEQUENCE: 118
atgcgtattc cgctggttgg taaagaaccg attgaagccg aagatatggg ttttaccctg      60
attcatgaac atctgcgtgt ttttagcgaa gcagttcgtt atcagtggcc ccatctgtat     120
aatgaagatg aagaactgcg taatgccgtt aatgaagtta acgtgccat gcagtttggt      180 gttaaaacca ttgttgatcc gaccgttatg ggtattggtc gtgatattcg ctttatggaa     240
aaagttgtga aaccaccgg tattaatctg gttgcaggca ccggtattta tttttgtg       300 gatctgccgt ttatttcct gaaccgcagc attgatgaaa ttgccgacct gtttattcat     360
gatttaaaag aaggtattca ggcaaccagc aataaagccg ttttgtgaa aattgcagcc     420 gatgaaccgg gtattaccaa agatgtggaa aaagtcattc gtgcagcagc cattacccat     480
aaagaagcca agttccgat tattacccat agcaatgccc ataataatac cggtctggaa     540
gaacagcgta ttctgatgga agaaggtgtt gatccgggta aaattctgat ggtcatctg      600 ggtgataccg ataataccga ttatattaaa aaaattgccg ataaaggcag ctttattggt     660
ctggatcgtt atggtctgga catgtctctg ccggttgata acgtaatga accacccctg      720 aaactgatta agatggcta tagcgatcgc attatgatca gccatgatta ttgttgtacc     780
attgatctgg gcaccgcacg tccggaactg aaaccgaaac tggcaccgcg ttggagcatg     840
gcactgattt ttgaagatac cattccgttt ctgaaaaaaa atggcgtgag cgaagaagtg     900
atcgatatta ttttcaaaga aaacccgaaa aaattcttta gctaa                    945

<210> SEQ ID NO 119
<211> LENGTH: 314
<212> TYPE: PRT
<213> ORGANISM: Sulfolobus islandicus

<400> SEQUENCE: 119

Met Arg Ile Pro Leu Val Gly Lys Glu Pro Ile Glu Ala Glu Asp Met
1               5                   10                  15

Gly Phe Thr Leu Ile His Glu His Leu Arg Val Phe Ser Glu Ala Val
            20                  25                  30

Arg Tyr Gln Trp Pro His Leu Tyr Asn Glu Asp Glu Glu Leu Arg Asn
        35                  40                  45

Ala Val Asn Glu Val Lys Arg Ala Met Gln Phe Gly Val Lys Thr Ile
    50                  55                  60

Val Asp Pro Thr Val Met Gly Ile Gly Arg Asp Ile Arg Phe Met Glu
65                  70                  75                  80

Lys Val Val Lys Thr Thr Gly Ile Asn Leu Val Ala Gly Thr Gly Ile
            85                  90                  95
```

Tyr Ile Phe Val Asp Leu Pro Phe Tyr Phe Leu Asn Arg Ser Ile Asp
                100                 105                 110

Glu Ile Ala Asp Leu Phe Ile His Asp Leu Lys Glu Gly Ile Gln Ala
            115                 120                 125

Thr Ser Asn Lys Ala Gly Phe Val Lys Ile Ala Ala Asp Glu Pro Gly
        130                 135                 140

Ile Thr Lys Asp Val Glu Lys Val Ile Arg Ala Ala Ile Thr His
145                 150                 155                 160

Lys Glu Ala Lys Val Pro Ile Ile Thr His Ser Asn Ala His Asn Asn
                165                 170                 175

Thr Gly Leu Glu Glu Gln Arg Ile Leu Met Glu Glu Gly Val Asp Pro
            180                 185                 190

Gly Lys Ile Leu Ile Gly His Leu Gly Asp Thr Asp Asn Thr Asp Tyr
        195                 200                 205

Ile Lys Lys Ile Ala Asp Lys Gly Ser Phe Ile Gly Leu Asp Arg Tyr
    210                 215                 220

Gly Leu Asp Met Ser Leu Pro Val Asp Lys Arg Asn Glu Thr Thr Leu
225                 230                 235                 240

Lys Leu Ile Lys Asp Gly Tyr Ser Asp Arg Ile Met Ile Ser His Asp
                245                 250                 255

Tyr Cys Cys Thr Ile Asp Leu Gly Thr Ala Arg Pro Glu Leu Lys Pro
            260                 265                 270

Lys Leu Ala Pro Arg Trp Ser Met Ala Leu Ile Phe Glu Asp Thr Ile
        275                 280                 285

Pro Phe Leu Lys Lys Asn Gly Val Ser Glu Glu Val Ile Asp Ile Ile
    290                 295                 300

Phe Lys Glu Asn Pro Lys Lys Phe Phe Ser
305                 310

<210> SEQ ID NO 120
<211> LENGTH: 945
<212> TYPE: DNA
<213> ORGANISM: Sulfolobus islandicus

<400> SEQUENCE: 120
atgcgtattc cgctggttgg taaagaaccg attgaagccg aagatatggg ttttaccctg    60
attcatgaac atctgcgtgt ttttagcgaa gcagttcgtt atcagtggcc ccatctgtat   120
aatgaagatg aagaactgcg taatgccgtt aatgaagtta acgtgccat gcagtttggt    180
gttaaaacca ttgttgatcc gagtgttatg ggtattggtc gtgatattcg ctttatggaa   240
aaagttgtga aaccaccgg tattaatctg gttgcaggca ccggtatttta tatttatgtg   300
gatctgccgt tttatttct gaaccgcagc attgatgaaa ttgccgacct gtttattcat   360
gatattaaag aaggtattca ggcaaccccg aataagccg ttttgtgaa aattgcagcc    420
gatgaaccgg gtattaccaa agatgtggaa aagttattc gtgcagcagc cattacccat   480
aaagaagcca agttccgat tattacccat agcaatgccc ataataatac cggtctggaa   540
gaacagcgta ttctgatgga agaaggtgtt gatccgggta aaattctgat tggtcatctg   600
ggtgataccg ataataccga ttatattaaa aaaattgccg ataaaggcag ctttattggt   660
ctggatcgtt atggtctgga catgtctctg ccggttgata acgtaatga accaccctg    720
aaactgatta agatggcta tagcgatcgc attatgatca gccatgatta ttgttgtacc   780
attgatatgg gcaccgcacg tccggaactg aaaccgaaac cggcaccgcg ttggagcatg   840

```
gcactgattt tgaagatac cattccgttt ctgaaaaaaa atggcgtgag cgaagaagtg    900
atcgatatta ttttcaaaga aaacccgaaa aaattcttta gctaa                   945
```

<210> SEQ ID NO 121
<211> LENGTH: 314
<212> TYPE: PRT
<213> ORGANISM: Sulfolobus islandicus

<400> SEQUENCE: 121

```
Met Arg Ile Pro Leu Val Gly Lys Glu Pro Ile Glu Ala Glu Asp Met
1               5                   10                  15

Gly Phe Thr Leu Ile His Glu His Leu Arg Val Phe Ser Glu Ala Val
                20                  25                  30

Arg Tyr Gln Trp Pro His Leu Tyr Asn Glu Asp Glu Glu Leu Arg Asn
            35                  40                  45

Ala Val Asn Glu Val Lys Arg Ala Met Gln Phe Gly Val Lys Thr Ile
        50                  55                  60

Val Asp Pro Ser Val Met Gly Ile Gly Arg Asp Ile Arg Phe Met Glu
65                  70                  75                  80

Lys Val Val Lys Thr Thr Gly Ile Asn Leu Val Ala Gly Thr Gly Ile
                85                  90                  95

Tyr Ile Tyr Val Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Ala
        115                 120                 125

Thr Pro Asn Lys Ala Gly Phe Val Lys Ile Ala Ala Asp Glu Pro Gly
130                 135                 140

Ile Thr Lys Asp Val Glu Lys Val Ile Arg Ala Ala Ile Thr His
145                 150                 155                 160

Lys Glu Ala Lys Val Pro Ile Ile Thr His Ser Asn Ala His Asn Asn
                165                 170                 175

Thr Gly Leu Glu Glu Gln Arg Ile Leu Met Glu Glu Gly Val Asp Pro
            180                 185                 190

Gly Lys Ile Leu Ile Gly His Leu Gly Asp Thr Asp Asn Thr Asp Tyr
        195                 200                 205

Ile Lys Lys Ile Ala Asp Lys Gly Ser Phe Ile Gly Leu Asp Arg Tyr
    210                 215                 220

Gly Leu Asp Met Ser Leu Pro Val Asp Lys Arg Asn Glu Thr Thr Leu
225                 230                 235                 240

Lys Leu Ile Lys Asp Gly Tyr Ser Asp Arg Ile Met Ile Ser His Asp
                245                 250                 255

Tyr Cys Cys Thr Ile Asp Met Gly Thr Ala Arg Pro Glu Leu Lys Pro
            260                 265                 270

Lys Pro Ala Pro Arg Trp Ser Met Ala Leu Ile Phe Glu Asp Thr Ile
        275                 280                 285

Pro Phe Leu Lys Lys Asn Gly Val Ser Glu Val Ile Asp Ile Ile
    290                 295                 300

Phe Lys Glu Asn Pro Lys Lys Phe Phe Ser
305                 310
```

<210> SEQ ID NO 122
<211> LENGTH: 945
<212> TYPE: DNA
<213> ORGANISM: Sulfolobus islandicus

<400> SEQUENCE: 122

```
atgcgtattc cgctggttgg taaagaaccg attgaagccg aagatatggg ttttaccctg    60
attcatgaac atctgcgtgt ttttagcgaa gcagttcgtt atcagtggcc tcatctgtat   120
aatgaagatg aagaactgcg taatgccgtt aatgaagtta aacgtgccat gcagtttggt   180
gttaaaacca ttgttgatcc gagtgttatg ggtctgggtc gtgatactcg ctttatggaa   240
aaagttgtga aaccaccggg tattaatctg gttgcaggca ccggtatttg gattttgtg    300 gatctgccgt tttattttct gaaccgcagc attgatgaaa ttgccgacct gtttattcat   360
gatattaaag aaggtattca ggcaaccagc aataaagccg gttttgtgaa aattgcagcc   420
gatgaaccgg gtattaccaa agatgtggaa aagttattc gtgcagcagc cattacccat    480
aaagaagcca agttccgat tattacccat agcaatgccc ataataatac cggtctggaa    540
gaacagcgta ttctgatgga agaaggtgtt gatccgggta aaattctgat tggtcatctg   600
ggtgataccg ataataccga ttatattaaa aaaattgccg ataaaggcag ctttattggt   660
ctggatcgtt atggtctgga catgtttctg ccggttgata acgtaatga accaccctg     720 aaactgatta agatggcta tagcgatcgc attatgatca gccatgatta ttgttgtacc   780
attgatctgg gcaccgcacg tccggaactg aaaccgaaac tggcaccgcg ttggagcatg   840
gcactgattt ttgaagatac cattccgttt ctgaaaaaaa atggcgtgag cgaagaagtg   900
atcgatatta ttttcaaaga aaacccgaaa aaattcttta gctaa                    945
```

<210> SEQ ID NO 123
<211> LENGTH: 314
<212> TYPE: PRT
<213> ORGANISM: Sulfolobus islandicus

<400> SEQUENCE: 123

```
Met Arg Ile Pro Leu Val Gly Lys Glu Pro Ile Glu Ala Glu Asp Met
1               5                   10                  15

Gly Phe Thr Leu Ile His Glu His Leu Arg Val Phe Ser Glu Ala Val
            20                  25                  30

Arg Tyr Gln Trp Pro His Leu Tyr Asn Glu Asp Glu Glu Leu Arg Asn
        35                  40                  45

Ala Val Asn Glu Val Lys Arg Ala Met Gln Phe Gly Val Lys Thr Ile
    50                  55                  60

Val Asp Pro Ser Val Met Gly Leu Gly Arg Asp Thr Arg Phe Met Glu
65                  70                  75                  80

Lys Val Val Lys Thr Thr Gly Ile Asn Leu Val Ala Gly Thr Gly Ile
                85                  90                  95

Trp Ile Phe Val Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Ala
        115                 120                 125

Thr Ser Asn Lys Ala Gly Phe Val Lys Ile Ala Ala Asp Glu Pro Gly
    130                 135                 140

Ile Thr Lys Asp Val Glu Lys Val Ile Arg Ala Ala Ile Thr His
145                 150                 155                 160

Lys Glu Ala Lys Val Pro Ile Ile Thr His Ser Asn Ala His Asn Asn
                165                 170                 175

Thr Gly Leu Glu Glu Gln Arg Ile Leu Met Glu Glu Gly Val Asp Pro
            180                 185                 190

Gly Lys Ile Leu Ile Gly His Leu Gly Asp Thr Asp Asn Thr Asp Tyr
        195                 200                 205
```

```
Ile Lys Lys Ile Ala Asp Lys Gly Ser Phe Ile Gly Leu Asp Arg Tyr
    210                 215                 220

Gly Leu Asp Met Phe Leu Pro Val Asp Lys Arg Asn Glu Thr Thr Leu
225                 230                 235                 240

Lys Leu Ile Lys Asp Gly Tyr Ser Asp Arg Ile Met Ile Ser His Asp
                245                 250                 255

Tyr Cys Cys Thr Ile Asp Leu Gly Thr Ala Arg Pro Glu Leu Lys Pro
            260                 265                 270

Lys Leu Ala Pro Arg Trp Ser Met Ala Leu Ile Phe Glu Asp Thr Ile
        275                 280                 285

Pro Phe Leu Lys Lys Asn Gly Val Ser Glu Val Ile Asp Ile Ile
    290                 295                 300

Phe Lys Glu Asn Pro Lys Lys Phe Phe Ser
305                 310
```

<210> SEQ ID NO 124
<211> LENGTH: 945
<212> TYPE: DNA
<213> ORGANISM: Sulfolobus islandicus

<400> SEQUENCE: 124

```
atgcgtattc cgctggttgg tgaagaaccg attgaagccg aagatatggg ttttaccctg      60
attcatgaac atctgcgtgt ttttagcgaa gcagttcgtt atcagtggcc tcatctgtat     120
aatgaagatg aagaactgcg taatgccgtt aatgaagtta acgtgccat gcagtttggt      180
gttaaaacca ttgttgatcc gaccgttatg ggtctgggtc gtgatattcg ctttatggaa     240
aaagttgtga aaccaccgg tattaatctg gttgcaggca ccggtatttg gattttgtg      300
gatctgccgt tttattttct gaaccgcagc attgatgaaa ttgccgacct gtttattcat     360
gatattaaag aaggtattca ggcaaccagc aataaagccg ttttgtgaa aattgcagcc     420
gatgaaccgg gtattaccaa agatgtggaa aaagttattc gtgcagcagc cattacccat    480
aaagaagcca agttccgat tattacccat agcaatgccc ataataatac cggtctggaa     540
gaacagcgta ttctgatgga agaaggtgtt gatccgggta aaattctgat tggtcatctg    600
ggtgataccg ataataccga ttatattaaa aaaattgccg ataaaggcag ctttattggt    660
ctggatcgtt atggtctgga catgtttctg ccggttgata acgtaatga accaccctg      720
aaactgatta agatggcta tagcgatcgc attatgatca gccatgatta tgttgtacc     780
attgattggg gcaccgcacg tccggaactg aaaccgaaac tggcaccgcg ttggagcatg    840
gcactgattt ttgaagatac cattccgttt ctgaaaaaaa atggcgtgag cgaagaagtg    900
atcgatatta ttttcaaaga aaacccgaaa aaattcttta gctaa                    945
```

<210> SEQ ID NO 125
<211> LENGTH: 314
<212> TYPE: PRT
<213> ORGANISM: Sulfolobus islandicus

<400> SEQUENCE: 125

```
Met Arg Ile Pro Leu Val Gly Glu Glu Pro Ile Glu Ala Glu Asp Met
1               5                   10                  15

Gly Phe Thr Leu Ile His Glu His Leu Arg Val Phe Ser Glu Ala Val
                20                  25                  30

Arg Tyr Gln Trp Pro His Leu Tyr Asn Glu Asp Glu Glu Leu Arg Asn
            35                  40                  45
```

Ala Val Asn Glu Val Lys Arg Ala Met Gln Phe Gly Val Lys Thr Ile
    50                  55                  60
Val Asp Pro Thr Val Met Gly Leu Gly Arg Asp Ile Arg Phe Met Glu
65                  70                  75                  80
Lys Val Val Lys Thr Thr Gly Ile Asn Leu Val Ala Gly Thr Gly Ile
                85                  90                  95
Trp Ile Phe Val Asp Leu Pro Phe Tyr Phe Leu Asn Arg Ser Ile Asp
            100                 105                 110
Glu Ile Ala Asp Leu Phe Ile His Asp Ile Lys Glu Gly Ile Gln Ala
        115                 120                 125
Thr Ser Asn Lys Ala Gly Phe Val Lys Ile Ala Ala Asp Glu Pro Gly
    130                 135                 140
Ile Thr Lys Asp Val Glu Lys Val Ile Arg Ala Ala Ile Thr His
145                 150                 155                 160
Lys Glu Ala Lys Val Pro Ile Ile Thr His Ser Asn Ala His Asn Asn
                165                 170                 175
Thr Gly Leu Glu Glu Gln Arg Ile Leu Met Glu Glu Gly Val Asp Pro
            180                 185                 190
Gly Lys Ile Leu Ile Gly His Leu Gly Asp Thr Asp Asn Thr Asp Tyr
        195                 200                 205
Ile Lys Lys Ile Ala Asp Lys Gly Ser Phe Ile Gly Leu Asp Arg Tyr
    210                 215                 220
Gly Leu Asp Met Phe Leu Pro Val Asp Lys Arg Asn Glu Thr Thr Leu
225                 230                 235                 240
Lys Leu Ile Lys Asp Gly Tyr Ser Asp Arg Ile Met Ile Ser His Asp
                245                 250                 255
Tyr Cys Cys Thr Ile Asp Trp Gly Thr Ala Arg Pro Glu Leu Lys Pro
            260                 265                 270
Lys Leu Ala Pro Arg Trp Ser Met Ala Leu Ile Phe Glu Asp Thr Ile
        275                 280                 285
Pro Phe Leu Lys Lys Asn Gly Val Ser Glu Val Ile Asp Ile Ile
    290                 295                 300
Phe Lys Glu Asn Pro Lys Lys Phe Phe Ser
305                 310

<210> SEQ ID NO 126
<211> LENGTH: 945
<212> TYPE: DNA
<213> ORGANISM: Sulfolobus islandicus

<400> SEQUENCE: 126

```
atgcgtattc cgctggttgg taaagaaccg attgaagccg aagatatggg ttttacccty     60
attcatgaac atctgcgtgt ttttagcgaa gcagttcgtt atcagtggcc tcatctgtat    120
aatgaagatg aagaactgcg taatgccgtt aatgaagtta acgtgccat gcagtttggt    180
gttaaaacca ttgttgatcc gaccgttatg ggtattggtc gtgatattcg ctttatggaa    240
aaagttgtga aaccaccggg tattaatctg gttgcaggca ccggtattta tatttatgtg    300
gatctgccgt tttatttct gaaccgcagc attgatgaaa ttgccgacct gtttattcat    360
gatattaaag aaggtattca ggcaaccagc aataaagccg gttttgtgaa attgcagcc    420
gatgaaccgg gtattaccaa agatgtggaa aaagttattc gtgcagcagc cattacccat    480
aaagaagcca agttccgat tattacccat agcaatgccc ataataatac cggtctggaa    540
gaacagcgta ttctgatgga agaaggtgtt gatccgggta aaattctgat tggtcatctg    600
```

```
ggtgataccg ataataccga ttatattaaa aaaattgccg ataaaggcag ctttattggt    660
ctggatcgtt atggtctgga cctgtttctg ccggttgata acgtaatga aaccaccctg     720 aaactgatta agatggcta tagcgatcgc attatgatca gccatgatta ttgttgtacc     780
attgattttg gcaccgcacg tccggaactg aaaccgaaac tggcaccgcg ttggagcatg    840
gcactgattt ttgaagatac cattccgttt ctgaaaaaaa atggcgtgag cgaagaagtg    900
atcgatatta ttttcaaaga aaacccgaaa aaattcttta gctaa                   945
```

```
<210> SEQ ID NO 127
<211> LENGTH: 314
<212> TYPE: PRT
<213> ORGANISM: Sulfolobus islandicus

<400> SEQUENCE: 127

Met Arg Ile Pro Leu Val Gly Lys Glu Pro Ile Glu Ala Glu Asp Met
1               5                   10                  15

Gly Phe Thr Leu Ile His Glu His Leu Arg Val Phe Ser Glu Ala Val
            20                  25                  30

Arg Tyr Gln Trp Pro His Leu Tyr Asn Glu Asp Glu Leu Arg Asn
        35                  40                  45

Ala Val Asn Glu Val Lys Arg Ala Met Gln Phe Gly Val Lys Thr Ile
    50                  55                  60

Val Asp Pro Thr Val Met Gly Ile Gly Arg Asp Ile Arg Phe Met Glu
65                  70                  75                  80

Lys Val Val Lys Thr Thr Gly Ile Asn Leu Val Ala Gly Thr Gly Ile
                85                  90                  95

Tyr Ile Tyr Val Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Ala
        115                 120                 125

Thr Ser Asn Lys Ala Gly Phe Val Lys Ile Ala Ala Asp Glu Pro Gly
    130                 135                 140

Ile Thr Lys Asp Val Glu Lys Val Ile Arg Ala Ala Ile Thr His
145                 150                 155                 160

Lys Glu Ala Lys Val Pro Ile Ile Thr His Ser Asn Ala His Asn Asn
                165                 170                 175

Thr Gly Leu Glu Glu Gln Arg Ile Leu Met Glu Glu Gly Val Asp Pro
            180                 185                 190

Gly Lys Ile Leu Ile Gly His Leu Gly Asp Thr Asp Asn Thr Asp Tyr
        195                 200                 205

Ile Lys Lys Ile Ala Asp Lys Gly Ser Phe Ile Gly Leu Asp Arg Tyr
    210                 215                 220

Gly Leu Asp Leu Phe Leu Pro Val Asp Lys Arg Asn Glu Thr Thr Leu
225                 230                 235                 240

Lys Leu Ile Lys Asp Gly Tyr Ser Asp Arg Ile Met Ile Ser His Asp
                245                 250                 255

Tyr Cys Cys Thr Ile Asp Phe Gly Thr Ala Arg Pro Glu Leu Lys Pro
            260                 265                 270

Lys Leu Ala Pro Arg Trp Ser Met Ala Leu Ile Phe Glu Asp Thr Ile
        275                 280                 285

Pro Phe Leu Lys Lys Asn Gly Val Ser Glu Glu Val Ile Asp Ile Ile
    290                 295                 300

Phe Lys Glu Asn Pro Lys Lys Phe Phe Ser
305                 310
```

<210> SEQ ID NO 128
<211> LENGTH: 945
<212> TYPE: DNA
<213> ORGANISM: Sulfolobus islandicus

<400> SEQUENCE: 128

```
atgcgtattc cgctggttgg taaagaaccg attgaagccg aagatatggg ttttaccctg      60
attcatgaac atctgcgtgt ttttagcgaa gcagttcgtt atcagtggcc tcatctgtat     120
aatgaagatg aagaactgcg taatgccgtt aatgaagtta acgtgccat gcagtttggt      180
gttaaaacca ttgttgatcc gagtgttatg ggtctgggtc gtgatattcg ctttatggaa     240
aaagttgtga aaccaccgg tattaatctg gttgcaggca ccggtatttg gattttgtg       300
gatctgccgt tttatttttct gaaccgcagc attgatgaaa ttgccgacct gtttattcat    360
gatattaaag aaggtattca ggcaaccccg aataaagccg ttttgtgaa aattgcagcc      420
gatgaaccgg gtattaccaa agatgtggaa aaagttattc gtgcagcagc cattacccat     480
aaagaagcca agttccgat tattacccat agcaatgccc ataataatac cggtctggaa      540
gaacagcgta ttctgatgga agaaggtgtt gatccgggta aaattctgat tggtcatctg     600
ggtgataccg ataataccga ttatattaaa aaaattgccg ataaaggcag ctttattggt     660
ctggatcgtt atggtctgga catgtttctg ccggttgata acgtaatga accaccctg      720
aaactgatta agatggcta tagcgatcgc attatgatca gccatgatta ttgttgtacc     780
attgattggg gcaccgcacg tccggaactg aaaccgaaac tggcaccgcg ttggagcatg     840
gcactgattt ttgaagatac cattccgttt ctgaaaaaaa atggcgtgag cgaagaagtg     900
atcgatatta ttttcaaaga aaacccgaaa aaattcttta gctaa                    945
```

<210> SEQ ID NO 129
<211> LENGTH: 314
<212> TYPE: PRT
<213> ORGANISM: Sulfolobus islandicus

<400> SEQUENCE: 129

Met Arg Ile Pro Leu Val Gly Lys Glu Pro Ile Glu Ala Glu Asp Met
1               5                   10                  15

Gly Phe Thr Leu Ile His Glu His Leu Arg Val Phe Ser Glu Ala Val
            20                  25                  30

Arg Tyr Gln Trp Pro His Leu Tyr Asn Glu Asp Glu Glu Leu Arg Asn
        35                  40                  45

Ala Val Asn Glu Val Lys Arg Ala Met Gln Phe Gly Val Lys Thr Ile
    50                  55                  60

Val Asp Pro Ser Val Met Gly Leu Gly Arg Asp Ile Arg Phe Met Glu
65                  70                  75                  80

Lys Val Val Lys Thr Thr Gly Ile Asn Leu Val Ala Gly Thr Gly Ile
                85                  90                  95

Trp Ile Phe Val Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Ala
        115                 120                 125

Thr Pro Asn Lys Ala Gly Phe Val Lys Ile Ala Ala Asp Glu Pro Gly
    130                 135                 140

Ile Thr Lys Asp Val Glu Lys Val Ile Arg Ala Ala Ala Ile Thr His
145                 150                 155                 160

```
Lys Glu Ala Lys Val Pro Ile Ile Thr His Ser Asn Ala His Asn Asn
            165                 170                 175

Thr Gly Leu Glu Glu Gln Arg Ile Leu Met Glu Gly Val Asp Pro
        180                 185                 190

Gly Lys Ile Leu Ile Gly His Leu Gly Asp Thr Asp Asn Thr Asp Tyr
        195                 200                 205

Ile Lys Lys Ile Ala Asp Lys Gly Ser Phe Ile Gly Leu Asp Arg Tyr
        210                 215                 220

Gly Leu Asp Met Phe Leu Pro Val Asp Lys Arg Asn Glu Thr Thr Leu
225                 230                 235                 240

Lys Leu Ile Lys Asp Gly Tyr Ser Asp Arg Ile Met Ile Ser His Asp
                245                 250                 255

Tyr Cys Cys Thr Ile Asp Trp Gly Thr Ala Arg Pro Glu Leu Lys Pro
                260                 265                 270

Lys Leu Ala Pro Arg Trp Ser Met Ala Leu Ile Phe Glu Asp Thr Ile
                275                 280                 285

Pro Phe Leu Lys Lys Asn Gly Val Ser Glu Val Ile Asp Ile Ile
            290                 295                 300

Phe Lys Glu Asn Pro Lys Lys Phe Phe Ser
305                 310

<210> SEQ ID NO 130
<211> LENGTH: 945
<212> TYPE: DNA
<213> ORGANISM: Sulfolobus islandicus

<400> SEQUENCE: 130
atgcgtattc cgctggttgg taaagaaccg attgaagccg aagatatggg ttttaccctg    60
attcatgaac atctgcgtgc atttagcgaa gcagttcgtt atcagtggcc tcatctgtat   120
aatgaagatg aagaactgcg taatgccgtt aatgaagtta acgtgccat gcagtttggt   180 gttaaaacca ttgttgatcc gaccgttatg ggtctgggtc gtgatattcg ctttatggaa   240
aaagttgtga aaccaccgg tattaatctg gttgcaggca ccggtattta tatttatgtg   300
gatctgccgt tttatttct gaaccgcagc attgatgaaa ttgccgacct gtttattcat   360
gatattaaag aaggtattca ggcaaccagc aataaagccg ttttgtgaa aattgcagcc   420 gatgaaccgg gtattaccaa agatgtggaa aaagttattc gtgcagcagc cattacccat   480
aaagaagcca agttccgat tattacccat agcaatgccc ataataatac cggtctggaa   540
gaacagcgta ttctgatgga agaaggtgtt gatccgggta aaattctgat tggtcatctg   600
ggtgataccg ataataccga ttatattaaa aaaattgccg ataaaggcag ctttattggt   660
ctggatcgtt atggtgtgga cctgtttctg ccggttgata acgtaatga accacccctg   720 aaactgatta agatggcta tagcgatcgc attatgatca gccatgatta tgttgtacc   780 attgatctgg gcaccgcacg tccggaactg aaaccgaaac tggcaccgcg ttggagcatg   840
gcactaattt ttgaagatac cattccgttt ctgaaaaaaa atggcgtgag cgaagaagtg   900
atcgatatta ttttcaaaga aaacccgaaa aaattctta gctaa                    945

<210> SEQ ID NO 131
<211> LENGTH: 314
<212> TYPE: PRT
<213> ORGANISM: Sulfolobus islandicus

<400> SEQUENCE: 131

Met Arg Ile Pro Leu Val Gly Lys Glu Pro Ile Glu Ala Glu Asp Met
```

```
    1               5                  10                 15
Gly Phe Thr Leu Ile His Glu His Leu Arg Ala Phe Ser Glu Ala Val
                20                 25                 30
Arg Tyr Gln Trp Pro His Leu Tyr Asn Glu Asp Glu Leu Arg Asn
            35                 40                 45
Ala Val Asn Glu Val Lys Arg Ala Met Gln Phe Gly Val Lys Thr Ile
        50                 55                 60
Val Asp Pro Thr Val Met Gly Leu Gly Arg Asp Ile Arg Phe Met Glu
65                 70                 75                 80
Lys Val Val Lys Thr Thr Gly Ile Asn Leu Val Ala Gly Thr Gly Ile
                85                 90                 95
Tyr Ile Tyr Val Asp Leu Pro Phe Tyr Phe Leu Asn Arg Ser Ile Asp
                100                105                110
Glu Ile Ala Asp Leu Phe Ile His Asp Ile Lys Glu Gly Ile Gln Ala
                115                120                125
Thr Ser Asn Lys Ala Gly Phe Val Lys Ile Ala Ala Asp Glu Pro Gly
            130                135                140
Ile Thr Lys Asp Val Glu Lys Val Ile Arg Ala Ala Ile Thr His
145                150                155                160
Lys Glu Ala Lys Val Pro Ile Ile Thr His Ser Asn Ala His Asn Asn
                165                170                175
Thr Gly Leu Glu Glu Gln Arg Ile Leu Met Glu Glu Gly Val Asp Pro
            180                185                190
Gly Lys Ile Leu Ile Gly His Leu Gly Asp Thr Asp Asn Thr Asp Tyr
            195                200                205
Ile Lys Lys Ile Ala Asp Lys Gly Ser Phe Ile Gly Leu Asp Arg Tyr
        210                215                220
Gly Val Asp Leu Phe Leu Pro Val Asp Lys Arg Asn Glu Thr Thr Leu
225                230                235                240
Lys Leu Ile Lys Asp Gly Tyr Ser Asp Arg Ile Met Ile Ser His Asp
                245                250                255
Tyr Cys Cys Thr Ile Asp Leu Gly Thr Ala Arg Pro Glu Leu Lys Pro
                260                265                270
Lys Leu Ala Pro Arg Trp Ser Met Ala Leu Ile Phe Glu Asp Thr Ile
            275                280                285
Pro Phe Leu Lys Lys Asn Gly Val Ser Glu Val Ile Asp Ile Ile
            290                295                300
Phe Lys Glu Asn Pro Lys Lys Phe Phe Ser
305                310

<210> SEQ ID NO 132
<211> LENGTH: 945
<212> TYPE: DNA
<213> ORGANISM: Sulfolobus islandicus

<400> SEQUENCE: 132
atgcgtattc cgctggttgg taaagaaccg attgaagccg aagatatggg ttttacccctg    60 attcatgaac atctgcgtgt ttttagcgaa gcagttcgtt atcagtggcc tcatctgtat   120
aatgaagatg aagaactgcg taatgccgtt aatgaagtta acgtgccat gcagtttggt    180 gttaaaacca ttgttgatgt gagtgttatg ggtctgggtc gtgatattcg ctttatggaa   240
aaagttgtga aaaccaccgg tattaatctg gttgcaggca ccggtatttg gattttgtg    300 gatctgccgt tttatttct gaaccgcagc attgatgaaa ttgccgacct gtttattcat   360
```

-continued

```
gatattaaag aaggtattca ggcaaccagc aataaagccg gttttgtgaa aattgcagcc    420
gatgaaccgg gtattaccaa agatgtggag aaagttattc gtgcagcagc cattacccat    480
aaagaagcca agttccgat tattacccat agcaatgccc ataataatac cggtctggaa     540
gaacagcgta ttctgatgga agaaggtgtt gatccgggta aaattctgat tggtcatctg    600
ggtgataccg ataataccga ttatattaaa aaaattgccg ataaaggcag ctttattggt    660
ctggatcgtt atggtctgga catgtttctg ccggttgata acgtaatga accaccctg     720
aaactgatta agatggcta tagcgatcgc attatgatca gccatgatta tgcttgtacc    780
attgatctgg gcaccgcacg tccggaactg aaaccgaaac tggcaccgcg ttggagcacg    840
gcactgattt ttgaagatac cattccgttt ctgaaaaaaa atggcgtgag cgaagaagtg    900
atcgatatta ttttcaaaga aaacccgaaa aaattcttta gctaa                  945
```

<210> SEQ ID NO 133
<211> LENGTH: 314
<212> TYPE: PRT
<213> ORGANISM: Sulfolobus islandicus

<400> SEQUENCE: 133

```
Met Arg Ile Pro Leu Val Gly Lys Glu Pro Ile Glu Ala Glu Asp Met
1               5                   10                  15

Gly Phe Thr Leu Ile His Glu His Leu Arg Val Phe Ser Glu Ala Val
            20                  25                  30

Arg Tyr Gln Trp Pro His Leu Tyr Asn Glu Asp Glu Leu Arg Asn
        35                  40                  45

Ala Val Asn Glu Val Lys Arg Ala Met Gln Phe Gly Val Lys Thr Ile
    50                  55                  60

Val Asp Val Ser Val Met Gly Leu Gly Arg Asp Ile Arg Phe Met Glu
65                  70                  75                  80

Lys Val Val Lys Thr Thr Gly Ile Asn Leu Val Ala Gly Thr Gly Ile
                85                  90                  95

Trp Ile Phe Val Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Ala
        115                 120                 125

Thr Ser Asn Lys Ala Gly Phe Val Lys Ile Ala Ala Asp Glu Pro Gly
    130                 135                 140

Ile Thr Lys Asp Val Glu Lys Val Ile Arg Ala Ala Ile Thr His
145                 150                 155                 160

Lys Glu Ala Lys Val Pro Ile Ile Thr His Ser Asn Ala His Asn Asn
                165                 170                 175

Thr Gly Leu Glu Glu Gln Arg Ile Leu Met Glu Glu Gly Val Asp Pro
            180                 185                 190

Gly Lys Ile Leu Ile Gly His Leu Gly Asp Thr Asp Asn Thr Asp Tyr
        195                 200                 205

Ile Lys Lys Ile Ala Asp Lys Gly Ser Phe Ile Gly Leu Asp Arg Tyr
    210                 215                 220

Gly Leu Asp Met Phe Leu Pro Val Asp Lys Arg Asn Glu Thr Thr Leu
225                 230                 235                 240

Lys Leu Ile Lys Asp Gly Tyr Ser Asp Arg Ile Met Ile Ser His Asp
                245                 250                 255

Tyr Ala Cys Thr Ile Asp Leu Gly Thr Ala Arg Pro Glu Leu Lys Pro
            260                 265                 270
```

Lys Leu Ala Pro Arg Trp Ser Thr Ala Leu Ile Phe Glu Asp Thr Ile
           275                 280                 285

Pro Phe Leu Lys Lys Asn Gly Val Ser Glu Glu Val Ile Asp Ile Ile
        290                 295                 300

Phe Lys Glu Asn Pro Lys Lys Phe Phe Ser
305                 310

<210> SEQ ID NO 134
<211> LENGTH: 945
<212> TYPE: DNA
<213> ORGANISM: Sulfolobus islandicus

<400> SEQUENCE: 134
atgcgtattc cgctggttgg taaagaaccg attgaagccg aagatatggg ttttacccfg      60 attcatgaac atctgcgtgt ttttagcgaa gcagttcgtt atcagtggcc tcatctgtat     120
aatgaagatg aagaactgcg taatgccgtt aatgaagtta acgtgccat gcagtttggt      180 gttaaaacca ttgttgatcc gagtgttatg ggtctgggtc gtgatattcg ctttatggaa     240
aaagttgtga aaccaccgg tattaatctg gttgcaggca ccggtatttg gattttttgtg     300 gatctgccgt ttattttttct gaaccgcagc attgatgaaa ttgccgacct gtttattcat    360
gatattaaag aaggtattca ggcaaccccg aataaagccg ttttttgtgaa aattgcagct    420 gatgaaccgg gtattaccaa agatgtggaa aaagttattc gtgcagcagc cattacccat    480
aaagaagcca atgttccgat tattacccat agcaatgccc ataataatac cggtctggaa    540
gaacagcgta ttctgatgga agaaggtgtt gatccgggta aaattctgat tggtcatctg    600
ggtgataccg ataataccga ttatattaaa aaaattgccg ataaaggcag ctttattggt    660
ctggatcgtt atggtgtgga cctgtttctg ccggttgata acgtaatga accacccfg      720 aaactgatta agatggcta tagcgatcgc attatgatca gccatgatta ttgttgtacc     780
attgatatgg gcaccgcacg tccggaactg aaaccgaaac tggcaccgcg ttggagcatg    840
gcactgattt ttgaagatac cattccgttt ctgaaaaaaa atggcgtgag cgaagaagtg    900
atcgatatta ttttcaaaga aaacccgaaa aaattctttta gctaa                    945

<210> SEQ ID NO 135
<211> LENGTH: 314
<212> TYPE: PRT
<213> ORGANISM: Sulfolobus islandicus

<400> SEQUENCE: 135

Met Arg Ile Pro Leu Val Gly Lys Glu Pro Ile Glu Ala Glu Asp Met
1               5                   10                  15

Gly Phe Thr Leu Ile His Glu His Leu Arg Val Phe Ser Glu Ala Val
            20                  25                  30

Arg Tyr Gln Trp Pro His Leu Tyr Asn Glu Asp Glu Glu Leu Arg Asn
        35                  40                  45

Ala Val Asn Glu Val Lys Arg Ala Met Gln Phe Gly Val Lys Thr Ile
    50                  55                  60

Val Asp Pro Ser Val Met Gly Leu Gly Arg Asp Ile Arg Phe Met Glu
65                  70                  75                  80

Lys Val Val Lys Thr Thr Gly Ile Asn Leu Val Ala Gly Thr Gly Ile
                85                  90                  95

Trp Ile Phe Val Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Ala

```
                115                 120                 125
Thr Pro Asn Lys Ala Gly Phe Val Lys Ile Ala Ala Asp Glu Pro Gly
    130                 135                 140

Ile Thr Lys Asp Val Glu Lys Val Ile Arg Ala Ala Ile Thr His
145                 150                 155                 160

Lys Glu Ala Asn Val Pro Ile Ile Thr His Ser Asn Ala His Asn Asn
                165                 170                 175

Thr Gly Leu Glu Glu Gln Arg Ile Leu Met Glu Glu Gly Val Asp Pro
            180                 185                 190

Gly Lys Ile Leu Ile Gly His Leu Gly Asp Thr Asp Asn Thr Asp Tyr
        195                 200                 205

Ile Lys Lys Ile Ala Asp Lys Gly Ser Phe Ile Gly Leu Asp Arg Tyr
    210                 215                 220

Gly Val Asp Leu Phe Leu Pro Val Asp Lys Arg Asn Glu Thr Thr Leu
225                 230                 235                 240

Lys Leu Ile Lys Asp Gly Tyr Ser Asp Arg Ile Met Ile Ser His Asp
                245                 250                 255

Tyr Cys Cys Thr Ile Asp Met Gly Thr Ala Arg Pro Glu Leu Lys Pro
            260                 265                 270

Lys Leu Ala Pro Arg Trp Ser Met Ala Leu Ile Phe Glu Asp Thr Ile
        275                 280                 285

Pro Phe Leu Lys Lys Asn Gly Val Ser Glu Glu Val Ile Asp Ile Ile
    290                 295                 300

Phe Lys Glu Asn Pro Lys Lys Phe Phe Ser
305                 310

<210> SEQ ID NO 136
<211> LENGTH: 945
<212> TYPE: DNA
<213> ORGANISM: Sulfolobus islandicus

<400> SEQUENCE: 136
atgcgtattc cgctggttgg taaagaaccg attgaagccg aagatatggg ttttacccctg      60
attcatgaac atctgcgtgt ttttagcgaa gcagttcgtt atcagtggcc ccatctgtat     120
aatgaagatg aagaactgcg taatgccgtt aatgaagtta acgtgccat gcagtttggt      180
gttaaaaccca ttgttgatcc gagtgttatg ggtattggtc gtgatattcg ctttatggaa     240
aaagttgtga aaccaccgg tattaatctg gttgcaggca ccggtatttg gattttgtgt     300
gatctgccgt tttatttct gaaccgcagc attgatgaaa ttgccgacct gtttattcat     360
gatattaaag aaggtattca ggcaaccccg aataaagccg gttttgtgaa aattgcagcc     420
gatgaaccgg gtattaccaa agatgtggaa aaagttattc gtgcagcagc cattaccccat     480
aaagaagcca agttccgat tattacccat agcaatgccc ataataatac cggtctggaa     540
gaacagcgta ttctgatgga agaaggtgtt gatccgggta aaattctgat tggtcatctg     600
ggtgataccg ataataccga ttatattaaa aaaattgccg ataaaggcag ctttattggt     660
ctggatcgtt atggtctgga cctgtttctg ccggttgata acgtaatga accacccctg     720
aaactgatta agatggcta tagcgatcgc attatgatca gccatgatta ttgttgtacc     780
attgattggg gcaccgcacg tccggaactg aaaccgaaac tggcaccgcg ttggagcatg     840
gcactgattt ttgaagatac cattccgttt ctgaaaaaaa atggcgtgag cgaagaagtg     900
atcgatatta ttttcaaaga aaacccgaaa aaattcttta gctaa                     945
```

```
<210> SEQ ID NO 137
<211> LENGTH: 314
<212> TYPE: PRT
<213> ORGANISM: Sulfolobus islandicus

<400> SEQUENCE: 137
```

Met Arg Ile Pro Leu Val Gly Lys Glu Pro Ile Glu Ala Glu Asp Met
1               5                   10                  15

Gly Phe Thr Leu Ile His Glu His Leu Arg Val Phe Ser Glu Ala Val
            20                  25                  30

Arg Tyr Gln Trp Pro His Leu Tyr Asn Glu Asp Glu Glu Leu Arg Asn
        35                  40                  45

Ala Val Asn Glu Val Lys Arg Ala Met Gln Phe Gly Val Lys Thr Ile
    50                  55                  60

Val Asp Pro Ser Val Met Gly Ile Gly Arg Asp Ile Arg Phe Met Glu
65                  70                  75                  80

Lys Val Val Lys Thr Thr Gly Ile Asn Leu Val Ala Gly Thr Gly Ile
                85                  90                  95

Trp Ile Phe Val Asp Leu Pro Phe Tyr Phe Leu Asn Arg Ser Ile Asp
            100                 105                 110

Glu Ile Ala Asp Leu Phe Ile His Asp Ile Lys Glu Gly Ile Gln Ala
        115                 120                 125

Thr Pro Asn Lys Ala Gly Phe Val Lys Ile Ala Ala Asp Glu Pro Gly
    130                 135                 140

Ile Thr Lys Asp Val Glu Lys Val Ile Arg Ala Ala Ile Thr His
145                 150                 155                 160

Lys Glu Ala Lys Val Pro Ile Ile Thr His Ser Asn Ala His Asn Asn
                165                 170                 175

Thr Gly Leu Glu Glu Gln Arg Ile Leu Met Glu Glu Gly Val Asp Pro
            180                 185                 190

Gly Lys Ile Leu Ile Gly His Leu Gly Asp Thr Asp Asn Thr Asp Tyr
        195                 200                 205

Ile Lys Lys Ile Ala Asp Lys Gly Ser Phe Ile Gly Leu Asp Arg Tyr
    210                 215                 220

Gly Leu Asp Leu Phe Leu Pro Val Asp Lys Arg Asn Glu Thr Thr Leu
225                 230                 235                 240

Lys Leu Ile Lys Asp Gly Tyr Ser Asp Arg Ile Met Ile Ser His Asp
                245                 250                 255

Tyr Cys Cys Thr Ile Asp Trp Gly Thr Ala Arg Pro Glu Leu Lys Pro
            260                 265                 270

Lys Leu Ala Pro Arg Trp Ser Met Ala Leu Ile Phe Glu Asp Thr Ile
        275                 280                 285

Pro Phe Leu Lys Lys Asn Gly Val Ser Glu Glu Val Ile Asp Ile Ile
    290                 295                 300

Phe Lys Glu Asn Pro Lys Lys Phe Phe Ser
305                 310

```
<210> SEQ ID NO 138
<211> LENGTH: 948
<212> TYPE: DNA
<213> ORGANISM: Sulfolobus solfataricus

<400> SEQUENCE: 138
```
atggcgcgca ttccgctggt tggtaaagat agcattgaaa gcaaagatat tggctttacc        60
ctgattcatg aacatctgcg tgttttagc gaagcagttc gtcagcagtg gcctcatctg       120

```
tataatgaag atgaagaatt tcgcaatgcc gtgaatgaag ttaaacgtgc aatgcagttt      180
ggcgttaaaa ccattgttga tccgaccgtt atgggtctgg gtcgtgatat tcgttttatg      240
gaaaaagttg tgaaagccac cggcattaat ctggttgcag gcaccggtat ttatatttat      300
atcgatctgc cgtttgattt tctgaatcgc agcattgatg aaattgccga cctgtttatt      360
catgatatta agaaggcat tcagggcacc ctgaataaag caggttttgt taaaattgca      420
gccgatgaac cggtattac caaagatgtt gaaaaagtta ttcgtgcagc agccattgcc      480
aataaagaaa ccaaagttcc gattattacc catagcaatg cccataataa taccggtctg      540
gaacagcagc gtattctgac cgaagaaggt gtggatccgg gtaaaattct gattggtcat      600
ctgggtgata ccgataatat cgattatatc aaaaaaattg ccgataaagg cagctttatt      660
ggtctggatc gttatggtct ggacctgttt ctgccggttg ataaacgtaa tgaaaccacc      720
ctgcgcctga ttaaagatgg ttatagcgat aaaattatga ttagccatga ttattgctgc      780
accattgata tgggcaccgc aaaaccggaa tataaaccga aactggcacc gcgttggagc      840 attccctga tttttgaaga tacaattccg tttctgaaac gcaatggtgt taatgaagaa      900
gtgattgcca ccattttta agaaaatccg aaaaaattct ttagctaa                    948
```

<210> SEQ ID NO 139
<211> LENGTH: 315
<212> TYPE: PRT
<213> ORGANISM: Sulfolobus solfataricus

<400> SEQUENCE: 139

```
Met Ala Arg Ile Pro Leu Val Gly Lys Asp Ser Ile Glu Ser Lys Asp
1               5                   10                  15

Ile Gly Phe Thr Leu Ile His Glu His Leu Arg Val Phe Ser Glu Ala
            20                  25                  30

Val Arg Gln Gln Trp Pro His Leu Tyr Asn Glu Asp Glu Glu Phe Arg
        35                  40                  45

Asn Ala Val Asn Glu Val Lys Arg Ala Met Gln Phe Gly Val Lys Thr
    50                  55                  60

Ile Val Asp Pro Thr Val Met Gly Leu Gly Arg Asp Ile Arg Phe Met
65                  70                  75                  80

Glu Lys Val Val Lys Ala Thr Gly Ile Asn Leu Val Ala Gly Thr Gly
                85                  90                  95

Ile Tyr Ile Tyr Ile Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Gly Thr Leu Asn Lys Ala Gly Phe Val Lys Ile Ala Ala Asp Glu Pro
    130                 135                 140

Gly Ile Thr Lys Asp Val Glu Lys Val Ile Arg Ala Ala Ile Ala
145                 150                 155                 160

Asn Lys Glu Thr Lys Val Pro Ile Ile Thr His Ser Asn Ala His Asn
                165                 170                 175

Asn Thr Gly Leu Glu Gln Gln Arg Ile Leu Thr Glu Glu Gly Val Asp
            180                 185                 190

Pro Gly Lys Ile Leu Ile Gly His Leu Gly Asp Thr Asp Asn Ile Asp
        195                 200                 205

Tyr Ile Lys Lys Ile Ala Asp Lys Gly Ser Phe Ile Gly Leu Asp Arg
    210                 215                 220

Tyr Gly Leu Asp Leu Phe Leu Pro Val Asp Lys Arg Asn Glu Thr Thr
```

```
                225                 230                 235                 240
Leu Arg Leu Ile Lys Asp Gly Tyr Ser Asp Lys Ile Met Ile Ser His
                    245                 250                 255

Asp Tyr Cys Cys Thr Ile Asp Met Gly Thr Ala Lys Pro Glu Tyr Lys
                260                 265                 270

Pro Lys Leu Ala Pro Arg Trp Ser Ile Thr Leu Ile Phe Glu Asp Thr
            275                 280                 285

Ile Pro Phe Leu Lys Arg Asn Gly Val Asn Glu Glu Val Ile Ala Thr
        290                 295                 300

Ile Phe Lys Glu Asn Pro Lys Lys Phe Phe Ser
305                 310                 315

<210> SEQ ID NO 140
<211> LENGTH: 948
<212> TYPE: DNA
<213> ORGANISM: Sulfolobus solfataricus

<400> SEQUENCE: 140
atggcgcgca ttccgctggt tggtaaagat agcattgaaa gcaaagatat ggctttacc      60 ctgattcatg aacatctgcg tgtttttagc gaagcagttc gtcagcagtg gcctcatctg    120
tataatgaag atgaagaatt cgcaatgcc gtgaatgaag ttaaacgtgc aatgcagttt     180
ggcgttaaaa ccattgttga tccgaccgtt atgggtctgg tcgtgatat cgtttttatg     240 gaaaaagttg tgaaagccac cggcattaat ctggttgcag caccggtat ttatatttat    300 atcgatctgc gttttatttt ctgaatcgc agcattgatg aaattgccga cctgtttatt     360
catgatatta agaaggcat tcagggcacc ctgaataaag caggttttgt taaaattgca    420
gccgatgaac cgggtattac caaagatgtt gaaaaagtta tcgtgcagc agccattgcc    480 aataaagaaa ccaaagttcc gattattacc catagcaatg cccataataa taccggtctg    540
gaacagcagc gtattctgac cgaagaaggt gtggatccgg gtaaaattct gattggtcat    600
ctgggtgata ccgataatat cgattatatc aaaaaaattg ccgataaagg cagctttatt    660
ggtctggatc gttatggtct ggacctgttt ctgccggttg ataaacgtaa tgaaaccacc    720
ctgcgcctga ttaaagatgg ttatagcgat aaaattatga ttagccatga ttattgctgc    780
accattgatc tgggcaccgc aaaaccggaa tataaaccga aactggcacc gcgttggagc    840 attccctga tttttgaaga tacaattccg tttctgaaac gcaatggtgt taatgaagaa    900
gtgattgcca ccattttaa agaaaatccg aaaaaattct ttagctaa                 948

<210> SEQ ID NO 141
<211> LENGTH: 315
<212> TYPE: PRT
<213> ORGANISM: Sulfolobus solfataricus

<400> SEQUENCE: 141

Met Ala Arg Ile Pro Leu Val Gly Lys Asp Ser Ile Glu Ser Lys Asp
1               5                  10                  15

Ile Gly Phe Thr Leu Ile His Glu His Leu Arg Val Phe Ser Glu Ala
            20                  25                  30

Val Arg Gln Gln Trp Pro His Leu Tyr Asn Glu Asp Glu Glu Phe Arg
        35                  40                  45

Asn Ala Val Asn Glu Val Lys Arg Ala Met Gln Phe Gly Val Lys Thr
    50                  55                  60

Ile Val Asp Pro Thr Val Met Gly Leu Gly Arg Asp Ile Arg Phe Met
65                  70                  75                  80
```

```
Glu Lys Val Val Lys Ala Thr Gly Ile Asn Leu Val Ala Gly Thr Gly
                85                  90                  95

Ile Tyr Ile Tyr Ile Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Gly Thr Leu Asn Lys Ala Gly Phe Val Lys Ile Ala Ala Asp Glu Pro
    130                 135                 140

Gly Ile Thr Lys Asp Val Glu Lys Val Ile Arg Ala Ala Ile Ala
145                 150                 155                 160

Asn Lys Glu Thr Lys Val Pro Ile Ile Thr His Ser Asn Ala His Asn
                165                 170                 175

Asn Thr Gly Leu Glu Gln Gln Arg Ile Leu Thr Glu Glu Gly Val Asp
            180                 185                 190

Pro Gly Lys Ile Leu Ile Gly His Leu Gly Asp Thr Asp Asn Ile Asp
        195                 200                 205

Tyr Ile Lys Lys Ile Ala Asp Lys Gly Ser Phe Ile Gly Leu Asp Arg
    210                 215                 220

Tyr Gly Leu Asp Leu Phe Leu Pro Val Asp Lys Arg Asn Glu Thr Thr
225                 230                 235                 240

Leu Arg Leu Ile Lys Asp Gly Tyr Ser Asp Lys Ile Met Ile Ser His
                245                 250                 255

Asp Tyr Cys Cys Thr Ile Asp Leu Gly Thr Ala Lys Pro Glu Tyr Lys
            260                 265                 270

Pro Lys Leu Ala Pro Arg Trp Ser Ile Thr Leu Ile Phe Glu Asp Thr
        275                 280                 285

Ile Pro Phe Leu Lys Arg Asn Gly Val Asn Glu Glu Val Ile Ala Thr
    290                 295                 300

Ile Phe Lys Glu Asn Pro Lys Lys Phe Phe Ser
305                 310                 315

<210> SEQ ID NO 142
<211> LENGTH: 948
<212> TYPE: DNA
<213> ORGANISM: Sulfolobus solfataricus

<400> SEQUENCE: 142
atggcgcgca ttccgctggt tggtaaagat agcattgaaa gcaaagatat tggctttacc        60
ctgattcatg aacatctgcg tgtttttagc gaagcagttc gtcagcagtg gcctcatctg       120
tataatgaag atgaagaatt cgcaatgcc gtgaatgaag ttaaacgtgc aatgcagttt        180
ggcgttaaaa ccattgttga tccgaccgtt atgggtctgg tcgtgatat cgtttttatg        240 gaaaaagttg tgaaagccac cggcattaat ctggttgcag caccggtat ttatatttat        300 atcgatctgc cgtttatttt tctgaatcgc agcattgatg aaattgccga cctgtttatt       360
catgatatta agaaggcat tcagggcacc ctgaataaag caggttttgt taaaattgca        420
gccgatgaac cgggtattac caaagatgtt gaaaaagtta tcgtgcagc agccattgcc        480 aataaagaaa ccaaagttcc gattattacc catagcaatg cccataataa taccggtctg       540
gaacagcagc gtattctgac cgaagaaggt gtggatccgg gtaaaattct gattggtcat       600
ctgggtgata ccgataatat cgattatatc aaaaaaattg ccgataaagg cagctttatt       660
ggtctggatc gttatggtct ggacctgttt ctgccggttg ataaacgtaa tgaaaccacc       720
ctgcgcctga ttaagatgg ttatagcgat aaaattatga ttagccatga ttattgctgc       780
```
accattgatg caggcaccgc aaaaccggaa tataaaccga aactggcacc gcgttggagc     840
attaccctga ttttgaaga tacaattccg tttctgaaac gcaatggtgt taatgaagaa      900
gtgattgcca ccattttaa agaaaatccg aaaaaattct ttagctaa                  948

```
<210> SEQ ID NO 143
<211> LENGTH: 315
<212> TYPE: PRT
<213> ORGANISM: Sulfolobus solfataricus

<400> SEQUENCE: 143
```

Met Ala Arg Ile Pro Leu Val Gly Lys Asp Ser Ile Glu Ser Lys Asp
1               5                   10                  15

Ile Gly Phe Thr Leu Ile His Glu His Leu Arg Val Phe Ser Glu Ala
            20                  25                  30

Val Arg Gln Gln Trp Pro His Leu Tyr Asn Glu Asp Glu Glu Phe Arg
        35                  40                  45

Asn Ala Val Asn Glu Val Lys Arg Ala Met Gln Phe Gly Val Lys Thr
    50                  55                  60

Ile Val Asp Pro Thr Val Met Gly Leu Gly Arg Asp Ile Arg Phe Met
65                  70                  75                  80

Glu Lys Val Val Lys Ala Thr Gly Ile Asn Leu Val Ala Gly Thr Gly
                85                  90                  95

Ile Tyr Ile Tyr Ile Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Gly Thr Leu Asn Lys Ala Gly Phe Val Lys Ile Ala Ala Asp Glu Pro
    130                 135                 140

Gly Ile Thr Lys Asp Val Glu Lys Val Ile Arg Ala Ala Ala Ile Ala
145                 150                 155                 160

Asn Lys Glu Thr Lys Val Pro Ile Ile Thr His Ser Asn Ala His Asn
                165                 170                 175

Asn Thr Gly Leu Glu Gln Gln Arg Ile Leu Thr Glu Glu Gly Val Asp
            180                 185                 190

Pro Gly Lys Ile Leu Ile Gly His Leu Gly Asp Thr Asp Asn Ile Asp
        195                 200                 205

Tyr Ile Lys Lys Ile Ala Asp Lys Gly Ser Phe Ile Gly Leu Asp Arg
    210                 215                 220

Tyr Gly Leu Asp Leu Phe Leu Pro Val Asp Lys Arg Asn Glu Thr Thr
225                 230                 235                 240

Leu Arg Leu Ile Lys Asp Gly Tyr Ser Asp Lys Ile Met Ile Ser His
                245                 250                 255

Asp Tyr Cys Cys Thr Ile Asp Ala Gly Thr Ala Lys Pro Glu Tyr Lys
            260                 265                 270

Pro Lys Leu Ala Pro Arg Trp Ser Ile Thr Leu Ile Phe Glu Asp Thr
        275                 280                 285

Ile Pro Phe Leu Lys Arg Asn Gly Val Asn Glu Glu Val Ile Ala Thr
    290                 295                 300

Ile Phe Lys Glu Asn Pro Lys Lys Phe Phe Ser
305                 310                 315

```
<210> SEQ ID NO 144
<211> LENGTH: 948
<212> TYPE: DNA
```

<213> ORGANISM: Sulfolobus solfataricus

<400> SEQUENCE: 144

```
atggcgcgca ttccgctggt tggtaaagat agcattgaaa gcaaagatat tggctttacc      60
ctgattcatg aacatctgcg tgtttttagc gaagcagttc gtcagcagtg gcctcatctg     120
tataatgaag atgaagaatt tcgcaatgcc gtgaatgaag ttaaacgtgc aatgcagttt     180
ggcgttaaaa ccattgttga tccgaccgtt atgggtctgg gtcgtgatat tcgttttatg     240
gaaaaagttg tgaaagccac cggcattaat ctggttgcag gcaccggtat ttatatttat     300
atcgatctgc cgtttttattt tctgaatcgc agcattgatg aaattgccga cctgtttatt     360
catgatatta agaaggcat tcagggcacc ctgaataaag caggttttgt taaaattgca     420
gccgatgaac cgggtattac caaagatgtt gaaaaagtta ttcgtgcagc agccattgcc     480
aataaagaaa ccaaagttcc gattattacc catagcaatg cccataataa taccggtctg     540
gaacagcagc gtattctgac cgaagaaggt gtggatccgg gtaaaattct gattggtcat     600
ctgggtgata ccgataatat cgattatatc aaaaaaattg ccgataaagg cagctttatt     660
ggtctggatc gttatggtct ggacctgttt ctgccggttg ataaacgtaa tgaaaccacc     720
ctgcgcctga ttaaagatgg ttatagcgat aaaattatga ttagccatga ttattgctgc     780
accattgata ttggcaccgc aaaaccggaa tataaaccga actggcaccg cgttggagc     840
attccctga ttttttgaaga tacaattccg tttctgaaac gcaatggtgt taatgaagaa     900
gtgattgcca ccattttta agaaaatccg aaaaaattct ttagctaa                  948
```

<210> SEQ ID NO 145
<211> LENGTH: 315
<212> TYPE: PRT
<213> ORGANISM: Sulfolobus solfataricus

<400> SEQUENCE: 145

```
Met Ala Arg Ile Pro Leu Val Gly Lys Asp Ser Ile Glu Ser Lys Asp
1               5                   10                  15

Ile Gly Phe Thr Leu Ile His Glu His Leu Arg Val Phe Ser Glu Ala
            20                  25                  30

Val Arg Gln Gln Trp Pro His Leu Tyr Asn Glu Asp Glu Glu Phe Arg
        35                  40                  45

Asn Ala Val Asn Glu Val Lys Arg Ala Met Gln Phe Gly Val Lys Thr
    50                  55                  60

Ile Val Asp Pro Thr Val Met Gly Leu Gly Arg Asp Ile Arg Phe Met
65                  70                  75                  80

Glu Lys Val Val Lys Ala Thr Gly Ile Asn Leu Val Ala Gly Thr Gly
                85                  90                  95

Ile Tyr Ile Tyr Ile Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Gly Thr Leu Asn Lys Ala Gly Phe Val Lys Ile Ala Ala Asp Glu Pro
    130                 135                 140

Gly Ile Thr Lys Asp Val Glu Lys Val Ile Arg Ala Ala Ala Ile Ala
145                 150                 155                 160

Asn Lys Glu Thr Lys Val Pro Ile Ile Thr His Ser Asn Ala His Asn
                165                 170                 175

Asn Thr Gly Leu Glu Gln Gln Arg Ile Leu Thr Glu Glu Gly Val Asp
            180                 185                 190
```

```
Pro Gly Lys Ile Leu Ile Gly His Leu Gly Asp Thr Asp Asn Ile Asp
        195                 200                 205

Tyr Ile Lys Lys Ile Ala Asp Lys Gly Ser Phe Ile Gly Leu Asp Arg
        210                 215                 220

Tyr Gly Leu Asp Leu Phe Leu Pro Val Asp Lys Arg Asn Glu Thr Thr
225                 230                 235                 240

Leu Arg Leu Ile Lys Asp Gly Tyr Ser Asp Lys Ile Met Ile Ser His
                245                 250                 255

Asp Tyr Cys Cys Thr Ile Asp Ile Gly Thr Ala Lys Pro Glu Tyr Lys
                260                 265                 270

Pro Lys Leu Ala Pro Arg Trp Ser Ile Thr Leu Ile Phe Glu Asp Thr
            275                 280                 285

Ile Pro Phe Leu Lys Arg Asn Gly Val Asn Glu Glu Val Ile Ala Thr
        290                 295                 300

Ile Phe Lys Glu Asn Pro Lys Lys Phe Phe Ser
305                 310                 315

<210> SEQ ID NO 146
<211> LENGTH: 948
<212> TYPE: DNA
<213> ORGANISM: Sulfolobus solfataricus

<400> SEQUENCE: 146
atggcgcgca ttccgctggt tggtaaagat agcattgaaa gcaaagatat tggctttacc      60
ctgattcatg aacatctgcg tgtttttagc gaagcagttc gtcagcagtg gcctcatctg     120
tataatgaag atgaagaatt cgcaatgcc gtgaatgaag ttaaacgtgc aatgcagttt      180
ggcgttaaaa ccattgttga tccgaccgtt atgggtctgg tcgtgatat cgtttttatg      240 gaaaaagttg tgaaagccac cggcattaat ctggttgcag caccggtat ttatatttat      300 atcgatctgc gttttatttt tctgaatcgc agcattgatg aaattgccga cctgtttatt      360
catgatatta agaaggcat tcagggcacc ctgaataaag caggttttgt taaaattgca      420
gccgatgaac cgggtattac caaagatgtt gaaaaagtta tcgtgcagc agccattgcc      480 aataaagaaa ccaaagttcc gattattacc atagcaatg cccataataa taccggtctg      540
gaacagcagc gtattctgac cgaagaaggt gtggatccgg tgaaaattct gattggtcat     600
ctgggtgata ccgataatat cgattatatc aaaaaaattg ccgataaagg cagctttat     660 ggtctggatc gttatggtct ggacctgttt ctgccggttg ataaacgtaa tgaaaccacc      720
ctgcgcctga ttaagatgg ttatagcgat aaaattatga ttagccatga ttattgctgc      780
accattgatg ttggcaccgc aaaaccggaa tataaaccga aactggcacc gcgttggagc      840
attaccctga ttttgaaga tacaattccg tttctgaaac gcaatggtgt taatgaagaa      900
gtgattgcca ccatttttaa agaaaatccg aaaaaattct ttagctaa                  948

<210> SEQ ID NO 147
<211> LENGTH: 315
<212> TYPE: PRT
<213> ORGANISM: Sulfolobus solfataricus

<400> SEQUENCE: 147

Met Ala Arg Ile Pro Leu Val Gly Lys Asp Ser Ile Glu Ser Lys Asp
1               5                   10                  15

Ile Gly Phe Thr Leu Ile His Glu His Leu Arg Val Phe Ser Glu Ala
            20                  25                  30
```

Val Arg Gln Gln Trp Pro His Leu Tyr Asn Glu Asp Glu Glu Phe Arg
              35                  40                  45

Asn Ala Val Asn Glu Val Lys Arg Ala Met Gln Phe Gly Val Lys Thr
 50                  55                  60

Ile Val Asp Pro Thr Val Met Gly Leu Gly Arg Asp Ile Arg Phe Met
 65                  70                  75                  80

Glu Lys Val Val Lys Ala Thr Gly Ile Asn Leu Val Ala Gly Thr Gly
                 85                  90                  95

Ile Tyr Ile Tyr Ile Asp Leu Pro Phe Tyr Phe Leu Asn Arg Ser Ile
                100                 105                 110

Asp Glu Ile Ala Asp Leu Phe Ile His Asp Ile Lys Glu Gly Ile Gln
                115                 120                 125

Gly Thr Leu Asn Lys Ala Gly Phe Val Lys Ile Ala Ala Asp Glu Pro
130                 135                 140

Gly Ile Thr Lys Asp Val Glu Lys Val Ile Arg Ala Ala Ile Ala
145                 150                 155                 160

Asn Lys Glu Thr Lys Val Pro Ile Ile Thr His Ser Asn Ala His Asn
                165                 170                 175

Asn Thr Gly Leu Glu Gln Gln Arg Ile Leu Thr Glu Glu Gly Val Asp
                180                 185                 190

Pro Gly Lys Ile Leu Ile Gly His Leu Gly Asp Thr Asp Asn Ile Asp
                195                 200                 205

Tyr Ile Lys Lys Ile Ala Asp Lys Gly Ser Phe Ile Gly Leu Asp Arg
                210                 215                 220

Tyr Gly Leu Asp Leu Phe Leu Pro Val Asp Lys Arg Asn Glu Thr Thr
225                 230                 235                 240

Leu Arg Leu Ile Lys Asp Gly Tyr Ser Asp Lys Ile Met Ile Ser His
                245                 250                 255

Asp Tyr Cys Cys Thr Ile Asp Val Gly Thr Ala Lys Pro Glu Tyr Lys
                260                 265                 270

Pro Lys Leu Ala Pro Arg Trp Ser Ile Thr Leu Ile Phe Glu Asp Thr
                275                 280                 285

Ile Pro Phe Leu Lys Arg Asn Gly Val Asn Glu Glu Val Ile Ala Thr
290                 295                 300

Ile Phe Lys Glu Asn Pro Lys Lys Phe Phe Ser
305                 310                 315

<210> SEQ ID NO 148
<211> LENGTH: 948
<212> TYPE: DNA
<213> ORGANISM: Sulfolobus solfataricus

<400> SEQUENCE: 148
atggcgcgca ttccgctggt tggtaaagat agcattgaaa gcaaagatat tggctttacc    60
ctgattcatg aacatctgcg tgttttagc gaagcagttc gtcagcagtg gcctcatctg   120
tataatgaag atgaagaatt cgcaatgcc gtgaatgaag ttaaacgtgc aatgcagttt   180
ggcgttaaaa ccattgttga tccgaccgtt atgggtctgg tcgtgatat cgttttatg   240 gaaaaagttg tgaaagccac cggcattaat ctggttgcag gcaccggtat ttatatttat   300
atcgatctgc cgttttattt tctgaatcgc agcattgatg aaattgccga cctgtttatt   360
catgatatta agaaggcat tcagggcacc ctgaataaag caggttttgt taaaattgca   420
gccgatgaac cgggtattac caagatgtt gaaaaagtta tcgtgcagc agccattgcc   480 aataaagaaa ccaaagttcc gattattacc catagcaatg cccataataa taccggtctg   540

```
gaacagcagc gtattctgac cgaagaaggt gtggatccgg gtaaaattct gattggtcat    600
ctgggtgata ccgataatat cgattatatc aaaaaaattg ccgataaagg cagctttatt    660
ggtctggatc gttatggtct ggacctgttt ctgccggttg ataaacgtaa tgaaaccacc    720
ctgcgcctga ttaagatgg ttatagcgat aaaattatga ttagccatga ttattgctgc    780
accattgata ccggcaccgc aaaaccggaa tataaaccga aactggcacc gcgttggagc    840
attaccctga tttttgaaga tacaattccg tttctgaaac gcaatggtgt taatgaagaa    900
gtgattgcca ccatttttaa agaaaatccg aaaaaattct ttagctaa                948
```

<210> SEQ ID NO 149
<211> LENGTH: 315
<212> TYPE: PRT
<213> ORGANISM: Sulfolobus solfataricus

<400> SEQUENCE: 149

```
Met Ala Arg Ile Pro Leu Val Gly Lys Asp Ser Ile Glu Ser Lys Asp
1               5                   10                  15

Ile Gly Phe Thr Leu Ile His Glu His Leu Arg Val Phe Ser Glu Ala
            20                  25                  30

Val Arg Gln Gln Trp Pro His Leu Tyr Asn Glu Asp Glu Glu Phe Arg
        35                  40                  45

Asn Ala Val Asn Glu Val Lys Arg Ala Met Gln Phe Gly Val Lys Thr
    50                  55                  60

Ile Val Asp Pro Thr Val Met Gly Leu Gly Arg Asp Ile Arg Phe Met
65                  70                  75                  80

Glu Lys Val Val Lys Ala Thr Gly Ile Asn Leu Val Ala Gly Thr Gly
                85                  90                  95

Ile Tyr Ile Tyr Ile Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Gly Thr Leu Asn Lys Ala Gly Phe Val Lys Ile Ala Ala Asp Glu Pro
    130                 135                 140

Gly Ile Thr Lys Asp Val Glu Lys Val Ile Arg Ala Ala Ile Ala
145                 150                 155                 160

Asn Lys Glu Thr Lys Val Pro Ile Ile Thr His Ser Asn Ala His Asn
                165                 170                 175

Asn Thr Gly Leu Glu Gln Gln Arg Ile Leu Thr Glu Glu Gly Val Asp
            180                 185                 190

Pro Gly Lys Ile Leu Ile Gly His Leu Gly Asp Thr Asp Asn Ile Asp
        195                 200                 205

Tyr Ile Lys Lys Ile Ala Asp Lys Gly Ser Phe Ile Gly Leu Asp Arg
    210                 215                 220

Tyr Gly Leu Asp Leu Phe Leu Pro Val Asp Lys Arg Asn Glu Thr Thr
225                 230                 235                 240

Leu Arg Leu Ile Lys Asp Gly Tyr Ser Asp Lys Ile Met Ile Ser His
                245                 250                 255

Asp Tyr Cys Cys Thr Ile Asp Thr Gly Thr Ala Lys Pro Glu Tyr Lys
            260                 265                 270

Pro Lys Leu Ala Pro Arg Trp Ser Ile Thr Leu Ile Phe Glu Asp Thr
        275                 280                 285

Ile Pro Phe Leu Lys Arg Asn Gly Val Asn Glu Glu Val Ile Ala Thr
    290                 295                 300
```

Ile Phe Lys Glu Asn Pro Lys Lys Phe Phe Ser
305                 310                 315

<210> SEQ ID NO 150
<211> LENGTH: 948
<212> TYPE: DNA
<213> ORGANISM: Sulfolobus solfataricus

<400> SEQUENCE: 150

| | | | | | |
|---|---|---|---|---|---|
| atggcgcgca | ttccgctggt | tggtaaagat | agcattgaaa | gcaaagatat | tggctttacc | 60 |
| ctgattcatg | aacatctgcg | tgtttttagc | gaagcagttc | gtcagcagtg | gcctcatctg | 120 |
| tataatgaag | atgaagaatt | tcgcaatgcc | gtgaatgaag | ttaaacgtgc | aatgcagttt | 180 |
| ggcgttaaaa | ccattgttga | tccgaccgtt | atgggtctgg | gtcgtgatat | tcgttttatg | 240 |
| gaaaaagttg | tgaaagccac | cggcattaat | ctggttgcag | gcaccggtat | ttatatttat | 300 |
| atcgatctgc | cgtttattt | tctgaatcgc | agcattgatg | aaattgccga | cctgtttatt | 360 |
| catgatatta | agaaggcat | tcagggcacc | ctgaataaag | caggttttgt | taaaattgca | 420 |
| gccgatgaac | cgggtattac | caaagatgtt | gaaaaagtta | tcgtgcagc | agccattgcc | 480 |
| aataaagaaa | ccaaagttcc | gattattacc | atagcaatg | cccataataa | taccggtctg | 540 |
| aacagcagc | gtattctgac | cgaagaaggt | gtggatccgg | gtaaaattct | gattggtcat | 600 |
| ctgggtgata | ccgataatat | cgattatatc | aaaaaaattg | ccgataaagg | cagctttatt | 660 |
| ggtctggatc | gttatggtct | ggacctgttt | ctgccggttg | ataaacgtaa | tgaaaccacc | 720 |
| ctgcgcctga | ttaaagatgg | ttatagcgat | aaaattatga | ttagccatga | ttatctgtgc | 780 |
| acctttgatg | caggcaccgc | aaaaccggaa | tataaaccga | actggcacc | gcgttggagc | 840 |
| attaccctga | ttttgaaga | tacaattccg | tttctgaaac | gcaatggtgt | taatgaagaa | 900 |
| gtgattgcca | ccatttttaa | agaaaatccg | aaaaaattct | ttagctaa | | 948 |

<210> SEQ ID NO 151
<211> LENGTH: 315
<212> TYPE: PRT
<213> ORGANISM: Sulfolobus solfataricus

<400> SEQUENCE: 151

Met Ala Arg Ile Pro Leu Val Gly Lys Asp Ser Ile Glu Ser Lys Asp
1               5                   10                  15

Ile Gly Phe Thr Leu Ile His Glu His Leu Arg Val Phe Ser Glu Ala
                20                  25                  30

Val Arg Gln Gln Trp Pro His Leu Tyr Asn Glu Asp Glu Glu Phe Arg
            35                  40                  45

Asn Ala Val Asn Glu Val Lys Arg Ala Met Gln Phe Gly Val Lys Thr
        50                  55                  60

Ile Val Asp Pro Thr Val Met Gly Leu Gly Arg Asp Ile Arg Phe Met
65                  70                  75                  80

Glu Lys Val Val Lys Ala Thr Gly Ile Asn Leu Val Ala Gly Thr Gly
                85                  90                  95

Ile Tyr Ile Tyr Ile Asp Leu Pro Phe Tyr Phe Leu Asn Arg Ser Ile
                100                 105                 110

Asp Glu Ile Ala Asp Leu Phe Ile His Asp Ile Lys Glu Gly Ile Gln
            115                 120                 125

Gly Thr Leu Asn Lys Ala Gly Phe Val Lys Ile Ala Ala Asp Glu Pro
        130                 135                 140

Gly Ile Thr Lys Asp Val Glu Lys Val Ile Arg Ala Ala Ala Ile Ala
145                 150                 155                 160

Asn Lys Glu Thr Lys Val Pro Ile Ile Thr His Ser Asn Ala His Asn
            165                 170                 175

Asn Thr Gly Leu Glu Gln Gln Arg Ile Leu Thr Glu Glu Gly Val Asp
        180                 185                 190

Pro Gly Lys Ile Leu Ile Gly His Leu Gly Asp Thr Asp Asn Ile Asp
    195                 200                 205

Tyr Ile Lys Lys Ile Ala Asp Lys Gly Ser Phe Ile Gly Leu Asp Arg
210                 215                 220

Tyr Gly Leu Asp Leu Phe Leu Pro Val Asp Lys Arg Asn Glu Thr Thr
225                 230                 235                 240

Leu Arg Leu Ile Lys Asp Gly Tyr Ser Asp Lys Ile Met Ile Ser His
                245                 250                 255

Asp Tyr Leu Cys Thr Phe Asp Ala Gly Thr Ala Lys Pro Glu Tyr Lys
            260                 265                 270

Pro Lys Leu Ala Pro Arg Trp Ser Ile Thr Leu Ile Phe Glu Asp Thr
        275                 280                 285

Ile Pro Phe Leu Lys Arg Asn Gly Val Asn Glu Glu Val Ile Ala Thr
290                 295                 300

Ile Phe Lys Glu Asn Pro Lys Lys Phe Phe Ser
305                 310                 315

<210> SEQ ID NO 152
<211> LENGTH: 951
<212> TYPE: DNA
<213> ORGANISM: Sulfolobus solfataricus

<400> SEQUENCE: 152
atggcgcgca ttccgctggt tggtaaagat agcattgaaa gcaaagatat tggctttacc      60
ctgattcatg aacatctgcg tgcatttagc gaagcagttc gtcagcagtg gcctcatctg     120
tataatgaag atgaagaatt tcgcaatgcc gtgaatgaag ttaaacgtgc aatgcagttt     180
ggcgttaaaa ccattgttga tccgaccgtt atgggtctgg tcgtgatat tcgttttatg      240
gaaaaagttg tgaaagccac cggcattaat ctggttgcag caccggtat ttggattat      300
atcgatctgc gttttatttt ctgaatcgc agcattgatg aaattgccga cctgtttatt     360
catgatatta agaaggcat tcagggcacc ctgaataaag caggttttgt taaaattgca    420
gccgatgaac cgggtattac caaagatgtt gaaaaagtta tcgtgcagc agccattgcc     480
aataaagaaa ccaaagttcc gattattacc catagcaatg cccataataa taccggtctg    540
gaacagcagc gtattctgac cgaagaaggt gtggatccgg gtaaaattct gattggtcat    600
ctgggtgata ccgataatat cgattatatc aaaaaaattg ccgataaagg cagctttat    660
ggtctggatc gttatggtct ggacatgttt ctgccggttg ataaacgtaa tgaaaccacc    720
ctgcgcctga ttaagatgg ttatagcgat aaaattatga ttagccatga ttattgctgc    780
accattgata tgggcaccgc aaaaccggaa tataaaccga actggcaccg cgttggagc    840
attaccctga ttttgaaga tacaattccg tttctgaaac gcaatggtgt taatgaagaa    900
gtgattgcca ccattttaa agaaaatccg aaaaaattct ttagctaata a              951

<210> SEQ ID NO 153
<211> LENGTH: 315
<212> TYPE: PRT
<213> ORGANISM: Sulfolobus solfataricus

<400> SEQUENCE: 153

| | | | | | | | | | | | | | | |
|---|---|---|---|---|---|---|---|---|---|---|---|---|---|---|
| Met | Ala | Arg | Ile | Pro | Leu | Val | Gly | Lys | Asp | Ser | Ile | Glu | Ser | Lys | Asp |
| 1 | | | | 5 | | | | | 10 | | | | | 15 | |
| Ile | Gly | Phe | Thr | Leu | Ile | His | Glu | His | Leu | Arg | Ala | Phe | Ser | Glu | Ala |
| | | | 20 | | | | | 25 | | | | | 30 | | |
| Val | Arg | Gln | Gln | Trp | Pro | His | Leu | Tyr | Asn | Glu | Asp | Glu | Phe | Arg | |
| | | 35 | | | | | 40 | | | | | 45 | | | |
| Asn | Ala | Val | Asn | Glu | Val | Lys | Arg | Ala | Met | Gln | Phe | Gly | Val | Lys | Thr |
| | 50 | | | | | 55 | | | | | 60 | | | | |
| Ile | Val | Asp | Pro | Thr | Val | Met | Gly | Leu | Gly | Arg | Asp | Ile | Arg | Phe | Met |
| 65 | | | | | 70 | | | | | 75 | | | | | 80 |
| Glu | Lys | Val | Val | Lys | Ala | Thr | Gly | Ile | Asn | Leu | Val | Ala | Gly | Thr | Gly |
| | | | | 85 | | | | | 90 | | | | | 95 | |
| Ile | Trp | Ile | Tyr | Ile | Asp | Leu | Pro | Phe | Tyr | Phe | Leu | Asn | Arg | Ser | Ile |
| | | | 100 | | | | | 105 | | | | | 110 | | |
| Asp | Glu | Ile | Ala | Asp | Leu | Phe | Ile | His | Asp | Ile | Lys | Glu | Gly | Ile | Gln |
| | | | 115 | | | | | 120 | | | | | 125 | | |
| Gly | Thr | Leu | Asn | Lys | Ala | Gly | Phe | Val | Lys | Ile | Ala | Ala | Asp | Glu | Pro |
| | 130 | | | | | 135 | | | | | 140 | | | | |
| Gly | Ile | Thr | Lys | Asp | Val | Glu | Lys | Val | Ile | Arg | Ala | Ala | Ile | Ala | |
| 145 | | | | | 150 | | | | | 155 | | | | | 160 |
| Asn | Lys | Glu | Thr | Lys | Val | Pro | Ile | Ile | Thr | His | Ser | Asn | Ala | His | Asn |
| | | | | 165 | | | | | 170 | | | | | 175 | |
| Asn | Thr | Gly | Leu | Glu | Gln | Gln | Arg | Ile | Leu | Thr | Glu | Glu | Gly | Val | Asp |
| | | | 180 | | | | | 185 | | | | | 190 | | |
| Pro | Gly | Lys | Ile | Leu | Ile | Gly | His | Leu | Gly | Asp | Thr | Asp | Asn | Ile | Asp |
| | | 195 | | | | | 200 | | | | | 205 | | | |
| Tyr | Ile | Lys | Lys | Ile | Ala | Asp | Lys | Gly | Ser | Phe | Ile | Gly | Leu | Asp | Arg |
| | 210 | | | | | 215 | | | | | 220 | | | | |
| Tyr | Gly | Leu | Asp | Met | Phe | Leu | Pro | Val | Asp | Lys | Arg | Asn | Glu | Thr | Thr |
| 225 | | | | | 230 | | | | | 235 | | | | | 240 |
| Leu | Arg | Leu | Ile | Lys | Asp | Gly | Tyr | Ser | Asp | Lys | Ile | Met | Ile | Ser | His |
| | | | | 245 | | | | | 250 | | | | | 255 | |
| Asp | Tyr | Cys | Cys | Thr | Ile | Asp | Met | Gly | Thr | Ala | Lys | Pro | Glu | Tyr | Lys |
| | | | 260 | | | | | 265 | | | | | 270 | | |
| Pro | Lys | Leu | Ala | Pro | Arg | Trp | Ser | Ile | Thr | Leu | Ile | Phe | Glu | Asp | Thr |
| | | 275 | | | | | 280 | | | | | 285 | | | |
| Ile | Pro | Phe | Leu | Lys | Arg | Asn | Gly | Val | Asn | Glu | Glu | Val | Ile | Ala | Thr |
| | 290 | | | | | 295 | | | | | 300 | | | | |
| Ile | Phe | Lys | Glu | Asn | Pro | Lys | Lys | Phe | Phe | Ser | | | | | |
| 305 | | | | | 310 | | | | | 315 | | | | | |

<210> SEQ ID NO 154
<211> LENGTH: 948
<212> TYPE: DNA
<213> ORGANISM: Sulfolobus solfataricus

<400> SEQUENCE: 154

```
atggcgcgca ttccgctggt tggtaaagat agcattgaaa gcaaagatat tggctttacc    60
ctgattcatg aacatctgcg tgcatttagc gaagcagttc gtcagcagtg gcctcatctg   120
tataatgaag atgaagaatt cgcaatgcc gtgaatgaag ttaaacgtgc aatgcagttt   180
ggcgttaaaa ccattgttga tccgaccgtt atgggtctgg gtcgtgatat cgtttttatg   240
gaaaaagttg tgaaagccac cggcattaat ctggttgcag gcaccggtat ttggatttat   300
```

```
atcgatctgc cgtttttattt tctgaatcgc agcattgatg aaattgccga cctgttattt      360
catgatatta agaaggcat tcagggcacc ctgaataaag caggttttgt taaaattgca       420
gccgatgaac cgggtattac caaagatgtt gaaaaagtta ttcgtgcagc agccattgcc      480
aataaagaaa ccaaagttcc gattattacc catagcaatg cccataataa taccggtctg      540
gaacagcagc gtattctgac cgaagaaggt gtggatccgg gtaaaattct gattggtcat      600
ctgggtgata ccgataatat cgattatatc aaaaaaattg ccgataaagg cagctttatt      660
ggtctggatc gttatggtct ggacctgttt ctgccggttg ataaacgtaa tgaaaccacc      720
ctgcgcctga ttaaagatgg ttatagcgat aaaattatga ttagccatga ttattgctgc      780
accattgatc tgggcaccgc aaaaccggaa tataaaccga actggcaccg cgttggagc       840
actaccctga tttttgaaga tacaattccg tttctgaaac gcaatggtgt taatgaagaa      900
gtgattgcca ccattttttaa agaaaatccg aaaaaattct ttagctaa                  948
```

<210> SEQ ID NO 155
<211> LENGTH: 315
<212> TYPE: PRT
<213> ORGANISM: Sulfolobus solfataricus

<400> SEQUENCE: 155

```
Met Ala Arg Ile Pro Leu Val Gly Lys Asp Ser Ile Glu Ser Lys Asp
1               5                   10                  15

Ile Gly Phe Thr Leu Ile His Glu His Leu Arg Ala Phe Ser Glu Ala
            20                  25                  30

Val Arg Gln Gln Trp Pro His Leu Tyr Asn Glu Asp Glu Phe Arg
        35                  40                  45

Asn Ala Val Asn Glu Val Lys Arg Ala Met Gln Phe Gly Val Lys Thr
    50                  55                  60

Ile Val Asp Pro Thr Val Met Gly Leu Gly Arg Asp Ile Arg Phe Met
65                  70                  75                  80

Glu Lys Val Val Lys Ala Thr Gly Ile Asn Leu Val Ala Gly Thr Gly
                85                  90                  95

Ile Trp Ile Tyr Ile Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Gly Thr Leu Asn Lys Ala Gly Phe Val Lys Ile Ala Ala Asp Glu Pro
    130                 135                 140

Gly Ile Thr Lys Asp Val Glu Lys Val Ile Arg Ala Ala Ala Ile Ala
145                 150                 155                 160

Asn Lys Glu Thr Lys Val Pro Ile Ile Thr His Ser Asn Ala His Asn
                165                 170                 175

Asn Thr Gly Leu Glu Gln Gln Arg Ile Leu Thr Glu Glu Gly Val Asp
            180                 185                 190

Pro Gly Lys Ile Leu Ile Gly His Leu Gly Asp Thr Asp Asn Ile Asp
        195                 200                 205

Tyr Ile Lys Lys Ile Ala Asp Lys Gly Ser Phe Ile Gly Leu Asp Arg
    210                 215                 220

Tyr Gly Leu Asp Leu Phe Leu Pro Val Asp Lys Arg Asn Glu Thr Thr
225                 230                 235                 240

Leu Arg Leu Ile Lys Asp Gly Tyr Ser Asp Lys Ile Met Ile Ser His
                245                 250                 255
```

Asp Tyr Cys Cys Thr Ile Asp Leu Gly Thr Ala Lys Pro Glu Tyr Lys
            260                 265                 270

Pro Lys Leu Ala Pro Arg Trp Ser Thr Thr Leu Ile Phe Glu Asp Thr
        275                 280                 285

Ile Pro Phe Leu Lys Arg Asn Gly Val Asn Glu Val Ile Ala Thr
    290                 295                 300

Ile Phe Lys Glu Asn Pro Lys Lys Phe Phe Ser
305                 310                 315

<210> SEQ ID NO 156
<211> LENGTH: 951
<212> TYPE: DNA
<213> ORGANISM: Sulfolobus solfataricus

<400> SEQUENCE: 156
atggcgcgca ttccgctggt tggtaaagat agcattgaaa gcaaagatat tggctttacc      60
ctgattcatg aacatctgcg tgtttttagc gaagcagttc gtcagcagtg gcctcatctg     120
tataatgaag atgaagaact tcgcaatgcc gtgaatgaag ttaaacgtgc aatgcagttt     180
ggcgttaaaa ccattgttga tccgaccgtt atgggtctgg tcgtgatat tcgttttatg     240 gaaaaagttg tgaaagccac cggcattaat ctggttgcag caccggtat ttatatttat     300 atcgatctgc cgttttattt tctgaatcgc agcattgatg aaattgccga cctgtttatt     360
catgatatta agaaggcat tcagggcacc ctgaataaag caggttttgt taaaattgca     420
gccgatgaac cgggtattac caaagatgtt gaaaaagtta ttcgtgcagc agccattgcc     480
aataaagaaa ccaaagttcc gattattacc atagcaatg cccataataa taccggtctg     540
gaacagcagc gtattctgac cgaagaaggt gtggatccgg gtaaaattct gattggtcat     600
ctgggtgata ccgataatat cgattatatc aaaaaaattg ccgataaagg cagctttatt     660
ggtctggatc gttatggtct ggacctgttt ctgccggttg ataaacgtaa tgaaaccacc     720
ctgcgcctga ttaaagatgg ttatagcgat aaaattatga ttagccatga ttatgcctgc     780
accattgata tgggcaccgc aaaaccggaa tataaccga aactggcacc gcgttggagc     840
actaccctga ttttgaaga tacaattccg tttctgaaac gcaatggtgt taatgaagaa     900
gtgattgcca ccatttttaa agaaaatccg aaaaaattct ttagctaata a                951

<210> SEQ ID NO 157
<211> LENGTH: 315
<212> TYPE: PRT
<213> ORGANISM: Sulfolobus solfataricus

<400> SEQUENCE: 157

Met Ala Arg Ile Pro Leu Val Gly Lys Asp Ser Ile Glu Ser Lys Asp
1               5                   10                  15

Ile Gly Phe Thr Leu Ile His Glu His Leu Arg Val Phe Ser Glu Ala
            20                  25                  30

Val Arg Gln Gln Trp Pro His Leu Tyr Asn Glu Asp Glu Glu Leu Arg
        35                  40                  45

Asn Ala Val Asn Glu Val Lys Arg Ala Met Gln Phe Gly Val Lys Thr
    50                  55                  60

Ile Val Asp Pro Thr Val Met Gly Leu Gly Arg Asp Ile Arg Phe Met
65                  70                  75                  80

Glu Lys Val Val Lys Ala Thr Gly Ile Asn Leu Val Ala Gly Thr Gly
                85                  90                  95

Ile Tyr Ile Tyr Ile Asp Leu Pro Phe Tyr Phe Leu Asn Arg Ser Ile

|  |  |  | 100 |  |  |  | 105 |  |  |  | 110 |  |
|---|---|---|---|---|---|---|---|---|---|---|---|---|
| Asp | Glu | Ile | Ala | Asp | Leu | Phe | Ile | His | Asp | Ile | Lys | Glu | Gly | Ile | Gln |
|  |  |  | 115 |  |  |  | 120 |  |  |  | 125 |  |

Gly Thr Leu Asn Lys Ala Gly Phe Val Lys Ile Ala Ala Asp Glu Pro
    130                 135                 140

Gly Ile Thr Lys Asp Val Glu Lys Val Ile Arg Ala Ala Ala Ile Ala
145                 150                 155                 160

Asn Lys Glu Thr Lys Val Pro Ile Ile Thr His Ser Asn Ala His Asn
            165                 170                 175

Asn Thr Gly Leu Glu Gln Gln Arg Ile Leu Thr Glu Glu Val Asp
            180                 185                 190

Pro Gly Lys Ile Leu Ile Gly His Leu Gly Asp Thr Asp Asn Ile Asp
            195                 200                 205

Tyr Ile Lys Lys Ile Ala Asp Lys Gly Ser Phe Ile Gly Leu Asp Arg
            210                 215                 220

Tyr Gly Leu Asp Leu Phe Leu Pro Val Asp Lys Arg Asn Glu Thr Thr
225                 230                 235                 240

Leu Arg Leu Ile Lys Asp Gly Tyr Ser Asp Lys Ile Met Ile Ser His
            245                 250                 255

Asp Tyr Ala Cys Thr Ile Asp Met Gly Thr Ala Lys Pro Glu Tyr Lys
            260                 265                 270

Pro Lys Leu Ala Pro Arg Trp Ser Thr Thr Leu Ile Phe Glu Asp Thr
            275                 280                 285

Ile Pro Phe Leu Lys Arg Asn Gly Val Asn Glu Glu Val Ile Ala Thr
290                 295                 300

Ile Phe Lys Glu Asn Pro Lys Lys Phe Phe Ser
305                 310                 315

<210> SEQ ID NO 158
<211> LENGTH: 951
<212> TYPE: DNA
<213> ORGANISM: Sulfolobus solfataricus

<400> SEQUENCE: 158

```
atggcgcgca ttccgctggt tggtaaagat agcattgaaa gcaaagatat tggctttacc     60
ctgattcatg aacatctgcg tgcatttagc gaagcagttc gtcagcagtg gcctcatctg    120
tataatgaag atgaagaatt cgcaatgcc gtgaatgaag ttaaacgtgc aatgcagttt    180
ggcgttaaaa ccattgttga tccgaccgtt atgggtctgg tcgtgatac tcgttttatg    240
gaaaaagttg tgaaagccac cggcattaat ctggttgcag gcaccggtat ttggattttt    300
atcgatctgc cgttttattt tctgaatcgc agcattgatg aaattgccga cctgtttatt    360
catgatatta agaaggcat tcagggcacc ccgaataaag caggttttgt taaaattgca    420
gccgatgaac cgggtattac caaagatgtt gaaaaagtta tcgtgcagc agccattgcc    480
aataaagaaa ccaaagttcc gattattacc catagcaatg cccataataa taccggtctg    540
gaacagcagc gtattctgac cgaagaaggt gtggatccgg gtaaaattct gattggtcat    600
ctgggtgata ccgataatat cgattatatc aaaaaaattg ccgataaagg cagctttatt    660
ggtctggatc gttatggtgt ggacctgttt ctgccggttg ataaacgtaa tgaaaccacc    720
ctgcgcctga ttaaagatgg ttatagcgat aaaattatga ttagccatga ttattgctgc    780
accattgatt gggcaccgc aaaaccggaa tataaaccga actggcaccg cgttggagc    840
attaccctga ttttgaaga tacaattccg tttctgaaac gcaatggtgt taatgaagaa    900
```
gtgattgcca ccattttaa agaaaatccg aaaaaattct ttagctaata a       951

<210> SEQ ID NO 159
<211> LENGTH: 315
<212> TYPE: PRT
<213> ORGANISM: Sulfolobus solfataricus

<400> SEQUENCE: 159

Met Ala Arg Ile Pro Leu Val Gly Lys Asp Ser Ile Glu Ser Lys Asp
1               5                   10                  15

Ile Gly Phe Thr Leu Ile His Glu His Leu Arg Ala Phe Ser Glu Ala
            20                  25                  30

Val Arg Gln Gln Trp Pro His Leu Tyr Asn Glu Asp Glu Glu Phe Arg
        35                  40                  45

Asn Ala Val Asn Glu Val Lys Arg Ala Met Gln Phe Gly Val Lys Thr
    50                  55                  60

Ile Val Asp Pro Thr Val Met Gly Leu Gly Arg Asp Thr Arg Phe Met
65                  70                  75                  80

Glu Lys Val Val Lys Ala Thr Gly Ile Asn Leu Val Ala Gly Thr Gly
                85                  90                  95

Ile Trp Ile Phe Ile Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Gly Thr Pro Asn Lys Ala Gly Phe Val Lys Ile Ala Ala Asp Glu Pro
    130                 135                 140

Gly Ile Thr Lys Asp Val Glu Lys Val Ile Arg Ala Ala Ala Ile Ala
145                 150                 155                 160

Asn Lys Glu Thr Lys Val Pro Ile Ile Thr His Ser Asn Ala His Asn
                165                 170                 175

Asn Thr Gly Leu Glu Gln Gln Arg Ile Leu Thr Glu Glu Gly Val Asp
            180                 185                 190

Pro Gly Lys Ile Leu Ile Gly His Leu Gly Asp Thr Asp Asn Ile Asp
        195                 200                 205

Tyr Ile Lys Lys Ile Ala Asp Lys Gly Ser Phe Ile Gly Leu Asp Arg
    210                 215                 220

Tyr Gly Val Asp Leu Phe Leu Pro Val Asp Lys Arg Asn Glu Thr Thr
225                 230                 235                 240

Leu Arg Leu Ile Lys Asp Gly Tyr Ser Asp Lys Ile Met Ile Ser His
                245                 250                 255

Asp Tyr Cys Cys Thr Ile Asp Trp Gly Thr Ala Lys Pro Glu Tyr Lys
            260                 265                 270

Pro Lys Leu Ala Pro Arg Trp Ser Ile Thr Leu Ile Phe Glu Asp Thr
        275                 280                 285

Ile Pro Phe Leu Lys Arg Asn Gly Val Asn Glu Glu Val Ile Ala Thr
    290                 295                 300

Ile Phe Lys Glu Asn Pro Lys Lys Phe Phe Ser
305                 310                 315

<210> SEQ ID NO 160
<211> LENGTH: 951
<212> TYPE: DNA
<213> ORGANISM: Sulfolobus solfataricus

<400> SEQUENCE: 160
atggcgcgca ttccgctggt tggtaaagat agcattgaaa gcaaagatat tggctttacc       60

```
ctgattcatg aacatctgcg tgtttttagc gaagcagttc gtcagcagtg gccccatctg    120
tataatgaag atgaagaatt cgcaatgcc gtgaatgaag ttaaacgtgc aatgcagttt    180
ggcgttaaaa ccattgttga tccgaccgtt atgggtattg gtcgtgatat tcgttttatg    240
gaaaaagttg tgaaagccac cggcattaat ctggttgcag gcaccggtat ttatattttt    300
atcgatctgc cgtttatt cctgaatcgc agcattgatg aaattgccga cctgtttatt      360
catgatttaa aagaaggcat tcagggcacc ctgaataaag caggttttgt taaaattgca    420
gccgatgaac cgggtattac caaagatgtt gaaaaagtca ttcgtgcagc agccattgcc    480
aataaagaaa ccaaagttcc gattattacc catagcaatg cccataataa taccggtctg    540
gaacagcagc gtattctgac cgaagaaggt gtggatccgg gtaaaattct gattggtcat    600
ctgggtgata ccgataatat cgattatatc aaaaaaattg ccgataaagg cagctttatt    660
ggtctggatc gttatggtct ggacatgtct ctgccggttg ataaacgtaa tgaaaccacc    720
ctgcgcctga ttaaagatgg ttatagcgat aaaattatga ttagccatga ttattgctgc    780
accattgatc tgggcaccgc aaaaccggaa tataaaccga aactggcacc gcgttggagc    840
attaccctga ttttgaaga tacaattccg tttctgaaac gcaatggtgt taatgaagaa    900
gtgattgcca ccattttaa agaaaatccg aaaaaattct ttagctaata a              951
```

<210> SEQ ID NO 161
<211> LENGTH: 315
<212> TYPE: PRT
<213> ORGANISM: Sulfolobus solfataricus

<400> SEQUENCE: 161

```
Met Ala Arg Ile Pro Leu Val Gly Lys Asp Ser Ile Glu Ser Lys Asp
1               5                   10                  15

Ile Gly Phe Thr Leu Ile His Glu His Leu Arg Val Phe Ser Glu Ala
            20                  25                  30

Val Arg Gln Gln Trp Pro His Leu Tyr Asn Glu Asp Glu Glu Phe Arg
        35                  40                  45

Asn Ala Val Asn Glu Val Lys Arg Ala Met Gln Phe Gly Val Lys Thr
    50                  55                  60

Ile Val Asp Pro Thr Val Met Gly Ile Gly Arg Asp Ile Arg Phe Met
65                  70                  75                  80

Glu Lys Val Val Lys Ala Thr Gly Ile Asn Leu Val Ala Gly Thr Gly
                85                  90                  95

Ile Tyr Ile Phe Ile Asp Leu Pro Phe Tyr Phe Leu Asn Arg Ser Ile
            100                 105                 110

Asp Glu Ile Ala Asp Leu Phe Ile His Asp Leu Lys Glu Gly Ile Gln
        115                 120                 125

Gly Thr Leu Asn Lys Ala Gly Phe Val Lys Ile Ala Ala Asp Glu Pro
    130                 135                 140

Gly Ile Thr Lys Asp Val Glu Lys Val Ile Arg Ala Ala Ala Ile Ala
145                 150                 155                 160

Asn Lys Glu Thr Lys Val Pro Ile Ile Thr His Ser Asn Ala His Asn
                165                 170                 175

Asn Thr Gly Leu Glu Gln Gln Arg Ile Leu Thr Glu Glu Gly Val Asp
            180                 185                 190

Pro Gly Lys Ile Leu Ile Gly His Leu Gly Asp Thr Asp Asn Ile Asp
        195                 200                 205

Tyr Ile Lys Lys Ile Ala Asp Lys Gly Ser Phe Ile Gly Leu Asp Arg
```

Tyr Gly Leu Asp Met Ser Leu Pro Val Asp Lys Arg Asn Glu Thr Thr
225                 230                 235                 240

Leu Arg Leu Ile Lys Asp Gly Tyr Ser Asp Lys Ile Met Ile Ser His
            245                 250                 255

Asp Tyr Cys Cys Thr Ile Asp Leu Gly Thr Ala Lys Pro Glu Tyr Lys
            260                 265                 270

Pro Lys Leu Ala Pro Arg Trp Ser Ile Thr Leu Ile Phe Glu Asp Thr
            275                 280                 285

Ile Pro Phe Leu Lys Arg Asn Gly Val Asn Glu Glu Val Ile Ala Thr
            290                 295                 300

Ile Phe Lys Glu Asn Pro Lys Lys Phe Phe Ser
305                 310                 315

<210> SEQ ID NO 162
<211> LENGTH: 948
<212> TYPE: DNA
<213> ORGANISM: Sulfolobus solfataricus

<400> SEQUENCE: 162
atggcgcgca ttccgctggt tggtaaagat agcattgaaa gcaaagatat tggctttacc      60
ctgattcatg aacatctgcg tgttttagc gaagcagttc gtcagcagtg gccccatctg     120
tataatgaag atgaagaatt cgcaatgcc gtgaatgaag ttaaacgtgc aatgcagttt     180
ggcgttaaaa ccattgttga tccgagtgtt atgggtattg tcgtgatat cgttttatg     240
gaaaaagttg tgaaagccac cggcattaat ctggttgcag caccggtat ttatatttat     300
atcgatctgc gttttatttt tctgaatcgc agcattgatg aaattgccga cctgtttatt     360
catgatatta agaaggcat tcagggcacc ccgaataaag caggttttgt taaaattgca     420
gccgatgaac cgggtattac caaagatgtt gaaaaagtta tcgtgcagc agccattgcc     480
aataaagaaa ccaaagttcc gattattacc catagcaatg cccataataa taccggtctg     540
gaacagcagc gtattctgac gaagaaggt gtggatccgg gtaaaattct gattggtcat     600
ctgggtgata ccgataatat cgattatatc aaaaaaattg ccgataaagg cagctttatt     660
ggtctggatc gttatggtct ggacatgtct ctgccggttg ataaacgtaa tgaaaccacc     720
ctgcgcctga ttaaagatgg ttatagcgat aaaattatga ttagccatga ttattgctgc     780
accattgata tgggcaccgc aaaaccggaa tataaaccga aaccggcacc gcgttggagc     840
attaccctga ttttgaaga tacaattccg tttctgaaac gcaatggtgt taatgaagaa     900
gtgattgcca ccatttttaa agaaaatccg aaaaaattct ttagctaa                 948

<210> SEQ ID NO 163
<211> LENGTH: 315
<212> TYPE: PRT
<213> ORGANISM: Sulfolobus solfataricus

<400> SEQUENCE: 163

Met Ala Arg Ile Pro Leu Val Gly Lys Asp Ser Ile Glu Ser Lys Asp
1               5                   10                  15

Ile Gly Phe Thr Leu Ile His Glu His Leu Arg Val Phe Ser Glu Ala
            20                  25                  30

Val Arg Gln Gln Trp Pro His Leu Tyr Asn Glu Asp Glu Glu Phe Arg
        35                  40                  45

Asn Ala Val Asn Glu Val Lys Arg Ala Met Gln Phe Gly Val Lys Thr
    50                  55                  60

```
Ile Val Asp Pro Ser Val Met Gly Ile Gly Arg Asp Ile Arg Phe Met
 65                  70                  75                  80

Glu Lys Val Val Lys Ala Thr Gly Ile Asn Leu Val Ala Gly Thr Gly
                 85                  90                  95

Ile Tyr Ile Tyr Ile Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Gly Thr Pro Asn Lys Ala Gly Phe Val Lys Ile Ala Ala Asp Glu Pro
    130                 135                 140

Gly Ile Thr Lys Asp Val Glu Lys Val Ile Arg Ala Ala Ile Ala
145                 150                 155                 160

Asn Lys Glu Thr Lys Val Pro Ile Ile Thr His Ser Asn Ala His Asn
                165                 170                 175

Asn Thr Gly Leu Glu Gln Gln Arg Ile Leu Thr Glu Glu Gly Val Asp
            180                 185                 190

Pro Gly Lys Ile Leu Ile Gly His Leu Gly Asp Thr Asp Asn Ile Asp
        195                 200                 205

Tyr Ile Lys Lys Ile Ala Asp Lys Gly Ser Phe Ile Gly Leu Asp Arg
    210                 215                 220

Tyr Gly Leu Asp Met Ser Leu Pro Val Asp Lys Arg Asn Glu Thr Thr
225                 230                 235                 240

Leu Arg Leu Ile Lys Asp Gly Tyr Ser Asp Lys Ile Met Ile Ser His
                245                 250                 255

Asp Tyr Cys Cys Thr Ile Asp Met Gly Thr Ala Lys Pro Glu Tyr Lys
            260                 265                 270

Pro Lys Pro Ala Pro Arg Trp Ser Ile Thr Leu Ile Phe Glu Asp Thr
        275                 280                 285

Ile Pro Phe Leu Lys Arg Asn Gly Val Asn Glu Glu Val Ile Ala Thr
    290                 295                 300

Ile Phe Lys Glu Asn Pro Lys Lys Phe Phe Ser
305                 310                 315
```

<210> SEQ ID NO 164
<211> LENGTH: 948
<212> TYPE: DNA
<213> ORGANISM: Sulfolobus solfataricus

<400> SEQUENCE: 164

```
atggcgcgca ttccgctggt tggtaaagat agcattgaaa gcaaagatat tggctttacc    60
ctgattcatg aacatctgcg tgttttttagc gaagcagttc gtcagcagtg gcctcatctg   120
tataatgaag atgaagaatt tcgcaatgcc gtgaatgaag ttaaacgtgc aatgcagttt   180
ggcgttaaaa ccattgttga tccgagtgtt atgggtctgg tcgtgatac tcgttttatg    240 gaaaaagttg tgaaagccac cggcattaat ctggttgcag gcaccggtat ttggattttt   300
atcgatctgc cgttttattt tctgaatcgc agcattgatg aaattgccga cctgtttatt   360
catgatatta agaaggcat tcagggcacc ctgaataaag caggttttgt taaaattgca   420
gccgatgaac cgggtattac caagatgtt gaaaaagtta ttcgtgcagc agccattgcc   480
aataaagaaa ccaaagttcc gattattacc catagcaatg cccataataa taccggtctg   540
gaacagcagc gtattctgac cgaagaaggt gtggatccgg gtaaaattct gattggtcat   600
ctgggtgata ccgataatat cgattatatc aaaaaaattg ccgataaagg cagctttatt   660
```

```
ggtctggatc gttatggtct ggacatgttt ctgccggttg ataaacgtaa tgaaaccacc    720
ctgcgcctga ttaaagatgg ttatagcgat aaaattatga ttagccatga ttattgctgc    780
accattgatc tgggcaccgc aaaaccggaa tataaaccga actggcaccc gcgttggagc    840
attaccctga tttttgaaga tacaattccg tttctgaaac gcaatggtgt taatgaagaa    900
gtgattgcca ccatttttaa agaaaatccg aaaaaattct ttagctaa                 948
```

<210> SEQ ID NO 165
<211> LENGTH: 315
<212> TYPE: PRT
<213> ORGANISM: Sulfolobus solfataricus

<400> SEQUENCE: 165

```
Met Ala Arg Ile Pro Leu Val Gly Lys Asp Ser Ile Glu Ser Lys Asp
1               5                   10                  15

Ile Gly Phe Thr Leu Ile His Glu His Leu Arg Val Phe Ser Glu Ala
                20                  25                  30

Val Arg Gln Gln Trp Pro His Leu Tyr Asn Glu Asp Glu Glu Phe Arg
            35                  40                  45

Asn Ala Val Asn Glu Val Lys Arg Ala Met Gln Phe Gly Val Lys Thr
    50                  55                  60

Ile Val Asp Pro Ser Val Met Gly Leu Gly Arg Asp Thr Arg Phe Met
65                  70                  75                  80

Glu Lys Val Val Lys Ala Thr Gly Ile Asn Leu Val Ala Gly Thr Gly
                85                  90                  95

Ile Trp Ile Phe Ile Asp Leu Pro Phe Tyr Phe Leu Asn Arg Ser Ile
                100                 105                 110

Asp Glu Ile Ala Asp Leu Phe Ile His Asp Ile Lys Glu Gly Ile Gln
            115                 120                 125

Gly Thr Leu Asn Lys Ala Gly Phe Val Lys Ile Ala Ala Asp Glu Pro
    130                 135                 140

Gly Ile Thr Lys Asp Val Glu Lys Val Ile Arg Ala Ala Ala Ile Ala
145                 150                 155                 160

Asn Lys Glu Thr Lys Val Pro Ile Ile Thr His Ser Asn Ala His Asn
                165                 170                 175

Asn Thr Gly Leu Glu Gln Gln Arg Ile Leu Thr Glu Glu Gly Val Asp
            180                 185                 190

Pro Gly Lys Ile Leu Ile Gly His Leu Gly Asp Thr Asp Asn Ile Asp
    195                 200                 205

Tyr Ile Lys Lys Ile Ala Asp Lys Gly Ser Phe Ile Gly Leu Asp Arg
210                 215                 220

Tyr Gly Leu Asp Met Phe Leu Pro Val Asp Lys Arg Asn Glu Thr Thr
225                 230                 235                 240

Leu Arg Leu Ile Lys Asp Gly Tyr Ser Asp Lys Ile Met Ile Ser His
                245                 250                 255

Asp Tyr Cys Cys Thr Ile Asp Leu Gly Thr Ala Lys Pro Glu Tyr Lys
            260                 265                 270

Pro Lys Leu Ala Pro Arg Trp Ser Ile Thr Leu Ile Phe Glu Asp Thr
    275                 280                 285

Ile Pro Phe Leu Lys Arg Asn Gly Val Asn Glu Glu Val Ile Ala Thr
290                 295                 300

Ile Phe Lys Glu Asn Pro Lys Lys Phe Phe Ser
305                 310                 315
```

<210> SEQ ID NO 166
<211> LENGTH: 948
<212> TYPE: DNA
<213> ORGANISM: Sulfolobus solfataricus

<400> SEQUENCE: 166

```
atggcgcgca ttccgctggt tggtgaagat agcattgaaa gcaaagatat tggctttacc      60
ctgattcatg aacatctgcg tgttttagc gaagcagttc gtcagcagtg cctcatctg      120
tataatgaag atgaagaact tcgcaatgcc gtgaatgaag ttaaacgtgc aatgcagttt      180
ggcgttaaaa ccattgttga tccgaccgtt atgggtctgg tcgtgatat cgttttatg       240
gaaaaagttg tgaaagccac cggcattaat ctggttgcag gcaccggtat ttggattttt      300
atcgatctgc cgttttattt tctgaatcgc agcattgatg aaattgccga cctgtttatt      360
catgatatta agaaggcat tcagggcacc ctgaataaag caggttttgt taaaattgca      420
gccgatgaac cgggtattac caaagatgtt gaaaaagtta ttcgtgcagc agccattgcc      480
aataaagaaa ccaaagttcc gattattacc atagcaatg cccataataa taccggtctg      540
gaacagcagc gtattctgac cgaagaaggt gtggatccgg gtaaaattct gattggtcat      600
ctgggtgata ccgataatat cgattatatc aaaaaaattg ccgataaagg cagctttatt      660
ggtctggatc gttatggtct ggacatgttt ctgccggttg ataaacgtaa tgaaaccacc      720
ctgcgcctga ttaaagatgg ttatagcgat aaaattatga ttagccatga ttattgctgc      780
accattgatt ggggcaccgc aaaaccggaa tataaaccga actggcaccg cgttggagc      840
attaccctga ttttgaaga tacaattccg tttctgaaac gcaatggtgt taatgaagaa      900
gtgattgcca ccatttttaa agaaaatccg aaaaaattct ttagctaa                  948
```

<210> SEQ ID NO 167
<211> LENGTH: 315
<212> TYPE: PRT
<213> ORGANISM: Sulfolobus solfataricus

<400> SEQUENCE: 167

Met Ala Arg Ile Pro Leu Val Gly Glu Asp Ser Ile Glu Ser Lys Asp
1               5                   10                  15

Ile Gly Phe Thr Leu Ile His Glu His Leu Arg Val Phe Ser Glu Ala
            20                  25                  30

Val Arg Gln Gln Trp Pro His Leu Tyr Asn Glu Asp Glu Glu Leu Arg
        35                  40                  45

Asn Ala Val Asn Glu Val Lys Arg Ala Met Gln Phe Gly Val Lys Thr
    50                  55                  60

Ile Val Asp Pro Thr Val Met Gly Leu Gly Arg Asp Ile Arg Phe Met
65                  70                  75                  80

Glu Lys Val Val Lys Ala Thr Gly Ile Asn Leu Val Ala Gly Thr Gly
                85                  90                  95

Ile Trp Ile Phe Ile Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Gly Thr Leu Asn Lys Ala Gly Phe Val Lys Ile Ala Ala Asp Glu Pro
    130                 135                 140

Gly Ile Thr Lys Asp Val Glu Lys Val Ile Arg Ala Ala Ala Ile Ala
145                 150                 155                 160

Asn Lys Glu Thr Lys Val Pro Ile Ile Thr His Ser Asn Ala His Asn
                165                 170                 175

Asn Thr Gly Leu Glu Gln Gln Arg Ile Leu Thr Glu Gly Val Asp
                180                 185                 190

Pro Gly Lys Ile Leu Ile Gly His Leu Gly Asp Thr Asp Asn Ile Asp
            195                 200                 205

Tyr Ile Lys Lys Ile Ala Asp Lys Gly Ser Phe Ile Gly Leu Asp Arg
210                 215                 220

Tyr Gly Leu Asp Met Phe Leu Pro Val Asp Lys Arg Asn Glu Thr Thr
225                 230                 235                 240

Leu Arg Leu Ile Lys Asp Gly Tyr Ser Asp Lys Ile Met Ile Ser His
                245                 250                 255

Asp Tyr Cys Cys Thr Ile Asp Trp Gly Thr Ala Lys Pro Glu Tyr Lys
            260                 265                 270

Pro Lys Leu Ala Pro Arg Trp Ser Ile Thr Leu Ile Phe Glu Asp Thr
        275                 280                 285

Ile Pro Phe Leu Lys Arg Asn Gly Val Asn Glu Val Ile Ala Thr
    290                 295                 300

Ile Phe Lys Glu Asn Pro Lys Lys Phe Phe Ser
305                 310                 315

<210> SEQ ID NO 168
<211> LENGTH: 948
<212> TYPE: DNA
<213> ORGANISM: Sulfolobus solfataricus

<400> SEQUENCE: 168
atggcgcgca ttccgctggt tggtaaagat agcattgaaa gcaaagatat tggctttacc      60
ctgattcatg aacatctgcg tgttttagc gaagcagttc gtcagcagtg gcctcatctg      120
tataatgaag atgaagaatt tcgcaatgcc gtgaatgaag ttaaacgtgc aatgcagttt      180
ggcgttaaaa ccattgttga tccgaccgtt atgggtattg gtcgtgatat cgttttatg      240 gaaaaagttg tgaaagccac cggcattaat ctggttgcag caccggtat ttatatttat      300 atcgatctgc gtttttattt tctgaatcgc agcattgatg aaattgccga cctgtttatt      360
catgatatta agaaggcat tcagggcacc ctgaataaag caggttttgt taaaattgca      420
gccgatgaac cgggtattac caaagatgtt gaaaaagtta ttcgtgcagc agccattgcc      480
aataaagaaa ccaaagttcc gattattacc catagcaatg cccataataa taccggtctg      540
gaacagcagc gtattctgac cgaagaaggt gtggatccgg gtaaaattct gattggtcat      600
ctgggtgata ccgataatat cgattatatc aaaaaaattg ccgataaagg cagctttatt      660
ggtctggatc gttatggtct ggacctgttt ctgccggttg ataaacgtaa tgaaaccacc      720
ctgcgcctga ttaaagatgg ttatagcgat aaaattatga ttagccatga ttattgctgc      780
accattgatt ttggcaccgc aaaaccggaa tataaaccga aactggcacc gcgttggagc      840
attaccctga tttttgaaga tacaattccg tttctgaaac gcaatggtgt aatgaagaa      900 gtgattgcca ccattttaa agaaaatccg aaaaaattct ttagctaa                   948

<210> SEQ ID NO 169
<211> LENGTH: 315
<212> TYPE: PRT
<213> ORGANISM: Sulfolobus solfataricus

<400> SEQUENCE: 169

Met Ala Arg Ile Pro Leu Val Gly Lys Asp Ser Ile Glu Ser Lys Asp
1               5                   10                  15

```
Ile Gly Phe Thr Leu Ile His Glu His Leu Arg Val Phe Ser Glu Ala
             20                  25                  30

Val Arg Gln Gln Trp Pro His Leu Tyr Asn Glu Asp Glu Phe Arg
         35                  40                  45

Asn Ala Val Asn Glu Val Lys Arg Ala Met Gln Phe Gly Val Lys Thr
 50                  55                  60

Ile Val Asp Pro Thr Val Met Gly Ile Gly Arg Asp Ile Arg Phe Met
 65                  70                  75                  80

Glu Lys Val Val Lys Ala Thr Gly Ile Asn Leu Val Ala Gly Thr Gly
                 85                  90                  95

Ile Tyr Ile Tyr Ile Asp Leu Pro Phe Tyr Phe Leu Asn Arg Ser Ile
                100                 105                 110

Asp Glu Ile Ala Asp Leu Phe Ile His Asp Ile Lys Glu Gly Ile Gln
            115                 120                 125

Gly Thr Leu Asn Lys Ala Gly Phe Val Lys Ile Ala Ala Asp Glu Pro
        130                 135                 140

Gly Ile Thr Lys Asp Val Glu Lys Val Ile Arg Ala Ala Ala Ile Ala
145                 150                 155                 160

Asn Lys Glu Thr Lys Val Pro Ile Ile Thr His Ser Asn Ala His Asn
                165                 170                 175

Asn Thr Gly Leu Glu Gln Gln Arg Ile Leu Thr Glu Glu Gly Val Asp
            180                 185                 190

Pro Gly Lys Ile Leu Ile Gly His Leu Gly Asp Thr Asp Asn Ile Asp
        195                 200                 205

Tyr Ile Lys Lys Ile Ala Asp Lys Gly Ser Phe Ile Gly Leu Asp Arg
210                 215                 220

Tyr Gly Leu Asp Leu Phe Leu Pro Val Asp Lys Arg Asn Glu Thr Thr
225                 230                 235                 240

Leu Arg Leu Ile Lys Asp Gly Tyr Ser Asp Lys Ile Met Ile Ser His
                245                 250                 255

Asp Tyr Cys Cys Thr Ile Asp Phe Gly Thr Ala Lys Pro Glu Tyr Lys
            260                 265                 270

Pro Lys Leu Ala Pro Arg Trp Ser Ile Thr Leu Ile Phe Glu Asp Thr
        275                 280                 285

Ile Pro Phe Leu Lys Arg Asn Gly Val Asn Glu Glu Val Ile Ala Thr
290                 295                 300

Ile Phe Lys Glu Asn Pro Lys Lys Phe Phe Ser
305                 310                 315

<210> SEQ ID NO 170
<211> LENGTH: 948
<212> TYPE: DNA
<213> ORGANISM: Sulfolobus solfataricus

<400> SEQUENCE: 170
atggcgcgca ttccgctggt tggtaaagat agcattgaaa gcaaagatat tggctttacc    60
ctgattcatg aacatctgcg tgttttagc gaagcagttc gtcagcagtg gcctcatctg   120
tataatgaag atgaagaatt cgcaatgcc gtgaatgaag ttaaacgtgc aatgcagttt   180
ggcgttaaaa ccattgttga tccgagtgtt atgggtctgg tcgtgatat cgtttttatg   240 gaaaaagttg tgaaagccac cggcattaat ctggttgcag caccggtat ttggattttt   300 atcgatctgc cgttttattt tctgaatcga agcattgatg aaattgccga cctgtttatt   360
catgatatta agaaggcat tcagggcacc ccgaataaag caggttttgt taaaattgca   420
```

```
gccgatgaac cgggtattac caaagatgtt gaaaaagtta ttcgtgcagc agccattgcc      480
aataaagaaa ccaaagttcc gattattacc catagcaatg cccataataa taccggtctg      540
gaacagcagc gtattctgac cgaagaaggt gtggatccgg gtaaaattct gattggtcat      600
ctgggtgata ccgataatat cgattatatc aaaaaaattg ccgataaagg cagctttatt      660
ggtctggatc gttatggtct ggacatgttt ctgccggttg ataaacgtaa tgaaaccacc      720
ctgcgcctga ttaaagatgg ttatagcgat aaaattatga ttagccatga ttattgctgc      780
accattgatt ggggcaccgc aaaaccggaa tataaaccga aactggcacc gcgttggagc      840
attaccctga ttttgaaga tacaattccg tttctgaaac gcaatggtgt taatgaagaa      900
gtgattgcca ccattttaa agaaaatccg aaaaaattct ttagctaa                    948
```

<210> SEQ ID NO 171
<211> LENGTH: 315
<212> TYPE: PRT
<213> ORGANISM: Sulfolobus solfataricus

<400> SEQUENCE: 171

```
Met Ala Arg Ile Pro Leu Val Gly Lys Asp Ser Ile Glu Ser Lys Asp
1               5                   10                  15

Ile Gly Phe Thr Leu Ile His Glu His Leu Arg Val Phe Ser Glu Ala
            20                  25                  30

Val Arg Gln Gln Trp Pro His Leu Tyr Asn Glu Asp Glu Phe Arg
        35                  40                  45

Asn Ala Val Asn Glu Val Lys Arg Ala Met Gln Phe Gly Val Lys Thr
    50                  55                  60

Ile Val Asp Pro Ser Val Met Gly Leu Gly Arg Asp Ile Arg Phe Met
65                  70                  75                  80

Glu Lys Val Val Lys Ala Thr Gly Ile Asn Leu Val Ala Gly Thr Gly
                85                  90                  95

Ile Trp Ile Phe Ile Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Gly Thr Pro Asn Lys Ala Gly Phe Val Lys Ile Ala Ala Asp Glu Pro
    130                 135                 140

Gly Ile Thr Lys Asp Val Glu Lys Val Ile Arg Ala Ala Ala Ile Ala
145                 150                 155                 160

Asn Lys Glu Thr Lys Val Pro Ile Ile Thr His Ser Asn Ala His Asn
                165                 170                 175

Asn Thr Gly Leu Glu Gln Gln Arg Ile Leu Thr Glu Glu Gly Val Asp
            180                 185                 190

Pro Gly Lys Ile Leu Ile Gly His Leu Gly Asp Thr Asp Asn Ile Asp
        195                 200                 205

Tyr Ile Lys Lys Ile Ala Asp Lys Gly Ser Phe Ile Gly Leu Asp Arg
    210                 215                 220

Tyr Gly Leu Asp Met Phe Leu Pro Val Asp Lys Arg Asn Glu Thr Thr
225                 230                 235                 240

Leu Arg Leu Ile Lys Asp Gly Tyr Ser Asp Lys Ile Met Ile Ser His
                245                 250                 255

Asp Tyr Cys Cys Thr Ile Asp Trp Gly Thr Ala Lys Pro Glu Tyr Lys
            260                 265                 270

Pro Lys Leu Ala Pro Arg Trp Ser Ile Thr Leu Ile Phe Glu Asp Thr
        275                 280                 285
```

Ile Pro Phe Leu Lys Arg Asn Gly Val Asn Glu Val Ile Ala Thr
    290                 295                 300

Ile Phe Lys Glu Asn Pro Lys Lys Phe Phe Ser
305                 310                 315

<210> SEQ ID NO 172
<211> LENGTH: 948
<212> TYPE: DNA
<213> ORGANISM: Sulfolobus solfataricus

<400> SEQUENCE: 172

```
atggcgcgca ttccgctggt tgtaaagat agcattgaaa gcaaagatat tggctttacc      60
ctgattcatg aacatctgcg tgcatttagc gaagcagttc gtcagcagtg gcctcatctg     120
tataatgaag atgaagaact tcgcaatgcc gtgaatgaag ttaaacgtgc aatgcagttt     180
ggcgttaaaa ccattgttga tccgaccgtt atgggtctgg gtcgtgatat cgtttttatg     240
gaaaaagttg tgaaagccac cggcattaat ctggttgcag gcaccggtat ttatattat      300
atcgatctgc cgttttattt tctgaatcgc agcattgatg aaattgccga cctgtttatt     360
catgatatta agaaggcat tcagggcacc ctgaataaag caggttttgt taaaattgca     420
gccgatgaac cgggtattac caaagatgtt gaaaaagtta tcgtgcagc agccattgcc     480
aataaagaaa ccaaagttcc gattattacc catagcaatg cccataataa taccggtctg     540
gaacagcagc gtattctgac cgaagaaggt gtggatccgg gtaaaattct gattggtcat     600
ctgggtgata ccgataatat cgattatatc aaaaaaattg ccgataaagg cagctttatt     660
ggtctggatc gttatggtgt ggacctgttt ctgccggttg ataaacgtaa tgaaaccacc     720
ctgcgcctga ttaaagatgg ttatagcgat aaaattatga ttagccatga ttattgctgc     780
accattgatc tgggcaccgc aaaaccggaa tataaaccga aactggcacc gcgttggagc     840
attaccctaa ttttttgaaga tacaattccg tttctgaaac gcaatggtgt taatgaagaa     900
gtgattgcca ccatttttaa agaaaatccg aaaaaattct ttagctaa                  948
```

<210> SEQ ID NO 173
<211> LENGTH: 315
<212> TYPE: PRT
<213> ORGANISM: Sulfolobus solfataricus

<400> SEQUENCE: 173

Met Ala Arg Ile Pro Leu Val Gly Lys Asp Ser Ile Glu Ser Lys Asp
1               5                   10                  15

Ile Gly Phe Thr Leu Ile His Glu His Leu Arg Ala Phe Ser Glu Ala
            20                  25                  30

Val Arg Gln Gln Trp Pro His Leu Tyr Asn Glu Asp Glu Glu Leu Arg
        35                  40                  45

Asn Ala Val Asn Glu Val Lys Arg Ala Met Gln Phe Gly Val Lys Thr
    50                  55                  60

Ile Val Asp Pro Thr Val Met Gly Leu Gly Arg Asp Ile Arg Phe Met
65                  70                  75                  80

Glu Lys Val Val Lys Ala Thr Gly Ile Asn Leu Val Ala Gly Thr Gly
            85                  90                  95

Ile Tyr Ile Tyr Ile Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

```
Gly Thr Leu Asn Lys Ala Gly Phe Val Lys Ile Ala Ala Asp Glu Pro
130                 135                 140

Gly Ile Thr Lys Asp Val Glu Lys Val Ile Arg Ala Ala Ile Ala
145                 150                 155                 160

Asn Lys Glu Thr Lys Val Pro Ile Ile Thr His Ser Asn Ala His Asn
                165                 170                 175

Asn Thr Gly Leu Glu Gln Gln Arg Ile Leu Thr Glu Glu Gly Val Asp
            180                 185                 190

Pro Gly Lys Ile Leu Ile Gly His Leu Gly Asp Thr Asp Asn Ile Asp
        195                 200                 205

Tyr Ile Lys Lys Ile Ala Asp Lys Gly Ser Phe Ile Gly Leu Asp Arg
210                 215                 220

Tyr Gly Val Asp Leu Phe Leu Pro Val Asp Lys Arg Asn Glu Thr Thr
225                 230                 235                 240

Leu Arg Leu Ile Lys Asp Gly Tyr Ser Asp Lys Ile Met Ile Ser His
                245                 250                 255

Asp Tyr Cys Cys Thr Ile Asp Leu Gly Thr Ala Lys Pro Glu Tyr Lys
            260                 265                 270

Pro Lys Leu Ala Pro Arg Trp Ser Ile Thr Leu Ile Phe Glu Asp Thr
        275                 280                 285

Ile Pro Phe Leu Lys Arg Asn Gly Val Asn Glu Glu Val Ile Ala Thr
290                 295                 300

Ile Phe Lys Glu Asn Pro Lys Lys Phe Phe Ser
305                 310                 315
```

<210> SEQ ID NO 174
<211> LENGTH: 948
<212> TYPE: DNA
<213> ORGANISM: Sulfolobus solfataricus

<400> SEQUENCE: 174

```
atggcgcgca ttccgctggt tggtaaagat agcattgaaa gcaaagatat tggctttacc      60
ctgattcatg aacatctgcg tgttttagc gaagcagttc gtcagcagtg gcctcatctg     120
tataatgaag atgaagaatt tcgcaatgcc gtgaatgaag ttaaacgtgc aatgcagttt     180
ggcgttaaaa ccattgttga tgtgagtgtt atgggtctgg tcgtgatat cgttttatg      240
gaaaaagttg tgaaagccac cggcattaat ctggttgcag caccggtat ttggattttt      300
atcgatctgc cgttttattt tctgaatcgc agcattgatg aaattgccga cctgtttatt     360
catgatatta agaaggcat tcagggcacc ctgaataaag caggttttgt taaaattgca     420
gccgatgaac cgggtattac caaagatgtt gagaaagtta ttcgtgcagc agccattgcc     480
aataaagaaa ccaaagttcc gattattacc catagcaatg cccataataa taccggtctg     540
gaacagcagc gtattctgac cgaagaaggt gtggatccgg gtaaaattct gattggtcat     600
ctgggtgata ccgataatat cgattatatc aaaaaaattg ccgataaagg cagctttatt     660
ggtctggatc gttatggtct ggacatgttt ctgccggttg ataaacgtaa tgaaaccacc     720
ctgcgcctga ttaaagatgg ttatagcgat aaaattatga ttagccatga ttatgcctgc     780
accattgatc tgggcaccgc aaaaccggaa tataaaccga actggcaccg cgttggagc      840
actaccctga ttttgaaga tacaattccg tttctgaaac gcaatggtgt aatgaagaa      900
gtgattgcca ccattttaa agaaaatccg aaaaaattct ttagctaa                  948
```

<210> SEQ ID NO 175
<211> LENGTH: 315

```
<212> TYPE: PRT
<213> ORGANISM: Sulfolobus solfataricus

<400> SEQUENCE: 175

Met Ala Arg Ile Pro Leu Val Gly Lys Asp Ser Ile Glu Ser Lys Asp
1               5                   10                  15

Ile Gly Phe Thr Leu Ile His Glu His Leu Arg Val Phe Ser Glu Ala
            20                  25                  30

Val Arg Gln Gln Trp Pro His Leu Tyr Asn Glu Asp Glu Glu Phe Arg
        35                  40                  45

Asn Ala Val Asn Glu Val Lys Arg Ala Met Gln Phe Gly Val Lys Thr
    50                  55                  60

Ile Val Asp Val Ser Val Met Gly Leu Gly Arg Asp Ile Arg Phe Met
65                  70                  75                  80

Glu Lys Val Val Lys Ala Thr Gly Ile Asn Leu Val Ala Gly Thr Gly
                85                  90                  95

Ile Trp Ile Phe Ile Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Gly Thr Leu Asn Lys Ala Gly Phe Val Lys Ile Ala Ala Asp Glu Pro
    130                 135                 140

Gly Ile Thr Lys Asp Val Glu Lys Val Ile Arg Ala Ala Ile Ala
145                 150                 155                 160

Asn Lys Glu Thr Lys Val Pro Ile Ile Thr His Ser Asn Ala His Asn
                165                 170                 175

Asn Thr Gly Leu Glu Gln Gln Arg Ile Leu Thr Glu Glu Gly Val Asp
            180                 185                 190

Pro Gly Lys Ile Leu Ile Gly His Leu Gly Asp Thr Asp Asn Ile Asp
        195                 200                 205

Tyr Ile Lys Lys Ile Ala Asp Lys Gly Ser Phe Ile Gly Leu Asp Arg
    210                 215                 220

Tyr Gly Leu Asp Met Phe Leu Pro Val Asp Lys Arg Asn Glu Thr Thr
225                 230                 235                 240

Leu Arg Leu Ile Lys Asp Gly Tyr Ser Asp Lys Ile Met Ile Ser His
                245                 250                 255

Asp Tyr Ala Cys Thr Ile Asp Leu Gly Thr Ala Lys Pro Glu Tyr Lys
            260                 265                 270

Pro Lys Leu Ala Pro Arg Trp Ser Thr Thr Leu Ile Phe Glu Asp Thr
        275                 280                 285

Ile Pro Phe Leu Lys Arg Asn Gly Val Asn Glu Glu Val Ile Ala Thr
    290                 295                 300

Ile Phe Lys Glu Asn Pro Lys Lys Phe Phe Ser
305                 310                 315

<210> SEQ ID NO 176
<211> LENGTH: 948
<212> TYPE: DNA
<213> ORGANISM: Sulfolobus solfataricus

<400> SEQUENCE: 176
atggcgcgca ttccgctggt tggtaaagat agcattgaaa gcaaagatat tggctttacc      60
ctgattcatg aacatctgcg tgtttttagc gaagcagttc gtcagcagtg gcctcatctg     120
tataatgaag atgaagaact tcgcaatgcc gtgaatgaag ttaaacgtgc aatgcagttt     180
```

```
ggcgttaaaa ccattgttga tccgagtgtt atgggtctgg gtcgtgatat tcgttttatg    240
gaaaaagttg tgaaagccac cggcattaat ctggttgcag gcaccggtat ttggattttt    300
atcgatctgc cgttttattt tctgaatcgc agcattgatg aaattgccga cctgtttatt    360
catgatatta agaaggcat tcagggcacc ccgaataaag caggttttgt taaaattgca    420
gctgatgaac cgggtattac caaagatgtt gaaaaagtta ttcgtgcagc agccattgcc    480
aataaagaaa ccaatgttcc gattattacc catagcaatg cccataataa taccggtctg    540
gaacagcagc gtattctgac cgaagaaggt gtggatccgg gtaaaattct gattggtcat    600
ctgggtgata ccgataatat cgattatatc aaaaaaattg ccgataaagg cagctttatt    660
ggtctggatc gttatggtgt ggacctgttt ctgccggttg ataaacgtaa tgaaaccacc    720
ctgcgcctga ttaaagatgg ttatagcgat aaaattatga ttagccatga ttattgctgc    780
accattgata tgggcaccgc aaaaccggaa tataaaccga actggcaccg cgttggagc    840 attaccctga tttttgaaga tacaattccg tttctgaaac gcaatggtgt taatgaagaa    900
gtgattgcca ccattttaa agaaaatccg aaaaaattct ttagctaa                 948
```

<210> SEQ ID NO 177
<211> LENGTH: 315
<212> TYPE: PRT
<213> ORGANISM: Sulfolobus solfataricus

<400> SEQUENCE: 177

```
Met Ala Arg Ile Pro Leu Val Gly Lys Asp Ser Ile Glu Ser Lys Asp
1               5                   10                  15

Ile Gly Phe Thr Leu Ile His Glu His Leu Arg Val Phe Ser Glu Ala
            20                  25                  30

Val Arg Gln Gln Trp Pro His Leu Tyr Asn Glu Asp Glu Glu Leu Arg
        35                  40                  45

Asn Ala Val Asn Glu Val Lys Arg Ala Met Gln Phe Gly Val Lys Thr
    50                  55                  60

Ile Val Asp Pro Ser Val Met Gly Leu Gly Arg Asp Ile Arg Phe Met
65                  70                  75                  80

Glu Lys Val Val Lys Ala Thr Gly Ile Asn Leu Val Ala Gly Thr Gly
                85                  90                  95

Ile Trp Ile Phe Ile Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Gly Thr Pro Asn Lys Ala Gly Phe Val Lys Ile Ala Ala Asp Glu Pro
    130                 135                 140

Gly Ile Thr Lys Asp Val Glu Lys Val Ile Arg Ala Ala Ala Ile Ala
145                 150                 155                 160

Asn Lys Glu Thr Asn Val Pro Ile Ile Thr His Ser Asn Ala His Asn
                165                 170                 175

Asn Thr Gly Leu Glu Gln Gln Arg Ile Leu Thr Glu Glu Gly Val Asp
            180                 185                 190

Pro Gly Lys Ile Leu Ile Gly His Leu Gly Asp Thr Asp Asn Ile Asp
        195                 200                 205

Tyr Ile Lys Lys Ile Ala Asp Lys Gly Ser Phe Ile Gly Leu Asp Arg
    210                 215                 220

Tyr Gly Val Asp Leu Phe Leu Pro Val Asp Lys Arg Asn Glu Thr Thr
225                 230                 235                 240
```

```
Leu Arg Leu Ile Lys Asp Gly Tyr Ser Asp Lys Ile Met Ile Ser His
                245                 250                 255

Asp Tyr Cys Cys Thr Ile Asp Met Gly Thr Ala Lys Pro Glu Tyr Lys
            260                 265                 270

Pro Lys Leu Ala Pro Arg Trp Ser Ile Thr Leu Ile Phe Glu Asp Thr
        275                 280                 285

Ile Pro Phe Leu Lys Arg Asn Gly Val Asn Glu Val Ile Ala Thr
    290                 295                 300

Ile Phe Lys Glu Asn Pro Lys Lys Phe Phe Ser
305                 310                 315

<210> SEQ ID NO 178
<211> LENGTH: 948
<212> TYPE: DNA
<213> ORGANISM: Sulfolobus solfataricus

<400> SEQUENCE: 178
atggcgcgca ttccgctggt tggtaaagat agcattgaaa gcaaagatat tggctttacc      60
ctgattcatg aacatctgcg tgttttagc gaagcagttc gtcagcagtg gccccatctg     120
tataatgaag atgaagaatt cgcaatgcc gtgaatgaag ttaaacgtgc aatgcagttt     180
ggcgttaaaa ccattgttga tccgagtgtt atgggtattg gtcgtgatat cgtttttatg     240
gaaaaagttg tgaaagccac cggcattaat ctggttgcag caccggtat ttggattttt      300 atcgatctgc gttttatttt tctgaatcgc agcattgatg aaattgccga cctgtttatt     360
catgatatta agaaggcat tcagggcacc ccgaataaag caggttttgt taaaattgca     420
gccgatgaac cgggtattac caaagatgtt gaaaaagtta tcgtgcagc agccattgcc      480 aataaagaaa ccaaagttcc gattattacc atagcaatg cccataataa taccggtctg     540
gaacagcagc gtattctgac cgaagaaggt gtggatccgg taaaattct gattggtcat     600 ctgggtgata ccgataatat cgattatatc aaaaaaattg ccgataaagg cagctttatt     660
ggtctggatc gttatggtct ggacctgttt ctgccggttg ataaacgtaa tgaaaccacc     720
ctgcgcctga ttaaagatgg ttatagcgat aaaattatga ttagccatga ttattgctgc     780
accattgatt ggggcaccgc aaaaccggaa tataaaccga actggcaccg cgttggagc     840 attaccctga ttttgaaga tacaattccg tttctgaaac gcaatggtgt taatgaagaa     900
gtgattgcca ccatttttaa agaaaatccg aaaaaattct ttagctaa                  948

<210> SEQ ID NO 179
<211> LENGTH: 315
<212> TYPE: PRT
<213> ORGANISM: Sulfolobus solfataricus

<400> SEQUENCE: 179

Met Ala Arg Ile Pro Leu Val Gly Lys Asp Ser Ile Glu Ser Lys Asp
1               5                   10                  15

Ile Gly Phe Thr Leu Ile His Glu His Leu Arg Val Phe Ser Glu Ala
            20                  25                  30

Val Arg Gln Gln Trp Pro His Leu Tyr Asn Glu Asp Glu Glu Phe Arg
        35                  40                  45

Asn Ala Val Asn Glu Val Lys Arg Ala Met Gln Phe Gly Val Lys Thr
    50                  55                  60

Ile Val Asp Pro Ser Val Met Gly Ile Gly Arg Asp Ile Arg Phe Met
65                  70                  75                  80

Glu Lys Val Val Lys Ala Thr Gly Ile Asn Leu Val Ala Gly Thr Gly
```

```
                    85                  90                  95
Ile Trp Ile Phe Ile Asp Leu Pro Phe Tyr Phe Leu Asn Arg Ser Ile
                100                 105                 110

Asp Glu Ile Ala Asp Leu Phe Ile His Asp Ile Lys Glu Gly Ile Gln
                115                 120                 125

Gly Thr Pro Asn Lys Ala Gly Phe Val Lys Ile Ala Ala Asp Glu Pro
                130                 135                 140

Gly Ile Thr Lys Asp Val Glu Lys Val Ile Arg Ala Ala Ala Ile Ala
145                 150                 155                 160

Asn Lys Glu Thr Lys Val Pro Ile Ile Thr His Ser Asn Ala His Asn
                165                 170                 175

Asn Thr Gly Leu Glu Gln Gln Arg Ile Leu Thr Glu Gly Val Asp
                180                 185                 190

Pro Gly Lys Ile Leu Ile Gly His Leu Gly Asp Thr Asp Asn Ile Asp
                195                 200                 205

Tyr Ile Lys Lys Ile Ala Asp Lys Gly Ser Phe Ile Gly Leu Asp Arg
                210                 215                 220

Tyr Gly Leu Asp Leu Phe Leu Pro Val Asp Lys Arg Asn Glu Thr Thr
225                 230                 235                 240

Leu Arg Leu Ile Lys Asp Gly Tyr Ser Asp Lys Ile Met Ile Ser His
                245                 250                 255

Asp Tyr Cys Cys Thr Ile Asp Trp Gly Thr Ala Lys Pro Glu Tyr Lys
                260                 265                 270

Pro Lys Leu Ala Pro Arg Trp Ser Ile Thr Leu Ile Phe Glu Asp Thr
                275                 280                 285

Ile Pro Phe Leu Lys Arg Asn Gly Val Asn Glu Glu Val Ile Ala Thr
                290                 295                 300

Ile Phe Lys Glu Asn Pro Lys Lys Phe Phe Ser
305                 310                 315

<210> SEQ ID NO 180
<211> LENGTH: 951
<212> TYPE: DNA
<213> ORGANISM: Sulfolobus acidocaldarius

<400> SEQUENCE: 180
atggcgacca aaattccgct ggttggtaaa ggtgaaatta gtccgggtga atgggttttt      60
accctgattc atgaacatct gcgtgttttt agcgaaccgg tgcgttatca gtggcctcat     120
ctgtataatg aagatgaaga actgaaaaac gccgtgaacg aagtgaaaac cattatgagc     180
tatggcgtta aaaccattgt tgatccgacc gttatgggtc tgggtcgtga tattcgtttt     240
agtgaaaaag tggtgaaaga aaccggcatt aatgttattg cagcaaccgg tctgtatacc     300
tataccgatc tgccgttttt tttcaatggt cgtagcctgg aagaaattgc agaactgctg     360
atccacgata tcaaaaaagg tattcagggc accaataatc gtgcgggttt tatcaaagtt     420
gcagcagatg aaccgggtat tacccgtgat gttgaacgtg caattcgtgc agcagcaatt     480
gcacagaaag aaacaaatgt tccgattatc acccatagca atgcacataa tggcaccggt     540
ctggaacagc agcgtattct gatggaagaa ggtgtggatc cgggtcgtgt tctgattggt     600
catctgggtg ataccgataa cgtggactac atcaaaaaaa tcgcagataa aggtagcttt     660
gttggcctgg atcgctatgg tctggacctg tttctgccga ttgataaacg taatgaagtt     720
ctgctgaaac tgatcaaaga tggttatctg gatcgtatta ggtgagcca ggattattgt     780
tgtaccattg attttggtat tgccaaaccg aatataaaac cgaaactggc accgaaatgg     840
```

```
tcaatgagcc tgattttac cgatgtgatt ccgagcatta acgtgccgg tgttaccgat      900 gaacagctgc atgtgatttt tgttaaaaat ccggcacgcc tgtttagctg a             951
```

<210> SEQ ID NO 181
<211> LENGTH: 316
<212> TYPE: PRT
<213> ORGANISM: Sulfolobus acidocaldarius

<400> SEQUENCE: 181

```
Met Ala Thr Lys Ile Pro Leu Val Gly Lys Gly Glu Ile Ser Pro Gly
1               5                   10                  15

Glu Met Gly Phe Thr Leu Ile His Glu His Leu Arg Val Phe Ser Glu
            20                  25                  30

Pro Val Arg Tyr Gln Trp Pro His Leu Tyr Asn Glu Asp Glu Glu Leu
        35                  40                  45

Lys Asn Ala Val Asn Glu Val Lys Thr Ile Met Ser Tyr Gly Val Lys
    50                  55                  60

Thr Ile Val Asp Pro Thr Val Met Gly Leu Gly Arg Asp Ile Arg Phe
65                  70                  75                  80

Ser Glu Lys Val Val Lys Glu Thr Gly Ile Asn Val Ile Ala Ala Thr
                85                  90                  95

Gly Leu Tyr Thr Tyr Thr Asp Leu Pro Phe Phe Phe Asn Gly Arg Ser
            100                 105                 110

Leu Glu Glu Ile Ala Glu Leu Leu Ile His Asp Ile Lys Lys Gly Ile
        115                 120                 125

Gln Gly Thr Asn Asn Arg Ala Gly Phe Ile Lys Val Ala Ala Asp Glu
    130                 135                 140

Pro Gly Ile Thr Arg Asp Val Glu Arg Ala Ile Arg Ala Ala Ala Ile
145                 150                 155                 160

Ala Gln Lys Glu Thr Asn Val Pro Ile Ile Thr His Ser Asn Ala His
                165                 170                 175

Asn Gly Thr Gly Leu Glu Gln Gln Arg Ile Leu Met Glu Glu Gly Val
            180                 185                 190

Asp Pro Gly Arg Val Leu Ile Gly His Leu Gly Asp Thr Asp Asn Val
        195                 200                 205

Asp Tyr Ile Lys Lys Ile Ala Asp Lys Gly Ser Phe Val Gly Leu Asp
    210                 215                 220

Arg Tyr Gly Leu Asp Leu Phe Leu Pro Ile Asp Lys Arg Asn Glu Val
225                 230                 235                 240

Leu Leu Lys Leu Ile Lys Asp Gly Tyr Leu Asp Arg Ile Met Val Ser
                245                 250                 255

Gln Asp Tyr Cys Cys Thr Ile Asp Phe Gly Ile Ala Lys Pro Glu Tyr
            260                 265                 270

Lys Pro Lys Leu Ala Pro Lys Trp Ser Met Ser Leu Ile Phe Thr Asp
        275                 280                 285

Val Ile Pro Ser Ile Lys Arg Ala Gly Val Thr Asp Glu Gln Leu His
    290                 295                 300

Val Ile Phe Val Lys Asn Pro Ala Arg Leu Phe Ser
305                 310                 315
```

<210> SEQ ID NO 182
<211> LENGTH: 951
<212> TYPE: DNA
<213> ORGANISM: Sulfolobus acidocaldarius

<400> SEQUENCE: 182

```
atggcgacca aaattccgct ggttggtaaa ggtgaaatta gtccgggtga atgggttttt      60
accctgattc atgaacatct gcgtgttttt agcgaaccgg tgcgttatca gtggcctcat     120
ctgtataatg aagatgaaga actgaaaaac gccgtgaacg aagtgaaaac cattatgagc     180
tatggcgtta aaccattgt tgatccgacc gttatgggtc tgggtcgtga tattcgtttt      240
agtgaaaaag tggtgaaaga aaccggcatt aatgttattg cagcaaccgg tctgtatacc     300
tataccgatc tgccgttttt tttcaatggt cgtagcctgg aagaaattgc agaactgctg     360
atccacgata tcaaaaaagg tattcagggc accaataatc gtgcgggttt tatcaaagtt     420
gcagcagatg aaccgggtat tacccgtgat gttgaacgtg caattcgtgc agcagcaatt     480
gcacagaaag aaacaaatgt tccgattatc acccatagca atgcacataa tggcaccggt     540
ctggaacagc agcgtattct gatggaagaa ggtgtggatc cgggtcgtgt tctgattggt     600
catctgggtg ataccgataa cgtggactac atcaaaaaaa tcgcagataa aggtagcttt     660
gttggcctgg atcgctatgg tctggacctg tttctgccga ttgataaacg taatgaagtt     720
ctgctgaaac tgatcaaaga tggttatctg gatcgtatta tggtgagcca ggattattgt     780
tgtaccattg atatgggtat tgccaaaccg aatataaaac cgaaactggc accgaaatgg     840
tcaatgagcc tgattttttac cgatgtgatt ccgagcatta acgtgccgg tgttaccgat      900
gaacagctgc atgtgattt tgttaaaaat ccggcacgcc tgtttagctg a              951
```

<210> SEQ ID NO 183
<211> LENGTH: 316
<212> TYPE: PRT
<213> ORGANISM: Sulfolobus acidocaldarius

<400> SEQUENCE: 183

```
Met Ala Thr Lys Ile Pro Leu Val Gly Lys Gly Glu Ile Ser Pro Gly
1               5                   10                  15

Glu Met Gly Phe Thr Leu Ile His Glu His Leu Arg Val Phe Ser Glu
            20                  25                  30

Pro Val Arg Tyr Gln Trp Pro His Leu Tyr Asn Glu Asp Glu Glu Leu
        35                  40                  45

Lys Asn Ala Val Asn Glu Val Lys Thr Ile Met Ser Tyr Gly Val Lys
    50                  55                  60

Thr Ile Val Asp Pro Thr Val Met Gly Leu Gly Arg Asp Ile Arg Phe
65                  70                  75                  80

Ser Glu Lys Val Val Lys Glu Thr Gly Ile Asn Val Ile Ala Ala Thr
                85                  90                  95

Gly Leu Tyr Thr Tyr Thr Asp Leu Pro Phe Phe Phe Asn Gly Arg Ser
            100                 105                 110

Leu Glu Glu Ile Ala Glu Leu Leu Ile His Asp Ile Lys Lys Gly Ile
        115                 120                 125

Gln Gly Thr Asn Asn Arg Ala Gly Phe Ile Lys Val Ala Ala Asp Glu
    130                 135                 140

Pro Gly Ile Thr Arg Asp Val Glu Arg Ala Ile Arg Ala Ala Ile
145                 150                 155                 160

Ala Gln Lys Glu Thr Asn Val Pro Ile Ile Thr His Ser Asn Ala His
                165                 170                 175

Asn Gly Thr Gly Leu Glu Gln Gln Arg Ile Leu Met Glu Glu Gly Val
            180                 185                 190

Asp Pro Gly Arg Val Leu Ile Gly His Leu Gly Asp Thr Asp Asn Val
```

|  | 195 |  |  |  | 200 |  |  |  | 205 |  |  |
|---|---|---|---|---|---|---|---|---|---|---|---|

Asp Tyr Ile Lys Lys Ile Ala Asp Lys Gly Ser Phe Val Gly Leu Asp
    210                 215                 220

Arg Tyr Gly Leu Asp Leu Phe Leu Pro Ile Asp Lys Arg Asn Glu Val
225                 230                 235                 240

Leu Leu Lys Leu Ile Lys Asp Gly Tyr Leu Asp Arg Ile Met Val Ser
                245                 250                 255

Gln Asp Tyr Cys Cys Thr Ile Asp Met Gly Ile Ala Lys Pro Glu Tyr
            260                 265                 270

Lys Pro Lys Leu Ala Pro Lys Trp Ser Met Ser Leu Ile Phe Thr Asp
        275                 280                 285

Val Ile Pro Ser Ile Lys Arg Ala Gly Val Thr Asp Glu Gln Leu His
    290                 295                 300

Val Ile Phe Val Lys Asn Pro Ala Arg Leu Phe Ser
305                 310                 315

<210> SEQ ID NO 184
<211> LENGTH: 951
<212> TYPE: DNA
<213> ORGANISM: Sulfolobus acidocaldarius

<400> SEQUENCE: 184

```
atggcgacca aaattccgct ggttggtaaa ggtgaaatta gtccgggtga atgggtttt      60
accctgattc atgaacatct gcgtgttttt agcgaaccgg tgcgttatca gtggcctcat    120
ctgtataatg aagatgaaga actgaaaaac gccgtgaacg aagtgaaaac cattatgagc    180
tatggcgtta aaaccattgt tgatccgacc gttatgggtc tgggtcgtga tattcgtttt    240
agtgaaaaag tggtgaaaga aaccggcatt aatgttattg cagcaaccgg tctgtatacc    300
tataccgatc tgccgttttt tttcaatggt cgtagcctgg aagaaattgc agaactgctg    360
atccacgata tcaaaaaagg tattcagggc accaataatc gtgcgggttt tatcaaagtt    420
gcagcagatg aaccgggtat tacccgtgat gttgaacgtg caattcgtgc agcagcaatt    480
gcacagaaag aaacaaatgt tccgattatc acccatagca atgcacataa tggcaccggt    540
ctggaacagc agcgtattct gatggaagaa ggtgtggatc cgggtcgtgt tctgattggt    600
catctgggtg ataccgataa cgtggactac atcaaaaaaa tcgcagataa aggtagcttt    660
gttggcctgg atcgctatgg tctggacctg tttctgccga ttgataaacg taatgaagtt    720
ctgctgaaac tgatcaaaga tggttatctg gatcgtatta tggtgagcca ggattattgt    780
tgtaccattg atctgggtat tgccaaaccg gaatataaac cgaaactggc accgaaatgg    840
tcaatgagcc tgattttttac cgatgtgatt ccgagcatta aacgtgccgg tgttaccgat    900
gaacagctgc atgtgatttt tgttaaaaat ccggcacgcc tgtttagctg a              951
```

<210> SEQ ID NO 185
<211> LENGTH: 316
<212> TYPE: PRT
<213> ORGANISM: Sulfolobus acidocaldarius

<400> SEQUENCE: 185

Met Ala Thr Lys Ile Pro Leu Val Gly Lys Gly Glu Ile Ser Pro Gly
1               5                   10                  15

Glu Met Gly Phe Thr Leu Ile His Glu His Leu Arg Val Phe Ser Glu
            20                  25                  30

Pro Val Arg Tyr Gln Trp Pro His Leu Tyr Asn Glu Asp Glu Glu Leu
        35                  40                  45

Lys Asn Ala Val Asn Glu Val Lys Thr Ile Met Ser Tyr Gly Val Lys
                50                  55                  60

Thr Ile Val Asp Pro Thr Val Met Gly Leu Gly Arg Asp Ile Arg Phe
 65                  70                  75                  80

Ser Glu Lys Val Val Lys Glu Thr Gly Ile Asn Val Ile Ala Ala Thr
                    85                  90                  95

Gly Leu Tyr Thr Tyr Thr Asp Leu Pro Phe Phe Asn Gly Arg Ser
                100                 105                 110

Leu Glu Glu Ile Ala Glu Leu Leu Ile His Asp Ile Lys Lys Gly Ile
            115                 120                 125

Gln Gly Thr Asn Asn Arg Ala Gly Phe Ile Lys Val Ala Ala Asp Glu
        130                 135                 140

Pro Gly Ile Thr Arg Asp Val Glu Arg Ala Ile Arg Ala Ala Ile
145                 150                 155                 160

Ala Gln Lys Glu Thr Asn Val Pro Ile Ile Thr His Ser Asn Ala His
                165                 170                 175

Asn Gly Thr Gly Leu Glu Gln Gln Arg Ile Leu Met Glu Glu Gly Val
            180                 185                 190

Asp Pro Gly Arg Val Leu Ile Gly His Leu Gly Asp Thr Asp Asn Val
        195                 200                 205

Asp Tyr Ile Lys Lys Ile Ala Asp Lys Gly Ser Phe Val Gly Leu Asp
210                 215                 220

Arg Tyr Gly Leu Asp Leu Phe Leu Pro Ile Asp Lys Arg Asn Glu Val
225                 230                 235                 240

Leu Leu Lys Leu Ile Lys Asp Gly Tyr Leu Asp Arg Ile Met Val Ser
                245                 250                 255

Gln Asp Tyr Cys Cys Thr Ile Asp Leu Gly Ile Ala Lys Pro Glu Tyr
            260                 265                 270

Lys Pro Lys Leu Ala Pro Lys Trp Ser Met Ser Leu Ile Phe Thr Asp
        275                 280                 285

Val Ile Pro Ser Ile Lys Arg Ala Gly Val Thr Asp Glu Gln Leu His
290                 295                 300

Val Ile Phe Val Lys Asn Pro Ala Arg Leu Phe Ser
305                 310                 315

<210> SEQ ID NO 186
<211> LENGTH: 951
<212> TYPE: DNA
<213> ORGANISM: Sulfolobus acidocaldarius

<400> SEQUENCE: 186
atggcgacca aaattccgct ggttggtaaa ggtgaaatta gtccgggtga atgggtttt      60 accctgattc atgaacatct gcgtgttttt agcgaaccgg tgcgttatca gtggcctcat     120
ctgtataatg aagatgaaga actgaaaaac gccgtgaacg aagtgaaaac cattatgagc     180
tatggcgtta aaaccattgt tgatccgacc gttatgggtc tgggtcgtga tattcgtttt     240
agtgaaaaag tggtgaaaga aaccggcatt aatgttattg cagcaaccgg tctgtatacc     300
tataccgatc tgccgttttt tttcaatggt cgtagcctgg aagaaattgc agaactgctg     360
atccacgata tcaaaaaagg tattcagggc accaataatc gtgcgggttt tatcaaagtt     420
gcagcagatg aaccgggtat tacccgtgat gttgaacgtg caattcgtgc agcagcaatt     480
gcacagaaag aaacaaatgt tccgattatc acccatagca atgcacataa tggcaccggt     540
ctggaacagc agcgtattct gatggaagaa ggtgtggatc cgggtcgtgt tctgattggt     600

-continued

```
catctgggtg ataccgataa cgtggactac atcaaaaaaa tcgcagataa aggtagcttt    660
gttggcctgg atcgctatgg tctggacctg tttctgccga ttgataaacg taatgaagtt    720
ctgctgaaac tgatcaaaga tggttatctg gatcgtatta tggtgagcca ggattattgt    780
tgtaccattg atgcaggtat tgccaaaccg aatataaaac cgaaactggc accgaaatgg    840
tcaatgagcc tgatttttac cgatgtgatt ccgagcatta aacgtgccgg tgttaccgat    900
gaacagctgc atgtgatttt tgttaaaaat ccggcacgcc tgtttagctg a             951
```

<210> SEQ ID NO 187
<211> LENGTH: 316
<212> TYPE: PRT
<213> ORGANISM: Sulfolobus acidocaldarius

<400> SEQUENCE: 187

Met Ala Thr Lys Ile Pro Leu Val Gly Lys Gly Glu Ile Ser Pro Gly
1               5                   10                  15

Glu Met Gly Phe Thr Leu Ile His Glu His Leu Arg Val Phe Ser Glu
            20                  25                  30

Pro Val Arg Tyr Gln Trp Pro His Leu Tyr Asn Glu Asp Glu Glu Leu
        35                  40                  45

Lys Asn Ala Val Asn Glu Val Lys Thr Ile Met Ser Tyr Gly Val Lys
    50                  55                  60

Thr Ile Val Asp Pro Thr Val Met Gly Leu Gly Arg Asp Ile Arg Phe
65                  70                  75                  80

Ser Glu Lys Val Val Lys Glu Thr Gly Ile Asn Val Ile Ala Ala Thr
                85                  90                  95

Gly Leu Tyr Thr Tyr Thr Asp Leu Pro Phe Phe Phe Asn Gly Arg Ser
            100                 105                 110

Leu Glu Glu Ile Ala Glu Leu Leu Ile His Asp Ile Lys Lys Gly Ile
        115                 120                 125

Gln Gly Thr Asn Asn Arg Ala Gly Phe Ile Lys Val Ala Ala Asp Glu
    130                 135                 140

Pro Gly Ile Thr Arg Asp Val Glu Arg Ala Ile Arg Ala Ala Ala Ile
145                 150                 155                 160

Ala Gln Lys Glu Thr Asn Val Pro Ile Ile Thr His Ser Asn Ala His
                165                 170                 175

Asn Gly Thr Gly Leu Glu Gln Gln Arg Ile Leu Met Glu Glu Gly Val
            180                 185                 190

Asp Pro Gly Arg Val Leu Ile Gly His Leu Gly Asp Thr Asp Asn Val
        195                 200                 205

Asp Tyr Ile Lys Lys Ile Ala Asp Lys Gly Ser Phe Val Gly Leu Asp
    210                 215                 220

Arg Tyr Gly Leu Asp Leu Phe Leu Pro Ile Asp Lys Arg Asn Glu Val
225                 230                 235                 240

Leu Leu Lys Leu Ile Lys Asp Gly Tyr Leu Asp Arg Ile Met Val Ser
                245                 250                 255

Gln Asp Tyr Cys Cys Thr Ile Asp Ala Gly Ile Ala Lys Pro Glu Tyr
            260                 265                 270

Lys Pro Lys Leu Ala Pro Lys Trp Ser Met Ser Leu Ile Phe Thr Asp
        275                 280                 285

Val Ile Pro Ser Ile Lys Arg Ala Gly Val Thr Asp Glu Gln Leu His
    290                 295                 300

Val Ile Phe Val Lys Asn Pro Ala Arg Leu Phe Ser

<210> SEQ ID NO 188
<211> LENGTH: 951
<212> TYPE: DNA
<213> ORGANISM: Sulfolobus acidocaldarius

<400> SEQUENCE: 188

```
atggcgacca aaattccgct ggttggtaaa ggtgaaatta gtccgggtga atgggttt      60
accctgattc atgaacatct gcgtgttttt agcgaaccgg tgcgttatca gtggcctcat     120
ctgtataatg aagatgaaga actgaaaaac gccgtgaacg aagtgaaaac cattatgagc     180
tatggcgtta aaaccattgt tgatccgacc gttatgggtc tgggtcgtga tattcgtttt     240
agtgaaaaag tggtgaaaga aaccggcatt aatgttattg cagcaaccgg tctgtatacc     300
tataccgatc tgccgttttt tttcaatggt cgtagcctgg aagaaattgc agaactgctg     360
atccacgata tcaaaaaagg tattcagggc accaataatc gtgcgggttt tatcaaagtt     420
gcagcagatg aaccgggtat tacccgtgat gttgaacgtg caattcgtgc agcagcaatt     480
gcacagaaag aaacaaatgt tccgattatc acccatagca atgcacataa tggcaccggt     540
ctggaacagc agcgtattct gatggaagaa ggtgtggatc cgggtcgtgt tctgattggt     600
catctgggtg ataccgataa cgtggactac atcaaaaaaa tcgcagataa aggtagcttt     660
gttggcctgg atcgctatgg tctggacctg tttctgccga ttgataaacg taatgaagtt     720
ctgctgaaac tgatcaaaga tggttatctg gatcgtatta tggtgagcca ggattattgt     780
tgtaccattg atattggtat tgccaaaccg aatataaac cgaaactggc accgaaatgg     840
tcaatgagcc tgattttac cgatgtgatt ccgagcatta acgtgccgg tgttaccgat      900
gaacagctgc atgtgatttt tgttaaaaat ccggcacgcc tgtttagctg a             951
```

<210> SEQ ID NO 189
<211> LENGTH: 316
<212> TYPE: PRT
<213> ORGANISM: Sulfolobus acidocaldarius

<400> SEQUENCE: 189

```
Met Ala Thr Lys Ile Pro Leu Val Gly Lys Gly Glu Ile Ser Pro Gly
1               5                   10                  15

Glu Met Gly Phe Thr Leu Ile His Glu His Leu Arg Val Phe Ser Glu
            20                  25                  30

Pro Val Arg Tyr Gln Trp Pro His Leu Tyr Asn Glu Asp Glu Glu Leu
        35                  40                  45

Lys Asn Ala Val Asn Glu Val Lys Thr Ile Met Ser Tyr Gly Val Lys
    50                  55                  60

Thr Ile Val Asp Pro Thr Val Met Gly Leu Gly Arg Asp Ile Arg Phe
65                  70                  75                  80

Ser Glu Lys Val Val Lys Glu Thr Gly Ile Asn Val Ile Ala Ala Thr
                85                  90                  95

Gly Leu Tyr Thr Tyr Thr Asp Leu Pro Phe Phe Phe Asn Gly Arg Ser
            100                 105                 110

Leu Glu Glu Ile Ala Glu Leu Leu Ile His Asp Ile Lys Lys Gly Ile
        115                 120                 125

Gln Gly Thr Asn Asn Arg Ala Gly Phe Ile Lys Val Ala Ala Asp Glu
    130                 135                 140

Pro Gly Ile Thr Arg Asp Val Glu Arg Ala Ile Arg Ala Ala Ala Ile
145                 150                 155                 160
```

```
Ala Gln Lys Glu Thr Asn Val Pro Ile Ile Thr His Ser Asn Ala His
            165                 170                 175

Asn Gly Thr Gly Leu Glu Gln Gln Arg Ile Leu Met Glu Glu Gly Val
        180                 185                 190

Asp Pro Gly Arg Val Leu Ile Gly His Leu Gly Asp Thr Asp Asn Val
    195                 200                 205

Asp Tyr Ile Lys Lys Ile Ala Asp Lys Gly Ser Phe Val Gly Leu Asp
210                 215                 220

Arg Tyr Gly Leu Asp Leu Phe Leu Pro Ile Asp Lys Arg Asn Glu Val
225                 230                 235                 240

Leu Leu Lys Leu Ile Lys Asp Gly Tyr Leu Asp Arg Ile Met Val Ser
                245                 250                 255

Gln Asp Tyr Cys Cys Thr Ile Asp Ile Gly Ile Ala Lys Pro Glu Tyr
            260                 265                 270

Lys Pro Lys Leu Ala Pro Lys Trp Ser Met Ser Leu Ile Phe Thr Asp
        275                 280                 285

Val Ile Pro Ser Ile Lys Arg Ala Gly Val Thr Asp Glu Gln Leu His
    290                 295                 300

Val Ile Phe Val Lys Asn Pro Ala Arg Leu Phe Ser
305                 310                 315

<210> SEQ ID NO 190
<211> LENGTH: 951
<212> TYPE: DNA
<213> ORGANISM: Sulfolobus acidocaldarius

<400> SEQUENCE: 190
atggcgacca aaattccgct ggttggtaaa ggtgaaatta gtccgggtga atgggtttt      60 accctgattc atgaacatct gcgtgttttt agcgaaccgg tgcgttatca gtggcctcat    120
ctgtataatg aagatgaaga actgaaaaac gccgtgaacg aagtgaaaac cattatgagc    180
tatggcgtta aaaccattgt tgatccgacc gttatgggtc tgggtcgtga tattcgtttt    240
agtgaaaaag tggtgaaaga aaccggcatt aatgttattg cagcaaccgg tctgtatacc    300
tataccgatc tgccgttttt tttcaatggt cgtagcctgg aagaaattgc agaactgctg    360
atccacgata tcaaaaaagg tattcagggc accaataatc gtgcgggttt tatcaaagtt    420
gcagcagatg aaccgggtat tacccgtgat gttgaacgtg caattcgtgc agcagcaatt    480
gcacagaaag aaacaaatgt tccgattatc acccatagca atgcacataa tggcaccggt    540
ctggaacagc agcgtattct gatggaagaa ggtgtggatc cgggtcgtgt tctgattggt    600
catctgggtg ataccgataa cgtggactac atcaaaaaaa tcgcagataa aggtagcttt    660
gttggcctgg atcgctatgg tctggacctg tttctgccga ttgataaacg taatgaagtt    720
ctgctgaaac tgatcaaaga tggttatctg gatcgtatta tggtgagcca ggattattgt    780
tgtaccattg atgttggtat tgccaaaccg gaatataaac cgaaactggc accgaaatgg    840
tcaatgagcc tgattttta cgatgtgatt ccgagcatta aacgtgccgg tgttaccgat    900
gaacagctgc atgtgatttt tgttaaaaat ccggcacgcc tgtttagctg a              951

<210> SEQ ID NO 191
<211> LENGTH: 316
<212> TYPE: PRT
<213> ORGANISM: Sulfolobus acidocaldarius

<400> SEQUENCE: 191
```

```
Met Ala Thr Lys Ile Pro Leu Val Gly Lys Gly Glu Ile Ser Pro Gly
1               5                   10                  15

Glu Met Gly Phe Thr Leu Ile His Glu His Leu Arg Val Phe Ser Glu
            20                  25                  30

Pro Val Arg Tyr Gln Trp Pro His Leu Tyr Asn Glu Asp Glu Glu Leu
        35                  40                  45

Lys Asn Ala Val Asn Glu Val Lys Thr Ile Met Ser Tyr Gly Val Lys
    50                  55                  60

Thr Ile Val Asp Pro Thr Val Met Gly Leu Gly Arg Asp Ile Arg Phe
65                  70                  75                  80

Ser Glu Lys Val Val Lys Glu Thr Gly Ile Asn Val Ile Ala Ala Thr
                85                  90                  95

Gly Leu Tyr Thr Tyr Thr Asp Leu Pro Phe Phe Phe Asn Gly Arg Ser
            100                 105                 110

Leu Glu Glu Ile Ala Glu Leu Leu Ile His Asp Ile Lys Lys Gly Ile
        115                 120                 125

Gln Gly Thr Asn Asn Arg Ala Gly Phe Ile Lys Val Ala Ala Asp Glu
    130                 135                 140

Pro Gly Ile Thr Arg Asp Val Glu Arg Ala Ile Arg Ala Ala Ile
145                 150                 155                 160

Ala Gln Lys Glu Thr Asn Val Pro Ile Ile Thr His Ser Asn Ala His
                165                 170                 175

Asn Gly Thr Gly Leu Glu Gln Gln Arg Ile Leu Met Glu Glu Gly Val
            180                 185                 190

Asp Pro Gly Arg Val Leu Ile Gly His Leu Gly Asp Thr Asp Asn Val
        195                 200                 205

Asp Tyr Ile Lys Lys Ile Ala Asp Lys Gly Ser Phe Val Gly Leu Asp
    210                 215                 220

Arg Tyr Gly Leu Asp Leu Phe Leu Pro Ile Asp Lys Arg Asn Glu Val
225                 230                 235                 240

Leu Leu Lys Leu Ile Lys Asp Gly Tyr Leu Asp Arg Ile Met Val Ser
                245                 250                 255

Gln Asp Tyr Cys Cys Thr Ile Asp Val Gly Ile Ala Lys Pro Glu Tyr
            260                 265                 270

Lys Pro Lys Leu Ala Pro Lys Trp Ser Met Ser Leu Ile Phe Thr Asp
        275                 280                 285

Val Ile Pro Ser Ile Lys Arg Ala Gly Val Thr Asp Glu Gln Leu His
    290                 295                 300

Val Ile Phe Val Lys Asn Pro Ala Arg Leu Phe Ser
305                 310                 315

<210> SEQ ID NO 192
<211> LENGTH: 951
<212> TYPE: DNA
<213> ORGANISM: Sulfolobus acidocaldarius

<400> SEQUENCE: 192
atggcgacca aaattccgct ggttggtaaa ggtgaaatta gtccgggtga atgggtttt     60 accctgattc atgaacatct gcgtgttttt agcgaaccgg tgcgttatca gtggcctcat    120
ctgtataatg aagatgaaga actgaaaaac gccgtgaacg aagtgaaaac cattatgagc    180
tatggcgtta aaaccattgt tgatccgacc gttatgggtc tgggtcgtga tattcgtttt    240
agtgaaaaag tggtgaaaga aaccggcatt aatgttattg cagcaaccgg tctgtatacc    300
tataccgatc tgccgttttt tttcaatggt cgtagcctgg aagaaattgc agaactgctg    360
```

-continued

```
atccacgata tcaaaaaagg tattcagggc accaataatc gtgcgggttt tatcaaagtt      420
gcagcagatg aaccgggtat tacccgtgat gttgaacgtg caattcgtgc agcagcaatt      480
gcacagaaag aaacaaatgt tccgattatc acccatagca atgcacataa tggcaccggt      540
ctggaacagc agcgtattct gatggaagaa ggtgtggatc gggtcgtgt tctgattggt       600
catctgggtg ataccgataa cgtggactac atcaaaaaaa tcgcagataa aggtagcttt      660
gttggcctgg atcgctatgg tctggacctg tttctgccga ttgataaacg taatgaagtt      720
ctgctgaaac tgatcaaaga tggttatctg gatcgtatta tggtgagcca ggattattgt      780
tgtaccattg ataccggtat tgccaaaccg aatataaac cgaaactggc accgaaatgg       840
tcaatgagcc tgattttac cgatgtgatt ccgagcatta acgtgccgg tgttaccgat        900
gaacagctgc atgtgatttt tgttaaaaat ccggcacgcc tgtttagctg a               951
```

<210> SEQ ID NO 193
<211> LENGTH: 316
<212> TYPE: PRT
<213> ORGANISM: Sulfolobus acidocaldarius

<400> SEQUENCE: 193

```
Met Ala Thr Lys Ile Pro Leu Val Gly Lys Gly Glu Ile Ser Pro Gly
1               5                   10                  15

Glu Met Gly Phe Thr Leu Ile His Glu His Leu Arg Val Phe Ser Glu
                20                  25                  30

Pro Val Arg Tyr Gln Trp Pro His Leu Tyr Asn Glu Asp Glu Glu Leu
            35                  40                  45

Lys Asn Ala Val Asn Glu Val Lys Thr Ile Met Ser Tyr Gly Val Lys
        50                  55                  60

Thr Ile Val Asp Pro Thr Val Met Gly Leu Gly Arg Asp Ile Arg Phe
65                  70                  75                  80

Ser Glu Lys Val Val Lys Glu Thr Gly Ile Asn Val Ile Ala Ala Thr
                85                  90                  95

Gly Leu Tyr Thr Tyr Thr Asp Leu Pro Phe Phe Phe Asn Gly Arg Ser
                100                 105                 110

Leu Glu Glu Ile Ala Glu Leu Leu Ile His Asp Ile Lys Lys Gly Ile
            115                 120                 125

Gln Gly Thr Asn Asn Arg Ala Gly Phe Ile Lys Val Ala Ala Asp Glu
        130                 135                 140

Pro Gly Ile Thr Arg Asp Val Glu Arg Ala Ile Arg Ala Ala Ile
145                 150                 155                 160

Ala Gln Lys Glu Thr Asn Val Pro Ile Ile Thr His Ser Asn Ala His
                165                 170                 175

Asn Gly Thr Gly Leu Glu Gln Gln Arg Ile Leu Met Glu Glu Gly Val
                180                 185                 190

Asp Pro Gly Arg Val Leu Ile Gly His Leu Gly Asp Thr Asp Asn Val
            195                 200                 205

Asp Tyr Ile Lys Lys Ile Ala Asp Lys Gly Ser Phe Val Gly Leu Asp
        210                 215                 220

Arg Tyr Gly Leu Asp Leu Phe Leu Pro Ile Asp Lys Arg Asn Glu Val
225                 230                 235                 240

Leu Leu Lys Leu Ile Lys Asp Gly Tyr Leu Asp Arg Ile Met Val Ser
                245                 250                 255

Gln Asp Tyr Cys Cys Thr Ile Asp Thr Gly Ile Ala Lys Pro Glu Tyr
                260                 265                 270
```

Lys Pro Lys Leu Ala Pro Lys Trp Ser Met Ser Leu Ile Phe Thr Asp
            275                 280                 285

Val Ile Pro Ser Ile Lys Arg Ala Gly Val Thr Asp Glu Gln Leu His
    290                 295                 300

Val Ile Phe Val Lys Asn Pro Ala Arg Leu Phe Ser
305                 310                 315

<210> SEQ ID NO 194
<211> LENGTH: 954
<212> TYPE: DNA
<213> ORGANISM: Sulfolobus acidocaldarius

<400> SEQUENCE: 194

| | | | | | |
|---|---|---|---|---|---|
| atggcgacca | aaattccgct | ggttggtaaa | ggtgaaatta | gtccgggtga | atgggtttt | 60 |
| accctgattc | atgaacatct | gcgtgttttt | agcgaaccgg | tgcgttatca | gtggcctcat | 120 |
| ctgtataatg | aagatgaaga | actgaaaaac | gccgtgaacg | aagtgaaaac | cattatgagc | 180 |
| tatggcgtta | aaaccattgt | tgatccgacc | gttatgggtc | tgggtcgtga | tattcgtttt | 240 |
| agtgaaaaag | tggtgaaaga | aaccggcatt | aatgttattg | cagcaaccgg | tctgtatacc | 300 |
| tataccgatc | tgccgttttt | tttcaatggt | cgtagcctgg | aagaaattgc | agaactgctg | 360 |
| atccacgata | tcaaaaaagg | tattcagggc | accaataatc | gtgcgggttt | tatcaaagtt | 420 |
| gcagcagatg | aaccgggtat | tacccgtgat | gttgaacgtg | caattcgtgc | agcagcaatt | 480 |
| gcacagaaag | aaacaaatgt | tccgattatc | acccatagca | atgcacataa | tggcaccggt | 540 |
| ctggaacagc | agcgtattct | gatggaagaa | ggtgtggatc | cgggtcgtgt | tctgattggt | 600 |
| catctgggtg | ataccgataa | cgtggactac | atcaaaaaaa | tcgcagataa | aggtagcttt | 660 |
| gttggcctgg | atcgctatgg | tctggacctg | tttctgccga | ttgataaacg | taatgaagtt | 720 |
| ctgctgaaac | tgatcaaaga | tggttatctg | gatcgtatta | tggtgagcca | ggattatctg | 780 |
| tgtacctttg | atgcaggtat | tgccaaaccg | gaatataaac | cgaaactggc | accgaaatgg | 840 |
| tcaatgagcc | tgatttttac | cgatgtgatt | ccgagcatta | aacgtgccgg | tgttaccgat | 900 |
| gaacagctgc | atgtgatttt | tgttaaaaat | ccggcacgcc | tgtttagctg | ataa | 954 |

<210> SEQ ID NO 195
<211> LENGTH: 316
<212> TYPE: PRT
<213> ORGANISM: Sulfolobus acidocaldarius

<400> SEQUENCE: 195

Met Ala Thr Lys Ile Pro Leu Val Gly Lys Gly Glu Ile Ser Pro Gly
1               5                   10                  15

Glu Met Gly Phe Thr Leu Ile His Glu His Leu Arg Val Phe Ser Glu
            20                  25                  30

Pro Val Arg Tyr Gln Trp Pro His Leu Tyr Asn Glu Asp Glu Glu Leu
        35                  40                  45

Lys Asn Ala Val Asn Glu Val Lys Thr Ile Met Ser Tyr Gly Val Lys
    50                  55                  60

Thr Ile Val Asp Pro Thr Val Met Gly Leu Gly Arg Asp Ile Arg Phe
65                  70                  75                  80

Ser Glu Lys Val Val Lys Glu Thr Gly Ile Asn Val Ile Ala Ala Thr
                85                  90                  95

Gly Leu Tyr Thr Tyr Thr Asp Leu Pro Phe Phe Phe Asn Gly Arg Ser
            100                 105                 110

| | | | | | | | | | | | |
|---|---|---|---|---|---|---|---|---|---|---|---|
|Leu|Glu|Glu|Ile|Ala|Glu|Leu|Leu|Ile|His|Asp|Ile|Lys|Lys|Gly|Ile|
| |115| | | |120| | | |125| | | | | | |
|Gln|Gly|Thr|Asn|Asn|Arg|Ala|Gly|Phe|Ile|Lys|Val|Ala|Ala|Asp|Glu|
| | |130| | | |135| | | |140| | | | | |
|Pro|Gly|Ile|Thr|Arg|Asp|Val|Glu|Arg|Ala|Ile|Arg|Ala|Ala|Ile|
|145| | | |150| | | |155| | | |160| | | |
|Ala|Gln|Lys|Glu|Thr|Asn|Val|Pro|Ile|Ile|Thr|His|Ser|Asn|Ala|His|
| | | | |165| | | |170| | | |175| | | |
|Asn|Gly|Thr|Gly|Leu|Glu|Gln|Gln|Arg|Ile|Leu|Met|Glu|Glu|Gly|Val|
| | | |180| | | |185| | | |190| | | | |
|Asp|Pro|Gly|Arg|Val|Leu|Ile|Gly|His|Leu|Gly|Asp|Thr|Asp|Asn|Val|
| | |195| | | |200| | | |205| | | | | |
|Asp|Tyr|Ile|Lys|Lys|Ile|Ala|Asp|Lys|Gly|Ser|Phe|Val|Gly|Leu|Asp|
| |210| | | |215| | | |220| | | | | | |
|Arg|Tyr|Gly|Leu|Asp|Leu|Phe|Leu|Pro|Ile|Asp|Lys|Arg|Asn|Glu|Val|
|225| | | |230| | | |235| | | |240| | | |
|Leu|Leu|Lys|Leu|Ile|Lys|Asp|Gly|Tyr|Leu|Asp|Arg|Ile|Met|Val|Ser|
| | | |245| | | |250| | | |255| | | | |
|Gln|Asp|Tyr|Leu|Cys|Thr|Phe|Asp|Ala|Gly|Ile|Ala|Lys|Pro|Glu|Tyr|
| | |260| | | |265| | | |270| | | | | |
|Lys|Pro|Lys|Leu|Ala|Pro|Lys|Trp|Ser|Met|Ser|Leu|Ile|Phe|Thr|Asp|
| |275| | | |280| | | |285| | | | | | |
|Val|Ile|Pro|Ser|Ile|Lys|Arg|Ala|Gly|Val|Thr|Asp|Glu|Gln|Leu|His|
| |290| | | |295| | | |300| | | | | | |
|Val|Ile|Phe|Val|Lys|Asn|Pro|Ala|Arg|Leu|Phe|Ser|
|305| | | |310| | | |315| | | | |

<210> SEQ ID NO 196
<211> LENGTH: 954
<212> TYPE: DNA
<213> ORGANISM: Sulfolobus acidocaldarius

<400> SEQUENCE: 196

```
atggcgacca aaattccgct ggttggtaaa ggtgaaatta gtccgggtga atgggttttt      60
accctgattc atgaacatct gcgtgcattt agcgaaccgg tgcgttatca gtggcctcat     120
ctgtataatg aagatgaaga actgaaaaac gccgtgaacg aagtgaaaac cattatgagc     180
tatggcgtta aaaccattgt tgatccgacc gttatgggtc tgggtcgtga tattcgtttt     240
agtgaaaaag tggtgaaaga accggcatt aatgttattg cagcaaccgg tctgtggacc     300
tataccgatc tgccgttttt tttcaatggt cgtagcctgg aagaaattgc agaactgctg     360
atccacgata tcaaaaaagg tattcagggc accaataatc gtgcgggttt tatcaaagtt     420
gcagcagatg aaccgggtat tacccgtgat gttgaacgtg caattcgtgc agcagcaatt     480
gcacagaaag aaacaaatgt tccgattatc acccatagca atgcacataa tggcaccggt     540
ctgaacagc agcgtattct gatggaagaa ggtgtggatc cgggtcgtgt tctgattggt     600
catctgggtg ataccgataa cgtggactac atcaaaaaaa tcgcagataa aggtagcttt     660
gttggcctgg atcgctatgg tctggacatg tttctgccga ttgataaacg taatgaagtt     720
ctgctgaaac tgatcaaaga tggttatctg gatcgtatta tggtgagcca ggattattgt     780
tgtaccattg atatgggtat tgccaaaccg gaatataaac cgaaactggc accgaaatgg     840
tcaatgagcc tgattttttac cgatgtgatt ccgagcatta aacgtgccgg tgttaccgat     900
gaacagctgc atgtgatttt tgttaaaaat ccggcacgcc tgtttagctg ataa           954
```

<210> SEQ ID NO 197
<211> LENGTH: 316
<212> TYPE: PRT
<213> ORGANISM: Sulfolobus acidocaldarius

<400> SEQUENCE: 197

Met Ala Thr Lys Ile Pro Leu Val Gly Lys Gly Glu Ile Ser Pro Gly
1               5                   10                  15

Glu Met Gly Phe Thr Leu Ile His Glu His Leu Arg Ala Phe Ser Glu
            20                  25                  30

Pro Val Arg Tyr Gln Trp Pro His Leu Tyr Asn Glu Asp Glu Glu Leu
        35                  40                  45

Lys Asn Ala Val Asn Glu Val Lys Thr Ile Met Ser Tyr Gly Val Lys
    50                  55                  60

Thr Ile Val Asp Pro Thr Val Met Gly Leu Gly Arg Asp Ile Arg Phe
65                  70                  75                  80

Ser Glu Lys Val Val Lys Glu Thr Gly Ile Asn Val Ile Ala Ala Thr
                85                  90                  95

Gly Leu Trp Thr Tyr Thr Asp Leu Pro Phe Phe Asn Gly Arg Ser
            100                 105                 110

Leu Glu Glu Ile Ala Glu Leu Leu Ile His Asp Ile Lys Lys Gly Ile
        115                 120                 125

Gln Gly Thr Asn Asn Arg Ala Gly Phe Ile Lys Val Ala Ala Asp Glu
    130                 135                 140

Pro Gly Ile Thr Arg Asp Val Glu Arg Ala Ile Arg Ala Ala Ile
145                 150                 155                 160

Ala Gln Lys Glu Thr Asn Val Pro Ile Ile Thr His Ser Asn Ala His
                165                 170                 175

Asn Gly Thr Gly Leu Glu Gln Gln Arg Ile Leu Met Glu Glu Gly Val
            180                 185                 190

Asp Pro Gly Arg Val Leu Ile Gly His Leu Gly Asp Thr Asp Asn Val
        195                 200                 205

Asp Tyr Ile Lys Lys Ile Ala Asp Lys Gly Ser Phe Val Gly Leu Asp
    210                 215                 220

Arg Tyr Gly Leu Asp Met Phe Leu Pro Ile Asp Lys Arg Asn Glu Val
225                 230                 235                 240

Leu Leu Lys Leu Ile Lys Asp Gly Tyr Leu Asp Arg Ile Met Val Ser
                245                 250                 255

Gln Asp Tyr Cys Cys Thr Ile Asp Met Gly Ile Ala Lys Pro Glu Tyr
            260                 265                 270

Lys Pro Lys Leu Ala Pro Lys Trp Ser Met Ser Leu Ile Phe Thr Asp
        275                 280                 285

Val Ile Pro Ser Ile Lys Arg Ala Gly Val Thr Asp Glu Gln Leu His
    290                 295                 300

Val Ile Phe Val Lys Asn Pro Ala Arg Leu Phe Ser
305                 310                 315

<210> SEQ ID NO 198
<211> LENGTH: 954
<212> TYPE: DNA
<213> ORGANISM: Sulfolobus acidocaldarius

<400> SEQUENCE: 198
atggcgacca aaattccgct ggttggtaaa ggtgaaatta gtccgggtga atgggttttt      60
accctgattc atgaacatct gcgtgcattt agcgaaccgg tgcgttatca gtggcctcat     120

```
ctgtataatg aagatgaaga actgaaaaac gccgtgaacg aagtgaaaac cattatgagc    180
tatggcgtta aaaccattgt tgatccgacc gttatgggtc tgggtcgtga tattcgtttt    240
agtgaaaaag tggtgaaaga accggcatt aatgttattg cagcaaccgg tctgtggacc     300
tataccgatc tgccgttttt tttcaatggt cgtagcctgg aagaaattgc agaactgctg    360
atccacgata tcaaaaaagg tattcagggc accaataatc gtgcgggttt tatcaaagtt    420
gcagcagatg aaccgggtat tacccgtgat gttgaacgtg caattcgtgc agcagcaatt    480
gcacagaaag aaacaaatgt tccgattatc acccatagca atgcacataa tggcaccggt    540
ctggaacagc agcgtattct gatggaagaa ggtgtggatc cgggtcgtgt tctgattggt    600
catctgggtg ataccgataa cgtggactac atcaaaaaaa tcgcagataa aggtagcttt    660
gttggcctgg atcgctatgg tctggacctg tttctgccga ttgataaacg taatgaagtt    720
ctgctgaaac tgatcaaaga tggttatctg gatcgtatta tggtgagcca ggattattgt    780
tgtaccattg atctgggtat tgccaaaccg aatataaaac cgaaactggc accgaaatgg    840
tcaacgagcc tgattttac cgatgtgatt ccgagcatta acgtgccgg tgttaccgat     900 gaacagctgc atgtgatttt tgttaaaaat ccggcacgcc tgtttagctg ataa          954

<210> SEQ ID NO 199
<211> LENGTH: 316
<212> TYPE: PRT
<213> ORGANISM: Sulfolobus acidocaldarius

<400> SEQUENCE: 199

Met Ala Thr Lys Ile Pro Leu Val Gly Lys Gly Glu Ile Ser Pro Gly
1               5                   10                  15

Glu Met Gly Phe Thr Leu Ile His Glu His Leu Arg Ala Phe Ser Glu
            20                  25                  30

Pro Val Arg Tyr Gln Trp Pro His Leu Tyr Asn Glu Asp Glu Glu Leu
        35                  40                  45

Lys Asn Ala Val Asn Glu Val Lys Thr Ile Met Ser Tyr Gly Val Lys
    50                  55                  60

Thr Ile Val Asp Pro Thr Val Met Gly Leu Gly Arg Asp Ile Arg Phe
65                  70                  75                  80

Ser Glu Lys Val Val Lys Glu Thr Gly Ile Asn Val Ile Ala Ala Thr
                85                  90                  95

Gly Leu Trp Thr Tyr Thr Asp Leu Pro Phe Phe Asn Gly Arg Ser
            100                 105                 110

Leu Glu Glu Ile Ala Glu Leu Leu Ile His Asp Ile Lys Lys Gly Ile
        115                 120                 125

Gln Gly Thr Asn Asn Arg Ala Gly Phe Ile Lys Val Ala Ala Asp Glu
    130                 135                 140

Pro Gly Ile Thr Arg Asp Val Glu Arg Ala Ile Arg Ala Ala Ile
145                 150                 155                 160

Ala Gln Lys Glu Thr Asn Val Pro Ile Ile Thr His Ser Asn Ala His
                165                 170                 175

Asn Gly Thr Gly Leu Glu Gln Gln Arg Ile Leu Met Glu Glu Gly Val
            180                 185                 190

Asp Pro Gly Arg Val Leu Ile Gly His Leu Gly Asp Thr Asp Asn Val
        195                 200                 205

Asp Tyr Ile Lys Lys Ile Ala Asp Lys Gly Ser Phe Val Gly Leu Asp
    210                 215                 220
```

```
Arg Tyr Gly Leu Asp Leu Phe Leu Pro Ile Asp Lys Arg Asn Glu Val
225                 230                 235                 240

Leu Leu Lys Leu Ile Lys Asp Gly Tyr Leu Asp Arg Ile Met Val Ser
            245                 250                 255

Gln Asp Tyr Cys Cys Thr Ile Asp Leu Gly Ile Ala Lys Pro Glu Tyr
            260                 265                 270

Lys Pro Lys Leu Ala Pro Lys Trp Ser Thr Ser Leu Ile Phe Thr Asp
        275                 280                 285

Val Ile Pro Ser Ile Lys Arg Ala Gly Val Thr Asp Glu Gln Leu His
290                 295                 300

Val Ile Phe Val Lys Asn Pro Ala Arg Leu Phe Ser
305                 310                 315

<210> SEQ ID NO 200
<211> LENGTH: 954
<212> TYPE: DNA
<213> ORGANISM: Sulfolobus acidocaldarius

<400> SEQUENCE: 200
atggcgacca aaattccgct ggttggtaaa ggtgaaatta gtccgggtga atgggtttt      60 accctgattc atgaacatct gcgtgttttt agcgaaccgg tgcgttatca gtggcctcat    120
ctgtataatg aagatgaaga actgaaaaac gccgtgaacg aagtgaaaac cattatgagc    180
tatggcgtta aaaccattgt tgatccgacc gttatgggtc tgggtcgtga tattcgtttt    240
agtgaaaaag tggtgaaaga accggcatt aatgttattg cagcaaccgg tctgtatacc     300
tataccgatc tgccgttttt tttcaatggt cgtagcctgg aagaaattgc agaactgctg    360
atccacgata tcaaaaaagg tattcagggc accaataatc gtgcgggttt tatcaaagtt    420
gcagcagatg aaccgggtat tacccgtgat gttgaacgtg caattcgtgc agcagcaatt    480
gcacagaaag aaacaaatgt tccgattatc acccatagca tgcacataa tggcaccggt     540 ctggaacagc agcgtattct gatggaagaa ggtgtggatc cgggtcgtgt tctgattggt    600
catctgggtg ataccgataa cgtggactac atcaaaaaaa tcgcagataa aggtagcttt    660
gttggcctgg atcgctatgg tctggacctg tttctgccga ttgataaacg taatgaagtt    720 ctgctgaaaac tgatcaaaga tggttatctg atcgtatta tggtgagcca ggattatgct    780
tgtaccattg atatgggtat tgccaaaccg aatataaac cgaaactggc accgaaatgg     840
tcaacgagcc tgattttta cgatgtgatt ccgagcatta acgtgccgg tgttaccgat      900 gaacagctgc atgtgatttt tgttaaaaat ccggcacgcc tgtttagctg ataa           954

<210> SEQ ID NO 201
<211> LENGTH: 316
<212> TYPE: PRT
<213> ORGANISM: Sulfolobus acidocaldarius

<400> SEQUENCE: 201

Met Ala Thr Lys Ile Pro Leu Val Gly Lys Gly Glu Ile Ser Pro Gly
1               5                   10                  15

Glu Met Gly Phe Thr Leu Ile His Glu His Leu Arg Val Phe Ser Glu
            20                  25                  30

Pro Val Arg Tyr Gln Trp Pro His Leu Tyr Asn Glu Asp Glu Glu Leu
        35                  40                  45

Lys Asn Ala Val Asn Glu Val Lys Thr Ile Met Ser Tyr Gly Val Lys
    50                  55                  60

Thr Ile Val Asp Pro Thr Val Met Gly Leu Gly Arg Asp Ile Arg Phe
```

```
                65                  70                  75                  80
Ser Glu Lys Val Val Lys Glu Thr Gly Ile Asn Val Ile Ala Ala Thr
                    85                  90                  95

Gly Leu Tyr Thr Tyr Thr Asp Leu Pro Phe Phe Asn Gly Arg Ser
            100                 105                 110

Leu Glu Glu Ile Ala Glu Leu Leu Ile His Asp Ile Lys Lys Gly Ile
        115                 120                 125

Gln Gly Thr Asn Asn Arg Ala Gly Phe Ile Lys Val Ala Ala Asp Glu
    130                 135                 140

Pro Gly Ile Thr Arg Asp Val Glu Arg Ala Ile Arg Ala Ala Ile
145                 150                 155                 160

Ala Gln Lys Glu Thr Asn Val Pro Ile Ile Thr His Ser Asn Ala His
                165                 170                 175

Asn Gly Thr Gly Leu Glu Gln Gln Arg Ile Leu Met Glu Glu Gly Val
            180                 185                 190

Asp Pro Gly Arg Val Leu Ile Gly His Leu Gly Asp Thr Asp Asn Val
        195                 200                 205

Asp Tyr Ile Lys Lys Ile Ala Asp Lys Gly Ser Phe Val Gly Leu Asp
    210                 215                 220

Arg Tyr Gly Leu Asp Leu Phe Leu Pro Ile Asp Lys Arg Asn Glu Val
225                 230                 235                 240

Leu Leu Lys Leu Ile Lys Asp Gly Tyr Leu Asp Arg Ile Met Val Ser
                245                 250                 255

Gln Asp Tyr Ala Cys Thr Ile Asp Met Gly Ile Ala Lys Pro Glu Tyr
            260                 265                 270

Lys Pro Lys Leu Ala Pro Lys Trp Ser Thr Ser Leu Ile Phe Thr Asp
        275                 280                 285

Val Ile Pro Ser Ile Lys Arg Ala Gly Val Thr Asp Glu Gln Leu His
    290                 295                 300

Val Ile Phe Val Lys Asn Pro Ala Arg Leu Phe Ser
305                 310                 315

<210> SEQ ID NO 202
<211> LENGTH: 954
<212> TYPE: DNA
<213> ORGANISM: Sulfolobus acidocaldarius

<400> SEQUENCE: 202
atggcgacca aaattccgct ggttggtaaa ggtgaaatta gtccgggtga atgggttttt    60
accctgattc atgaacatct gcgtgcattt agcgaaccgg tgcgttatca gtggcctcat   120
ctgtataatg aagatgaaga actgaaaaac gccgtgaacg aagtgaaaac cattatgagc   180
tatggcgtta aaaccattgt tgatccgacc gttatgggtc tgggtcgtga tactcgtttt   240
agtgaaaaag tggtgaaaga accggcatt aatgttattg cagcaaccgg tctgtggacc   300
tttaccgatc tgccgttttt tttcaatggt cgtagcctgg aagaaattgc agaactgctg   360
atccacgata tcaaaaaagg tattcagggc accccgaatc gtgcgggttt tatcaaagtt   420
gcagcagatg aaccgggtat tacccgtgat gttgaacgtg caattcgtgc agcagcaatt   480
gcacagaaag aaacaaatgt tccgattatc acccatagca tgcacataa tggcaccggt   540 ctggaacagc agcgtattct gatggaagaa ggtgtggatc cgggtcgtgt tctgattggt   600
catctgggtg ataccgataa cgtggactac atcaaaaaaa tcgcagataa aggtagcttt   660
gttggcctgg atcgctatgg tgtggacctg tttctgccga ttgataaacg taatgaagtt   720
```

```
ctgctgaaac tgatcaaaga tggttatctg gatcgtatta tggtgagcca ggattattgt    780
tgtaccattg attggggtat tgccaaaccg gaatataaac cgaaactggc accgaaatgg    840
tcaatgagcc tgattttttac cgatgtgatt ccgagcatta acgtgccgg tgttaccgat    900 gaacagctgc atgtgatttt tgttaaaaat ccggcacgcc tgtttagctg ataa          954
```

<210> SEQ ID NO 203
<211> LENGTH: 316
<212> TYPE: PRT
<213> ORGANISM: Sulfolobus acidocaldarius

<400> SEQUENCE: 203

```
Met Ala Thr Lys Ile Pro Leu Val Gly Lys Gly Glu Ile Ser Pro Gly
1               5                   10                  15

Glu Met Gly Phe Thr Leu Ile His Glu His Leu Arg Ala Phe Ser Glu
                20                  25                  30

Pro Val Arg Tyr Gln Trp Pro His Leu Tyr Asn Glu Asp Glu Glu Leu
            35                  40                  45

Lys Asn Ala Val Asn Glu Val Lys Thr Ile Met Ser Tyr Gly Val Lys
        50                  55                  60

Thr Ile Val Asp Pro Thr Val Met Gly Leu Gly Arg Asp Thr Arg Phe
65                  70                  75                  80

Ser Glu Lys Val Val Lys Glu Thr Gly Ile Asn Val Ile Ala Ala Thr
                85                  90                  95

Gly Leu Trp Thr Phe Thr Asp Leu Pro Phe Phe Asn Gly Arg Ser
                100                 105                 110

Leu Glu Glu Ile Ala Glu Leu Leu Ile His Asp Ile Lys Lys Gly Ile
            115                 120                 125

Gln Gly Thr Pro Asn Arg Ala Gly Phe Ile Lys Val Ala Ala Asp Glu
        130                 135                 140

Pro Gly Ile Thr Arg Asp Val Glu Arg Ala Ile Arg Ala Ala Ile
145                 150                 155                 160

Ala Gln Lys Glu Thr Asn Val Pro Ile Ile Thr His Ser Asn Ala His
                165                 170                 175

Asn Gly Thr Gly Leu Glu Gln Gln Arg Ile Leu Met Glu Glu Gly Val
            180                 185                 190

Asp Pro Gly Arg Val Leu Ile Gly His Leu Gly Asp Thr Asp Asn Val
        195                 200                 205

Asp Tyr Ile Lys Lys Ile Ala Asp Lys Gly Ser Phe Val Gly Leu Asp
    210                 215                 220

Arg Tyr Gly Val Asp Leu Phe Leu Pro Ile Asp Lys Arg Asn Glu Val
225                 230                 235                 240

Leu Leu Lys Leu Ile Lys Asp Gly Tyr Leu Asp Arg Ile Met Val Ser
                245                 250                 255

Gln Asp Tyr Cys Cys Thr Ile Asp Trp Gly Ile Ala Lys Pro Glu Tyr
            260                 265                 270

Lys Pro Lys Leu Ala Pro Lys Trp Ser Met Ser Leu Ile Phe Thr Asp
        275                 280                 285

Val Ile Pro Ser Ile Lys Arg Ala Gly Val Thr Asp Glu Gln Leu His
    290                 295                 300

Val Ile Phe Val Lys Asn Pro Ala Arg Leu Phe Ser
305                 310                 315
```

<210> SEQ ID NO 204
<211> LENGTH: 954

```
<212> TYPE: DNA
<213> ORGANISM: Sulfolobus acidocaldarius

<400> SEQUENCE: 204
atggcgacca aaattccgct ggttggtaaa ggtgaaatta gtccgggtga atgggttttt      60
accctgattc atgaacatct gcgtgttttt agcgaaccgg tgcgttatca gtggccccat     120
ctgtataatg aagatgaaga actgaaaaac gccgtgaacg aagtgaaaac cattatgagc     180
tatggcgtta aaaccattgt tgatccgacc gttatgggta ttggtcgtga tattcgtttt     240
agtgaaaaag tggtgaaaga accggcatt aatgttattg cagcaaccgg tctgtatacc      300
tttaccgatc tgccgttttt tttcaatggt cgtagcctgg aagaaattgc agaactgctg     360
atccacgatt taaaaaaagg tattcagggc accaataatc gtgcgggttt tatcaaagtt     420
gcagcagatg aaccgggtat tacccgtgat gttgaacgtg ccattcgtgc agcagcaatt     480
gcacagaaag aaacaaatgt tccgattatc acccatagca atgcacataa tggcaccggt     540
ctggaacagc agcgtattct gatggaagaa ggtgtggatc cgggtcgtgt tctgattggt     600
catctgggtg ataccgataa cgtggactac atcaaaaaaa tcgcagataa aggtagcttt     660
gttggcctgg atcgctatgg tctggacatg tctctgccga ttgataaacg taatgaagtt     720
ctgctgaaac tgatcaaaga tggttatctg atcgtatta tggtgagcca ggattattgt      780
tgtaccattg atctgggtat tgccaaaccg aatataaac cgaaactggc accgaaatgg      840
tcaatgagcc tgattttac cgatgtgatt ccgagcatta acgtgccgg tgttaccgat       900 gaacagctgc atgtgatttt tgttaaaaat ccggcacgcc tgtttagctg ataa            954

<210> SEQ ID NO 205
<211> LENGTH: 316
<212> TYPE: PRT
<213> ORGANISM: Sulfolobus acidocaldarius

<400> SEQUENCE: 205

Met Ala Thr Lys Ile Pro Leu Val Gly Lys Gly Glu Ile Ser Pro Gly
1               5                   10                  15

Glu Met Gly Phe Thr Leu Ile His Glu His Leu Arg Val Phe Ser Glu
            20                  25                  30

Pro Val Arg Tyr Gln Trp Pro His Leu Tyr Asn Glu Asp Glu Glu Leu
        35                  40                  45

Lys Asn Ala Val Asn Glu Val Lys Thr Ile Met Ser Tyr Gly Val Lys
    50                  55                  60

Thr Ile Val Asp Pro Thr Val Met Gly Ile Gly Arg Asp Ile Arg Phe
65                  70                  75                  80

Ser Glu Lys Val Val Lys Glu Thr Gly Ile Asn Val Ile Ala Ala Thr
                85                  90                  95

Gly Leu Tyr Thr Phe Thr Asp Leu Pro Phe Phe Phe Asn Gly Arg Ser
            100                 105                 110

Leu Glu Glu Ile Ala Glu Leu Leu Ile His Asp Leu Lys Lys Gly Ile
        115                 120                 125

Gln Gly Thr Asn Asn Arg Ala Gly Phe Ile Lys Val Ala Ala Asp Glu
    130                 135                 140

Pro Gly Ile Thr Arg Asp Val Glu Arg Ala Ile Arg Ala Ala Ala Ile
145                 150                 155                 160

Ala Gln Lys Glu Thr Asn Val Pro Ile Ile Thr His Ser Asn Ala His
                165                 170                 175

Asn Gly Thr Gly Leu Glu Gln Gln Arg Ile Leu Met Glu Glu Gly Val
```

```
                    180                 185                 190
Asp Pro Gly Arg Val Leu Ile Gly His Leu Gly Asp Thr Asp Asn Val
                195                 200                 205

Asp Tyr Ile Lys Lys Ile Ala Asp Lys Gly Ser Phe Val Gly Leu Asp
            210                 215                 220

Arg Tyr Gly Leu Asp Met Ser Leu Pro Ile Asp Lys Arg Asn Glu Val
225                 230                 235                 240

Leu Leu Lys Leu Ile Lys Asp Gly Tyr Leu Asp Arg Ile Met Val Ser
                245                 250                 255

Gln Asp Tyr Cys Cys Thr Ile Asp Leu Gly Ile Ala Lys Pro Glu Tyr
            260                 265                 270

Lys Pro Lys Leu Ala Pro Lys Trp Ser Met Ser Leu Ile Phe Thr Asp
            275                 280                 285

Val Ile Pro Ser Ile Lys Arg Ala Gly Val Thr Asp Glu Gln Leu His
            290                 295                 300

Val Ile Phe Val Lys Asn Pro Ala Arg Leu Phe Ser
305                 310                 315
```

<210> SEQ ID NO 206
<211> LENGTH: 954
<212> TYPE: DNA
<213> ORGANISM: Sulfolobus acidocaldarius

<400> SEQUENCE: 206

```
atggcgacca aaattccgct ggttggtaaa ggtgaaatta gtccgggtga atgggtttt     60
accctgattc atgaacatct gcgtgttttt agcgaaccgg tgcgttatca gtggcccat   120
ctgtataatg aagatgaaga actgaaaaac gccgtgaacg aagtgaaaac cattatgagc   180
tatgccgtta aaaccattgt tgatccgagt gttatgggta ttggtcgtga tattcgtttt   240
agtgaaaaag tggtgaaaga aaccggcatt aatgttattg cagcaaccgg tctgtatacc   300
tataccgatc tgccgttttt tttcaatggt cgtagcctgg aagaaattgc agaactgctg   360
atccacgata tcaaaaaagg tattcagggc accccgaatc gtgcgggttt tatcaaagtt   420
gcagcagatg aaccgggtat tacccgtgat gttgaacgtg caattcgtgc agcagcaatt   480
gcacagaaag aaacaaatgt tccgattatc acccatagca atgcacataa tggcaccggt   540
ctggaacagc agcgtattct gatggaagaa ggtgtggatc cgggtcgtgt tctgattggt   600
catctgggtg ataccgataa cgtggactac atcaaaaaaa tcgcagataa aggtagcttt   660
gttggcctgg atcgctatgg tctggacatg tctctgccga ttgataaacg taatgaagtt   720
ctgctgaaac tgatcaaaga tggttatctg gatcgtatta tggtgagcca ggattattgt   780
tgtaccattg atatgggtat tgccaaaccg aatataaaac cgaaaccggc accgaaatgg   840
tcaatgagcc tgattttac cgatgtgatt ccgagcatta acgtgccggt gttaccgat    900
gaacagctgc atgtgatttt tgttaaaaat ccggcacgcc tgtttagctg ataa          954
```

<210> SEQ ID NO 207
<211> LENGTH: 316
<212> TYPE: PRT
<213> ORGANISM: Sulfolobus acidocaldarius

<400> SEQUENCE: 207

```
Met Ala Thr Lys Ile Pro Leu Val Gly Lys Gly Glu Ile Ser Pro Gly
1               5                   10                  15

Glu Met Gly Phe Thr Leu Ile His Glu His Leu Arg Val Phe Ser Glu
                20                  25                  30
```

Pro Val Arg Tyr Gln Trp Pro His Leu Tyr Asn Glu Asp Glu Glu Leu
                35                  40                  45
Lys Asn Ala Val Asn Glu Val Lys Thr Ile Met Ser Tyr Gly Val Lys
     50                  55                  60
Thr Ile Val Asp Pro Ser Val Met Gly Ile Gly Arg Asp Ile Arg Phe
65                  70                  75                  80
Ser Glu Lys Val Val Lys Glu Thr Gly Ile Asn Val Ile Ala Ala Thr
                85                  90                  95
Gly Leu Tyr Thr Tyr Thr Asp Leu Pro Phe Phe Asn Gly Arg Ser
                100                 105                 110
Leu Glu Glu Ile Ala Glu Leu Leu Ile His Asp Ile Lys Lys Gly Ile
                115                 120                 125
Gln Gly Thr Pro Asn Arg Ala Gly Phe Ile Lys Val Ala Ala Asp Glu
                130                 135                 140
Pro Gly Ile Thr Arg Asp Val Glu Arg Ala Ile Arg Ala Ala Ala Ile
145                 150                 155                 160
Ala Gln Lys Glu Thr Asn Val Pro Ile Ile Thr His Ser Asn Ala His
                165                 170                 175
Asn Gly Thr Gly Leu Glu Gln Gln Arg Ile Leu Met Glu Glu Gly Val
                180                 185                 190
Asp Pro Gly Arg Val Leu Ile Gly His Leu Gly Asp Thr Asp Asn Val
                195                 200                 205
Asp Tyr Ile Lys Lys Ile Ala Asp Lys Gly Ser Phe Val Gly Leu Asp
                210                 215                 220
Arg Tyr Gly Leu Asp Met Ser Leu Pro Ile Asp Lys Arg Asn Glu Val
225                 230                 235                 240
Leu Leu Lys Leu Ile Lys Asp Gly Tyr Leu Asp Arg Ile Met Val Ser
                245                 250                 255
Gln Asp Tyr Cys Cys Thr Ile Asp Met Gly Ile Ala Lys Pro Glu Tyr
                260                 265                 270
Lys Pro Lys Pro Ala Pro Lys Trp Ser Met Ser Leu Ile Phe Thr Asp
                275                 280                 285
Val Ile Pro Ser Ile Lys Arg Ala Gly Val Thr Asp Glu Gln Leu His
                290                 295                 300
Val Ile Phe Val Lys Asn Pro Ala Arg Leu Phe Ser
305                 310                 315

<210> SEQ ID NO 208
<211> LENGTH: 954
<212> TYPE: DNA
<213> ORGANISM: Sulfolobus acidocaldarius

<400> SEQUENCE: 208
atggcgacca aaattccgct ggttggtaaa ggtgaaatta gtccgggtga atgggtttt      60 accctgattc atgaacatct gcgtgttttt agcgaaccgg tgcgttatca gtggcctcat     120
ctgtataatg aagatgaaga actgaaaaac gccgtgaacg aagtgaaaac cattatgagc     180
tatggcgtta aaaccattgt tgatccgagt gttatgggtc tgggtcgtga tactcgtttt     240
agtgaaaaag tggtgaaaga aaccggcatt aatgttattg cagcaaccgg tctgtggacc     300
tttaccgatc tgccgttttt tttcaatggt cgtagcctgg aagaaattgc agaactgctg     360
atccacgata tcaaaaaagg tattcagggc accaataatc gtgcgggttt atcaaagtt      420 gcagcagatg aaccgggtat taccccgtgat gttgaacgtg caattcgtgc agcagcaatt     480

```
gcacagaaag aaacaaatgt tccgattatc acccatagca atgcacataa tggcaccggt    540
ctggaacagc agcgtattct gatggaagaa ggtgtggatc cgggtcgtgt tctgattggt    600
catctgggtg ataccgataa cgtggactac atcaaaaaaa tcgcagataa aggtagcttt    660
gttggcctgg atcgctatgg tctggacatg tttctgccga ttgataaacg taatgaagtt    720
ctgctgaaac tgatcaaaga tggttatctg gatcgtatta tggtgagcca ggattattgt    780
tgtaccattg atctgggtat tgccaaaccg aatataaaac cgaaactggc accgaaatgg    840
tcaatgagcc tgattttttac cgatgtgatt ccgagcatta acgtgccggt gttaccgat    900 gaacagctgc atgtgatttt tgttaaaaat ccggcacgcc tgtttagctg ataa          954
```

<210> SEQ ID NO 209
<211> LENGTH: 316
<212> TYPE: PRT
<213> ORGANISM: Sulfolobus acidocaldarius

<400> SEQUENCE: 209

```
Met Ala Thr Lys Ile Pro Leu Val Gly Lys Gly Glu Ile Ser Pro Gly
1               5                   10                  15

Glu Met Gly Phe Thr Leu Ile His Glu His Leu Arg Val Phe Ser Glu
            20                  25                  30

Pro Val Arg Tyr Gln Trp Pro His Leu Tyr Asn Glu Asp Glu Glu Leu
        35                  40                  45

Lys Asn Ala Val Asn Glu Val Lys Thr Ile Met Ser Tyr Gly Val Lys
    50                  55                  60

Thr Ile Val Asp Pro Ser Val Met Gly Leu Gly Arg Asp Thr Arg Phe
65                  70                  75                  80

Ser Glu Lys Val Val Lys Glu Thr Gly Ile Asn Val Ile Ala Ala Thr
                85                  90                  95

Gly Leu Trp Thr Phe Thr Asp Leu Pro Phe Phe Phe Asn Gly Arg Ser
            100                 105                 110

Leu Glu Glu Ile Ala Glu Leu Leu Ile His Asp Ile Lys Lys Gly Ile
        115                 120                 125

Gln Gly Thr Asn Asn Arg Ala Gly Phe Ile Lys Val Ala Ala Asp Glu
    130                 135                 140

Pro Gly Ile Thr Arg Asp Val Glu Arg Ala Ile Arg Ala Ala Ala Ile
145                 150                 155                 160

Ala Gln Lys Glu Thr Asn Val Pro Ile Ile Thr His Ser Asn Ala His
                165                 170                 175

Asn Gly Thr Gly Leu Glu Gln Gln Arg Ile Leu Met Glu Glu Gly Val
            180                 185                 190

Asp Pro Gly Arg Val Leu Ile Gly His Leu Gly Asp Thr Asp Asn Val
        195                 200                 205

Asp Tyr Ile Lys Lys Ile Ala Asp Lys Gly Ser Phe Val Gly Leu Asp
    210                 215                 220

Arg Tyr Gly Leu Asp Met Phe Leu Pro Ile Asp Lys Arg Asn Glu Val
225                 230                 235                 240

Leu Leu Lys Leu Ile Lys Asp Gly Tyr Leu Asp Arg Ile Met Val Ser
                245                 250                 255

Gln Asp Tyr Cys Cys Thr Ile Asp Leu Gly Ile Ala Lys Pro Glu Tyr
            260                 265                 270

Lys Pro Lys Leu Ala Pro Lys Trp Ser Met Ser Leu Ile Phe Thr Asp
        275                 280                 285

Val Ile Pro Ser Ile Lys Arg Ala Gly Val Thr Asp Glu Gln Leu His
```

Val Ile Phe Val Lys Asn Pro Ala Arg Leu Phe Ser
305                 310                 315

<210> SEQ ID NO 210
<211> LENGTH: 954
<212> TYPE: DNA
<213> ORGANISM: Sulfolobus acidocaldarius

<400> SEQUENCE: 210

```
atggcgacca aaattccgct ggttggtgaa ggtgaaatta gtccgggtga atgggtttt      60
accctgattc atgaacatct gcgtgttttt agcgaaccgg tgcgttatca gtggcctcat    120
ctgtataatg aagatgaaga actgaaaaac gccgtgaacg aagtgaaaac cattatgagc    180
tatggcgtta aaaccattgt tgatccgacc gttatgggtc tgggtcgtga tattcgtttt    240
agtgaaaaag tggtgaaaga accggcatt aatgttattg cagcaaccgg tctgtggacc     300
tttaccgatc tgccgttttt tttcaatggt cgtagcctgg aagaaattgc agaactgctg    360
atccacgata tcaaaaaagg tattcagggc accaataatc gtgcgggttt tatcaaagtt    420
gcagcagata aaccgggtat tacccgtgat gttgaacgtg caattcgtgc agcagcaatt    480
gcacagaaag aaacaaatgt tccgattatc acccatagca atgcacataa tggcaccggt    540
ctggaacagc agcgtattct gatggaagaa ggtgtggatc cgggtcgtgt tctgattggt    600
catctgggtg ataccgataa cgtggactac atcaaaaaaa tcgcagataa aggtagcttt    660
gttggcctgg atcgctatgg tctggacatg tttctgccga ttgataaacg taatgaagtt    720
ctgctgaaac tgatcaaaga tggttatctg atcgtatta tggtgagcca ggattattgt    780
tgtaccattg attggggtat tgccaaaccg aatataaac cgaaactggc accgaaatgg    840
tcaatgagcc tgattttac cgatgtgatt ccgagcatta acgtgccgg tgttaccgat      900
gaacagctgc atgtgatttt tgttaaaaat ccggcacgcc tgtttagctg ataa           954
```

<210> SEQ ID NO 211
<211> LENGTH: 316
<212> TYPE: PRT
<213> ORGANISM: Sulfolobus acidocaldarius

<400> SEQUENCE: 211

Met Ala Thr Lys Ile Pro Leu Val Gly Glu Gly Glu Ile Ser Pro Gly
1               5                   10                  15

Glu Met Gly Phe Thr Leu Ile His Glu His Leu Arg Val Phe Ser Glu
                20                  25                  30

Pro Val Arg Tyr Gln Trp Pro His Leu Tyr Asn Glu Asp Glu Glu Leu
            35                  40                  45

Lys Asn Ala Val Asn Glu Val Lys Thr Ile Met Ser Tyr Gly Val Lys
        50                  55                  60

Thr Ile Val Asp Pro Thr Val Met Gly Leu Gly Arg Asp Ile Arg Phe
65                  70                  75                  80

Ser Glu Lys Val Val Lys Glu Thr Gly Ile Asn Val Ile Ala Ala Thr
                85                  90                  95

Gly Leu Trp Thr Phe Thr Asp Leu Pro Phe Phe Phe Asn Gly Arg Ser
            100                 105                 110

Leu Glu Glu Ile Ala Glu Leu Leu Ile His Asp Ile Lys Lys Gly Ile
        115                 120                 125

Gln Gly Thr Asn Asn Arg Ala Gly Phe Ile Lys Val Ala Ala Asp Glu
    130                 135                 140

Pro Gly Ile Thr Arg Asp Val Glu Arg Ala Ile Arg Ala Ala Ala Ile
145                 150                 155                 160

Ala Gln Lys Glu Thr Asn Val Pro Ile Ile Thr His Ser Asn Ala His
            165                 170                 175

Asn Gly Thr Gly Leu Glu Gln Gln Arg Ile Leu Met Glu Gly Val
        180                 185                 190

Asp Pro Gly Arg Val Leu Ile Gly His Leu Gly Asp Thr Asp Asn Val
    195                 200                 205

Asp Tyr Ile Lys Lys Ile Ala Asp Lys Gly Ser Phe Val Gly Leu Asp
210                 215                 220

Arg Tyr Gly Leu Asp Met Phe Leu Pro Ile Asp Lys Arg Asn Glu Val
225                 230                 235                 240

Leu Leu Lys Leu Ile Lys Asp Gly Tyr Leu Asp Arg Ile Met Val Ser
                245                 250                 255

Gln Asp Tyr Cys Cys Thr Ile Asp Trp Gly Ile Ala Lys Pro Glu Tyr
            260                 265                 270

Lys Pro Lys Leu Ala Pro Lys Trp Ser Met Ser Leu Ile Phe Thr Asp
        275                 280                 285

Val Ile Pro Ser Ile Lys Arg Ala Gly Val Thr Asp Glu Gln Leu His
    290                 295                 300

Val Ile Phe Val Lys Asn Pro Ala Arg Leu Phe Ser
305                 310                 315

<210> SEQ ID NO 212
<211> LENGTH: 953
<212> TYPE: DNA
<213> ORGANISM: Sulfolobus acidocaldarius

<400> SEQUENCE: 212
atggcgacca aaattccgct ggttggtaaa ggtgaaatta gtccgggtga atgggttttt      60
accctgattc atgaacatct gcgtgttttt agcgaaccgg tgcgttatca gtggcctcat     120
ctgtataatg aagatgaaga actgaaaaac gccgtgaacg aagtgaaaac cattatgagc     180
tatggcgtta aaaccattgt tgatccgacc gttatgggta ttggtcgtga tattcgtttt     240
agtgaaaaag tggtgaaaga accggcatt aatgttattg cagcaaccgg tctgtatacc      300
tataccgatc tgccgttttt tttcaatggt cgtagcctgg aagaaattgc agaactgctg     360
atccacgata tcaaaaaagg tattcagggc accaataatc gtgcgggttt tatcaaagtt     420
gcagcagata accgggtat acccgtgat gttaacgtg caattcgtgc agcagcaatt        480
gcacagaaag aaacaaatgt tccgattatc acccatagca atgcacataa tggcaccggt     540
ctggaacagc agcgtattct gatggaagaa ggtgtggatc cgggtcgtgt tctgattggt     600
catctgggtg ataccgataa cgtggactac atcaaaaaaa tcgcagataa aggtagcttt     660
gttggcctgg atcgctatgg tctggacctg tttctgccga ttgataaacg taatgaagtt     720
ctgctgaaac tgatcaaaga tggttatctg atcgtatta tggtgagcca ggattattgt     780
tgtaccattg attttggtat tgccaaaccg aatataaac cgaaactggc accgaaatgg      840
tcaatgagcc tgattttac cgatgtgatt ccgagcatta acgtgccgg tgttaccgat       900 gaacagctgc atgtgatttt tgttaaaaat ccggcacgcc tgtttagctg aaa            953

<210> SEQ ID NO 213
<211> LENGTH: 316
<212> TYPE: PRT
<213> ORGANISM: Sulfolobus acidocaldarius

<400> SEQUENCE: 213

Met Ala Thr Lys Ile Pro Leu Val Gly Lys Gly Glu Ile Ser Pro Gly
1               5                   10                  15

Glu Met Gly Phe Thr Leu Ile His Glu His Leu Arg Val Phe Ser Glu
            20                  25                  30

Pro Val Arg Tyr Gln Trp Pro His Leu Tyr Asn Glu Asp Glu Glu Leu
        35                  40                  45

Lys Asn Ala Val Asn Glu Val Lys Thr Ile Met Ser Tyr Gly Val Lys
    50                  55                  60

Thr Ile Val Asp Pro Thr Val Met Gly Ile Gly Arg Asp Ile Arg Phe
65                  70                  75                  80

Ser Glu Lys Val Val Lys Glu Thr Gly Ile Asn Val Ile Ala Ala Thr
                85                  90                  95

Gly Leu Tyr Thr Tyr Thr Asp Leu Pro Phe Phe Asn Gly Arg Ser
            100                 105                 110

Leu Glu Glu Ile Ala Glu Leu Leu Ile His Asp Ile Lys Lys Gly Ile
            115                 120                 125

Gln Gly Thr Asn Asn Arg Ala Gly Phe Ile Lys Val Ala Ala Asp Glu
    130                 135                 140

Pro Gly Ile Thr Arg Asp Val Glu Arg Ala Ile Arg Ala Ala Ala Ile
145                 150                 155                 160

Ala Gln Lys Glu Thr Asn Val Pro Ile Ile Thr His Ser Asn Ala His
                165                 170                 175

Asn Gly Thr Gly Leu Glu Gln Gln Arg Ile Leu Met Glu Glu Gly Val
            180                 185                 190

Asp Pro Gly Arg Val Leu Ile Gly His Leu Gly Asp Thr Asp Asn Val
        195                 200                 205

Asp Tyr Ile Lys Lys Ile Ala Asp Lys Gly Ser Phe Val Gly Leu Asp
    210                 215                 220

Arg Tyr Gly Leu Asp Leu Phe Leu Pro Ile Asp Lys Arg Asn Glu Val
225                 230                 235                 240

Leu Leu Lys Leu Ile Lys Asp Gly Tyr Leu Asp Arg Ile Met Val Ser
                245                 250                 255

Gln Asp Tyr Cys Cys Thr Ile Asp Phe Gly Ile Ala Lys Pro Glu Tyr
            260                 265                 270

Lys Pro Lys Leu Ala Pro Lys Trp Ser Met Ser Leu Ile Phe Thr Asp
        275                 280                 285

Val Ile Pro Ser Ile Lys Arg Ala Gly Val Thr Asp Glu Gln Leu His
    290                 295                 300

Val Ile Phe Val Lys Asn Pro Ala Arg Leu Phe Ser
305                 310                 315

<210> SEQ ID NO 214
<211> LENGTH: 954
<212> TYPE: DNA
<213> ORGANISM: Sulfolobus acidocaldarius

<400> SEQUENCE: 214
atggcgacca aaattccgct ggttggtaaa ggtgaaatta gtccgggtga atgggttttt    60
accctgattc atgaacatct gcgtgttttt agcgaaccgg tgcgttatca gtggcctcat   120
ctgtataatg aagatgaaga actgaaaaac gccgtgaacg aagtgaaaac cattatgagc   180
tatggcgtta aaccattgt tgatccgagt gttatgggtc tgggtcgtga tattcgtttt   240

```
agtgaaaaag tggtgaaaga aaccggcatt aatgttattg cagcaaccgg tctgtggacc    300
tttaccgatc tgccgttttt tttcaatggt cgtagcctgg aagaaattgc agaactgctg    360
atccacgata tcaaaaaagg tattcagggc accccgaatc gtgcgggttt tatcaaagtt    420
gcagcagata aaccgggtat tacccgtgat gttgaacgtg caattcgtgc agcagcaatt    480
gcacagaaag aaacaaatgt tccgattatc acccatagca atgcacataa tggcaccggt    540
ctggaacagc agcgtattct gatggaagaa ggtgtggatc cgggtcgtgt tctgattggt    600
catctgggtg ataccgataa cgtggactac atcaaaaaaa tcgcagataa aggtagcttt    660
gttggcctgg atcgctatgg tctggacatg tttctgccga ttgataaacg taatgaagtt    720
ctgctgaaac tgatcaaaga tggttatctg gatcgtatta tggtgagcca ggattattgt    780
tgtaccattg attggggtat tgccaaaccg aatataaaac cgaaactggc accgaaatgg    840
tcaatgagcc tgattttac cgatgtgatt ccgagcatta acgtgccgg tgttaccgat    900 gaacagctgc atgtgatttt tgttaaaaat ccggcacgcc tgtttagctg ataa    954
```

<210> SEQ ID NO 215
<211> LENGTH: 316
<212> TYPE: PRT
<213> ORGANISM: Sulfolobus acidocaldarius

<400> SEQUENCE: 215

```
Met Ala Thr Lys Ile Pro Leu Val Gly Lys Gly Glu Ile Ser Pro Gly
 1               5                  10                  15

Glu Met Gly Phe Thr Leu Ile His Glu His Leu Arg Val Phe Ser Glu
                20                  25                  30

Pro Val Arg Tyr Gln Trp Pro His Leu Tyr Asn Glu Asp Glu Glu Leu
            35                  40                  45

Lys Asn Ala Val Asn Glu Val Lys Thr Ile Met Ser Tyr Gly Val Lys
        50                  55                  60

Thr Ile Val Asp Pro Ser Val Met Gly Leu Gly Arg Asp Ile Arg Phe
65                  70                  75                  80

Ser Glu Lys Val Val Lys Glu Thr Gly Ile Asn Val Ile Ala Ala Thr
                85                  90                  95

Gly Leu Trp Thr Phe Thr Asp Leu Pro Phe Phe Asn Gly Arg Ser
                100                 105                 110

Leu Glu Glu Ile Ala Glu Leu Leu Ile His Asp Ile Lys Lys Gly Ile
            115                 120                 125

Gln Gly Thr Pro Asn Arg Ala Gly Phe Ile Lys Val Ala Ala Asp Glu
        130                 135                 140

Pro Gly Ile Thr Arg Asp Val Glu Arg Ala Ile Arg Ala Ala Ile
145                 150                 155                 160

Ala Gln Lys Glu Thr Asn Val Pro Ile Ile Thr His Ser Asn Ala His
                165                 170                 175

Asn Gly Thr Gly Leu Glu Gln Gln Arg Ile Leu Met Glu Glu Gly Val
            180                 185                 190

Asp Pro Gly Arg Val Leu Ile Gly His Leu Gly Asp Thr Asp Asn Val
        195                 200                 205

Asp Tyr Ile Lys Lys Ile Ala Asp Lys Gly Ser Phe Val Gly Leu Asp
    210                 215                 220

Arg Tyr Gly Leu Asp Met Phe Leu Pro Ile Asp Lys Arg Asn Glu Val
225                 230                 235                 240

Leu Leu Lys Leu Ile Lys Asp Gly Tyr Leu Asp Arg Ile Met Val Ser
                245                 250                 255
```

Gln Asp Tyr Cys Cys Thr Ile Asp Trp Gly Ile Ala Lys Pro Glu Tyr
            260                 265                 270

Lys Pro Lys Leu Ala Pro Lys Trp Ser Met Ser Leu Ile Phe Thr Asp
        275                 280                 285

Val Ile Pro Ser Ile Lys Arg Ala Gly Val Thr Asp Glu Gln Leu His
290                 295                 300

Val Ile Phe Val Lys Asn Pro Ala Arg Leu Phe Ser
305                 310                 315

<210> SEQ ID NO 216
<211> LENGTH: 954
<212> TYPE: DNA
<213> ORGANISM: Sulfolobus acidocaldarius

<400> SEQUENCE: 216

| | | |
|---|---|---|
| atggcgacca aaattccgct ggttggtaaa ggtgaaatta gtccgggtga atgggttttt | 60 |
| accctgattc atgaacatct gcgtgcattt agcgaaccgg tgcgttatca gtggcctcat | 120 |
| ctgtataatg aagatgaaga actgaaaaac gccgtgaacg aagtgaaaac cattatgagc | 180 |
| tatggcgtta aaaccattgt tgatccgacc gttatgggtc tgggtcgtga tattcgtttt | 240 |
| agtgaaaaag tggtgaaaga accggcatt aatgttattg cagcaaccgg tctgtatacc | 300 |
| tataccgatc tgccgttttt tttcaatggt cgtagcctgg aagaaattgc agaactgctg | 360 |
| atccacgata tcaaaaaagg tattcagggc accaataatc gtgcgggttt tatcaaagtt | 420 |
| gcagcagatg aaccgggtat tacccgtgat gttgaacgtg caattcgtgc agcagcaatt | 480 |
| gcacagaaag aaacaaatgt tccgattatc acccatagca atgcacataa tggcaccggt | 540 |
| ctggaacagc agcgtattct gatggaagaa ggtgtggatc cgggtcgtgt tctgattggt | 600 |
| catctgggtg ataccgataa cgtggactac atcaaaaaaa tcgcagataa aggtagcttt | 660 |
| gttggcctgg atcgctatgg tgtggacctg tttctgccga ttgataaacg taatgaagtt | 720 |
| ctgctgaaac tgatcaaaga tggttatctg atcgtattta tggtgagcca ggattattgt | 780 |
| tgtaccattg atctgggtat tgccaaaccg gaatataaac cgaaactggc accgaaatgg | 840 |
| tcaatgagcc taatttttac cgatgtgatt ccgagcatta acgtgccggt gttaccgat | 900 |
| gaacagctgc atgtgatttt tgttaaaaat ccggcacgcc tgtttagctg ataa | 954 |

<210> SEQ ID NO 217
<211> LENGTH: 316
<212> TYPE: PRT
<213> ORGANISM: Sulfolobus acidocaldarius

<400> SEQUENCE: 217

Met Ala Thr Lys Ile Pro Leu Val Gly Lys Gly Glu Ile Ser Pro Gly
1               5                   10                  15

Glu Met Gly Phe Thr Leu Ile His Glu His Leu Arg Ala Phe Ser Glu
            20                  25                  30

Pro Val Arg Tyr Gln Trp Pro His Leu Tyr Asn Glu Asp Glu Glu Leu
        35                  40                  45

Lys Asn Ala Val Asn Glu Val Lys Thr Ile Met Ser Tyr Gly Val Lys
    50                  55                  60

Thr Ile Val Asp Pro Thr Val Met Gly Leu Gly Arg Asp Ile Arg Phe
65                  70                  75                  80

Ser Glu Lys Val Val Lys Glu Thr Gly Ile Asn Val Ile Ala Ala Thr
                85                  90                  95

```
Gly Leu Tyr Thr Tyr Thr Asp Leu Pro Phe Phe Asn Gly Arg Ser
            100                 105                 110

Leu Glu Glu Ile Ala Glu Leu Leu Ile His Asp Ile Lys Lys Gly Ile
        115                 120                 125

Gln Gly Thr Asn Asn Arg Ala Gly Phe Ile Lys Val Ala Ala Asp Glu
    130                 135                 140

Pro Gly Ile Thr Arg Asp Val Glu Arg Ala Ile Arg Ala Ala Ile
145                 150                 155                 160

Ala Gln Lys Glu Thr Asn Val Pro Ile Ile Thr His Ser Asn Ala His
                165                 170                 175

Asn Gly Thr Gly Leu Glu Gln Gln Arg Ile Leu Met Glu Glu Gly Val
            180                 185                 190

Asp Pro Gly Arg Val Leu Ile Gly His Leu Gly Asp Thr Asp Asn Val
        195                 200                 205

Asp Tyr Ile Lys Lys Ile Ala Asp Lys Gly Ser Phe Val Gly Leu Asp
    210                 215                 220

Arg Tyr Gly Val Asp Leu Phe Leu Pro Ile Asp Lys Arg Asn Glu Val
225                 230                 235                 240

Leu Leu Lys Leu Ile Lys Asp Gly Tyr Leu Asp Arg Ile Met Val Ser
                245                 250                 255

Gln Asp Tyr Cys Cys Thr Ile Asp Leu Gly Ile Ala Lys Pro Glu Tyr
            260                 265                 270

Lys Pro Lys Leu Ala Pro Lys Trp Ser Met Ser Leu Ile Phe Thr Asp
        275                 280                 285

Val Ile Pro Ser Ile Lys Arg Ala Gly Val Thr Asp Glu Gln Leu His
    290                 295                 300

Val Ile Phe Val Lys Asn Pro Ala Arg Leu Phe Ser
305                 310                 315

<210> SEQ ID NO 218
<211> LENGTH: 954
<212> TYPE: DNA
<213> ORGANISM: Sulfolobus acidocaldarius

<400> SEQUENCE: 218
atggcgacca aaattccgct ggttggtaaa ggtgaaatta gtccgggtga atgggtttt      60 accctgattc atgaacatct gcgtgttttt agcgaaccgg tgcgttatca gtggcctcat    120
ctgtataatg aagatgaaga actgaaaaac gccgtgaacg aagtgaaaac cattatgagc    180
tatggcgtta aaaccattgt tgatgtgagt gttatgggtc tgggtcgtga tattcgtttt    240
agtgaaaaag tggtgaaaga accggcatt aatgttattg cagcaaccgg tctgtggacc     300
tttaccgatc tgccgttttt tttcaatggt cgtagcctgg aagaaattgc agaactgctg    360
atccacgata tcaaaaaagg tattcagggc accaataatc gtgcgggttt tatcaaagtt    420
gcagcagatg aaccgggtat tacccgtgat gttgagcgtg caattcgtgc agcagcaatt    480
gcacagaaag aaacaaatgt tccgattatc acccatagca tgcacataa tggcaccggt    540 ctggaacagc agcgtattct gatggaagaa ggtgtggatc cgggtcgtgt tctgattggt    600
catctgggtg ataccgataa cgtggactac atcaaaaaaa tcgcagataa aggtagcttt    660
gttggcctgg atcgctatgg tctggacatg tttctgccga ttgataaacg taatgaagtt    720
ctgctgaaac tgatcaaaga tggttatctg gatcgtatta tggtgagcca ggattatgct    780
tgtaccattg atctgggtat tgccaaaccg gaatataaac cgaaactggc accgaaatgg    840
tcaacgagcc tgattttac cgatgtgatt ccgagcatta acgtgccgg tgttaccgat      900
```
gaacagctgc atgtgatttt tgttaaaaat ccggcacgcc tgtttagctg ataa            954

<210> SEQ ID NO 219
<211> LENGTH: 316
<212> TYPE: PRT
<213> ORGANISM: Sulfolobus acidocaldarius

<400> SEQUENCE: 219

Met Ala Thr Lys Ile Pro Leu Val Gly Lys Gly Glu Ile Ser Pro Gly
1               5                   10                  15

Glu Met Gly Phe Thr Leu Ile His Glu His Leu Arg Val Phe Ser Glu
            20                  25                  30

Pro Val Arg Tyr Gln Trp Pro His Leu Tyr Asn Glu Asp Glu Glu Leu
        35                  40                  45

Lys Asn Ala Val Asn Glu Val Lys Thr Ile Met Ser Tyr Gly Val Lys
    50                  55                  60

Thr Ile Val Asp Val Ser Val Met Gly Leu Gly Arg Asp Ile Arg Phe
65                  70                  75                  80

Ser Glu Lys Val Val Lys Glu Thr Gly Ile Asn Val Ile Ala Ala Thr
                85                  90                  95

Gly Leu Trp Thr Phe Thr Asp Leu Pro Phe Phe Asn Gly Arg Ser
            100                 105                 110

Leu Glu Glu Ile Ala Glu Leu Leu Ile His Asp Ile Lys Lys Gly Ile
        115                 120                 125

Gln Gly Thr Asn Asn Arg Ala Gly Phe Ile Lys Val Ala Ala Asp Glu
    130                 135                 140

Pro Gly Ile Thr Arg Asp Val Glu Arg Ala Ile Arg Ala Ala Ile
145                 150                 155                 160

Ala Gln Lys Glu Thr Asn Val Pro Ile Ile Thr His Ser Asn Ala His
                165                 170                 175

Asn Gly Thr Gly Leu Glu Gln Gln Arg Ile Leu Met Glu Glu Gly Val
            180                 185                 190

Asp Pro Gly Arg Val Leu Ile Gly His Leu Gly Asp Thr Asp Asn Val
        195                 200                 205

Asp Tyr Ile Lys Lys Ile Ala Asp Lys Gly Ser Phe Val Gly Leu Asp
    210                 215                 220

Arg Tyr Gly Leu Asp Met Phe Leu Pro Ile Asp Lys Arg Asn Glu Val
225                 230                 235                 240

Leu Leu Lys Leu Ile Lys Asp Gly Tyr Leu Asp Arg Ile Met Val Ser
                245                 250                 255

Gln Asp Tyr Ala Cys Thr Ile Asp Leu Gly Ile Ala Lys Pro Glu Tyr
            260                 265                 270

Lys Pro Lys Leu Ala Pro Lys Trp Ser Thr Ser Leu Ile Phe Thr Asp
        275                 280                 285

Val Ile Pro Ser Ile Lys Arg Ala Gly Val Thr Asp Glu Gln Leu His
    290                 295                 300

Val Ile Phe Val Lys Asn Pro Ala Arg Leu Phe Ser
305                 310                 315

<210> SEQ ID NO 220
<211> LENGTH: 954
<212> TYPE: DNA
<213> ORGANISM: Sulfolobus acidocaldarius

<400> SEQUENCE: 220

```
atggcgacca aaattccgct ggttggtaaa ggtgaaatta gtccgggtga atgggttttt    60
accctgattc atgaacatct gcgtgttttt agcgaaccgg tgcgttatca gtggcctcat   120
ctgtataatg aagatgaaga actgaaaaac gccgtgaacg aagtgaaaac cattatgagc   180
tatggcgtta aaaccattgt tgatccgagt gttatgggtc tgggtcgtga tattcgtttt   240
agtgaaaaag tggtgaaaga aaccggcatt aatgttattg cagcaaccgg tctgtggacc   300
tttaccgatc tgccgttttt tttcaatggt cgtagcctgg aagaaattgc agaactgctg   360
atccacgata tcaaaaaagg tattcagggc accccgaatc gtgcgggttt tatcaaagtt   420
gcagctgatg aaccgggtat tacccgtgat gttgaacgtg caattcgtgc agcagcaatt   480
gcacagaaag aaacaaatgt tccgattatc acccatagca atgcacataa tggcaccggt   540
ctggaacagc agcgtattct gatggaagaa ggtgtggatc cgggtcgtgt tctgattggt   600
catctgggtg ataccgataa cgtggactac atcaaaaaaa tcgcagataa aggtagcttt   660
gttggcctgg atcgctatgg tgtggacctg tttctgccga ttgataaacg taatgaagtt   720
ctgctgaaac tgatcaaaga tggttatctg atcgtatta tggtgagcca ggattattgt   780
tgtaccattg atatgggtat tgccaaaccg aatataaac cgaaactggc accgaaatgg   840
tcaatgagcc tgattttttac cgatgtgatt ccgagcatta acgtgccgg tgttaccgat   900
gaacagctgc atgtgatttt tgttaaaaat ccggcacgcc tgtttagctg ataa          954
```

<210> SEQ ID NO 221
<211> LENGTH: 316
<212> TYPE: PRT
<213> ORGANISM: Sulfolobus acidocaldarius

<400> SEQUENCE: 221

```
Met Ala Thr Lys Ile Pro Leu Val Gly Lys Gly Glu Ile Ser Pro Gly
 1               5                  10                  15
Glu Met Gly Phe Thr Leu Ile His Glu His Leu Arg Val Phe Ser Glu
            20                  25                  30
Pro Val Arg Tyr Gln Trp Pro His Leu Tyr Asn Glu Asp Glu Glu Leu
        35                  40                  45
Lys Asn Ala Val Asn Glu Val Lys Thr Ile Met Ser Tyr Gly Val Lys
    50                  55                  60
Thr Ile Val Asp Pro Ser Val Met Gly Leu Gly Arg Asp Ile Arg Phe
65                  70                  75                  80
Ser Glu Lys Val Val Lys Glu Thr Gly Ile Asn Val Ile Ala Ala Thr
                85                  90                  95
Gly Leu Trp Thr Phe Thr Asp Leu Pro Phe Phe Phe Asn Gly Arg Ser
            100                 105                 110
Leu Glu Glu Ile Ala Glu Leu Leu Ile His Asp Ile Lys Lys Gly Ile
        115                 120                 125
Gln Gly Thr Pro Asn Arg Ala Gly Phe Ile Lys Val Ala Ala Asp Glu
    130                 135                 140
Pro Gly Ile Thr Arg Asp Val Glu Arg Ala Ile Arg Ala Ala Ala Ile
145                 150                 155                 160
Ala Gln Lys Glu Thr Asn Val Pro Ile Ile Thr His Ser Asn Ala His
                165                 170                 175
Asn Gly Thr Gly Leu Glu Gln Gln Arg Ile Leu Met Glu Glu Gly Val
            180                 185                 190
Asp Pro Gly Arg Val Leu Ile Gly His Leu Gly Asp Thr Asp Asn Val
        195                 200                 205
```

Asp Tyr Ile Lys Lys Ile Ala Asp Lys Gly Ser Phe Val Gly Leu Asp
    210                 215                 220

Arg Tyr Gly Val Asp Leu Phe Leu Pro Ile Asp Lys Arg Asn Glu Val
225                 230                 235                 240

Leu Leu Lys Leu Ile Lys Asp Gly Tyr Leu Asp Arg Ile Met Val Ser
            245                 250                 255

Gln Asp Tyr Cys Cys Thr Ile Asp Met Gly Ile Ala Lys Pro Glu Tyr
            260                 265                 270

Lys Pro Lys Leu Ala Pro Lys Trp Ser Met Ser Leu Ile Phe Thr Asp
            275                 280                 285

Val Ile Pro Ser Ile Lys Arg Ala Gly Val Thr Asp Glu Gln Leu His
290                 295                 300

Val Ile Phe Val Lys Asn Pro Ala Arg Leu Phe Ser
305                 310                 315

<210> SEQ ID NO 222
<211> LENGTH: 954
<212> TYPE: DNA
<213> ORGANISM: Sulfolobus acidocaldarius

<400> SEQUENCE: 222
atggcgacca aaattccgct ggttggtaaa ggtgaaatta gtccgggtga atgggtttt     60 accctgattc atgaacatct gcgtgttttt agcgaaccgg tgcgttatca gtggccccat    120
ctgtataatg aagatgaaga actgaaaaac gccgtgaacg aagtgaaaac cattatgagc    180
tatggcgtta aaaccattgt tgatccgagt gttatgggta ttggtcgtga tattcgtttt    240
agtgaaaaag tggtgaaaga accggcatt aatgttattg cagcaaccgg tctgtggacc    300
tttaccgatc tgccgttttt tttcaatggt cgtagcctgg aagaaattgc agaactgctg    360
atccacgata tcaaaaaagg tattcagggc accccgaatc gtgcgggttt tatcaaagtt    420
gcagcagatg aaccgggtat tacccgtgat gttgaacgtg caattcgtgc agcagcaatt    480
gcacagaaag aaacaaatgt tccgattatc acccatagca atgcacataa tggcaccggt    540
ctggaacagc agcgtattct gatggaagaa ggtgtggatc cgggtcgtgt tctgattggt    600
catctgggtg ataccgataa cgtggactac atcaaaaaaa tcgcagataa aggtagcttt    660
gttggcctgg atcgctatgg tctggacctg tttctgccga ttgataaacg taatgaagtt    720
ctgctgaaac tgatcaaaga tggttatctg gatcgtatta tggtgagcca ggattattgt    780
tgtaccattg attggggtat tgccaaaccg gaatataaac cgaaactggc accgaaatgg    840
tcaatgagcc tgattttac cgatgtgatt ccgagcatta aacgtgccgg tgttaccgat    900
gaacagctgc atgtgatttt tgttaaaaat ccggcacgcc tgtttagctg ataa          954

<210> SEQ ID NO 223
<211> LENGTH: 316
<212> TYPE: PRT
<213> ORGANISM: Sulfolobus acidocaldarius

<400> SEQUENCE: 223

Met Ala Thr Lys Ile Pro Leu Val Gly Lys Gly Glu Ile Ser Pro Gly
1               5                   10                  15

Glu Met Gly Phe Thr Leu Ile His Glu His Leu Arg Val Phe Ser Glu
            20                  25                  30

Pro Val Arg Tyr Gln Trp Pro His Leu Tyr Asn Glu Asp Glu Glu Leu
        35                  40                  45

Lys Asn Ala Val Asn Glu Val Lys Thr Ile Met Ser Tyr Gly Val Lys

|   |   |   |   |   | 50  |   |   |   |   | 55  |   |   |   |   | 60  |   |   |   |
|---|---|---|---|---|---|---|---|---|---|---|---|---|---|---|---|---|---|---|

Thr Ile Val Asp Pro Ser Val Met Gly Ile Gly Arg Asp Ile Arg Phe
65                  70                  75                  80

Ser Glu Lys Val Val Lys Glu Thr Gly Ile Asn Val Ile Ala Ala Thr
                85                  90                  95

Gly Leu Trp Thr Phe Thr Asp Leu Pro Phe Phe Phe Asn Gly Arg Ser
            100                 105                 110

Leu Glu Glu Ile Ala Glu Leu Leu Ile His Asp Ile Lys Lys Gly Ile
        115                 120                 125

Gln Gly Thr Pro Asn Arg Ala Gly Phe Ile Lys Val Ala Ala Asp Glu
    130                 135                 140

Pro Gly Ile Thr Arg Asp Val Glu Arg Ala Ile Arg Ala Ala Ala Ile
145                 150                 155                 160

Ala Gln Lys Glu Thr Asn Val Pro Ile Ile Thr His Ser Asn Ala His
                165                 170                 175

Asn Gly Thr Gly Leu Glu Gln Gln Arg Ile Leu Met Glu Glu Gly Val
            180                 185                 190

Asp Pro Gly Arg Val Leu Ile Gly His Leu Gly Asp Thr Asp Asn Val
        195                 200                 205

Asp Tyr Ile Lys Lys Ile Ala Asp Lys Gly Ser Phe Val Gly Leu Asp
    210                 215                 220

Arg Tyr Gly Leu Asp Leu Phe Leu Pro Ile Asp Lys Arg Asn Glu Val
225                 230                 235                 240

Leu Leu Lys Leu Ile Lys Asp Gly Tyr Leu Asp Arg Ile Met Val Ser
                245                 250                 255

Gln Asp Tyr Cys Cys Thr Ile Asp Trp Gly Ile Ala Lys Pro Glu Tyr
            260                 265                 270

Lys Pro Lys Leu Ala Pro Lys Trp Ser Met Ser Leu Ile Phe Thr Asp
        275                 280                 285

Val Ile Pro Ser Ile Lys Arg Ala Gly Val Thr Asp Glu Gln Leu His
    290                 295                 300

Val Ile Phe Val Lys Asn Pro Ala Arg Leu Phe Ser
305                 310                 315

<210> SEQ ID NO 224
<211> LENGTH: 948
<212> TYPE: DNA
<213> ORGANISM: Sulfolobus islandicus

<400> SEQUENCE: 224
atggcgcgta ttccgctggt tggtaaagaa ccgattgaag ccgaagatat gggttttacc     60
ctgattcatg aacatctgcg tgttttagc gaagcagttc gttatcagtg gcctcatctg    120
tataatgaag atgaagaact gcgtaatgcc gttaatgaag ttaaacgtgc catgcagttt    180
ggtgttaaaa ccattgttga tccgaccgtt atgggtctgg tcgtgatat tcgctttatg    240 gaaaaagttg tgaaaaccac cggtattaat ctggttgcag caccggtat ttatatttat    300 gtggatctgc gttttattt tctgaaccgc agcattgatg aaattgccga cctgtttatt    360
catgatatta agaaggtat tcaggcaacc agcaataaag ccggttttgt gaaaattgca    420
gccgatgaac cgggtattac caaagatgtg gaaaaagtta ttcgtgcagc agccattacc    480
cataaagaag ccaaagttcc gattattacc catagcaatg cccataataa taccggtctg    540
gaagaacagc gtattctgat ggaagaaggt gttgatccgg gtaaaattct gattggtcat    600
ctgggtgata ccgataatac cgattatatt aaaaaaattg ccgataaagg cagctttatt    660

```
ggtctggatc gttatggtct ggacctgttt ctgccggttg ataaacgtaa tgaaaccacc    720
ctgaaactga ttaagatgg ctatagcgat cgcattatga tcagccatga ttattgttgt    780
accattgatt ttggcaccgc acgtccggaa ctgaaaccga aactggcacc gcgttggagc    840
atggcactga tttttgaaga taccattccg tttctgaaaa aaaatggcgt gagcgaagaa    900
gtgatcgata ttattttcaa agaaaacccg aaaaaattct ttagctaa              948
```

<210> SEQ ID NO 225
<211> LENGTH: 315
<212> TYPE: PRT
<213> ORGANISM: Sulfolobus islandicus

<400> SEQUENCE: 225

```
Met Ala Arg Ile Pro Leu Val Gly Lys Glu Pro Ile Glu Ala Glu Asp
1               5                   10                  15

Met Gly Phe Thr Leu Ile His Glu His Leu Arg Val Phe Ser Glu Ala
            20                  25                  30

Val Arg Tyr Gln Trp Pro His Leu Tyr Asn Glu Asp Glu Glu Leu Arg
        35                  40                  45

Asn Ala Val Asn Glu Val Lys Arg Ala Met Gln Phe Gly Val Lys Thr
    50                  55                  60

Ile Val Asp Pro Thr Val Met Gly Leu Gly Arg Asp Ile Arg Phe Met
65                  70                  75                  80

Glu Lys Val Val Lys Thr Thr Gly Ile Asn Leu Val Ala Gly Thr Gly
                85                  90                  95

Ile Tyr Ile Tyr Val Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Ala Thr Ser Asn Lys Ala Gly Phe Val Lys Ile Ala Ala Asp Glu Pro
    130                 135                 140

Gly Ile Thr Lys Asp Val Glu Lys Val Ile Arg Ala Ala Ile Thr
145                 150                 155                 160

His Lys Glu Ala Lys Val Pro Ile Ile Thr His Ser Asn Ala His Asn
                165                 170                 175

Asn Thr Gly Leu Glu Glu Gln Arg Ile Leu Met Glu Glu Gly Val Asp
            180                 185                 190

Pro Gly Lys Ile Leu Ile Gly His Leu Gly Asp Thr Asp Asn Thr Asp
        195                 200                 205

Tyr Ile Lys Lys Ile Ala Asp Lys Gly Ser Phe Ile Gly Leu Asp Arg
    210                 215                 220

Tyr Gly Leu Asp Leu Phe Leu Pro Val Asp Lys Arg Asn Glu Thr Thr
225                 230                 235                 240

Leu Lys Leu Ile Lys Asp Gly Tyr Ser Asp Arg Ile Met Ile Ser His
                245                 250                 255

Asp Tyr Cys Cys Thr Ile Asp Phe Gly Thr Ala Arg Pro Glu Leu Lys
            260                 265                 270

Pro Lys Leu Ala Pro Arg Trp Ser Met Ala Leu Ile Phe Glu Asp Thr
        275                 280                 285

Ile Pro Phe Leu Lys Lys Asn Gly Val Ser Glu Glu Val Ile Asp Ile
    290                 295                 300

Ile Phe Lys Glu Asn Pro Lys Lys Phe Phe Ser
305                 310                 315
```

<210> SEQ ID NO 226
<211> LENGTH: 948
<212> TYPE: DNA
<213> ORGANISM: Sulfolobus islandicus

<400> SEQUENCE: 226

```
atggcgcgta ttccgctggt tggtaaagaa ccgattgaag ccgaagatat gggttttacc     60
ctgattcatg aacatctgcg tgttttagc gaagcagttc gttatcagtg cctcatctg    120
tataatgaag atgaagaact gcgtaatgcc gttaatgaag ttaaacgtgc catgcagttt    180
ggtgttaaaa ccattgttga tccgaccgtt atgggtctgg tcgtgatat cgctttatg     240
gaaaaagttg tgaaaaccac cggtattaat ctggttgcag gcaccggtat ttatatttat    300
gtggatctgc cgttttattt tctgaaccgc agcattgatg aaattgccga cctgtttatt    360
catgatatta agaaggtat tcaggcaacc agcaataaag ccggttttgt gaaaattgca    420
gccgatgaac cgggtattac caaagatgtg gaaaaagtta ttcgtgcagc agccattacc    480
cataaagaag ccaaagttcc gattattacc catagcaatg cccataataa taccggtctg    540
gaagaacagc gtattctgat ggaagaaggt gttgatccgg gtaaaattct gattggtcat    600
ctgggtgata ccgataatac cgattatatt aaaaaaattg ccgataaagg cagctttatt    660
ggtctggatc gttatggtct ggacctgttt ctgccggttg ataaacgtaa tgaaaccacc    720
ctgaaactga ttaagatgg ctatagcgat cgcattatga tcagccatga ttattgttgt    780
accattgata tgggcaccgc acgtccggaa ctgaaaccga actggcaacc gcgttggagc    840
atggcactga tttttgaaga taccattccg tttctgaaaa aaaatggcgt gagcgaagaa    900
gtgatcgata ttatttttcaa agaaaacccg aaaaaaattct ttagctaa                948
```

<210> SEQ ID NO 227
<211> LENGTH: 315
<212> TYPE: PRT
<213> ORGANISM: Sulfolobus islandicus

<400> SEQUENCE: 227

```
Met Ala Arg Ile Pro Leu Val Gly Lys Glu Pro Ile Glu Ala Glu Asp
1               5                   10                  15

Met Gly Phe Thr Leu Ile His Glu His Leu Arg Val Phe Ser Glu Ala
            20                  25                  30

Val Arg Tyr Gln Trp Pro His Leu Tyr Asn Glu Asp Glu Glu Leu Arg
        35                  40                  45

Asn Ala Val Asn Glu Val Lys Arg Ala Met Gln Phe Gly Val Lys Thr
    50                  55                  60

Ile Val Asp Pro Thr Val Met Gly Leu Gly Arg Asp Ile Arg Phe Met
65                  70                  75                  80

Glu Lys Val Val Lys Thr Thr Gly Ile Asn Leu Val Ala Gly Thr Gly
                85                  90                  95

Ile Tyr Ile Tyr Val Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Ala Thr Ser Asn Lys Ala Gly Phe Val Lys Ile Ala Asp Glu Pro
    130                 135                 140

Gly Ile Thr Lys Asp Val Glu Lys Val Ile Arg Ala Ala Ala Ile Thr
145                 150                 155                 160

His Lys Glu Ala Lys Val Pro Ile Ile Thr His Ser Asn Ala His Asn
```

```
                     165                 170                 175
Asn Thr Gly Leu Glu Glu Gln Arg Ile Leu Met Glu Glu Gly Val Asp
                 180                 185                 190

Pro Gly Lys Ile Leu Ile Gly His Leu Gly Asp Thr Asp Asn Thr Asp
             195                 200                 205

Tyr Ile Lys Lys Ile Ala Asp Lys Gly Ser Phe Ile Gly Leu Asp Arg
         210                 215                 220

Tyr Gly Leu Asp Leu Phe Leu Pro Val Asp Lys Arg Asn Glu Thr Thr
225                 230                 235                 240

Leu Lys Leu Ile Lys Asp Gly Tyr Ser Asp Arg Ile Met Ile Ser His
                 245                 250                 255

Asp Tyr Cys Cys Thr Ile Asp Met Gly Thr Ala Arg Pro Glu Leu Lys
                 260                 265                 270

Pro Lys Leu Ala Pro Arg Trp Ser Met Ala Leu Ile Phe Glu Asp Thr
                 275                 280                 285

Ile Pro Phe Leu Lys Lys Asn Gly Val Ser Glu Val Ile Asp Ile
             290                 295                 300

Ile Phe Lys Glu Asn Pro Lys Lys Phe Phe Ser
305                 310                 315

<210> SEQ ID NO 228
<211> LENGTH: 948
<212> TYPE: DNA
<213> ORGANISM: Sulfolobus islandicus

<400> SEQUENCE: 228
atggcgcgta ttccgctggt tggtaaagaa ccgattgaag ccgaagatat gggttttacc      60
ctgattcatg aacatctgcg tgtttttagc gaagcagttc gttatcagtg gcctcatctg     120
tataatgaag atgaagaact gcgtaatgcc gttaatgaag ttaaacgtgc catgcagttt     180
ggtgttaaaa ccattgttga tccgaccgtt atgggtctgg tcgtgatat cgctttatg     240
gaaaaagttg tgaaaaccac cggtattaat ctggttgcag gcaccggtat ttatatttat     300
gtggatctgc gttttatttt tctgaaccgc agcattgatg aaattgccga cctgtttatt     360
catgatatta agaaggtat tcaggcaacc agcaataaag ccggttttgt gaaaattgca     420
gccgatgaac cgggtattac caaagatgtg gaaaaagtta ttcgtgcagc agccattacc     480
cataaagaag ccaaagttcc gattattacc atagcaatg cccataataa taccggtctg     540
gaagaacagc gtattctgat ggaagaaggt gttgatccgg gtaaaattct gattggtcat     600
ctgggtgata ccgataatac cgattatatt aaaaaaattg ccgataaagg cagctttatt     660
ggtctggatc gttatggtct ggacctgttt ctgccggttg ataaacgtaa tgaaaccacc     720
ctgaaactga ttaagatgg ctatagcgat cgcattatga tcagccatga ttattgttgt     780
accattgatc tgggcaccgc acgtccggaa ctgaaaccga actggcacc gcgttggagc     840
atggcactga ttttgaaga taccattccg tttctgaaaa aaaatggcgt gagcgaagaa     900
gtgatcgata ttatttttcaa agaaaacccg aaaaaattct ttagctaa              948

<210> SEQ ID NO 229
<211> LENGTH: 315
<212> TYPE: PRT
<213> ORGANISM: Sulfolobus islandicus

<400> SEQUENCE: 229

Met Ala Arg Ile Pro Leu Val Gly Lys Glu Pro Ile Glu Ala Glu Asp
1               5                   10                  15
```

```
Met Gly Phe Thr Leu Ile His Glu His Leu Arg Val Phe Ser Glu Ala
              20                  25                  30
Val Arg Tyr Gln Trp Pro His Leu Tyr Asn Glu Asp Glu Leu Arg
         35                  40                  45
Asn Ala Val Asn Glu Val Lys Arg Ala Met Gln Phe Gly Val Lys Thr
 50                  55                  60
Ile Val Asp Pro Thr Val Met Gly Leu Gly Arg Asp Ile Arg Phe Met
 65                  70                  75                  80
Glu Lys Val Val Lys Thr Thr Gly Ile Asn Leu Val Ala Gly Thr Gly
                 85                  90                  95
Ile Tyr Ile Tyr Val Asp Leu Pro Phe Tyr Phe Leu Asn Arg Ser Ile
                100                 105                 110
Asp Glu Ile Ala Asp Leu Phe Ile His Asp Ile Lys Glu Gly Ile Gln
                115                 120                 125
Ala Thr Ser Asn Lys Ala Gly Phe Val Lys Ile Ala Ala Asp Glu Pro
130                 135                 140
Gly Ile Thr Lys Asp Val Glu Lys Val Ile Arg Ala Ala Ile Thr
145                 150                 155                 160
His Lys Glu Ala Lys Val Pro Ile Ile Thr His Ser Asn Ala His Asn
                165                 170                 175
Asn Thr Gly Leu Glu Glu Gln Arg Ile Leu Met Glu Glu Gly Val Asp
                180                 185                 190
Pro Gly Lys Ile Leu Ile Gly His Leu Gly Asp Thr Asp Asn Thr Asp
                195                 200                 205
Tyr Ile Lys Lys Ile Ala Asp Lys Gly Ser Phe Ile Gly Leu Asp Arg
                210                 215                 220
Tyr Gly Leu Asp Leu Phe Leu Pro Val Asp Lys Arg Asn Glu Thr Thr
225                 230                 235                 240
Leu Lys Leu Ile Lys Asp Gly Tyr Ser Asp Arg Ile Met Ile Ser His
                245                 250                 255
Asp Tyr Cys Cys Thr Ile Asp Leu Gly Thr Ala Arg Pro Glu Leu Lys
                260                 265                 270
Pro Lys Leu Ala Pro Arg Trp Ser Met Ala Leu Ile Phe Glu Asp Thr
                275                 280                 285
Ile Pro Phe Leu Lys Lys Asn Gly Val Ser Glu Glu Val Ile Asp Ile
                290                 295                 300
Ile Phe Lys Glu Asn Pro Lys Lys Phe Phe Ser
305                 310                 315
```

<210> SEQ ID NO 230
<211> LENGTH: 948
<212> TYPE: DNA
<213> ORGANISM: Sulfolobus islandicus

<400> SEQUENCE: 230

```
atggcgcgta ttccgctggt tggtaaagaa ccgattgaag ccgaagatat gggttttacc    60
ctgattcatg aacatctgcg tgttttagc gaagcagttc gttatcagtg gcctcatctg   120
tataatgaag atgaagaact gcgtaatgcc gttaatgaag ttaaacgtgc catgcagttt   180
ggtgttaaaa ccattgttga tccgaccgtt atgggtctgg gtcgtgatat cgctttatg   240
gaaaaagttg tgaaaccac cggtattaat ctggttgcag gcaccggtat ttatatttat   300
gtggatctgc cgttttattt tctgaaccgc agcattgatg aaattgccga cctgtttatt   360
catgatatta agaaggtat tcaggcaacc agcaataaag ccggttttgt gaaaattgca   420
```

-continued

```
gccgatgaac cgggtattac caaagatgtg gaaaaagtta ttcgtgcagc agccattacc    480
cataaagaag ccaaagttcc gattattacc catagcaatg cccataataa taccggtctg    540
gaagaacagc gtattctgat ggaagaaggt gttgatccgg gtaaaattct gattggtcat    600
ctgggtgata ccgataatac cgattatatt aaaaaaattg ccgataaagg cagctttatt    660
ggtctggatc gttatggtct ggacctgttt ctgccggttg ataaacgtaa tgaaaccacc    720
ctgaaactga ttaaagatgg ctatagcgat cgcattatga tcagccatga ttattgttgt    780
accattgatg caggcaccgc acgtccggaa ctgaaaccga actggcaccg cgttggagc     840 atggcactga tttttgaaga taccattccg tttctgaaaa aaaatggcgt gagcgaagaa    900
gtgatcgata ttattttcaa agaaaacccg aaaaaattct ttagctaa                 948
```

<210> SEQ ID NO 231
<211> LENGTH: 315
<212> TYPE: PRT
<213> ORGANISM: Sulfolobus islandicus

<400> SEQUENCE: 231

```
Met Ala Arg Ile Pro Leu Val Gly Lys Glu Pro Ile Glu Ala Glu Asp
1               5                   10                  15

Met Gly Phe Thr Leu Ile His Glu His Leu Arg Val Phe Ser Glu Ala
                20                  25                  30

Val Arg Tyr Gln Trp Pro His Leu Tyr Asn Glu Asp Glu Glu Leu Arg
            35                  40                  45

Asn Ala Val Asn Glu Val Lys Arg Ala Met Gln Phe Gly Val Lys Thr
        50                  55                  60

Ile Val Asp Pro Thr Val Met Gly Leu Gly Arg Asp Ile Arg Phe Met
65                  70                  75                  80

Glu Lys Val Val Lys Thr Thr Gly Ile Asn Leu Val Ala Gly Thr Gly
                85                  90                  95

Ile Tyr Ile Tyr Val Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Ala Thr Ser Asn Lys Ala Gly Phe Val Lys Ile Ala Ala Asp Glu Pro
    130                 135                 140

Gly Ile Thr Lys Asp Val Glu Lys Val Ile Arg Ala Ala Ile Thr
145                 150                 155                 160

His Lys Glu Ala Lys Val Pro Ile Ile Thr His Ser Asn Ala His Asn
                165                 170                 175

Asn Thr Gly Leu Glu Glu Gln Arg Ile Leu Met Glu Glu Gly Val Asp
            180                 185                 190

Pro Gly Lys Ile Leu Ile Gly His Leu Gly Asp Thr Asp Asn Thr Asp
        195                 200                 205

Tyr Ile Lys Lys Ile Ala Asp Lys Gly Ser Phe Ile Gly Leu Asp Arg
    210                 215                 220

Tyr Gly Leu Asp Leu Phe Leu Pro Val Asp Lys Arg Asn Glu Thr Thr
225                 230                 235                 240

Leu Lys Leu Ile Lys Asp Gly Tyr Ser Asp Arg Ile Met Ile Ser His
                245                 250                 255

Asp Tyr Cys Cys Thr Ile Asp Ala Gly Thr Ala Arg Pro Glu Leu Lys
            260                 265                 270

Pro Lys Leu Ala Pro Arg Trp Ser Met Ala Leu Ile Phe Glu Asp Thr
```

```
              275                 280                 285
Ile Pro Phe Leu Lys Lys Asn Gly Val Ser Glu Val Ile Asp Ile
      290                 295                 300

Ile Phe Lys Glu Asn Pro Lys Lys Phe Phe Ser
305                 310                 315

<210> SEQ ID NO 232
<211> LENGTH: 948
<212> TYPE: DNA
<213> ORGANISM: Sulfolobus islandicus

<400> SEQUENCE: 232
atggcgcgta ttccgctggt tggtaaagaa ccgattgaag ccgaagatat gggttttacc      60
ctgattcatg aacatctgcg tgtttttagc gaagcagttc gttatcagtg gcctcatctg     120
tataatgaag atgaagaact gcgtaatgcc gttaatgaag ttaaacgtgc catgcagttt     180
ggtgttaaaa ccattgttga tccgaccgtt atgggtctgg gtcgtgatat tcgctttatg     240
gaaaaagttg tgaaaaccac cggtattaat ctggttgcag gcaccggtat ttatatttat     300
gtggatctgc cgtttatttt tctgaaccgc agcattgatg aaattgccga cctgtttatt     360
catgatatta agaaggtat tcaggcaacc agcaataaag ccggttttgt gaaaattgca     420
gccgatgaac cgggtattac caaagatgtg gaaaaagtta ttcgtgcagc agccattacc     480
cataaagaag ccaaagttcc gattattacc catagcaatg cccataataa taccggtctg     540
gaagaacagc gtattctgat ggaagaaggt gttgatccgg gtaaaattct gattggtcat     600
ctgggtgata ccgataatac cgattatatt aaaaaaattg ccgataaagg cagctttatt     660
ggtctggatc gttatggtct ggacctgttt ctgccggttg ataaacgtaa tgaaaccacc     720
ctgaaactga ttaaagatgg ctatagcgat cgcattatga tcagccatga ttattgttgt     780
accattgata ttggcaccgc acgtccggaa ctgaaaccga actggcaccg cgttggagc     840 atggcactga tttttgaaga taccattccg tttctgaaaa aaaatggcgt gagcgaagaa     900
gtgatcgata ttatttttcaa agaaaacccg aaaaaattct ttagctaa                 948

<210> SEQ ID NO 233
<211> LENGTH: 315
<212> TYPE: PRT
<213> ORGANISM: Sulfolobus islandicus

<400> SEQUENCE: 233

Met Ala Arg Ile Pro Leu Val Gly Lys Glu Pro Ile Glu Ala Glu Asp
1               5                  10                  15

Met Gly Phe Thr Leu Ile His Glu His Leu Arg Val Phe Ser Glu Ala
            20                  25                  30

Val Arg Tyr Gln Trp Pro His Leu Tyr Asn Glu Asp Glu Glu Leu Arg
        35                  40                  45

Asn Ala Val Asn Glu Val Lys Arg Ala Met Gln Phe Gly Val Lys Thr
    50                  55                  60

Ile Val Asp Pro Thr Val Met Gly Leu Gly Arg Asp Ile Arg Phe Met
65                  70                  75                  80

Glu Lys Val Val Lys Thr Thr Gly Ile Asn Leu Val Ala Gly Thr Gly
                85                  90                  95

Ile Tyr Ile Tyr Val Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125
```

Ala Thr Ser Asn Lys Ala Gly Phe Val Lys Ile Ala Ala Asp Glu Pro
    130                 135                 140

Gly Ile Thr Lys Asp Val Glu Lys Val Ile Arg Ala Ala Ala Ile Thr
145                 150                 155                 160

His Lys Glu Ala Lys Val Pro Ile Ile Thr His Ser Asn Ala His Asn
                165                 170                 175

Asn Thr Gly Leu Glu Glu Gln Arg Ile Leu Met Glu Glu Gly Val Asp
            180                 185                 190

Pro Gly Lys Ile Leu Ile Gly His Leu Gly Asp Thr Asp Asn Thr Asp
        195                 200                 205

Tyr Ile Lys Lys Ile Ala Asp Lys Gly Ser Phe Ile Gly Leu Asp Arg
    210                 215                 220

Tyr Gly Leu Asp Leu Phe Leu Pro Val Asp Lys Arg Asn Glu Thr Thr
225                 230                 235                 240

Leu Lys Leu Ile Lys Asp Gly Tyr Ser Asp Arg Ile Met Ile Ser His
                245                 250                 255

Asp Tyr Cys Cys Thr Ile Asp Ile Gly Thr Ala Arg Pro Glu Leu Lys
            260                 265                 270

Pro Lys Leu Ala Pro Arg Trp Ser Met Ala Leu Ile Phe Glu Asp Thr
        275                 280                 285

Ile Pro Phe Leu Lys Lys Asn Gly Val Ser Glu Glu Val Ile Asp Ile
    290                 295                 300

Ile Phe Lys Glu Asn Pro Lys Lys Phe Phe Ser
305                 310                 315

<210> SEQ ID NO 234
<211> LENGTH: 948
<212> TYPE: DNA
<213> ORGANISM: Sulfolobus islandicus

<400> SEQUENCE: 234
atggcgcgta ttccgctggt tggtaaagaa ccgattgaag ccgaagatat gggttttacc      60
ctgattcatg aacatctgcg tgtttttagc gaagcagttc gttatcagtg gcctcatctg     120
tataatgaag atgaagaact gcgtaatgcc gttaatgaag ttaaacgtgc catgcagttt     180
ggtgttaaaa ccattgttga tccgaccgtt atgggtctgg tcgtgatat cgctttatg      240
gaaaaagttg tgaaaaccac cggtattaat ctggttgcag caccggtat ttatatttat     300
gtggatctgc gttttatttt tctgaaccgc agcattgatg aaattgccga cctgtttatt     360
catgatatta agaaggtat tcaggcaacc agcaataaag ccggttttgt gaaaattgca     420
gccgatgaac cgggtattac caaagatgtg aaaaagtta ttcgtgcagc agccattacc     480
cataaagaag ccaaagttcc gattattacc atagcaatg cccataataa taccggtctg     540
gaagaacagc gtattctgat ggaagaaggt gttgatccgg gtaaaattct gattggtcat     600
ctgggtgata ccgataatac cgattatatt aaaaaaattg ccgataaagg cagctttatt     660
ggtctggatc gttatggtct ggacctgttt ctgccggttg ataaacgtaa tgaaaccacc     720
ctgaaactga ttaaagatgg ctatagcgat cgcattatga tcagccatga ttattgttgt     780
accattgatg ttggcaccgc acgtccggaa ctgaaaccga actggcaccg cgttggagc     840
atggcactga ttttgaaga taccattccg tttctgaaaa aaatggcgt gagcgaagaa     900
gtgatcgata ttatttttcaa agaaaacccg aaaaaattct ttagctaa                 948

<210> SEQ ID NO 235

<211> LENGTH: 315
<212> TYPE: PRT
<213> ORGANISM: Sulfolobus islandicus

<400> SEQUENCE: 235

Met Ala Arg Ile Pro Leu Val Gly Lys Glu Pro Ile Glu Ala Glu Asp
1               5                   10                  15
Met Gly Phe Thr Leu Ile His Glu His Leu Arg Val Phe Ser Glu Ala
            20                  25                  30
Val Arg Tyr Gln Trp Pro His Leu Tyr Asn Glu Asp Glu Glu Leu Arg
        35                  40                  45
Asn Ala Val Asn Glu Val Lys Arg Ala Met Gln Phe Gly Val Lys Thr
    50                  55                  60
Ile Val Asp Pro Thr Val Met Gly Leu Gly Arg Asp Ile Arg Phe Met
65                  70                  75                  80
Glu Lys Val Val Lys Thr Thr Gly Ile Asn Leu Val Ala Gly Thr Gly
                85                  90                  95
Ile Tyr Ile Tyr Val Asp Leu Pro Phe Tyr Phe Leu Asn Arg Ser Ile
            100                 105                 110
Asp Glu Ile Ala Asp Leu Phe Ile His Asp Ile Lys Glu Gly Ile Gln
        115                 120                 125
Ala Thr Ser Asn Lys Ala Gly Phe Val Lys Ile Ala Ala Asp Glu Pro
    130                 135                 140
Gly Ile Thr Lys Asp Val Glu Lys Val Ile Arg Ala Ala Ala Ile Thr
145                 150                 155                 160
His Lys Glu Ala Lys Val Pro Ile Ile Thr His Ser Asn Ala His Asn
                165                 170                 175
Asn Thr Gly Leu Glu Glu Gln Arg Ile Leu Met Glu Glu Gly Val Asp
            180                 185                 190
Pro Gly Lys Ile Leu Ile Gly His Leu Gly Asp Thr Asp Asn Thr Asp
        195                 200                 205
Tyr Ile Lys Lys Ile Ala Asp Lys Gly Ser Phe Ile Gly Leu Asp Arg
    210                 215                 220
Tyr Gly Leu Asp Leu Phe Leu Pro Val Asp Lys Arg Asn Glu Thr Thr
225                 230                 235                 240
Leu Lys Leu Ile Lys Asp Gly Tyr Ser Asp Arg Ile Met Ile Ser His
                245                 250                 255
Asp Tyr Cys Cys Thr Ile Asp Val Gly Thr Ala Arg Pro Glu Leu Lys
            260                 265                 270
Pro Lys Leu Ala Pro Arg Trp Ser Met Ala Leu Ile Phe Glu Asp Thr
        275                 280                 285
Ile Pro Phe Leu Lys Lys Asn Gly Val Ser Glu Glu Val Ile Asp Ile
    290                 295                 300
Ile Phe Lys Glu Asn Pro Lys Lys Phe Phe Ser
305                 310                 315

<210> SEQ ID NO 236
<211> LENGTH: 948
<212> TYPE: DNA
<213> ORGANISM: Sulfolobus islandicus

<400> SEQUENCE: 236
atggcgcgta ttccgctggt tggtaaagaa ccgattgaag ccgaagatat gggttttacc      60
ctgattcatg aacatctgcg tgttttagc gaagcagttc gttatcagtg gcctcatctg     120
tataatgaag atgaagaact gcgtaatgcc gttaatgaag ttaaacgtgc catgcagttt     180

```
ggtgttaaaa ccattgttga tccgaccgtt atgggtctgg gtcgtgatat tcgctttatg      240
gaaaaagttg tgaaaccac cggtattaat ctggttgcag caccggtat ttatatttat      300 gtggatctgc cgttttattt tctgaaccgc agcattgatg aaattgccga cctgtttatt      360
catgatatta agaaggtat tcaggcaacc agcaataaag ccggttttgt gaaaattgca      420
gccgatgaac cgggtattac caaagatgtg gaaaaagtta ttcgtgcagc agccattacc      480
cataaagaag ccaaagttcc gattattacc catagcaatg cccataataa taccggtctg      540
gaagaacagc gtattctgat ggaagaaggt gttgatccgg gtaaaattct gattggtcat      600
ctgggtgata ccgataatac cgattatatt aaaaaaattg ccgataaagg cagctttatt      660
ggtctggatc gttatggtct ggacctgttt ctgccggttg ataaacgtaa tgaaaccacc      720
ctgaaactga ttaaagatgg ctatagcgat cgcattatga tcagccatga ttattgttgt      780
accattgata ccggcaccgc acgtccggaa ctgaaaccga actggcacc gcgttggagc      840 atggcactga ttttgaaga taccattccg tttctgaaaa aaaatggcgt gagcgaagaa      900
gtgatcgata ttattttcaa agaaaacccg aaaaaattct ttagctaa                 948
```

<210> SEQ ID NO 237
<211> LENGTH: 315
<212> TYPE: PRT
<213> ORGANISM: Sulfolobus islandicus

<400> SEQUENCE: 237

```
Met Ala Arg Ile Pro Leu Val Gly Lys Glu Pro Ile Glu Ala Glu Asp
1               5                   10                  15

Met Gly Phe Thr Leu Ile His Glu His Leu Arg Val Phe Ser Glu Ala
            20                  25                  30

Val Arg Tyr Gln Trp Pro His Leu Tyr Asn Glu Asp Glu Glu Leu Arg
        35                  40                  45

Asn Ala Val Asn Glu Val Lys Arg Ala Met Gln Phe Gly Val Lys Thr
    50                  55                  60

Ile Val Asp Pro Thr Val Met Gly Leu Gly Arg Asp Ile Arg Phe Met
65                  70                  75                  80

Glu Lys Val Val Lys Thr Thr Gly Ile Asn Leu Val Ala Gly Thr Gly
                85                  90                  95

Ile Tyr Ile Tyr Val Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Ala Thr Ser Asn Lys Ala Gly Phe Val Lys Ile Ala Ala Asp Glu Pro
    130                 135                 140

Gly Ile Thr Lys Asp Val Glu Lys Val Ile Arg Ala Ala Ala Ile Thr
145                 150                 155                 160

His Lys Glu Ala Lys Val Pro Ile Ile Thr His Ser Asn Ala His Asn
                165                 170                 175

Asn Thr Gly Leu Glu Glu Gln Arg Ile Leu Met Glu Glu Gly Val Asp
            180                 185                 190

Pro Gly Lys Ile Leu Ile Gly His Leu Gly Asp Thr Asp Asn Thr Asp
        195                 200                 205

Tyr Ile Lys Lys Ile Ala Asp Lys Gly Ser Phe Ile Gly Leu Asp Arg
    210                 215                 220

Tyr Gly Leu Asp Leu Phe Leu Pro Val Asp Lys Arg Asn Glu Thr Thr
225                 230                 235                 240
```

```
Leu Lys Leu Ile Lys Asp Gly Tyr Ser Asp Arg Ile Met Ile Ser His
            245                 250                 255

Asp Tyr Cys Cys Thr Ile Asp Thr Gly Thr Ala Arg Pro Glu Leu Lys
            260                 265                 270

Pro Lys Leu Ala Pro Arg Trp Ser Met Ala Leu Ile Phe Glu Asp Thr
            275                 280                 285

Ile Pro Phe Leu Lys Lys Asn Gly Val Ser Glu Glu Val Ile Asp Ile
            290                 295                 300

Ile Phe Lys Glu Asn Pro Lys Lys Phe Phe Ser
305                 310                 315
```

<210> SEQ ID NO 238
<211> LENGTH: 948
<212> TYPE: DNA
<213> ORGANISM: Sulfolobus islandicus

<400> SEQUENCE: 238

```
atggcgcgta ttccgctggt tggtaaagaa ccgattgaag ccgaagatat gggttttacc    60
ctgattcatg aacatctgcg tgtttttagc gaagcagttc gttatcagtg gcctcatctg   120
tataatgaag atgaagaact gcgtaatgcc gttaatgaag ttaaacgtgc catgcagttt   180
ggtgttaaaa ccattgttga tccgaccgtt atgggtctgg gtcgtgatat tcgctttatg   240
gaaaaagttg tgaaaaccac cggtattaat ctggttgcag caccggtat ttatatttat   300
gtggatctgc gtttttattt tctgaaccgc agcattgatg aaattgccga cctgtttatt   360
catgatatta agaaggtat tcaggcaacc agcaataaag ccggttttgt gaaaattgca   420
gccgatgaac cgggtattac caaagatgtg gaaaaagtta ttcgtgcagc agccattacc   480
cataaagaag ccaaagttcc gattattacc catagcaatg cccataataa taccggtctg   540
gaagaacagc gtattctgat ggaagaaggt gttgatccgg gtaaaattct gattggtcat   600
ctgggtgata ccgataatac cgattatatt aaaaaaattg ccgataaagg cagctttatt   660
ggtctggatc gttatggtct ggacctgttt ctgccggttg ataacgtaa tgaaaccacc   720
ctgaaactga ttaaagatgg ctatagcgat cgcattatga tcagccatga ttatctgtgt   780
acctttgatg caggcaccgc acgtccggaa ctgaaaccga actggcacc gcgttggagc   840
atggcactga ttttgaaga taccattccg tttctgaaaa aaaatggcgt gagcgaagaa   900
gtgatcgata ttatttttcaa agaaaacccg aaaaaattct ttagctaa               948
```

<210> SEQ ID NO 239
<211> LENGTH: 315
<212> TYPE: PRT
<213> ORGANISM: Sulfolobus islandicus

<400> SEQUENCE: 239

```
Met Ala Arg Ile Pro Leu Val Gly Lys Glu Pro Ile Glu Ala Glu Asp
1               5                  10                  15

Met Gly Phe Thr Leu Ile His Glu His Leu Arg Val Phe Ser Glu Ala
            20                  25                  30

Val Arg Tyr Gln Trp Pro His Leu Tyr Asn Glu Asp Glu Glu Leu Arg
        35                  40                  45

Asn Ala Val Asn Glu Val Lys Arg Ala Met Gln Phe Gly Val Lys Thr
    50                  55                  60

Ile Val Asp Pro Thr Val Met Gly Leu Gly Arg Asp Ile Arg Phe Met
65                  70                  75                  80
```

```
Glu Lys Val Val Lys Thr Thr Gly Ile Asn Leu Val Ala Gly Thr Gly
                85                  90                  95

Ile Tyr Ile Tyr Val Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Ala Thr Ser Asn Lys Ala Gly Phe Val Lys Ile Ala Ala Asp Glu Pro
    130                 135                 140

Gly Ile Thr Lys Asp Val Glu Lys Val Ile Arg Ala Ala Ala Ile Thr
145                 150                 155                 160

His Lys Glu Ala Lys Val Pro Ile Ile Thr His Ser Asn Ala His Asn
                165                 170                 175

Asn Thr Gly Leu Glu Glu Gln Arg Ile Leu Met Glu Glu Gly Val Asp
            180                 185                 190

Pro Gly Lys Ile Leu Ile Gly His Leu Gly Asp Thr Asp Asn Thr Asp
        195                 200                 205

Tyr Ile Lys Lys Ile Ala Asp Lys Gly Ser Phe Ile Gly Leu Asp Arg
    210                 215                 220

Tyr Gly Leu Asp Leu Phe Leu Pro Val Asp Lys Arg Asn Glu Thr Thr
225                 230                 235                 240

Leu Lys Leu Ile Lys Asp Gly Tyr Ser Asp Arg Ile Met Ile Ser His
                245                 250                 255

Asp Tyr Leu Cys Thr Phe Asp Ala Gly Thr Ala Arg Pro Glu Leu Lys
            260                 265                 270

Pro Lys Leu Ala Pro Arg Trp Ser Met Ala Leu Ile Phe Glu Asp Thr
        275                 280                 285

Ile Pro Phe Leu Lys Lys Asn Gly Val Ser Glu Glu Val Ile Asp Ile
    290                 295                 300

Ile Phe Lys Glu Asn Pro Lys Lys Phe Phe Ser
305                 310                 315

<210> SEQ ID NO 240
<211> LENGTH: 948
<212> TYPE: DNA
<213> ORGANISM: Sulfolobus islandicus

<400> SEQUENCE: 240
atggcgcgta ttccgctggt tgtaaagaa ccgattgaag ccgaagatat gggttttacc      60
ctgattcatg aacatctgcg tgcatttagc gaagcagttc gttatcagtg gcctcatctg     120
tataatgaag atgaagaact gcgtaatgcc gttaatgaag ttaaacgtgc catgcagttt     180
ggtgttaaaa ccattgttga tccgaccgtt atgggtctgg tcgtgatat cgctttatg      240 gaaaaagttg tgaaaccac cggtattaat ctggttgcag caccggtat ttggatttat      300 gtggatctgc cgtttttattt tctgaaccgc agcattgatg aaattgccga cctgtttatt     360
catgatatta agaaggtat tcaggcaacc agcaataaag ccggttttgt gaaaattgca     420
gccgatgaac cgggtattac caaagatgtg gaaaaagtta ttcgtgcagc agccattacc     480
cataaagaag ccaaagttcc gattattacc catagcaatg cccataataa taccggtctg     540
gaagaacagc gtattctgat ggaagaaggt gttgatccgg gtaaaattct gattggtcat     600
ctgggtgata ccgataatac cgattatatt aaaaaaattg ccgataaagg cagctttatt     660
ggtctggatc gttatggtct ggacatgttt ctgccggttg ataaacgtaa tgaaaccacc     720
ctgaaactga ttaagatgg ctatagcgat cgcattatga tcagccatga ttattgttgt     780
```

```
accattgata tgggcaccgc acgtccggaa ctgaaaccga aactggcacc gcgttggagc    840
atggcactga ttttttgaaga taccattccg tttctgaaaa aaaatggcgt gagcgaagaa    900
gtgatcgata ttattttcaa agaaaacccg aaaaaattct ttagctaa                  948
```

<210> SEQ ID NO 241
<211> LENGTH: 315
<212> TYPE: PRT
<213> ORGANISM: Sulfolobus islandicus

<400> SEQUENCE: 241

```
Met Ala Arg Ile Pro Leu Val Gly Lys Glu Pro Ile Glu Ala Glu Asp
1               5                   10                  15

Met Gly Phe Thr Leu Ile His Glu His Leu Arg Ala Phe Ser Glu Ala
            20                  25                  30

Val Arg Tyr Gln Trp Pro His Leu Tyr Asn Glu Asp Glu Glu Leu Arg
        35                  40                  45

Asn Ala Val Asn Glu Val Lys Arg Ala Met Gln Phe Gly Val Lys Thr
    50                  55                  60

Ile Val Asp Pro Thr Val Met Gly Leu Gly Arg Asp Ile Arg Phe Met
65                  70                  75                  80

Glu Lys Val Val Lys Thr Thr Gly Ile Asn Leu Val Ala Gly Thr Gly
                85                  90                  95

Ile Trp Ile Tyr Val Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Ala Thr Ser Asn Lys Ala Gly Phe Val Lys Ile Ala Ala Asp Glu Pro
    130                 135                 140

Gly Ile Thr Lys Asp Val Glu Lys Val Ile Arg Ala Ala Ile Thr
145                 150                 155                 160

His Lys Glu Ala Lys Val Pro Ile Ile Thr His Ser Asn Ala His Asn
                165                 170                 175

Asn Thr Gly Leu Glu Glu Gln Arg Ile Leu Met Glu Glu Gly Val Asp
            180                 185                 190

Pro Gly Lys Ile Leu Ile Gly His Leu Gly Asp Thr Asp Asn Thr Asp
        195                 200                 205

Tyr Ile Lys Lys Ile Ala Asp Lys Gly Ser Phe Ile Gly Leu Asp Arg
    210                 215                 220

Tyr Gly Leu Asp Met Phe Leu Pro Val Asp Lys Arg Asn Glu Thr Thr
225                 230                 235                 240

Leu Lys Leu Ile Lys Asp Gly Tyr Ser Asp Arg Ile Met Ile Ser His
                245                 250                 255

Asp Tyr Cys Cys Thr Ile Asp Met Gly Thr Ala Arg Pro Glu Leu Lys
            260                 265                 270

Pro Lys Leu Ala Pro Arg Trp Ser Met Ala Leu Ile Phe Glu Asp Thr
        275                 280                 285

Ile Pro Phe Leu Lys Lys Asn Gly Val Ser Glu Glu Val Ile Asp Ile
    290                 295                 300

Ile Phe Lys Glu Asn Pro Lys Lys Phe Phe Ser
305                 310                 315
```

<210> SEQ ID NO 242
<211> LENGTH: 948
<212> TYPE: DNA
<213> ORGANISM: Sulfolobus islandicus

<400> SEQUENCE: 242

```
atggcgcgta ttccgctggt tggtaaagaa ccgattgaag ccgaagatat gggttttacc    60
ctgattcatg aacatctgcg tgcatttagc gaagcagttc gttatcagtg gcctcatctg   120
tataatgaag atgaagaact gcgtaatgcc gttaatgaag ttaaacgtgc catgcagttt   180
ggtgttaaaa ccattgttga tccgaccgtt atgggtctgg tcgtgatat tcgctttatg   240
gaaaaagttg tgaaaaccac cggtattaat ctggttgcag gcaccggtat ttggatttat   300
gtggatctgc cgtttatttt tctgaaccgc agcattgatg aaattgccga cctgtttatt   360
catgatatta agaaggtat tcaggcaacc agcaataaag ccggttttgt gaaaattgca   420
gccgatgaac cgggtattac caaagatgtg gaaaaagtta ttcgtgcagc agccattacc   480
cataaagaag ccaaagttcc gattattacc catagcaatg cccataataa taccggtctg   540
gaagaacagc gtattctgat ggaagaaggt gttgatccgg gtaaaattct gattggtcat   600
ctgggtgata ccgataatac cgattatatt aaaaaaattg ccgataaagg cagctttat   660
ggtctggatc gttatggtct ggacctgttt ctgccggttg ataaacgtaa tgaaaccacc   720
ctgaaactga ttaaagatgg ctatagcgat cgcattatga tcagccatga ttattgttgt   780
accattgatc tgggcaccgc acgtccggaa ctgaaaccga actggcacc gcgttggagc   840
acggcactga tttttgaaga taccattccg tttctgaaaa aaaatggcgt gagcgaagaa   900
gtgatcgata ttatttttcaa agaaaacccg aaaaaattct ttagctaa              948
```

<210> SEQ ID NO 243
<211> LENGTH: 315
<212> TYPE: PRT
<213> ORGANISM: Sulfolobus islandicus

<400> SEQUENCE: 243

```
Met Ala Arg Ile Pro Leu Val Gly Lys Glu Pro Ile Glu Ala Glu Asp
1               5                   10                  15

Met Gly Phe Thr Leu Ile His Glu His Leu Arg Ala Phe Ser Glu Ala
            20                  25                  30

Val Arg Tyr Gln Trp Pro His Leu Tyr Asn Glu Asp Glu Glu Leu Arg
        35                  40                  45

Asn Ala Val Asn Glu Val Lys Arg Ala Met Gln Phe Gly Val Lys Thr
    50                  55                  60

Ile Val Asp Pro Thr Val Met Gly Leu Gly Arg Asp Ile Arg Phe Met
65                  70                  75                  80

Glu Lys Val Val Lys Thr Thr Gly Ile Asn Leu Val Ala Gly Thr Gly
                85                  90                  95

Ile Trp Ile Tyr Val Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Ala Thr Ser Asn Lys Ala Gly Phe Val Lys Ile Ala Ala Asp Glu Pro
    130                 135                 140

Gly Ile Thr Lys Asp Val Glu Lys Val Ile Arg Ala Ala Ala Ile Thr
145                 150                 155                 160

His Lys Glu Ala Lys Val Pro Ile Ile Thr His Ser Asn Ala His Asn
                165                 170                 175

Asn Thr Gly Leu Glu Glu Gln Arg Ile Leu Met Glu Glu Gly Val Asp
            180                 185                 190
```

Pro Gly Lys Ile Leu Ile Gly His Leu Gly Asp Thr Asp Asn Thr Asp
        195                 200                 205

Tyr Ile Lys Lys Ile Ala Asp Lys Gly Ser Phe Ile Gly Leu Asp Arg
210                 215                 220

Tyr Gly Leu Asp Leu Phe Leu Pro Val Asp Lys Arg Asn Glu Thr Thr
225                 230                 235                 240

Leu Lys Leu Ile Lys Asp Gly Tyr Ser Asp Arg Ile Met Ile Ser His
                245                 250                 255

Asp Tyr Cys Cys Thr Ile Asp Leu Gly Thr Ala Arg Pro Glu Leu Lys
            260                 265                 270

Pro Lys Leu Ala Pro Arg Trp Ser Thr Ala Leu Ile Phe Glu Asp Thr
        275                 280                 285

Ile Pro Phe Leu Lys Lys Asn Gly Val Ser Glu Val Ile Asp Ile
    290                 295                 300

Ile Phe Lys Glu Asn Pro Lys Lys Phe Phe Ser
305                 310                 315

<210> SEQ ID NO 244
<211> LENGTH: 948
<212> TYPE: DNA
<213> ORGANISM: Sulfolobus islandicus

<400> SEQUENCE: 244
atggcgcgta ttccgctggt tggtaaagaa ccgattgaag ccgaagatat gggttttacc      60
ctgattcatg aacatctgcg tgttttagc gaagcagttc gttatcagtg gcctcatctg     120
tataatgaag atgaagaact gcgtaatgcc gttaatgaag ttaaacgtgc catgcagttt     180
ggtgttaaaa ccattgttga tccgaccgtt atgggtctgg tcgtgatat cgctttatg     240
gaaaaagttg tgaaaccac cggtattaat ctggttgcag caccggtat ttatatttat     300
gtggatctgc gttttatt tctgaaccgc agcattgatg aaattgccga cctgtttatt     360
catgatatta agaaggtat tcaggcaacc agcaataaag ccggttttgt gaaaattgca     420
gccgatgaac cgggtattac caaagatgtg aaaaagtta ttcgtgcagc agccattacc     480
cataaagaag ccaaagttcc gattattacc catagcaatg cccataataa taccggtctg     540
gaagaacagc gtattctgat ggaagaaggt gttgatccgg gtaaaattct gattggtcat     600
ctgggtgata ccgataatac cgattatatt aaaaaaattg ccgataaagg cagctttatt     660
ggtctggatc gttatggtct ggacctgttt ctgccggttg ataaacgtaa tgaaaccacc     720
ctgaaactga ttaaagatgg ctatagcgat cgcattatga tcagccatga ttatgcttgt     780
accattgata tgggcaccgc acgtccggaa ctgaaaccga actggcacc gcgttggagc     840
acggcactga ttttgaaga taccattccg tttctgaaaa aaaatggcgt gagcgaagaa     900
gtgatcgata tattttcaa agaaaacccg aaaaaattct ttagctaa                  948

<210> SEQ ID NO 245
<211> LENGTH: 315
<212> TYPE: PRT
<213> ORGANISM: Sulfolobus islandicus

<400> SEQUENCE: 245

Met Ala Arg Ile Pro Leu Val Gly Lys Glu Pro Ile Glu Ala Glu Asp
1               5                   10                  15

Met Gly Phe Thr Leu Ile His Glu His Leu Arg Val Phe Ser Glu Ala
            20                  25                  30

Val Arg Tyr Gln Trp Pro His Leu Tyr Asn Glu Asp Glu Glu Leu Arg

```
              35                  40                  45
Asn Ala Val Asn Glu Val Lys Arg Ala Met Gln Phe Gly Val Lys Thr
 50                  55                  60

Ile Val Asp Pro Thr Val Met Gly Leu Gly Arg Asp Ile Arg Phe Met
 65                  70                  75                  80

Glu Lys Val Val Lys Thr Thr Gly Ile Asn Leu Val Ala Gly Thr Gly
                 85                  90                  95

Ile Tyr Ile Tyr Val Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Ala Thr Ser Asn Lys Ala Gly Phe Val Lys Ile Ala Ala Asp Glu Pro
    130                 135                 140

Gly Ile Thr Lys Asp Val Glu Lys Val Ile Arg Ala Ala Ile Thr
145                 150                 155                 160

His Lys Glu Ala Lys Val Pro Ile Ile Thr His Ser Asn Ala His Asn
                165                 170                 175

Asn Thr Gly Leu Glu Glu Gln Arg Ile Leu Met Glu Glu Gly Val Asp
            180                 185                 190

Pro Gly Lys Ile Leu Ile Gly His Leu Gly Asp Thr Asp Asn Thr Asp
        195                 200                 205

Tyr Ile Lys Lys Ile Ala Asp Lys Gly Ser Phe Ile Gly Leu Asp Arg
    210                 215                 220

Tyr Gly Leu Asp Leu Phe Leu Pro Val Asp Lys Arg Asn Glu Thr Thr
225                 230                 235                 240

Leu Lys Leu Ile Lys Asp Gly Tyr Ser Asp Arg Ile Met Ile Ser His
                245                 250                 255

Asp Tyr Ala Cys Thr Ile Asp Met Gly Thr Ala Arg Pro Glu Leu Lys
            260                 265                 270

Pro Lys Leu Ala Pro Arg Trp Ser Thr Ala Leu Ile Phe Glu Asp Thr
        275                 280                 285

Ile Pro Phe Leu Lys Lys Asn Gly Val Ser Glu Glu Val Ile Asp Ile
    290                 295                 300

Ile Phe Lys Glu Asn Pro Lys Lys Phe Phe Ser
305                 310                 315

<210> SEQ ID NO 246
<211> LENGTH: 948
<212> TYPE: DNA
<213> ORGANISM: Sulfolobus islandicus

<400> SEQUENCE: 246
atggcgcgta ttccgctggt tggtaaagaa ccgattgaag ccgaagatat gggttttacc      60
ctgattcatg aacatctgcg tgcatttagc gaagcagttc gttatcagtg gcctcatctg     120
tataatgaag atgaagaact gcgtaatgcc gttaatgaag ttaaacgtgc catgcagttt     180
ggtgttaaaa ccattgttga tccgaccgtt atgggtctgg gtcgtgatac tcgctttatg     240
gaaaaagttg tgaaaaccac cggtattaat ctggttgcag gcaccggtat ttggattttt     300
gtggatctgc cgttttattt tctgaaccgc agcattgatg aaattgccga cctgtttatt     360
catgatatta agaaggtat tcaggcaacc ccgaataaag ccggttttgt gaaaattgca     420
gccgatgaac cgggtattac caagatgtg gaaaaagtta ttcgtgcagc agccattacc     480
cataaagaag ccaaagttcc gattattacc catagcaatg cccataataa taccggtctg     540
```

```
gaagaacagc gtattctgat ggaagaaggt gttgatccgg gtaaaattct gattggtcat    600
ctgggtgata ccgataatac cgattatatt aaaaaaattg ccgataaagg cagctttatt    660
ggtctggatc gttatggtgt ggacctgttt ctgccggttg ataaacgtaa tgaaaccacc    720
ctgaaactga ttaaagatgg ctatagcgat cgcattatga tcagccatga ttattgttgt    780
accattgatt ggggcaccgc acgtccggaa ctgaaaccga actggcaccg cgttggagc     840 atggcactga ttttgaaga taccattccg tttctgaaaa aaatggcgt gagcgaagaa      900 gtgatcgata ttattttcaa agaaaacccg aaaaaattct ttagctaa                 948
```

<210> SEQ ID NO 247
<211> LENGTH: 315
<212> TYPE: PRT
<213> ORGANISM: Sulfolobus islandicus

<400> SEQUENCE: 247

```
Met Ala Arg Ile Pro Leu Val Gly Lys Glu Pro Ile Glu Ala Glu Asp
1               5                   10                  15

Met Gly Phe Thr Leu Ile His Glu His Leu Arg Ala Phe Ser Glu Ala
            20                  25                  30

Val Arg Tyr Gln Trp Pro His Leu Tyr Asn Glu Asp Glu Glu Leu Arg
        35                  40                  45

Asn Ala Val Asn Glu Val Lys Arg Ala Met Gln Phe Gly Val Lys Thr
    50                  55                  60

Ile Val Asp Pro Thr Val Met Gly Leu Gly Arg Asp Thr Arg Phe Met
65                  70                  75                  80

Glu Lys Val Val Lys Thr Thr Gly Ile Asn Leu Val Ala Gly Thr Gly
                85                  90                  95

Ile Trp Ile Phe Val Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Ala Thr Pro Asn Lys Ala Gly Phe Val Lys Ile Ala Ala Asp Glu Pro
    130                 135                 140

Gly Ile Thr Lys Asp Val Glu Lys Val Ile Arg Ala Ala Ala Ile Thr
145                 150                 155                 160

His Lys Glu Ala Lys Val Pro Ile Ile Thr His Ser Asn Ala His Asn
                165                 170                 175

Asn Thr Gly Leu Glu Glu Gln Arg Ile Leu Met Glu Glu Gly Val Asp
            180                 185                 190

Pro Gly Lys Ile Leu Ile Gly His Leu Gly Asp Thr Asp Asn Thr Asp
        195                 200                 205

Tyr Ile Lys Lys Ile Ala Asp Lys Gly Ser Phe Ile Gly Leu Asp Arg
    210                 215                 220

Tyr Gly Val Asp Leu Phe Leu Pro Val Asp Lys Arg Asn Glu Thr Thr
225                 230                 235                 240

Leu Lys Leu Ile Lys Asp Gly Tyr Ser Asp Arg Ile Met Ile Ser His
                245                 250                 255

Asp Tyr Cys Cys Thr Ile Asp Trp Gly Thr Ala Arg Pro Glu Leu Lys
            260                 265                 270

Pro Lys Leu Ala Pro Arg Trp Ser Met Ala Leu Ile Phe Glu Asp Thr
        275                 280                 285

Ile Pro Phe Leu Lys Lys Asn Gly Val Ser Glu Glu Val Ile Asp Ile
    290                 295                 300
```

Ile Phe Lys Glu Asn Pro Lys Lys Phe Phe Ser
305                 310                 315

<210> SEQ ID NO 248
<211> LENGTH: 948
<212> TYPE: DNA
<213> ORGANISM: Sulfolobus islandicus

<400> SEQUENCE: 248

| | | | | | |
|---|---|---|---|---|---|
| atggcgcgta | ttccgctggt | tggtaaagaa | ccgattgaag | ccgaagatat | gggttttacc | 60 |
| ctgattcatg | aacatctgcg | tgtttttagc | gaagcagttc | gttatcagtg | gccccatctg | 120 |
| tataatgaag | atgaagaact | gcgtaatgcc | gttaatgaag | ttaaacgtgc | catgcagttt | 180 |
| ggtgttaaaa | ccattgttga | tccgaccgtt | atgggtattg | gtcgtgatat | tcgctttatg | 240 |
| gaaaaagttg | tgaaaaccac | cggtattaat | ctggttgcag | gcaccggtat | ttatattttt | 300 |
| gtggatctgc | cgtttatttt | cctgaaccgc | agcattgatg | aaattgccga | cctgtttatt | 360 |
| catgatttaa | aagaaggtat | tcaggcaacc | agcaataaag | ccggttttgt | gaaaattgca | 420 |
| gccgatgaac | cgggtattac | caaagatgtg | gaaaaagtca | ttcgtgcagc | agccattacc | 480 |
| cataaagaag | ccaaagttcc | gattattacc | atagcaatg | cccataataa | taccggtctg | 540 |
| gaagaacagc | gtattctgat | ggaagaaggt | gttgatccgg | gtaaaattct | gattggtcat | 600 |
| ctgggtgata | ccgataatac | cgattatatt | aaaaaaattg | ccgataaagg | cagctttatt | 660 |
| ggtctggatc | gttatggtct | ggacatgtct | ctgccggttg | ataaacgtaa | tgaaaccacc | 720 |
| ctgaaactga | ttaaagatgg | ctatagcgat | cgcattatga | tcagccatga | ttattgttgt | 780 |
| accattgatc | tgggcaccgc | acgtccggaa | ctgaaaccga | aactggcacc | gcgttggagc | 840 |
| atggcactga | tttttgaaga | taccattccg | tttctgaaaa | aaaatggcgt | gagcgaagaa | 900 |
| gtgatcgata | ttatttttcaa | agaaaacccg | aaaaaattct | ttagctaa | | 948 |

<210> SEQ ID NO 249
<211> LENGTH: 315
<212> TYPE: PRT
<213> ORGANISM: Sulfolobus islandicus

<400> SEQUENCE: 249

Met Ala Arg Ile Pro Leu Val Gly Lys Glu Pro Ile Glu Ala Glu Asp
1               5                   10                  15

Met Gly Phe Thr Leu Ile His Glu His Leu Arg Val Phe Ser Glu Ala
            20                  25                  30

Val Arg Tyr Gln Trp Pro His Leu Tyr Asn Glu Asp Glu Glu Leu Arg
        35                  40                  45

Asn Ala Val Asn Glu Val Lys Arg Ala Met Gln Phe Gly Val Lys Thr
    50                  55                  60

Ile Val Asp Pro Thr Val Met Gly Ile Gly Arg Asp Ile Arg Phe Met
65                  70                  75                  80

Glu Lys Val Val Lys Thr Thr Gly Ile Asn Leu Val Ala Gly Thr Gly
                85                  90                  95

Ile Tyr Ile Phe Val Asp Leu Pro Phe Tyr Phe Leu Asn Arg Ser Ile
            100                 105                 110

Asp Glu Ile Ala Asp Leu Phe Ile His Asp Leu Lys Glu Gly Ile Gln
        115                 120                 125

Ala Thr Ser Asn Lys Ala Gly Phe Val Lys Ile Ala Ala Asp Glu Pro
    130                 135                 140

Gly Ile Thr Lys Asp Val Glu Lys Val Ile Arg Ala Ala Ala Ile Thr

```
                145                 150                 155                 160
His Lys Glu Ala Lys Val Pro Ile Ile Thr His Ser Asn Ala His Asn
                    165                 170                 175

Asn Thr Gly Leu Glu Glu Gln Arg Ile Leu Met Glu Glu Gly Val Asp
                180                 185                 190

Pro Gly Lys Ile Leu Ile Gly His Leu Gly Asp Thr Asp Asn Thr Asp
            195                 200                 205

Tyr Ile Lys Lys Ile Ala Asp Lys Gly Ser Phe Ile Gly Leu Asp Arg
        210                 215                 220

Tyr Gly Leu Asp Met Ser Leu Pro Val Asp Lys Arg Asn Glu Thr Thr
225                 230                 235                 240

Leu Lys Leu Ile Lys Asp Gly Tyr Ser Asp Arg Ile Met Ile Ser His
                245                 250                 255

Asp Tyr Cys Cys Thr Ile Asp Leu Gly Thr Ala Arg Pro Glu Leu Lys
                    260                 265                 270

Pro Lys Leu Ala Pro Arg Trp Ser Met Ala Leu Ile Phe Glu Asp Thr
                275                 280                 285

Ile Pro Phe Leu Lys Lys Asn Gly Val Ser Glu Glu Val Ile Asp Ile
            290                 295                 300

Ile Phe Lys Glu Asn Pro Lys Lys Phe Phe Ser
305                 310                 315

<210> SEQ ID NO 250
<211> LENGTH: 948
<212> TYPE: DNA
<213> ORGANISM: Sulfolobus islandicus

<400> SEQUENCE: 250
atggcgcgta ttccgctggt tggtaaagaa ccgattgaag ccgaagatat gggttttacc      60
ctgattcatg aacatctgcg tgttttagc gaagcagttc gttatcagtg gccccatctg     120
tataatgaag atgaagaact gcgtaatgcc gttaatgaag ttaaacgtgc catgcagttt     180
ggtgttaaaa ccattgttga tccgagtgtt atgggtattg gtcgtgatat cgctttatg     240
gaaaaagttg tgaaaaccac cggtattaat ctggttgcag caccggtat ttatatttat     300
gtggatctgc gtttttattt tctgaaccgc agcattgatg aaattgccga cctgttattt     360
catgatatta agaaggtat tcaggcaacc ccgaataaag ccggtttttgt gaaaattgca     420
gccgatgaac cgggtattac caaagatgtg gaaaaagtta ttcgtgcagc agccattacc     480
cataaagaag ccaaagttcc gattattacc catagcaatg cccataataa taccggtctg     540
gaagaacagc gtattctgat ggaagaaggt gttgatccgg gtaaaattct gattggtcat     600
ctgggtgata ccgataatac cgattatatt aaaaaaattg ccgataaagg cagctttatt     660
ggtctggatc gttatggtct ggacatgtct ctgccggttg ataaacgtaa tgaaaccacc     720
ctgaaactga ttaaagatgg ctatagcgat cgcattatga tcagccatga ttattgttgt     780
accattgata tgggcaccgc acgtccggaa ctgaaaccga accggcaccc gcgttggagc     840
atggcactga ttttgaaga taccattccg tttctgaaaa aaatggcgt gagcgaagaa     900
gtgatcgata ttatttttcaa agaaaacccg aaaaaattct ttagctaa               948

<210> SEQ ID NO 251
<211> LENGTH: 315
<212> TYPE: PRT
<213> ORGANISM: Sulfolobus islandicus

<400> SEQUENCE: 251
```

```
Met Ala Arg Ile Pro Leu Val Gly Lys Glu Pro Ile Glu Ala Glu Asp
1               5                   10                  15

Met Gly Phe Thr Leu Ile His Glu His Leu Arg Val Phe Ser Glu Ala
            20                  25                  30

Val Arg Tyr Gln Trp Pro His Leu Tyr Asn Glu Asp Glu Glu Leu Arg
        35                  40                  45

Asn Ala Val Asn Glu Val Lys Arg Ala Met Gln Phe Gly Val Lys Thr
    50                  55                  60

Ile Val Asp Pro Ser Val Met Gly Ile Gly Arg Asp Ile Arg Phe Met
65              70                  75                  80

Glu Lys Val Val Lys Thr Thr Gly Ile Asn Leu Val Ala Gly Thr Gly
            85                  90                  95

Ile Tyr Ile Tyr Val Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
            115                 120                 125

Ala Thr Pro Asn Lys Ala Gly Phe Val Lys Ile Ala Ala Asp Glu Pro
    130                 135                 140

Gly Ile Thr Lys Asp Val Glu Lys Val Ile Arg Ala Ala Ala Ile Thr
145                 150                 155                 160

His Lys Glu Ala Lys Val Pro Ile Ile Thr His Ser Asn Ala His Asn
                165                 170                 175

Asn Thr Gly Leu Glu Glu Gln Arg Ile Leu Met Glu Glu Gly Val Asp
            180                 185                 190

Pro Gly Lys Ile Leu Ile Gly His Leu Gly Asp Thr Asp Asn Thr Asp
        195                 200                 205

Tyr Ile Lys Lys Ile Ala Asp Lys Gly Ser Phe Ile Gly Leu Asp Arg
210                 215                 220

Tyr Gly Leu Asp Met Ser Leu Pro Val Asp Lys Arg Asn Glu Thr Thr
225                 230                 235                 240

Leu Lys Leu Ile Lys Asp Gly Tyr Ser Asp Arg Ile Met Ile Ser His
                245                 250                 255

Asp Tyr Cys Cys Thr Ile Asp Met Gly Thr Ala Arg Pro Glu Leu Lys
            260                 265                 270

Pro Lys Pro Ala Pro Arg Trp Ser Met Ala Leu Ile Phe Glu Asp Thr
        275                 280                 285

Ile Pro Phe Leu Lys Lys Asn Gly Val Ser Glu Val Ile Asp Ile
    290                 295                 300

Ile Phe Lys Glu Asn Pro Lys Lys Phe Phe Ser
305                 310                 315
```

<210> SEQ ID NO 252
<211> LENGTH: 948
<212> TYPE: DNA
<213> ORGANISM: Sulfolobus islandicus

<400> SEQUENCE: 252

```
atggcgcgta ttccgctggt tggtaaagaa ccgattgaag ccgaagatat gggttttacc      60
ctgattcatg aacatctgcg tgtttttagc gaagcagttc gttatcagtg gcctcatctg     120
tataatgaag atgaagaact gcgtaatgcc gttaatgaag ttaaacgtgc catgcagttt     180
ggtgttaaaa ccattgttga tccgagtgtt atgggtctgg tcgtgatac tcgctttatg     240 gaaaaagttg tgaaaccac cggtattaat ctggttgcag gcaccggtat ttggattttt     300
```

-continued

```
gtggatctgc cgttttattt tctgaaccgc agcattgatg aaattgccga cctgttatt    360 catgatatta agaaggtat tcaggcaacc agcaataaag ccggttttgt gaaaattgca    420
gccgatgaac cgggtattac caaagatgtg gaaaaagtta ttcgtgcagc agccattacc    480
cataaagaag ccaaagttcc gattattacc catagcaatg cccataataa taccggtctg    540
gaagaacagc gtattctgat ggaagaaggt gttgatccgg gtaaaattct gattggtcat    600
ctgggtgata ccgataatac cgattatatt aaaaaaattg ccgataaagg cagctttatt    660
ggtctggatc gttatggtct ggacatgttt ctgccggttg ataaacgtaa tgaaaccacc    720
ctgaaactga ttaaagatgg ctatagcgat cgcattatga tcagccatga ttattgttgt    780
accattgatc tgggcaccgc acgtccggaa ctgaaaccga actggcacc gcgttggagc     840 atggcactga tttttgaaga taccattccg tttctgaaaa aaaatggcgt gagcgaagaa    900
gtgatcgata ttatttcaa agaaaacccg aaaaaattct ttagctaa                 948
```

<210> SEQ ID NO 253
<211> LENGTH: 315
<212> TYPE: PRT
<213> ORGANISM: Sulfolobus islandicus

<400> SEQUENCE: 253

```
Met Ala Arg Ile Pro Leu Val Gly Lys Glu Pro Ile Glu Ala Glu Asp
1               5                   10                  15

Met Gly Phe Thr Leu Ile His Glu His Leu Arg Val Phe Ser Glu Ala
                20                  25                  30

Val Arg Tyr Gln Trp Pro His Leu Tyr Asn Glu Asp Glu Glu Leu Arg
            35                  40                  45

Asn Ala Val Asn Glu Val Lys Arg Ala Met Gln Phe Gly Val Lys Thr
        50                  55                  60

Ile Val Asp Pro Ser Val Met Gly Leu Gly Arg Asp Thr Arg Phe Met
65                  70                  75                  80

Glu Lys Val Val Lys Thr Thr Gly Ile Asn Leu Val Ala Gly Thr Gly
                85                  90                  95

Ile Trp Ile Phe Val Asp Leu Pro Phe Tyr Phe Leu Asn Arg Ser Ile
                100                 105                 110

Asp Glu Ile Ala Asp Leu Phe Ile His Asp Ile Lys Glu Gly Ile Gln
            115                 120                 125

Ala Thr Ser Asn Lys Ala Gly Phe Val Lys Ile Ala Ala Asp Glu Pro
        130                 135                 140

Gly Ile Thr Lys Asp Val Glu Lys Val Ile Arg Ala Ala Ala Ile Thr
145                 150                 155                 160

His Lys Glu Ala Lys Val Pro Ile Ile Thr His Ser Asn Ala His Asn
                165                 170                 175

Asn Thr Gly Leu Glu Glu Gln Arg Ile Leu Met Glu Glu Gly Val Asp
            180                 185                 190

Pro Gly Lys Ile Leu Ile Gly His Leu Gly Asp Thr Asp Asn Thr Asp
        195                 200                 205

Tyr Ile Lys Lys Ile Ala Asp Lys Gly Ser Phe Ile Gly Leu Asp Arg
    210                 215                 220

Tyr Gly Leu Asp Met Phe Leu Pro Val Asp Lys Arg Asn Glu Thr Thr
225                 230                 235                 240

Leu Lys Leu Ile Lys Asp Gly Tyr Ser Asp Arg Ile Met Ile Ser His
                245                 250                 255

Asp Tyr Cys Cys Thr Ile Asp Leu Gly Thr Ala Arg Pro Glu Leu Lys
```

Pro Lys Leu Ala Pro Arg Trp Ser Met Ala Leu Ile Phe Glu Asp Thr
              275                 280                 285

Ile Pro Phe Leu Lys Lys Asn Gly Val Ser Glu Val Ile Asp Ile
          290                 295                 300

Ile Phe Lys Glu Asn Pro Lys Lys Phe Phe Ser
305                 310                 315

<210> SEQ ID NO 254
<211> LENGTH: 948
<212> TYPE: DNA
<213> ORGANISM: Sulfolobus islandicus

<400> SEQUENCE: 254

```
atggcgcgta ttccgctggt tggtgaagaa ccgattgaag ccgaagatat gggttttacc      60
ctgattcatg aacatctgcg tgttttagc gaagcagttc gttatcagtg gcctcatctg     120
tataatgaag atgaagaact gcgtaatgcc gttaatgaag ttaaacgtgc catgcagttt     180
ggtgttaaaa ccattgttga tccgaccgtt atgggtctgg gtcgtgatat cgctttatg     240
gaaaaagttg tgaaaccac cggtattaat ctggttgcag caccggtat ttggattttt     300
gtggatctgc cgttttattt tctgaaccgc agcattgatg aaattgccga cctgtttatt     360
catgatatta agaaggtat tcaggcaacc agcaataaag ccggttttgt gaaaattgca     420
gccgatgaac cgggtattac caaagatgtg gaaaaagtta ttcgtgcagc agccattacc     480
cataaagaag ccaaagttcc gattattacc atagcaatg cccataataa taccggtctg     540
gaagaacagc gtattctgat ggaagaaggt gttgatccgg gtaaaattct gattggtcat     600
ctgggtgata ccgataatac cgattatatt aaaaaaattg ccgataaagg cagctttatt     660
ggtctggatc gttatggtct ggacatgttt ctgccggttg ataaacgtaa tgaaaccacc     720
ctgaaactga ttaaagatgg ctatagcgat cgcattatga tcagccatga ttattgttgt     780
accattgatt ggggcaccgc acgtccggaa ctgaaaccga actggcaccg cgttggagc     840
atggcactga tttttgaaga taccattccg tttctgaaaa aaatggcgt gagcgaagaa     900
gtgatcgata ttattttcaa agaaaacccg aaaaaattct ttagctaa                 948
```

<210> SEQ ID NO 255
<211> LENGTH: 315
<212> TYPE: PRT
<213> ORGANISM: Sulfolobus islandicus

<400> SEQUENCE: 255

Met Ala Arg Ile Pro Leu Val Gly Glu Glu Pro Ile Glu Ala Glu Asp
1               5                   10                  15

Met Gly Phe Thr Leu Ile His Glu His Leu Arg Val Phe Ser Glu Ala
              20                  25                  30

Val Arg Tyr Gln Trp Pro His Leu Tyr Asn Glu Asp Glu Glu Leu Arg
          35                  40                  45

Asn Ala Val Asn Glu Val Lys Arg Ala Met Gln Phe Gly Val Lys Thr
      50                  55                  60

Ile Val Asp Pro Thr Val Met Gly Leu Gly Arg Asp Ile Arg Phe Met
65                  70                  75                  80

Glu Lys Val Val Lys Thr Thr Gly Ile Asn Leu Val Ala Gly Thr Gly
              85                  90                  95

Ile Trp Ile Phe Val Asp Leu Pro Phe Tyr Phe Leu Asn Arg Ser Ile
              100                 105                 110

```
Asp Glu Ile Ala Asp Leu Phe Ile His Asp Ile Lys Glu Gly Ile Gln
            115                 120                 125

Ala Thr Ser Asn Lys Ala Gly Phe Val Lys Ile Ala Ala Asp Glu Pro
        130                 135                 140

Gly Ile Thr Lys Asp Val Glu Lys Val Ile Arg Ala Ala Ile Thr
145                 150                 155                 160

His Lys Glu Ala Lys Val Pro Ile Ile Thr His Ser Asn Ala His Asn
                165                 170                 175

Asn Thr Gly Leu Glu Glu Gln Arg Ile Leu Met Glu Glu Gly Val Asp
            180                 185                 190

Pro Gly Lys Ile Leu Ile Gly His Leu Gly Asp Thr Asp Asn Thr Asp
        195                 200                 205

Tyr Ile Lys Lys Ile Ala Asp Lys Gly Ser Phe Ile Gly Leu Asp Arg
    210                 215                 220

Tyr Gly Leu Asp Met Phe Leu Pro Val Asp Lys Arg Asn Glu Thr Thr
225                 230                 235                 240

Leu Lys Leu Ile Lys Asp Gly Tyr Ser Asp Arg Ile Met Ile Ser His
                245                 250                 255

Asp Tyr Cys Cys Thr Ile Asp Trp Gly Thr Ala Arg Pro Glu Leu Lys
            260                 265                 270

Pro Lys Leu Ala Pro Arg Trp Ser Met Ala Leu Ile Phe Glu Asp Thr
        275                 280                 285

Ile Pro Phe Leu Lys Lys Asn Gly Val Ser Glu Val Ile Asp Ile
    290                 295                 300

Ile Phe Lys Glu Asn Pro Lys Lys Phe Phe Ser
305                 310                 315

<210> SEQ ID NO 256
<211> LENGTH: 948
<212> TYPE: DNA
<213> ORGANISM: Sulfolobus islandicus

<400> SEQUENCE: 256
atggcgcgta ttccgctggt tggtaaagaa ccgattgaag ccgaagatat gggttttacc      60
ctgattcatg aacatctgcg tgttttagc gaagcagttc gttatcagtg gcctcatctg     120
tataatgaag atgaagaact gcgtaatgcc gttaatgaag ttaaacgtgc catgcagttt     180
ggtgttaaaa ccattgttga tccgaccgtt atgggtattg gtcgtgatat cgctttatg     240
gaaaaagttg tgaaaccac cggtattaat ctggttgcag caccggtat ttatatttat     300
gtggatctgc cgttttattt tctgaaccgc agcattgatg aaattgccga cctgtttatt     360
catgatatta agaaggtat tcaggcaacc agcaataaag ccggttttgt gaaaattgca     420
gccgatgaac cgggtattac caaagatgtg gaaaaagtta ttcgtgcagc agccattacc     480
cataaagaag ccaaagttcc gattattacc catagcaatg cccataataa taccggtctg     540
gaagaacagc gtattctgat ggaagaaggt gttgatccgg gtaaaattct gattggtcat     600
ctgggtgata ccgataatac cgattatatt aaaaaaattg ccgataaagg cagctttatt     660
ggtctggatc gttatggtct ggacctgttt ctgccggttg ataaacgtaa tgaaaccacc     720
ctgaaactga ttaaagatgg ctatagcgat cgcattatga tcagccatga ttattgttgt     780
accattgatt ttggcaccgc acgtccggaa ctgaaaccga aactggcacc gcgttggagc     840
atggcactga ttttgaaga taccattccg tttctgaaaa aaaatggcgt gagcgaagaa     900
gtgatcgata ttattttcaa agaaaacccg aaaaaattct ttagctaa                  948
```

<210> SEQ ID NO 257
<211> LENGTH: 315
<212> TYPE: PRT
<213> ORGANISM: Sulfolobus islandicus

<400> SEQUENCE: 257

| Met | Ala | Arg | Ile | Pro | Leu | Val | Gly | Lys | Glu | Pro | Ile | Glu | Ala | Glu | Asp |
|---|---|---|---|---|---|---|---|---|---|---|---|---|---|---|---|
| 1 | | | | 5 | | | | | 10 | | | | | 15 | |

Met Gly Phe Thr Leu Ile His Glu His Leu Arg Val Phe Ser Glu Ala
            20                  25                  30

Val Arg Tyr Gln Trp Pro His Leu Tyr Asn Glu Asp Glu Glu Leu Arg
        35                  40                  45

Asn Ala Val Asn Glu Val Lys Arg Ala Met Gln Phe Gly Val Lys Thr
    50                  55                  60

Ile Val Asp Pro Thr Val Met Gly Ile Gly Arg Asp Ile Arg Phe Met
65                  70                  75                  80

Glu Lys Val Val Lys Thr Thr Gly Ile Asn Leu Val Ala Gly Thr Gly
                85                  90                  95

Ile Tyr Ile Tyr Val Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Ala Thr Ser Asn Lys Ala Gly Phe Val Lys Ile Ala Ala Asp Glu Pro
    130                 135                 140

Gly Ile Thr Lys Asp Val Glu Lys Val Ile Arg Ala Ala Ala Ile Thr
145                 150                 155                 160

His Lys Glu Ala Lys Val Pro Ile Ile Thr His Ser Asn Ala His Asn
                165                 170                 175

Asn Thr Gly Leu Glu Glu Gln Arg Ile Leu Met Glu Glu Gly Val Asp
            180                 185                 190

Pro Gly Lys Ile Leu Ile Gly His Leu Gly Asp Thr Asp Asn Thr Asp
        195                 200                 205

Tyr Ile Lys Lys Ile Ala Asp Lys Gly Ser Phe Ile Gly Leu Asp Arg
    210                 215                 220

Tyr Gly Leu Asp Leu Phe Leu Pro Val Asp Lys Arg Asn Glu Thr Thr
225                 230                 235                 240

Leu Lys Leu Ile Lys Asp Gly Tyr Ser Asp Arg Ile Met Ile Ser His
                245                 250                 255

Asp Tyr Cys Cys Thr Ile Asp Phe Gly Thr Ala Arg Pro Glu Leu Lys
            260                 265                 270

Pro Lys Leu Ala Pro Arg Trp Ser Met Ala Leu Ile Phe Glu Asp Thr
        275                 280                 285

Ile Pro Phe Leu Lys Lys Asn Gly Val Ser Glu Glu Val Ile Asp Ile
    290                 295                 300

Ile Phe Lys Glu Asn Pro Lys Lys Phe Phe Ser
305                 310                 315

<210> SEQ ID NO 258
<211> LENGTH: 948
<212> TYPE: DNA
<213> ORGANISM: Sulfolobus islandicus

<400> SEQUENCE: 258
atggcgcgta ttccgctggt tggtaaagaa ccgattgaag ccgaagatat gggttttacc      60

-continued

```
ctgattcatg aacatctgcg tgttttagc gaagcagttc gttatcagtg gcctcatctg    120
tataatgaag atgaagaact gcgtaatgcc gttaatgaag ttaaacgtgc catgcagttt    180
ggtgttaaaa ccattgttga tccgagtgtt atgggtctgg gtcgtgatat cgctttatg     240 gaaaaagttg tgaaaccac cggtattaat ctggttgcag gcaccggtat ttggattttt     300
gtggatctgc cgttttattt tctgaaccgc agcattgatg aaattgccga cctgtttatt    360
catgatatta agaaggtat tcaggcaacc ccgaataaag ccggttttgt gaaaattgca     420
gccgatgaac cgggtattac caaagatgtg gaaaaagtta ttcgtgcagc agccattacc    480
cataaagaag ccaaagttcc gattattacc catagcaatg cccataataa taccggtctg    540
gaagaacagc gtattctgat ggaagaaggt gttgatccgg gtaaaattct gattggtcat    600
ctgggtgata ccgataatac cgattatatt aaaaaaattg ccgataaagg cagctttatt    660
ggtctggatc gttatggtct ggacatgttt ctgccggttg ataaacgtaa tgaaaccacc    720
ctgaaactga ttaaagatgg ctatagcgat cgcattatga tcagccatga ttattgttgt    780
accattgatt ggggcaccgc acgtccggaa ctgaaaccga actggcaccg cgttggagc     840 atggcactga tttttgaaga taccattccg tttctgaaaa aaaatggcgt gagcgaagaa    900
gtgatcgata ttatttttcaa agaaaacccg aaaaaattct ttagctaa                948
```

<210> SEQ ID NO 259
<211> LENGTH: 315
<212> TYPE: PRT
<213> ORGANISM: Sulfolobus islandicus

<400> SEQUENCE: 259

```
Met Ala Arg Ile Pro Leu Val Gly Lys Glu Pro Ile Glu Ala Glu Asp
1               5                  10                  15

Met Gly Phe Thr Leu Ile His Glu His Leu Arg Val Phe Ser Glu Ala
            20                  25                  30

Val Arg Tyr Gln Trp Pro His Leu Tyr Asn Glu Asp Glu Glu Leu Arg
        35                  40                  45

Asn Ala Val Asn Glu Val Lys Arg Ala Met Gln Phe Gly Val Lys Thr
    50                  55                  60

Ile Val Asp Pro Ser Val Met Gly Leu Gly Arg Asp Ile Arg Phe Met
65                  70                  75                  80

Glu Lys Val Val Lys Thr Thr Gly Ile Asn Leu Val Ala Gly Thr Gly
                85                  90                  95

Ile Trp Ile Phe Val Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Ala Thr Pro Asn Lys Ala Gly Phe Val Lys Ile Ala Asp Glu Pro
    130                 135                 140

Gly Ile Thr Lys Asp Val Glu Lys Val Ile Arg Ala Ala Ala Ile Thr
145                 150                 155                 160

His Lys Glu Ala Lys Val Pro Ile Ile Thr His Ser Asn Ala His Asn
                165                 170                 175

Asn Thr Gly Leu Glu Glu Gln Arg Ile Leu Met Glu Glu Gly Val Asp
            180                 185                 190

Pro Gly Lys Ile Leu Ile Gly His Leu Gly Asp Thr Asp Asn Thr Asp
        195                 200                 205

Tyr Ile Lys Lys Ile Ala Asp Lys Gly Ser Phe Ile Gly Leu Asp Arg
    210                 215                 220
```

```
Tyr Gly Leu Asp Met Phe Leu Pro Val Asp Lys Arg Asn Glu Thr Thr
225                 230                 235                 240

Leu Lys Leu Ile Lys Asp Gly Tyr Ser Asp Arg Ile Met Ile Ser His
            245                 250                 255

Asp Tyr Cys Cys Thr Ile Asp Trp Gly Thr Ala Arg Pro Glu Leu Lys
            260                 265                 270

Pro Lys Leu Ala Pro Arg Trp Ser Met Ala Leu Ile Phe Glu Asp Thr
            275                 280                 285

Ile Pro Phe Leu Lys Lys Asn Gly Val Ser Glu Val Ile Asp Ile
            290                 295                 300

Ile Phe Lys Glu Asn Pro Lys Lys Phe Phe Ser
305                 310                 315

<210> SEQ ID NO 260
<211> LENGTH: 948
<212> TYPE: DNA
<213> ORGANISM: Sulfolobus islandicus

<400> SEQUENCE: 260
atggcgcgta ttccgctggt tggtaaagaa ccgattgaag ccgaagatat gggttttacc        60
ctgattcatg aacatctgcg tgcatttagc gaagcagttc gttatcagtg gcctcatctg       120
tataatgaag atgaagaact gcgtaatgcc gttaatgaag ttaaacgtgc catgcagttt       180
ggtgttaaaa ccattgttga tccgaccgtt atgggtctgg tcgtgatat cgctttatg       240 gaaaaagttg tgaaaccac cggtattaat ctggttgcag caccggtat ttatatttat       300 gtggatctgc cgttttattt tctgaaccgc agcattgatg aaattgccga cctgtttatt       360
catgatatta agaaggtat tcaggcaacc agcaataaag ccggttttgt gaaaattgca       420
gccgatgaac cgggtattac caaagatgtg gaaaaagtta ttcgtgcagc agccattacc       480
cataaagaag ccaaagttcc gattattacc catagcaatg cccataataa taccggtctg       540
gaagaacagc gtattctgat ggaagaaggt gttgatccgg gtaaaattct gattggtcat       600
ctgggtgata ccgataatac cgattatatt aaaaaaattg ccgataaagg cagctttatt       660
ggtctggatc gttatggtgt ggacctgttt ctgccggttg ataaacgtaa tgaaaccacc       720
ctgaaactga ttaaagatgg ctatagcgat cgcattatga tcagccatga ttattgttgt       780
accattgatc tgggcaccgc acgtccggaa ctgaaaccga actggcaccgc cgttggagc       840 atggcactaa ttttgaaga taccattccg tttctgaaaa aaaatggcgt gagcgaagaa       900
gtgatcgata ttattttcaa agaaaacccg aaaaaattct ttagctaa                    948

<210> SEQ ID NO 261
<211> LENGTH: 315
<212> TYPE: PRT
<213> ORGANISM: Sulfolobus islandicus

<400> SEQUENCE: 261

Met Ala Arg Ile Pro Leu Val Gly Lys Glu Pro Ile Glu Ala Glu Asp
1               5                   10                  15

Met Gly Phe Thr Leu Ile His Glu His Leu Arg Ala Phe Ser Glu Ala
            20                  25                  30

Val Arg Tyr Gln Trp Pro His Leu Tyr Asn Glu Asp Glu Glu Leu Arg
        35                  40                  45

Asn Ala Val Asn Glu Val Lys Arg Ala Met Gln Phe Gly Val Lys Thr
    50                  55                  60
```

```
Ile Val Asp Pro Thr Val Met Gly Leu Gly Arg Asp Ile Arg Phe Met
65                  70                  75                  80

Glu Lys Val Val Lys Thr Thr Gly Ile Asn Leu Val Ala Gly Thr Gly
                85                  90                  95

Ile Tyr Ile Tyr Val Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Ala Thr Ser Asn Lys Ala Gly Phe Val Lys Ile Ala Ala Asp Glu Pro
    130                 135                 140

Gly Ile Thr Lys Asp Val Glu Lys Val Ile Arg Ala Ala Ala Ile Thr
145                 150                 155                 160

His Lys Glu Ala Lys Val Pro Ile Ile Thr His Ser Asn Ala His Asn
                165                 170                 175

Asn Thr Gly Leu Glu Glu Gln Arg Ile Leu Met Glu Glu Gly Val Asp
            180                 185                 190

Pro Gly Lys Ile Leu Ile Gly His Leu Gly Asp Thr Asp Asn Thr Asp
        195                 200                 205

Tyr Ile Lys Lys Ile Ala Asp Lys Gly Ser Phe Ile Gly Leu Asp Arg
    210                 215                 220

Tyr Gly Val Asp Leu Phe Leu Pro Val Asp Lys Arg Asn Glu Thr Thr
225                 230                 235                 240

Leu Lys Leu Ile Lys Asp Gly Tyr Ser Asp Arg Ile Met Ile Ser His
                245                 250                 255

Asp Tyr Cys Cys Thr Ile Asp Leu Gly Thr Ala Arg Pro Glu Leu Lys
            260                 265                 270

Pro Lys Leu Ala Pro Arg Trp Ser Met Ala Leu Ile Phe Glu Asp Thr
        275                 280                 285

Ile Pro Phe Leu Lys Lys Asn Gly Val Ser Glu Glu Val Ile Asp Ile
    290                 295                 300

Ile Phe Lys Glu Asn Pro Lys Lys Phe Phe Ser
305                 310                 315

<210> SEQ ID NO 262
<211> LENGTH: 948
<212> TYPE: DNA
<213> ORGANISM: Sulfolobus islandicus

<400> SEQUENCE: 262
atggcgcgta ttccgctggt tggtaaagaa ccgattgaag ccgaagatat gggttttacc      60
ctgattcatg aacatctgcg tgttttagc gaagcagttc gttatcagtg gcctcatctg     120
tataatgaag atgaagaact gcgtaatgcc gttaatgaag ttaaacgtgc catgcagttt     180
ggtgttaaaa ccattgttga tgtgagtgtt atgggtctgg tcgtgatat cgctttatg      240 gaaaaagttg tgaaaccac cggtattaat ctggttgcag gcaccggtat ttggattttt     300
gtggatctgc cgttttattt tctgaaccgc agcattgatg aaattgccga cctgtttatt     360
catgatatta agaaggtat tcaggcaacc agcaataaag ccggttttgt gaaaattgca     420
gccgatgaac cgggtattac caaagatgtg gagaaagtta ttcgtgcagc agccattacc     480
cataaagaag ccaaagttcc gattattacc catagcaatg cccataataa taccggtctg     540
gaagaacagc gtattctgat ggaagaaggt gttgatccgg gtaaaattct gattggtcat     600
ctgggtgata ccgataatac cgattatatt aaaaaaattg ccgataaagg cagctttatt     660
ggtctggatc gttatggtct ggacatgttt ctgccggttg ataaacgtaa tgaaaccacc     720
```

```
ctgaaactga ttaaagatgg ctatagcgat cgcattatga tcagccatga ttatgcttgt    780
accattgatc tgggcaccgc acgtccggaa ctgaaaccga actggcacc gcgttggagc     840 acggcactga tttttgaaga taccattccg tttctgaaaa aaatggcgt gagcgaagaa     900 gtgatcgata ttattttcaa agaaaacccg aaaaaattct ttagctaa                 948
```

<210> SEQ ID NO 263
<211> LENGTH: 315
<212> TYPE: PRT
<213> ORGANISM: Sulfolobus islandicus

<400> SEQUENCE: 263

```
Met Ala Arg Ile Pro Leu Val Gly Lys Glu Pro Ile Glu Ala Glu Asp
 1               5                  10                  15

Met Gly Phe Thr Leu Ile His Glu His Leu Arg Val Phe Ser Glu Ala
            20                  25                  30

Val Arg Tyr Gln Trp Pro His Leu Tyr Asn Glu Asp Glu Glu Leu Arg
        35                  40                  45

Asn Ala Val Asn Glu Val Lys Arg Ala Met Gln Phe Gly Val Lys Thr
    50                  55                  60

Ile Val Asp Val Ser Val Met Gly Leu Gly Arg Asp Ile Arg Phe Met
65                  70                  75                  80

Glu Lys Val Val Lys Thr Thr Gly Ile Asn Leu Val Ala Gly Thr Gly
                85                  90                  95

Ile Trp Ile Phe Val Asp Leu Pro Phe Tyr Phe Leu Asn Arg Ser Ile
           100                 105                 110

Asp Glu Ile Ala Asp Leu Phe Ile His Asp Ile Lys Glu Gly Ile Gln
       115                 120                 125

Ala Thr Ser Asn Lys Ala Gly Phe Val Lys Ile Ala Ala Asp Glu Pro
   130                 135                 140

Gly Ile Thr Lys Asp Val Glu Lys Val Ile Arg Ala Ala Ala Ile Thr
145                 150                 155                 160

His Lys Glu Ala Lys Val Pro Ile Ile Thr His Ser Asn Ala His Asn
                165                 170                 175

Asn Thr Gly Leu Glu Glu Gln Arg Ile Leu Met Glu Glu Gly Val Asp
           180                 185                 190

Pro Gly Lys Ile Leu Ile Gly His Leu Gly Asp Thr Asp Asn Thr Asp
       195                 200                 205

Tyr Ile Lys Lys Ile Ala Asp Lys Gly Ser Phe Ile Gly Leu Asp Arg
   210                 215                 220

Tyr Gly Leu Asp Met Phe Leu Pro Val Asp Lys Arg Asn Glu Thr Thr
225                 230                 235                 240

Leu Lys Leu Ile Lys Asp Gly Tyr Ser Asp Arg Ile Met Ile Ser His
                245                 250                 255

Asp Tyr Ala Cys Thr Ile Asp Leu Gly Thr Ala Arg Pro Glu Leu Lys
           260                 265                 270

Pro Lys Leu Ala Pro Arg Trp Ser Thr Ala Leu Ile Phe Glu Asp Thr
       275                 280                 285

Ile Pro Phe Leu Lys Lys Asn Gly Val Ser Glu Glu Val Ile Asp Ile
   290                 295                 300

Ile Phe Lys Glu Asn Pro Lys Lys Phe Phe Ser
305                 310                 315
```

<210> SEQ ID NO 264

<211> LENGTH: 948
<212> TYPE: DNA
<213> ORGANISM: Sulfolobus islandicus

<400> SEQUENCE: 264

```
atggcgcgta ttccgctggt tggtaaagaa ccgattgaag ccgaagatat gggttttacc      60
ctgattcatg aacatctgcg tgtttttagc gaagcagttc gttatcagtg gcctcatctg     120
tataatgaag atgaagaact gcgtaatgcc gttaatgaag ttaaacgtgc catgcagttt     180
ggtgttaaaa ccattgttga tccgagtgtt atgggtctgg gtcgtgatat tcgctttatg     240
gaaaaagttg tgaaaccac cggtattaat ctggttgcag gcaccggtat ttggattttt     300
gtggatctgc cgttttattt tctgaaccgc agcattgatg aaattgccga cctgtttatt     360
catgatatta agaaggtat tcaggcaacc ccgaataaag ccggttttgt gaaaattgca     420
gctgatgaac cgggtattac caaagatgtg gaaaaagtta ttcgtgcagc agccattacc     480
cataaagaag ccaatgttcc gattattacc catagcaatg cccataataa taccggtctg     540
gaagaacagc gtattctgat ggaagaaggt gttgatccgg gtaaaattct gattggtcat     600
ctgggtgata ccgataatac cgattatatt aaaaaaattg ccgataaagg cagctttatt     660
ggtctggatc gttatggtgt ggacctgttt ctgccggttg ataaacgtaa tgaaaccacc     720
ctgaaactga ttaaagatgg ctatagcgat cgcattatga tcagccatga ttattgttgt     780
accattgata tgggcaccgc acgtccggaa ctgaaaccga actggcaccg cgttggagc      840
atggcactga ttttgaaga taccattccg tttctgaaaa aaaatggcgt gagcgaagaa     900
gtgatcgata tattttcaa agaaaaccg aaaaaattct ttagctaa                   948
```

<210> SEQ ID NO 265
<211> LENGTH: 315
<212> TYPE: PRT
<213> ORGANISM: Sulfolobus islandicus

<400> SEQUENCE: 265

```
Met Ala Arg Ile Pro Leu Val Gly Lys Glu Pro Ile Glu Ala Glu Asp
 1               5                  10                  15
Met Gly Phe Thr Leu Ile His Glu His Leu Arg Val Phe Ser Glu Ala
                20                  25                  30
Val Arg Tyr Gln Trp Pro His Leu Tyr Asn Glu Asp Glu Glu Leu Arg
            35                  40                  45
Asn Ala Val Asn Glu Val Lys Arg Ala Met Gln Phe Gly Val Lys Thr
        50                  55                  60
Ile Val Asp Pro Ser Val Met Gly Leu Gly Arg Asp Ile Arg Phe Met
65                  70                  75                  80
Glu Lys Val Val Lys Thr Thr Gly Ile Asn Leu Val Ala Gly Thr Gly
                85                  90                  95
Ile Trp Ile Phe Val Asp Leu Pro Phe Tyr Phe Leu Asn Arg Ser Ile
            100                 105                 110
Asp Glu Ile Ala Asp Leu Phe Ile His Asp Ile Lys Glu Gly Ile Gln
        115                 120                 125
Ala Thr Pro Asn Lys Ala Gly Phe Val Lys Ile Ala Ala Asp Glu Pro
    130                 135                 140
Gly Ile Thr Lys Asp Val Glu Lys Val Ile Arg Ala Ala Ile Thr
145                 150                 155                 160
His Lys Glu Ala Asn Val Pro Ile Ile Thr His Ser Asn Ala His Asn
                165                 170                 175
```

```
Asn Thr Gly Leu Glu Gln Arg Ile Leu Met Glu Glu Gly Val Asp
            180                 185                 190
Pro Gly Lys Ile Leu Ile Gly His Leu Gly Asp Thr Asp Asn Thr Asp
        195                 200                 205
Tyr Ile Lys Lys Ile Ala Asp Lys Gly Ser Phe Ile Gly Leu Asp Arg
    210                 215                 220
Tyr Gly Val Asp Leu Phe Leu Pro Val Asp Lys Arg Asn Glu Thr Thr
225                 230                 235                 240
Leu Lys Leu Ile Lys Asp Gly Tyr Ser Asp Arg Ile Met Ile Ser His
                245                 250                 255
Asp Tyr Cys Cys Thr Ile Asp Met Gly Thr Ala Arg Pro Glu Leu Lys
            260                 265                 270
Pro Lys Leu Ala Pro Arg Trp Ser Met Ala Leu Ile Phe Glu Asp Thr
        275                 280                 285
Ile Pro Phe Leu Lys Lys Asn Gly Val Ser Glu Glu Val Ile Asp Ile
    290                 295                 300
Ile Phe Lys Glu Asn Pro Lys Lys Phe Phe Ser
305                 310                 315

<210> SEQ ID NO 266
<211> LENGTH: 948
<212> TYPE: DNA
<213> ORGANISM: Sulfolobus islandicus

<400> SEQUENCE: 266
atggcgcgta ttccgctggt tggtaaagaa ccgattgaag ccgaagatat gggttttacc      60
ctgattcatg aacatctgcg tgttttagc gaagcagttc gttatcagtg gccccatctg     120
tataatgaag atgaagaact gcgtaatgcc gttaatgaag ttaaacgtgc catgcagttt     180
ggtgttaaaa ccattgttga tccgagtgtt atgggtattg gtcgtgatat cgctttatg     240
gaaaaagttg tgaaaaccac cggtattaat ctggttgcag caccggtat ttggattttt     300
gtggatctgc cgttttattt tctgaaccgc agcattgatg aaattgccga cctgtttatt     360
catgatatta agaaggtat tcaggcaacc ccgaataaag ccggttttgt gaaaattgca     420
gccgatgaac cgggtattac caaagatgtg aaaaagtta tcgtgcagc agccattacc     480
cataaagaag ccaaagttcc gattattacc catagcaatg cccataataa taccggtctg     540
gaagaacagc gtattctgat ggaagaaggt gttgatccgg gtaaaattct gattggtcat     600
ctgggtgata ccgataatac cgattatatt aaaaaaattg ccgataaagg cagctttatt     660
ggtctggatc gttatggtct ggacctgttt ctgccggttg ataaacgtaa tgaaaccacc     720
ctgaaactga ttaaagatgg ctatagcgat cgcattatga tcagccatga ttattgttgt     780
accattgatt ggggcaccgc acgtccggaa ctgaaaccga actggcaccg cgttggagc     840
atggcactga ttttgaaga taccattccg tttctgaaaa aaaatggcgt gagcgaagaa     900
gtgatcgata ttatttttcaa agaaaacccg aaaaaattct tagctaa                948

<210> SEQ ID NO 267
<211> LENGTH: 315
<212> TYPE: PRT
<213> ORGANISM: Sulfolobus islandicus

<400> SEQUENCE: 267

Met Ala Arg Ile Pro Leu Val Gly Lys Glu Pro Ile Glu Ala Glu Asp
1               5                   10                  15
Met Gly Phe Thr Leu Ile His Glu His Leu Arg Val Phe Ser Glu Ala
```

| | | 20 | | | | 25 | | | | 30 | | |
|---|---|---|---|---|---|---|---|---|---|---|---|---|

Val Arg Tyr Gln Trp Pro His Leu Tyr Asn Glu Asp Glu Glu Leu Arg
    35                  40                  45

Asn Ala Val Asn Glu Val Lys Arg Ala Met Gln Phe Gly Val Lys Thr
 50                  55                  60

Ile Val Asp Pro Ser Val Met Gly Ile Gly Arg Asp Ile Arg Phe Met
65                  70                  75                  80

Glu Lys Val Val Lys Thr Thr Gly Ile Asn Leu Val Ala Gly Thr Gly
                 85                  90                  95

Ile Trp Ile Phe Val Asp Leu Pro Phe Tyr Phe Leu Asn Arg Ser Ile
            100                 105                 110

Asp Glu Ile Ala Asp Leu Phe Ile His Asp Ile Lys Glu Gly Ile Gln
        115                 120                 125

Ala Thr Pro Asn Lys Ala Gly Phe Val Lys Ile Ala Ala Asp Glu Pro
    130                 135                 140

Gly Ile Thr Lys Asp Val Glu Lys Val Ile Arg Ala Ala Ala Ile Thr
145                 150                 155                 160

His Lys Glu Ala Lys Val Pro Ile Ile Thr His Ser Asn Ala His Asn
                165                 170                 175

Asn Thr Gly Leu Glu Glu Gln Arg Ile Leu Met Glu Glu Gly Val Asp
            180                 185                 190

Pro Gly Lys Ile Leu Ile Gly His Leu Gly Asp Thr Asp Asn Thr Asp
        195                 200                 205

Tyr Ile Lys Lys Ile Ala Asp Lys Gly Ser Phe Ile Gly Leu Asp Arg
    210                 215                 220

Tyr Gly Leu Asp Leu Phe Leu Pro Val Asp Lys Arg Asn Glu Thr Thr
225                 230                 235                 240

Leu Lys Leu Ile Lys Asp Gly Tyr Ser Asp Arg Ile Met Ile Ser His
                245                 250                 255

Asp Tyr Cys Cys Thr Ile Asp Trp Gly Thr Ala Arg Pro Glu Leu Lys
            260                 265                 270

Pro Lys Leu Ala Pro Arg Trp Ser Met Ala Leu Ile Phe Glu Asp Thr
        275                 280                 285

Ile Pro Phe Leu Lys Lys Asn Gly Val Ser Glu Glu Val Ile Asp Ile
    290                 295                 300

Ile Phe Lys Glu Asn Pro Lys Lys Phe Phe Ser
305                 310                 315

<210> SEQ ID NO 268
<211> LENGTH: 30
<212> TYPE: DNA
<213> ORGANISM: Artificial Sequence
<220> FEATURE:
<223> OTHER INFORMATION: W263M-F

<400> SEQUENCE: 268
tgcaccattg atatgggcac cgcaaaaccg                                     30

<210> SEQ ID NO 269
<211> LENGTH: 30
<212> TYPE: DNA
<213> ORGANISM: Artificial Sequence
<220> FEATURE:
<223> OTHER INFORMATION: W263M-R

<400> SEQUENCE: 269
cggttttgcg gtgcccatat caatggtgca                                     30

<210> SEQ ID NO 270
<211> LENGTH: 30
<212> TYPE: DNA
<213> ORGANISM: Artificial Sequence
<220> FEATURE:
<223> OTHER INFORMATION: W263L-F

<400> SEQUENCE: 270
tgcaccattg atctgggcac cgcaaaaccg                                     30

<210> SEQ ID NO 271
<211> LENGTH: 30
<212> TYPE: DNA
<213> ORGANISM: Artificial Sequence
<220> FEATURE:
<223> OTHER INFORMATION: W263L-R

<400> SEQUENCE: 271
cggttttgcg gtgcccagat caatggtgca                                     30

<210> SEQ ID NO 272
<211> LENGTH: 30
<212> TYPE: DNA
<213> ORGANISM: Artificial Sequence
<220> FEATURE:
<223> OTHER INFORMATION: W263A-F

<400> SEQUENCE: 272
tgcaccattg atgcaggcac cgcaaaaccg                                     30

<210> SEQ ID NO 273
<211> LENGTH: 30
<212> TYPE: DNA
<213> ORGANISM: Artificial Sequence
<220> FEATURE:
<223> OTHER INFORMATION: W263A-R

<400> SEQUENCE: 273
cggttttgcg gtgcctgcat caatggtgca                                     30

<210> SEQ ID NO 274
<211> LENGTH: 30
<212> TYPE: DNA
<213> ORGANISM: Artificial Sequence
<220> FEATURE:
<223> OTHER INFORMATION: W263I-F

<400> SEQUENCE: 274
tgcaccattg atattggcac cgcaaaaccg                                     30

<210> SEQ ID NO 275
<211> LENGTH: 30
<212> TYPE: DNA
<213> ORGANISM: Artificial Sequence
<220> FEATURE:
<223> OTHER INFORMATION: W263I-R

<400> SEQUENCE: 275
cggttttgcg gtgccaatat caatggtgca                                     30

<210> SEQ ID NO 276
<211> LENGTH: 30
<212> TYPE: DNA
<213> ORGANISM: Artificial Sequence
<220> FEATURE:

<223> OTHER INFORMATION: W263V-F

<400> SEQUENCE: 276
tgcaccattg atgttggcac cgcaaaaccg                               30

<210> SEQ ID NO 277
<211> LENGTH: 30
<212> TYPE: DNA
<213> ORGANISM: Artificial Sequence
<220> FEATURE:
<223> OTHER INFORMATION: W263V-R

<400> SEQUENCE: 277
cggttttgcg gtgccaacat caatggtgca                               30

<210> SEQ ID NO 278
<211> LENGTH: 30
<212> TYPE: DNA
<213> ORGANISM: Artificial Sequence
<220> FEATURE:
<223> OTHER INFORMATION: W263T-F

<400> SEQUENCE: 278
tgcaccattg ataccggcac cgcaaaaccg                               30

<210> SEQ ID NO 279
<211> LENGTH: 30
<212> TYPE: DNA
<213> ORGANISM: Artificial Sequence
<220> FEATURE:
<223> OTHER INFORMATION: W263T-R

<400> SEQUENCE: 279
cggttttgcg gtgccggtat caatggtgca                               30

<210> SEQ ID NO 280
<211> LENGTH: 30
<212> TYPE: DNA
<213> ORGANISM: Artificial Sequence
<220> FEATURE:
<223> OTHER INFORMATION: C258L-F

<400> SEQUENCE: 280
attagccatg attatctgtg caccattgat                               30

<210> SEQ ID NO 281
<211> LENGTH: 30
<212> TYPE: DNA
<213> ORGANISM: Artificial Sequence
<220> FEATURE:
<223> OTHER INFORMATION: C258L-R

<400> SEQUENCE: 281
atcaatggtg cacagataat catggctaat                               30

<210> SEQ ID NO 282
<211> LENGTH: 30
<212> TYPE: DNA
<213> ORGANISM: Artificial Sequence
<220> FEATURE:
<223> OTHER INFORMATION: I261F-F

<400> SEQUENCE: 282
gattattgct gcacctttga ttgggggcacc                              30

-continued

```
<210> SEQ ID NO 283
<211> LENGTH: 30
<212> TYPE: DNA
<213> ORGANISM: Artificial Sequence
<220> FEATURE:
<223> OTHER INFORMATION: I261F-R

<400> SEQUENCE: 283
ggtgccccaa tcaaaggtgc agcaataatc                                      30

<210> SEQ ID NO 284
<211> LENGTH: 30
<212> TYPE: DNA
<213> ORGANISM: Artificial Sequence
<220> FEATURE:
<223> OTHER INFORMATION: V27A-F

<400> SEQUENCE: 284
gaacatctgc gtgcatttag cgaagcagtt                                      30

<210> SEQ ID NO 285
<211> LENGTH: 30
<212> TYPE: DNA
<213> ORGANISM: Artificial Sequence
<220> FEATURE:
<223> OTHER INFORMATION: V27A-R

<400> SEQUENCE: 285
aactgcttcg ctaaatgcac gcagatgttc                                      30

<210> SEQ ID NO 286
<211> LENGTH: 33
<212> TYPE: DNA
<213> ORGANISM: Artificial Sequence
<220> FEATURE:
<223> OTHER INFORMATION: Y97W-F

<400> SEQUENCE: 286
ggcaccggta tttggattta tatcgatctg ccg                                  33

<210> SEQ ID NO 287
<211> LENGTH: 33
<212> TYPE: DNA
<213> ORGANISM: Artificial Sequence
<220> FEATURE:
<223> OTHER INFORMATION: Y97W-R

<400> SEQUENCE: 287
cggcagatcg atataaatcc aaataccggt gcc                                  33

<210> SEQ ID NO 288
<211> LENGTH: 33
<212> TYPE: DNA
<213> ORGANISM: Artificial Sequence
<220> FEATURE:
<223> OTHER INFORMATION: L228M-F

<400> SEQUENCE: 288
gatcgttatg gtctggacat gtttctgccg gtt                                  33

<210> SEQ ID NO 289
<211> LENGTH: 33
<212> TYPE: DNA
<213> ORGANISM: Artificial Sequence
<220> FEATURE:
<223> OTHER INFORMATION: L228M-R
```

<400> SEQUENCE: 289
aaccggcaga aacatgtcca gaccataacg atc                          33

<210> SEQ ID NO 290
<211> LENGTH: 31
<212> TYPE: DNA
<213> ORGANISM: Artificial Sequence
<220> FEATURE:
<223> OTHER INFORMATION: I280T-F

<400> SEQUENCE: 290
gcaccgcgtt ggagcactac cctgattttt g                            31

<210> SEQ ID NO 291
<211> LENGTH: 31
<212> TYPE: DNA
<213> ORGANISM: Artificial Sequence
<220> FEATURE:
<223> OTHER INFORMATION: I280T-R

<400> SEQUENCE: 291
caaaaatcag ggtagtgctc caacgcggtg c                            31

<210> SEQ ID NO 292
<211> LENGTH: 43
<212> TYPE: DNA
<213> ORGANISM: Artificial Sequence
<220> FEATURE:
<223> OTHER INFORMATION: F46L-F

<400> SEQUENCE: 292
ctgtataatg aagatgaaga actgcgcaat gccgtgaatg aag                43

<210> SEQ ID NO 293
<211> LENGTH: 43
<212> TYPE: DNA
<213> ORGANISM: Artificial Sequence
<220> FEATURE:
<223> OTHER INFORMATION: F46L-R

<400> SEQUENCE: 293
cttcattcac ggcattgcgc agttcttcat cttcattata cag                43

<210> SEQ ID NO 294
<211> LENGTH: 45
<212> TYPE: DNA
<213> ORGANISM: Artificial Sequence
<220> FEATURE:
<223> OTHER INFORMATION: I76T-F

<400> SEQUENCE: 294
gttatgggtc tgggtcgtga tactcgtttt atggaaaaag ttgtg              45

<210> SEQ ID NO 295
<211> LENGTH: 45
<212> TYPE: DNA
<213> ORGANISM: Artificial Sequence
<220> FEATURE:
<223> OTHER INFORMATION: I76T-R

<400> SEQUENCE: 295
cacaactttt tccataaaac gagtatcacg acccagaccc ataac              45

<210> SEQ ID NO 296
<211> LENGTH: 33

```
<212> TYPE: DNA
<213> ORGANISM: Artificial Sequence
<220> FEATURE:
<223> OTHER INFORMATION: Y99F-F

<400> SEQUENCE: 296
ggcaccggta tttatatttt tatcgatctg ccg                              33

<210> SEQ ID NO 297
<211> LENGTH: 33
<212> TYPE: DNA
<213> ORGANISM: Artificial Sequence
<220> FEATURE:
<223> OTHER INFORMATION: Y99F-R

<400> SEQUENCE: 297
cggcagatcg ataaaaatat aaataccggt gcc                              33

<210> SEQ ID NO 298
<211> LENGTH: 34
<212> TYPE: DNA
<213> ORGANISM: Artificial Sequence
<220> FEATURE:
<223> OTHER INFORMATION: L130P-F

<400> SEQUENCE: 298
ggcattcagg gcaccccgaa taaagcaggt tttg                             34

<210> SEQ ID NO 299
<211> LENGTH: 34
<212> TYPE: DNA
<213> ORGANISM: Artificial Sequence
<220> FEATURE:
<223> OTHER INFORMATION: L130P-R

<400> SEQUENCE: 299
caaaacctgc tttattcggg gtgccctgaa tgcc                             34

<210> SEQ ID NO 300
<211> LENGTH: 33
<212> TYPE: DNA
<213> ORGANISM: Artificial Sequence
<220> FEATURE:
<223> OTHER INFORMATION: L226V-F

<400> SEQUENCE: 300
gatcgttatg gtgtggacct gtttctgccg gtt                              33

<210> SEQ ID NO 301
<211> LENGTH: 33
<212> TYPE: DNA
<213> ORGANISM: Artificial Sequence
<220> FEATURE:
<223> OTHER INFORMATION: L226V-R

<400> SEQUENCE: 301
aaccggcaga aacaggtcca caccataacg atc                              33

<210> SEQ ID NO 302
<211> LENGTH: 30
<212> TYPE: DNA
<213> ORGANISM: Artificial Sequence
<220> FEATURE:
<223> OTHER INFORMATION: L72I-F

<400> SEQUENCE: 302
```

```
gttatgggta ttggtcgtga tattcgtttt                                30

<210> SEQ ID NO 303
<211> LENGTH: 30
<212> TYPE: DNA
<213> ORGANISM: Artificial Sequence
<220> FEATURE:
<223> OTHER INFORMATION: L72I-R

<400> SEQUENCE: 303
aaaacgaata tcacgaccaa tacccataac                                30

<210> SEQ ID NO 304
<211> LENGTH: 33
<212> TYPE: DNA
<213> ORGANISM: Artificial Sequence
<220> FEATURE:
<223> OTHER INFORMATION: F229S-F

<400> SEQUENCE: 304
gatcgttatg gtctggacct gtctctgccg gtt                            33

<210> SEQ ID NO 305
<211> LENGTH: 33
<212> TYPE: DNA
<213> ORGANISM: Artificial Sequence
<220> FEATURE:
<223> OTHER INFORMATION: F229S-R

<400> SEQUENCE: 305
aaccggcaga gacaggtcca gaccataacg atc                            33

<210> SEQ ID NO 306
<211> LENGTH: 30
<212> TYPE: DNA
<213> ORGANISM: Artificial Sequence
<220> FEATURE:
<223> OTHER INFORMATION: T68S-F

<400> SEQUENCE: 306
aaaaccattg ttgatccgag tgttatgggt                                30

<210> SEQ ID NO 307
<211> LENGTH: 30
<212> TYPE: DNA
<213> ORGANISM: Artificial Sequence
<220> FEATURE:
<223> OTHER INFORMATION: T68S-R

<400> SEQUENCE: 307
acccataaca ctcggatcaa caatggtttt                                30

<210> SEQ ID NO 308
<211> LENGTH: 33
<212> TYPE: DNA
<213> ORGANISM: Artificial Sequence
<220> FEATURE:
<223> OTHER INFORMATION: K8E-F

<400> SEQUENCE: 308
cattccgctg gttggtgaag atagcattga aag                            33

<210> SEQ ID NO 309
<211> LENGTH: 33
<212> TYPE: DNA
<213> ORGANISM: Artificial Sequence
```

```
<220> FEATURE:
<223> OTHER INFORMATION: K8E-R

<400> SEQUENCE: 309
ctttcaatgc tatcttcacc aaccagcgga atg                                    33

<210> SEQ ID NO 310
<211> LENGTH: 30
<212> TYPE: DNA
<213> ORGANISM: Artificial Sequence
<220> FEATURE:
<223> OTHER INFORMATION: P67S-F

<400> SEQUENCE: 310
aaaaccattg ttgattcgac cgttatgggt                                        30

<210> SEQ ID NO 311
<211> LENGTH: 30
<212> TYPE: DNA
<213> ORGANISM: Artificial Sequence
<220> FEATURE:
<223> OTHER INFORMATION: P67S-R

<400> SEQUENCE: 311
acccataacg gtcgaatcaa caatggtttt                                        30

<210> SEQ ID NO 312
<211> LENGTH: 32
<212> TYPE: DNA
<213> ORGANISM: Artificial Sequence
<220> FEATURE:
<223> OTHER INFORMATION: K164N-F

<400> SEQUENCE: 312
caataaagaa accaatgttc cgattattac cc                                     32

<210> SEQ ID NO 313
<211> LENGTH: 32
<212> TYPE: DNA
<213> ORGANISM: Artificial Sequence
<220> FEATURE:
<223> OTHER INFORMATION: K164N-R

<400> SEQUENCE: 313
gggtaataat cggaacattg gtttctttat tg                                     32
```

SULFOLOBAL PHOSPHOTRIESTERASE-LIKE (PLL) LACTONASES ACTIVITY HAVING ENHANCED PROPERTIES AND THE USES THEREOF

The present invention relates to Sulfolobal Phosphotriesterase-Like Lactonases (PLL) activity having enhanced properties and the uses thereof, notably as bioscavenger of organophosphorus compounds or as quorum quencher of the bacteria using lactones to communicate.

Organophosphate (OPs) insecticides have become the most widely used insecticides available today. OPs are used in agriculture, at home, in gardens, and in veterinary practice. Since most of these compounds inhibit some esterase enzymes, exposure to OPs can lead to serious toxicity by multiple routes. Irreversible inhibition of acetylcholinesterase by OPs, a key enzyme of the mammalian nervous system, causes severe damage for all vertebrates. Loss of enzyme function leads to accumulation of acetylcholine in different compartments of the body causing muscle contraction, paralysis and respiratory depression. Increased pulmonary secretions with respiratory failure are the usual causes of death from organophosphate poisoning.

Some of OPs have also been developed by armies before the World War II. The discovery of OPs with improved toxicity and/or higher stability has lead to the development of chemical warfar agents (CWA) such as sarin, soman, tabun or VX. Moreover, OPs insecticides, being easily accessible and not so less toxic as compared to CWA OPs, constitute an important risk for the population. Faced with these growing threats, the development of anti-dotes has never been more urgent.

OPs are efficiently absorbed by inhalation, ingestion, and skin penetration because of the hydrophobicity of these molecules. The occurrence of poisoning depends on the absorption rate of the compound. Symptoms of acute OPs poisoning develop during or after exposure, within minutes to hours, depending of the method of the contact. Exposure by inhalation results in the fastest appearance of toxic symptoms, followed by the gastrointestinal route and finally dermal route.

Protective suits and masks do not always offer an effective protection against OPs. In patients poisoned by OPs contamination of skin, clothing or hair, decontamination must proceed with surgical soap or laundry detergents. Treatment of highly contaminated persons results in administering atropine or diazepam which antagonize the effects of excessive concentrations of acetylcholine at end-organs having muscarinic receptors. Unfortunately, atropine remains ineffective against nicotinic actions, specifically muscle weakness and respiratory depression in case of severe poisoning. Pralidoxime, a cholinesterase reactivator, relieves the nicotinic as well as the muscarinic effects of OPs poisoning when administering less than 48 hours after poisoning. The use of this compound remains uneffective against sarin which holds a very quickly effect once inhaled. Clearing airway and improving tissue oxygenation is also very helpful.

Although some progress in prophylaxia has been made with the abovementioned techniques, existing protection and the treatments for these poisoning nevertheless remain unsatisfactory.

The first OPs-hydrolases have been identified in several bacteria in the early 90's (Cheng et al., 1993, Appl. Environ. Microbiol., 59: 3138-3140, Raveh et al., 1993, Biochem Pharmacol., 45: 2465-2474). These enzymes are able to catalyze the hydrolysis of phosphoester bounds in OPs. Unfortunately, due to their low stoichiometric binding capacity to OPs, huge quantity of enzymes is needed to cure the poisoning individuals. This renders the use of these enzymes disproportionate and quite expensive.

Some other microbial enzymes generally called phosphotriesterases (PTEs) show preferences for organophosphorous compounds with P—O or P—S bonds. These enzymes are members of the aminohydrolase superfamily, enzymes catalyzing hydrolysis of a broad range of compounds with different chemical properties (phosphoesters, esters, amides, etc). Their coding genes, opd (organo phosphate degradation), were isolated in soil bacteria such as *Pseudomonas diminuta*, also called *Brevundominas diminuta* (Munnecke et al., 1976; Appl. Environ. Microbiol., 32: 7-13), *Flavobacterium sp.* (Sethunathan et al., 1973, Can J Microbiol, 19: 873-875) and *Agrobacterium radiobacter* (Horne et al., 2003, FEMS Microbiol Lett, 222: 1-8), and genes similar to opd were also identified in Archaea (Merone et al., 2005, Extremophiles, 9: 297-305). The catalytic properties of hyperthermophilic PTEs are extensively studied because of their ability to hydrolyze pesticides and several nerve agents (Jackson et al., 2005, Biochem Biophys Acta, 1752: 56-64/ Jackson et al., 2008, J Mol Biol, 375: 1189-1196/Wong et al., 2007, Biochemistry, 46: 13352-13369/Elias et al., 2008, J Mol Biol, 379: 1017-1028/Pompea et al., 2009, Extremophiles, 13: 461-470). The hyperthermophilic PTEs have the advantage of being very stable and inexpensive to produce due to their capacity to resist to organic solvents or detergents at moderate temperature. Thus, hyperthermophilic PTEs are promising for the development of a bioscavenger for neurotoxic agents such as OPs.

Recently, three hyperthermophilic PTEs were isolated and purified from *Sulfolobus sp.*: SsoPox was isolated from *Sulfolobus solfataricus* (Merone et al., 2005, Extremophiles, 9: 297-305), SacPox was isolated from *Sulfolobus acidicaldarius* (Porzio et al., 2007, Biochimie, 89: 625-636) and SisLac (also called SisPox) was isolated from *Sulfolobus islandicus* (Gotthard et al., 2011, Acta Crystallogr Sect F Struct Biol Cryst Commun 67: 354-357/Hiblot et al., 2012, PLoS One 7: e47028). SsoPox, SacPox and SisLac are members of an enzyme family called phosphotriesterase-Like Lactonase (PLL). Phylogenetic and biochemical studies have revealed that SsoPox and SisLac enzymes are native lactonases endowed with promiscuous paraoxonase activity and more generally with organophosphate hydrolase activity (Afriat et al., 2006, Biochemistry, 45: 13677-13686/ Elias et al., 2012, J Biol Chem., 287(1): 11-20). Despite PTEs and PLLs enzymes exhibit the same $(\beta/\alpha)_8$ barrel fold or so-called TIM barrel, their ability to hydrolyze different kinds of substrates such as lactones or OPs is different.

Lactones are signalling molecules synthesized by bacteria which allow them to detect the population density. This cell-to-cell communication process is termed quorum sensing (QS) and is well known to modulate many key biological functions of bacteria including biofilm formation (Popat et al., 2008, British Medical Bulletin, 87: 63-75). This link between QS and virulence is central to the pathogenesis of many bacterial infections, including *P. aeruginosa* (Sakuragi et al., 2007, J Bacteriol, 189: 5383-5386) but also *A. baumanii* (Stacy et al., 2012, ACS Chem Biol, 7(10): 1719-1728), *Bulkolderia sp.* (McKeon et al., 2011, J Infect Dis, February 1; 203(3):383-92), *Vibrio sp.* (Augustine et al., 2010, Arch Microbiol 192(12): 1019-1022) or *E. caratovora* (Dong et al., 2001, Nature, 411: 813-817). Interfering with QS system, also called quorum quenching, is a promising approach to control bacterial diseases in plants and animals (Dong et al., 2001, nature, 411: 813-817). N-acylhomoserine lactones (AHLs) are molecules that mediate bacterial communication for many Gram negative bacteria and some Archaeal organisms (Zhang et al., 2012, ISME J., Jul; 6(7):1336-44). It classically regulates infection and virulence functions. These molecules accumulate in the media to reach a certain threshold for which the transcriptional profile of the bacteria is altered (Hentzer et al., 2003, Embo J, 22: 3803-3815). By hydrolyzing AHLs, lactonases like PLLs can quench the AHL-mediated communication between bacteria, as seen for human paraoxonases (Ma et al., 2009, Appl Microbiol Biotechnol, 83: 135-141) or AiiA lactonase (Dong et al., 2001, Nature, 411: 813-817). Because of their dual catalytic activities, lactonases and phosphotriesterases, PLLs constitute highly attractive candidate for biotechnological utilization as quorum quenching agent or OPs bioscavenger.

In WO 2008/145865, the inventors of the present invention provide novel PTEs being more active vis-à-vis the OPs by introducing mutations in close vicinity of the active site of SsoPox. The main aim of this work was to obtain new enzymes with catalytic performance close to the ones of mesophilic PTEs.

Surprisingly, the inventors discovered that the introduction of mutations in several β sheets or loops of the PLLs enzymes could increase not only the OPs hydrolyse activity but also the lactonases activity of said enzymes.

One aspect of the present invention is to provide, novel mutated hyperthermophilic PTEs having a lactonase activity, having the advantages of being both:
  more active vis-à-vis the OPs, or more active vis-à-vis the AHLs, or more active vis-à-vis the OPs and vis-à-vis the AHLs than the wild type hyperthermophilic PTEs,
  more stable and less expensive to produce than the mesophilic PTEs.

Another aspect of the present invention contemplates a method for the establishment of a library of mutated hyperthermophilic PTE variants.

Another aspect of the present invention is to provide efficient tools for the decontamination of OPs polluted surfaces of materials, of the skin, of hairs or mucous membranes. Said tools can be compositions, bioscavengers, cartridge decontamination, kit of decontamination, impregnated materials with new mutated hyperthermophilic PTEs.

Another aspect of the present invention is to provide vectors and host cells able to synthesize the new mutated hyperthermophilic PTEs in large scale with a reduced cost.

Yet another aspect of the present invention is directed to the use of new mutated hyperthermophilic PTEs as bioscavengers within the context of the decontamination of the surfaces of materials, of the skin or mucous membranes contaminated with organophosphorus compounds, or within the context of the pollution control of water polluted with organophosphorus compounds, or within the context of the destruction of stocks of neurotoxic agents.

Still another aspect of the present invention is to provide compositions comprising new mutated hyperthermophilic PTEs for their use in the treatment of diseases caused by bacteria using AHLs to communicate. The expression bacteria relates not only to bacteria but also to Archae.

A subject of the invention is mutated hyperthermophilic PTE having a lactonase activity derived from a hyperthermophilic phosphotriesterase corresponding to the consensus sequence of SEQ ID NO: 1, said mutated PTE comprise the at least one mutation selected from the group consisting of: substitutions of the glycine G in position 9, the lysine K in position 10, the valine V in position 29, the phenylalanine F or leucine L in position 48, the lysine K in position 56, the proline P in position 69, the threonine T in position 70, the leucine L in position 74, the isoleucine I in position 78, the valine V in position 85, the tyrosine Y in position 99, the tyrosine Y in position 101, the isoleucine I in position 124, the leucine L or serine S or asparagine N in position 132, the aspartic acid D in position 143, the lysine K or asparagine N in position 166, the isoleucine I in position 169, the aspartic acid D in position 193, the glycine G in position 195, the arginine R in position 225, the glycine G in position 227, the leucine L in position 228, the leucine L in position 230, the phenylalanine F in position 231, the leucine L in position 232, the tyrosine Y position 259, the cysteine C in position 260, the cysteine C in position 261, the threonine T in position 262, the isoleucine I in position 263, the aspartic acid D in position 264, the tryptophane W in position 265, the glycine G in position 266, the threonine T or isoleucine I in position 267, the alanine A in position 268, the lysine K or arginine R in position 269, the proline P in position 270, the glutamic acid E in position 271, the tyrosine Y or leucine L in position 272, the lysine K in position 273, the proline P in position 274, the lysine K in position 275, the leucine L in position 276, the alanine A in position 277, the proline P in position 278, the arginine R or lysine K in position 279, the tryptophan W in position 280, the serine S in position 281, the isoleucine I or methionine M in position 282, the threonine T or alanine A or serine S in position 283, the leucine L in position 284, the isoleucine I in position 285, the asparagine N or serine S or threonine T in position 299, of SEQ ID NO: 1 by any other natural amino acid different from the one(s) described in the consensus sequence,
with an exception for positions 48, 132, 166, 267, 269, 272, 279, 282, 283 and 299 where the substitution can be done with one amino acid described in the consensus sequence only if said substitution on said positions is always associated with at least another substitution chosen among the above-mentioned positions, or by any other non-natural amino acid, with the proviso that when the at least one mutation is selected from the group consisting of substitutions of the tyrosine Y in position 99, the tyrosine Y in position 101, the arginine R in position 225, the cysteine C in position 260, then the said at least one mutation is always associated with at least one mutation selected from the group consisting of substitutions of the glycine G in position 9, the lysine K in position 10, the phenylalanine F or leucine L in position 48, the lysine K in position 56, the isoleucine I in position 78, the valine V in position 85, the isoleucine I in position 124, the leucine L or serine S or asparagine N in position 132, the lysine K or asparagine N in position 166, the isoleucine I in position 169, the aspartic acid D in position 193, the glycine G in position 195, the leucine L in position 230, the leucine L in position 232, the tyrosine Y in position 259, the cysteine C in position 261, the threonine T in position 262, the isoleucine I in position 263, the aspartic acid D in position 264, the glycine G in position 266, the threonine T or isoleucine I in position 267, the alanine A in position 268, the lysine K or arginine R in position 269, the proline P in position 270, the glutamic acid E in position 271, the tyrosine Y or leucine L in position 272, the lysine K in position 273, the proline P in position 274, the lysine K in position 275, the leucine L in position 276, the alanine A in position 277, the proline P in position 278, the arginine R or lysine K in position 279, the serine S in position 281, the isoleucine I or methionine M in position 282, the threonine T or alanine A or serine S in position 283, the leucine L in position 284, the isoleucine I in position 285, the asparagine N or serine S or threonine T in position 299, and with the proviso that when the at least one mutation selected from the group consisting of substitutions of the valine V in position 29, the proline P in position 69, the threonine T in position 70, the leucine L in position 74, the aspartic acid D in position 143, the glycine G in position 227, the leucine L in position 228, the phenylalanine F in position 231, the tryptophane W in position 265, the tryptophane W in position 280 is associated with the at least one mutation selected from the group consisting of the substitutions of the tyrosine Y in position 99, the tyrosine Y in position 101, the arginine R in position 225, the cysteine C in position 260 to form associated mutations, then the said associated mutations are always associated with at least one mutation selected from the group consisting of substitutions of the glycine G in position 9, the lysine K in position 10, the phenylalanine F or leucine L in position 48, the lysine K in position 56, the isoleucine I in position 78, the valine V in position 85, the isoleucine I in position 124, the leucine L or serine S or asparagine N in position 132, the lysine K or asparagine N in position 166, the isoleucine I in position 169, the aspartic acid D in position 193, the glycine G in position 195, the leucine L in position 230, the leucine L in position 232, the tyrosine Y in position 259, the cysteine C in position 261, the threonine T in position 262, the isoleucine I in position 263, the aspartic acid D in position 264, the glycine G in position 266, the threonine T or isoleucine I in position 267, the alanine A in position 268, the lysine K or arginine R in position 269, the proline P in position 270, the glutamic acid E in position 271, the tyrosine Y or leucine L in position 272, the lysine K in position 273, the proline P in position 274, the lysine K in position 275, the leucine L in position 276, the alanine A in position 277, the proline P in position 278, the arginine R or lysine K in position 279, the serine S in position 281, the isoleucine I or methionine M in position 282, the threonine T or alanine A or serine S in position 283, the leucine L in position 284, the isoleucine I in position 285, the asparagine N or serine S or threonine T in position 299.

PTEs are zinc-metalloproteases that were originally identified for their ability to hydrolyse phosphotriesterase-containing organophosphorous compounds, but recently more members of this family were found to possess lactonase activity as well. Lactonase activity is the ability to hydrolyze the ester bound in the lactone ring.

The expression "mutated hyperthermophilic PTE having a lactonase activity" relates to any enzyme having both lactonase and phosphotriesterase catalytic activities, said enzymes being isolated from thermophilic or hyperthermophilic bacteria belonging to the PLLs or PTEs superfamilies. By "superfamily" is meant a large group of proteins sharing the same fold (topology and secondary structure elements), and the same active site architecture. A superfamily is comprised of dozens of groups of proteins sharing the same three dimensional structure and functions, each group exhibiting a different function. These functions typically share a common element (e.g. a key chemical step in enzyme catalysis) and also the active site residues executing this element. By "thermophilic bacteria" are meant bacteria living between 45° C. to 120° C. By "hyperthermophilic bacteria" is meant bacteria for which the optimal temperatures are above 80° C. The thermostability of the enzymes isolated from thermophilic or hyperthermophilic bacteria confers them the advantage of being inexpensive to produce, on the one hand because they are stable in organic solvents which make them more suitable for industrial processes, and, on the other hand, because they are very inexpensive to purify by the technique of heating the cell lysates of the cells producing the above-mentioned enzymes; a large yield and high purity are thus obtained in one stage.

Lactonase and phosphotriesterase catalytic activities can be tested on their respective substrata according to methods disclosed in experimental part of the invention.

The introduction of an amino acid residue in position 2 of SEQ ID NO: 1 results from the experimental protocols used to perform the differents mutated hyperthermophilic PTEs, notably due to the choice of restriction enzyme in the cloning site of vectors for the building of the mutated hyperthermophilic PTEs. For example, the use of NcoI restriction enzyme in the cloning site of said vectors leads to the addition of the alanine residue in position 2 of SEQ ID NO: 1 in order to avoid a change in the reading frame. The introduction of said alanine residue in position 2 of SEQ ID NO: 1 has no effect in the activity of either the wild type or the mutated hyperthermophilic PTEs. It means that two mutated hyperthermophilic PTEs having a sequence derived from SEQ ID NO: 1, one bearing an added alanine residue in position 2, the other one being free of said alanine residue in position 2 share exactly the same enzymatic activity in terms of performance.

For positions 48, 132, 166, 267, 269, 272, 279, 282, 283 and 299, the substitution can be done with one of the amino acid described in the consensus sequence, i.e. already existing in natural hyperthermophilic PTEs only if said substitution on said positions is always associated with at least any other substitution chosen among the above-mentioned position. For example, if phenylalanine F in position 48 is substituted by a leucine L, then another substitution should be done at least in any of the 52 other positions as disclosed.

The first proviso aims to exclude a single mutation at positions Y99, Y101, R225 or C260 of SEQ ID NO: 1. When the natural amino acid at one of the above-mentioned position is mutated, then it is always associated with at least one the 39 substitutions in position G9, K10, F/L48, K56, I78, V85, I124, L/S/N132, K/N166, I169, D193, G195, L230, L232, Y259, C261, T262, I263, D264, G266, T/I267, A268, K/R269, P270, E271, Y/L272, K273, P274, K275, L276, A277, P278, R/K279, S281, I/M282, T/A/S283, L284, I285, N/S/T299 of SEQ ID NO: 1.

The second proviso aims to exclude all the combinations of at least one mutation selected from the group consisting of substitution of the valine V in position 29, substitution of the proline P in position 69, substitution of the threonine T in position 70, substitution of the leucine L in position 74, substitution of the aspartic acid D in position 143, substitution of the glycine G in position 227, substitution of the leucine L in position 228, substitution of the phenylalanine F in position 231, substitution of the tryptophane W in position 265, substitution of the tryptophane W in position 280 associated with at least one mutation selected from the group consisting of the tyrosine Y in position 99, substitution of the tyrosine Y in position 101, substitution of the arginine R in position 225, substitution of the cysteine C in position 260 of SEQ ID NO: 1. When such a combination of mutations occurred, then it is always associated with at least one the 39 substitutions in position G9, K10, F/L48, K56, I78, V85, I124, L/S/N132, K/N166, I169, D193, G195, L230, L232, Y259, C261, T262, I263, D264, G266, T/I267, A268, K/R269, P270, E271, Y/L272, K273, P274, K275, L276, A277, P278, R/K279, S281, I/M282, T/A/S283, L284, I285, N/S/T299 of SEQ ID NO: 1.

The aim of the above-mentioned proviso is to exclude some specific mutated hyperthermophilic phosphotriesterase (PTEs) previously disclosed by the inventor in WO 2008/145865.

The mutated hyperthermophilic phosphotriesterase (PTEs) having a lactonase activity of the invention have the advantage of being more active than the wild type hyperthermophilic phosphotriesterase (PTEs) having a lactonase activity from which they derived not only within the context of hydrolysis of OPs but also within the context of the treatment of diseases caused by bacteria using AHLs to communicate, notably by hydrolysis of AHLs.

The hyperthermophilic PTEs having a lactonase activity of the present invention also have the advantage of being more active:
within the context of the hydrolysis of the OPs, and/or,
within the context of quorum quenching, i.e. within the context of resistance to pathogen infections,
than the wild type hyperthermophilic PTEs from which they derived.

In a preferred embodiment, the mutated hyperthermophilic phosphotriesterase (PTE) having a lactonase activity derived from a hyperthermophilic phosphotriesterase according to the present invention, wherein the amino acid in position 2 in SEQ ID NO: 1 is missing, said mutated PTE comprise the at least one mutation selected from the group consisting of: substitutions of the glycine G in position 8, the lysine K in position 9, the valine V in position 28, the phenylalanine F or leucine L in position 47, the lysine K in position 55, the proline P in position 68, the threonine T in position 69, the leucine L in position 73, the isoleucine I in position 77, the valine V in position 84, the tyrosine Y in position 98, the tyrosine Y in position 100, the isoleucine I in position 123, the leucine L or serine S or asparagine N in position 131, the aspartic acid D in position 142, the lysine K or asparagine N in position 165, the isoleucine I in position 168, the aspartic acid D in position 192, the glycine G in position 194, the arginine R in position 224, the glycine G in position 226, the leucine L in position 227, the leucine L in position 229, the phenylalanine F in position 230, the leucine L in position 231, the tyrosine Y position 258, the cysteine C in position 259, the cysteine C in position 260, the threonine T in position 261, the isoleucine I in position 262, the aspartic acid D in position 263, the tryptophane W in position 264, the glycine G in position 265, the threonine T or isoleucine I in position 266, the alanine A in position 267, the lysine K or arginine R in position 268, the proline P in position 269, the glutamic acid E in position 270, the tyrosine Y or leucine L in position 271, the lysine K in position 272, the proline P in position 273, the lysine K in position 274, the leucine L in position 275, the alanine A in position 276, the proline P in position 277, the arginine R or lysine K in position 278, the tryptophan W in position 279, the serine S in position 280, the isoleucine I or methionine M in position 281, the threonine T or alanine A or serine S in position 282, the leucine L in position 283, the isoleucine I in position 284, the asparagine N or serine S or threonine T in position 298, of SEQ ID NO: 1 by any other natural amino acid different from the one(s) described in the consensus sequence,
with an exception for positions 47, 131, 165, 266, 268, 271, 278, 281, 282 and 298 where the substitution can be done with one amino acid described in the consensus sequence only if said substitution on said positions is always associated with at least another substitution chosen among the above-mentioned positions, or by any other non-natural amino acid, with the proviso that when the at least one mutation is selected from the group consisting of substitutions of the tyrosine Y in position 98, the tyrosine Y in position 100, the arginine R in position 224, the cysteine C in position 259, then the said at least one mutation is always associated with at least one mutation selected from the group consisting of substitutions of the glycine G in position 8, the lysine K in position 9, the phenylalanine F or leucine L in position 47, the lysine K in position 55, the isoleucine I in position 77, the valine V in position 84, the isoleucine I in position 123, the leucine L or serine S or asparagine N in position 131, the lysine K or asparagine N in position 165, the isoleucine I in position 168, the aspartic acid D in position 192, the glycine G in position 194, the leucine L in position 229, the leucine L in position 231, the tyrosine Y in position 258, the cysteine C in position 260, the threonine T in position 261, the isoleucine I in position 262, the aspartic acid D in position 263, the glycine G in position 265, the threonine T or isoleucine I in position 266, the alanine A in position 267, the lysine K or arginine R in position 268, the proline P in position 269, the glutamic acid E in position 270, the tyrosine Y or leucine L in position 271, the lysine K in position 272, the proline P in position 273, the lysine K in position 274, the leucine L in position 275, the alanine A in position 276, the proline P in position 277, the arginine R or lysine K in position 278, the serine S in position 280, the isoleucine I or methionine M in position 281, the threonine T or alanine A or serine S in position 282, the leucine L in position 283, the isoleucine I in position 284, the asparagine N or serine S or threonine T in position 298,
and with the proviso that when the at least one mutation selected from the group consisting of substitutions of the valine V in position 28, the proline P in position 68, the threonine T in position 69, the leucine L in position 73, the aspartic acid D in position 142, the glycine G in position 226, the leucine L in position 227, the phenylalanine F in position 230, the tryptophane W in position 264, the tryptophane W in position 279 is associated with the at least one mutation selected from the group consisting of the substitutions of the tyrosine Y in position 98, the tyrosine Y in position 100, the arginine R in position 224, the cysteine C in position 259 to form associated mutations, then the said associated mutations are always associated with at least one mutation selected from the group consisting of substitutions of the glycine G in position 8, the lysine K in position 9, the phenylalanine F or leucine L in position 47, the lysine K in position 55, the isoleucine I in position 77, the valine V in position 84, the isoleucine I in position 123, the leucine L or serine S or asparagine N in position 131, the lysine K or asparagine N in position 165, the isoleucine I in position 168, the aspartic acid D in position 192, the glycine G in position 194, the leucine L in position 229, the leucine L in position 231, the tyrosine Y in position 258, the cysteine C in position 260, the threonine T in position 261, the isoleucine I in position 262, the aspartic acid D in position 263, the glycine G in position 265, the threonine T or isoleucine I in position 266, the alanine A in position 267, the lysine K or arginine R in position 268, the proline P in position 269, the glutamic acid E in position 270, the tyrosine Y or leucine L in position 271, the lysine K in position 272, the proline P in position 273, the lysine K in position 274, the leucine L in position 275, the alanine A in position 276, the proline P in position 277, the arginine R or lysine K in position 278, the serine S in position 280, the isoleucine I or methionine M in position 281, the threonine T or alanine A or serine S in position 282, the leucine L in position 283, the isoleucine I in position 284, the asparagine N or serine S or threonine T in position 298.

In this preferred embodiment, the alanine residue in position 2 is absent of the SEQ ID NO: 1.

The first proviso aims to exclude a single mutation at positions Y98, Y100, R224 or C259 of SEQ ID NO: 1. When the natural amino acid at one of the above-mentioned position is mutated, then it is always associated with at least one the 39 substitutions in position G8, K9, F/L47, K55, I77, V84, I123, L/S/N131, K/N165, I168, D192, G194, L229, L231, Y258, C260, T261, I262, D263, G265, T/I266, A267, K/R268, P269, E270, Y/L271, K272, P273, K274, L275, A276, P277, R/K278, S280, I/M281, T/A/S282, L283, I284, N/S/T298 of SEQ ID NO: 1.

The second proviso aims to exclude all the combinations of at least one mutation selected from the group consisting of substitution of the valine V in position 28, substitution of the proline P in position 68, substitution of the threonine T in position 69, substitution of the leucine L in position 73, substitution of the aspartic acid D in position 142, substitution of the glycine G in position 226, substitution of the leucine L in position 227, substitution of the phenylalanine F in position 230, substitution of the tryptophane W in position 264, substitution of the tryptophane W in position 279 associated with at least one mutation selected from the group consisting of the tyrosine Y in position 98, substitution of the tyrosine Y in position 100, substitution of the arginine R in position 224, substitution of the cysteine C in position 259 of SEQ ID NO: 1. When such a combination of mutations occurred, then it is always associated with at least one the 39 substitutions in position G8, K9, F/L47, K55, I77, V84, I123, L/S/N131, K/N165, I168, D192, G194, L229, L231, Y258, C260, T261, I262, D263, G265, T/I266, A267, K/R268, P269, E270, Y/L271, K272, P273, K274, L275, A276, P277, R/K278, S280, I/M281, T/A/S282, L283, I284, N/S/T298 of SEQ ID NO: 1.

In a more preferred embodiment, the mutated hyperthermophilic PTEs having a lactonase activity according to the present invention corresponding to the sequence of SEQ ID NO : 3 or having at least 70% or more identity to the amino acid sequence of SEQ ID NO: 3, said mutated PTE comprise the at least one mutation selected from the group consisting of: substitutions of the glycine G in position 7, the lysine K in position 8, the valine V in position 27, the phenylalanine F in position 46, the lysine K in position 54, the proline P in position 67, the threonine T in position 68, the leucine L in position 72, the isoleucine I in position 76, the valine V in position 83, the tyrosine Y in position 97, the tyrosine Y in position 99, the isoleucine I in position 122, the leucine L in position 130, the aspartic acid D in position 141, the lysine K in position 164, the isoleucine I in position 167, the aspartic acid D in position 191, the glycine G in position 193, the arginine R in position 223, the glycine G in position 225, the leucine L in position 226, the leucine L in position 228, the phenylalanine F in position 229, the leucine L in position 230, the tyrosine Y position 257, the cysteine C in position 258, the cysteine C in position 259, the threonine T in position 260, the isoleucine I in position 261, the aspartic acid D in position 262, the tryptophane W in position 263, the glycine G in position 264, the threonine T in position 265, the alanine A in position 266, the lysine K in position 267, the proline P in position 268, the glutamic acid E in position 269, the tyrosine Y in position 270, the lysine K in position 271, the proline P in position 272, the lysine K in position 273, the leucine L in position 274, the alanine A in position 275, the proline P in position 276, the arginine R in position 277, the tryptophan W in position 278, the serine S in position 279, the isoleucine I in position 280, the threonine T in position 281, the leucine L in position 282, the isoleucine I in position 283, the asparagine N in position 297, of SEQ ID NO : 3 by any other natural or non-natural amino acid, with the proviso that when the at least one mutation is selected from the group consisting of substitutions of the tyrosine Y in position 97, the tyrosine Y in position 99, the arginine R in position 223, the cysteine C in position 258, then the said at least one mutation is always associated with at least one mutation selected from the group consisting of substitutions of the glycine G in position 7, the lysine K in position 8, the phenylalanine F in position 46, the lysine K in position 54, the isoleucine I in position 76, the valine V in position 83, the isoleucine I in position 122, the leucine L in position 130, the lysine K in position 164, the isoleucine I in position 167, the aspartic acid D in position 191, the glycine G in position 193, the leucine L in position 228, the leucine L in position 230, the tyrosine Y in position 257, the cysteine C in position 259, the threonine T in position 260, the isoleucine I in position 261, the aspartic acid D in position 262, the glycine G in position 264, the threonine T in position 265, the alanine A in position 266, the lysine K in position 267, the proline P in position 268, the glutamic acid E in position 269, the tyrosine Y in position 270, the lysine K in position 271, the proline P in position 272, the lysine K in position 273, the leucine L in position 274, the alanine A in position 275, the proline P in position 276, the arginine R in position 277, the serine S in position 279, the isoleucine I in position 280, the threonine T in position 281, the leucine L in position 282, the isoleucine I in position 283, the asparagine N in position 297, and with the proviso that when the at least one mutation selected from the group consisting of substitutions of the valine V in position 27, the proline P in position 67, the threonine T in position 68, the leucine L in position 72, the aspartic acid D in position 141, the glycine G in position 225, the leucine L in position 226, the phenylalanine F in position 229, the tryptophane W in position 263, the tryptophane W in position 278 is associated with the at least one mutation selected from the group consisting of the substitutions of the tyrosine Y in position 97, the tyrosine Y in position 99, the arginine R in position 223, the cysteine C in position 258 to form associated mutations, then the said associated mutations are always associated with at least one mutation selected from the group consisting of substitutions of the glycine G in position 7, the lysine K in position 8, the phenylalanine F in position 46, the lysine K in position 54, the isoleucine I in position 76, the valine V in position 83, the isoleucine I in position 122, the leucine L in position 130, the lysine K in position 164, the isoleucine I in position 167, the aspartic acid D in position 191, the glycine G in position 193, the leucine L in position 228, the leucine L in position 230, the tyrosine Y in position 257, the cysteine C in position 259, the threonine T in position 260, the isoleucine I in position 261, the aspartic acid D in position 262, the glycine G in position 264, the threonine T in position 265, the alanine A in position 266, the lysine K in position 267, the proline P in position 268, the glutamic acid E in position 269, the tyrosine Y in position 270, the lysine K in position 271, the proline P in position 272, the lysine K in position 273, the leucine L in position 274, the alanine A in position 275, the proline P in position 276, the arginine R in position 277, the serine S in position 279, the isoleucine I in position 280, the threonine T in position 281, the leucine L in position 282, the isoleucine I in position 283, the asparagine N in position 297.

In this more preferred embodiment, the alanine residue in position 2 and the threonine residue in position 3 are absent of the SEQ ID NO: 1.

The first proviso aims to exclude a single mutation at positions Y97, Y99, R223 or C258 of SEQ ID NO: 1. When the natural amino acid at one of the above-mentioned position is mutated, then it is always associated with at least one the 39 substitutions in position G7, K8, F46, K54, I76, V83, I122, L130, K164, I167, D191, G193, L228, L230, Y257, C259, T260, I261, D262, G264, T265, A266, K267, P268, E269, Y270, K271, P272, K273, L274, A275, P276, R277, S279, I280, T281, L282, I283, N297 of SEQ ID NO: 1.

The second proviso aims to exclude all the combinations of at least one mutation selected from the group consisting of substitution of the valine V in position 27, substitution of the proline P in position 67, substitution of the threonine T in position 68, substitution of the leucine L in position 72, substitution of the aspartic acid D in position 141, substitution of the glycine G in position 225, substitution of the leucine L in position 226, substitution of the phenylalanine F in position 229, substitution of the tryptophane W in position 263, substitution of the tryptophane W in position 278 associated with at least one mutation selected from the group consisting of the tyrosine Y in position 97, substitution of the tyrosine Y in position 99, substitution of the arginine R in position 223, substitution of the cysteine C in position 258 of SEQ ID NO: 1. When such a combination of mutations occurred, then it is always associated with at least one the 39 substitutions in position G7, K8, F46, K54, I76, V83, I122, L130, K164, I167, D191, G193, L228, L230, Y257, C259, T260, I261, D262, G264, T265, A266, K267, P268, E269, Y270, K271, P272, K273, L274, A275, P276, R277, S279, I280, T281, L282, I283, N297 of SEQ ID NO: 1.

The invention relates more particularly to the above-mentioned mutated hyperthermophilic PTEs having a lactonase activity, derived from a hyperthermophilic phosphotriesterase according to the present invention, wherein the amino acid in position 2 in SEQ ID NO: 1 is missing, said mutated PTEs comprise the at least one mutation selected from the group consisting of: substitutions of the valine V in position 28, the proline P in position 68, the threonine T in position 69, the leucine L in position 73, the tyrosine Y in position 98, the tyrosine Y in position 100, the aspartic acid D in position 142, the arginine R in position 224, the glycine G in position 226, the leucine L in position 227, the phenylalanine F in position 230, the cysteine C in position 259, the tryptophane W in position 264 and the tryptophan W in position 279, of SEQ ID NO: 1 by any other natural amino acid different from the one(s) described in the consensus sequence or by any other non-natural amino acid.

In an even more specific embodiment, the above-mentioned mutated hyperthermophilic PTEs having a lactonase activity, derived from a hyperthermophilic phosphotriesterase according to the present invention, wherein the amino acid in position 2 in SEQ ID NO: 1 is missing, comprise only one mutation, said mutation being selected from the group consisting of: substitutions of the valine V in position 28, the proline P in position 68, the threonine T in position 69, the leucine L in position 73, the aspartic acid D in position 142, the glycine G in position 226, the leucine L in position 227, the phenylalanine F in position 230, the tryptophane W in position 264 and the tryptophan W in position 279, of SEQ ID NO: 1 by any other natural amino acid different from the one(s) described in the consensus sequence or by any other non-natural amino acid.

In a more specific embodiment, the above-mentioned mutated hyperthermophilic PTEs having a lactonase activity, derived from a hyperthermophilic phosphotriesterase according to the present invention, wherein the amino acid in position 2 in SEQ ID NO: 1 is missing, comprise the at least one mutation selected from the group consisting of: substitutions of the glycine G in position 8, the lysine K in position 9, the phenylalanine F or leucine L in position 47, the lysine K in position 55, the isoleucine I in position 77, the valine V in position 84, the isoleucine I in position 123, the leucine L or serine S or asparagine N in position 131, the lysine K or asparagine N in position 165, the isoleucine I in position 168, the aspartic acid D in position 192, the glycine G in position 194, the leucine L in position 229, the leucine L in position 231, the tyrosine Y position 258, the cysteine C in position 260, the threonine T in position 261, the isoleucine I in position 262, the aspartic acid D in position 263, the glycine G in position 265, the threonine T or isoleucine I in position 266, the alanine A in position 267, the lysine K or arginine R in position 268, the proline P in position 269, the glutamic acid E in position 270, the tyrosine Y or leucine L in position 271, the lysine K in position 272, the proline P in position 273, the lysine K in position 274, the leucine L in position 275, the alanine A in position 276, the proline P in position 277, the arginine R or lysine K in position 278, the serine S in position 280, the isoleucine I or methionine M in position 281, the threonine T or alanine A or serine S in position 282, the leucine L in position 283, the isoleucine I in position 284 and the asparagine N or serine S or threonine T in position 298, of SEQ ID NO: 1 by any other natural amino acid different from the one(s) described in the consensus sequence or by any other non-natural amino acid.

In an even more specific embodiment, the above-mentioned mutated hyperthermophilic PTEs having a lactonase activity, derived from a hyperthermophilic phosphotriesterase according to the present invention, wherein the amino acid in position 2 in SEQ ID NO: 1 is missing, comprise only one mutation, said mutation being selected from the group consisting of: substitutions of the glycine G in position 8, the lysine K in position 9, the phenylalanine F or leucine L in position 47, the lysine K in position 55, the isoleucine I in position 77, the valine V in position 84, the isoleucine I in position 123, the leucine L or serine S or asparagine N in position 131, the lysine K or asparagine N in position 165, the isoleucine I in position 168, the aspartic acid D in position 192, the glycine G in position 194, the leucine L in position 229, the leucine L in position 231, the tyrosine Y position 258, the cysteine C in position 260, the threonine T in position 261, the isoleucine I in position 262, the aspartic acid D in position 263, the glycine G in position 265, the threonine T or isoleucine I in position 266, the alanine A in position 267, the lysine K or arginine R in position 268, the proline P in position 269, the glutamic acid E in position 270, the tyrosine Y or leucine L in position 271, the lysine K in position 272, the proline P in position 273, the lysine K in position 274, the leucine L in position 275, the alanine A in position 276, the proline P in position 277, the arginine R or lysine K in position 278, the serine S in position 280, the isoleucine I or methionine M in position 281, the threonine T or alanine A or serine S in position 282, the leucine L in position 283, the isoleucine I in position 284 and the asparagine N or serine S or threonine T in position 298, of SEQ ID NO: 1 by any other natural amino acid different from the one(s) described in the consensus sequence or by any other non-natural amino acid.

A more particular subject of the invention is the above-mentioned mutated hyperthermophilic PTEs having a lactonase activity, derived from the hyperthermophilic PTE of *Sulfolobus solfataricus* corresponding to the sequence SEQ ID NO: 3, or from the hyperthermophilic PTE of *Sulfolobus acidocaldarius* corresponding to the sequence SEQ ID NO:

5, or from the hyperthermophilic PTE of *Sulfolobus islandicus* corresponding to the sequence SEQ ID NO: 7, said sequences SEQ ID NO: 3, SEQ ID NO: 5 and SEQ ID NO: 7 belonging to the consensus sequence SEQ ID NO: 1, the amino acids in position 2 in SEQ ID NO: 1 being missing from SEQ ID NO: 5 and the amino acids in position 2 and 3 in SEQ ID NO: 1 being missing from SEQ ID NO: 3 and SEQ ID NO: 7.

The invention relates more particularly to the above-mentioned mutated hyperthermophilic PTEs having a lactonase activity, derived from a hyperthermophilic phosphotriesterase according to the present invention, wherein the amino acid in position 2 in SEQ ID NO: 1 is missing, and wherein the at least one mutation is selected from the group consisting of:

substitution of the glycine G in position 8 by a non-bulky amino acid selected from the group consisting of PLIVADCSTN, in particular STA, notably S, substitution of the lysine K in position 9 by a charged amino acid selected from the group consisting of RHDEC, in particular EDR, notably E, substitution of the valine V in position 28 by a non-bulky amino acid selected from the group consisting of GPLIADCSTN or by a hydrophobic amino acid selected from the group consisting of ILMFGAPWYC, in particular GIFA, notably A, substitution of the phenylalanine F in position 47 by a non-bulky amino acid selected from the group consisting of GPLIVADCSTN or by a polar amino acid selected from the group consisting of WYSTCQNRKHDE, in particular LYW, notably L, or substitution of the leucine L in position 47 by a non-bulky amino acid selected from the group consisting of GPIVADCSTN or by a polar amino acid selected from the group consisting of WYSTCQNRKHDE, in particular YW, substitution of the lysine K in position 55 by a bulky amino acid selected from the group consisting of EHRQYWFM or by a hydrophobic amino acid selected from the group consisting of VILMFGAPWYC, in particular IRL, notably I, substitution of the threonine T in position 69 by a non-bulky amino acid selected from the group consisting of GPLIVADCSN, in particular VAS, notably S, substitution of the leucine L in position 73 by a hydrophobic amino acid selected from the group consisting of VIMFGAPWYC, in particular CAMI, notably I, substitution of the isoleucine I in position 77 by a non-bulky amino acid selected from the group consisting of GPLVADCSTN, in particular PTV, notably T, substitution of the valine V in position 84 by a non-bulky amino acid selected from the group consisting of GPLIADCSTN or by a hydrophobic amino acid selected from the group consisting of ILMFGAPWYC, in particular AGI, notably A, substitution of the tyrosine Y in position 98 by a bulky amino acid selected from the group consisting of EHKRQWFM or by a hydrophobic amino acid selected from the group consisting of VILMFGAPWC, in particular FCLW, notably W, substitution of the tyrosine Y in position 100 by a bulky amino acid selected from the group consisting of EHKRQWFM or by a hydrophobic amino acid selected from the group consisting of VILMFGAPWC, in particular GEWF, notably F, substitution of the isoleucine I in position 123 by a non-bulky amino acid selected from the group consisting of GPLVADCSTN, in particular LAV, notably L, substitution of the leucine L or serine S or asparagine N in position 131 by a non-bulky amino acid selected from the group consisting of GPIVADCT, in particular PT, notably P, substitution of the aspartic acid D in position 142 by a polar amino acid selected from the group consisting of WYSTCQNRKHE, in particular SET, notably T, substitution of the lysine K in position 165 by a polar amino acid selected from the group consisting of WYSTCNQRHDE, in particular NQR, notably N, or substitution of the asparagine N in position 165 by a polar amino acid selected from the group consisting of WYSTCQRKHDE, in particular QR, substitution of the glycine G in position 194 by a non-bulky amino acid selected from the group consisting of PLIVADCSTN or by a polar amino acid selected from the group consisting of WYSTCNQRKHDE, in particular ST, notably S, substitution of the arginine R in position 224 by a non-bulky amino acid selected from the group consisting of GPLIVADCSTN or by a polar amino acid selected from the group consisting of WYSTCQNKHDE, in particular CSTAH, notably AC, substitution of the leucine L in position 227 by a non-bulky amino acid selected from the group consisting of GPIVADCSTN or by apolar amino acid selected from the group consisting of WYSTCQNRKHDE, in particular AIVH, notably V, substitution of the leucine L in position 229 by a non-bulky amino acid selected from the group consisting of GPIVADCSTN or by a hydrophobic amino acid selected from the group consisting of VIMFGAPWYC, in particular IM, notably M, substitution of the phenylalanine F in position 230 by a non-bulky amino acid selected from the group consisting of GPLIVADCSTN, in particular LTAS, notably S, substitution of the leucine L in position 231 by a non-bulky amino acid selected from the group consisting of GPIVADCSTN, in particular PVA, notably P, substitution of the cysteine C in position 259 by a hydrophobic amino acid selected from the group consisting of VILMFGAPWY, in particular YLIA, notably LA, substitution of the isoleucine I in position 262 by a hydrophobic amino acid selected from the group consisting of VLMFGAPWYC, in particular FWC, notably F, substitution of the tryptophane W in position 264 by a hydrophobic amino acid selected from the group consisting of VILMFGAPYC or by a non-bulky amino acid selected from the group consisting of GPLIVADCSTN, in particular ALMFCITV, notably F, with the proviso that the tryptophane W in position 264 can not be substituted by a phenylalanine F in SEQ ID NO: 3, substitution of the leucine L in position 275 by a hydrophobic amino acid selected from the group consisting of VIMFGAPWYC, in particular AVP, notably P, substitution of the alanine A in position 276 by a hydrophobic amino acid selected from the group consisting of VILMFGPWYC or by a non-bulky amino acid selected from the group consisting of GPLIVDCSTN, in particular NVMT, notably T, substitution of the isoleucine I or methionine M in position 281 by a non-bulky amino acid selected from the group consisting of GPLVADCSTN or by a hydrophobic amino acid selected from the group consisting of VLFGAPWYC, in particular TYP, notably T, substitution of the leucine L in position 283 by a bulky amino acid selected from the group consisting of EKHRQYWFM, in particular FMH, notably M, and substitution of the asparagine N or serine S or threonine T in position 298 by a polar amino acid selected from the group consisting of WYCQRKHDE, notably Q.

These 29 particular substitutions in position G8, K9, V28, F/L47, K55, T69, L73, I77, V84, Y98, Y100, I123, L/S/N131, D142, K/N165, G194, R224, L227, L229, F230, L231, C259, I262, W264, L275, A276, I/M281, L283 and N/S/T298 belong to the first set of substitutions called set 1.

These positions are considered as key positions to modulate enzymatic activities and are also implicated in AHLs substrates accommodation within the active site of the enzyme. Said positions had been identified by directed evolution strategy.

By the term "substitution" is meant the replacement of one amino acid by another. The substitutions can be conservative, i.e. the substituted amino acid is replaced by an amino acid of the same structure or with the same physico-chemical properties (polar, hydrophobic, acidic, basic amino acids) such that the three dimensional structure of the protein remains unchanged, or by contrast non conservative.

When set 1 is related to a sequence, it means that at least one substitution of said set occurs in said sequence.

The invention relates more particularly to the above-mentioned mutated hyperthermophilic PTE having a lactonase activity, derived from a hyperthermophilic phosphotriesterase according to the present invention, wherein the amino acid in position 2 in SEQ ID NO: 1 is missing, and wherein the at least one mutation is selected from the group consisting of:

substitution of the isoleucine I in position 168 by a non-bulky amino acid selected from the group consisting of GPLVADCSTN or by a hydrophobic amino acid selected from the group consisting of VLMFGAPWYC, in particular VAL, notably V, substitution of the aspartic acid D in position 192 by a non-bulky amino acid selected from the group consisting of GPLIVADCSTN or by a polar amino acid selected from the group consisting of WYSTCQNRKHE, in particular ST, notably S, substitution of the tyrosine Y position 258 by a non-bulky amino acid selected from the group consisting of GPLIVADCSTN or by a hydrophobic amino acid selected from the group consisting of VLMFGAPWC, in particular CSVW, notably C, substitution of the cysteine C in position 260 a non-bulky amino acid selected from the group consisting of GPLIVADSTN or by a hydrophobic amino acid selected from the group consisting of VILMFGAPWY, in particular SFWV, notably S, substitution of the threonine T in position 261 a non-bulky amino acid selected from the group consisting of GPLIVADCSN or by a polar amino acid selected from the group consisting of WYSCQNRKHE, in particular GH, notably G, substitution of the aspartic acid D in position 263 by a polar amino acid selected from the group consisting of WYSTCQNRKHE or by a non-bulky amino acid selected from the group consisting of GPLIVACSTN, in particular SLH, substitution of the glycine G in position 265 non-bulky amino acid selected from the group consisting of PLI-VADCSTN or by a hydrophobic amino acid selected from the group consisting of VILMFAPWYC, in particular AVP, substitution of the threonine T or isoleucine I in position 266 by a hydrophobic amino acid selected from the group consisting of VLMFGAPWYC or by a non-bulky amino acid selected from the group consisting of GPLVADCSN, in particular VWP, notably V, substitution of the alanine A in position 267 by a polar amino acid selected from the group consisting of WYSTCQNRKHDE, in particular NQ, notably N, substitution of the lysine K or arginine R in position 268 by a non-bulky amino acid selected from the group consisting of GPLIVADCSTN or by a hydrophobic amino acid selected from the group consisting of VILMFGAPWYC, in particular IAP, notably IP, substitution of the proline P in position 269 by a hydrophobic amino acid selected from the group consisting of VILMFGACWY, in particular MCL, notably M, substitution of the glutamic acid E in position 270 by a polar amino acid selected from the group consisting of WYSTCQNRKHD, in particular DQ, notably D, substitution of the tyrosine Y or leucine L in position 271 by a non-bulky amino acid selected from the group consisting of GPIVADCSTN or by a hydrophobic amino acid selected from the group consisting of VIM-FGAPWC, in particular VA, substitution of the lysine K in position 272 by a bulky amino acid selected from the group consisting of EHRQYWFM or by a hydrophobic amino acid selected from the group consisting of VILMFGAPWYC, in particular MLA, substitution of the proline P in position 273 by a non-bulky amino acid selected from the group consisting of GLIVADCSTN or by a polar amino acid selected from the group consisting of WYSTCQNRKHDE, in particular DEL, notably DL, substitution of the lysine K in position 274 by a non-bulky amino acid selected from the group consisting of GLIVADCSTN or by a polar amino acid selected from the group consisting of WYSTCQNRHD, in particular R, substitution of the proline P in position 277 by a bulky amino acid selected from the group consisting of EHKRQYWFM or by a hydrophobic amino acid selected from the group consisting of VILMFGAWYC, in particular KAV, notably K, substitution of the arginine R or lysine K in position 278 by a polar amino acid selected from the group consisting of WYSTCQNHDE, in particular DNQ, notably DN, substitution of the serine S in position 280 by a non-bulky amino acid selected from the group consisting of GPLIVADCTN or by a polar amino acid selected from the group consisting of WYTCQNRKHDE, in particular GH, substitution of the threonine T or alanine A or serine S in position 282 by a non-bulky amino acid selected from the group consisting of GPLIVDCN or by a hydrophobic amino acid selected from the group consisting of VILMFGPWYC, in particular LV, notably L, and substitution of the isoleucine I in position 284 non-bulky amino acid selected from the group consisting of GPLVADCSTN, in particular VAL, notably V.

These 21 particular substitutions in position I168, D192, Y258, C260, T261, D263, G265, T/I266, A267, K/R268, P269, E270, Y/L271, K272, P273, K274, P277, R/K278, S280, T/A/S282 and I284 belong to the second set of substitutions called set 2.

These positions are mainly implicated in AHLs substrata accommodation within the active site of the enzyme. They were selected by analyzing the evolutive history of this family of enzymes.

When set 2 is related to a sequence, it means that at least one substitution of said set occurs in said sequence.

The invention relates more particularly to the above-mentioned mutated hyperthermophilic PTE having a lactonase activity, derived from a hyperthermophilic phosphotriesterase according to the present invention, wherein the amino acid in position 2 in SEQ ID NO: 1 is missing, and wherein the at least one mutation is selected from the group consisting of:
  substitution of the proline P in position 68 by a non-bulky amino acid selected from the group consisting of GLIVADCSTN, in particular GAV,
  substitution of the glycine G in position 226 by a non-bulky amino acid selected from the group consisting of PLIVADCSTN, in particular AVP,
  and substitution of the tryptophan W in position 279 by a hydrophobic amino acid selected from the group consisting of VILMFGAPYC or by a charged amino acid selected from the group consisting of RKHDEC, in particular RKDI, notably R.

These 3 particular substitutions in position P68, G226 and W279 belong to the third set of substitutions called set 3.

These positions are highly suspected as being implicated in enzymatic activities of the enzyme.

When set 3 is related to a sequence, it means that at least one substitution of said set occurs in said sequence.

The invention relates even more particularly to the above-mentioned mutated hyperthermophilic PTE having a lactonase activity, derived from a hyperthermophilic phosphotriesterase according to the present invention, wherein the amino acid in position 2 in SEQ ID NO: 1 is missing, and wherein the at least one mutation selected from the group consisting of:
  substitution of the glycine G in position 8 by a non-bulky amino acid selected from the group consisting of PLIVADCSTN, in particular STA, notably S,
  substitution of the lysine K in position 9 by a charged amino acid selected from the group consisting of RHDEC, in particular EDR, notably E,
  substitution of the valine V in position 28 by a non-bulky amino acid selected from the group consisting of GPLIADCSTN or by a hydrophobic amino acid selected from the group consisting of ILMFGAPWYC, in particular GIFA, notably A,
  substitution of the phenylalanine F in position 47 by a non-bulky amino acid selected from the group consisting of GPLIVADCSTN or by a polar amino acid selected from the group consisting of WYSTCQNRKHDE, in particular LYW, notably L, or substitution of the leucine L in position 47 by a non-bulky amino acid selected from the group consisting of GPIVADCSTN or by a polar amino acid selected from the group consisting of WYSTCQNRKHDE, in particular YW,
  substitution of the lysine K in position 55 by a bulky amino acid selected from the group consisting of EHRQYWFM or by a hydrophobic amino acid selected from the group consisting of VILMFGAPWYC, in particular IRL, notably I,
  substitution of the threonine T in position 69 by a non-bulky amino acid selected from the group consisting of GPLIVADCSN, in particular VAS, notably S,
  substitution of the leucine L in position 73 by a hydrophobic amino acid selected from the group consisting of VIMFGAPWYC, in particular CAMI, notably I,
  substitution of the isoleucine I in position 77 by a non-bulky amino acid selected from the group consisting of GPLVADCSTN, in particular PTV, notably T,
  substitution of the valine V in position 84 by a non-bulky amino acid selected from the group consisting of GPLIADCSTN or by a hydrophobic amino acid selected from the group consisting of ILMFGAPWYC, in particular AGI, notably A,
  substitution of the tyrosine Y in position 98 by a bulky amino acid selected from the group consisting of EHKRQWFM or by a hydrophobic amino acid selected from the group consisting of VILMFGAPWC, in particular FCLW, notably W,
  substitution of the tyrosine Y in position 100 by a bulky amino acid selected from the group consisting of EHKRQWFM or by a hydrophobic amino acid selected from the group consisting of VILMFGAPWC, in particular GEWF, notably F,
  substitution of the isoleucine I in position 123 by a non-bulky amino acid selected from the group consisting of GPLVADCSTN, in particular LAV, notably L,
  substitution of the leucine L or serine S or asparagine N in position 131 by a non-bulky amino acid selected from the group consisting of GPIVADCT, in particular PT, notably P,
  substitution of the aspartic acid D in position 142 by a polar amino acid selected from the group consisting of WYSTCQNRKHE, in particular SET, notably T,
  substitution of the lysine K in position 165 by a polar amino acid selected from the group consisting of WYSTCNQRHDE, in particular NQR, notably N, or substitution of the asparagine N in position 165 by a polar amino acid selected from the group consisting of WYSTCQRKHDE, in particular QR,
  substitution of the glycine G in position 194 by a non-bulky amino acid selected from the group consisting of PLIVADCSTN or by a polar amino acid selected from the group consisting of WYSTCNQRKHDE, in particular ST, notably S,
  substitution of the arginine R in position 224 by a non-bulky amino acid selected from the group consisting of GPLIVADCSTN or by a polar amino acid selected from the group consisting of WYSTCQNKHDE, in particular CSTAH, notably AC,
  substitution of the leucine L in position 227 by a non-bulky amino acid selected from the group consisting of GPIVADCSTN or by apolar amino acid selected from the group consisting of WYSTCQNRKHDE, in particular AIVH, notably V,
  substitution of the leucine L in position 229 by a non-bulky amino acid selected from the group consisting of GPIVADCSTN or by a hydrophobic amino acid selected from the group consisting of VIMFGAPWYC, in particular IM, notably M,
  substitution of the phenylalanine F in position 230 by a non-bulky amino acid selected from the group consisting of GPLIVADCSTN, in particular LTAS, notably S,
  substitution of the leucine L in position 231 by a non-bulky amino acid selected from the group consisting of GPIVADCSTN, in particular PVA, notably P, substitution of the cysteine C in position 259 by a hydrophobic amino acid selected from the group consisting of VILMFGAPWY, in particular YLIA, notably LA, substitution of the isoleucine I in position 262 by a hydrophobic amino acid selected from the group consisting of VLMFGAPWYC, in particular FWC, notably F, substitution of the tryptophane W in position 264 by a hydrophobic amino acid selected from the group consisting of VILMFGAPYC or by a non-bulky amino acid selected from the group consisting of GPLIVADCSTN, in particular ALMFCITV, notably F, with the proviso that the tryptophane W in position 264 can not be substituted by a phenylalanine F in SEQ ID NO: 3, substitution of the leucine L in position 275 by a hydrophobic amino acid selected from the group consisting of VIMFGAPWYC, in particular AVP, notably P, substitution of the alanine A in position 276 by a hydrophobic amino acid selected from the group consisting of VILMFGPWYC or by a non-bulky amino acid selected from the group consisting of GPLIVDCSTN, in particular NVMT, notably T, substitution of the isoleucine I or methionine M in position 281 by a non-bulky amino acid selected from the group consisting of GPLVADCSTN or by a hydrophobic amino acid selected from the group consisting of VLFGAPWYC, in particular TYP, notably T, substitution of the leucine L in position 283 by a bulky amino acid selected from the group consisting of EKHRQYWFM, in particular FMH, notably M, and substitution of the asparagine N or serine S or threonine T in position 298 by a polar amino acid selected from the group consisting of WYCQRKHDE, notably Q, further comprises at least one mutation selected from the group consisting of:

substitution of the isoleucine I in position 168 by a non-bulky amino acid selected from the group consisting of GPLVADCSTN or by a hydrophobic amino acid selected from the group consisting of VLMFGAPWYC, in particular VAL, notably V, substitution of the aspartic acid D in position 192 by a non-bulky amino acid selected from the group consisting of GPLIVADCSTN or by a polar amino acid selected from the group consisting of WYSTCQNRKHE, in particular ST, notably S, substitution of the tyrosine Y position 258 by a non-bulky amino acid selected from the group consisting of GPLIVADCSTN or by a hydrophobic amino acid selected from the group consisting of VLMFGAPWC, in particular CSVW, notably C, substitution of the cysteine C in position 260 a non-bulky amino acid selected from the group consisting of GPLIVADSTN or by a hydrophobic amino acid selected from the group consisting of VILMFGAPWY, in particular SFWV, notably S, substitution of the threonine T in position 261 a non-bulky amino acid selected from the group consisting of GPLIVADCSN or by a polar amino acid selected from the group consisting of WYSCQNRKHE, in particular GH, notably G, substitution of the aspartic acid D in position 263 by a polar amino acid selected from the group consisting of WYSTCQNRKHE or by a non-bulky amino acid selected from the group consisting of GPLIVACSTN, in particular SLH, substitution of the glycine G in position 265 non-bulky amino acid selected from the group consisting of PLIVADCSTN or by a hydrophobic amino acid selected from the group consisting of VILMFAPWYC, in particular AVP, substitution of the threonine T or isoleucine I in position 266 by a hydrophobic amino acid selected from the group consisting of VLMFGAPWYC or by a non-bulky amino acid selected from the group consisting of GPLVADCSN, in particular VWP, notably V, substitution of the alanine A in position 267 by a polar amino acid selected from the group consisting of WYSTCQNRKHDE, in particular NQ, notably N, substitution of the lysine K or arginine R in position 268 by a non-bulky amino acid selected from the group consisting of GPLIVADCSTN or by a hydrophobic amino acid selected from the group consisting of VILMFGAPWYC, in particular IAP, notably IP, substitution of the proline P in position 269 by a hydrophobic amino acid selected from the group consisting of VILMFGACWY, in particular MCL, notably M, substitution of the glutamic acid E in position 270 by a polar amino acid selected from the group consisting of WYSTCQNRKHD, in particular DQ, notably D, substitution of the tyrosine Y or leucine L in position 271 by a non-bulky amino acid selected from the group consisting of GPIVADCSTN or by a hydrophobic amino acid selected from the group consisting of VIMFGAPWC, in particular VA, substitution of the lysine K in position 272 by a bulky amino acid selected from the group consisting of EHRQYWFM or by a hydrophobic amino acid selected from the group consisting of VILMFGAPWYC, in particular MLA, substitution of the proline P in position 273 by a non-bulky amino acid selected from the group consisting of GLIVADCSTN or by a polar amino acid selected from the group consisting of WYSTCQNRKHDE, in particular DEL, notably DL, substitution of the lysine K in position 274 by a non-bulky amino acid selected from the group consisting of GLIVADCSTN or by a polar amino acid selected from the group consisting of WYSTCQNRHD, in particular R, substitution of the proline P in position 277 by a bulky amino acid selected from the group consisting of EHKRQYWFM or by a hydrophobic amino acid selected from the group consisting of VILMFGAWYC, in particular KAV, notably K, substitution of the arginine R or lysine K in position 278 by a polar amino acid selected from the group consisting of WYSTCQNHDE, in particular DNQ, notably DN, substitution of the serine S in position 280 by a non-bulky amino acid selected from the group consisting of GPLIVADCTN or by a polar amino acid selected from the group consisting of WYTCQNRKHDE, in particular GH, substitution of the threonine T or alanine A or serine S in position 282 by a non-bulky amino acid selected from the group consisting of GPLIVDCN or by a hydrophobic amino acid selected from the group consisting of VILMFGPWYC, in particular LV, notably L, and substitution of the isoleucine I in position 284 non-bulky amino acid selected from the group consisting of GPLVADCSTN, in particular VAL, notably V.

It means that at least one substitution among the 29 particular substitutions of set 1 in position G8, K9, V28, F/L47, K55, T69, L73, I77, V84, Y98, Y100, I123, L/S/N131, D142, N165, G194, R224, L227, L229, F230, L231, C259, I262, W264, L275, A276, I/M281, L283 and N/S/T298 can be associated with at least one substitution among the 21 particular substitutions of set 2 in position I168, D192, Y258, C260, T261, D263, G265, T/I266, A267, K/R268, P269, E270, Y/L271, K272, P273, K274, P277, R/K278, S280, T/A/S282 and I284.

The invention relates even more particularly to the above-mentioned mutated hyperthermophilic PTE having a lactonase activity, derived from a hyperthermophilic phosphotriesterase according to the present invention, wherein the amino acid in position 2 in SEQ ID NO: 1 is missing, and wherein the at least one mutation selected from the group consisting of:

- substitution of the glycine G in position 8 by a non-bulky amino acid selected from the group consisting of PLIVADCSTN, in particular STA, notably S,
- substitution of the lysine K in position 9 by a charged amino acid selected from the group consisting of RHDEC, in particular EDR, notably E,
- substitution of the valine V in position 28 by a non-bulky amino acid selected from the group consisting of GPLIADCSTN or by a hydrophobic amino acid selected from the group consisting of ILMFGAPWYC, in particular GIFA, notably A,
- substitution of the phenylalanine F in position 47 by a non-bulky amino acid selected from the group consisting of GPLIVADCSTN or by a polar amino acid selected from the group consisting of WYSTCQNRKHDE, in particular LYW, notably L, or substitution of the leucine L in position 47 by a non-bulky amino acid selected from the group consisting of GPIVADCSTN or by a polar amino acid selected from the group consisting of WYSTCQNRKHDE, in particular YW,
- substitution of the lysine K in position 55 by a bulky amino acid selected from the group consisting of EHRQYWFM or by a hydrophobic amino acid selected from the group consisting of VILMFGAPWYC, in particular IRL, notably I,
- substitution of the threonine T in position 69 by a non-bulky amino acid selected from the group consisting of GPLIVADCSN, in particular VAS, notably S,
- substitution of the leucine L in position 73 by a hydrophobic amino acid selected from the group consisting of VIMFGAPWYC, in particular CAMI, notably I,
- substitution of the isoleucine I in position 77 by a non-bulky amino acid selected from the group consisting of GPLVADCSTN, in particular PTV, notably T,
- substitution of the valine V in position 84 by a non-bulky amino acid selected from the group consisting of GPLIADCSTN or by a hydrophobic amino acid selected from the group consisting of ILMFGAPWYC, in particular AGI, notably A,
- substitution of the tyrosine Y in position 98 by a bulky amino acid selected from the group consisting of EHKRQWFM or by a hydrophobic amino acid selected from the group consisting of VILMFGAPWC, in particular FCLW, notably W,
- substitution of the tyrosine Y in position 100 by a bulky amino acid selected from the group consisting of EHKRQWFM or by a hydrophobic amino acid selected from the group consisting of VILMFGAPWC, in particular GEWF, notably F,
- substitution of the isoleucine I in position 123 by a non-bulky amino acid selected from the group consisting of GPLVADCSTN, in particular LAV, notably L,
- substitution of the leucine L or serine S or asparagine N in position 131 by a non-bulky amino acid selected from the group consisting of GPIVADCT, in particular PT, notably P,
- substitution of the aspartic acid D in position 142 by a polar amino acid selected from the group consisting of WYSTCQNRKHE, in particular SET, notably T,
- substitution of the lysine K in position 165 by a polar amino acid selected from the group consisting of WYSTCNQRHDE, in particular NQR, notably N, or substitution of the asparagine N in position 165 by a polar amino acid selected from the group consisting of WYSTCQRKHDE, in particular QR,
- substitution of the glycine G in position 194 by a non-bulky amino acid selected from the group consisting of PLIVADCSTN or by a polar amino acid selected from the group consisting of WYSTCNQRKHDE, in particular ST, notably S,
- substitution of the arginine R in position 224 by a non-bulky amino acid selected from the group consisting of GPLIVADCSTN or by a polar amino acid selected from the group consisting of WYSTCQNKHDE, in particular CSTAH, notably AC,
- substitution of the leucine L in position 227 by a non-bulky amino acid selected from the group consisting of GPIVADCSTN or by apolar amino acid selected from the group consisting of WYSTCQNRKHDE, in particular AIVH, notably V,
- substitution of the leucine L in position 229 by a non-bulky amino acid selected from the group consisting of GPIVADCSTN or by a hydrophobic amino acid selected from the group consisting of VIMFGAPWYC, in particular IM, notably M,
- substitution of the phenylalanine F in position 230 by a non-bulky amino acid selected from the group consisting of GPLIVADCSTN, in particular LTAS, notably S,
- substitution of the leucine L in position 231 by a non-bulky amino acid selected from the group consisting of GPIVADCSTN, in particular PVA, notably P,
- substitution of the cysteine C in position 259 by a hydrophobic amino acid selected from the group consisting of VILMFGAPWY, in particular YLIA, notably LA,
- substitution of the isoleucine I in position 262 by a hydrophobic amino acid selected from the group consisting of VLMFGAPWYC, in particular FWC, notably F,
- substitution of the tryptophane W in position 264 by a hydrophobic amino acid selected from the group consisting of VILMFGAPYC or by a non-bulky amino acid selected from the group consisting of GPLIVADCSTN, in particular ALMFCITV, notably F, with the proviso that the tryptophane W in position 264 can not be substituted by a phenylalanine F in SEQ ID NO: 3,
- substitution of the leucine L in position 275 by a hydrophobic amino acid selected from the group consisting of VIMFGAPWYC, in particular AVP, notably P,
- substitution of the alanine A in position 276 by a hydrophobic amino acid selected from the group consisting of VILMFGPWYC or by a non-bulky amino acid selected from the group consisting of GPLIVDCSTN, in particular NVMT, notably T,
- substitution of the isoleucine I or methionine M in position 281 by a non-bulky amino acid selected from the group consisting of GPLVADCSTN or by a hydrophobic amino acid selected from the group consisting of VLFGAPWYC, in particular TYP, notably T, substitution of the leucine L in position 283 by a bulky amino acid selected from the group consisting of EKHRQYWFM, in particular FMH, notably M, and substitution of the asparagine N or serine S or threonine T in position 298 by a polar amino acid selected from the group consisting of WYCQRKHDE, notably Q, further comprises at least one mutation selected from the group consisting of:

substitution of the proline P in position 68 by a non-bulky amino acid selected from the group consisting of GLIVADCSTN, in particular GAV, substitution of the glycine G in position 226 by a non-bulky amino acid selected from the group consisting of PLIVADCSTN, in particular AVP, and substitution of the tryptophan W in position 279 by a hydrophobic amino acid selected from the group consisting of VILMFGAPYC or by a charged amino acid selected from the group consisting of RKHDEC, in particular RKDI, notably R.

It means that at least one substitution among the 29 particular substitutions of set 1 in position G8, K9, V28, F/L47, K55, T69, L73, I77, V84, Y98, Y100, I123, L/S/N131, D142, N165, G194, R224, L227, L229, F230, L231, C259, I262, W264, L275, A276, I/M281, L283 and N/S/T298 can be associated with at least one substitution among the 3 particular substitutions of set 3 in position P68, G226 and W279.

The invention relates even more particularly to the above-mentioned mutated hyperthermophilic PTE having a lactonase activity, derived from a hyperthermophilic phosphotriesterase according to the present invention, wherein the amino acid in position 2 in SEQ ID NO: 1 is missing, and wherein the at least one mutation selected from the group consisting of:

substitution of the glycine G in position 8 by a non-bulky amino acid selected from the group consisting of PLIVADCSTN, in particular STA, notably S, substitution of the lysine K in position 9 by a charged amino acid selected from the group consisting of RHDEC, in particular EDR, notably E, substitution of the valine V in position 28 by a non-bulky amino acid selected from the group consisting of GPLIADCSTN or by a hydrophobic amino acid selected from the group consisting of ILMFGAPWYC, in particular GIFA, notably A, substitution of the phenylalanine F in position 47 by a non-bulky amino acid selected from the group consisting of GPLIVADCSTN or by a polar amino acid selected from the group consisting of WYSTCQNRKHDE, in particular LYW, notably L, or substitution of the leucine L in position 47 by a non-bulky amino acid selected from the group consisting of GPIVADCSTN or by a polar amino acid selected from the group consisting of WYSTCQNRKHDE, in particular YW, substitution of the lysine K in position 55 by a bulky amino acid selected from the group consisting of EHRQYWFM or by a hydrophobic amino acid selected from the group consisting of VILMFGAPWYC, in particular IRL, notably I, substitution of the threonine T in position 69 by a non-bulky amino acid selected from the group consisting of GPLIVADCSN, in particular VAS, notably S, substitution of the leucine L in position 73 by a hydrophobic amino acid selected from the group consisting of VIMFGAPWYC, in particular CAMI, notably I, substitution of the isoleucine I in position 77 by a non-bulky amino acid selected from the group consisting of GPLVADCSTN, in particular PTV, notably T, substitution of the valine V in position 84 by a non-bulky amino acid selected from the group consisting of GPLIADCSTN or by a hydrophobic amino acid selected from the group consisting of ILMFGAPWYC, in particular AGI, notably A, substitution of the tyrosine Y in position 98 by a bulky amino acid selected from the group consisting of EHKRQWFM or by a hydrophobic amino acid selected from the group consisting of VILMFGAPWC, in particular FCLW, notably W, substitution of the tyrosine Y in position 100 by a bulky amino acid selected from the group consisting of EHKRQWFM or by a hydrophobic amino acid selected from the group consisting of VILMFGAPWC, in particular GEWF, notably F, substitution of the isoleucine I in position 123 by a non-bulky amino acid selected from the group consisting of GPLVADCSTN, in particular LAV, notably L, substitution of the leucine L or serine S or asparagine N in position 131 by a non-bulky amino acid selected from the group consisting of GPIVADCT, in particular PT, notably P, substitution of the aspartic acid D in position 142 by a polar amino acid selected from the group consisting of WYSTCQNRKHE, in particular SET, notably T, substitution of the lysine K in position 165 by a polar amino acid selected from the group consisting of WYSTCNQRHDE, in particular NQR, notably N, or substitution of the asparagine N in position 165 by a polar amino acid selected from the group consisting of WYSTCQRKHDE, in particular QR, substitution of the glycine G in position 194 by a non-bulky amino acid selected from the group consisting of PLIVADCSTN or by a polar amino acid selected from the group consisting of WYSTCNQRKHDE, in particular ST, notably S, substitution of the arginine R in position 224 by a non-bulky amino acid selected from the group consisting of GPLIVADCSTN or by a polar amino acid selected from the group consisting of WYSTCQNKHDE, in particular CSTAH, notably AC, substitution of the leucine L in position 227 by a non-bulky amino acid selected from the group consisting of GPIVADCSTN or by apolar amino acid selected from the group consisting of WYSTCQNRKHDE, in particular AIVH, notably V, substitution of the leucine L in position 229 by a non-bulky amino acid selected from the group consisting of GPIVADCSTN or by a hydrophobic amino acid selected from the group consisting of VIMFGAPWYC, in particular IM, notably M, substitution of the phenylalanine F in position 230 by a non-bulky amino acid selected from the group consisting of GPLIVADCSTN, in particular LTAS, notably S, substitution of the leucine L in position 231 by a non-bulky amino acid selected from the group consisting of GPIVADCSTN, in particular PVA, notably P, substitution of the cysteine C in position 259 by a hydrophobic amino acid selected from the group consisting of VILMFGAPWY, in particular YLIA, notably LA, substitution of the isoleucine I in position 262 by a hydrophobic amino acid selected from the group consisting of VLMFGAPWYC, in particular FWC, notably F, substitution of the tryptophane W in position 264 by a hydrophobic amino acid selected from the group consisting of VILMFGAPYC or by a non-bulky amino acid selected from the group consisting of GPLIVADCSTN, in particular ALMFCITV, notably F, with the proviso that the tryptophane W in position 264 can not be substituted by a phenylalanine F in SEQ ID NO: 3, substitution of the leucine L in position 275 by a hydrophobic amino acid selected from the group consisting of VIMFGAPWYC, in particular AVP, notably P, substitution of the alanine A in position 276 by a hydrophobic amino acid selected from the group consisting of VILMFGPWYC or by a non-bulky amino acid selected from the group consisting of GPLIVDCSTN, in particular NVMT, notably T, substitution of the isoleucine I or methionine M in position 281 by a non-bulky amino acid selected from the group consisting of GPLVADCSTN or by a hydrophobic amino acid selected from the group consisting of VLFGAPWYC, in particular TYP, notably T, substitution of the leucine L in position 283 by a bulky amino acid selected from the group consisting of EKHRQYWFM, in particular FMH, notably M, and substitution of the asparagine N or serine S or threonine T in position 298 by a polar amino acid selected from the group consisting of WYCQRKHDE, notably Q, further comprises at least one mutation selected from the group consisting of:

- substitution of the isoleucine I in position 168 by a non-bulky amino acid selected from the group consisting of GPLVADCSTN or by a hydrophobic amino acid selected from the group consisting of VLMFGAPWYC, in particular VAL, notably V,
- substitution of the aspartic acid D in position 192 by a non-bulky amino acid selected from the group consisting of GPLIVADCSTN or by a polar amino acid selected from the group consisting of WYSTCQNRKHE, in particular ST, notably S,
- substitution of the tyrosine Y position 258 by a non-bulky amino acid selected from the group consisting of GPLIVADCSTN or by a hydrophobic amino acid selected from the group consisting of VLMFGAPWC, in particular CSVW, notably C,
- substitution of the cysteine C in position 260 a non-bulky amino acid selected from the group consisting of GPLIVADSTN or by a hydrophobic amino acid selected from the group consisting of VILMFGAPWY, in particular SFWV, notably S,
- substitution of the threonine T in position 261 a non-bulky amino acid selected from the group consisting of GPLIVADCSN or by a polar amino acid selected from the group consisting of WYSCQNRKHE, in particular GH, notably G,
- substitution of the aspartic acid D in position 263 by a polar amino acid selected from the group consisting of WYSTCQNRKHE or by a non-bulky amino acid selected from the group consisting of GPLIVACSTN, in particular SLH,
- substitution of the glycine G in position 265 non-bulky amino acid selected from the group consisting of PLIVADCSTN or by a hydrophobic amino acid selected from the group consisting of VILMFAPWYC, in particular AVP,
- substitution of the threonine T or isoleucine I in position 266 by a hydrophobic amino acid selected from the group consisting of VLMFGAPWYC or by a non-bulky amino acid selected from the group consisting of GPLVADCSN, in particular VWP, notably V,
- substitution of the alanine A in position 267 by a polar amino acid selected from the group consisting of WYSTCQNRKHDE, in particular NQ, notably N,
- substitution of the lysine K or arginine R in position 268 by a non-bulky amino acid selected from the group consisting of GPLIVADCSTN or by a hydrophobic amino acid selected from the group consisting of VILMFGAPWYC, in particular IAP, notably IP,
- substitution of the proline P in position 269 by a hydrophobic amino acid selected from the group consisting of VILMFGACWY, in particular MCL, notably M,
- substitution of the glutamic acid E in position 270 by a polar amino acid selected from the group consisting of WYSTCQNRKHD, in particular DQ, notably D,
- substitution of the tyrosine Y or leucine L in position 271 by a non-bulky amino acid selected from the group consisting of GPIVADCSTN or by a hydrophobic amino acid selected from the group consisting of VIMFGAPWC, in particular VA,
- substitution of the lysine K in position 272 by a bulky amino acid selected from the group consisting of EHRQYWFM or by a hydrophobic amino acid selected from the group consisting of VILMFGAPWYC, in particular MLA,
- substitution of the proline P in position 273 by a non-bulky amino acid selected from the group consisting of GLIVADCSTN or by a polar amino acid selected from the group consisting of WYSTCQNRKHDE, in particular DEL, notably DL,
- substitution of the lysine K in position 274 by a non-bulky amino acid selected from the group consisting of GLIVADCSTN or by a polar amino acid selected from the group consisting of WYSTCQNRHD, in particular R,
- substitution of the proline P in position 277 by a bulky amino acid selected from the group consisting of EHKRQYWFM or by a hydrophobic amino acid selected from the group consisting of VILMFGAWYC, in particular KAV, notably K,
- substitution of the arginine R or lysine K in position 278 by a polar amino acid selected from the group consisting of WYSTCQNHDE, in particular DNQ, notably DN,
- substitution of the serine S in position 280 by a non-bulky amino acid selected from the group consisting of GPLIVADCTN or by a polar amino acid selected from the group consisting of WYTCQNRKHDE, in particular GH,
- substitution of the threonine T or alanine A or serine S in position 282 by a non-bulky amino acid selected from the group consisting of GPLIVDCN or by a hydrophobic amino acid selected from the group consisting of VILMFGPWYC, in particular LV, notably L,
- and substitution of the isoleucine I in position 284 non-bulky amino acid selected from the group consisting of GPLVADCSTN, in particular VAL, notably V, further comprises at least one mutation selected from the group consisting of:

- substitution of the proline P in position 68 by a non-bulky amino acid selected from the group consisting of GLIVADCSTN, in particular GAV,
- substitution of the glycine G in position 226 by a non-bulky amino acid selected from the group consisting of PLIVADCSTN, in particular AVP,
- and substitution of the tryptophan W in position 279 by a hydrophobic amino acid selected from the group consisting of VILMFGAPYC or by a charged amino acid selected from the group consisting of RKHDEC, in particular RKDI, notably R.

It means that at the at least one substitution among the 29 particular substitutions of set 1 in position G8, K9, V28, F/L47, K55, T69, L73, I77, V84, Y98, Y100, I123, L/S/N131, D142, N165, G194, R224, L227, L229, F230, L231, C259, I262, W264, L275, A276, I/M281, L283 and N/S/T298 can be associated with at least one substitution among the 21 particular substitutions of set 2 in position I168, D192, Y258, C260, T261, D263, G265, T/I266, A267, K/R268, P269, E270, Y/L271, K272, P273, K274, P277, R/K278, S280, T/A/S282 and I284 and with at least one substitution among the 3 particular substitutions of set 3 in position P68, G226 and W279.

The invention relates even more particularly to the above-mentioned mutated hyperthermophilic PTE having a lactonase activity, derived from a hyperthermophilic phosphotriesterase according to the present invention, wherein the amino acid in position 2 in SEQ ID NO: 1 is missing, and wherein the at least one mutation selected from the group consisting of:

substitution of the isoleucine I in position 168 by a non-bulky amino acid selected from the group consisting of GPLVADCSTN or by a hydrophobic amino acid selected from the group consisting of VLMFGAPWYC, in particular VAL, notably V, substitution of the aspartic acid D in position 192 by a non-bulky amino acid selected from the group consisting of GPLIVADCSTN or by a polar amino acid selected from the group consisting of WYSTCQNRKHE, in particular ST, notably S, substitution of the tyrosine Y position 258 by a non-bulky amino acid selected from the group consisting of GPLIVADCSTN or by a hydrophobic amino acid selected from the group consisting of VLMFGAPWC, in particular CSVW, notably C, substitution of the cysteine C in position 260 a non-bulky amino acid selected from the group consisting of GPLIVADSTN or by a hydrophobic amino acid selected from the group consisting of VILMFGAPWY, in particular SFWV, notably S, substitution of the threonine T in position 261 a non-bulky amino acid selected from the group consisting of GPLIVADCSN or by a polar amino acid selected from the group consisting of WYSCQNRKHE, in particular GH, notably G, substitution of the aspartic acid D in position 263 by a polar amino acid selected from the group consisting of WYSTCQNRKHE or by a non-bulky amino acid selected from the group consisting of GPLIVACSTN, in particular SLH, substitution of the glycine G in position 265 non-bulky amino acid selected from the group consisting of PLIVADCSTN or by a hydrophobic amino acid selected from the group consisting of VILMFAPWYC, in particular AVP, substitution of the threonine T or isoleucine I in position 266 by a hydrophobic amino acid selected from the group consisting of VLMFGAPWYC or by a non-bulky amino acid selected from the group consisting of GPLVADCSN, in particular VWP, notably V, substitution of the alanine A in position 267 by a polar amino acid selected from the group consisting of WYSTCQNRKHDE, in particular NQ, notably N, substitution of the lysine K or arginine R in position 268 by a non-bulky amino acid selected from the group consisting of GPLIVADCSTN or by a hydrophobic amino acid selected from the group consisting of VILMFGAPWYC, in particular IAP, notably IP, substitution of the proline P in position 269 by a hydrophobic amino acid selected from the group consisting of VILMFGACWY, in particular MCL, notably M, substitution of the glutamic acid E in position 270 by a polar amino acid selected from the group consisting of WYSTCQNRKHD, in particular DQ, notably D, substitution of the tyrosine Y or leucine L in position 271 by a non-bulky amino acid selected from the group consisting of GPIVADCSTN or by a hydrophobic amino acid selected from the group consisting of VIMFGAPWC, in particular VA, substitution of the lysine K in position 272 by a bulky amino acid selected from the group consisting of EHRQYWFM or by a hydrophobic amino acid selected from the group consisting of VILMFGAPWYC, in particular MLA, substitution of the proline P in position 273 by a non-bulky amino acid selected from the group consisting of GLIVADCSTN or by a polar amino acid selected from the group consisting of WYSTCQNRKHDE, in particular DEL, notably DL, substitution of the lysine K in position 274 by a non-bulky amino acid selected from the group consisting of GLIVADCSTN or by a polar amino acid selected from the group consisting of WYSTCQNRHD, in particular R, substitution of the proline P in position 277 by a bulky amino acid selected from the group consisting of EHKRQYWFM or by a hydrophobic amino acid selected from the group consisting of VILMFGAWYC, in particular KAV, notably K, substitution of the arginine R or lysine K in position 278 by a polar amino acid selected from the group consisting of WYSTCQNHDE, in particular DNQ, notably DN, substitution of the serine S in position 280 by a non-bulky amino acid selected from the group consisting of GPLIVADCTN or by a polar amino acid selected from the group consisting of WYTCQNRKHDE, in particular GH, substitution of the threonine T or alanine A or serine S in position 282 by a non-bulky amino acid selected from the group consisting of GPLIVDCN or by a hydrophobic amino acid selected from the group consisting of VILMFGPWYC, in particular LV, notably L, and substitution of the isoleucine I in position 284 non-bulky amino acid selected from the group consisting of GPLVADCSTN, in particular VAL, notably V, further comprises at least one mutation selected from the group consisting of:

substitution of the proline P in position 68 by a non-bulky amino acid selected from the group consisting of GLIVADCSTN, in particular GAV, substitution of the glycine G in position 226 by a non-bulky amino acid selected from the group consisting of PLIVADCSTN, in particular AVP, and substitution of the tryptophan W in position 279 by a hydrophobic amino acid selected from the group consisting of VILMFGAPYC or by a charged amino acid selected from the group consisting of RKHDEC, in particular RKDI, notably R.

It means that at the at least one substitution among the 21 particular substitutions of set 2 in position I168, D192, Y258, C260, T261, D263, G265, T/I266, A267, K/R268, P269, E270, Y/L271, K272, P273, K274, P277, R/K278, S280, T/A/S282 and I284 can be associated with at least one substitution among the 3 particular substitutions of set 3 in position P68, G226 and W279.

The invention relates more particularly to the above-mentioned mutated hyperthermophilic PTEs having a lactonase activity, derived from the hyperthermophilic PTE of *Sulfolobus solfataricus* corresponding to the sequence SEQ ID NO: 3, said mutated PTEs comprising the at least one mutation selected from the group consisting of: substitutions of the valine V in position 27, the proline P in position 67, the threonine T in position 68, the leucine L in position 72, the tyrosine Y in position 97, the tyrosine Y in position 99, the aspartic acid D in position 141, the arginine R in position 223, the glycine G in position 225, the leucine L in position 226, the phenylalanine F in position 229, the cysteine C in position 258, the tryptophane W in position 263 and the tryptophan W in position 278, of SEQ ID NO: 3 by any other natural or non-natural amino acid.

In an even more specific embodiment, the above-mentioned mutated hyperthermophilic PTEs having a lactonase activity, derived from the hyperthermophilic PTE of *Sulfolobus solfataricus* corresponding to the sequence SEQ ID NO: 3, comprise only one mutation, said mutation being selected from the group consisting of: substitutions of the valine V in position 27, the proline P in position 67, the threonine T in position 68, the leucine L in position 72, the aspartic acid D in position 141, the glycine G in position 225, the leucine L in position 226, the phenylalanine F in position 229, the tryptophane W in position 263 and the tryptophan W in position 278, of SEQ ID NO: 3 by any other natural or non-natural amino acid.

In a more specific embodiment, the above-mentioned mutated hyperthermophilic PTEs having a lactonase activity, derived from the hyperthermophilic PTE of *Sulfolobus solfataricus* corresponding to the sequence SEQ ID NO: 3, comprise the at least one mutation selected from the group consisting of: substitutions of the glycine G in position 7, the lysine K in position 8, the phenylalanine F in position 46, the lysine K in position 54, the isoleucine I in position 76, the valine V in position 83, the isoleucine I in position 122, the leucine L in position 130, the lysine K in position 164, the isoleucine I in position 167, the aspartic acid D in position 191, the glycine G in position 193, the leucine L in position 228, the leucine L in position 230, the tyrosine Y position 257, the cysteine C in position 259, the threonine T in position 260, the isoleucine I in position 261, the aspartic acid D in position 262, the glycine G in position 264, the threonine T in position 265, the alanine A in position 266, the lysine K in position 267, the proline P in position 268, the glutamic acid E in position 269, the tyrosine Y in position 270, the lysine K in position 271, the proline P in position 272, the lysine K in position 273, the leucine L in position 274, the alanine A in position 275, the proline P in position 276, the arginine R in position 277, the serine S in position 279, the isoleucine I in position 280, the threonine T in position 281, the leucine L in position 282, the isoleucine I in position 283 and the asparagine N in position 297, of SEQ ID NO: 3 by any other natural or non-natural amino acid.

In an even more specific embodiment, the above-mentioned mutated hyperthermophilic PTEs having a lactonase activity, derived from the hyperthermophilic PTE of *Sulfolobus solfataricus* corresponding to the sequence SEQ ID NO: 3, comprise only one mutation, said mutation being selected from the group consisting of: substitutions of the glycine G in position 7, the lysine K in position 8, the phenylalanine F in position 46, the lysine K in position 54, the isoleucine I in position 76, the valine V in position 83,
the isoleucine I in position 122, the leucine L in position 130, the lysine K in position 164, the isoleucine I in position 167, the aspartic acid D in position 191, the glycine G in position 193, the leucine L in position 228, the leucine L in position 230, the tyrosine Y position 257, the cysteine C in position 259, the threonine T in position 260, the isoleucine I in position 261, the aspartic acid D in position 262, the glycine G in position 264, the threonine T in position 265, the alanine A in position 266, the lysine K in position 267, the proline P in position 268, the glutamic acid E in position 269, the tyrosine Y in position 270, the lysine K in position 271, the proline P in position 272, the lysine K in position 273, the leucine L in position 274, the alanine A in position 275, the proline P in position 276, the arginine R in position 277, the serine S in position 279, the isoleucine I in position 280, the threonine T in position 281, the leucine L in position 282, the isoleucine I in position 283 and the asparagine N in position 297, of SEQ ID NO: 3 by any other natural or non-natural amino acid.

The invention relates more particularly to the above-mentioned mutated hyperthermophilic PTE having a lactonase activity, derived from the hyperthermophilic PTE of *Sulfolobus solfataricus* corresponding to the sequence SEQ ID NO: 3, and wherein the at least one mutation is selected from the group consisting of:

substitution of the glycine G in position 7 by a non-bulky amino acid selected from the group consisting of PLIVADCSTN, in particular STA, notably S, substitution of the lysine K in position 8 by a charged amino acid selected from the group consisting of RHDEC, in particular EDR, notably E, substitution of the valine V in position 27 by a non-bulky amino acid selected from the group consisting of GPLIADCSTN or by a hydrophobic amino acid selected from the group consisting of ILMFGAPWYC, in particular GIFA, notably A, substitution of the phenylalanine F in position 46 by a non-bulky amino acid selected from the group consisting of GPLIVADCSTN or by a polar amino acid selected from the group consisting of WYSTCQNRKHDE, in particular LYW, notably L, substitution of the lysine K in position 54 by a bulky amino acid selected from the group consisting of EHRQYWFM or by a hydrophobic amino acid selected from the group consisting of VILMFGAPWYC, in particular IRL, notably I, substitution of the threonine T in position 68 by a non-bulky amino acid selected from the group consisting of GPLIVADCSN, in particular VAS, notably S, substitution of the leucine L in position 72 by a hydrophobic amino acid selected from the group consisting of VIMFGAPWYC, in particular CAMI, notably I, substitution of the isoleucine I in position 76 by a non-bulky amino acid selected from the group consisting of GPLVADCSTN, in particular PTV, notably T, substitution of the valine V in position 83 by a non-bulky amino acid selected from the group consisting of GPLIADCSTN or by a hydrophobic amino acid selected from the group consisting of ILMFGAPWYC, in particular AGI, notably A, substitution of the tyrosine Y in position 97 by a bulky amino acid selected from the group consisting of EHKRQWFM or by a hydrophobic amino acid selected from the group consisting of VILMFGAPWC, in particular FCLW, notably W, substitution of the tyrosine Y in position 99 by a bulky amino acid selected from the group consisting of EHKRQWFM or by a hydrophobic amino acid selected from the group consisting of VILMFGAPWC, in particular GEWF, notably F, substitution of the isoleucine I in position 122 by a non-bulky amino acid selected from the group consisting of GPLVADCSTN, in particular LAV, notably L, substitution of the leucine L in position 130 by a non-bulky amino acid selected from the group consisting of GPLIVADCSTN, in particular PST, notably P, substitution of the aspartic acid D in position 141 by a polar amino acid selected from the group consisting of WYSTCQNRKHE, in particular SET, notably T, substitution of the lysine K in position 164 by a polar amino acid selected from the group consisting of WYSTCQNRHDE, in particular NQR, notably N, substitution of the glycine G in position 193 by a non-bulky amino acid selected from the group consisting of PLIVADCSTN or by a polar amino acid selected from the group consisting of WYSTCNQRKHDE, in particular ST, notably S, substitution of the arginine R in position 223 by a non-bulky amino acid selected from the group consisting of GPLIVADCSTN or by a polar amino acid selected from the group consisting of WYSTCQNKHDE, in particular CSTAH, notably AC, substitution of the leucine L in position 226 by a non-bulky amino acid selected from the group consisting of GPIVADCSTN or by apolar amino acid selected from the group consisting of WYSTCQNRKHDE, in particular AIVH, notably V, substitution of the leucine L in position 228 by a non-bulky amino acid selected from the group consisting of GPIVADCSTN or by a hydrophobic amino acid selected from the group consisting of VIMFGAPWYC, in particular IM, notably M, substitution of the phenylalanine F in position 229 by a non-bulky amino acid selected from the group consisting of GPLIVADCSTN, in particular LTAS, notably S, substitution of the leucine L in position 230 by a non-bulky amino acid selected from the group consisting of GPIVADCSTN, in particular PVA, notably P, substitution of the cysteine C in position 258 by a hydrophobic amino acid selected from the group consisting of VILMFGAPWY, in particular YLIA, notably LA, substitution of the isoleucine I in position 261 by a hydrophobic amino acid selected from the group consisting of VLMFGAPWYC, in particular FWC, notably F, substitution of the tryptophane W in position 263 by a non-bulky amino acid selected from the group consisting of GPLIVADCSTN or by a hydrophobic amino acid selected from the group consisting of VILMGAPYC, in particular ALMCITV, substitution of the leucine L in position 274 by a hydrophobic amino acid selected from the group consisting of VIMFGAPWYC, in particular AVP, notably P, substitution of the alanine A in position 275 by a hydrophobic amino acid selected from the group consisting of VILMFGPWYC or by a non-bulky amino acid selected from the group consisting of GPLIVDCSTN, in particular NVMT, notably T, substitution of the isoleucine I in position 280 by a non-bulky amino acid selected from the group consisting of GPLVADCSTN or by a hydrophobic amino acid selected from the group consisting of VLMFGAPWYC, in particular TMYP, notably T, substitution of the leucine L in position 282 by a bulky amino acid selected from the group consisting of EKHRQYWFM, in particular FMH, notably M, and substitution of the asparagine N in position 297 by a polar amino acid selected from the group consisting of WYSTCQRKHDE, in particular QST, notably S.

These 29 particular substitutions in position G7, K8, V27, F46, K54, T68, L72, I76, V83, Y97, Y99, I122, L130, D141, N164, G193, R223, L226, L228, F229, L230, C258, I261, W263, L274, A275, I280, L282 and N297 belong to the four set of substitutions called set 4.

The invention relates more particularly to the abovementioned mutated hyperthermophilic PTE having a lactonase activity, derived from the hyperthermophilic PTE of *Sulfolobus solfataricus* corresponding to the sequence SEQ ID NO: 3, and wherein the at least one mutation is selected from the group consisting of:

substitution of the isoleucine I in position 167 by a non-bulky amino acid selected from the group consisting of GPLVADCSTN or by a hydrophobic amino acid selected from the group consisting of VLMFGAPWYC, in particular VAL, notably V, substitution of the aspartic acid D in position 191 by a non-bulky amino acid selected from the group consisting of GPLIVADCSTN or by a polar amino acid selected from the group consisting of WYSTCQNRKHE, in particular ST, notably S, substitution of the tyrosine Y position 257 by a non-bulky amino acid selected from the group consisting of GPLIVADCSTN or by a hydrophobic amino acid selected from the group consisting of VLMFGAPWC, in particular CSVW, notably C, substitution of the cysteine C in position 259 a non-bulky amino acid selected from the group consisting of GPLIVADSTN or by a hydrophobic amino acid selected from the group consisting of VILMFGAPWY, in particular SFWV, notably S, substitution of the threonine T in position 260 a non-bulky amino acid selected from the group consisting of GPLIVADCSN or by a polar amino acid selected from the group consisting of WYSCQNRKHE, in particular GH, notably G, substitution of the aspartic acid D in position 262 by a polar amino acid selected from the group consisting of WYSTCQNRKHE or by a non-bulky amino acid selected from the group consisting of GPLIVADCSTN, in particular SLH, substitution of the glycine G in position 264 non-bulky amino acid selected from the group consisting of PLIVADCSTN or by a hydrophobic amino acid selected from the group consisting of VILMFAPWYC, in particular AVP, substitution of the threonine T in position 265 by a hydrophobic amino acid selected from the group consisting of VILMFGAPWYC or by a non-bulky amino acid selected from the group consisting of GPLIVADCSN, in particular VWP, notably V, substitution of the alanine A in position 266 by a polar amino acid selected from the group consisting of WYSTCQNRKHDE, in particular NQ, notably N, substitution of the lysine K in position 267 by a non-bulky amino acid selected from the group consisting of GPLIVADCSTN or by a hydrophobic amino acid selected from the group consisting of VILMFGAPWYC, in particular IAP, notably IP, substitution of the proline P in position 268 by a hydrophobic amino acid selected from the group consisting of VILMFGAWYC, in particular MCL, notably M, substitution of the glutamic acid E in position 269 by a polar amino acid selected from the group consisting of WYSTCQNRKHD, in particular DQ, notably D, substitution of the tyrosine Y in position 270 by a non-bulky amino acid selected from the group consisting of GPLIVADCSTN or by a hydrophobic amino acid selected from the group consisting of VILMFGAPWC, in particular VAL, substitution of the lysine K in position 271 by a bulky amino acid selected from the group consisting of EHRQYWFM or by a hydrophobic amino acid selected from the group consisting of VILMFGAPWYC, in particular MLA, substitution of the proline P in position 272 by a non-bulky amino acid selected from the group consisting of GLIVADCSTN or by a polar amino acid selected from the group consisting of WYSTCQNRKHDE, in particular DEL, notably DL, substitution of the lysine K in position 273 by a non-bulky amino acid selected from the group consisting of GPLIVADCSTN or by a polar amino acid selected from the group consisting of WYSTCQNRHD, in particular RP, substitution of the proline P in position 276 by a bulky amino acid selected from the group consisting of EHRQYWFM or by a hydrophobic amino acid selected from the group consisting of VILMFGAWYC, in particular KAV, notably K, substitution of the arginine R in position 277 by a polar amino acid selected from the group consisting of WYSTCQNKHDE, in particular DNQ, notably DN, substitution of the serine S in position 279 by a non-bulky amino acid selected from the group consisting of GPLIVADCTN or by a polar amino acid selected from the group consisting of WYTCQNRKHDE, in particular GH, substitution of the threonine T in position 281 by a non-bulky amino acid selected from the group consisting of GPLIVADCSN or by a hydrophobic amino acid selected from the group consisting of VILMFGAPWYC, in particular ALV, notably AL, and substitution of the isoleucine I in position 283 non-bulky amino acid selected from the group consisting of GPLIVADCSTN, in particular VAL, notably V.

These 21 particular substitutions in position I167, D191, Y257, C259, T260, D262, G264, T265, A266, K267, P268, E269, Y270, K271, P272, K273, P276, R277, S279, T281 and I283 belong to the Pith set of substitutions called set 5.

The invention relates more particularly to the above-mentioned mutated hyperthermophilic PTE having a lactonase activity, derived from the hyperthermophilic PTE of Sulfolobus solfataricus corresponding to the sequence SEQ ID NO: 3, and wherein the at least one mutation is selected from the group consisting of:

substitution of the proline P in position 67 by a non-bulky amino acid selected from the group consisting of GLIVADCSTN, in particular GAV, substitution of the glycine G in position 225 by a non-bulky amino acid selected from the group consisting of PLIVADCSTN, in particular AVP, and substitution of the tryptophan W in position 278 by a hydrophobic amino acid selected from the group consisting of VILMFGAPYC or by a charged amino acid selected from the group consisting of RKHDEC, in particular RKDI, notably R.

These 3 particular substitutions in position P67, G225 and W278 belong to the sixth set of substitutions called set 6.

The invention also relates to the above-mentioned mutated hyperthermophilic PTE having a lactonase activity, derived from the hyperthermophilic PTE of Sulfolobus solfataricus corresponding to the sequence SEQ ID NO: 3, wherein the at least one mutation selected from the group consisting of:

substitution of the glycine G in position 7 by a non-bulky amino acid selected from the group consisting of PLIVADCSTN, in particular STA, notably S, substitution of the lysine K in position 8 by a charged amino acid selected from the group consisting of RHDEC, in particular EDR, notably E, substitution of the valine V in position 27 by a non-bulky amino acid selected from the group consisting of GPLIADCSTN or by a hydrophobic amino acid selected from the group consisting of ILMFGAPWYC, in particular GIFA, notably A, substitution of the phenylalanine F in position 46 by a non-bulky amino acid selected from the group consisting of GPLIVADCSTN or by a polar amino acid selected from the group consisting of WYSTCQNRKHDE, in particular LYW, notably L, substitution of the lysine K in position 54 by a bulky amino acid selected from the group consisting of EHRQYWFM or by a hydrophobic amino acid selected from the group consisting of VILMFGAPWYC, in particular IRL, notably I, substitution of the threonine T in position 68 by a non-bulky amino acid selected from the group consisting of GPLIVADCSN, in particular VAS, notably S, substitution of the leucine L in position 72 by a hydrophobic amino acid selected from the group consisting of VIMFGAPWYC, in particular CAMI, notably I, substitution of the isoleucine I in position 76 by a non-bulky amino acid selected from the group consisting of GPLVADCSTN, in particular PTV, notably T, substitution of the valine V in position 83 by a non-bulky amino acid selected from the group consisting of GPLIADCSTN or by a hydrophobic amino acid selected from the group consisting of ILMFGAPWYC, in particular AGI, notably A, substitution of the tyrosine Y in position 97 by a bulky amino acid selected from the group consisting of EHKRQWFM or by a hydrophobic amino acid selected from the group consisting of VILMFGAPWC, in particular FCLW, notably W, substitution of the tyrosine Y in position 99 by a bulky amino acid selected from the group consisting of EHKRQWFM or by a hydrophobic amino acid selected from the group consisting of VILMFGAPWC, in particular GEWF, notably F, substitution of the isoleucine I in position 122 by a non-bulky amino acid selected from the group consisting of GPLVADCSTN, in particular LAV, notably L, substitution of the leucine L in position 130 by a non-bulky amino acid selected from the group consisting of GPLIVADCSTN, in particular PST, notably P, substitution of the aspartic acid D in position 141 by a polar amino acid selected from the group consisting of WYSTCQNRKHE, in particular SET, notably T, substitution of the lysine K in position 164 by a polar amino acid selected from the group consisting of WYSTCQNRHDE, in particular NQR, notably N, substitution of the glycine G in position 193 by a non-bulky amino acid selected from the group consisting of PLIVADCSTN or by a polar amino acid selected from the group consisting of WYSTCNQRKHDE, in particular ST, notably S, substitution of the arginine R in position 223 by a non-bulky amino acid selected from the group consisting of GPLIVADCSTN or by a polar amino acid selected from the group consisting of WYSTCQNRHDE, in particular CSTAH, notably AC, substitution of the leucine L in position 226 by a non-bulky amino acid selected from the group consisting of GPIVADCSTN or by apolar amino acid selected from the group consisting of WYSTCQNRKHDE, in particular AIVH, notably V, substitution of the leucine L in position 228 by a non-bulky amino acid selected from the group consisting of GPIVADCSTN or by a hydrophobic amino acid selected from the group consisting of VIMFGAPWYC, in particular IM, notably M, substitution of the phenylalanine F in position 229 by a non-bulky amino acid selected from the group consisting of GPLIVADCSTN, in particular LTAS, notably S, substitution of the leucine L in position 230 by a non-bulky amino acid selected from the group consisting of GPIVADCSTN, in particular PVA, notably P, substitution of the cysteine C in position 258 by a hydrophobic amino acid selected from the group consisting of VILMFGAPWY, in particular YLIA, notably LA, substitution of the isoleucine I in position 261 by a hydrophobic amino acid selected from the group consisting of VLMFGAPWYC, in particular FWC, notably F, substitution of the tryptophane W in position 263 by a non-bulky amino acid selected from the group consisting of GPLIVADCSTN or by a hydrophobic amino acid selected from the group consisting of VILMGAPYC, in particular ALMCITV, substitution of the leucine L in position 274 by a hydrophobic amino acid selected from the group consisting of VIMFGAPWYC, in particular AVP, notably P, substitution of the alanine A in position 275 by a hydrophobic amino acid selected from the group consisting of VILMFGPWYC or by a non-bulky amino acid selected from the group consisting of GPLIVDCSTN, in particular NVMT, notably T, substitution of the isoleucine I in position 280 by a non-bulky amino acid selected from the group consisting of GPLVADCSTN or by a hydrophobic amino acid selected from the group consisting of VLMFGAPWYC, in particular TMYP, notably T, substitution of the leucine L in position 282 by a bulky amino acid selected from the group consisting of EKHRQYWFM, in particular FMH, notably M, and substitution of the asparagine N in position 297 by a polar amino acid selected from the group consisting of WYSTCQRKHDE, in particular QST, notably S, further comprises at least one mutation selected from the group consisting of:

substitution of the isoleucine I in position 167 by a non-bulky amino acid selected from the group consisting of GPLVADCSTN or by a hydrophobic amino acid selected from the group consisting of VLMFGAPWYC, in particular VAL, notably V, substitution of the aspartic acid D in position 191 by a non-bulky amino acid selected from the group consisting of GPLIVADCSTN or by a polar amino acid selected from the group consisting of WYSTCQNRKHE, in particular ST, notably S, substitution of the tyrosine Y position 257 by a non-bulky amino acid selected from the group consisting of GPLIVADCSTN or by a hydrophobic amino acid selected from the group consisting of VLMFGAPWC, in particular CSVW, notably C, substitution of the cysteine C in position 259 a non-bulky amino acid selected from the group consisting of GPLIVADSTN or by a hydrophobic amino acid selected from the group consisting of VILMFGAPWY, in particular SFWV, notably S, substitution of the threonine T in position 260 a non-bulky amino acid selected from the group consisting of GPLIVADCSN or by a polar amino acid selected from the group consisting of WYSCQNRKHE, in particular GH, notably G, substitution of the aspartic acid D in position 262 by a polar amino acid selected from the group consisting of WYSTCQNRKHE or by a non-bulky amino acid selected from the group consisting of GPLIVADCSTN, in particular SLH, substitution of the glycine G in position 264 non-bulky amino acid selected from the group consisting of PLIVADCSTN or by a hydrophobic amino acid selected from the group consisting of VILMFAPWYC, in particular AVP, substitution of the threonine T in position 265 by a hydrophobic amino acid selected from the group consisting of VILMFGAPWYC or by a non-bulky amino acid selected from the group consisting of GPLIVADCSN, in particular VWP, notably V, substitution of the alanine A in position 266 by a polar amino acid selected from the group consisting of WYSTCQNRKHDE, in particular NQ, notably N, substitution of the lysine K in position 267 by a non-bulky amino acid selected from the group consisting of GPLIVADCSTN or by a hydrophobic amino acid selected from the group consisting of VILMFGAPWYC, in particular IAP, notably IP, substitution of the proline P in position 268 by a hydrophobic amino acid selected from the group consisting of VILMFGAWYC, in particular MCL, notably M, substitution of the glutamic acid E in position 269 by a polar amino acid selected from the group consisting of WYSTCQNRKHD, in particular DQ, notably D, substitution of the tyrosine Y in position 270 by a non-bulky amino acid selected from the group consisting of GPLIVADCSTN or by a hydrophobic amino acid selected from the group consisting of VILMFGAPWC, in particular VAL, substitution of the lysine K in position 271 by a bulky amino acid selected from the group consisting of EHRQYWFM or by a hydrophobic amino acid selected from the group consisting of VILMFGAPWYC, in particular MLA, substitution of the proline P in position 272 by a non-bulky amino acid selected from the group consisting of GLIVADCSTN or by a polar amino acid selected from the group consisting of WYSTCQNRKHDE, in particular DEL, notably DL, substitution of the lysine K in position 273 by a non-bulky amino acid selected from the group consisting of GPLIVADCSTN or by a polar amino acid selected from the group consisting of WYSTCQNRHD, in particular RP, substitution of the proline P in position 276 by a bulky amino acid selected from the group consisting of EHRQYWFM or by a hydrophobic amino acid selected from the group consisting of VILMFGAWYC, in particular KAV, notably K, substitution of the arginine R in position 277 by a polar amino acid selected from the group consisting of WYSTCQNKHDE, in particular DNQ, notably DN, substitution of the serine S in position 279 by a non-bulky amino acid selected from the group consisting of GPLIVADCTN or by a polar amino acid selected from the group consisting of WYTCQNRKHDE, in particular GH, substitution of the threonine T in position 281 by a non-bulky amino acid selected from the group consisting of GPLIVADCSN or by a hydrophobic amino acid selected from the group consisting of VILMFGAPWYC, in particular ALV, notably AL, and substitution of the isoleucine I in position 283 non-bulky amino acid selected from the group consisting of GPLVADCSTN, in particular VAL, notably V.

It means that at least one substitution among the 29 particular substitutions of set 4 in position G7, K8, V27, F46, K54, T68, L72, I76, V83, Y97, Y99, I122, L130, D141, N164, G193, R223, L226, L228, F229, L230, C258, I261, W263, L274, A275, I280, L282 and N297 can be associated with at least one substitution among the 21 particular substitutions of set 5 in position I167, D191, Y257, C259, T260, D262, G264, T265, A266, K267, P268, E269, Y270, K271, P272, K273, P276, R277, S279, T281.

The invention also relates to the above-mentioned mutated hyperthermophilic PTE having a lactonase activity, derived from the hyperthermophilic PTE of *Sulfolobus solfataricus* corresponding to the sequence SEQ ID NO: 3, wherein the at least one mutation selected from the group consisting of:

substitution of the glycine G in position 7 by a non-bulky amino acid selected from the group consisting of PLIVADCSTN, in particular STA, notably S, substitution of the lysine K in position 8 by a charged amino acid selected from the group consisting of RHDEC, in particular EDR, notably E, substitution of the valine V in position 27 by a non-bulky amino acid selected from the group consisting of GPLIADCSTN or by a hydrophobic amino acid selected from the group consisting of ILMFGAPWYC, in particular GIFA, notably A, substitution of the phenylalanine F in position 46 by a non-bulky amino acid selected from the group consisting of GPLIVADCSTN or by a polar amino acid selected from the group consisting of WYSTCQNRKHDE, in particular LYW, notably L, substitution of the lysine K in position 54 by a bulky amino acid selected from the group consisting of EHRQYWFM or by a hydrophobic amino acid selected from the group consisting of VILMFGAPWYC, in particular IRL, notably I, substitution of the threonine T in position 68 by a non-bulky amino acid selected from the group consisting of GPLIVADCSN, in particular VAS, notably S, substitution of the leucine L in position 72 by a hydrophobic amino acid selected from the group consisting of VIMFGAPWYC, in particular CAMI, notably I, substitution of the isoleucine I in position 76 by a non-bulky amino acid selected from the group consisting of GPLVADCSTN, in particular PTV, notably T, substitution of the valine V in position 83 by a non-bulky amino acid selected from the group consisting of GPLIADCSTN or by a hydrophobic amino acid selected from the group consisting of ILMFGAPWYC, in particular AGI, notably A, substitution of the tyrosine Y in position 97 by a bulky amino acid selected from the group consisting of EHKRQWFM or by a hydrophobic amino acid selected from the group consisting of VILMFGAPWC, in particular FCLW, notably W, substitution of the tyrosine Y in position 99 by a bulky amino acid selected from the group consisting of EHKRQWFM or by a hydrophobic amino acid selected from the group consisting of VILMFGAPWC, in particular GEWF, notably F, substitution of the isoleucine I in position 122 by a non-bulky amino acid selected from the group consisting of GPLVADCSTN, in particular LAV, notably L, substitution of the leucine L in position 130 by a non-bulky amino acid selected from the group consisting of GPLIVADCSTN, in particular PST, notably P, substitution of the aspartic acid D in position 141 by a polar amino acid selected from the group consisting of WYSTCQNRKHE, in particular SET, notably T, substitution of the lysine K in position 164 by a polar amino acid selected from the group consisting of WYSTCQNRHDE, in particular NQR, notably N, substitution of the glycine G in position 193 by a non-bulky amino acid selected from the group consisting of PLIVADCSTN or by a polar amino acid selected from the group consisting of WYSTCNQRKHDE, in particular ST, notably S, substitution of the arginine R in position 223 by a non-bulky amino acid selected from the group consisting of GPLIVADCSTN or by a polar amino acid selected from the group consisting of WYSTCQNKHDE, in particular CSTAH, notably AC, substitution of the leucine L in position 226 by a non-bulky amino acid selected from the group consisting of GPIVADCSTN or by apolar amino acid selected from the group consisting of WYSTCQNRKHDE, in particular AIVH, notably V, substitution of the leucine L in position 228 by a non-bulky amino acid selected from the group consisting of GPIVADCSTN or by a hydrophobic amino acid selected from the group consisting of VIMFGAPWYC, in particular IM, notably M, substitution of the phenylalanine F in position 229 by a non-bulky amino acid selected from the group consisting of GPLIVADCSTN, in particular LTAS, notably S, substitution of the leucine L in position 230 by a non-bulky amino acid selected from the group consisting of GPIVADCSTN, in particular PVA, notably P, substitution of the cysteine C in position 258 by a hydrophobic amino acid selected from the group consisting of VILMFGAPWY, in particular YLIA, notably LA, substitution of the isoleucine I in position 261 by a hydrophobic amino acid selected from the group consisting of VLMFGAPWYC, in particular FWC, notably F, substitution of the tryptophane W in position 263 by a non-bulky amino acid selected from the group consisting of GPLIVADCSTN or by a hydrophobic amino acid selected from the group consisting of VILMGAPYC, in particular ALMCITV, substitution of the leucine L in position 274 by a hydrophobic amino acid selected from the group consisting of VIMFGAPWYC, in particular AVP, notably P, substitution of the alanine A in position 275 by a hydrophobic amino acid selected from the group consisting of VILMFGPWYC or by a non-bulky amino acid selected from the group consisting of GPLIVDCSTN, in particular NVMT, notably T, substitution of the isoleucine I in position 280 by a non-bulky amino acid selected from the group consisting of GPLVADCSTN or by a hydrophobic amino acid selected from the group consisting of VLMFGAPWYC, in particular TMYP, notably T, substitution of the leucine L in position 282 by a bulky amino acid selected from the group consisting of EKHRQYWFM, in particular FMH, notably M, and substitution of the asparagine N in position 297 by a polar amino acid selected from the group consisting of WYSTCQRKHDE, in particular QST, notably S, further comprises at least one mutation selected from the group consisting of:

substitution of the proline P in position 67 by a non-bulky amino acid selected from the group consisting of GLIVADCSTN, in particular GAV, substitution of the glycine G in position 225 by a non-bulky amino acid selected from the group consisting of PLIVADCSTN, in particular AVP, and substitution of the tryptophan W in position 278 by a hydrophobic amino acid selected from the group consisting of VILMFGAPYC or by a charged amino acid selected from the group consisting of RKHDEC, in particular RKDI, notably R.

It means that at least one substitution among the 29 particular substitutions of set 4 in position G7, K8, V27, F46, K54, T68, L72, I76, V83, Y97, Y99, I122, L130, D141, N164, G193, R223, L226, L228, F229, L230, C258, I261, W263, L274, A275, I280, L282 and N297 can be associated with at least one substitution among the 3 particular substitutions of set 6 in position P67, G225 and W278.

The invention also relates to the above-mentioned mutated hyperthermophilic PTE having a lactonase activity, derived from the hyperthermophilic PTE of *Sulfolobus solfataricus* corresponding to the sequence SEQ ID NO: 3, wherein the at least one mutation selected from the group consisting of:

substitution of the glycine G in position 7 by a non-bulky amino acid selected from the group consisting of PLIVADCSTN, in particular STA, notably S, substitution of the lysine K in position 8 by a charged amino acid selected from the group consisting of RHDEC, in particular EDR, notably E, substitution of the valine V in position 27 by a non-bulky amino acid selected from the group consisting of GPLIADCSTN or by a hydrophobic amino acid selected from the group consisting of ILMFGAPWYC, in particular GIFA, notably A, substitution of the phenylalanine F in position 46 by a non-bulky amino acid selected from the group consisting of GPLIVADCSTN or by a polar amino acid selected from the group consisting of WYSTCQNRKHDE, in particular LYW, notably L, substitution of the lysine K in position 54 by a bulky amino acid selected from the group consisting of EHRQYWFM or by a hydrophobic amino acid selected from the group consisting of VILMFGAPWYC, in particular IRL, notably I, substitution of the threonine T in position 68 by a non-bulky amino acid selected from the group consisting of GPLIVADCSN, in particular VAS, notably S, substitution of the leucine L in position 72 by a hydrophobic amino acid selected from the group consisting of VIMFGAPWYC, in particular CAMI, notably I, substitution of the isoleucine I in position 76 by a non-bulky amino acid selected from the group consisting of GPLVADCSTN, in particular PTV, notably T, substitution of the valine V in position 83 by a non-bulky amino acid selected from the group consisting of GPLIADCSTN or by a hydrophobic amino acid selected from the group consisting of ILMFGAPWYC, in particular AGI, notably A, substitution of the tyrosine Y in position 97 by a bulky amino acid selected from the group consisting of EHKRQWFM or by a hydrophobic amino acid selected from the group consisting of VILMFGAPWC, in particular FCLW, notably W, substitution of the tyrosine Y in position 99 by a bulky amino acid selected from the group consisting of EHKRQWFM or by a hydrophobic amino acid selected from the group consisting of VILMFGAPWC, in particular GEWF, notably F, substitution of the isoleucine I in position 122 by a non-bulky amino acid selected from the group consisting of GPLVADCSTN, in particular LAV, notably L, substitution of the leucine L in position 130 by a non-bulky amino acid selected from the group consisting of GPLIVADCSTN, in particular PST, notably P, substitution of the aspartic acid D in position 141 by a polar amino acid selected from the group consisting of WYSTCQNRKHE, in particular SET, notably T, substitution of the lysine K in position 164 by a polar amino acid selected from the group consisting of WYSTCQNRHDE, in particular NQR, notably N, substitution of the glycine G in position 193 by a non-bulky amino acid selected from the group consisting of PLIVADCSTN or by a polar amino acid selected from the group consisting of WYSTCNQRKHDE, in particular ST, notably S, substitution of the arginine R in position 223 by a non-bulky amino acid selected from the group consisting of GPLIVADCSTN or by a polar amino acid selected from the group consisting of WYSTCQNKHDE, in particular CSTAH, notably AC, substitution of the leucine L in position 226 by a non-bulky amino acid selected from the group consisting of GPIVADCSTN or by apolar amino acid selected from the group consisting of WYSTCQNRKHDE, in particular AIVH, notably V, substitution of the leucine L in position 228 by a non-bulky amino acid selected from the group consisting of GPIVADCSTN or by a hydrophobic amino acid selected from the group consisting of VIMFGAPWYC, in particular IM, notably M, substitution of the phenylalanine F in position 229 by a non-bulky amino acid selected from the group consisting of GPLIVADCSTN, in particular LTAS, notably S, substitution of the leucine L in position 230 by a non-bulky amino acid selected from the group consisting of GPIVADCSTN, in particular PVA, notably P, substitution of the cysteine C in position 258 by a hydrophobic amino acid selected from the group consisting of VILMFGAPWY, in particular YLIA, notably LA, substitution of the isoleucine I in position 261 by a hydrophobic amino acid selected from the group consisting of VLMFGAPWYC, in particular FWC, notably F, substitution of the tryptophane W in position 263 by a non-bulky amino acid selected from the group consisting of GPLIVADCSTN or by a hydrophobic amino acid selected from the group consisting of VILMGAPYC, in particular ALMCITV, substitution of the leucine L in position 274 by a hydrophobic amino acid selected from the group consisting of VIMFGAPWYC, in particular AVP, notably P, substitution of the alanine A in position 275 by a hydrophobic amino acid selected from the group consisting of VILMFGPWYC or by a non-bulky amino acid selected from the group consisting of GPLIVDCSTN, in particular NVMT, notably T, substitution of the isoleucine I in position 280 by a non-bulky amino acid selected from the group consisting of GPLVADCSTN or by a hydrophobic amino acid selected from the group consisting of VLMFGAPWYC, in particular TMYP, notably T, substitution of the leucine L in position 282 by a bulky amino acid selected from the group consisting of EKHRQYWFM, in particular FMH, notably M, and substitution of the asparagine N in position 297 by a polar amino acid selected from the group consisting of WYSTCQRKHDE, in particular QST, notably S, further comprises at least one mutation selected from the group consisting of:

substitution of the isoleucine I in position 167 by a non-bulky amino acid selected from the group consisting of GPLVADCSTN or by a hydrophobic amino acid selected from the group consisting of VLMFGAPWYC, in particular VAL, notably V, substitution of the aspartic acid D in position 191 by a non-bulky amino acid selected from the group consisting of GPLIVADCSTN or by a polar amino acid selected from the group consisting of WYSTCQNRKHE, in particular ST, notably S, substitution of the tyrosine Y position 257 by a non-bulky amino acid selected from the group consisting of GPLIVADCSTN or by a hydrophobic amino acid selected from the group consisting of VLMFGAPWC, in particular CSVW, notably C, substitution of the cysteine C in position 259 a non-bulky amino acid selected from the group consisting of GPLIVADSTN or by a hydrophobic amino acid selected from the group consisting of VILMFGAPWY, in particular SFWV, notably S, substitution of the threonine T in position 260 a non-bulky amino acid selected from the group consisting of GPLIVADCSN or by a polar amino acid selected from the group consisting of WYSCQNRKHE, in particular GH, notably G, substitution of the aspartic acid D in position 262 by a polar amino acid selected from the group consisting of WYSTCQNRKHE or by a non-bulky amino acid selected from the group consisting of GPLIVADCSTN, in particular SLH, substitution of the glycine G in position 264 non-bulky amino acid selected from the group consisting of PLIVADCSTN or by a hydrophobic amino acid selected from the group consisting of VILMFAPWYC, in particular AVP, substitution of the threonine T in position 265 by a hydrophobic amino acid selected from the group consisting of VILMFGAPWYC or by a non-bulky amino acid selected from the group consisting of GPLIVADCSN, in particular VWP, notably V, substitution of the alanine A in position 266 by a polar amino acid selected from the group consisting of WYSTCQNRKHDE, in particular NQ, notably N, substitution of the lysine K in position 267 by a non-bulky amino acid selected from the group consisting of GPLIVADCSTN or by a hydrophobic amino acid selected from the group consisting of VILMFGAPWYC, in particular IAP, notably IP, substitution of the proline P in position 268 by a hydrophobic amino acid selected from the group consisting of VILMFGAWYC, in particular MCL, notably M, substitution of the glutamic acid E in position 269 by a polar amino acid selected from the group consisting of WYSTCQNRKHD, in particular DQ, notably D, substitution of the tyrosine Y in position 270 by a non-bulky amino acid selected from the group consisting of GPLIVADCSTN or by a hydrophobic amino acid selected from the group consisting of VILMFGAPWC, in particular VAL, substitution of the lysine K in position 271 by a bulky amino acid selected from the group consisting of EHRQYWFM or by a hydrophobic amino acid selected from the group consisting of VILMFGAPWYC, in particular MLA, substitution of the proline P in position 272 by a non-bulky amino acid selected from the group consisting of GLIVADCSTN or by a polar amino acid selected from the group consisting of WYSTCQNRKHDE, in particular DEL, notably DL, substitution of the lysine K in position 273 by a non-bulky amino acid selected from the group consisting of GPLIVADCSTN or by a polar amino acid selected from the group consisting of WYSTCQNRHD, in particular RP, substitution of the proline P in position 276 by a bulky amino acid selected from the group consisting of EHRQYWFM or by a hydrophobic amino acid selected from the group consisting of VILMFGAWYC, in particular KAV, notably K, substitution of the arginine R in position 277 by a polar amino acid selected from the group consisting of WYSTCQNKHDE, in particular DNQ, notably DN, substitution of the serine S in position 279 by a non-bulky amino acid selected from the group consisting of GPLIVADCTN or by a polar amino acid selected from the group consisting of WYTCQNRKHDE, in particular GH, substitution of the threonine T in position 281 by a non-bulky amino acid selected from the group consisting of GPLIVADCSN or by a hydrophobic amino acid selected from the group consisting of VILMFGAPWYC, in particular ALV, notably AL, and substitution of the isoleucine I in position 283 non-bulky amino acid selected from the group consisting of GPLVADCSTN, in particular VAL, notably V, further comprises at least one mutation selected from the group consisting of:

substitution of the proline P in position 67 by a non-bulky amino acid selected from the group consisting of GLIVADCSTN, in particular GAV, substitution of the glycine G in position 225 by a non-bulky amino acid selected from the group consisting of PLIVADCSTN, in particular AVP, and substitution of the tryptophan W in position 278 by a hydrophobic amino acid selected from the group consisting of VILMFGAPYC or by a charged amino acid selected from the group consisting of RKHDEC, in particular RKDI, notably R.

It means that at least one substitution among the 29 particular substitutions of set 4 in position G7, K8, V27, F46, K54, T68, L72, I76, V83, Y97, Y99, I122, L130, D141, N164, G193, R223, L226, L228, F229, L230, C258, I261, W263, L274, A275, I280, L282 and N297 can be associated with at least one substitution among the 21 particular substitutions of set 5 in position I167, D191, Y257, C259, T260, D262, G264, T265, A266, K267, P268, E269, Y270, K271, P272, K273, P276, R277, S279, T281 and with at least one substitution among the 3 particular substitutions of set 6 in position P67, G225 and W278.

The invention also relates to the above-mentioned mutated hyperthermophilic PTE having a lactonase activity, derived from the hyperthermophilic PTE of *Sulfolobus solfataricus* corresponding to the sequence SEQ ID NO: 3, wherein the at least one mutation selected from the group consisting of:

- substitution of the isoleucine I in position 167 by a non-bulky amino acid selected from the group consisting of GPLVADCSTN or by a hydrophobic amino acid selected from the group consisting of VLMFGAPWYC, in particular VAL, notably V,
- substitution of the aspartic acid D in position 191 by a non-bulky amino acid selected from the group consisting of GPLIVADCSTN or by a polar amino acid selected from the group consisting of WYSTCQNRKHE, in particular ST, notably S,
- substitution of the tyrosine Y position 257 by a non-bulky amino acid selected from the group consisting of GPLIVADCSTN or by a hydrophobic amino acid selected from the group consisting of VLMFGAPWC, in particular CSVW, notably C,
- substitution of the cysteine C in position 259 a non-bulky amino acid selected from the group consisting of GPLIVADSTN or by a hydrophobic amino acid selected from the group consisting of VILMFGAPWY, in particular SFWV, notably S,
- substitution of the threonine T in position 260 a non-bulky amino acid selected from the group consisting of GPLIVADCSN or by a polar amino acid selected from the group consisting of WYSCQNRKHE, in particular GH, notably G,
- substitution of the aspartic acid D in position 262 by a polar amino acid selected from the group consisting of WYSTCQNRKHE or by a non-bulky amino acid selected from the group consisting of GPLIVADCSTN, in particular SLH,
- substitution of the glycine G in position 264 non-bulky amino acid selected from the group consisting of PLIVADCSTN or by a hydrophobic amino acid selected from the group consisting of VILMFAPWYC, in particular AVP,
- substitution of the threonine T in position 265 by a hydrophobic amino acid selected from the group consisting of VILMFGAPWYC or by a non-bulky amino acid selected from the group consisting of GPLIVADCSN, in particular VWP, notably V,
- substitution of the alanine A in position 266 by a polar amino acid selected from the group consisting of WYSTCQNRKHDE, in particular NQ, notably N,
- substitution of the lysine K in position 267 by a non-bulky amino acid selected from the group consisting of GPLIVADCSTN or by a hydrophobic amino acid selected from the group consisting of VILMFGAPWYC, in particular IAP, notably IP,
- substitution of the proline P in position 268 by a hydrophobic amino acid selected from the group consisting of VILMFGAWYC, in particular MCL, notably M,
- substitution of the glutamic acid E in position 269 by a polar amino acid selected from the group consisting of WYSTCQNRKHD, in particular DQ, notably D,
- substitution of the tyrosine Y in position 270 by a non-bulky amino acid selected from the group consisting of GPLIVADCSTN or by a hydrophobic amino acid selected from the group consisting of VILMFGAPWC, in particular VAL,
- substitution of the lysine K in position 271 by a bulky amino acid selected from the group consisting of EHRQYWFM or by a hydrophobic amino acid selected from the group consisting of VILMFGAPWYC, in particular MLA,
- substitution of the proline P in position 272 by a non-bulky amino acid selected from the group consisting of GLIVADCSTN or by a polar amino acid selected from the group consisting of WYSTCQNRKHDE, in particular DEL, notably DL,
- substitution of the lysine K in position 273 by a non-bulky amino acid selected from the group consisting of GPLIVADCSTN or by a polar amino acid selected from the group consisting of WYSTCQNRHD, in particular RP,
- substitution of the proline P in position 276 by a bulky amino acid selected from the group consisting of EHRQYWFM or by a hydrophobic amino acid selected from the group consisting of VILMFGAWYC, in particular KAV, notably K,
- substitution of the arginine R in position 277 by a polar amino acid selected from the group consisting of WYSTCQNKHDE, in particular DNQ, notably DN,
- substitution of the serine S in position 279 by a non-bulky amino acid selected from the group consisting of GPLIVADCTN or by a polar amino acid selected from the group consisting of WYTCQNRKHDE, in particular GH,
- substitution of the threonine T in position 281 by a non-bulky amino acid selected from the group consisting of GPLIVADCSN or by a hydrophobic amino acid selected from the group consisting of VILMFGAPWYC, in particular ALV, notably AL,
- and substitution of the isoleucine I in position 283 non-bulky amino acid selected from the group consisting of GPLVADCSTN, in particular VAL, notably V, further comprises at least one mutation selected from the group consisting of:

- substitution of the proline P in position 67 by a non-bulky amino acid selected from the group consisting of GLIVADCSTN, in particular GAV,
- substitution of the glycine G in position 225 by a non-bulky amino acid selected from the group consisting of PLIVADCSTN, in particular AVP,
- and substitution of the tryptophan W in position 278 by a hydrophobic amino acid selected from the group consisting of VILMFGAPYC or by a charged amino acid selected from the group consisting of RKHDEC, in particular RKDI, notably R.

It means that the at least one substitution among the 21 particular substitutions of set 5 in position I167, D191, Y257, C259, T260, D262, G264, T265, A266, K267, P268, E269, Y270, K271, P272, K273, P276, R277, S279, T281 can be associated with at least one substitution among the 3 particular substitutions of set 6 in position P67, G225 and W278.

A more particular subject of the invention is mutated hyperthermophilic PTE having a lactonase activity according to the present invention, derived from the hyperthermophilic PTE of *Sulfolobus solfataricus* corresponding to the sequence SEQ ID NO: 3, said mutated hyperthermophilic PTE correspond to the following sequences:

SEQ ID NO: 9 corresponding to the SEQ ID NO: 3 comprising the following one mutation: substitution of the tryptophan W in position 263 by a methionine M, SEQ ID NO: 11 corresponding to the SEQ ID NO: 3 comprising the following one mutation: substitution of the tryptophan W in position 263 by a leucine L, SEQ ID NO: 13 corresponding to the SEQ ID NO: 3 comprising the following one mutation: substitution of the tryptophan W in position 263 by an alanine A, SEQ ID NO: 15 corresponding to the SEQ ID NO: 3 comprising the following one mutation: substitution of the tryptophan W in position 263 by an isoleucine I, SEQ ID NO: 17 corresponding to the SEQ ID NO: 3 comprising the following one mutation: substitution of the tryptophan W in position 263 by a valine V, SEQ ID NO: 19 corresponding to the SEQ ID NO: 3 comprising the following one mutation: substitution of the tryptophan W in position 263 by a threonine T, SEQ ID NO: 21 corresponding to the SEQ ID NO: 3 comprising the following three mutations: substitution of the cysteine C in position 258 by a leucine L, substitution of the isoleucine I in position 261 by a phenylalanine F, substitution of the tryptophan W in position 263 by an alanine A, SEQ ID NO: 23 corresponding to the SEQ ID NO: 3 comprising the following four mutations: substitution of the valine V in position 27 by an alanine A, substitution of the tyrosine Y in position 97 by a tryptophan W, substitution of the leucine L in position 228 by a methionine M, substitution of the tryptophan W in position 263 by a methionine M, SEQ ID NO: 25 corresponding to the SEQ ID NO: 3 comprising the following four mutations: substitution of the valine V in position 27 by an alanine A, substitution of the tyrosine Y in position 97 by a tryptophan W, substitution of the tryptophan W in position 263 by a leucine L, substitution of the isoleucine I in position 280 by a threonine T, SEQ ID NO: 27 corresponding to the SEQ ID NO: 3 comprising the following four mutations: substitution of the phenylalanine F in position 46 by a leucine L, substitution of the cytosine C in position 258 by an alanine A, substitution of the tryptophan W in position 263 by a methionine M, substitution of the isoleucine I in position 280 by a threonine T, SEQ ID NO: 29 corresponding to the SEQ ID NO: 3 comprising the following six mutations: substitution of the valine V in position 27 by an alanine A, substitution of the isoleucine I in position 76 by a threonine T, substitution of the tyrosine Y in position 97 by a tryptophan W, substitution of the tyrosine Y in position 99 by a phenylalanine F, substitution of the leucine L in position 130 by a proline P, substitution of the leucine L in position 226 by a valine V, SEQ ID NO: 31 corresponding to the SEQ ID NO: 3 comprising the following six mutations: substitution of the leucine L in position 72 by an isoleucine I, substitution of the tyrosine Y in position 99 by a phenylalanine F, substitution of the isoleucine I in position 122 by a leucine L, substitution of the leucine L in position 228 by a methionine M, substitution of the phenylalanine F in position 229 by a serine S, substitution of the tryptophan W in position 263 by a leucine L, SEQ ID NO: 33 corresponding to the SEQ ID NO: 3 comprising the following seven mutations: substitution of the threonine T in position 68 by a serine S, substitution of the leucine L in position 72 by an isoleucine I, substitution of the leucine L in position 130 by a proline P, substitution of the leucine L in position 228 by a methionine M, substitution of the phenylalanine F in position 229 by a serine S, substitution of the tryptophan W in position 263 by a methionine M, substitution of the leucine L in position 274 by a proline P, SEQ ID NO: 35 corresponding to the SEQ ID NO: 3 comprising the following six mutations: substitution of the threonine T in position 68 by a serine S, substitution of the isoleucine I in position 76 by a threonine T, substitution of the tyrosine Y in position 97 by a tryptophan W, substitution of the tyrosine Y in position 99 by a phenylalanine F, substitution of the leucine L in position 228 by a methionine M, substitution of the tryptophan W in position 263 by a leucine L, SEQ ID NO: 37 corresponding to the SEQ ID NO: 3 comprising the following five mutations: substitution of the lysine K in position 8 by an glutamic acid E, substitution of the phenylalanine F in position 46 by a leucine L, substitution of the tyrosine Y in position 97 by a tryptophan W, substitution of the tyrosine Y in position 99 by a phenylalanine F, substitution of the leucine L in position 228 by a methionine M, SEQ ID NO: 39 corresponding to the SEQ ID NO: 3 comprising the following two mutations: substitution of the leucine L in position 72 by an isoleucine I, substitution of the tryptophan W in position 263 by a phenylalanine F, SEQ ID NO: 41 corresponding to the SEQ ID NO: 3 comprising the following five mutations: substitution of the threonine T in position 68 by a serine S, substitution of the tyrosine Y in position 97 by a tryptophan W, substitution of the tyrosine Y in position 99 by a phenylalanine F, substitution of the leucine L in position 130 by a proline P, substitution of the leucine L in position 228 by a methionine M, SEQ ID NO: 43 corresponding to the SEQ ID NO: 3 comprising the following four mutations: substitution of the valine V in position 27 by an alanine A, substitution of the phenylalanine F in position 46 by a leucine L, substitution of the leucine L in position 226 by a valine V, substitution the tryptophan W in position 263 by a leucine L, SEQ ID NO: 45 corresponding to the SEQ ID NO: 3 comprising the following eight mutations: substitution of the proline P in position 67 by a valine V, substitution of the threonine T in position 68 by a serine S, substitution of the tyrosine Y in position 97 by a tryptophan W, substitution of the tyrosine Y in position 99 by a phenylalanine F, substitution of the leucine L in position 228 by a methionine M, substitution of the cysteine C in position 258 by an alanine A, substitution the tryptophan W in position 263 by a leucine L, substitution of the isoleucine I in position 280 by a threonine T, SEQ ID NO: 47 corresponding to the SEQ ID NO: 3 comprising the following eight mutations: substitution of the phenylalanine F in position 46 by a leucine L, substitution of the threonine T in position 68 by a serine S, substitution of the tyrosine Y in position 97 by a tryptophan W, substitution of the tyrosine Y in position 99 by a phenylalanine F, substitution of the leucine L in position 130 by a proline P, substitution of the lysine K in position 164 by an asparagine N, substitution of the leucine L in position 226 by a valine V, substitution the tryptophan W in position 263 by a methionine M, SEQ ID NO: 49 corresponding to the SEQ ID NO: 3 comprising the following five mutations: substitution of the threonine T in position 68 by a serine S, substitution of the leucine L in position 72 by an isoleucine I, substitution of the tyrosine Y in position 97 by a tryptophan W, substitution of the tyrosine Y in position 99 by a phenylalanine F, substitution of the leucine L in position 130 by a proline P.

The coding sequence of the above-mentioned mutated hyperthermophilic PTE having a lactonase activity according to the present invention, derived from the hyperthermophilic PTE of Sulfolobus solfataricus corresponding to the sequence SEQ ID NO: 3 and corresponding to the following sequences SEQ ID NO: 8, 10, 12, 14, 16, 18, 20, 22, 24, 26, 28, 30, 32, 34, 36, 38, 40, 42, 44, 46, and 48 are also part of the invention.

The invention also related to mutated hyperthermophilic PTE having a lactonase activity according to the present invention, derived from the hyperthermophilic PTE of Sulfolobus solfataricus corresponding to the sequence SEQ ID NO: 3, said mutated hyperthermophilic PTE correspond to the following sequences SEQ ID NO: 139, 141, 143, 145, 147, 149, 151, 153, 155, 157, 159, 161, 163, 165, 167, 169, 171, 173, 175, 177 and 179 for the proteins and to their respective coding sequences SEQ ID NO: 138, 140, 142, 144, 146, 148, 150, 152, 154, 156, 158, 160, 162, 164, 166, 168, 170, 172, 174, 176 and 178.

A more particular subject of the invention is the above-mentioned mutated hyperthermophilic PTE having a lactonase activity, in which at least one of the amino acids involved in the salt bridges is modified by substitution, or deletion, such that the activation temperature of said mutated hyperthermophilic PTE having a lactonase activity is reduced compared with the activation temperature of the mutated hyperthermophilic PTE having a lactonase activity in which the amino acids involved in the salt bridges is unmodified.

By "substitution" is meant the replacement of an amino acid by another. By "deletion" is meant the removal of an amino acid, such that the protein sequence which has been subjected to said deletion is shorter than the sequence which has not been subjected to said deletion.

In a preferred embodiment, the amino acids involved in the salt bridges mentioned previously can be replaced by a sequence of at least two amino acids. This is then an "addition" and the protein sequence which has been subjected to said addition is longer than the sequence which has not been subjected to said addition.

The substitutions defined according to the invention relate equally to natural or non-natural (artificial) amino acids. Thus, the amino acids involved in salt bridges can be replaced by a natural or an artificial amino acid.

The invention relates more particularly to the above-mentioned mutated hyperthermophilic PTE having a lactonase activity, derived from the hyperthermophilic PTE of Sulfolobus solfataricus corresponding to the sequence SEQ ID NO: 3, further comprising at least one mutation corresponding to a substitution of at least one of the amino acids of the following amino acid pairs, the positions of which in SEQ ID NO: 3 are indicated hereafter, by another natural or non-natural amino acid: 2R/314S, 14K/12E, 26R/75D, 26R/42E, 33R/42E, 33R/45E, 55R/52E, 55R/285E, 74R/121D, 81K/42E, 81K/43D, 84K/80E, 109R/113E, 123K/162E, 147K/148D, 151K/148D, 154R/150E, 154R/187E, 154R/188E, 161K/188E, 183R/150E, 183R/187E, 183R/180E, 210K/245E, 215K/214D, 223R/256D, 223R/202D, 234K/204D, 235R/202D, 241R/245D, 245D/244K, 250K/249D, 277R/286D, 292K/298E, 310K/307E.

The invention relates also to the above-mentioned mutated hyperthermophilic PTEs having a lactonase activity, derived from the hyperthermophilic PTE of Sulfolobus acidocaldarius corresponding to the sequence SEQ ID NO: 5, said mutated PTEs comprising the at least one mutation selected from the group consisting of: substitutions of the glycine G in position 8, the lysine K in position 9, the valine V in position 28, the leucine L in position 47, the lysine K in position 55, the proline P in position 68, the threonine T in position 69, the leucine L in position 73, the isoleucine I in position 77, the valine V in position 84, the tyrosine Y in position 98, the tyrosine Y in position 100, the isoleucine I in position 123, the asparagine N in position 131, the aspartic acid D in position 142, the asparagine N in position 165, the isoleucine I in position 168, the aspartic acid D in position 192, the glycine G in position 194, the arginine R in position 224, the glycine G in position 226, the leucine L in position 227, the leucine L in position 229, the phenylalanine F in position 230, the leucine L in position 231, the tyrosine Y position 258, the cysteine C in position 259, the cysteine C in position 260, the threonine T in position 261, the isoleucine I in position 262, the aspartic acid D in position 263, the tryptophane W in position 264, the glycine G in position 265, the isoleucine I in position 266, the alanine A in position 267, the lysine K in position 268, the proline P in position 269, the glutamic acid E in position 270, the tyrosine Y in position 271, the lysine K in position 272, the proline P in position 273, the lysine K in position 274, the leucine L in position 275, the alanine A in position 276, the proline P in position 277, the lysine K in position 278, the tryptophan W in position 279, the serine S in position 280, the methionine M in position 281, the serine S in position 282, the leucine L in position 283, the isoleucine I in position 284 and the threonine T in position 298, of SEQ ID NO: 5 by any other natural or non-natural amino acid.

In a more specific embodiment, the above-mentioned mutated hyperthermophilic PTEs having a lactonase activity, derived from the hyperthermophilic PTE of Sulfolobus acidocaldarius corresponding to the sequence SEQ ID NO: 5, comprise the at least one mutation selected from the group consisting of: substitutions of the valine V in position 28, the proline P in position 68, the threonine T in position 69, the leucine L in position 73, the tyrosine Y in position 98, the tyrosine Y in position 100, the aspartic acid D in position 142, the arginine R in position 224, the glycine G in position 226, the leucine L in position 227, the phenylalanine F in position 230, the cysteine C in position 259, the tryptophane W in position 264 and the tryptophan W in position 279, of SEQ ID NO: 5 by any other natural or non-natural amino acid.

In an even more specific embodiment, the above-mentioned mutated hyperthermophilic PTEs having a lactonase activity, derived from the hyperthermophilic PTE of Sulfolobus acidocaldarius corresponding to the sequence SEQ ID NO: 5, comprise only one mutation, said mutation being selected from the group consisting of: substitutions of the valine V in position 28, the proline P in position 68, the threonine T in position 69, the leucine L in position 73, the aspartic acid D in position 142, the glycine G in position 226, the leucine L in position 227, the phenylalanine F in position 230, the tryptophane W in position 264, the tryptophan W in position 279, of SEQ ID NO : 5 by any other natural or non-natural amino acid.

In a more specific embodiment, the above-mentioned mutated hyperthermophilic PTEs having a lactonase activity, derived from the hyperthermophilic PTE of *Sulfolobus acidocaldarius* corresponding to the sequence SEQ ID NO: 5, comprise the at least one mutation selected from the group consisting of: substitutions of the glycine G in position 8, the lysine K in position 9, the leucine L in position 47, the lysine K in position 55, the isoleucine I in position 77, the valine V in position 84, the isoleucine I in position 123, the asparagine N in position 131, the asparagine N in position 165, the isoleucine I in position 168, the aspartic acid D in position 192, the glycine G in position 194, the leucine L in position 229, the leucine L in position 231, the tyrosine Y position 258, the cysteine C in position 260, the threonine T in position 261, the isoleucine I in position 262, the aspartic acid D in position 263, the glycine G in position 265, the isoleucine I in position 266, the alanine A in position 267, the lysine K in position 268, the proline P in position 269, the glutamic acid E in position 270, the tyrosine Y in position 271, the lysine K in position 272, the proline P in position 273, the lysine K in position 274, the leucine L in position 275, the alanine A in position 276, the proline P in position 277, the lysine K in position 278, the serine S in position 280, the methionine M in position 281, the serine S in position 282, the leucine L in position 283, the isoleucine I in position 284 and the threonine T in position 298, of SEQ ID NO : 5 by any other natural or non-natural amino acid.

In an even more specific embodiment, the above-mentioned mutated hyperthermophilic PTEs having a lactonase activity, derived from the hyperthermophilic PTE of *Sulfolobus acidocaldarius* corresponding to the sequence SEQ ID NO: 5, comprise only one mutation, said mutation being selected from the group consisting of: substitutions of the glycine G in position 8, the lysine K in position 9, the leucine L in position 47, the lysine K in position 55, the isoleucine I in position 77, the valine V in position 84, the isoleucine I in position 123, the asparagine N in position 131, the asparagine N in position 165, the isoleucine I in position 168, the aspartic acid D in position 192, the glycine G in position 194, the leucine L in position 229, the leucine L in position 231, the tyrosine Y position 258, the cysteine C in position 260, the threonine T in position 261, the isoleucine I in position 262, the aspartic acid D in position 263, the glycine G in position 265, the isoleucine I in position 266, the alanine A in position 267, the lysine K in position 268, the proline P in position 269, the glutamic acid E in position 270, the tyrosine Y in position 271, the lysine K in position 272, the proline P in position 273, the lysine K in position 274, the leucine L in position 275, the alanine A in position 276, the proline P in position 277, the lysine K in position 278, the serine S in position 280, the methionine M in position 281, the serine S in position 282, the leucine L in position 283, the isoleucine I in position 284, the threonine T in position 298, of SEQ ID NO : 5 by any other natural or non-natural amino acid.

The invention relates more particularly to the above-mentioned mutated hyperthermophilic PTE having a lactonase activity, derived from the hyperthermophilic PTE of *Sulfolobus acidocaldarius* corresponding to the sequence SEQ ID NO: 5, and wherein the at least one mutation is selected from the group consisting of:

substitution of the glycine G in position 8 by a non-bulky amino acid selected from the group consisting of PLIVADCSTN, in particular STA, notably S, substitution of the lysine K in position 9 by a charged amino acid selected from the group consisting of RHDEC, in particular EDR, notably E, substitution of the valine V in position 28 by a non-bulky amino acid selected from the group consisting of GPLIADCSTN or by a hydrophobic amino acid selected from the group consisting of ILMFGAPWYC, in particular GIFA, notably A, substitution of the leucine L in position 47 by a non-bulky amino acid selected from the group consisting of GPIVADCSTN or by a polar amino acid selected from the group consisting of WYSTCQNRKHDE, in particular YW, substitution of the lysine K in position 55 by a bulky amino acid selected from the group consisting of EHRQYWFM or by a hydrophobic amino acid selected from the group consisting of VILMFGAPWYC, in particular IRL, notably I, substitution of the threonine T in position 69 by a non-bulky amino acid selected from the group consisting of GPLIVADCSN, in particular VAS, notably S, substitution of the leucine L in position 73 by a hydrophobic amino acid selected from the group consisting of VIMFGAPWYC, in particular CAMI, notably I, substitution of the isoleucine I in position 77 by a non-bulky amino acid selected from the group consisting of GPLVADCSTN, in particular PTV, notably T, substitution of the valine V in position 84 by a non-bulky amino acid selected from the group consisting of GPLIADCSTN or by a hydrophobic amino acid selected from the group consisting of ILMFGAPWYC, in particular AGI, notably A, substitution of the tyrosine Y in position 98 by a bulky amino acid selected from the group consisting of EHKRQWFM or by a hydrophobic amino acid selected from the group consisting of VILMFGAPWC, in particular FCLW, notably W, substitution of the tyrosine Y in position 100 by a bulky amino acid selected from the group consisting of EHKRQWFM or by a hydrophobic amino acid selected from the group consisting of VILMFGAPWC, in particular GEWF, notably F, substitution of the isoleucine I in position 123 by a non-bulky amino acid selected from the group consisting of GPLVADCSTN, in particular LAV, notably L, substitution of the asparagine N in position 131 by a non-bulky amino acid selected from the group consisting of GPLIVADCSTN, in particular PST, notably P, substitution of the aspartic acid D in position 142 by a polar amino acid selected from the group consisting of WYSTCQNRKHE, in particular SET, notably T, substitution of the asparagine N in position 165 by a polar amino acid selected from the group consisting of WYSTCQRKHDE, in particular QR, substitution of the glycine G in position 194 by a non-bulky amino acid selected from the group consisting of PLIVADCSTN or by a polar amino acid selected from the group consisting of WYSTCNQRKHDE, in particular ST, notably S, substitution of the arginine R in position 224 by a non-bulky amino acid selected from the group consisting of GPLIVADCSTN or by a polar amino acid selected from the group consisting of WYSTCQNKHDE, in particular CSTAH, notably AC, substitution of the leucine L in position 227 by a non-bulky amino acid selected from the group consisting of GPIVADCSTN or by apolar amino acid selected from the group consisting of WYSTCQNRKHDE, in particular AIVH, notably V, substitution of the leucine L in position 229 by a non-bulky amino acid selected from the group consisting of GPIVADCSTN or by a hydrophobic amino acid selected from the group consisting of VIMFGAPWYC, in particular IM, notably M, substitution of the phenylalanine F in position 230 by a non-bulky amino acid selected from the group consisting of GPLIVADCSTN, in particular LTAS, notably S, substitution of the leucine L in position 231 by a non-bulky amino acid selected from the group consisting of GPIVADCSTN, in particular PVA, notably P, substitution of the cysteine C in position 259 by a hydrophobic amino acid selected from the group consisting of VILMFGAPWY, in particular YLIA, notably LA, substitution of the isoleucine I in position 262 by a hydrophobic amino acid selected from the group consisting of VLMFGAPWYC, in particular FWC, notably F, substitution of the tryptophane W in position 264 by a non-bulky amino acid selected from the group consisting of GPLIVADCSTN or by a hydrophobic amino acid selected from the group consisting of VILMFGAPYC, in particular ALMFCITV, notably F, substitution of the leucine L in position 275 by a hydrophobic amino acid selected from the group consisting of VIMFGAPWYC, in particular AVP, notably P, substitution of the alanine A in position 276 by a hydrophobic amino acid selected from the group consisting of VILMFGPWYC or by a non-bulky amino acid selected from the group consisting of GPLIVDCSTN, in particular NVMT, notably T, substitution of the methionine M in position 281 by a non-bulky amino acid selected from the group consisting of GPLIVADCSTN or by a hydrophobic amino acid selected from the group consisting of VILFGAPWYC, in particular TYP, notably T, substitution of the leucine L in position 283 by a bulky amino acid selected from the group consisting of EKHRQYWFM, in particular FMH, notably M, and substitution of the threonine T in position 298 by a polar amino acid selected from the group consisting of WYSCQNRKHDE, in particular QS, notably S.

These 29 particular substitutions in position G8, K9, V28, L47, K55, T69, L73, I77, V84, Y98, Y100, I123, N131, D142, N165, G194, R224, L227, L229, F230, L231, C259, I262, W264, L275, A276, M281, L283 and T298 belong to the seventh set of substitutions called set 7.

The invention relates more particularly to the above-mentioned mutated hyperthermophilic PTE having a lactonase activity, derived from the hyperthermophilic PTE of Sulfolobus acidocaldarius corresponding to the sequence SEQ ID NO: 5, and wherein the at least one mutation is selected from the group consisting of:

substitution of the isoleucine I in position 168 by a non-bulky amino acid selected from the group consisting of GPLIVADCSTN or by a hydrophobic amino acid selected from the group consisting of VLMFGAPWYC, in particular VAL, notably V, substitution of the aspartic acid D in position 192 by a non-bulky amino acid selected from the group consisting of GPLVADCSTN or by a polar amino acid selected from the group consisting of WYSTCQNRKHE, in particular ST, notably S, substitution of the tyrosine Y position 258 by a non-bulky amino acid selected from the group consisting of GPLIVADCSTN or by a hydrophobic amino acid selected from the group consisting of VLMFGAPWC, in particular CSVW, notably C, substitution of the cysteine C in position 260 a non-bulky amino acid selected from the group consisting of GPLIVADSTN or by a hydrophobic amino acid selected from the group consisting of VILMFGAPWY, in particular SFWV, notably S, substitution of the threonine T in position 261 a non-bulky amino acid selected from the group consisting of GPLIVADCSN or by a polar amino acid selected from the group consisting of WYSCQNRKHE, in particular GH, notably G, substitution of the aspartic acid D in position 263 by a polar amino acid selected from the group consisting of WYSTCQNRKHE or by a non-bulky amino acid selected from the group consisting of GPLIVACSTN, in particular SLH, substitution of the glycine G in position 265 non-bulky amino acid selected from the group consisting of PLIVADCSTN or by a hydrophobic amino acid selected from the group consisting of VILMFAPWYC, in particular AVP, substitution of the isoleucine I in position 266 by a hydrophobic amino acid selected from the group consisting of VLMFGAPWYC or by a non-bulky amino acid selected from the group consisting of GPLVADCSTN, in particular VWP, notably V, substitution of the alanine A in position 267 by a polar amino acid selected from the group consisting of WYSTCQNRKHDE, in particular NQ, notably N, substitution of the lysine K in position 268 by a non-bulky amino acid selected from the group consisting of GPLIVADCSTN or by a hydrophobic amino acid selected from the group consisting of VILMFGAPWYC, in particular IAP, notably IP, substitution of the proline P in position 269 by a hydrophobic amino acid selected from the group consisting of VILMFGAWYC, in particular MCL, notably M, substitution of the glutamic acid E in position 270 by a polar amino acid selected from the group consisting of WYSTCQNRKHD, in particular DQ, notably D, substitution of the tyrosine Y in position 271 by a non-bulky amino acid selected from the group consisting of GPLIVADCSTN or by a hydrophobic amino acid selected from the group consisting of VILMFGAPWC, in particular VAL, substitution of the lysine K in position 272 by a bulky amino acid selected from the group consisting of EHRQYWFM or by a hydrophobic amino acid selected from the group consisting of VILMFGAPWYC, in particular MLA, substitution of the proline P in position 273 by a non-bulky amino acid selected from the group consisting of GPLIVADCSTN or by a polar amino acid selected from the group consisting of WYSTCQNRKHDE, in particular DEL, notably DL, substitution of the lysine K in position 274 by a non-bulky amino acid selected from the group consisting of GPLIVADCSTN or by a polar amino acid selected from the group consisting of WYSTCQNRHD, in particular RP, substitution of the proline P in position 277 by a bulky amino acid selected from the group consisting of EHKRQYWFM or by a hydrophobic amino acid selected from the group consisting of VILMFGAWYC, in particular KAV, notably K, substitution of the lysine K in position 278 by a polar amino acid selected from the group consisting of WYSTCQNRHDE, in particular DNQ, notably DN, substitution of the serine S in position 280 by a non-bulky amino acid selected from the group consisting of GPLIVADCTN or by a polar amino acid selected from the group consisting of WYTCQNRKHDE, in particular GH, substitution of the serine S in position 282 by a non-bulky amino acid selected from the group consisting of GPLIVADCTN or by a hydrophobic amino acid selected from the group consisting of VILMFGAPWYC, in particular ALV, notably AL, and substitution of the isoleucine I in position 284 non-bulky amino acid selected from the group consisting of GPLVADCSTN, in particular VAL, notably V.

These 21 particular substitutions in position I168, D192, Y258, C260, T261, D263, G265, I266, A267, K268, P269, E270, Y/L271, K272, P273, K274, P277, K278, S280, S282 and I284 belong to the eighth set of substitutions called set 8.

The invention relates more particularly to the above-mentioned mutated hyperthermophilic PTE having a lactonase activity, derived from the hyperthermophilic PTE of *Sulfolobus acidocaldarius* corresponding to the sequence SEQ ID NO: 5, and wherein the at least one mutation is selected from the group consisting of:

substitution of the proline P in position 68 by a non-bulky amino acid selected from the group consisting of GLIVADCSTN, in particular GAV, substitution of the glycine G in position 226 by a non-bulky amino acid selected from the group consisting of PLIVADCSTN, in particular AVP, and substitution of the tryptophan W in position 279 by a hydrophobic amino acid selected from the group consisting of VILMFGAPYC or by a charged amino acid selected from the group consisting of RKHDEC, in particular RKDI, notably R. These 3 particular substitutions in position P68, G226 and W279 belong to the ninth set of substitutions called set 9.

The invention also relates to the above-mentioned mutated hyperthermophilic PTE having a lactonase activity, derived from the hyperthermophilic PTE of *Sulfolobus acidocaldarius* corresponding to the sequence SEQ ID NO: 5, and wherein the at least one mutation selected from the group consisting of:

substitution of the glycine G in position 8 by a non-bulky amino acid selected from the group consisting of PLIVADCSTN, in particular STA, notably S, substitution of the lysine K in position 9 by a charged amino acid selected from the group consisting of RHDEC, in particular EDR, notably E, substitution of the valine V in position 28 by a non-bulky amino acid selected from the group consisting of GPLIADCSTN or by a hydrophobic amino acid selected from the group consisting of ILMFGAPWYC, in particular GIFA, notably A, substitution of the leucine L in position 47 by a non-bulky amino acid selected from the group consisting of GPIVADCSTN or by a polar amino acid selected from the group consisting of WYSTCQNRKHDE, in particular YW, substitution of the lysine K in position 55 by a bulky amino acid selected from the group consisting of EHRQYWFM or by a hydrophobic amino acid selected from the group consisting of VILMFGAPWYC, in particular IRL, notably I, substitution of the threonine T in position 69 by a non-bulky amino acid selected from the group consisting of GPLIVADCSN, in particular VAS, notably S, substitution of the leucine L in position 73 by a hydrophobic amino acid selected from the group consisting of VIMFGAPWYC, in particular CAMI, notably I, substitution of the isoleucine I in position 77 by a non-bulky amino acid selected from the group consisting of GPLVADCSTN, in particular PTV, notably T, substitution of the valine V in position 84 by a non-bulky amino acid selected from the group consisting of GPLIADCSTN or by a hydrophobic amino acid selected from the group consisting of ILMFGAPWYC, in particular AGI, notably A, substitution of the tyrosine Y in position 98 by a bulky amino acid selected from the group consisting of EHKRQWFM or by a hydrophobic amino acid selected from the group consisting of VILMFGAPWC, in particular FCLW, notably W, substitution of the tyrosine Y in position 100 by a bulky amino acid selected from the group consisting of EHKRQWFM or by a hydrophobic amino acid selected from the group consisting of VILMFGAPWC, in particular GEWF, notably F, substitution of the isoleucine I in position 123 by a non-bulky amino acid selected from the group consisting of GPLVADCSTN, in particular LAV, notably L, substitution of the asparagine N in position 131 by a non-bulky amino acid selected from the group consisting of GPLIVADCSTN, in particular PST, notably P, substitution of the aspartic acid D in position 142 by a polar amino acid selected from the group consisting of WYSTCQNRKHE, in particular SET, notably T, substitution of the asparagine N in position 165 by a polar amino acid selected from the group consisting of WYSTCQRKHDE, in particular QR, substitution of the glycine G in position 194 by a non-bulky amino acid selected from the group consisting of PLIVADCSTN or by a polar amino acid selected from the group consisting of WYSTCNQRKHDE, in particular ST, notably S, substitution of the arginine R in position 224 by a non-bulky amino acid selected from the group consisting of GPLIVADCSTN or by a polar amino acid selected from the group consisting of WYSTCQNKHDE, in particular CSTAH, notably AC, substitution of the leucine L in position 227 by a non-bulky amino acid selected from the group consisting of GPIVADCSTN or by apolar amino acid selected from the group consisting of WYSTCQNRKHDE, in particular AIVH, notably V, substitution of the leucine L in position 229 by a non-bulky amino acid selected from the group consisting of GPIVADCSTN or by a hydrophobic amino acid selected from the group consisting of VIMFGAPWYC, in particular IM, notably M, substitution of the phenylalanine F in position 230 by a non-bulky amino acid selected from the group consisting of GPLIVADCSTN, in particular LTAS, notably S, substitution of the leucine L in position 231 by a non-bulky amino acid selected from the group consisting of GPIVADCSTN, in particular PVA, notably P, substitution of the cysteine C in position 259 by a hydrophobic amino acid selected from the group consisting of VILMFGAPWY, in particular YLIA, notably LA,
substitution of the isoleucine I in position 262 by a hydrophobic amino acid selected from the group consisting of VLMFGAPWYC, in particular FWC, notably F,
substitution of the tryptophane W in position 264 by a non-bulky amino acid selected from the group consisting of GPLIVADCSTN or by a hydrophobic amino acid selected from the group consisting of VILMFGAPYC, in particular ALMFCITV, notably F,
substitution of the leucine L in position 275 by a hydrophobic amino acid selected from the group consisting of VIMFGAPWYC, in particular AVP, notably P,
substitution of the alanine A in position 276 by a hydrophobic amino acid selected from the group consisting of VILMFGPWYC or by a non-bulky amino acid selected from the group consisting of GPLIVDCSTN, in particular NVMT, notably T,
substitution of the methionine M in position 281 by a non-bulky amino acid selected from the group consisting of GPLIVADCSTN or by a hydrophobic amino acid selected from the group consisting of VILFGAPWYC, in particular TYP, notably T,
substitution of the leucine L in position 283 by a bulky amino acid selected from the group consisting of EKHRQYWFM, in particular FMH, notably M,
and substitution of the threonine T in position 298 by a polar amino acid selected from the group consisting of WYSCQNRKHDE, in particular QS, notably S,
further comprises at least one mutation selected from the group consisting of:
substitution of the isoleucine I in position 168 by a non-bulky amino acid selected from the group consisting of GPLIVADCSTN or by a hydrophobic amino acid selected from the group consisting of VLMFGAPWYC, in particular VAL, notably V,
substitution of the aspartic acid D in position 192 by a non-bulky amino acid selected from the group consisting of GPLVADCSTN or by a polar amino acid selected from the group consisting of WYSTCQNRKHE, in particular ST, notably S,
substitution of the tyrosine Y position 258 by a non-bulky amino acid selected from the group consisting of GPLIVADCSTN or by a hydrophobic amino acid selected from the group consisting of VLMFGAPWC, in particular CSVW, notably C, substitution of the cysteine C in position 260 a non-bulky amino acid selected from the group consisting of GPLIVADSTN or by a hydrophobic amino acid selected from the group consisting of VILMFGAPWY, in particular SFWV, notably S, substitution of the threonine T in position 261 a non-bulky amino acid selected from the group consisting of GPLIVADCSN or by a polar amino acid selected from the group consisting of WYSCQNRKHE, in particular GH, notably G, substitution of the aspartic acid D in position 263 by a polar amino acid selected from the group consisting of WYSTCQNRKHE or by a non-bulky amino acid selected from the group consisting of GPLIVACSTN, in particular SLH, substitution of the glycine G in position 265 non-bulky amino acid selected from the group consisting of PLIVADCSTN or by a hydrophobic amino acid selected from the group consisting of VILMFAPWYC, in particular AVP, substitution of the isoleucine I in position 266 by a hydrophobic amino acid selected from the group consisting of VLMFGAPWYC or by a non-bulky amino acid selected from the group consisting of GPLVADCSTN, in particular VWP, notably V, substitution of the alanine A in position 267 by a polar amino acid selected from the group consisting of WYSTCQNRKHDE, in particular NQ, notably N, substitution of the lysine K in position 268 by a non-bulky amino acid selected from the group consisting of GPLIVADCSTN or by a hydrophobic amino acid selected from the group consisting of VILMFGAPWYC, in particular IAP, notably IP, substitution of the proline P in position 269 by a hydrophobic amino acid selected from the group consisting of VILMFGAWYC, in particular MCL, notably M, substitution of the glutamic acid E in position 270 by a polar amino acid selected from the group consisting of WYSTCQNRKHD, in particular DQ, notably D, substitution of the tyrosine Y in position 271 by a non-bulky amino acid selected from the group consisting of GPLIVADCSTN or by a hydrophobic amino acid selected from the group consisting of VILMFGAPWC, in particular VAL, substitution of the lysine K in position 272 by a bulky amino acid selected from the group consisting of EHRQYWFM or by a hydrophobic amino acid selected from the group consisting of VILMFGAPWYC, in particular MLA, substitution of the proline P in position 273 by a non-bulky amino acid selected from the group consisting of GPLIVADCSTN or by a polar amino acid selected from the group consisting of WYSTCQNRKHDE, in particular DEL, notably DL, substitution of the lysine K in position 274 by a non-bulky amino acid selected from the group consisting of GPLIVADCSTN or by a polar amino acid selected from the group consisting of WYSTCQNRHD, in particular RP, substitution of the proline P in position 277 by a bulky amino acid selected from the group consisting of EHKRQYWFM or by a hydrophobic amino acid selected from the group consisting of VILMFGAWYC, in particular KAY, notably K, substitution of the lysine K in position 278 by a polar amino acid selected from the group consisting of WYSTCQNRHDE, in particular DNQ, notably DN, substitution of the serine S in position 280 by a non-bulky amino acid selected from the group consisting of GPLIVADCTN or by a polar amino acid selected from the group consisting of WYTCQNRKHDE, in particular GH, substitution of the serine S in position 282 by a non-bulky amino acid selected from the group consisting of GPLIVADCTN or by a hydrophobic amino acid selected from the group consisting of VILMFGAPWYC, in particular ALV, notably AL, and substitution of the isoleucine I in position 284 non-bulky amino acid selected from the group consisting of GPLVADCSTN, in particular VAL, notably V.

It means that at least one substitution among the 29 particular substitutions of set 7 in position G8, K9, V28, L47, K55, T69, L73, I77, V84, Y98, Y100, I123, N131, D142, N165, G194, R224, L227, L229, F230, L231, C259, I262, W264, L275, A276, M281, L283 and T298 can be associated with at least one substitution among the 21 particular substitutions of set 8 in position I168, D192, Y258, C260, T261, D263, G265, I266, A267, K268, P269, E270, Y/L271, K272, P273, K274, P277, K278, S280, S282 and I284.

The invention also relates to the above-mentioned mutated hyperthermophilic PTE having a lactonase activity, derived from the hyperthermophilic PTE of *Sulfolobus acidocaldarius* corresponding to the sequence SEQ ID NO: 5, and wherein the at least one mutation is selected from the group consisting of:

substitution of the glycine G in position 8 by a non-bulky amino acid selected from the group consisting of PLIVADCSTN, in particular STA, notably S, substitution of the lysine K in position 9 by a charged amino acid selected from the group consisting of RHDEC, in particular EDR, notably E, substitution of the valine V in position 28 by a non-bulky amino acid selected from the group consisting of GPLIADCSTN or by a hydrophobic amino acid selected from the group consisting of ILMFGAPWYC, in particular GIFA, notably A, substitution of the leucine L in position 47 by a non-bulky amino acid selected from the group consisting of GPIVADCSTN or by a polar amino acid selected from the group consisting of WYSTCQNRKHDE, in particular YW, substitution of the lysine K in position 55 by a bulky amino acid selected from the group consisting of EHRQYWFM or by a hydrophobic amino acid selected from the group consisting of VILMFGAPWYC, in particular IRL, notably I, substitution of the threonine T in position 69 by a non-bulky amino acid selected from the group consisting of GPLIVADCSN, in particular VAS, notably S, substitution of the leucine L in position 73 by a hydrophobic amino acid selected from the group consisting of VIMFGAPWYC, in particular CAMI, notably I, substitution of the isoleucine I in position 77 by a non-bulky amino acid selected from the group consisting of GPLVADCSTN, in particular PTV, notably T, substitution of the valine V in position 84 by a non-bulky amino acid selected from the group consisting of GPLIADCSTN or by a hydrophobic amino acid selected from the group consisting of ILMFGAPWYC, in particular AGI, notably A, substitution of the tyrosine Y in position 98 by a bulky amino acid selected from the group consisting of EHKRQWFM or by a hydrophobic amino acid selected from the group consisting of VILMFGAPWC, in particular FCLW, notably W, substitution of the tyrosine Y in position 100 by a bulky amino acid selected from the group consisting of EHKRQWFM or by a hydrophobic amino acid selected from the group consisting of VILMFGAPWC, in particular GEWF, notably F, substitution of the isoleucine I in position 123 by a non-bulky amino acid selected from the group consisting of GPLVADCSTN, in particular LAV, notably L, substitution of the asparagine N in position 131 by a non-bulky amino acid selected from the group consisting of GPLIVADCSTN, in particular PST, notably P, substitution of the aspartic acid D in position 142 by a polar amino acid selected from the group consisting of WYSTCQNRKHE, in particular SET, notably T, substitution of the asparagine N in position 165 by a polar amino acid selected from the group consisting of WYSTCQRKHDE, in particular QR, substitution of the glycine G in position 194 by a non-bulky amino acid selected from the group consisting of PLIVADCSTN or by a polar amino acid selected from the group consisting of WYSTCNQRKHDE, in particular ST, notably S, substitution of the arginine R in position 224 by a non-bulky amino acid selected from the group consisting of GPLIVADCSTN or by a polar amino acid selected from the group consisting of WYSTCQNKHDE, in particular CSTAH, notably AC, substitution of the leucine L in position 227 by a non-bulky amino acid selected from the group consisting of GPIVADCSTN or by apolar amino acid selected from the group consisting of WYSTCQNRKHDE, in particular AIVH, notably V, substitution of the leucine L in position 229 by a non-bulky amino acid selected from the group consisting of GPIVADCSTN or by a hydrophobic amino acid selected from the group consisting of VIMFGAPWYC, in particular IM, notably M, substitution of the phenylalanine F in position 230 by a non-bulky amino acid selected from the group consisting of GPLIVADCSTN, in particular LTAS, notably S, substitution of the leucine L in position 231 by a non-bulky amino acid selected from the group consisting of GPIVADCSTN, in particular PVA, notably P, substitution of the cysteine C in position 259 by a hydrophobic amino acid selected from the group consisting of VILMFGAPWY, in particular YLIA, notably LA, substitution of the isoleucine I in position 262 by a hydrophobic amino acid selected from the group consisting of VLMFGAPWYC, in particular FWC, notably F, substitution of the tryptophane W in position 264 by a non-bulky amino acid selected from the group consisting of GPLIVADCSTN or by a hydrophobic amino acid selected from the group consisting of VILMFGAPYC, in particular ALMFCITV, notably F, substitution of the leucine L in position 275 by a hydrophobic amino acid selected from the group consisting of VIMFGAPWYC, in particular AVP, notably P, substitution of the alanine A in position 276 by a hydrophobic amino acid selected from the group consisting of VILMFGPWYC or by a non-bulky amino acid selected from the group consisting of GPLIVDCSTN, in particular NVMT, notably T, substitution of the methionine M in position 281 by a non-bulky amino acid selected from the group consisting of GPLIVADCSTN or by a hydrophobic amino acid selected from the group consisting of VILFGAPWYC, in particular TYP, notably T, substitution of the leucine L in position 283 by a bulky amino acid selected from the group consisting of EKHRQYWFM, in particular FMH, notably M, and substitution of the threonine T in position 298 by a polar amino acid selected from the group consisting of WYSCQNRKHDE, in particular QS, notably S, further comprises at least one mutation selected from the group consisting of:

substitution of the proline P in position 68 by a non-bulky amino acid selected from the group consisting of GLIVADCSTN, in particular GAV, substitution of the glycine G in position 226 by a non-bulky amino acid selected from the group consisting of PLIVADCSTN, in particular AVP, and substitution of the tryptophan W in position 279 by a hydrophobic amino acid selected from the group consisting of VILMFGAPYC or by a charged amino acid selected from the group consisting of RKHDEC, in particular RKDI, notably R.

It means that at least one substitution among the 29 particular substitutions of set 7 in position G8, K9, V28, L47, K55, T69, L73, I77, V84, Y98, Y100, I123, N131, D142, N165, G194, R224, L227, L229, F230, L231, C259, I262, W264, L275, A276, M281, L283 and T298 can be associated with at least one substitution among the 3 particular substitutions of set 9 in position P68, G226 and W279.

The invention also relates to the above-mentioned mutated hyperthermophilic PTE having a lactonase activity, derived from the hyperthermophilic PTE of *Sulfolobus acidocaldarius* corresponding to the sequence SEQ ID NO: 5, and wherein the at least one mutation selected from the group consisting of:

substitution of the glycine G in position 8 by a non-bulky amino acid selected from the group consisting of PLIVADCSTN, in particular STA, notably S, substitution of the lysine K in position 9 by a charged amino acid selected from the group consisting of RHDEC, in particular EDR, notably E, substitution of the valine V in position 28 by a non-bulky amino acid selected from the group consisting of GPLIADCSTN or by a hydrophobic amino acid selected from the group consisting of ILMFGAPWYC, in particular GIFA, notably A, substitution of the leucine L in position 47 by a non-bulky amino acid selected from the group consisting of GPIVADCSTN or by a polar amino acid selected from the group consisting of WYSTCQNRKHDE, in particular YW, substitution of the lysine K in position 55 by a bulky amino acid selected from the group consisting of EHRQYWFM or by a hydrophobic amino acid selected from the group consisting of VILMFGAPWYC, in particular IRL, notably I, substitution of the threonine T in position 69 by a non-bulky amino acid selected from the group consisting of GPLIVADCSN, in particular VAS, notably S, substitution of the leucine L in position 73 by a hydrophobic amino acid selected from the group consisting of VIMFGAPWYC, in particular CAMI, notably I, substitution of the isoleucine I in position 77 by a non-bulky amino acid selected from the group consisting of GPLVADCSTN, in particular PTV, notably T, substitution of the valine V in position 84 by a non-bulky amino acid selected from the group consisting of GPLIADCSTN or by a hydrophobic amino acid selected from the group consisting of ILMFGAPWYC, in particular AGI, notably A, substitution of the tyrosine Y in position 98 by a bulky amino acid selected from the group consisting of EHKRQWFM or by a hydrophobic amino acid selected from the group consisting of VILMFGAPWC, in particular FCLW, notably W, substitution of the tyrosine Y in position 100 by a bulky amino acid selected from the group consisting of EHKRQWFM or by a hydrophobic amino acid selected from the group consisting of VILMFGAPWC, in particular GEWF, notably F, substitution of the isoleucine I in position 123 by a non-bulky amino acid selected from the group consisting of GPLVADCSTN, in particular LAV, notably L, substitution of the asparagine N in position 131 by a non-bulky amino acid selected from the group consisting of GPLIVADCSTN, in particular PST, notably P, substitution of the aspartic acid D in position 142 by a polar amino acid selected from the group consisting of WYSTCQNRKHE, in particular SET, notably T, substitution of the asparagine N in position 165 by a polar amino acid selected from the group consisting of WYSTCQRKHDE, in particular QR, substitution of the glycine G in position 194 by a non-bulky amino acid selected from the group consisting of PLIVADCSTN or by a polar amino acid selected from the group consisting of WYSTCNQRKHDE, in particular ST, notably S, substitution of the arginine R in position 224 by a non-bulky amino acid selected from the group consisting of GPLIVADCSTN or by a polar amino acid selected from the group consisting of WYSTCQNKHDE, in particular CSTAH, notably AC, substitution of the leucine L in position 227 by a non-bulky amino acid selected from the group consisting of GPIVADCSTN or by apolar amino acid selected from the group consisting of WYSTCQNRKHDE, in particular AIVH, notably V, substitution of the leucine L in position 229 by a non-bulky amino acid selected from the group consisting of GPIVADCSTN or by a hydrophobic amino acid selected from the group consisting of VIMFGAPWYC, in particular IM, notably M, substitution of the phenylalanine F in position 230 by a non-bulky amino acid selected from the group consisting of GPLIVADCSTN, in particular LTAS, notably S, substitution of the leucine L in position 231 by a non-bulky amino acid selected from the group consisting of GPIVADCSTN, in particular PVA, notably P, substitution of the cysteine C in position 259 by a hydrophobic amino acid selected from the group consisting of VILMFGAPWY, in particular YLIA, notably LA, substitution of the isoleucine I in position 262 by a hydrophobic amino acid selected from the group consisting of VLMFGAPWYC, in particular FWC, notably F, substitution of the tryptophane W in position 264 by a non-bulky amino acid selected from the group consisting of GPLIVADCSTN or by a hydrophobic amino acid selected from the group consisting of VILMFGAPYC, in particular ALMFCITV, notably F, substitution of the leucine L in position 275 by a hydrophobic amino acid selected from the group consisting of VIMFGAPWYC, in particular AVP, notably P, substitution of the alanine A in position 276 by a hydrophobic amino acid selected from the group consisting of VILMFGPWYC or by a non-bulky amino acid selected from the group consisting of GPLIVDCSTN, in particular NVMT, notably T, substitution of the methionine M in position 281 by a non-bulky amino acid selected from the group consisting of GPLIVADCSTN or by a hydrophobic amino acid selected from the group consisting of VILFGAPWYC, in particular TYP, notably T, substitution of the leucine L in position 283 by a bulky amino acid selected from the group consisting of EKHRQYWFM, in particular FMH, notably M, and substitution of the threonine T in position 298 by a polar amino acid selected from the group consisting of WYSCQNRKHDE, in particular QS, notably S, further comprises at least one mutation selected from the group consisting of:

substitution of the isoleucine I in position 168 by a non-bulky amino acid selected from the group consisting of GPLIVADCSTN or by a hydrophobic amino acid selected from the group consisting of VLMFGAPWYC, in particular VAL, notably V, substitution of the aspartic acid D in position 192 by a non-bulky amino acid selected from the group consisting of GPLVADCSTN or by a polar amino acid selected from the group consisting of WYSTCQNRKHE, in particular ST, notably S, substitution of the tyrosine Y position 258 by a non-bulky amino acid selected from the group consisting of GPLIVADCSTN or by a hydrophobic amino acid selected from the group consisting of VLMFGAPWC, in particular CSVW, notably C, substitution of the cysteine C in position 260 a non-bulky amino acid selected from the group consisting of GPLIVADSTN or by a hydrophobic amino acid selected from the group consisting of VILMFGAPWY, in particular SFWV, notably S, substitution of the threonine T in position 261 a non-bulky amino acid selected from the group consisting of GPLIVADCSN or by a polar amino acid selected from the group consisting of WYSCQNRKHE, in particular GH, notably G, substitution of the aspartic acid D in position 263 by a polar amino acid selected from the group consisting of WYSTCQNRKHE or by a non-bulky amino acid selected from the group consisting of GPLIVACSTN, in particular SLH, substitution of the glycine G in position 265 non-bulky amino acid selected from the group consisting of PLIVADCSTN or by a hydrophobic amino acid selected from the group consisting of VILMFAPWYC, in particular AVP, substitution of the isoleucine I in position 266 by a hydrophobic amino acid selected from the group consisting of VLMFGAPWYC or by a non-bulky amino acid selected from the group consisting of GPLVADCSTN, in particular VWP, notably V, substitution of the alanine A in position 267 by a polar amino acid selected from the group consisting of WYSTCQNRKHDE, in particular NQ, notably N, substitution of the lysine K in position 268 by a non-bulky amino acid selected from the group consisting of GPLIVADCSTN or by a hydrophobic amino acid selected from the group consisting of VILMFGAPWYC, in particular IAP, notably IP, substitution of the proline P in position 269 by a hydrophobic amino acid selected from the group consisting of VILMFGAWYC, in particular MCL, notably M, substitution of the glutamic acid E in position 270 by a polar amino acid selected from the group consisting of WYSTCQNRKHD, in particular DQ, notably D, substitution of the tyrosine Y in position 271 by a non-bulky amino acid selected from the group consisting of GPLIVADCSTN or by a hydrophobic amino acid selected from the group consisting of VILMFGAPWC, in particular VAL, substitution of the lysine K in position 272 by a bulky amino acid selected from the group consisting of EHRQYWFM or by a hydrophobic amino acid selected from the group consisting of VILMFGAPWYC, in particular MLA, substitution of the proline P in position 273 by a non-bulky amino acid selected from the group consisting of GPLIVADCSTN or by a polar amino acid selected from the group consisting of WYSTCQNRKHDE, in particular DEL, notably DL, substitution of the lysine K in position 274 by a non-bulky amino acid selected from the group consisting of GPLIVADCSTN or by a polar amino acid selected from the group consisting of WYSTCQNRHD, in particular RP, substitution of the proline P in position 277 by a bulky amino acid selected from the group consisting of EHKRQYWFM or by a hydrophobic amino acid selected from the group consisting of VILMFGAWYC, in particular KAV, notably K, substitution of the lysine K in position 278 by a polar amino acid selected from the group consisting of WYSTCQNRHDE, in particular DNQ, notably DN, substitution of the serine S in position 280 by a non-bulky amino acid selected from the group consisting of GPLIVADCTN or by a polar amino acid selected from the group consisting of WYTCQNRKHDE, in particular GH, substitution of the serine S in position 282 by a non-bulky amino acid selected from the group consisting of GPLIVADCTN or by a hydrophobic amino acid selected from the group consisting of VILMFGAPWYC, in particular ALV, notably AL, and substitution of the isoleucine I in position 284 non-bulky amino acid selected from the group consisting of GPLVADCSTN, in particular VAL, notably V, further comprises at least one mutation selected from the group consisting of:

substitution of the proline P in position 68 by a non-bulky amino acid selected from the group consisting of GLIVADCSTN, in particular GAV, substitution of the glycine G in position 226 by a non-bulky amino acid selected from the group consisting of PLIVADCSTN, in particular AVP, and substitution of the tryptophan W in position 279 by a hydrophobic amino acid selected from the group consisting of VILMFGAPYC or by a charged amino acid selected from the group consisting of RKHDEC, in particular RKHDI, notably R.

It means that at least one substitution among the 29 particular substitutions of set 7 in position G8, K9, V28, L47, K55, T69, L73, I77, V84, Y98, Y100, I123, N131, D142, N165, G194, R224, L227, L229, F230, L231, C259, I262, W264, L275, A276, M281, L283 and T298 can be associated with at least one substitution among the 21 particular substitutions of set 8 in position I168, D192, Y258, C260, T261, D263, G265, I266, A267, K268, P269, E270, Y/L271, K272, P273, K274, P277, K278, S280, S282 and I284 and with at least at least one substitution among the 3 particular substitutions of set 9 in position P68, G226 and W279.

The invention also relates to the above-mentioned mutated hyperthermophilic PTE having a lactonase activity, derived from the hyperthermophilic PTE of *Sulfolobus acidocaldarius* corresponding to the sequence SEQ ID NO: 5, and wherein the at least one mutation selected from the group consisting of:

substitution of the isoleucine I in position 168 by a non-bulky amino acid selected from the group consisting of GPLIVADCSTN or by a hydrophobic amino acid selected from the group consisting of VLMFGAP-WYC, in particular VAL, notably V, substitution of the aspartic acid D in position 192 by a non-bulky amino acid selected from the group consisting of GPLVADCSTN or by a polar amino acid selected from the group consisting of WYSTCQN-RKHE, in particular ST, notably S, substitution of the tyrosine Y position 258 by a non-bulky amino acid selected from the group consisting of GPLI-VADCSTN or by a hydrophobic amino acid selected from the group consisting of VLMFGAPWC, in particular CSVW, notably C, substitution of the cysteine C in position 260 a non-bulky amino acid selected from the group consisting of GPLI-VADSTN or by a hydrophobic amino acid selected from the group consisting of VILMFGAPWY, in particular SFWV, notably S, substitution of the threonine T in position 261 a non-bulky amino acid selected from the group consisting of GPLI-VADCSN or by a polar amino acid selected from the group consisting of WYSCQNRKHE, in particular GH, notably G, substitution of the aspartic acid D in position 263 by a polar amino acid selected from the group consisting of WYSTCQNRKHE or by a non-bulky amino acid selected from the group consisting of GPLIVACSTN, in particular SLH, substitution of the glycine G in position 265 non-bulky amino acid selected from the group consisting of PLI-VADCSTN or by a hydrophobic amino acid selected from the group consisting of VILMFAPWYC, in particular AVP, substitution of the isoleucine I in position 266 by a hydrophobic amino acid selected from the group consisting of VLMFGAPWYC or by a non-bulky amino acid selected from the group consisting of GPLVAD-CSTN, in particular VWP, notably V, substitution of the alanine A in position 267 by a polar amino acid selected from the group consisting of WYSTCQNRKHDE, in particular NQ, notably N, substitution of the lysine K in position 268 by a non-bulky amino acid selected from the group consisting of GPLI-VADCSTN or by a hydrophobic amino acid selected from the group consisting of VILMFGAPWYC, in particular IAP, notably IP, substitution of the proline P in position 269 by a hydrophobic amino acid selected from the group consisting of VILMFGAWYC, in particular MCL, notably M, substitution of the glutamic acid E in position 270 by a polar amino acid selected from the group consisting of WYSTCQNRKHD, in particular DQ, notably D, substitution of the tyrosine Y in position 271 by a non-bulky amino acid selected from the group consisting of GPLIVADCSTN or by a hydrophobic amino acid selected from the group consisting of VILMFGAPWC, in particular VAL, substitution of the lysine K in position 272 by a bulky amino acid selected from the group consisting of EHRQYWFM or by a hydrophobic amino acid selected from the group consisting of VILMFGAPWYC, in particular MLA, substitution of the proline P in position 273 by a non-bulky amino acid selected from the group consisting of GPLIVADCSTN or by a polar amino acid selected from the group consisting of WYSTCQNRKHDE, in particular DEL, notably DL, substitution of the lysine K in position 274 by a non-bulky amino acid selected from the group consisting of GPLI-VADCSTN or by a polar amino acid selected from the group consisting of WYSTCQNRHD, in particular RP, substitution of the proline P in position 277 by a bulky amino acid selected from the group consisting of EHKRQYWFM or by a hydrophobic amino acid selected from the group consisting of VILMFGAWYC, in particular KAV, notably K, substitution of the lysine K in position 278 by a polar amino acid selected from the group consisting of WYSTCQNRHDE, in particular DNQ, notably DN, substitution of the serine S in position 280 by a non-bulky amino acid selected from the group consisting of GPLI-VADCTN or by a polar amino acid selected from the group consisting of WYTCQNRKHDE, in particular GH, substitution of the serine S in position 282 by a non-bulky amino acid selected from the group consisting of GPLI-VADCTN or by a hydrophobic amino acid selected from the group consisting of VILMFGAPWYC, in particular ALV, notably AL, and substitution of the isoleucine I in position 284 non-bulky amino acid selected from the group consisting of GPLVADCSTN, in particular VAL, notably V, further comprises at least one mutation selected from the group consisting of:

substitution of the proline P in position 68 by a non-bulky amino acid selected from the group consisting of GLI-VADCSTN, in particular GAV, substitution of the glycine G in position 226 by a non-bulky amino acid selected from the group consisting of PLIVADCSTN, in particular AVP, and substitution of the tryptophan W in position 279 by a hydrophobic amino acid selected from the group consisting of VILMFGAPYC or by a charged amino acid selected from the group consisting of RKHDEC, in particular RKDI, notably R.

It means that at least one substitution among the 21 particular substitutions of set 8 in position I168, D192, Y258, C260, T261, D263, G265, I266, A267, K268, P269, E270, Y/L271, K272, P273, K274, P277, K278, S280, S282 and I284 can be associated with at least at least one substitution among the 3 particular substitutions of set 9 in position P68, G226 and W279.

A more particular subject of the invention is mutated hyperthermophilic PTE having a lactonase activity according to the present invention, derived from the hyperthermophilic PTE of *Sulfolobus acidocaldarius* corresponding to the sequence SEQ ID NO: 5, said mutated hyperthermophilic PTE correspond to the following sequences:

SEQ ID NO: 51 corresponding to the SEQ ID NO: 5 comprising the following one mutation: substitution of the tryptophan W in position 264 by a phenylalanine F, SEQ ID NO: 53 corresponding to the SEQ ID NO: 5 comprising the following one mutation: substitution of the tryptophan W in position 264 by a methionine M, SEQ ID NO: 55 corresponding to the SEQ ID NO: 5 comprising the following one mutation: substitution of the tryptophan W in position 264 by a leucine L, SEQ ID NO: 57 corresponding to the SEQ ID NO: 5 comprising the following one mutation: substitution of the tryptophan W in position 264 by an alanine A, SEQ ID NO: 59 corresponding to the SEQ ID NO: 5 comprising the following one mutation: substitution of the tryptophan W in position 264 by an isoleucine I, SEQ ID NO: 61 corresponding to the SEQ ID NO: 5 comprising the following one mutation: substitution of the tryptophan W in position 264 by a valine V, SEQ ID NO: 63 corresponding to the SEQ ID NO: 5 comprising the following one mutation: substitution of the tryptophan W in position 264 by a threonine T, SEQ ID NO: 65 corresponding to the SEQ ID NO: 5 comprising the following three mutations: substitution of the cysteine C in position 259 by a leucine L, substitution of the isoleucine I in position 262 by a phenylalanine F, substitution of the tryptophan W in position 264 by an alanine A, SEQ ID NO: 67 corresponding to the SEQ ID NO: 5 comprising the following four mutations: substitution of the valine V in position 28 by an alanine A, substitution of the tyrosine Y in position 98 by a tryptophan W, substitution of the leucine L in position 229 by a methionine M, substitution of the tryptophan W in position 264 by a methionine M, SEQ ID NO: 69 corresponding to the SEQ ID NO: 5 comprising the following four mutations: substitution of the valine V in position 28 by an alanine A, substitution of the tyrosine Y in position 98 by a tryptophan W, substitution of the tryptophan W in position 264 by a leucine L, substitution of the methionine M in position 281 by a threonine T, SEQ ID NO: 71 corresponding to the SEQ ID NO: 5 comprising the following four mutations: substitution of the cytosine C in position 259 by an alanine A, substitution of the tryptophan W in position 264 by a methionine M, substitution of the methionine M in position 281 by a threonine T, SEQ ID NO: 73 corresponding to the SEQ ID NO: 5 comprising the following six mutations: substitution of the valine V in position 28 by an alanine A, substitution of the isoleucine I in position 77 by a threonine T, substitution of the tyrosine Y in position 98 by a tryptophan W, substitution of the tyrosine Y in position 100 by a phenylalanine F, substitution of the asparagine N in position 131 by a proline P, substitution of the leucine L in position 227 by a valine V, SEQ ID NO: 75 corresponding to the SEQ ID NO: 5 comprising the following six mutations: substitution of the leucine L in position 73 by an isoleucine I, substitution of the tyrosine Y in position 100 by a phenylalanine F, substitution of the isoleucine I in position 123 by a leucine L, substitution of the leucine L in position 229 by a methionine M, substitution of the phenylalanine F in position 230 by a serine S, substitution of the tryptophan W in position 264 by a leucine L, SEQ ID NO: 77 corresponding to the SEQ ID NO: 5 comprising the following seven mutations: substitution of the threonine T in position 69 by a serine S, substitution of the leucine L in position 73 by an isoleucine I, substitution of the asparagine N in position 131 by a proline P, substitution of the leucine L in position 229 by a methionine M, substitution of the phenylalanine F in position 230 by a serine S, substitution of the tryptophan W in position 264 by a methionine M, substitution of the leucine L in position 275 by a proline P, SEQ ID NO: 79 corresponding to the SEQ ID NO: 5 comprising the following six mutations: substitution of the threonine T in position 69 by a serine S, substitution of the isoleucine I in position 77 by a threonine T, substitution of the tyrosine Y in position 98 by a tryptophan W, substitution of the tyrosine Y in position 100 by a phenylalanine F, substitution of the leucine L in position 229 by a methionine M, substitution of the tryptophan W in position 264 by a leucine L, SEQ ID NO: 81 corresponding to the SEQ ID NO: 5 comprising the following five mutations: substitution of the lysine K in position 9 by a glutamic acid E, substitution of the tyrosine Y in position 98 by a tryptophan W, substitution of the tyrosine Y in position 100 by a phenylalanine F, substitution of the leucine L in position 229 by a methionine M, SEQ ID NO: 83 corresponding to the SEQ ID NO: 5 comprising the following two mutations: substitution of the leucine L in position 73 by an isoleucine I, substitution of the tryptophan W in position 264 by a phenylalanine F, SEQ ID NO: 85 corresponding to the SEQ ID NO: 5 comprising the following five mutations: substitution of the threonine T in position 69 by a serine S, substitution of the tyrosine Y in position 98 by a tryptophan W, substitution of the tyrosine Y in position 100 by a phenylalanine F, substitution of the asparagine N in position 131 by a proline P, substitution of the leucine L in position 229 by a methionine M, SEQ ID NO: 87 corresponding to the SEQ ID NO: 5 comprising the following four mutations: substitution of the valine V in position 28 by an alanine A, substitution of the leucine L in position 227 by a valine V, substitution the tryptophan W in position 264 by a leucine L, SEQ ID NO: 89 corresponding to the SEQ ID NO: 5 comprising the following eight mutations: substitution of the proline P in position 68 by a valine V, substitution of the threonine T in position 69 by a serine S, substitution of the tyrosine Y in position 98 by a tryptophan W, substitution of the tyrosine Y in position 100 by a phenylalanine F, substitution of the leucine L in position 229 by a methionine M, substitution of the cysteine C in position 259 by an alanine A, substitution the tryptophan W in position 264 by a leucine L, substitution of the methionine M in position 281 by a threonine T, SEQ ID NO: 91 corresponding to the SEQ ID NO: 5 comprising the following eight mutations: substitution of the threonine T in position 69 by a serine S, substitution of the tyrosine Y in position 98 by a tryptophan W, substitution of the tyrosine Y in position 100 by a phenylalanine F, substitution of the asparagine N in position 131 by a proline P, substitution of the leucine L in position 227 by a valine V, substitution the tryptophan W in position 264 by a methionine M, SEQ ID NO: 93 corresponding to the SEQ ID NO: 5 comprising the following five mutations: substitution of the threonine T in position 69 by a serine S, substitution of the leucine L in position 73 by an isoleucine I, substitution of the tyrosine Y in position 98 by a tryptophan W, substitution of the tyrosine Y in position 100 by a phenylalanine F, substitution of the asparagine N in position 131 by a proline P.

The coding sequence of the above-mentioned mutated hyperthermophilic PTE having a lactonase activity according to the present invention, derived from the hyperthermophilic PTE of *Sulfolobus acidocaldarius* corresponding to the sequence SEQ ID NO: 5 and corresponding to the following sequences SEQ ID NO: 50, 52, 54, 56, 58, 60, 62, 64, 66, 68, 70, 72, 74, 76, 78, 80, 82, 84, 86, 88, 90 and 92 are also part of the invention.

The invention also related to mutated hyperthermophilic PTE having a lactonase activity according to the present invention, derived from the hyperthermophilic PTE of *Sulfolobus acidocaldarius* corresponding to the sequence SEQ ID NO: 5, said mutated hyperthermophilic PTE correspond to the following sequences SEQ ID NO: 181, 183, 185, 187, 189, 191, 193, 195, 197, 199, 201, 203, 205, 207, 209, 21, 213, 215, 217, 219, 221 and 223 for the proteins and to their respective coding sequences SEQ ID NO: 180, 182, 184, 186, 188, 190, 192, 194, 196, 198, 200, 202, 204, 206, 208, 210, 212, 214, 216, 218, 220 and 222.

The invention relates more particularly to the above-mentioned mutated hyperthermophilic PTE having a lactonase activity, derived from the hyperthermophilic PTE of *Sulfolobus acidocaldarius* corresponding to the sequence SEQ ID NO: 5, further comprising at least one mutation corresponding to a substitution of at least one of the amino acids of the following amino acid pairs, the positions of which in SEQ ID NO: 5 are indicated hereafter, by another natural or non-natural amino acid: 3K/315S, 15G/13S, 27R/76D, 27R/43E, 34R/43E, 34R/46E, 56T/53E, 56T/286T, 75R/122D, 82K/43E, 82K/44D, 85K/81E, 110R/114E, 124K/163E, 148R/149D, 152R/149D, 155R/151E, 155R/188E, 155R/189E, 162R/189E, 184R/151E, 184R/188E, 184R/181E, 211K/246D, 216K/215D, 224R/257D, 224R/203D, 235K/205D, 236R/203D, 242K/246D, 246D/245K, 251R/250D, 278K/287D, 293K/299D, 311A/308K.

The invention relates also to the above-mentioned mutated hyperthermophilic PTEs having a lactonase activity, derived from the hyperthermophilic PTE of *Sulfolobus islandicus* corresponding to the sequence SEQ ID NO: 7, said mutated PTEs comprise the at least one mutation selected from the group consisting of: substitutions of the glycine G in position 7, the lysine K in position 8, the valine V in position 27, the leucine L in position 46, the lysine K in position 54, the proline P in position 67, the threonine T in position 68, the leucine L in position 72, the isoleucine I in position 76, the valine V in position 83, the tyrosine Y in position 97, the tyrosine Y in position 99, the isoleucine I in position 122, the serine S in position 130, the aspartic acid D in position 141, the lysine K in position 164, the isoleucine I in position 167, the aspartic acid D in position 191, the glycine G in position 193, the arginine R in position 223, the glycine G in position 225, the leucine L in position 226, the leucine L in position 228, the phenylalanine F in position 229, the leucine L in position 230, the tyrosine Y position 257, the cysteine C in position 258, the cysteine C in position 259, the threonine T in position 260, the isoleucine I in position 261, the aspartic acid D in position 262, the tryptophane W in position 263, the glycine G in position 264, the threonine T in position 265, the alanine A in position 266, the arginine R in position 267, the proline P in position 268, the glutamic acid E in position 269, the leucine L in position 270, the lysine K in position 271, the proline P in position 272, the lysine K in position 273, the leucine L in position 274, the alanine A in position 275, the proline P in position 276, the arginine R in position 277, the tryptophan W in position 278, the serine S in position 279, the methionine M in position 280, the alanine A in position 281, the serine S in position 282, the isoleucine I in position 283 and the serine S in position 297, of SEQ ID NO : 7 by any other natural or non-natural amino acid.

In a more specific embodiment, the above-mentioned mutated hyperthermophilic PTEs having a lactonase activity, derived from the hyperthermophilic PTE of *Sulfolobus islandicus* corresponding to the sequence SEQ ID NO: 7, comprise the at least one mutation selected from the group consisting of: substitutions of the valine V in position 27, the proline P in position 67, the threonine T in position 68, the leucine L in position 72, the tyrosine Y in position 97, the tyrosine Y in position 99, the aspartic acid D in position 141, the arginine R in position 223, the glycine G in position 225, the leucine L in position 226, the phenylalanine F in position 229, the cysteine C in position 258, the tryptophane W in position 263 and the tryptophan W in position 278, of SEQ ID NO: 7 by any other natural or non-natural amino acid.

In an even more specific embodiment, the above-mentioned mutated hyperthermophilic PTEs having a lactonase activity, derived from the hyperthermophilic PTE of *Sulfolobus islandicus* corresponding to the sequence SEQ ID NO: 7, comprise only one mutation, said mutation being selected from the group consisting of: substitutions of the valine V in position 27, the proline P in position 67, the threonine T in position 68, the leucine L in position 72, the aspartic acid D in position 141, the glycine G in position 225, the leucine L in position 226, the phenylalanine F in position 229, the tryptophane W in position 263 and the tryptophan W in position 278, of SEQ ID NO: 7 by any other natural or non-natural amino acid.

In an even more specific embodiment, the above-mentioned mutated hyperthermophilic PTEs having a lactonase activity, derived from the hyperthermophilic PTE of *Sulfolobus islandicus* corresponding to the sequence SEQ ID NO: 7, comprise the at least one mutation selected from the group consisting of: substitutions of the glycine G in position 7, the lysine K in position 8, the leucine L in position 46, the lysine K in position 54, the isoleucine I in position 76, the valine V in position 83, the isoleucine I in position 122, the serine S in position 130, the lysine K in position 164, the isoleucine I in position 167, the aspartic acid D in position 191, the glycine G in position 193, the leucine L in position 228, the leucine L in position 230, the tyrosine Y position 257, the cysteine C in position 259, the threonine T in position 260, the isoleucine I in position 261, the aspartic acid D in position 262, the glycine G in position 264, the threonine T in position 265, the alanine A in position 266, the arginine R in position 267, the proline P in position 268, the glutamic acid E in position 269, the leucine L in position 270, the lysine K in position 271, the proline P in position 272, the lysine K in position 273, the leucine L in position 274, the alanine A in position 275, the proline P in position 276, the arginine R in position 277, the serine S in position 279, the methionine M in position 280, the alanine A in position 281, the leucine L in position 282, the isoleucine I in position 283 and the serine S in position 297, of SEQ ID NO: 7 by any other natural or non-natural amino acid.

In an even more specific embodiment, the above-mentioned mutated hyperthermophilic PTEs having a lactonase activity, derived from the hyperthermophilic PTE of *Sulfolobus islandicus* corresponding to the sequence SEQ ID NO: 7, comprise only one mutation, said mutation being selected from the group consisting of: substitutions of the glycine G in position 7, the lysine K in position 8, the leucine L in position 46, the lysine K in position 54, the isoleucine I in position 76, the valine V in position 83, the isoleucine I in position 122, the serine S in position 130, the lysine K in position 164, the isoleucine I in position 167, the aspartic acid D in position 191, the glycine G in position 193, the leucine L in position 228, the leucine L in position 230, the tyrosine Y position 257, the cysteine C in position 259, the threonine T in position 260, the isoleucine I in position 261, the aspartic acid D in position 262, the glycine G in position 264, the threonine T in position 265, the alanine A in position 266, the arginine R in position 267, the proline P in position 268, the glutamic acid E in position 269, the leucine L in position 270, the lysine K in position 271, the proline P in position 272, the lysine K in position 273, the leucine L in position 274, the alanine A in position 275, the proline P in position 276, the arginine R in position 277, the serine S in position 279, the methionine M in position 280, the alanine A in position 281, the leucine L in position 282, the isoleucine I in position 283, the serine S in position 297, of SEQ ID NO: 7 by any other natural or non-natural amino acid.

The invention relates more particularly to the above-mentioned mutated hyperthermophilic PTE having a lactonase activity, derived from the hyperthermophilic PTE of *Sulfolobus islandicus* corresponding to the sequence SEQ ID NO: 7, and wherein the at least one mutation is selected from the group consisting of:

substitution of the glycine G in position 7 by a non-bulky amino acid selected from the group consisting of PLIVADCSTN, in particular STA, notably S, substitution of the lysine K in position 8 by a charged amino acid selected from the group consisting of RHDEC, in particular EDR, notably E, substitution of the valine V in position 27 by a non-bulky amino acid selected from the group consisting of GPLIADCSTN or by a hydrophobic amino acid selected from the group consisting of ILMFGAPWYC, in particular GIFA, notably A, substitution of the leucine L in position 46 by a non-bulky amino acid selected from the group consisting of GPIVADCSTN or by a polar amino acid selected from the group consisting of WYSTCQNRKHDE, in particular YW, substitution of the lysine K in position 54 by a bulky amino acid selected from the group consisting of EHRQYWFM or by a hydrophobic amino acid selected from the group consisting of VILMFGAPWYC, in particular IRL, notably I, substitution of the threonine T in position 68 by a non-bulky amino acid selected from the group consisting of GPLIVADCSN, in particular VAS, notably S, substitution of the leucine L in position 72 by a hydrophobic amino acid selected from the group consisting of VIMFGAPWYC, in particular CAMI, notably I, substitution of the isoleucine I in position 76 by a non-bulky amino acid selected from the group consisting of GPLVADCSTN, in particular PTV, notably T, substitution of the valine V in position 83 by a non-bulky amino acid selected from the group consisting of GPLIADCSTN or by a hydrophobic amino acid selected from the group consisting of ILMFGAPWYC, in particular AGI, notably A, substitution of the tyrosine Y in position 97 by a bulky amino acid selected from the group consisting of EHKRQWFM or by a hydrophobic amino acid selected from the group consisting of VILMFGAPWC, in particular FCLW, notably W, substitution of the tyrosine Y in position 99 by a bulky amino acid selected from the group consisting of EHKRQWFM or by a hydrophobic amino acid selected from the group consisting of VILMFGAPWC, in particular GEWF, notably F, substitution of the isoleucine I in position 122 by a non-bulky amino acid selected from the group consisting of GPLVADCSTN, in particular LAV, notably L, substitution of the serine S in position 130 by a non-bulky amino acid selected from the group consisting of GPLIVADCTN, in particular PT, notably P, substitution of the aspartic acid D in position 141 by a polar amino acid selected from the group consisting of WYSTCQNRKHE, in particular SET, notably T, substitution of the lysine K in position 164 by a polar amino acid selected from the group consisting of WYSTCQNRHDE, in particular NQR, notably N, substitution of the glycine G in position 193 by a non-bulky amino acid selected from the group consisting of PLIVADCSTN or by a polar amino acid selected from the group consisting of WYSTCNQRKHDE, in particular ST, notably S, substitution of the arginine R in position 223 by a non-bulky amino acid selected from the group consisting of GPLIVADCSTN or by a polar amino acid selected from the group consisting of WYSTCQNKHDE, in particular CSTAH, notably AC, substitution of the leucine L in position 226 by a non-bulky amino acid selected from the group consisting of GPIVADCSTN or by apolar amino acid selected from the group consisting of WYSTCQNRKHDE, in particular AIVH, notably V, substitution of the leucine L in position 228 by a non-bulky amino acid selected from the group consisting of GPIVADCSTN or by a hydrophobic amino acid selected from the group consisting of VIMFGAPWYC, in particular IM, notably M, substitution of the phenylalanine F in position 229 by a non-bulky amino acid selected from the group consisting of GPLIVADCSTN, in particular LTAS, notably S, substitution of the leucine L in position 230 by a non-bulky amino acid selected from the group consisting of GPIVADCSTN, in particular PVA, notably P, substitution of the cysteine C in position 258 by a hydrophobic amino acid selected from the group consisting of VILMFGAPWY, in particular YLIA, notably LA, substitution of the isoleucine I in position 261 by a hydrophobic amino acid selected from the group consisting of VLMFGAPWYC, in particular FWC, notably F, substitution of the tryptophane W in position 263 by a non-bulky amino acid selected from the group consisting of GPLIVDCSTN or by a hydrophobic amino acid selected from the group consisting of VILMFGAPYC, in particular ALMFCITV, notably F, substitution of the leucine L in position 274 by a hydrophobic amino acid selected from the group consisting of VIMFGAPWYC, in particular AVP, notably P, substitution of the alanine A in position 275 by a hydrophobic amino acid selected from the group consisting of VILMFGPWYC or by a non-bulky amino acid selected from the group consisting of GPLIVDCSTN, in particular NVMT, notably T, substitution of the methionine M in position 280 by a non-bulky amino acid selected from the group consisting of GPLIVADCSTN or by a hydrophobic amino acid selected from the group consisting of VLMFGAPWYC, in particular TYP, notably T, substitution of the leucine L in position 282 by a bulky amino acid selected from the group consisting of EKHRQYWFM, in particular FMH, notably M, and substitution of the serine S in position 297 by a polar amino acid selected from the group consisting of WYTCQNRKHDE, in particular QT.

These 29 particular substitutions in position G7, K8, V27, F46, K54, T68, L72, I76, V83, Y97, Y99, I122, S130, D141, K164, G193, R223, L226, L228, F229, L230, C258, I261, W263, L274, A275, M280, L282 and N297 belong to the tenth set of substitutions called set 10.

The invention relates more particularly to the above-mentioned mutated hyperthermophilic PTE having a lactonase activity, derived from the hyperthermophilic PTE of *Sulfolobus islandicus* corresponding to the sequence SEQ ID NO: 7, and wherein the at least one mutation is selected from the group consisting of:

- substitution of the isoleucine I in position 167 by a non-bulky amino acid selected from the group consisting of GPLVADCSTN or by a hydrophobic amino acid selected from the group consisting of VLMFGAPWYC, in particular VAL, notably V,
- substitution of the aspartic acid D in position 191 by a non-bulky amino acid selected from the group consisting of GPLIVADCSTN or by a polar amino acid selected from the group consisting of WYSTCQNRKHE, in particular ST, notably S,
- substitution of the tyrosine Y position 257 by a non-bulky amino acid selected from the group consisting of GPLIVADCSTN or by a hydrophobic amino acid selected from the group consisting of VLMFGAPWC, in particular CSVW, notably C,
- substitution of the cysteine C in position 259 a non-bulky amino acid selected from the group consisting of GPLIVADSTN or by a hydrophobic amino acid selected from the group consisting of VILMFGAPWY, in particular SFWV, notably S,
- substitution of the threonine T in position 260 a non-bulky amino acid selected from the group consisting of GPLIVADCSN or by a polar amino acid selected from the group consisting of WYSCQNRKHE, in particular GH, notably G,
- substitution of the aspartic acid D in position 262 by a polar amino acid selected from the group consisting of WYSTCQNRKHE or by a non-bulky amino acid selected from the group consisting of GPLIVADCSTN, in particular SLH,
- substitution of the glycine G in position 264 non-bulky amino acid selected from the group consisting of PLIVADCSTN or by a hydrophobic amino acid selected from the group consisting of VILMFAPWYC, in particular AVP,
- substitution of the threonine T in position 265 by a hydrophobic amino acid selected from the group consisting of VILMFGAPWYC or by a non-bulky amino acid selected from the group consisting of GPLIVADCSN, in particular VWP, notably V,
- substitution of the alanine A in position 266 by a polar amino acid selected from the group consisting of WYSTCQNRKHDE, in particular NQ, notably N,
- substitution of the arginine R in position 267 by a non-bulky amino acid selected from the group consisting of GPLIVADCSTN or by a hydrophobic amino acid selected from the group consisting of VILMFGAPWYC, in particular IAP, notably IP,
- substitution of the proline P in position 268 by a hydrophobic amino acid selected from the group consisting of VILMFGAWYC, in particular MCL, notably M,
- substitution of the glutamic acid E in position 269 by a polar amino acid selected from the group consisting of WYSTCQNRKHD, in particular DQ, notably D,
- substitution of the leucine L in position 270 by a non-bulky amino acid selected from the group consisting of GPIVADCSTN or by a hydrophobic amino acid selected from the group consisting of VILMFGAPWC, in particular VA,
- substitution of the lysine K in position 271 by a bulky amino acid selected from the group consisting of EHRQYWFM or by a hydrophobic amino acid selected from the group consisting of VILMFGAPWYC, in particular MLA,
- substitution of the proline P in position 272 by non-bulky amino acid selected from the group consisting of GPLIVADCSTN or by a polar amino acid selected from the group consisting of WYSTCQNRKHDE, in particular DEL, notably DL,
- substitution of the lysine K in position 273 by a non-bulky amino acid selected from the group consisting of GPLIVADCSTN or by a polar amino acid selected from the group consisting of WYSTCQNRHD, in particular RP,
- substitution of the proline P in position 276 by a bulky amino acid selected from the group consisting of EHKRQYWFM or by a hydrophobic amino acid selected from the group consisting of VILMFGAWYC, in particular KAV, notably K,
- substitution of the arginine R in position 277 by a polar amino acid selected from the group consisting of WYSTCQNKHDE, in particular DNQ, notably DN,
- substitution of the serine S in position 279 by a non-bulky amino acid selected from the group consisting of GPLIVADCTN or by a polar amino acid selected from the group consisting of WYTCQNRKHDE, in particular GH,
- substitution of the alanine A in position 281 by a non-bulky amino acid selected from the group consisting of GPLIVDCSTN or by a hydrophobic amino acid selected from the group consisting of VILMFGAPWYC, in particular ALV, notably AL,
- and substitution of the isoleucine I in position 283 non-bulky amino acid selected from the group consisting of GPLVADCSTN, in particular VAL, notably V.

These 21 particular substitutions in position I167, D191, Y257, C259, T260, D262, G264, T265, A266, R267, P268, E269, L270, K271, P272, K273, P276, R277, S279, A281 and I283 belong to the eleventh set of substitutions called set 11.

The invention relates more particularly to the above-mentioned mutated hyperthermophilic PTE having a lactonase activity, derived from the hyperthermophilic PTE of *Sulfolobus islandicus* corresponding to the sequence SEQ ID NO: 7, and wherein the at least one mutation is selected from the group consisting of:

- substitution of the proline P in position 67 by a non-bulky amino acid selected from the group consisting of GLIVADCSTN, in particular GAV,
- substitution of the glycine G in position 225 by a non-bulky amino acid selected from the group consisting of PLIVADCSTN, in particular AVP,
- and substitution of the tryptophan W in position 278 by a hydrophobic amino acid selected from the group consisting of VILMFGAPYC or by a charged amino acid selected from the group consisting of RKHDEC, in particular RKDI, notably R.

These 3 particular substitutions in position P67, G225 and W278 belong to the twelfth set of substitutions called set 12.

The invention also relates to the above-mentioned mutated hyperthermophilic PTE having a lactonase activity, derived from the hyperthermophilic PTE of *Sulfolobus islandicus* corresponding to the sequence SEQ ID NO: 7, wherein the at least one mutation selected from the group consisting of:

substitution of the glycine G in position 7 by a non-bulky amino acid selected from the group consisting of PLIVADCSTN, in particular STA, notably S, substitution of the lysine K in position 8 by a charged amino acid selected from the group consisting of RHDEC, in particular EDR, notably E, substitution of the valine V in position 27 by a non-bulky amino acid selected from the group consisting of GPLIADCSTN or by a hydrophobic amino acid selected from the group consisting of ILMFGAPWYC, in particular GIFA, notably A, substitution of the leucine L in position 46 by a non-bulky amino acid selected from the group consisting of GPIVADCSTN or by a polar amino acid selected from the group consisting of WYSTCQNRKHDE, in particular YW, substitution of the lysine K in position 54 by a bulky amino acid selected from the group consisting of EHRQYWFM or by a hydrophobic amino acid selected from the group consisting of VILMFGAPWYC, in particular IRL, notably I, substitution of the threonine T in position 68 by a non-bulky amino acid selected from the group consisting of GPLIVADCSN, in particular VAS, notably S, substitution of the leucine L in position 72 by a hydrophobic amino acid selected from the group consisting of VIMFGAPWYC, in particular CAMI, notably I, substitution of the isoleucine I in position 76 by a non-bulky amino acid selected from the group consisting of GPLVADCSTN, in particular PTV, notably T, substitution of the valine V in position 83 by a non-bulky amino acid selected from the group consisting of GPLIADCSTN or by a hydrophobic amino acid selected from the group consisting of ILMFGAPWYC, in particular AGI, notably A, substitution of the tyrosine Y in position 97 by a bulky amino acid selected from the group consisting of EHKRQWFM or by a hydrophobic amino acid selected from the group consisting of VILMFGAPWC, in particular FCLW, notably W, substitution of the tyrosine Y in position 99 by a bulky amino acid selected from the group consisting of EHKRQWFM or by a hydrophobic amino acid selected from the group consisting of VILMFGAPWC, in particular GEWF, notably F, substitution of the isoleucine I in position 122 by a non-bulky amino acid selected from the group consisting of GPLVADCSTN, in particular LAV, notably L, substitution of the serine S in position 130 by a non-bulky amino acid selected from the group consisting of GPLIVADCTN, in particular PT, notably P, substitution of the aspartic acid D in position 141 by a polar amino acid selected from the group consisting of WYSTCQNRKHE, in particular SET, notably T, substitution of the lysine K in position 164 by a polar amino acid selected from the group consisting of WYSTCQNRHDE, in particular NQR, notably N, substitution of the glycine G in position 193 by a non-bulky amino acid selected from the group consisting of PLIVADCSTN or by a polar amino acid selected from the group consisting of WYSTCNQRKHDE, in particular ST, notably S, substitution of the arginine R in position 223 by a non-bulky amino acid selected from the group consisting of GPLIVADCSTN or by a polar amino acid selected from the group consisting of WYSTCQNKHDE, in particular CSTAH, notably AC,
substitution of the leucine L in position 226 by a non-bulky amino acid selected from the group consisting of GPIVADCSTN or by apolar amino acid selected from the group consisting of WYSTCQNRKHDE, in particular AIVH, notably V,
substitution of the leucine L in position 228 by a non-bulky amino acid selected from the group consisting of GPIVADCSTN or by a hydrophobic amino acid selected from the group consisting of VIMFGAPWYC, in particular IM, notably M,
substitution of the phenylalanine F in position 229 by a non-bulky amino acid selected from the group consisting of GPLIVADCSTN, in particular LTAS, notably S,
substitution of the leucine L in position 230 by a non-bulky amino acid selected from the group consisting of GPIVADCSTN, in particular PVA, notably P,
substitution of the cysteine C in position 258 by a hydrophobic amino acid selected from the group consisting of VILMFGAPWY, in particular YLIA, notably LA,
substitution of the isoleucine I in position 261 by a hydrophobic amino acid selected from the group consisting of VLMFGAPWYC, in particular FWC, notably F,
substitution of the tryptophane W in position 263 by a non-bulky amino acid selected from the group consisting of GPLIVDCSTN or by a hydrophobic amino acid selected from the group consisting of VILMFGAPYC, in particular ALMFCITV, notably F,
substitution of the leucine L in position 274 by a hydrophobic amino acid selected from the group consisting of VIMFGAPWYC, in particular AVP, notably P,
substitution of the alanine A in position 275 by a hydrophobic amino acid selected from the group consisting of VILMFGPWYC or by a non-bulky amino acid selected from the group consisting of GPLIVDCSTN, in particular NVMT, notably T,
substitution of the methionine M in position 280 by a non-bulky amino acid selected from the group consisting of GPLIVADCSTN or by a hydrophobic amino acid selected from the group consisting of VLMFGAPWYC, in particular TYP, notably T,
substitution of the leucine L in position 282 by a bulky amino acid selected from the group consisting of EKHRQYWFM, in particular FMH, notably M,
and substitution of the serine S in position 297 by a polar amino acid selected from the group consisting of WYTCQNRKHDE, in particular QT, further comprises at least one mutation selected from the group consisting of:

substitution of the isoleucine I in position 167 by a non-bulky amino acid selected from the group consisting of GPLVADCSTN or by a hydrophobic amino acid selected from the group consisting of VLMFGAPWYC, in particular VAL, notably V,
substitution of the aspartic acid D in position 191 by a non-bulky amino acid selected from the group consisting of GPLIVADCSTN or by a polar amino acid selected from the group consisting of WYSTCQNRKHE, in particular ST, notably S,
substitution of the tyrosine Y position 257 by a non-bulky amino acid selected from the group consisting of GPLIVADCSTN or by a hydrophobic amino acid selected from the group consisting of VLMFGAPWC, in particular CSVW, notably C,
substitution of the cysteine C in position 259 a non-bulky amino acid selected from the group consisting of GPLI- VADSTN or by a hydrophobic amino acid selected from the group consisting of VILMFGAPWY, in particular SFWV, notably S, substitution of the threonine T in position 260 a non-bulky amino acid selected from the group consisting of GPLIVADCSN or by a polar amino acid selected from the group consisting of WYSCQNRKHE, in particular GH, notably G, substitution of the aspartic acid D in position 262 by a polar amino acid selected from the group consisting of WYSTCQNRKHE or by a non-bulky amino acid selected from the group consisting of GPLIVADCSTN, in particular SLH, substitution of the glycine G in position 264 non-bulky amino acid selected from the group consisting of PLIVADCSTN or by a hydrophobic amino acid selected from the group consisting of VILMFAPWYC, in particular AVP, substitution of the threonine T in position 265 by a hydrophobic amino acid selected from the group consisting of VILMFGAPWYC or by a non-bulky amino acid selected from the group consisting of GPLIVADCSN, in particular VWP, notably V, substitution of the alanine A in position 266 by a polar amino acid selected from the group consisting of WYSTCQNRKHDE, in particular NQ, notably N, substitution of the arginine R in position 267 by a non-bulky amino acid selected from the group consisting of GPLIVADCSTN or by a hydrophobic amino acid selected from the group consisting of VILMFGAPWYC, in particular IAP, notably IP, substitution of the proline P in position 268 by a hydrophobic amino acid selected from the group consisting of VILMFGAWYC, in particular MCL, notably M, substitution of the glutamic acid E in position 269 by a polar amino acid selected from the group consisting of WYSTCQNRKHD, in particular DQ, notably D, substitution of the leucine L in position 270 by a non-bulky amino acid selected from the group consisting of GPIVADCSTN or by a hydrophobic amino acid selected from the group consisting of VILMFGAPWC, in particular VA, substitution of the lysine K in position 271 by a bulky amino acid selected from the group consisting of EHRQYWFM or by a hydrophobic amino acid selected from the group consisting of VILMFGAPWYC, in particular MLA, substitution of the proline P in position 272 by non-bulky amino acid selected from the group consisting of GPLIVADCSTN or by a polar amino acid selected from the group consisting of WYSTCQNRKHDE, in particular DEL, notably DL, substitution of the lysine K in position 273 by a non-bulky amino acid selected from the group consisting of GPLIVADCSTN or by a polar amino acid selected from the group consisting of WYSTCQNRHD, in particular RP, substitution of the proline P in position 276 by a bulky amino acid selected from the group consisting of EHKRQYWFM or by a hydrophobic amino acid selected from the group consisting of VILMFGAWYC, in particular KAV, notably K, substitution of the arginine R in position 277 by a polar amino acid selected from the group consisting of WYSTCQNKHDE, in particular DNQ, notably DN, substitution of the serine S in position 279 by a non-bulky amino acid selected from the group consisting of GPLI-VADCTN or by a polar amino acid selected from the group consisting of WYTCQNRKHDE, in particular GH, substitution of the alanine A in position 281 by a non-bulky amino acid selected from the group consisting of GPLIVDCSTN or by a hydrophobic amino acid selected from the group consisting of VILMFGAPWYC, in particular ALV, notably AL, and substitution of the isoleucine I in position 283 non-bulky amino acid selected from the group consisting of GPLVADCSTN, in particular VAL, notably V.

It means that at least one substitution among the 29 particular substitutions of set 10 in position G7, K8, V27, F46, K54, T68, L72, I76, V83, Y97, Y99, I122, S130, D141, K164, G193, R223, L226, L228, F229, L230, C258, I261, W263, L274, A275, M280, L282 and N297 can be associated with at least one substitution among the 21 particular substitutions of set 11 in position I167, D191, Y257, C259, T260, D262, G264, T265, A266, R267, P268, E269, L270, K271, P272, K273, P276, R277, S279, A281 and I283.

The invention also relates to the above-mentioned mutated hyperthermophilic PTE having a lactonase activity, derived from the hyperthermophilic PTE of *Sulfolobus islandicus* corresponding to the sequence SEQ ID NO: 7, wherein the at least one mutation selected from the group consisting of:

substitution of the glycine G in position 7 by a non-bulky amino acid selected from the group consisting of PLIVADCSTN, in particular STA, notably S, substitution of the lysine K in position 8 by a charged amino acid selected from the group consisting of RHDEC, in particular EDR, notably E, substitution of the valine V in position 27 by a non-bulky amino acid selected from the group consisting of GPLIADCSTN or by a hydrophobic amino acid selected from the group consisting of ILMFGAPWYC, in particular GIFA, notably A, substitution of the leucine L in position 46 by a non-bulky amino acid selected from the group consisting of GPIVADCSTN or by a polar amino acid selected from the group consisting of WYSTCQNRKHDE, in particular YW, substitution of the lysine K in position 54 by a bulky amino acid selected from the group consisting of EHRQYWFM or by a hydrophobic amino acid selected from the group consisting of VILMFGAPWYC, in particular IRL, notably I, substitution of the threonine T in position 68 by a non-bulky amino acid selected from the group consisting of GPLIVADCSN, in particular VAS, notably S, substitution of the leucine L in position 72 by a hydrophobic amino acid selected from the group consisting of VIMFGAPWYC, in particular CAMI, notably I, substitution of the isoleucine I in position 76 by a non-bulky amino acid selected from the group consisting of GPLVADCSTN, in particular PTV, notably T, substitution of the valine V in position 83 by a non-bulky amino acid selected from the group consisting of GPLIADCSTN or by a hydrophobic amino acid selected from the group consisting of ILMFGAPWYC, in particular AGI, notably A, substitution of the tyrosine Y in position 97 by a bulky amino acid selected from the group consisting of EHKRQWFM or by a hydrophobic amino acid selected from the group consisting of VILMFGAPWC, in particular FCLW, notably W, substitution of the tyrosine Y in position 99 by a bulky amino acid selected from the group consisting of EHKRQWFM or by a hydrophobic amino acid selected from the group consisting of VILMFGAPWC, in particular GEWF, notably F, substitution of the isoleucine I in position 122 by a non-bulky amino acid selected from the group consisting of GPLVADCSTN, in particular LAV, notably L, substitution of the serine S in position 130 by a non-bulky amino acid selected from the group consisting of GPLIVADCTN, in particular PT, notably P, substitution of the aspartic acid D in position 141 by a polar amino acid selected from the group consisting of WYSTCQNRKHE, in particular SET, notably T, substitution of the lysine K in position 164 by a polar amino acid selected from the group consisting of WYSTCQNRHDE, in particular NQR, notably N, substitution of the glycine G in position 193 by a non-bulky amino acid selected from the group consisting of PLIVADCSTN or by a polar amino acid selected from the group consisting of WYSTCNQRKHDE, in particular ST, notably S, substitution of the arginine R in position 223 by a non-bulky amino acid selected from the group consisting of GPLIVADCSTN or by a polar amino acid selected from the group consisting of WYSTCQNKHDE, in particular CSTAH, notably AC, substitution of the leucine L in position 226 by a non-bulky amino acid selected from the group consisting of GPIVADCSTN or by apolar amino acid selected from the group consisting of WYSTCQNRKHDE, in particular AIVH, notably V, substitution of the leucine L in position 228 by a non-bulky amino acid selected from the group consisting of GPIVADCSTN or by a hydrophobic amino acid selected from the group consisting of VIMFGAPWYC, in particular IM, notably M, substitution of the phenylalanine F in position 229 by a non-bulky amino acid selected from the group consisting of GPLIVADCSTN, in particular LTAS, notably S, substitution of the leucine L in position 230 by a non-bulky amino acid selected from the group consisting of GPIVADCSTN, in particular PVA, notably P, substitution of the cysteine C in position 258 by a hydrophobic amino acid selected from the group consisting of VILMFGAPWY, in particular YLIA, notably LA, substitution of the isoleucine I in position 261 by a hydrophobic amino acid selected from the group consisting of VLMFGAPWYC, in particular FWC, notably F, substitution of the tryptophane W in position 263 by a non-bulky amino acid selected from the group consisting of GPLIVDCSTN or by a hydrophobic amino acid selected from the group consisting of VILMFGAPYC, in particular ALMFCITV, notably F, substitution of the leucine L in position 274 by a hydrophobic amino acid selected from the group consisting of VIMFGAPWYC, in particular AVP, notably P, substitution of the alanine A in position 275 by a hydrophobic amino acid selected from the group consisting of VILMFGPWYC or by a non-bulky amino acid selected from the group consisting of GPLIVDCSTN, in particular NVMT, notably T, substitution of the methionine M in position 280 by a non-bulky amino acid selected from the group consisting of GPLIVADCSTN or by a hydrophobic amino acid selected from the group consisting of VLMFGAPWYC, in particular TYP, notably T, substitution of the leucine L in position 282 by a bulky amino acid selected from the group consisting of EKHRQYWFM, in particular FMH, notably M, and substitution of the serine S in position 297 by a polar amino acid selected from the group consisting of WYTCQNRKHDE, in particular QT, further comprises at least one mutation selected from the group consisting of:

substitution of the proline P in position 67 by a non-bulky amino acid selected from the group consisting of GLIVADCSTN, in particular GAV, substitution of the glycine G in position 225 by a non-bulky amino acid selected from the group consisting of PLIVADCSTN, in particular AVP, and substitution of the tryptophan W in position 278 by a hydrophobic amino acid selected from the group consisting of VILMFGAPYC or by a charged amino acid selected from the group consisting of RKHDEC, in particular RKDI, notably R.

It means that at least one substitution among the 29 particular substitutions of set 10 in position G7, K8, V27, F46, K54, T68, L72, I76, V83, Y97, Y99, I122, S130, D141, K164, G193, R223, L226, L228, F229, L230, C258, I261, W263, L274, A275, M280, L282 and N297 can be associated with at least one substitution among the, K273, P276, R277, S279, A281 and I283 and with at least one substitution among the 3 particular substitutions of set 12 in position P67, G225 and W278.

The invention also relates to the above-mentioned mutated hyperthermophilic PTE having a lactonase activity, derived from the hyperthermophilic PTE of *Sulfolobus islandicus* corresponding to the sequence SEQ ID NO: 7, wherein the at least one mutation selected from the group consisting of:

substitution of the glycine G in position 7 by a non-bulky amino acid selected from the group consisting of PLIVADCSTN, in particular STA, notably S, substitution of the lysine K in position 8 by a charged amino acid selected from the group consisting of RHDEC, in particular EDR, notably E, substitution of the valine V in position 27 by a non-bulky amino acid selected from the group consisting of GPLIADCSTN or by a hydrophobic amino acid selected from the group consisting of ILMFGAPWYC, in particular GIFA, notably A, substitution of the leucine L in position 46 by a non-bulky amino acid selected from the group consisting of GPIVADCSTN or by a polar amino acid selected from the group consisting of WYSTCQNRKHDE, in particular YW, substitution of the lysine K in position 54 by a bulky amino acid selected from the group consisting of EHRQYWFM or by a hydrophobic amino acid selected from the group consisting of VILMFGAPWYC, in particular IRL, notably I, substitution of the threonine T in position 68 by a non-bulky amino acid selected from the group consisting of GPLIVADCSN, in particular VAS, notably S, substitution of the leucine L in position 72 by a hydrophobic amino acid selected from the group consisting of VIMFGAPWYC, in particular CAMI, notably I, substitution of the isoleucine I in position 76 by a non-bulky amino acid selected from the group consisting of GPLVADCSTN, in particular PTV, notably T, substitution of the valine V in position 83 by a non-bulky amino acid selected from the group consisting of GPLIADCSTN or by a hydrophobic amino acid selected from the group consisting of ILMFGAPWYC, in particular AGI, notably A, substitution of the tyrosine Y in position 97 by a bulky amino acid selected from the group consisting of EHKRQWFM or by a hydrophobic amino acid selected from the group consisting of VILMFGAPWC, in particular FCLW, notably W, substitution of the tyrosine Y in position 99 by a bulky amino acid selected from the group consisting of EHKRQWFM or by a hydrophobic amino acid selected from the group consisting of VILMFGAPWC, in particular GEWF, notably F, substitution of the isoleucine I in position 122 by a non-bulky amino acid selected from the group consisting of GPLVADCSTN, in particular LAV, notably L, substitution of the serine S in position 130 by a non-bulky amino acid selected from the group consisting of GPLIVADCTN, in particular PT, notably P, substitution of the aspartic acid D in position 141 by a polar amino acid selected from the group consisting of WYSTCQNRKHE, in particular SET, notably T, substitution of the lysine K in position 164 by a polar amino acid selected from the group consisting of WYSTCQNRHDE, in particular NQR, notably N, substitution of the glycine G in position 193 by a non-bulky amino acid selected from the group consisting of PLIVADCSTN or by a polar amino acid selected from the group consisting of WYSTCNQRKHDE, in particular ST, notably S, substitution of the arginine R in position 223 by a non-bulky amino acid selected from the group consisting of GPLIVADCSTN or by a polar amino acid selected from the group consisting of WYSTCQNKHDE, in particular CSTAH, notably AC, substitution of the leucine L in position 226 by a non-bulky amino acid selected from the group consisting of GPIVADCSTN or by apolar amino acid selected from the group consisting of WYSTCQNRKHDE, in particular AIVH, notably V, substitution of the leucine L in position 228 by a non-bulky amino acid selected from the group consisting of GPIVADCSTN or by a hydrophobic amino acid selected from the group consisting of VIMFGAPWYC, in particular IM, notably M, substitution of the phenylalanine F in position 229 by a non-bulky amino acid selected from the group consisting of GPLIVADCSTN, in particular LTAS, notably S, substitution of the leucine L in position 230 by a non-bulky amino acid selected from the group consisting of GPIVADCSTN, in particular PVA, notably P, substitution of the cysteine C in position 258 by a hydrophobic amino acid selected from the group consisting of VILMFGAPWY, in particular YLIA, notably LA, substitution of the isoleucine I in position 261 by a hydrophobic amino acid selected from the group consisting of VLMFGAPWYC, in particular FWC, notably F, substitution of the tryptophane W in position 263 by a non-bulky amino acid selected from the group consisting of GPLIVDCSTN or by a hydrophobic amino acid selected from the group consisting of VILMFGAPYC, in particular ALMFCITV, notably F, substitution of the leucine L in position 274 by a hydrophobic amino acid selected from the group consisting of VIMFGAPWYC, in particular AVP, notably P, substitution of the alanine A in position 275 by a hydrophobic amino acid selected from the group consisting of VILMFGPWYC or by a non-bulky amino acid selected from the group consisting of GPLIVDCSTN, in particular NVMT, notably T, substitution of the methionine M in position 280 by a non-bulky amino acid selected from the group consisting of GPLIVADCSTN or by a hydrophobic amino acid selected from the group consisting of VLMFGAPWYC, in particular TYP, notably T, substitution of the leucine L in position 282 by a bulky amino acid selected from the group consisting of EKHRQYWFM, in particular FMH, notably M, and substitution of the serine S in position 297 by a polar amino acid selected from the group consisting of WYTCQNRKHDE, in particular QT, further comprises at least one mutation selected from the group consisting of:

substitution of the isoleucine I in position 167 by a non-bulky amino acid selected from the group consisting of GPLVADCSTN or by a hydrophobic amino acid selected from the group consisting of VLMFGAPWYC, in particular VAL, notably V, substitution of the aspartic acid D in position 191 by a non-bulky amino acid selected from the group consisting of GPLIVADCSTN or by a polar amino acid selected from the group consisting of WYSTCQNRKHE, in particular ST, notably S, substitution of the tyrosine Y position 257 by a non-bulky amino acid selected from the group consisting of GPLIVADCSTN or by a hydrophobic amino acid selected from the group consisting of VLMFGAPWC, in particular CSVW, notably C, substitution of the cysteine C in position 259 a non-bulky amino acid selected from the group consisting of GPLIVADSTN or by a hydrophobic amino acid selected from the group consisting of VILMFGAPWY, in particular SFWV, notably S, substitution of the threonine T in position 260 a non-bulky amino acid selected from the group consisting of GPLIVADCSN or by a polar amino acid selected from the group consisting of WYSCQNRKHE, in particular GH, notably G, substitution of the aspartic acid D in position 262 by a polar amino acid selected from the group consisting of WYSTCQNRKHE or by a non-bulky amino acid selected from the group consisting of GPLIVADCSTN, in particular SLH, substitution of the glycine G in position 264 non-bulky amino acid selected from the group consisting of PLIVADCSTN or by a hydrophobic amino acid selected from the group consisting of VILMFAPWYC, in particular AVP, substitution of the threonine T in position 265 by a hydrophobic amino acid selected from the group consisting of VILMFGAPWYC or by a non-bulky amino acid selected from the group consisting of GPLIVADCSN, in particular VWP, notably V, substitution of the alanine A in position 266 by a polar amino acid selected from the group consisting of WYSTCQNRKHDE, in particular NQ, notably N, substitution of the arginine R in position 267 by a non-bulky amino acid selected from the group consisting of GPLIVADCSTN or by a hydrophobic amino acid selected from the group consisting of VILMFGAP-WYC, in particular TAP, notably IP, substitution of the proline P in position 268 by a hydrophobic amino acid selected from the group consisting of VILMFGAWYC, in particular MCL, notably M, substitution of the glutamic acid E in position 269 by a polar amino acid selected from the group consisting of WYSTCQNRKHD, in particular DQ, notably D, substitution of the leucine L in position 270 by a non-bulky amino acid selected from the group consisting of GPIVADCSTN or by a hydrophobic amino acid selected from the group consisting of VILMFGAPWC, in particular VA, substitution of the lysine K in position 271 by a bulky amino acid selected from the group consisting of EHRQYWFM or by a hydrophobic amino acid selected from the group consisting of VILMFGAPWYC, in particular MLA, substitution of the proline P in position 272 by non-bulky amino acid selected from the group consisting of GPLIVADCSTN or by a polar amino acid selected from the group consisting of WYSTCQNRKHDE, in particular DEL, notably DL, substitution of the lysine K in position 273 by a non-bulky amino acid selected from the group consisting of GPLIVADCSTN or by a polar amino acid selected from the group consisting of WYSTCQNRHD, in particular RP, substitution of the proline P in position 276 by a bulky amino acid selected from the group consisting of EHKRQYWFM or by a hydrophobic amino acid selected from the group consisting of VILMFGAWYC, in particular KAV, notably K, substitution of the arginine R in position 277 by a polar amino acid selected from the group consisting of WYSTCQNKHDE, in particular DNQ, notably DN, substitution of the serine S in position 279 by a non-bulky amino acid selected from the group consisting of GPLIVADCTN or by a polar amino acid selected from the group consisting of WYTCQNRKHDE, in particular GH, substitution of the alanine A in position 281 by a non-bulky amino acid selected from the group consisting of GPLIVDCSTN or by a hydrophobic amino acid selected from the group consisting of VILMFGAPWYC, in particular ALV, notably AL, and substitution of the isoleucine I in position 283 non-bulky amino acid selected from the group consisting of GPLVADCSTN, in particular VAL, notably V, further comprises at least one mutation selected from the group consisting of:

substitution of the proline P in position 67 by a non-bulky amino acid selected from the group consisting of GLIVADCSTN, in particular GAV, substitution of the glycine G in position 225 by a non-bulky amino acid selected from the group consisting of PLIVADCSTN, in particular AVP, and substitution of the tryptophan W in position 278 by a hydrophobic amino acid selected from the group consisting of VILMFGAPYC or by a charged amino acid selected from the group consisting of RKHDEC, in particular RKDI, notably R.

It means that at least one substitution among the 29 particular substitutions of set 10 in position G7, K8, V27, F46, K54, T68, L72, I76, V83, Y97, Y99, I122, S130, D141, K164, G193, R223, L226, L228, F229, L230, C258, I261, W263, L274, A275, M280, L282 and N297 can be associated with at least one substitution among the 21 particular substitutions of set 11 in position I167, D191, Y257, C259, T260, D262, G264, T265, A266, R267, P268, E269, L270, K271, P272, K273, P276, R277, S279, A281 and I283 and with at least one substitution among the 3 particular substitutions of set 12 in position P67, G225 and W278.

The invention also relates to the above-mentioned mutated hyperthermophilic PTE having a lactonase activity, derived from the hyperthermophilic PTE of *Sulfolobus islandicus* corresponding to the sequence SEQ ID NO: 7, wherein the at least one mutation selected from the group consisting of:

substitution of the isoleucine I in position 167 by a non-bulky amino acid selected from the group consisting of GPLVADCSTN or by a hydrophobic amino acid selected from the group consisting of VLMFGAP-WYC, in particular VAL, notably V, substitution of the aspartic acid D in position 191 by a non-bulky amino acid selected from the group consisting of GPLIVADCSTN or by a polar amino acid selected from the group consisting of WYSTCQN-RKHE, in particular ST, notably S, substitution of the tyrosine Y position 257 by a non-bulky amino acid selected from the group consisting of GPLIVADCSTN or by a hydrophobic amino acid selected from the group consisting of VLMFGAPWC, in particular CSVW, notably C, substitution of the cysteine C in position 259 a non-bulky amino acid selected from the group consisting of GPLIVADSTN or by a hydrophobic amino acid selected from the group consisting of VILMFGAPWY, in particular SFWV, notably S, substitution of the threonine T in position 260 a non-bulky amino acid selected from the group consisting of GPLIVADCSN or by a polar amino acid selected from the group consisting of WYSCQNRKHE, in particular GH, notably G, substitution of the aspartic acid D in position 262 by a polar amino acid selected from the group consisting of WYSTCQNRKHE or by a non-bulky amino acid selected from the group consisting of GPLIVADCSTN, in particular SLH, substitution of the glycine G in position 264 non-bulky amino acid selected from the group consisting of PLIVADCSTN or by a hydrophobic amino acid selected from the group consisting of VILMFAPWYC, in particular AVP, substitution of the threonine T in position 265 by a hydrophobic amino acid selected from the group consisting of VILMFGAPWYC or by a non-bulky amino acid selected from the group consisting of GPLIVADCSN, in particular VWP, notably V, substitution of the alanine A in position 266 by a polar amino acid selected from the group consisting of WYSTCQNRKHDE, in particular NQ, notably N, substitution of the arginine R in position 267 by a non-bulky amino acid selected from the group consisting of GPLIVADCSTN or by a hydrophobic amino acid selected from the group consisting of VILMFGAP-WYC, in particular IAP, notably IP, substitution of the proline P in position 268 by a hydrophobic amino acid selected from the group consisting of VILMFGAWYC, in particular MCL, notably M, substitution of the glutamic acid E in position 269 by a polar amino acid selected from the group consisting of WYSTCQNRKHD, in particular DQ, notably D, substitution of the leucine L in position 270 by a non-bulky amino acid selected from the group consisting of GPIVADCSTN or by a hydrophobic amino acid selected from the group consisting of VILMFGAPWC, in particular VA, substitution of the lysine K in position 271 by a bulky amino acid selected from the group consisting of EHRQYWFM or by a hydrophobic amino acid selected from the group consisting of VILMFGAPWYC, in particular MLA, substitution of the proline P in position 272 by non-bulky amino acid selected from the group consisting of GPLIVADCSTN or by a polar amino acid selected from the group consisting of WYSTCQNRKHDE, in particular DEL, notably DL, substitution of the lysine K in position 273 by a non-bulky amino acid selected from the group consisting of GPLIVADCSTN or by a polar amino acid selected from the group consisting of WYSTCQNRHD, in particular RP, substitution of the proline P in position 276 by a bulky amino acid selected from the group consisting of EHKRQYWFM or by a hydrophobic amino acid selected from the group consisting of VILMFGAWYC, in particular KAV, notably K, substitution of the arginine R in position 277 by a polar amino acid selected from the group consisting of WYSTCQNKHDE, in particular DNQ, notably DN, substitution of the serine S in position 279 by a non-bulky amino acid selected from the group consisting of GPLIVADCTN or by a polar amino acid selected from the group consisting of WYTCQNRKHDE, in particular GH, substitution of the alanine A in position 281 by a non-bulky amino acid selected from the group consisting of GPLIVDCSTN or by a hydrophobic amino acid selected from the group consisting of VILMFGAPWYC, in particular ALV, notably AL, and substitution of the isoleucine I in position 283 non-bulky amino acid selected from the group consisting of GPLVADCSTN, in particular VAL, notably V, further comprises at least one mutation selected from the group consisting of:

substitution of the proline P in position 67 by a non-bulky amino acid selected from the group consisting of GLIVADCSTN, in particular GAV, substitution of the glycine G in position 225 by a non-bulky amino acid selected from the group consisting of PLIVADCSTN, in particular AVP, and substitution of the tryptophan W in position 278 by a hydrophobic amino acid selected from the group consisting of VILMFGAPYC or by a charged amino acid selected from the group consisting of RKHDEC, in particular RKDI, notably R.

It means that at least one substitution among the 21 particular substitutions of set 11 in position I167, D191, Y257, C259, T260, D262, G264, T265, A266, R267, P268, E269, L270, K271, P272, K273, P276, R277, S279, A281 and I283 can be associated with at least one substitution among the 3 particular substitutions of set 12 in position P67, G225 and W278.

A more particular subject of the invention is mutated hyperthermophilic PTE having a lactonase activity according to the present invention, derived from the hyperthermophilic PTE of *Sulfolobus islandicus* corresponding to the sequence SEQ ID NO: 7, said mutated hyperthermophilic PTE correspond to the following sequences:

SEQ ID NO: 95 corresponding to the SEQ ID NO: 7 comprising the following one mutation: substitution of the tryptophan W in position 263 by a phenylalanine F, SEQ ID NO: 97 corresponding to the SEQ ID NO: 7 comprising the following one mutation: substitution of the tryptophan W in position 263 by a methionine M, SEQ ID NO: 99 corresponding to the SEQ ID NO: 7 comprising the following one mutation: substitution of the tryptophan W in position 263 by a leucine L, SEQ ID NO: 101 corresponding to the SEQ ID NO: 7 comprising the following one mutation: substitution of the tryptophan W in position 263 by an alanine A, SEQ ID NO: 103 corresponding to the SEQ ID NO: 7 comprising the following one mutation: substitution of the tryptophan W in position 263 by an isoleucine I, SEQ ID NO: 105 corresponding to the SEQ ID NO: 7 comprising the following one mutation: substitution of the tryptophan W in position 263 by a valine V, SEQ ID NO: 107 corresponding to the SEQ ID NO: 7 comprising the following one mutation: substitution of the tryptophan W in position 263 by a threonine T, SEQ ID NO: 109 corresponding to the SEQ ID NO: 7 comprising the following three mutations: substitution of the cysteine C in position 258 by a leucine L, substitution of the isoleucine I in position 261 by a phenylalanine F, substitution of the tryptophan W in position 263 by an alanine A, SEQ ID NO: 111 corresponding to the SEQ ID NO: 7 comprising the following four mutations: substitution of the valine V in position 27 by an alanine A, substitution of the tyrosine Y in position 97 by a tryptophan W, substitution of the leucine L in position 228 by a methionine M, substitution of the tryptophan W in position 263 by a methionine M, SEQ ID NO: 113 corresponding to the SEQ ID NO: 7 comprising the following four mutations: substitution of the valine V in position 27 by an alanine A, substitution of the tyrosine Y in position 97 by a tryptophan W, substitution of the tryptophan W in position 263 by a leucine L, substitution of the methionine M in position 280 by a threonine T, SEQ ID NO: 115 corresponding to the SEQ ID NO: 7 comprising the following four mutations: substitution of the cytosine C in position 258 by an alanine A, substitution of the tryptophan W in position 263 by a methionine M, substitution of the methionine M in position 280 by a threonine T, SEQ ID NO: 117 corresponding to the SEQ ID NO: 7 comprising the following six mutations: substitution of the valine V in position 27 by an alanine A, substitution of the isoleucine I in position 76 by a threonine T, substitution of the tyrosine Y in position 97 by a tryptophan W, substitution of the tyrosine Y in position 99 by a phenylalanine F, substitution of the serine S in position 130 by a proline P, substitution of the leucine L in position 226 by a valine V, SEQ ID NO: 119 corresponding to the SEQ ID NO: 7 comprising the following six mutations: substitution of the leucine L in position 72 by an isoleucine I, substitution of the tyrosine Y in position 99 by a phenylalanine F, substitution of the isoleucine I in position 122 by a leucine L, substitution of the leucine L in position 228 by a methionine M, substitution of the phenylalanine F in position 229 by a serine S, substitution of the tryptophan W in position 263 by a leucine L, SEQ ID NO: 121 corresponding to the SEQ ID NO: 7 comprising the following seven mutations: substitution of the threonine T in position 68 by a serine S, substitution of the leucine L in position 72 by an isoleucine I, substitution of the serine S in position 130 by a proline P, substitution of the leucine L in position 228 by a methionine M, substitution of the phenylalanine F in position 229 by a serine S, substitution of the tryptophan W in position 263 by a methionine M, substitution of the leucine L in position 274 by a proline P, SEQ ID NO: 123 corresponding to the SEQ ID NO: 7 comprising the following six mutations: substitution of the threonine T in position 68 by a serine S, substitution of the isoleucine I in position 76 by a threonine T, substitution of the tyrosine Y in position 97 by a tryptophan W, substitution of the tyrosine Y in position 99 by a phenylalanine F, substitution of the leucine L in position 228 by a methionine M, substitution of the tryptophan W in position 263 by a leucine L, SEQ ID NO: 125 corresponding to the SEQ. ID NO: 7 comprising the following five mutations: substitution of the lysine K in position 8 by an glutamic acid E, substitution of the tyrosine Y in position 97 by a tryptophan W, substitution of the tyrosine Y in position 99 by a phenylalanine F, substitution of the leucine L in position 228 by a methionine M, SEQ ID NO: 127 corresponding to the SEQ ID NO: 7 comprising the following two mutations: substitution of the leucine L in position 72 by an isoleucine I, substitution of the tryptophan W in position 263 by a phenylalanine F, SEQ ID NO: 129 corresponding to the SEQ ID NO: 7 comprising the following five mutations: substitution of the threonine T in position 68 by a serine S, substitution of the tyrosine Y in position 97 by a tryptophan W, substitution of the tyrosine Y in position 99 by a phenylalanine F, substitution of the serine S in position 130 by a proline P, substitution of the leucine L in position 228 by a methionine M, SEQ ID NO: 131 corresponding to the SEQ ID NO: 7 comprising the following four mutations: substitution of the valine V in position 27 by an alanine A, substitution of the leucine L in position 226 by a valine V, substitution the tryptophan W in position 263 by a leucine L, SEQ ID NO: 133 corresponding to the SEQ ID NO: 7 comprising the following eight mutations: substitution of the proline P in position 67 by a valine V, substitution of the threonine T in position 68 by a serine S, substitution of the tyrosine Y in position 97 by a tryptophan W, substitution of the tyrosine Y in position 99 by a phenylalanine F, substitution of the leucine L in position 228 by a methionine M, substitution of the cysteine C in position 258 by an alanine A, substitution the tryptophan W in position 263 by a leucine L, substitution of the methionine M in position 280 by a threonine T, SEQ ID NO: 135 corresponding to the SEQ ID NO: 7 comprising the following eight mutations: substitution of the threonine T in position 68 by a serine S, substitution of the tyrosine Y in position 97 by a tryptophan W, substitution of the tyrosine Y in position 99 by a phenylalanine F, substitution of the serine S in position 130 by a proline P, substitution of the lysine K in position 164 by an asparagine N, substitution of the leucine L in position 226 by a valine V, substitution the tryptophan W in position 263 by a methionine M, SEQ ID NO: 137 corresponding to the SEQ ID NO: 7 comprising the following five mutations: substitution of the threonine T in position 68 by a serine S, substitution of the leucine L in position 72 by an isoleucine I, substitution of the tyrosine Y in position 97 by a tryptophan W, substitution of the tyrosine Y in position 99 by a phenylalanine F, substitution of the serine S in position 130 by a proline P.

The coding sequence of the above-mentioned mutated hyperthermophilic PTE having a lactonase activity according to the present invention, derived from the hyperthermophilic PTE of *Sulfolobus islandicus* corresponding to the sequence SEQ ID NO: 7 and corresponding to the following sequences SEQ ID NO: 94, 96, 98, 100, 102, 104, 106, 108, 110, 112, 114, 116, 118, 120, 122, 124, 126, 128, 130, 132, 134 and 136 are also part of the invention.

The invention also related to mutated hyperthermophilic PTE having a lactonase activity according to the present invention, derived from the hyperthermophilic PTE of *Sulfolobus islandicus* corresponding to the sequence SEQ ID NO: 7, said mutated hyperthermophilic PTE corresponding to the following sequences SEQ ID NO: 225, 227, 229, 231, 233, 235, 237, 239, 241, 243, 245, 247, 249, 251, 253, 255, 257, 259, 261, 263, 265 and 267 for the proteins and to their respective coding sequences SEQ ID NO: 224, 226, 228, 230, 232, 234, 236, 238, 240, 242, 244, 246, 248, 250, 252, 254, 256, 258, 260, 262, 264 and 266.

The invention relates more particularly to the above-mentioned mutated hyperthermophilic PTE having a lactonase activity, derived from the hyperthermophilic PTE of *Sulfolobus islandicus* corresponding to the sequence SEQ ID NO: 7, further comprising at least one mutation corresponding to a substitution of at least one of the amino acids of the following amino acid pairs, the positions of which in SEQ ID NO: 7 are indicated hereafter, by another natural or non-natural amino acid: 2R/314S, 14E/12E, 26R/75D, 26R/42E, 33R/42E, 33R/45E, 55R/52E, 55R/285E, 74R/121D, 81K/42E, 81K/43D, 84K/80E, 109R/113E, 123K/162E, 147K/148D, 151K/148D, 154R/150E, 154R/187E, 154R/188E, 161K/188E, 183R/150E, 183R/187E, 183R/180E, 210K/245D, 215K/214D, 223R/256D, 223R/202D, 234K/204D, 235R/202D, 241K/245D, 245D/244K, 250R/249D, 277R/286D, 292K/298E, 310K/307E.

The invention also relates to a mutated hyperthermophilic phosphotriesterase having a lactonase activity derived from a hyperthermophilic phosphotriesterase defined by the consensus sequence SEQ ID NO : 1, said mutated hyperthermophilic phosphotriesterase having a single mutation being a substitution of the tryptophan W in position 265 of the consensus sequence SEQ ID NO : 1.

In an embodiment, the invention relates to a mutated hyperthermophilic phosphotriesterase as defined above, said mutated hyperthermophilic phosphotriesterase having a single mutation being a substitution of the tryptophan W in position 265 of the consensus sequence SEQ ID NO : 1 by a threonine T.

In an embodiment, the invention relates to a mutated hyperthermophilic phosphotriesterase as defined above, said mutated hyperthermophilic phosphotriesterase having a single mutation being a substitution of the tryptophan W in position 263 of the sequence SEQ ID NO : 3 by an isoleucine I, a valine V, a threonine T or an alanine A.

The invention also relates to the isolated nucleic acid sequence encoding the mutated hyperthermophilic PTE having a lactonase activity as defined above.

A subject of the invention is also the vectors comprising the nucleic acid encoding the mutated hyperthermophilic PTE having a lactonase activity as defined above. Such vectors can be plasmids, cosmids, phagemids or any other tool useful for cloning and expressing a nucleic acid.

The invention also relates to host cells, in particular bacteria, transformed by using the vector as defined above, such that their genome contains nucleotide sequences encoding the mutated hyperthermophilic PTE having a lactonase activity as defined above, said mutated hyperthermophilic PTE having a lactonase activity being produced in the cytoplasm of the host cells or secreted at their surface.

A subject of the invention is also is a method for generating a library of mutated hyperthermophilic PTE variants having a lactonase activity comprising:
  introducing into a population of host cells of a plurality of vectors comprising a nucleic acid sequence encoding the mutated hyperthermophilic PTE having a lactonase activity,
  culturing the population of host cells in an appropriate culture media,
  expressing the polypeptide in the said cultured host cell,
  recovering a plurality of mutated hyperthermophilic PTE variants.

The invention also relates to a library of mutated hyperthermophilic PTE variants having a lactonase activity obtainable by the method for generating a library of mutated hyperthermophilic PTE variants having a lactonase activity as disclosed above.

The aim of said library is to provide polypeptide variants of mutated hyperthermophilic PTE having a lactonase activity with enhanced phenotypic properties relative to those of the wild-type hyperthermophilic PTE having a lactonase activity from which they derived.

The invention also relates to the use of a mutation to increase a lactonase catalytic activity of a hyperthermophilic phosphotriesterase which has a sequence corresponding to the consensus sequence of SEQ ID NO : 1, wherein the amino acid W in position 265 is substituted by an amino acid chosen in the group consisting of the amino acids isoleucine I, valine V, threonine T or alanine A, to obtain a mutated hyperthermophilic phosphotriesterase which has an increased lactonase catalytic activity in comparison of the lactonase activity of said hyperthermophilic phosphotriesterase corresponding to the consensus sequence of SEQ ID NO : 1.

The invention also relates to the use of a single mutation to increase a lactonase catalytic activity of a hyperthermophilic phosphotriesterase which has a sequence corresponding to the consensus sequence of SEQ ID NO : 1, wherein the amino acid W in position 265 is substituted by an amino acid chosen in the group consisting of the amino acids isoleucine I, valine V, threonine T or alanine A, to obtain a mutated hyperthermophilic phosphotriesterase which has an increased lactonase catalytic activity in comparison of the lactonase activity of said hyperthermophilic phosphotriesterase corresponding to the consensus sequence of SEQ ID NO : 1.

The invention also relates to a process for increasing a lactonase catalytic activity of a hyperthermophilic phosphotriesterase which has a sequence corresponding to the consensus sequence of SEQ ID NO : 1, comprising a step of substitution of the amino acid W in position 265 by an amino acid chosen in the group consisting of the amino acids isoleucine I, valine V, threonine T or alanine A, to obtain a mutated hyperthermophilic phosphotriesterase which has an increased lactonase catalytic activity in comparison of the lactonase activity of said hyperthermophilic phosphotriesterase corresponding to the consensus sequence of SEQ ID NO : 1.

The invention also relates to a process for increasing a lactonase catalytic activity of a hyperthermophilic phosphotriesterase which has a sequence corresponding to the consensus sequence of SEQ ID NO : 1, comprising a step of a single substitution of the amino acid W in position 265 by an amino acid chosen in the group consisting of the amino acids isoleucine I, valine V, threonine T or alanine A, to obtain a mutated hyperthermophilic phosphotriesterase which has an increased lactonase catalytic activity in comparison of the lactonase activity of said hyperthermophilic phosphotriesterase corresponding to the consensus sequence of SEQ ID NO : 1.

The expression "a lactonase catalytic activity" refers to the hydrolysis of lactones, in particular N-acylhomoserine lactones (AHLs), which mediate bacterial communication for many Gram negative bacteria and some Archaeal organisms.

The expression "an increased lactonase catalytic activity" means that, for the hydrolysis of an AHL, the mutated hyperthermophilic PTE has a higher value of the ratio $K_{cat}/K_M$ in comparison of the value of the ratio $K_{cat}/K_M$ of the non-mutated hyperthermophilic PTE of which it derives.

Preferably, $K_{cat}/K_M$ of the mutated hyperthermophilic PTE is increased of at least two times, more preferably between 25 and 70 times, in comparison of the non mutated hyperthermophilic PTE.

In an embodiment, the invention concerns the use, or the process, as defined above, wherein said hyperthermophilic phosphotriesterase is a wild-type hyperthermophilic phosphotriesterase.

In an embodiment, the invention concerns the use, or the process, as defined above, wherein hydrolyzis of 3-oxo-C12 AHL by said mutated hyperthermophilic phosphotriesterase is increased by at least 2 times, in particular from 25 to 70 times, in comparison of hydrolyzis of 3-oxo-C12 AHL by said hyperthermophilic phosphotriesterase.

Preferably, $K_{cat}/K_M$ of the mutated hyperthermophilic PTE is increased of at least two times, more preferably between 25 and 70 times, in comparison of the non mutated hyperthermophilic PTE.

In an embodiment, the invention concerns the use, or the process, as defined above, wherein said mutated hyperthermophilic phosphotriesterase has a thermostability, which is substantially similar to the thermostability of said hyperthermophilic phosphotriesterase.

The expression "thermostability" refers to the ability of the PTE to resist to high temperatures, in particular above 70° C., more particularly between 70° C. and 120° C. At these temperatures, the 3D structure of the PTE is maintained, and these enzymes are still active and able to hydrolyze OPs or lactones.

Classically, mutations which modify the catalytic activities of the PTEs are associated with a loss of the thermostability in the mutated PTE in comparison of the non-mutated PTE. However, the mutated PTEs of the invention have a thermostability which is substantially similar to the thermostability of said hyperthermophilic phosphotriesterase.

The thermostability of the PTE can be verified by determining the melting temperature.

The melting temperature of the mutated PTE of the invention is higher than 80° C., preferably higher than 85° C., preferably higher than 90° C.

This melting temperature can be measured by circular dichroism spectroscopy.

In an embodiment, the invention concerns the use, or the process, as defined above, wherein the amino acid in position 2 in SEQ ID NO : 1 is missing.

In an embodiment, the invention concerns the use, or the process, as defined above, wherein said hyperthermophilic phosphotriesterase is chosen in the group consisting of SEQ ID NO : 3 from *Sulfolobus solfataricus*, SEQ ID NO : 5 from *Sulfolobus acidocalaricus*, or from SEQ ID NO : 7 *Sulfolobus islandicus*, wherein said sequences SEQ ID NO : 3, SEQ ID NO : 5 and SEQ ID NO : 7 belong to the consensus SEQ ID NO : 1, the amino acid in position 2 in SEQ ID NO : 1 being missing from SEQ ID NO: 5 and the amino acids in position 2 and 3 in SEQ ID NO: 1 being missing from SEQ ID NO: 3 and SEQ ID NO: 7.

In an embodiment, the invention concerns the use, or the process, as defined above, wherein at least the amino acid W in position 265 is substituted by an amino acid chosen in the group consisting of the amino acids isoleucine I, valine V, threonine T or alanine A.

In an embodiment, the invention concerns the use, or the process, as defined above, wherein said amino acid W in position 265 is substituted by an amino acid Isoleucine I.

In an embodiment, the invention concerns the use, or the process, as defined above, wherein said mutated hyperthermophilic phosphotriesterase further comprises at least one additional substitution, said at least one additional substitution being selected from the group consisting of substitutions in positions G9, K10, V29, F/L48, K56, P69, T70, L74, I78, V85, I124, L/S/N132, D143, K/N166, I169, D193, G195, G227, L228, L230, F231, L232, Y259, C261, T262, I263, D264, G266, T/I267, A268, K/R269, P270, E271, Y/L272, K273, P274, K275, L276, A277, P278, R/K279, W280, S281, I/M282, T/A/S283, L284, I285, N/S/T299 of SEQ ID NO: 1.

In an embodiment, the invention concerns the use, or the process, as defined above, wherein said mutated hyperthermophilic phosphotriesterase further comprises at least one additional substitution, said at least one additional substitution being selected from the group consisting of substitutions in positions G9, K10, V29, F/L48, K56, P69, T70, L74, I78, V85, I124, L/S/N132, D143, K/N166, I169, D193, G195, G227, L228, L230, F231, L232, Y259, C261, T262, I263, D264, G266, T/I267, A268, K/R269, P270, E271, Y/L272, K273, P274, K275, L276, A277, P278, W280, S281, I/M282, T/A/S283, L284, I285, N/S/T299 of SEQ ID NO: 1.

In an embodiment, the invention concerns the use, or the process, as defined above, wherein said mutated hyperthermophilic phosphotriesterase further comprises at least one supplementary substitution, said at least one supplementary substitution being selected from the group consisting of substitutions in positions Y99, Y101, R225 and C260 of SEQ ID NO: 1.

In an embodiment, the invention concerns the use, or the process, as defined above, said mutated hyperthermophilic PTE corresponding to the following sequences: SEQ ID NO: 13, SEQ ID NO: 15, SEQ ID NO: 17, SEQ ID NO: 19, SEQ ID NO: 57, SEQ ID NO: 59, SEQ ID NO: 61, SEQ ID NO: 63, SEQ ID NO: 101, SEQ ID NO: 103, SEQ ID NO: 105, SEQ ID NO: 107.

In an embodiment, the invention concerns the use, or the process, as defined above, said mutated hyperthermophilic PTE corresponding to the following sequences: SEQ ID NO: 21, SEQ ID NO: 65 or SEQ ID NO: 109.

The invention also relates to compositions comprising the mutated hyperthermophilic PTE having a lactonase activity as defined above.

In a preferred embodiment, the compositions as defined above comprising the mutated hyperthermophilic PTE having a lactonase activity further comprise at least one detergent.

In a more preferred embodiment, the above mentioned composition comprising both the mutated hyperthermophilic PTE having a lactonase activity and at least one detergent can be used as laundry detergent to clean up materials impregnated with OPs compounds.

An aspect of the invention concerns the use of the mutated hyperthermophilic PTE of the invention for the decontamination of the organophosphorous compounds. This aspect is based on the capacity of the mutated hyperthermophilic PTE to catalyze the hydrolysis of phosphoester bounds in OPs.

Therefore, the invention also relates to the use of a mutated hyperthermophilic PTE having a lactonase activity as defined above, or of host cells as defined above, as bioscavengers:
- within the context of the decontamination of the surfaces of materials, of the skin or mucous membranes contaminated with organophosphorous compounds, or
- within the context of the prevention or treatment of an external or of an internal poisoning by ingestion or inhalation of organophosphorous compounds,
- within the context of the pollution control of water polluted with organophosphorus compounds, or
- within the context of the destruction of stocks of neurotoxic agents.

In an embodiment, the invention relates to the use as defined above, wherein said mutated hyperthermophilic PTE are chosen among the group consisting of: SEQ ID NO : 9, SEQ ID NO : 11, SEQ ID NO : 23, SEQ ID NO : 27, SEQ ID NO : 29, SEQ ID NO : 31, SEQ ID NO : 53, SEQ ID NO : 55, SEQ ID NO : 67, SEQ ID NO : 71, SEQ ID NO : 73, SEQ ID NO : 75, SEQ ID NO : 97, SEQ ID NO : 99, SEQ ID NO : 111, SEQ ID NO :115, SEQ ID NO : 117, SEQ ID NO : 119.

In an embodiment, the invention relates to the use as defined above, wherein said mutated hyperthermophilic PTE are chosen among the group consisting of: SEQ ID NO : 9, SEQ ID NO : 11, SEQ ID NO : 23, SEQ ID NO : 27, SEQ ID NO : 29, SEQ ID NO : 31, SEQ ID NO : 53, SEQ ID NO : 55, SEQ ID NO : 67, SEQ ID NO : 71, SEQ ID NO : 73, SEQ ID NO : 75, SEQ ID NO : 97, SEQ ID NO : 99, SEQ ID NO : 111, SEQ ID NO :115, SEQ ID NO : 117, SEQ ID NO : 119, SEQ ID NO : 21, SEQ ID NO : 65 and SEQ ID NO : 109.

A subject of the invention is also materials impregnated with mutated hyperthermophilic PTE having a lactonase activity as defined above, in liquid or solid form, such as gloves, various garments, wipes, spray foams.

Another subject of the invention is kits of decontamination of the surfaces of the materials, of the skins or mucous membranes, contaminated with organophosphorus compounds, or for the pollution control of water polluted with organophosphorus compounds, said kit comprising mutated hyperthermophilic PTE having a lactonase activity as defined above, or materials impregnated with mutated hyperthermophilic PTE having a lactonase activity as defined above.

A subject of the invention is also bioscavengers of organophosphorus compounds comprising mutated hyperthermophilic PTE having a lactonase activity as defined above.

The invention also related to cartridges for external decontamination inside which mutated hyperthermophilic PTE having a lactonase activity as defined above are grafted.

Said cartridges can be used for decontaminating the blood of an individual poisoned with OPs compounds.

Another aspect of the invention concerns the use of the mutated hyperthermophilic PTE of the invention as antibacterial agents. This aspect is based on the capacity of the mutated hyperthermophilic PTE of the invention to hydrolyze lactones and, thus, to disrupt the quorum sensing of micro-organisms using homoserin lactone substrates to communicate.

Therefore, the invention concerns the use of a mutated hyperthermophilic phosphotriesterase as defined above to disrupt quorum-sensing in bacteria.

In an embodiment, the invention concerns the use of a mutated hyperthermophilic phosphotriesterase, which has a sequence corresponding to the consensus sequence of SEQ ID NO : 1, wherein the amino acid W in position 265 is substituted by an amino acid chosen in the group consisting of the amino acids isoleucine I, valine V, threonine T or alanine A, which has an increased lactonase catalytic activity in comparison of the lactonase activity of said hyperthermophilic phosphotriesterase corresponding to the consensus sequence of SEQ ID NO : 1.

In an embodiment, the invention concerns the use of a mutated hyperthermophilic phosphotriesterase as defined above to disrupt quorum-sensing in bacteria, said mutated hyperthermophilic PTE being chosen in the group consisting of: SEQ ID NO: 13, SEQ ID NO: 15, SEQ ID NO: 17, SEQ ID NO: 19, SEQ ID NO: 57, SEQ ID NO: 59, SEQ ID NO: 61, SEQ ID NO: 63, SEQ ID NO: 101, SEQ ID NO: 103, SEQ ID NO: 105, SEQ ID NO: 107.

In an embodiment, the invention concerns the use of a mutated hyperthermophilic phosphotriesterase as defined above to disrupt quorum-sensing in bacteria, said mutated hyperthermophilic PTE being chosen in the group consisting of: SEQ ID NO: 21, SEQ ID NO: 65 and SEQ ID NO: 109.

In an embodiment, the invention concerns the use of a mutated hyperthermophilic phosphotriesterase as defined above to disrupt quorum-sensing in bacteria, said mutated hyperthermophilic PTE being chosen in the group consisting of: SEQ ID NO : 9, SEQ ID NO : 11, SEQ ID NO : 23, SEQ ID NO : 27, SEQ ID NO : 29, SEQ ID NO : 31, SEQ ID NO : 53, SEQ ID NO : 55, SEQ ID NO : 67, SEQ ID NO : 71, SEQ ID NO : 73, SEQ ID NO : 75, SEQ ID NO : 97, SEQ ID NO : 99, SEQ ID NO : 111, SEQ ID NO : 115, SEQ ID NO : 117, SEQ ID NO : 119, SEQ ID NO : 21, SEQ ID NO : 65 and SEQ ID NO :109.

In an embodiment, the invention concerns the use of a mutated hyperthermophilic PTE of the invention to limit the formation of biofilms, notably in boats or other sea equipments.

In particular, a mutated hyperthermophilic PTE can be added to painting media in order to limit the formation of biofilms, notably in boats or other sea equipments.

In an embodiment, the invention concerns the use of a mutated hyperthermophilic PTE of the invention to inhibit the fire blight in plants or to inhibit the rotting of vegetables.

Fire blight in plants is due to infections by bacteria of the genus *Erwinia*, whereas rotting of vegetables is due to infections by bacteria of the genus *Serratia*.
Colonization of plants and vegetables by *Erwinia* and *Serratia* bacteria both involve a quorum sensing based on lactone substrates. Such lactone substrates can be hydrolysed by PTE to prevent and/or to treat *Erwinia* and *Serratia* infections.

A subject of the invention is also a phytosanitary composition comprising as active ingredient at least one mutated hyperthermophilic PTE as defined above.

A subject of the invention is also an antibacterial composition comprising as an active ingredient at least one mutated hyperthermophilic PTE as defined above.

The invention is also related to pharmaceutical compositions comprising as active ingredient at least one mutated hyperthermophilic PTE having a lactonase activity as defined above in combination with a pharmaceutically acceptable vehicle.

The invention also relates to pharmaceutical compositions for their use in the treatment of pathology due to the presence of bacteria, notably pneumonia or nosocomial diseases.

The invention also relates to pharmaceutical compositions for their use in the treatment of dental plaque.

The invention also relates to pharmaceutical compositions for their use as eye drops in the treatment of eye infections or eye surface healing.

In a preferred embodiment, pharmaceutical compositions as defined above comprising the mutated hyperthermophilic PTE having a lactonase activity further comprise at least one antibiotic selected from the group consisting of gentamycine, ciprofloxacin, ceftazidime, imipenem, tobramycine.

In a more preferred embodiment, pharmaceutical compositions as defined above are presented in a form which can be administered by injectable route, in particular in solution or packaged or pegylated, or by topical route, in particular in the form of an ointment, aerosol or wipes.

The invention also related to use of materials impregnated with or comprising the mutated hyperthermophilic PTE having a lactonase activity, as antiseptics for the decontamination of the surface bacterial infection.

The invention also relates to compositions or pharmaceutical composition comprising the mutated hyperthermophilic PTE having a lactonase activity for its use in the treatment of bacterial infections caused by bacteria using homoserin lactone substrates to communicate, in particular in the blood, wounds, burn, skin, biomaterial-body contact area.

A subject of the invention is also a method for disrupting the quorum sensing of micro-organisms using homoserin lactone substrates to communicate, said method consisting of administering to a patient in need thereof a sufficient amount of composition or pharmaceutical composition comprising the mutated hyperthermophilic PTE having a lactonase activity as defined above.

Another subject of the invention is also a mutated hyperthermophilic PTE as defined above for its use as a medicament.

In an embodiment, the invention concerns a mutated hyperthermophilic PTE as defined above, for its use in the treatment of bacterial infections.

In an embodiment, the invention concerns a mutated hyperthermophilic PTE as defined above for its use in the treatment of pneumonia or nosocomial diseases, caused by bacteria using homoserin lactone substrates to communicate, in particular in the blood, wounds, burn, skin, biomaterial-body contact area.

In an embodiment, the invention concerns a mutated hyperthermophilic PTE as defined above for its use in the treatment of dental plaque.

In an embodiment, the invention concerns a mutated hyperthermophilic PTE as defined above for its use in the treatment of eye infections or eye surface healing.

The invention is further illustrated by the following figures and examples of the phosphotriesterase of *Sulfolobus solfataricus*, and mutations made to the latter within the context of the preparation of mutated hyperthermophilic PTE having a lactonase activity as defined above according to the invention. These examples are not intended to be limitation of the invention.

FIGURES

FIG. 1: Chemical structure of SsoPox substrates

The chemical structure of paraoxon (A.), CMP-coumarin (B.), 3-oxo-C12 AHL (C.), 3-oxo-C10 AHL (D.), undecanoic-δ-lactone (E.) and undecanoic-γ-lactone (F.) are presented.

FIG. 2: SsoPox phosphotriesterase activity screening and characterization

Relative phosphotriesterase activities of W263 saturation site variants have been screened with 1 mM (A.) and 100 µM (B.) of paraoxon substrate and 50 µM (C.) of CMP-coumarin substrate. The best variants (i.e. SsoPox W263F, W263M, W263A and W263L) have been characterized for paraoxon hydrolysis and catalytic efficiencies have been compared to SsoPox wt (D.).

FIG. 3: SsoPox lactonase activity screening and characterization

A. Schematic representation of $P.$ $aeruginosa$ based lactonase activity screening method. Relative lactonase activity of W263 saturation sites variants have been screened for 3-oxo-C12 AHL hydrolysis (B.). The best variants (i.e. SsoPox W263I, W263V, W263T and W263A) have been characterized for 3-oxo-C12 AHL hydrolysis and catalytic efficiencies have been compared to SsoPox wt (C.)

FIG. 4: A. SsoPox W263I mediated inhibition of lasB transcription.

The chart shows expression in treated cultures expressed as the percentage of lasB expression in untreated control (no SsoPox W263I), and represents data averaged from three independent experiments, each with three technical replicates; error bars represent 95% confidence intervals. Student's T test $p=<0.05$ for SsoPoxW263I. All T tests for comparison of baseline with highest dose of enzyme.

Figure 5:
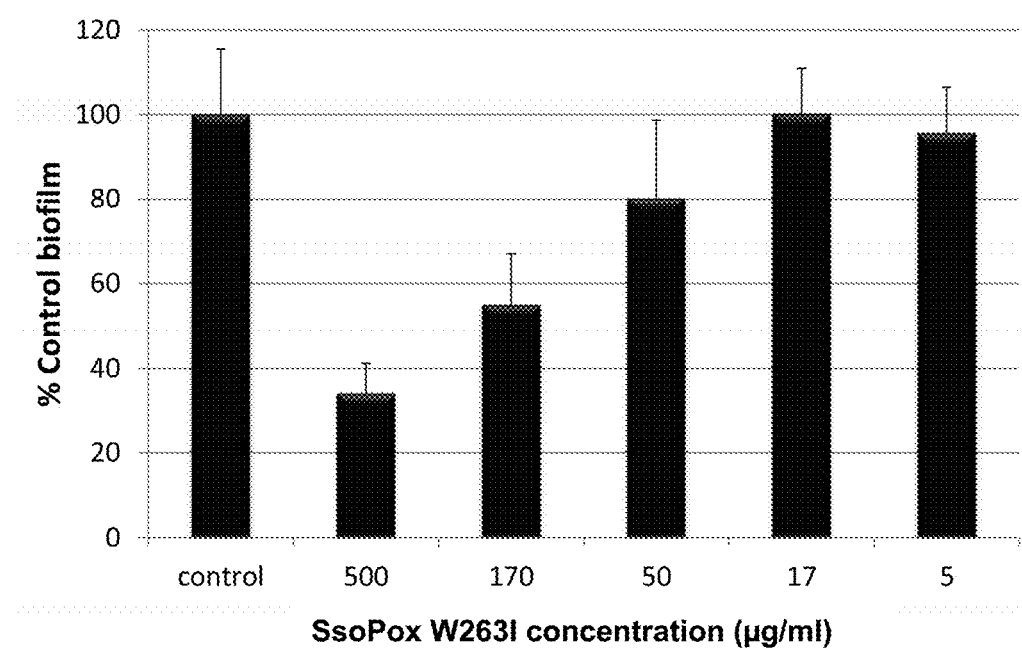

FIG. 5: Inhibition of PAO1 biofilm formation by SsoPoxW263I.

Biofilms were grown in an MBEC device as described in the methods section. Inhibition of $P.$ $aeruginosa$ biofilm formation by SsoPox W263I is seen in a dose-dependent fashion: Student's T test $p=<0.05$ for SsoPoxW263I.

Figure 6:
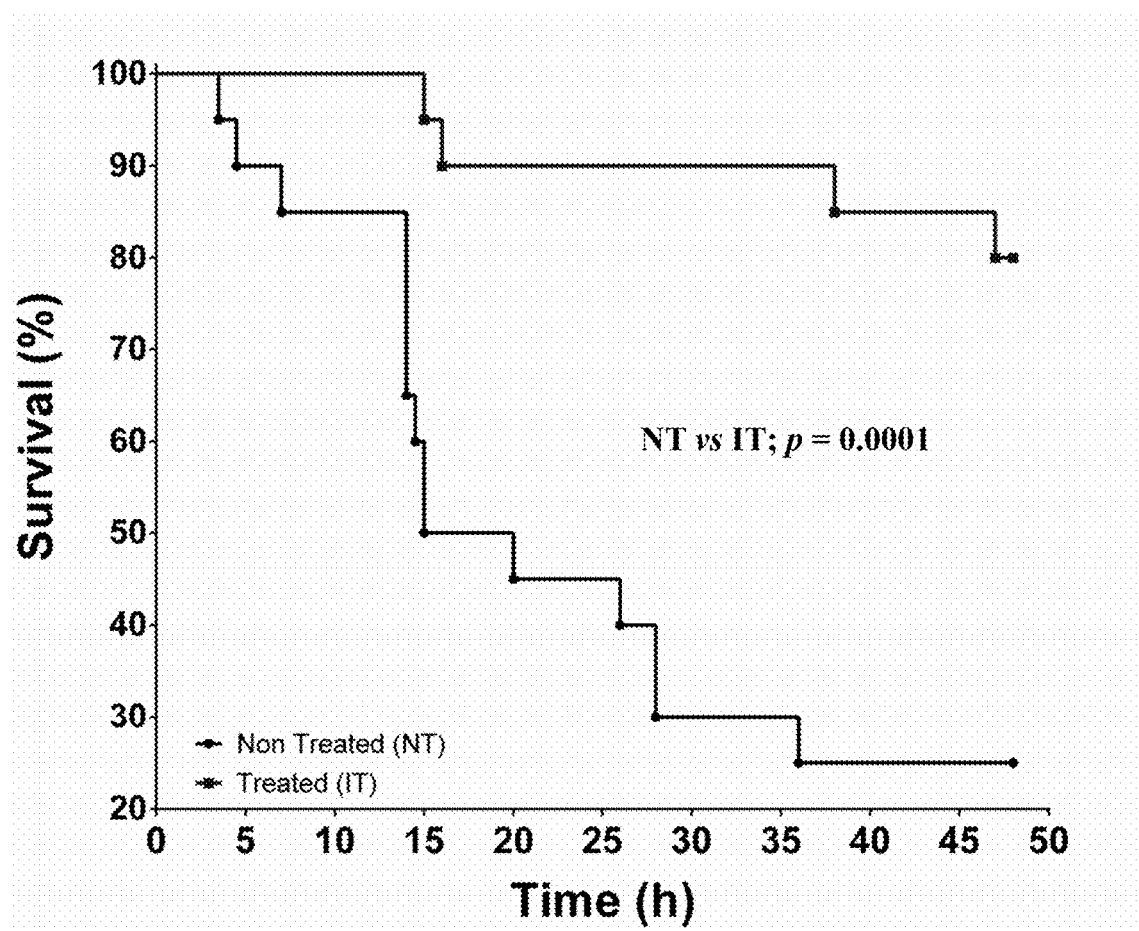

FIG. 6. Forty-eight hour survival curves of the 2 groups of animals after infection. Animals were infected with $10^8$ CFU/mL (300 µL) of $P.$ $aeruginosa$ PAO1 and non-treated (NT) or immediately-treated (IT) with SsoPoxW263I.

FIG. 7: Lung histological examination after infection

Pathological mapping of lungs representative of non-treated (NT) (A), differed-treatment (DT) (B) and immediate-treatment (IT) (C) groups: photomicrographs of pathological Giemsa staining X 100 of the lung sections. Mean histological severity score (HSS) was of (mean±SD) 2.64±0.4 for the NT group, 1.27±0.6 for the IT group (p=0.005 vs. NT) and 2.32±0.4 for the DT group (p=NS vs. NT).

EXAMPLES

Example 1

In this example, SsoPox variants have been experimentally produced and characterized.

1—Experimental Procedure 1.1—Initial Material

SsoPox coding gene is optimized for $Escherichia$ $coli$ expression and was synthesized by GeneArt (Life Technologies, France)[1]. The gene was subsequently cloned into a custom version of pET32b (Novagen) (=pET32b-ΔTrx-SsoPox) NcoI and NotI as cloning sites. The SsoPox sequence has been verified by sequencage (Sequencage plateforme, Timone, Marseille, France). Both plasmids have been used for evolution protocols.

1.2—Site Directed Mutagenesis

A saturation site of position W263 of SsoPox was ordered to service provider (GeneArt, Invitrogen; Germany) from the initially used plasmid pET22b-SsoPox. Each variant were checked by sequencing and provided as $Escherichia$ $coli$ DH5α cell glycerol stocks. The 20 plasmids (pET22b-SsoPox-W263X) have been purified from $E.$ $coli$ DH5α cells and transformed into BL21(DE$_3$)-pLysS strain by electroporation for activity screening and into BL21(DE3)-pGro7/EL (TaKaRa) for high amount production/purification (see concerning section below).

For others site directed mutagenesis or saturation site of selected positions, pfu Turbo polymerase (Agilent) has been used to amplify the overall plasmid using primers incorporating wanted variations. PCR composition has been performed as advised by the customer in a final volume of 25 µL and amplification was performed from 100 ng of plasmid. The PCR protocol was the following:

| | | |
|---|---|---|
| 95° C. | 10' | 1X |
| 95° C. | 45" | |
| 50° C. | 1' | 30X |
| 68° C. | 15' | |
| 68° C. | 20' | 1X |
| 14° C. | ∞ | 1X |

Remaining initial plasmids were removed by DpnI enzymatic digestion (1 µl; Fermentas) during 45' at 37° C. After inactivation of 20' at 90° C., DNA was purified (QIAquick PCR Purification Kit; Qiagen) to obtain about 30 µL of variable amount of DNA. 5 µL of purified DNA was then transformed into $Escherichia$ $coli$ electrocompetent cells (50 µL; $E.$ $cloni$; Lucigen), recovered in 1 mL of SOC medium during 1 h at 37° C. and then plated on agar medium supplemented with ampicillin (100 µg/mL). Several clones were sequenced to verify the well-performed mutagenesis (Sequencage plateforme, Timone, Marseille, France) and verified plasmids were transformed into $E.$ $coli$ strain BL21 (DE$_3$)-pGro7/GroEL (TaKaRa) for high amount production/purification and analysis (see concerning section below).

1.3—Directed Evolution Process

Directed evolution protocol has been performed using the GeneMorph® II Random Mutagenesis Kit in 25 µL final, using primers T7-promotor (TAA TAC GAC TCA CTA TAG GG) and T7-RP (GCT AGT TAT TGC TCA GCG G) and 500 ng of matrix (correspond to 6 µg of pET32b-ΔTrx-SsoPox plasmid). Others PCR elements have been performed as advised by the customer recommendations. The PCR protocol was the following:

| | | |
|---|---|---|
| 95° C. | 5' | 1X |
| 95° C. | 30" | |
| 55° C. | 30" | 30X |
| 72° C. | 4' | |
| 72° C. | 10' | 1X |
| 14° C. | ∞ | 1X |

Remaining plasmid was then digested by DpnI enzyme (1 µl; Fermentas) during 45' at 37° C. and then inactivated 20', 90° C. DNA was then purified (QIAquick PCR Purification Kit; Qiagen) to obtain about 50 µL of DNA at 100 ng/µL. For the next steps please refer to part "clonage and bank generation".

1.4—Method

SsoPox coding gene has been amplified from pET32b-ΔTrx-SsoPox plasmid by PCR (500 μL RedTaq; Sigma) using primers T7-promotor (TAA TAC GAC TCA CTA TAG GG) and T7-RP (GCT AGT TAT TGC TCA GCG G). The PCR protocol was the following:

| 95° C. | 2' | 1X |
|---|---|---|
| 95° C. | 30" | |
| 55° C. | 1.5' | 25X |
| 72° C. | 1.2' | |
| 72° C. | 7' | 1X |
| 16° C. | ∞ | 1X |

Remaining plasmid was then digested by DpnI enzyme (1 μl; Fermentas) during 45' at 37° C. and then inactivated 20', 90° C. DNA was then purified (QIAquick PCR Purification Kit; Qiagen) to obtain about 100 μL, of DNA at 200 ng/μL. 15 μL of DNA (~3 μg) was digested by 2 UE of DNAseI (TaKaRa) in buffer TrisHCl 100 mM pH 7.5, MnCl$_2$ 10 mM at 20° C. during 30", 1' and 2'. Digestions were stopped by 10' incubation at 90° C. in presence of EDTA 60 mM. After spin down, DNA aliquots were pooled and run on electrophoresis agarose (2%; w/v) gel in TAE buffer during 15' at 50 mA. Fragments consisting of average size of 70 bp (from 50 to 150 pb) were excised from gel and purified using D-Tube™ Dyalizer Maxi (Calbiochem) devices.

DNA extracted from gel (concentration >12 ng/μL) was used as matrix in "assembly PCR" consisting of 100 ng of matrix, 2 pmol of primers incorporating mutations and using 2.5 UE of Pfu Turbo polymerase (Agilent) with a final volume of 25 μl. The primer mix was composed of an oligonucleotide mix consisting of equivalent amount of modified positions. The PCR protocol was the following:

| 94° C. | 2' | 1X |
|---|---|---|
| 94° C. | 30" | |
| 65° C. | 1.5' | |
| 62° C. | 1.5' | |
| 59° C. | 1.5' | |
| 56° C. | 1.5' | |
| 53° C. | 1.5' | 35X |
| 50° C. | 1.5' | |
| 47° C. | 1.5' | |
| 45° C. | 1.5' | |
| 41° C. | 1.5' | |
| 72° C. | 45" | |
| 72° C. | 7' | 1X |
| 4° C. | ∞ | 1X |

The primer incorporating mutations in the directions 5'-3' are as follows:

TABLE 1

Listing of primers used to create SsoPox variants

| SEQ ID NO | Primer | Sequence 5'-3' |
|---|---|---|
| SEQ ID NO: 268 | W263M-F | TGCACCATTGATATG GGCACCGCAAAACCG |
| SEQ ID NO: 269 | W263M-R | CGGTTTTGCGGTGCC CATATCAATGGTGCA |
| SEQ ID NO: 270 | W263L-F | TGCACCATTGATCTG GGCACCGCAAAACCG |
| SEQ ID NO: 271 | W263L-R | CGGTTTTGCGGTGCC CAGATCAATGGTGCA |
| SEQ ID NO: 272 | W263A-F | TGCACCATTGATGCA GGCACCGCAAAACCG |
| SEQ ID NO: 273 | W263A-R | CGGTTTTGCGGTGCC TGCATCAATGGTGCA |
| SEQ ID NO: 274 | W263I-F | TGCACCATTGATATT GGCACCGCAAAACCG |
| SEQ ID NO: 275 | W263I-R | CGGTTTTGCGGTGCC AATATCAATGGTGCA |
| SEQ ID NO: 276 | W263V-F | TGCACCATTGATGTT GGCACCGCAAAACCG |
| SEQ ID NO: 277 | W263V-R | CGGTTTTGCGGTGCC AACATCAATGGTGCA |
| SEQ ID NO: 278 | W263T-F | TGCACCATTGATACC GGCACCGCAAAACCG |
| SEQ ID NO: 279 | W263T-R | CGGTTTTGCGGTGCC GGTATCAATGGTGCA |
| SEQ ID NO: 280 | C258L-F | ATTAGCCATGATTAT CTGTGCACCATTGAT |
| SEQ ID NO: 281 | C258L-R | ATCAATGGTGCACAG ATAATCATGGCTAAT |
| SEQ ID NO: 282 | I261F-F | GATTATTGCTGCACC TTTGATTGGGCACC |
| SEQ ID NO: 283 | I261F-R | GGTGCCCAATCAAA GGTGCAGCAATAATC |
| SEQ ID NO: 284 | V27A-F | GAACATCTGCGTGCA TTTAGCGAAGCAGTT |
| SEQ ID NO: 285 | V27A-R | AACTGCTTCGCTAAA TGCACGCAGATGTTC |
| SEQ ID NO: 286 | Y97W-F | GGCACCGGTATTTGG ATTTATATCGATCTG CCG |
| SEQ ID NO: 287 | Y97W-R | CGGCAGATCGATATA AATCCAAATACCGGT GCC |
| SEQ ID NO: 288 | L228M-F | GATCGTTATGGTCTG GACATGTTTCTGCCG GTT |
| SEQ ID NO: 289 | L228M-R | AACCGGCAGAAACAT GTCCAGACCATAACG ATC |
| SEQ ID NO: 290 | I280T-F | GCACCGCGTTGGAGC ACTACCCTGATTTTT G |
| SEQ ID NO: 291 | I280T-R | CAAAAATCAGGGTAG TGCTCCAACGCGGTG C |
| SEQ ID NO: 292 | F46L-F | CTGTATAATGAAGAT GAAGAACTGCGCAAT GCCGTGAATGAAG |
| SEQ ID NO: 293 | F46L-R | CTTCATTCACGGCAT TGCGCAGTTCTTCAT CTTCATTATACAG |

TABLE 1-continued

Listing of primers used to create SsoPox variants

| SEQ ID NO | Primer | Sequence 5'-3' |
|---|---|---|
| SEQ ID NO: 294 | I76T-F | GTTATGGGTCTGGGT CGTGATACTCGTTTT ATGGAAAAGTTGTG |
| SEQ ID NO: 295 | I76T-R | CACAACTTTTTCCAT AAAACGAGTATCACG ACCCAGACCCATAAC |
| SEQ ID NO: 296 | Y99F-F | GGCACCGGTATTTAT ATTTTTATCGATCTG CCG |
| SEQ ID NO: 297 | Y99F-R | CGGCAGATCGATAAA AATATAAATACCGGT GCC |
| SEQ ID NO: 298 | L130P-F | GGCATTCAGGGCACC CCGAATAAAGCAGGT TTTG |
| SEQ ID NO: 299 | L130P-R | CAAAACCTGCTTTAT TCGGGGTGCCCTGAA TGCC |
| SEQ ID NO: 300 | L226V-F | GATCGTTATGGTGTG GACCTGTTTCTGCCG GTT |
| SEQ ID NO: 301 | L226V-R | AACCGGCAGAAACAG GTCCACACCATAACG ATC |
| SEQ ID NO: 302 | L72I-F | GTTATGGGTATTGGT CGTGATATTCGTTTT |
| SEQ ID NO: 303 | L72I-R | AAAACGAATATCACG ACCAATACCCATAAC |
| SEQ ID NO: 304 | F229S-F | GATCGTTATGGTCTG GACCTGTCTCTGCCG GTT |
| SEQ ID NO: 305 | F229S-R | AACCGGCAGAGACAG GTCCAGACCATAACG ATC |
| SEQ ID NO: 306 | T68S-F | AAAACCATTGTTGAT CCGAGTGTTATGGGT |
| SEQ ID NO: 307 | T68S-R | ACCCATAACACTCGG ATCAACAATGGTTTT |
| SEQ ID NO: 308 | K8E-F | CATTCCGCTGGTTGG TGAAGATAGCATTGA AAG |
| SEQ ID NO: 309 | K8E-R | CTTTCAATGCTATCT TCACCAACCAGCGGA ATG |
| SEQ ID NO: 310 | P67S-F | AAAACCATTGTTGAT TCGACCGTTATGGGT |
| SEQ ID NO: 311 | P67S-R | ACCCATAACGGTCGA ATCAACAATGGTTTT |
| SEQ ID NO: 312 | K164N-F | CAATAAAGAAACCAA TGTTCCGATTATTAC CC |
| SEQ ID NO: 313 | K164N-R | GGGTAATAATCGGAA CATTGGTTTCTTTAT TG |

Finally, assembly PCR was used as matrix for "nested PCR". 1 µL of assembly PCR was used as classical PCR (50 µL, RedTaq; Sigma) with cloning primers SsoPox-lib-pET-5' (ATGCGCATTCCGCTGGTTGG) and SsoPox-lib-pET-3' ( TTATTAGCTAAAGAATTTTTTCGGATTTTC). The PCR protocol was the following:

| 95° C. | 2' | 1X |
|---|---|---|
| 95° C. | 30" | 25X |
| 65° C. | 1.5' | |
| 72° C. | 7' | 1X |
| 16° C. | ∞ | 1X |

1.5—Clonage and Bank Generation

PCR product has been purified using extraction kit (QIAquick PCR Purification Kit; Qiagen) and then digested for 45' at 37° C. by NcoI Fastdigest and NotI Fastdigest enzymes (12UE of each enzyme; Fermentas). Enzymes were then inactivated by 20' incubation at 90° C. and then purified (QIAquick PCR Purification Kit; Qiagen) to be cloned into pET32b-Δtrx plasmid at the corresponding restriction sites previously dephosphorylated as recommended by the customer (10 UE/µl CIP; NEB). Ligation has been performed in a molar ratio 1:3 with 50 ng of plasmid using T4-DNA ligase during 16 h at 16° C. (20 UE; NEB).

After ligation, ligase was inactivated 20' at 90° C. and then purified from salts by classical alcohol precipitation and recovered in 10 µL of water. *Escherichia coli* electrocompetent cells (50 µL; *E. cloni*; Lucingen) were electroporated with 5 µL of purified ligation and recovered in 1 mL of SOC medium for 1 h at 37° C. All 1 mL was then plated on agar selected medium (ampicillin 100 µg/mL) and incubated overnight at 37° C.

Obtaining transformation efficiency higher than $10^4$ colonies on agar plate, the colonies were then harvested using 1 mL of plasmidic extraction kit solution 1 (Qiaprep Spin Miniprep kit; Quiagen) and plasmids were then extracted from cells following the recommended procedure. The plasmid pool obtained constituting the bank, 100 ng were used to electroporate 50 µL of electrocompetent BL21(DE3)-pGro7/EL (TaKaRa). After 1 h of recovering in SOC medium at 37° C., cells were plated on agar plate added of ampicillin (100 µg/mL) and chloramphenicol (37 µg/mL).

2—Screening Procedure

Microcultures consisting of 600 µL of ZYP medium [3,4] supplemented by ampicillin (100 µg/mL) and chloramphenicol (34 µg/mL) are inoculated by a tip picked colony in 96 well plates. Cultures grew at 37° C. under 1 600 rpm agitation for 5 h before activation mediated by temperature transition to 25° C. and addition of $CoCl_2$ (0.2 mM) and arabinose (0.2%, w/v). After overnight growth, tips were removed and used to pick separated colony on agar plate (ampicilin 100 µg/mL; chloramphenicol 34 µg/mL) for strain conservation. Cultures were centrifuged to keep cell pellets which were resuspended in lysis buffer consisting of 50 mM HEPES pH 8, 150 mM NaCl, $CoCl_2$ 0.2 mM, Lysozyme 0.25 PMSF 0.1 mM DNAseI 10 µg/ml and $MgSO_4$ 20 mM. Cells were disrupted by freezing/thawing steps and cells debris were removed by centrifugation (13 000 g, 4° C., 30'). Partial purification of the protein was performed exploiting SsoPox hyperthermostability [5] by 15 minutes incubation at 70° C. Aggregated proteins were harvested by centrifugation (13 000 g, 25° C., 30').

2.1—Phosphotriesterase Activity Screening

Phosphotriesterase activity screening was mediate by monitoring chromophoric phosphotriester hydrolysis (paraoxon, methyl-paroxon, parathion, methyl parathion (1 mM or 100 µM,Fluka). Kinetics experiments were performed for 10' monitoring phosphotriester ($\varepsilon_{405\ nm}$=17 000 $M^{-1}cm^{-1}$) hydrolysis at 25° C. using a microplate reader (Synergy HT; BioTek, USA) and the Gen5.1 software in a 6.2 mm path length cell for 200 µL reaction in 96-well plate. Standard assays were performed in pte buffer (50 mM HEPES pH 8, 150 mM NaCl, 0.2 mM $CoCl_2$).

2.2—Lactonase Activity Screening

Lactonase activity screening was mediated by a genetically modified strain PAO1 of *Pseudomonas aeruginosa* (PAO1-ΔlasI-JP2). The JP2 plasmid encodes proteins coding for bioluminescence production in presence of 3-oxo-C12 AHLs in *P. aeruginosa*; the lasI gene, responsible of 3-oxo-C12 AHLs synthesis in wt *P. aeruginosa*, is deleted. SsoPox variants (5 µL of tenfold diluted partially purified variants) are mixed in 100 µL of pte buffer with 3-oxo-C12 AHL (100 nM) and incubated 20 minutes at room temperature. A volume of 450 µL of LB media (Trimethoprime lactate 300 µg/mL) was inoculated by overnight preculture of *P. aeruginosa* PAO1-ΔlasI-JP2 (1/50) and supplemented with the mixture protein/AHLs (50 µL). The final theoretical concentration of 3-oxo-C12 AHLs is 20 nM, prior to enzymatic hydrolysis by SsoPox. After 270 minutes of culture at 37° C., cell density ($OD_{600\ nm}$) and bioluminescence (460-40 nm; intensity 100) of 200 µL aliquots of culture are measured in a 96-well plate using a microplate reader (Synergy HT, BioTek, USA) monitored by Gen5.1 software. Controls consist in the same experiment without enzyme and/or without AHLs.

Best hits were re-plated and then placed in microcultures as previously explained despite each clones were represented four times. The previous protocol was performed as identic to confirm the results. However, lysis buffer and pte buffer doesn't contain $CoCl_2$ salt to avoid affinity loss for the metals by the enzyme during the improvement process.

3—Improvement Confirmation and Analysis

The best variants were then sequenced (Sequencage plateforme, Timone, Marseille, France) and produce in larger amount for catalytic properties analysis. Genes or plasmids selected for the best improvement can have been used to perform the next round of diversity generation (i.e. go back to the first sections).

The high amount of protein production was performed using *E. coli* strain BL21(DE$_3$)-pGro7/GroEL (TaKaRa). Productions have been performed in 500 mL of ZYP medium [3] (100 µg/ml ampicilline, 34 µg/ml chloramphenicol) as previously explained [4,6,7], 0.2% (w/v) arabinose (Sigma-Aldrich; France) was added to induce the expression of the chaperones GroEL/ES and temperature transition to 25° C. was performed. Purification was performed as previously explained [7]. Briefly, a single step of 30' incubation at 70° C. was performed, followed by differential ammonium sulfate precipitation, dialysis and exclusion size chromatography. Proteins were quantified using nanospectrophotometer (nanodrop, thermofisher scientific, France) using protein molar extinction coefficient generated using protein primary sequence in PROT-PARAM (expasy tool softwares) [8].

3.1—Kinetics Generalities

Catalytic parameters were evaluated at 25° C., and recorded with a microplate reader (Synergy HT, BioTek, USA) and the Gen5.1 software in a 6.2 mm path length cell for 200 µL reaction in 96-well plate as previously explained [6]. Catalytic parameters were obtained by fitting the data to the Michaelis-Menten (MM) equation [9] using Graph-Pad Prism 5 software. When $V_{max}$ could not be reached in the experiments, the catalytic efficiency was obtained by fitting the linear part of MM plot to a linear regression using Graph-Pad Prism 5 software.

3.2—Phosphotriesterase Activity Characterization

Standard assays were performed in pte buffer measuring time course hydrolysis of PNP derivative of OPs ($\varepsilon_{405\ nm}$=17 000 $M^{-1}cm^{-1}$), nerve agents coumarin derivatives (CMP-coumarin, IMP-coumarin, PinP-coumarin) [10]($\varepsilon_{412\ nm}$=37 000 $M^{-1}cm^{-1}$) or malathion bu adding 2 mM DTNB in the buffer ($\varepsilon_{412\ nm}$=13 700 $M^{-1}cm^{-1}$). Kinetics have also been performed in pte buffer added of 0.1 and/or 0.01% of SDS as previously exemplified [1].

3.3—Lactonase Activity Characterization

The lactonase kinetics were performed using a previously described protocol [6]. The time course hydrolysis of lactones were performed in lac buffer (Bicine 2.5 mM pH 8.3, NaCl 150 mM, $CoCl_2$ 0.2 mM, Cresol purple 0.25 mM and 0.5% DMSO) over a concentration range 0-2 mM for AHLs. Cresol purple ($pK_a$ 8.3 at 25° C.) is a pH indicator used to follow lactone ring hydrolysis by acidification of the medium. Molar coefficient extinction at 577 nm was evaluated recording absorbance of the buffer over an acetic acid range of concentration 0-0.35 mM.

3.4—Melting Temperature Determination

Circular Dichroism spectra were recorded as previously explained [6] using a Jasco J-810 spectropolarimeter equipped with a Pelletier type temperature control system (Jasco PTC-4235) in a 1 mm thick quartz cell and using the Spectra Manager software. Briefly, measurements were performed in 10 mM sodium phosphate buffer at pH 8 with a protein concentration of 0.1 mg/mL. Denaturation was recorded at 222 nm by increasing the temperature from 20 to 95° C. (at 5° C./min) in 10 mM sodium phosphate buffer at pH 8 containing increasing concentrations (1.5-4 M) of guanidinium chloride. The theoretical Tm without guanidinium chloride was extrapolated by a linear fit using the GraphPadPrism 5 software.

2—Results 2.1—Phosphotriesterase and Lactonase Activity Screening

It has been previously highlighted that some residues in SsoPox active site are deleterious for phosphotriesterase activity compared to *P. diminuta* PTE active site (Hiblot et al., 2012, PloS One 7(10), e47028). In particular, W263 make a steric hindrance in SsoPox active site blocking the entry of OPs. However, it has been shown that W263F variation allowed a phosphotriesterase activity improvement despite that Trp and Phe are both cumbersome residues[5]. This raises the question of the real impact of variation at position W263. Indeed, W263 position is located at the dimer interface and on the active site capping loop positioning the lactone ring in SsoPox complexed structure with HTL[6]. Thus, variations at this position have been study to better understand their structural impacts allowing activity improvement.

Phosphotriesterase and Lactonase Activities Screening

A saturation site of the W263 position has been performed in the aim to screen phosphotriesterase and lactonase activities. Each variant have been produced in small amount (3 mL) and partially purified exploiting the natural thermoresistance of SsoPox to perform activity screening.

Phosphotriesterase Activity Screening

The ability of each variant to hydrolyse paraoxon substrate (FIG. 1-A) has been evaluated with 1 mM and 100 μM with same tendencies observed. The most efficient variants were respectively SsoPox W263L, W263M and W263F with specific activities enhancements ranging between 30-50 and 20-35 times respectively at 1 mM and 100 μM, compared to SsoPox wt. Moreover, it is interesting to note that the native enzyme (W263) is the less efficient among the saturation site variants for paraoxon hydrolysis (after W263K).

CMP-coumarin (FIG. 1-C) is a cyclosarin derivative used also to evaluate the ability of variants to hydrolyse nerve agents (50 μM). The SsoPox variants W263F, W263M and W263L exhibit the best specific activities (FIG. 2-C). The improvements range between 4 and 11 times compared to SsoPox wt.

due to exogenously added 3-oxo-C12 AHLs. Thus, if a lactonase is pre-incubated with 3-oxo-C12 AHLs, the bioluminescence will be inversely proportional to lactonase (3-oxo-C12 AHLase) activity.

Using this screening method, SsoPox W263A, W263I, W263T and W263V have been selected for a potential lactonase activity improvement (FIG. 3-B). The amplitude of the ameliorations in our conditions of screening can't be evaluated. Selected variations implicate small and mainly hydrophobic residues. These four variants form the group "lactonase selected variants".

2.2—Enzymatic Characterization of SsoPox Variants
2.2.1—Single Position Variants Confirmation of screening results has been allowed by enzymatic characterisation of phosphotriesterase and lactonase selected variants. They have been produced and purified in large amount. Their catalytic parameters have been characterized for lactone (3-oxo-C12 AHL (l)) and phosphotriester (Paraoxon) substrates (Table 2).

TABLE 2

Lactonase and phosphotriesterase activity of W263 variants of SsoPox (ND corresponds to not determined value).

| | SsoPox variant | $k_{cat}$ (s$^{-1}$) | $K_M$ (μM) | $K_I$ (μM) | $k_{cat}/K_M$ (M$^{-1}$s$^{-1}$) | Enhancement/wt |
|---|---|---|---|---|---|---|
| Paraoxon | Wt | 12.59 ± 1.26 | 24250 ± 3716 | — | 5.19(±1.31) × 10$^2$ | 1 |
| | W263F | 8.47 ± 0.53 | 700 ± 146 | — | 1.21(±0.33) × 10$^4$ | 23.3 |
| | W263M | 6.82 ± 0.57 | 931 ± 163 | — | 7.33(±1.9) × 10$^3$ | 14.1 |
| | W263L | ND | ND | — | 2.37(±0.33) × 10$^3$ | 4.6 |
| | W263I | ND | ND | — | 1.21(±0.59) × 10$^3$ | 2.3 |
| | W263V | ND | ND | — | 8.83(±0.3) × 10$^2$ | 1.7 |
| | W263T | ND | ND | — | 1.06(±0.03) × 10$^3$ | 2.0 |
| | W263A | 5.29 ± 0.69 | 1491 ± 351 | — | 3.55(±1.30) × 10$^3$ | 6.8 |
| 3-oxo- | Wt | (9.9 ± 1.2) × 10$^{-1}$ | 335 ± 10.4 | — | 2.96(±0.99) × 10$^3$ | 1 |
| | W263F | (6.6 ± 0.3) × 10$^{-1}$ | 146 ± 33 | — | 4.52(±1.04) × 10$^3$ | 1.5 |
| | W263M | ND | ND | ND | ND | 0 |
| | W263L | ND | ND | ND | ND | 0 |
| | W263I | 2.89 ± 0.08 | 17.8 ± 4.87 | — | 1.62(±0.45) × 10$^5$ | 54.7 |
| | W263V | 4.82 ± 0.11 | 24.7 ± 5.2 | — | 1.95(±0.44) × 10$^5$ | 65.8 |
| | W263T | 10.4 ± 0.35 | 137 ± 19 | — | 7.56(±1.08) × 10$^4$ | 25.6 |
| | W263A | 20.4 ± 1.21 | 1640 ± 170 | — | 1.25(±0.15) × 10$^3$ | 0.42 |

In conclusion, SsoPox W263F, W263L and W263M seem the best able to improve phosphotriesters hydrolysis. Variations implicate mainly hydrophobic residues with variable cumbersome. These proteins will form the group "phosphotriesterase selected variants".

Lactonase Activity Screening

It has been postulated that reduction of steric hindrance is not the only explanation for phosphotriesterase activity improvement of SsoPox W263F. So, variation at this position could allow a lactonase activity improvement. In the aim to explore this issue, a lactonase activity screening method has been developed. This screen is based on P. aeruginosa PAO1 derivative strain deleted for lasI gene and carrying a JP2 plasmid allowing to produce bioluminescence in presence of 3-oxo-C12 AHLs (l) (FIG. 1-C) (a main lactone implicated in P. aeruginosa quorum sensing system). In few words, this strain doesn't produce by itself 3-oxo-C12 AHLs and, thus, doesn't generate intrinsically bioluminescence. The bioluminescence intensity in experiment is only Phosphotriesterase Activity Characterization Phosphotriesterase activity of wt SsoPox has been characterized in a previous study (Hiblot et al., 2012, PloS One 7(10), e47028). As already observed in screening experiments, catalytic efficiencies of all selected variants were higher than the wt protein for paraoxon (Table 2). Among the phosphotriesterase selected variants, SsoPox W263F exhibits the highest paraoxonase catalytic efficiency ($k_{cat}/K_M$=1.21(±0.33)×10$^4$ M$^{-1}$s$^{-1}$) followed by SsoPox W263M and SsoPox W263L with respective enhancements of 23.3, 14.1 and 4.6 times compared to wt enzyme (Table 2, FIG. 2-D). Among the lactonase selected variants, only SsoPox W263A ($k_{cat}/K_M$=3.55(±1.30)×10$^3$ M$^{-1}$s$^{-1}$) exhibits a higher paraoxonase catalytic efficiency than the SsoPox W263L phosphotriesterase selected variant (6.8 times improvement compared to wt enzyme).

SsoPox W263L variant was selected for its phosphotriesterase activity improvement. Owing its potential for phosphotriester hydrolysis, its ability to hydrolyze different nerve agent derivatives has been addressed (Table 3).

TABLE 3

Phosphodiesterase activity of W263L variant of SsoPox. ND corresponds to not determined value. For paraoxon and methyl-parathion in presence of SDS, experimental data were fitted to substrate inhibition equation because of amore suitable fit than with classical MM equation. As a consequence, the calculated catalytic efficiencies are available only at low substrate concentration.

|  | SsoPox W263L | | | |
|---|---|---|---|---|
|  | $k_{cat}(s^{-1})$ | $K_M$ (µM) | $K_I$ (µM) | $k_{cat}/K_M(M^{-1}s^{-1})$ |
| Paraoxon | 3.13 ± 0.25 | 985 ± 169 | — | 3.18(±0.60) × $10^3$ |
| Paraoxon + SDS 0.01% | 8.89 ± 0.99 | 141 ± 33 | 1700 ± 453 | 6.29(±1.62) × $10^4$ |
| Paraoxon + DOC 0.01% | 3.17 ± 0.18 | 244 ± 55 | — | 1.30(±0.30) × $10^4$ |
| Methyl-paraoxon | ND | ND | ND | 3.16(±0.10) × $10^4$ |
| Methyl-paraoxon + SDS 0.01% | ND | ND | ND | 1.69(±0.04) × $10^5$ |
| Methyl-parathion + SDS 0.01% | 1.22(±0.13) × $10^{-1}$ | 168 ± 31 | 1920 ± 676 | 728 ± 156 |

It has been shown that anionic detergents, like SDS, were able to enhance the phosphotriesterase activity of SsoPox (Hiblot et al., 2012, PloS One 7(10), e47028). Paraoxon hydrolysis by SsoPox W263L in presence of SDS at 0.01% ($k_{cat}/K_M$=6.29(±1.62)×$10^4$ $M^{-1}s^{-1}$) has been compared to the paraoxon hydrolysis by wt enzyme ($k_{cat}/K_M$=6.41 (±1.51)×$10^3$ $M^{-1}s^{-1}$). The catalytic efficiency improvement induced by SDS on SsoPox W263L (19.8 times) is higher than one observed for wt SsoPox (12.4 times). It was proposed that activity improvement by SDS is due to global flexibilisation of the protein (Hiblot et al., 2012, PloS One 7(10), e47028). The higher improvement observed for SsoPox W263L could be due to variation-induced flexibility mimicking partially the SDS-induced flexibility. Indeed, leucine being less cumbersome than Trp, the phosphotriesterase improvement can be imputed to steric hindrance reduction.

Moreover, SDS at 0.01% is also able to enhance methyl-paraoxon hydrolysis by SsoPox W263L (5.3 times).

Deoxycholate acid (DOC), a mild detergent, is less effective than the SDS in increasing the paraoxon hydrolysis by the SsoPox W263L ($k_{cat}/K_M$=1.30(±0.30)×$10^4$).

Lactonase Activity Characterization

Chemically different lactone substrates have been used in the aim to understand the lactonase activity improvement of SsoPox. AHLs and γ/δ-lactones (oxo-lactones) are differently acylated on the lactone cycle (FIG. 1). We have studied AHLs with different size chains. 3-oxo-C10 AHLs (l) (FIG. 1-D) are 10 times better substrate for wt enzyme compared to 3-oxo-C12 AHL (l) (respectively, $k_{cat}/K_M$=3.16(±0.40)× $10^4$ $M^{-1}s^{-1}$ and $k_{cat}/K_M$=2.96(±0.99)×$10^3$ $M^{-1}s^{-1}$; data not shown) for which variants have been screened. Two different oxo-lactones exhibiting different ring sizes have also been studied. Wt SsoPox exhibits a 10 times higher catalytic efficiency with undecanoic-δ-lactones (r) (6 atoms ring-size) than with undecanoic-γ-lactones (r) (5 atoms ring-size) (respectively, $k_{cat}/K_M$=6.72(±2.54)×$10^4$ $M^{-1}s^{-1}$ and $k_{cat}/K_M$=2.36 (±0.38)×$10^3$ $M^{-1}s^{-1}$; data not shown).

Directed evolution allows to "select what you screen for". Giving that best lactonase variants were selected on their ability do hydrolyse 3-oxo-C12 AHL, kinetic characterisations of the 3-oxo-C12 AHLase activity has been performed (Table 2). Results obtained allows to confine that lactonase selected variants exhibit 3-oxo-C12 AHLase improved catalytic efficiencies compared to SsoPox wt. These improvements range from 26 times for SsoPox W263T to 66 times for SsoPox W263V with a $k_{cat}/K_M$=1.95(±0.44)×$10^5$ $M^{-1}s^{-1}$ that is the best referred to our knowledge (FIG. 3-C). Concerning the phosphotriesterase selected variants, none of them presents enhanced 3-oxo-C12 AHLase catalytic efficiencies, only SsoPox W263F presents an efficiency equivalent to the wt enzyme. SsoPox W263L, W263A and W263M lost the ability to hydrolyse this molecule. The extent of the improvements observed makes of 3-oxo-C12 a potential promiscuous substrate.

Series of complementary results have been obtained for 3-oxo-C12 AHL, 3-oxo-C10 AHL, δ-lactone and undecanoic-γ-lactone substrates (see table 2').

TABLE 2'

Lactonase activities of W263 variants of SsoPox (ND corresponds to not determined value).

|  | SsoPox variant | $k_{cat}$ ($s^{-1}$) | $K_M$ (µM) | $K_I$ (µM) | $k_{cat}/K_M$ ($M^{-1}s^{-1}$) | Enhancement/wt |
|---|---|---|---|---|---|---|
| 3-oxo-C12 AHL (l) (XII) | wt | 1.01 ± 0.13 | 456 ± 128 | — | 2.22(±0.68) × $10^3$ | 1 |
|  | W263F | 0.41 ± 0.02 | 146 ± 33 | — | 2.81(±0.65) × $10^3$ | 1.3 ± 0.5 |
|  | W263M | ND | ND | — | ND | ND |
|  | W263L | ND | ND | — | ND | ND |
|  | W263I | 1.80 ± 0.05 | 17.8 ± 4.9 | — | 1.0l(±0.28) × $10^5$ | 45.5 ± 18.8 |
|  | W263V | 3.00 ± 0.07 | 24.7 ± 5.2 | — | 1.21(±0.26) × $10^5$ | 54.5 ± 20.4 |
|  | W263T | 6.44 ± 0.22 | 137 ± 19 | — | 4.70(±0.67) × $10^4$ | 21.2 ± 7.2 |
| 3-oxo-C10 AHL (l) (XI) | wt | 4.52 ± 0.10 | 143 ± 15 | — | 3.16(±0.40) × $10^4$ | 1 |
|  | W263F | 3.96 ± 0.18 | 288 ± 56 | — | 1.38(±0.28) × $10^4$ | 4.4(±1.0) × $10^{-1}$ |
|  | W263M | ND | ND | — | ND | 0 |
|  | W263L | ND | ND | — | ND | 0 |
|  | W263I | (6.00 ± 0.90) × $10^{-1}$ | 1605 ± 443 | — | 3.74(±1.17) × $10^2$ | 1.2(±0.4) × $10^{-2}$ |
|  | W263V | (1.90 ± 0.09) × $10^{-1}$ | 1346 ± 298 | — | 1.41(±0.32) × $10^2$ | 4.5(±1.2)$10^{-3}$ |
|  | W263T | (1.07 ± 0.16) × $10^{-1}$ | 1000 ± 343 | — | 1.06(±0.40) × $10^2$ | 3.4(±1.3)$10^{-3}$ |

TABLE 2'-continued

Lactonase activities of W263 variants of SsoPox (ND corresponds to not determined value).

| | SsoPox variant | $k_{cat}$ (s$^{-1}$) | $K_M$ (µM) | $K_I$ (µM) | $k_{cat}/K_M$ (M$^{-1}$s$^{-1}$) | Enhancement/wt |
|---|---|---|---|---|---|---|
| Undecanoic-δ-lactone (r) (XX) | wt | 7.38 ± 0.28 | 94 ± 18 | — | 7.86(±1.53) × 10$^4$ | 1 |
| | W263F | (6.65 ± 0.32) × 10$^1$ | 135.2 ± 52.8 | — | 4.92(±1.93) × 10$^5$ | 6.3 ± 2.7 |
| | W263M | (7.12 ± 0.66) × 10$^1$ | 161 ± 47 | 7 400 ± 2 475 | 4.42(±1.35) × 10$^5$ | 5.6 ± 2.0 |
| | W263L | (5.68 ± 0.58) × 10$^1$ | 219 ± 62 | 4 253 ± 1 152 | 2.59(±0.78) × 10$^5$ | 3.3 ± 1.2 |
| | W263I | (5.80 ± 0.74) × 10$^1$ | <10 | 803 ± 213 | >5.80(±0.74) × 10$^6$ | >73.8 ± 17.2 |
| | W263V | (4.48 ± 0.50) × 10$^1$ | 57 ± 16 | 789 ± 186 | 7.92(±2.34) × 10$^5$ | 10.1 ± 3.6 |
| | W263T | (9.33 ± 0.80) × 10$^1$ | 130 ± 41 | 3047 ± 576 | 7.17(±2.34) × 10$^5$ | 9.1 ± 3.5 |
| Undecanoic-γ-lactone (r) (XVI) | wt | 4.95 ± 0.26 | 2 099 ± 230 | — | 2.36 (±0.38) × 10$^3$ | 1 |
| | W263F | 4.63 ± 0.27 | 373 ± 111 | — | 1.24(±0.38) × 10$^4$ | 5.3 ± 1.8 |
| | W263M | 4.25 ± 0.22 | 334 ± 61 | — | 1.27(±0.24) × 10$^4$ | 5.4 ± 1.3 |
| | W263L | 3.92 ± 0.17 | 371.8 ± 69.2 | — | 1.05(±0.20) × 10$^4$ | 4.4 ± 1.1 |
| | W263I | 1.94 ± 0.08 | 361 ± 47 | — | 5.37(±0.73) × 10$^3$ | 2.3 ± 0.5 |
| | W263V | 5.64 ± 0.53 | 1 760 ± 404 | — | 3.20(±0.80) × 10$^3$ | 1.4 ± 0.4 |
| | W263T | 4.55 ± 0.10 | 13.0 ± 4.2 | — | 3.49(±1.13) × 10$^5$ | 147.9 ± 53.5 |

Thermostability

The melting temperatures have been determined by circular dichroism spectroscopy for the wt SsoPox enzyme and the single position variants. Resultants are given below:

wt: 104° C.
W263F: 91.8±1.7° C.
W263M: 85.3±0.9° C.
W263L: 92.0±2.1° C.
W263T: 89.2±0.4° C.
W263V: 84.1±1.6° C.
W263I: 87.8±1.2° C.

2.2.2—Multiple Positions Variants

Some of the above mentioned mutated hyperthermophilic phosphotriesterase (PTE) having a lactonase activity derived from a hyperthermophilic phosphotriesterase corresponding to the sequence of SEQ ID NO: 3 have been tested for their ability to hydrolyse either OPs or AHLs compounds. The results of their enzymatic activities are presented hereafter.

Five mutated hyperthermophilic phosphotriesterase (PTE) having a lactonase activity derived from the hyperthermophilic PTE of Sulfolobus solfataricus corresponding to the sequence SEQ ID NO: 3 have been tested for their phosphotriesterase activity. The evaluation of phosphotriesterase activity has been performed using ethyl-paraoxon, methyl-paraoxon, ethyl-parathion, methyl-parathion and malathion. Results are presented in tables 4 and 5 hereafter.

TABLE 5

Phosphodiesterase activity of variants of SsoPox αsC6 and αsD6. Catalytic avtivity is expressed in M$^{-1}$s$^{-1}$ (ND = not detected, VLH = very low hydrolysis).

| Substrat | SsoPox wt | αsC6 SEQ ID NO: 31 | αsD6 SEQ ID NO: 23 |
|---|---|---|---|
| Ethyl-Paraoxon | 5.19(±1.31) · 10$^2$ | 2.86(±0.17) · 10$^4$ | 6.22(±1.01) · 10$^4$ |
| Methyl-Paraoxon | 1.27(±0.7) · 10$^3$ | 3.11(±1.32) · 10$^4$ | 2.04(±0.59) · 10$^4$ |
| Ethyl-Parathion | ND | 1.10(±0.20) · 10$^2$ | 6.05(±1.50) · 10$^3$ |
| Methyl-Parathion | 9.09 ± 0.9 | 24.8 ± 3.9 | 2.01(±0.36) · 10$^4$ |
| Malathion | 5.56 ± 1.26 | 7.7(±5.94) · 10$^2$ | 4.20(±0.49) · 10$^2$ |

Among the phosphotriesterase selected variants, SsoPox αsD6 exhibits the highest paraoxonase catalytic efficiency for ethyl-paraoxon, ethyl-parathion and methyl parathion. SsoPox αsC6 exhibits the highest paraoxonase catalytic efficiency for malathion. Unlike SsoPox wt, SsoPox αsA6, αsB5, αsC6 and αsD6 are now able to hydrolyze methyl parathion.

SsoPox αsD6 is probably the most interesting variant of SsoPox for its capacity to hydrolyze several OPs substrates.

Example 2

In this example, we tested whether the variant SsoPox W263I, which has an improved ability to hydrolyze 3-oxo-

TABLE 4

Phosphodiesterase activity of variants of SsoPox αsA1, αsA6, αsB5. Catalytic avtivity is expressed in M$^{-1}$s$^{-1}$ (ND = not detected, VLH = very low hydrolysis).

| Substrat | SsoPox wt | αsA1 SEQ ID NO: 21 | αsA6 SEQ ID NO: 27 | αsB5 SEQ ID NO: 29 |
|---|---|---|---|---|
| Ethyl-Paraoxon | 5.19(±1.31) · 10$^2$ | 3.37(±0.94) · 10$^4$ | 3.61(±1.69) · 10$^3$ | 4.98(±0.94) · 10$^4$ |
| Methyl-Paraoxon | 1.27(±0.7) · 10$^3$ | 2.29(±1.09) · 10$^4$ | 1.08(±0.30) · 10$^4$ | 4.31(±0.14) · 10$^3$ |
| Ethyl-Parathion | ND | VLH | 2.39(±0.47) · 10$^2$ | 9.32(±1.44) · 10$^2$ |
| Methyl-Parathion | 9.09 ± 0.9 | 3.68(±0.5) · 10$^1$ | 61 ± 15 | 9.49(±1.15) · 10$^2$ |
| Malathion | 5.56 ± 1.26 | 3.2 ± 0.7 | ND | 31.1 ± 7.7 |

C12 AHLs could decrease *P. aeruginosa* biofilm formation and virulence factor production in vitro, and reduce mortality in vivo. We present evidence that lactonase-mediated quorum quenching inhibits virulence and decreases lethality of *P. aeruginosa* in a rat pulmonary infection model.

1—Experimental Procedure 1.1—*P. aeruginosa* Culture

The laboratory strain PAO1 (ATCC reference 15692) was used in all experiments. Strains were grown in LB (BD, France) medium and were maintained at −80° C. in 50% LB broth and 50% glycerol. *P. aeruginosa* PAO1 carrying a chromosomally integrated PlasB-luxCDABE reporter construct [11] was maintained in the same way as the wild-type strain. Strains were grown at 37° C. in Luria-Bertani (LB) medium (BD, France) with shaking (200 rpm). LB was solidified with 1.5 bacto agar when required.

For in vivo studies, at the time of the experiments, aliquots containing the bacteria were thawed and cultured on a COS (Biomerieux, France) (Columbia with 5% Sheep blood) agar plate. Ten fresh colonies were sampled and cultured overnight at 37° C. in triptych soy broth (TSB, Biomerieux, France) with continuous agitating until the $OD_{600\ nm}=1$ with cultured PAO1. Serial dilution was subsequently performed to adjust the bacterial amount and exact concentrations were confirmed by plating serial dilutions on the appropriate culture medium and counting colonies. Inoculums of $10^8$ CFU/ml were used for all animal infections.

1.2—Biofilm Formation Assays

Cultures of *P. aeruginosa* PAO1 (18 hours) were diluted 1:50 in 10% TSB and dispensed into the wells of a Calgary Biofilm Device 96 well plate (Innovotech Inc., Edmonton, Canada). To test inhibition of biofilm formation, three-fold dilution series (50 µg down to 0.5 µg of SsoPox W263I) was added to the wells. Plates were incubated for 4 hours with rocking at 120 Hz at 37° C. The biofilms were stained with 1% crystal violet. Crystal violet was dissolved from biofilms in 100% ethanol and quantified by measuring absorbance at 600 nm [14]. *P. aeruginosa* PAO1 planktonic growth was also measured at 600 nm.

1.3—LasB Reporter System

Aliquots of *P. aeruginosa* PAO1 carrying PlasB-luxCD-ABE from an 18 hr old culture were placed in wells of a 96 well plate, after which dilutions from 50 µg to 0.05 µg of SsoPox W263I were added. Plates were incubated at 37° C. for 90 minutes, with shaking every 10 minutes during which luminescence was measured every 10 minutes to determine activity of the quorum sensing reporter.

1.4—Animal General Procedure

Adult Sprague-Dawley male pathogen-free rats weighting 250 to 300 g from SAS Janvier (Le-Genest-St-Isle, France) were housed in individual plastic cages placed in a ventilated pressurized cabinet (A-BOX 160, Noroit, Rezé, France) with free access to water and standard diet food. Animals were anesthetized with 5% Sevoflurane® (Abbott, Rungis, France) in 100% oxygen (anesthetizing box, Harvard Apparatus, Les Ulis, France). Their trachea was exposed and intubated using a 16-gauge catheter for drug and/or bacterial administration. Awaken animals were housed back in the same condition as initially and were weighed daily. At the end of each experiment, euthanasia was performed with an intra-peritoneal injection of a lethal dose of thiopental (Panpharma, France).

1.5—Rat Tolerance of Inhaled SsoPox W263I

The tolerance of SsoPox administered by intra-tracheal route was attested in a preliminary study on 3 groups of animals (n=3 per group) receiving 250 µl of SsoPox W263I at a concentration of either 0.1, 1 or 10 mg/ml and compared to 5 controls receiving 250 µl of phosphate buffered saline (PBS; Biomerieux; France). One animal of each group was sacrificed after 6, 24 and 48 hours. Surviving animals were sacrificed after 48 hours. Lungs were removed after death and their macroscopic aspect was noted, then they were preserved in formaldehyde for histological assessment.

1.6—Rat Respiratory Infection Model and SsoPox W263I Treatment

Three groups of 20 animals were infected by intra tracheal inoculation of 250 µl of a solution of PBS containing $10^8$ CFU/ml of *P. aeruginosa* PAO1. At the same time, a first group received 250 additional µl of PBS into the trachea (non-treated group: NT), another group received 250 µl of SsoPox W263I at a concentration of 1 mg/ml (immediate treatment group: IT). In the last group, animals received 250 µl of SsoPox W263I at 1 mg/ml 3 hours later (deferred treatment group: DT). SsoPox W263I and additional PBS were delivered intratracheally using the same anesthetic procedure as for the infection.

1.7—Lung Processing After infection, animals were observed for 2 days and spontaneous mortality was noted. Surviving rats were euthanized after 48 hours. After death, lungs were removed aseptically. Right lung was homogenized in PBS for bacterial culture. Left lung was preserved for histological analysis.

1.8—Histological Severity Score (HSS)

Examination was performed by a pathologist blinded to the group identity (H. L.). An HSS was calculated based on the number of bronchopneumonia lesions (0, no lesions; 1, 30 lesions/lung; 2, ≥30 lesions/lung; 3, confluent lesions of bronchopneumonia), as previously reported [13].

1.9—Statistics

The number of studied animals (20 animals per group) was calculated based on a mortality reduction from 80% in the NT group infected with PAO1 (known from literature data [12]) to an expected mortality rate of 50% in the treated groups, with 90% statistical power and a two-sided alpha value of 0.05.

2—Results 2.1—Decreases of lasB Expression and Biofilm Formation by SsoPox W263I We measured lasB transcription in a *P. aeruginosa* PAO1 strain carrying the chromosomally integrated PlasB-luxCD-ABE reporter construct. The gene lasB codes for elastase, a classical virulence factor regulated by quorum sensing. Addition of SsoPox W263I into *P. aeruginosa* PAO1 cultures significantly reduced lasB transcription (FIG. 4). SsoPox W263I-mediated lasB inhibition exhibited a dose-dependent profile with a half inhibition concentration ($[C_{1/2}]$) of the enzyme around 0.5 µg/mL (FIG. 4).

Biofilm development is also regulated in part by quorum sensing. The effect of SsoPox W263I on the ability of *P. aeruginosa* to form biofilms was investigated. Our results show that the lactonase inhibits biofilm formation in a dose-dependent manner, with a $[C_{1/2}]$ of approximately 170 µg/mL (FIG. 5).

2.2—SsoPox W263I Protects Rats from *P. aeruginosa* PAO1 Pneumonia

The effects of SsoPox treatment on rat respiratory tissues were investigated. Tracheal instillation of SsoPox W263I was well tolerated—no spontaneous mortality was observed regardless of the dose administered (up to 2.5 mg). Lungs removed after treatment showed no macroscopic signs of injury and histological analysis showed normal lung parenchyma. SsoPox W263I caused no observable acute inflammatory reactions in the rat respiratory parenchyma.

The influence of SsoPox W263I on *P. aeruginosa* pulmonary infection was investigated in two groups of 20 rats. In the non-treated group (NT), the mortality rate after inoculation with *P. aeruginosa* was 75% (15/20). When the rats were treated with SsoPox (1 mg/mL) immediately after inoculation with *P. aeruginosa* (IT), the mortality was significantly reduced to 20% (4/20) (p=0.0001 vs NT) (FIG. 6). In addition we observed that loss of body weight, measured from the day of inoculation with *P. aeruginosa* until the day of death, was significantly less in the IT group than in the NT group (11.3±12 g vs. 20.4±9.3 g respectively; p=0.01). The DT group lost 25.6±1.82 g of body weight (p=0.77 vs NT group). Moreover, mean time to death was significantly longer in the DT group as compared to the control group (37±13 vs. 25±16 hours; p=0.01).

Consistent with the increased survival of the IT group, we noted that the lungs of the animals in the IT group had less inflammatory damage as compared to the NT group (FIG. 7): HSS (1.27±0.6 vs. 2.64±0.4; p=0.005). In the DT group, the mean HSS was not different from the NT group.

Example 3

The ecotoxicity of SsoPox has been tested on the viability and development of oyster larvae (*Crassostrea gigas*) and sea urchins larvae (*Paracentrotus lividus*) during 24 hours and 48 hours respectively. Experiments have been done using 10 mg/l, 1 mg/l, 100 µg/l, 10 µg/l, 1 µg/l or 100 ng/l of SsoPox and two samples of at least 100 larvae have been analyzed. CuSO4 has been used as a toxic control.
In the case of the urchin larvae, no effects have been observed at any of the tested concentrations.
In the case of the oyster larvae, no effects have been observed for a concentration equal or lower to 1 mg/L, only 10% of the population is affected at a concentration of 2.9 mg/L (sample 1) or 3.5 mg/L (sample 2).
These results indicate that high concentrations of SsoPox are not toxic for living organisms and thus, the use of SsoPox in sea environment can be considered favorably.

REFERENCES

1. Hiblot J, Gotthard G, Chabriere E, Elias M (2012) Characterisation of the organophosphate hydrolase catalytic activity of SsoPox. Sci Rep 2: 779.

3. Studier F W (2005) Protein production by auto-induction in high density shaking cultures. Protein Expr Purif 41: 207-234.

4. Gotthard G, Hiblot J, Elias M, Chabriere E (2011) Crystallization and preliminary X-ray diffraction analysis of the hyperthermophilic *Sulfolobus islandicus* lactonase. Acta Crystallogr Sect F Struct Biol Cryst Commun 67: 354-357.

5. Del Vecchio P, Elias M, Merone L, Graziano G, Dupuy J, et al. (2009) Structural determinants of the high thermal stability of SsoPox from the hyperthermophilic archaeon *Sulfolobus solfataricus*. Extremophiles 13: 461-470.

6. Hiblot J, Gotthard G, Chabriere E, Elias M (2012) Structural and Enzymatic characterization of the lactonase SisLac from *Sulfolobus islandicus*. PLoS One 7: e47028.

7. Hiblot J, Gotthard G, Chabriere E, Elias M (2012) Characterisation of the organophosphate hydrolase catalytic activity of SsoPox. Sci Rep 2.

8. Gasteiger E, Hoogland C, Gattiker A, Duvaud S, Wilkins M R, et al. (2005) Protein Identification and Analysis Tools on the ExPASy Server. In: Walker J M, editor. The proteomics protocols handbook: Humana Press.

9. Copeland R A (2000) Enzymes, A Practical Introduction to Structure, Mechanism, and Data Analysis. New York, Chichester, Weiheim, Brisbane, Singapore, Toronto: WILEY-VCH. 390.

10. Ashani Y, Gupta R D, Goldsmith M, Silman I, Sussman J L, et al. (2010) Stereo-specific synthesis of analogs of nerve agents and their utilization for selection and characterization of paraoxonase (PON1) catalytic scavengers. Chem Biol Interact 187: 362-369.

11. Darch S E, West S A, Winzer K, Diggle S P (2012) Density-dependent fitness benefits in quorum-sensing bacterial populations. Proc Natl Acad Sci USA 109: 8259-8263.

12. Lesprit P, Faurisson F, Join-Lambert O, Roudot-Thoraval F, Foglino M, et al. (2003) Role of the quorum-sensing system in experimental pneumonia due to *Pseudomonas aeruginosa* in rats. Am J Respir Crit Care Med 167: 1478-1482.

13. Marquette C H, Wermert D, Wallet F, Copin M C, Tonnel A B (1999) Characterization of an animal model of ventilator-acquired pneumonia. Chest 115: 200-209.

14. O'Toole G A, Kolter R (1998) Initiation of biofilm formation in *Pseudomonas fluorescens* WCS365 proceeds via multiple, convergent signalling pathways: a genetic analysis. Mol Microbiol 28: 449-461.

The invention claimed is:

1. A mutated hyperthermophilic phosphotriesterase, said mutated hyperthermophilic phosphotriesterase has an increased lactonase catalytic activity in comparison of the lactonase activity of a non-mutated hyperthermophilic phosphotriesterase, wherein the non-mutated hyperthermophilic phosphotriesterase is a wild-type phosphotriesterase corresponding to the consensus sequence of SEQ ID NO:1, wherein the amino acid W in position 265 is substituted by an amino acid selected from the group consisting of the amino acids isoleucine I, valine V, threonine T and alanine A within the mutated hyperthermophilic phosphotriesterase.

2. The mutated hyperthermophilic phosphotriesterase according to claim 1, wherein hydrolyzis of 3-oxo-C12 AHL by said mutated hyperthermophilic phosphotriesterase is increased by at least 2 times, in comparison of hydrolyzis of 3-oxo-C12 AHL by said non-mutated hyperthermophilic phosphotriesterase.

3. The mutated hyperthermophilic phosphotriesterase according to claim 1, wherein said mutated hyperthermophilic phosphotriesterase has a thermostability, which is substantially similar to the thermostability of said non-mutated hyperthermophilic phosphotriesterase.

4. The mutated hyperthermophilic phosphotriesterase according to claim 1, wherein the amino acid in position 2 in SEQ ID NO : 1 is missing.

5. The mutated hyperthermophilic phosphotriesterase according to claim 1, wherein said non-mutated hyperthermophilic phosphotriesterase is selected from the group consisting of SEQ ID NO : 3 from Sulfolobus solfataricus, SEQ ID NO : 5 from Sulfolobus acidocalaricus, and from SEQ ID NO : 7 Sulfolobus islandicus,
   wherein said sequences SEQ ID NO : 3, SEQ ID NO : 5 and SEQ ID NO : 7 belong to the consensus SEQ ID NO : 1, and for said mutated hyperthermophilic phosphotriesterase the amino acid in position 2 in SEQ ID NO: 1 being missing from SEQ ID NO: 5 and the amino acids in position 2 and 3 in SEQ ID NO: 1 being missing from SEQ ID NO: 3 and SEQ ID NO: 7.

6. The mutated hyperthermophilic phosphotriesterase according to claim 1, wherein said amino acid W in position 265 is substituted by an amino acid Isoleucine I.

7. The mutated hyperthermophilic phosphotriesterase according to claim 1, said mutated hyperthermophilic PTE selected from the group consisting of : SEQ ID NO: 13, SEQ ID NO: 15, SEQ ID NO: 17, SEQ ID NO: 19, SEQ ID NO: 57, SEQ ID NO: 59, SEQ ID NO: 61, SEQ ID NO: 63, SEQ ID NO: 101, SEQ ID NO: 103, SEQ ID NO: 105 and SEQ ID NO: 107.

8. A method of disrupting quorum-sensing in bacteria comprising administering a sufficient amount of the mutated hyperthermophilic phosphotriesterase as defined in claim 1.

9. The method according to claims 8, wherein the mutated hyperthermophilic phosphotriesterase is administered to boats or other sea equipment and limits the formation of biofilms in boats or other sea equipment.

10. The method according to claims 8, wherein the mutated hyperthermophilic phosphotriesterase is administered to plants or vegetables and inhibits fire blight in plants or rotting of vegetables.

11. A phytosanitary composition comprising as active ingredient at least one mutated hyperthermophilic phosphotriesterase as defined in claim 1.

12. An antibacterial composition comprising as active ingredient at least one mutated hyperthermophilic phosphotriesterase as defined in claim 1.

13. A pharmaceutical composition comprising as active ingredient at least one mutated hyperthermophilic phosphotriesterase as defined in claim 1, in association with a pharmaceutically acceptable vehicle.

14. The pharmaceutical composition according to claim 13, further comprising at least one antibiotic selected from the group consisting of gentamycine, ciprofloxacin, ceftazidime, imipenem, and tobramycine.

15. A medicament comprising hyperthermophilic phosphotriesteraseas defined in claim 1.

16. A method of treating bacterial infections, comprising administering to a patient in need thereof an effective amount of the mutated hyperthermophilic phosphotriesterase as defined in claim 1.

17. A method of treating pneumonia or nosocomial diseases, caused by bacteria using homoserin lactone substrates to communicate, in particular in the blood, wounds, burn, skin, biomaterial-body contact area, comprising administering to a patient in need thereof an effective amount of the mutated hyperthermophilic phosphotriesterase as defined in claim 1.

18. A method of treating dental plaque comprising administering to a patient in need thereof an effective amount of the mutated hyperthermophilic phosphotriesterase as defined in claim 1.

19. A method of treating eye infections or eye surface healing comprising administering to a patient in need thereof an effective amount of the mutated hyperthermophilic phosphotriesterase as defined in claim 1.

20. A mutated hyperthermophilic phosphotriesterase, said mutated hyperthermophilic phosphotriesterase has an increased lactonase catalytic activity in comparison of the lactonase activity of a non-mutated hyperthermophilic phosphotriesterase, wherein the non-mutated hyperthermophilic phosphotriesterase is a wild-type phosphotriesterase corresponding to the consensus sequence of SEQ ID NO:1, wherein the amino acid W in position 265 is the single substitution within the mutated hyperthermophilic phosphotriesterase.

21. The mutated hyperthermophilic phosphotriesterase according to claim 20, said mutated hyperthermophilic phosphotriesterase having a single mutation being a substitution of the tryptophan W in position 265 of the consensus sequence SEQ ID NO : 1 by a threonine T.

22. The mutated hyperthermophilic phosphotriesterase according to claim 20, said mutated hyperthermophilic phosphotriesterase having a single mutation being a substitution of the tryptophan W in position 263 of the sequence SEQ ID NO : 3 by an isoleucine I, a valine V, a threonine T or an alanine A.

* * * * *